United States Patent
Bartberger et al.

(10) Patent No.: US 11,332,459 B2
(45) Date of Patent: May 17, 2022

(54) BENZIMIDAZOLE DERIVATIVES AND THEIR USES

(71) Applicant: TEIJIN PHARMA LIMITED, Tokyo (JP)

(72) Inventors: Michael D. Bartberger, Sherman Oaks, CA (US); Nagasree Chakka, Lexington, MA (US); Hua Gao, Canton, MA (US); Angel Guzman-Perez, Belmont, MA (US); Daniel B. Horne, Natick, MA (US); Zihao Hua, Andover, MA (US); Madeleine Kieffer, Burlingame, CA (US); Daniel C. H. Lin, Redwood City, CA (US); Benjamin Charles Milgram, Cambridge, MA (US); Jane Panteleev, Charlestown, MA (US); Laurie Schenkel, Somerville, MA (US); John Stellwagen, Beverly, MA (US); Matthew Weiss, Boston, MA (US); Ryan D. White, Somerville, MA (US); Wei Zhao, Westford, MA (US)

(73) Assignee: TEIJIN PHARMA LIMITED, Tokyo (JP)

( * ) Notice: Subject to any disclaimer, the term of this patent is extended or adjusted under 35 U.S.C. 154(b) by 0 days.

(21) Appl. No.: 16/754,349

(22) PCT Filed: Oct. 18, 2018

(86) PCT No.: PCT/US2018/056484
§ 371 (c)(1),
(2) Date: Apr. 7, 2020

(87) PCT Pub. No.: WO2019/079578
PCT Pub. Date: Apr. 25, 2019

(65) Prior Publication Data
US 2020/0308145 A1    Oct. 1, 2020

Related U.S. Application Data

(60) Provisional application No. 62/671,090, filed on May 14, 2018, provisional application No. 62/574,465, filed on Oct. 19, 2017.

(51) Int. Cl.
| | | |
|---|---|---|
| C07D 401/14 | (2006.01) | |
| A61K 31/4545 | (2006.01) | |
| C07D 401/04 | (2006.01) | |
| C07D 403/04 | (2006.01) | |
| C07D 413/14 | (2006.01) | |
| C07D 471/04 | (2006.01) | |
| C07D 471/10 | (2006.01) | |
| C07D 498/04 | (2006.01) | |

(52) U.S. Cl.
CPC ......... *C07D 401/14* (2013.01); *C07D 401/04* (2013.01); *C07D 403/04* (2013.01); *C07D 413/14* (2013.01); *C07D 471/04* (2013.01); *C07D 471/10* (2013.01); *C07D 498/04* (2013.01)

(58) Field of Classification Search
CPC .............. C07D 401/14; A61K 31/4545; A61K 31/506; A61P 9/12; A61P 13/12
USPC .................... 546/193; 514/318, 256; 544/333
See application file for complete search history.

(56) References Cited

U.S. PATENT DOCUMENTS

| | | |
|---|---|---|
| 4,857,536 A | 8/1989 | Manoury et al. |
| 7,541,477 B2 | 6/2009 | Moriya et al. |
| 8,003,668 B2 | 8/2011 | Defossa et al. |
| 8,163,774 B2 | 4/2012 | Defossa et al. |
| 9,388,192 B2 | 7/2016 | Czardybon et al. |
| 9,828,348 B2 | 11/2017 | Tafesse et al. |
| 10,501,421 B1 * | 12/2019 | Fesik .................. C07D 409/04 |

(Continued)

FOREIGN PATENT DOCUMENTS

| | | |
|---|---|---|
| EP | 1 863 790 B1 | 3/2006 |
| EP | 2 368 876 A1 | 3/2010 |

(Continued)

OTHER PUBLICATIONS

Coon et al., Brain-Penetrating 2-Aminobenzimidazole $H_1$-Antihistamines for the Treatment of Insomnia, Bioorganic & Medicinal Chemistry Letters (2009) 19:4380-4384.

(Continued)

*Primary Examiner* — Charanjit Aulakh
(74) *Attorney, Agent, or Firm* — Mintz Levin Cohn Ferris Glovsky and Popeo PC

(57) ABSTRACT

The present invention relates to inhibitors of Transient Receptor Potential Channel 6 (TRPC6) protein activity. The present invention provides a compound of formula (I) or a pharmaceutically acceptable salt thereof, pharmaceutical compositions comprising a compound of the invention, a method for manufacturing compounds of the invention and therapeutic uses thereof.

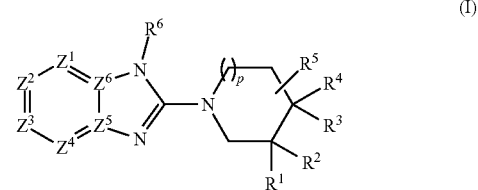

(I)

16 Claims, No Drawings

(56) References Cited

U.S. PATENT DOCUMENTS

| | | |
|---|---|---|
| 2004/0106655 A1 | 6/2004 | Kitajima et al. |
| 2004/0152690 A1 | 8/2004 | Balan et al. |
| 2006/0247253 A1 | 11/2006 | Leban et al. |
| 2010/0267717 A1 | 10/2010 | Leban et al. |
| 2013/0303462 A1 | 11/2013 | Klein et al. |

FOREIGN PATENT DOCUMENTS

| | | |
|---|---|---|
| WO | WO 1996/06845 A1 | 3/1996 |
| WO | WO 2003/033486 A1 | 4/2003 |
| WO | WO 2003/039440 A3 | 5/2003 |
| WO | WO 2005/103029 A1 | 11/2005 |
| WO | WO 2006/010283 A1 | 2/2006 |
| WO | WO 2006/099942 A3 | 9/2006 |
| WO | WO 2006/128670 A1 | 12/2006 |
| WO | WO 2007/041833 A2 | 4/2007 |
| WO | WO 2008/003667 A2 | 1/2008 |
| WO | WO 2008/023239 A1 | 2/2008 |
| WO | WO 2008/097428 A3 | 8/2008 |
| WO | WO 2008/100977 A3 | 8/2008 |
| WO | WO 2008/153701 A1 | 12/2008 |
| WO | WO 2009/018280 A2 | 2/2009 |
| WO | WO 2009/089234 A3 | 7/2009 |
| WO | WO 2010/104306 A2 | 9/2010 |
| WO | WO 2010/144742 A3 | 12/2010 |
| WO | WO 2011/023812 A1 | 3/2011 |
| WO | WO 2011/107474 A1 | 9/2011 |
| WO | WO 3023/012478 A1 | 1/2012 |
| WO | WO 2012/080729 A2 | 6/2012 |
| WO | WO 2012/098281 A3 | 7/2012 |
| WO | WO 2012/116440 A1 | 9/2012 |
| WO | WO 2014/027053 A1 | 2/2014 |
| WO | WO 2014/127350 A1 | 8/2014 |
| WO | WO 2014/160183 A1 | 10/2014 |
| WO | WO 2015/002754 A2 | 1/2015 |
| WO | WO 2016/016421 A1 | 2/2016 |
| WO | WO 2016/168598 A1 | 10/2016 |
| WO | WO 2017/052394 A1 | 3/2017 |
| WO | WO 2017/060488 A1 | 4/2017 |
| WO | WO 2017/064068 A1 | 4/2017 |
| WO | WO 2017/144909 A1 | 8/2017 |
| WO | WO 2018/039384 A1 | 3/2018 |

OTHER PUBLICATIONS

Frid et al., Prediction of drug-related cardiac adverse effects in humans-B: Use of QSAR programs for early detection of drug-induced cardiac toxicities, Regulatory Toxicology and Pharmacology (2010), 56(3):276-289.

Kuang et al., 254C>G: a TRPC6 Promoter Variation Associated with Enhanced Transcription and Steroid-Resistant Nephrotic Syndrome in Chinese Children, Pediatric Research (2013), 74(5):511-516.

Kurukulasuriya et al., Xanthine Mimetics as Potent Dipeptideyl Peptidase IV Inhibitors, Bioorganic & Medicinal Chemistry Letters (2006), 16:6226-6230.

Mackay et al., Acute Lung Injury and Acute Respiratory Distress Syndrome, Continuing Education in Anesthesia, Critical Care & Pain (2009), 9(5): 152-156.

Yu et al., A Functional Single-Nucleotide Polymorphism in the TRPC6 Gene Promoter Associated with Idiopathic Pulmonary Arterial Hypertension, Circulation (2009), 119:2313-2322.

Zhu et al., Identification and optimization of 2-aminobenzimidazole derivatives as novel inhibitors of TRPC4 and TRPC5 channels, British Journal of Pharmacology (2015), 172(14:3495-3509.

PUBCHEM, Substance Record for SID 46514183. Available Date Jan. 19, 2008. [retrieved on Nov. 15, 2018], Retrieved from the internet: https://pubchem.ncbi.nlm.nih.gov/substance/46514183 entire document.

PUBCHEM CID: 19786480; 1-(4-Fuoro-benzyl)-2-piperazin-1-yl-1H-benzoimidazole; Create date Dec. 5, 2007; 12 pages.

PUBCHEM CID: 71632022; Tert-butyl (1-(1-!4-cyanobenzyl)-1H-benzo[d]imidazole-2-yl)piperidin-3-yl)carbamate; Create date Aug. 8, 2013; 8 pages.

PUBCHEM CID: 71647030; Tert-butyl (1-(1-(4-cyanobenzyl)-1H-benzo[d]imidazole-2-yl)piperidin-3-yl)(methyl)carbamate; Create date Aug. 8, 2013; 8 pages.

PUBCHEM CID: 97166949; Tert-butyl N-[(3R)-1-[1-[(4-cyanophenyl)methyl]benzimidazol-2-yl]piperidin-3-yl]-N-methylcarbamate; Create date Dec. 11, 2015; 9 pages.

PUBCHEM CID: 97166950; Tert-butyl N-[(3S)-1-[1-[(4-cyanophenyl)methyl]benzimidazol-2-yl]piperidin-3-yl]-N-methylcarbamate; Create date Dec. 11, 2015; 9 pages.

PUBCHEM CID: 97174051; Tert-butyl N-[(3R)-1-[1-[(4-cyanophenyl)methyl]benzimidazol-2-yl]iperidin-3-yl]carbamate; Create date Dec. 11, 2015; 9 pages.

PUBCHEM CID: 97174052; Tert-butyl N-[(3S)-1-[1-[(4-cyanophenyl)methyl]benzimidazol-2-yl]piperidin-3-yl]carbamate; Create date Dec. 11, 2015; 9 pages.

Search Report dated Sep. 24, 2021 issued in corresponding Singapore Appl 11202003502V; 2 pages.

Lavrador-Erb, Karine et al., "The discovery and structure-activity relationships of 2-(piperidin-3-yl)-1H-benzimidazoles as selective, CNS penetrating Hi-antihistamines for insomnia," *Bioorganic & Medicinal Chemistry Letters* (Mar. 10, 2010) 20:2916-2919.

* cited by examiner

BENZIMIDAZOLE DERIVATIVES AND THEIR USES

CROSS-REFERENCE TO RELATED APPLICATIONS

This application is the U.S. National Phase of International Application No. PCT/US2018/056484 and published in English, which claims the benefit of U.S. Provisional Application No. 62/671,090, filed May 14, 2018 and U.S. Provisional Application No. 62/574,465, filed Oct. 19, 2017, each of which is incorporated by reference herein.

The present invention relates generally to Transient Receptor Potential Canonical (TRPC) Channel proteins, and more particularly to inhibitors of Transient Receptor Potential Channel 6 (TRPC6) protein activity, pharmaceutical compositions comprising said inhibitors and to methods of using such inhibitors.

BACKGROUND OF THE INVENTION

The TRPC6 channel, a member of the Transient receptor potential (TRP) family, which is a non-selective cation-permeable channel, is activated by diacylglycerol and the like produced by activation of phospholipase C and exerts physiological and pathophysiological effects. TRPC6 has effects such as cardiac pathological hypertrophy and fibrosis, progression of myocardial damage in muscular dystrophy, acute pulmonary vasoconstriction, pathological progression in chronic hypoxia-induced pulmonary hypertension, allergic airway response, migration of cells such as neutrophils, increased permeability of endothelial cells on inflammation, pathological flattening of podocytes and progression of glomerular injury, and proliferation or infiltration of malignant tumors, and is diversely distributed in the brain, heart, lungs, kidneys, placenta, ovaries, spleen, and the like (see for example J. Clin. Invest. 116:3114-3126, 2006; Dev. Cell. 23:705-715, 2012; Circ. Res. 114:823-832, 2014; Proc. Natl. Acd. Sci. USA 103:19093-19098, 2006; J. Cardiovasc. Pharmacol. 57:140-147, 2011; Hypertension 63:173-80, 2014; Clin. Exp. Allergy 38:1548-1558, 2008; Acta. Physiol. 195:3-11, 2009; J. Exp. Med. 209:1953-1968, 2011; Arterioscler. Thromb. Vasc. Biol. 33:2121-2129, 2013; PLoS ONE 5: e12859, 2010; Expert. Opin. Ther. Targets. 14:513-27, 2010; and BMC Cancer 13:116, 2013). In familial focal segmental glomerulosclerosis (FSGS), gain-of-function mutants of TRPC6 have been identified, and in steroid resistant nephrotic syndrome or idiopathic pulmonary arterial hypertension patients, a single nucleotide polymorphism in the promoter region that increases mRNA expression of TRPC6 has been identified (see for example: Pediatr Res. 2013 November; 74(5):511-6 and Circulation. 2009 May 5; 119(17):2313-2322). Thus, it is considered that hyperfunction and increased expression of TRPC6 contribute to pathological progression of nephrotic syndrome, pulmonary hypertension and the like (see for example Science 308:1801-1804, 2005; Nat. Genet. 37:739-744, 2005; PLoS One 4: e7771, 2009; Clin. J. Am. Soc. Nephrol. 6:1139-1148, 2011; Mol. Biol. Cell. 22:1824-1835, 2011; BMC Nephrol. 14:104, 2013; Pediatr. Res. 74:511-516, 2013; and Nephrol. Dial. Transplant. 28:1830-1838, 2013). Furthermore, increased expression of TRPC6 has been reported in minimal change nephrotic syndrome, membranous nephropathy, and diabetic nephropathy (see, ) for example, Circulation 119:2313-2322, 2009; J. Am. Soc. Nephrol. 18:29-36, 2007; and Nephrol. Dial. Transplant. 27:921-929, 2012).

New approaches are needed to modulate TRPC6 activity and more particularly inhibit TRPC6 activity in the prevention and/or treatment of nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS) heart failure, stroke, malignant tumor, and muscular dystrophy. There remains a need for agents that exploit different mechanisms of action and may have better outcomes in terms of relief of symptoms, safety, and patient mortality, both short-term and long-term.

SUMMARY OF THE INVENTION

The present invention provides compounds which inhibit TRPC proteins, and more specifically inhibit TRPC6 proteins. The present invention provides, in one aspect, benzimidazole compounds which inhibit TRPC6 activity. Inhibition of TRPC6 activity may be particularly desirable in the treatment or prevention of a variety of diseases including nephrotic syndrome, focal segmental glomerulosclerosis, membranous nephropathy, diabetic nephropathy, heart failure, stroke, acute lung injury, acute respiratory distress syndrome (ARDS) and acute renal failure.

The invention provides, in one aspect, substituted benzimidazole compounds which modulate the activity of TRPC6. Preferably, the substituted benzimidazole compounds of the invention are TRPC6 inhibitors.

The substituted benzimidazole compounds of the invention are compounds and salts according to Formula (I):

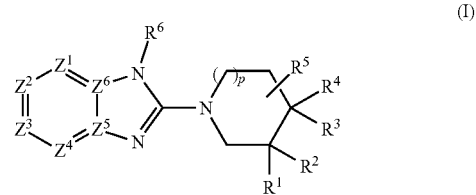

(I)

Also provided is a pharmaceutical composition comprising a pharmaceutically acceptable excipient, carrier or adjuvant and at least one compound of Formula (I) or subformulae thereof. Pharmaceutical compositions provided by the invention are suitable for use in the treatment of disease modulated by TRPC6 activity. In certain aspects the pharmaceutical compositions of the invention are suitable for use in the treatment of, e.g., treatment of nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, heart failure, stroke, malignant tumor or muscular dystrophy.

Also provided is a packaged pharmaceutical composition, comprising a pharmaceutical composition comprising a pharmaceutically acceptable excipient, carrier or adjuvant and at least one compound of formula (I) or subformulae thereof, and instructions for using the composition to treat a patient suffering from a disease mediated by TRPC6 activity or more particularly to treat a patient suffering from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS) heart failure, stroke, malignant tumor or muscular dystrophy. In certain instances, the patient is suffering from nephrotic syndrome, membranous nephropathy, and acute renal failure.

Also provided is a method of treating or preventing disease in a mammal which method comprises administering to a mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof.

Also provided is a method for modulating TRPC6 activity in a mammal, which method comprises administering to the mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof. Another aspect of the invention relates to a method of treating a TRPC6-mediated disease or disorder, the method comprising administering a TRPC6 inhibitor of the invention to a patient in need of therapy. In certain embodiments, the TRPC6 mediated disease or disorder is selected from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor or muscular dystrophy. In certain instances, the patient is suffering from nephrotic syndrome, membranous nephropathy, and acute renal failure.

Also provided is the use, in the manufacture of a medicament for treating or preventing disease mediated by TRPC6 activity, of at least one compound of formula I or subformulae thereof.

Other aspects and embodiments will be apparent to those skilled in the art form the following detailed description.

DETAILED DESCRIPTION OF THE INVENTION

The invention related generally to compounds of Formula I and salts and tautomers thereof which inhibit TRPC protein activity and more particularly inhibit TRPC6 protein activity. In particular, the invention relates to compounds which selectively inhibit TRPC6 protein activity.

In a first embodiment, the invention provides a compound or pharmaceutically acceptable salt thereof, according to Formula I:

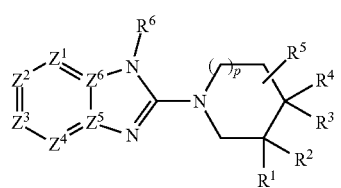
(I)

Wherein
p is 0 or 1;
when p is 0, then $R^1$ is hydrogen, $C_1$-$C_6$alkyl, halogen or hydroxy; $R^2$ is amino or amino$C_1$-$C_4$alkyl; $R^3$ is hydrogen; and $R^4$ is hydrogen, $C_1$-$C_6$alkyl or phenyl; or when p is 0, then $R^1$ and $R^3$, taken in combination, form a fused $C_3$-$C_6$cycloalkyl ring or a fused 4 to 6 member heterocycle ring having 1 or 2 ring heteroatoms independently selected from N, O or S, which cycloalkyl or heterocycle is optionally substituted with amino; $R^2$ is hydrogen, $C_1$-$C_6$alkyl or amino$C_1$-$C_4$alkyl; and $R^4$ is hydrogen; or when p is 1, then $R^1$ is $NHR^{1a}$; $R^{1a}$ is hydrogen, $C_1$-$C_4$alkyl, $C_3$-$C_7$cycloalkyl, hydroxy$C_1$-$C_4$alkyl, or 4 to 6 member heterocycloalkyl having one ring heteroatom selected from N, O or S; $R^2$ is hydrogen, $C_1$-$C_4$alkyl, hydroxy$C_1$-$C_4$alkyl or $C(O)NH_2$; $R^3$ is hydrogen, halogen, $C_1$-$C_4$alkyl, $C_1$-$C_4$alkoxy or hydroxy; and $R^4$ is hydrogen, $C_1$-$C_4$alkyl or halogen; or when p is 0 or 1, then $CR^1R^2$, taken in combination, form a spirocyclic 4 to 6 member heterocycloalkyl; $R^3$ is hydrogen, halogen, $C_1$-$C_4$alkyl, $C_1$-$C_4$alkoxy, or hydroxy; and $R^4$ is hydrogen or halogen; or when p is 1, then $R^1$ and $R^3$, taken in combination, form a fused 4 to 6 member heterocycle or a fused 3 to 7 member carbocycle, which heterocycle comprises a ring nitrogen atom and optionally 0 or 1 additional ring heteroatoms selected from N, O and S, and which carbocycle is substituted with amino; and $R^2$ is hydrogen; and $R^4$ is hydrogen, halogen or hydroxy;

$R^5$ represents 1 or 2 substituents independently selected from hydrogen, halogen, hydroxy, amino, $C_1$-$C_6$alkyl or $C_1$-$C_6$alkoxy;

$R^6$ is —$(CR^7R^8)$-A; or $R^6$ is a 4 to 7 member lactam which is optionally substituted with one or two substituents independently selected from the group consisting of hydroxy, $C_1$-$C_6$alkyl, $C_2$-$C_6$alkenyl, $C_2$-$C_6$alkynyl, $C_3$-$C_6$cycloalkyl, halo$C_1$-$C_6$alkyl, $C_1$-$C_6$alkoxy, halo$C_1$-$C_6$alkoxy, hydroxy$C_1$-$C_6$alkyl, $C_1$-$C_6$alkoxy$C_1$-$C_6$alkyl, phenyl, 4 to 7 member heterocycle having 1 ring atoms selected from N, O or S and 0 or 1 additional ring N atoms or 5 or 6 member heteroaryl having one ring heteroatom selected from N, O or S and 0 or 1 additional ring nitrogen atom, wherein the heteroaryl, heterocycle or phenyl group is optionally substituted with 0, 1 or 2 $C_1$-$C_6$alkyl or halogen; or $R^6$ is a partially unsaturated 9 or 10 member bicyclic carbocycle, which is optionally substituted with 1 or 2 substituents independently selected from halogen, cyano, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, $C(O)NH_2$ and $C(O)NHC_1$-$C_6$alkyl;

A is 5 or 6 member heteroaryl, which heteroaryl comprises one ring heteroatom selected from N, O or S and 0, 1 or 2 additional ring nitrogen atoms, which heteroaryl is optionally substituted with 0, 1, 2, 3 or 4 groups independently selected from halogen, cyano, $C_1$-$C_6$alkyl, $C_2$-$C_6$alkenyl, $C_2$-$C_6$alkynyl, $C_3$-$C_6$cycloalkyl, halo$C_1$-$C_6$alkyl, $C_1$-$C_6$alkoxy, halo$C_1$-$C_6$alkoxy, $C(O)N(R^4)_2$, $S(O)_2$ $C_1$-$C_6$alkyl, phenyl or 5 or 6 member heteroaryl having one ring heteroatom selected from N, O or S and 0, 1 or 2 additional ring nitrogen atoms, wherein the optional heteroaryl or phenyl substituent is further substituted with 0, 1 or 2 $C_1$-$C_6$alkyl; or A is phenyl substituted with 1, 2 or 3 substituents independently selected from halogen, $C_1$-$C_6$alkyl, $C_2$-$C_6$alkenyl, $C_2$-$C_6$alkynyl, halo$C_1$-$C_6$alkyl, cyano$C_1$-$C_6$alkyl, $C_1$-$C_6$alkoxy, halo$C_1$-$C_6$alkoxy, cyano$C_1$-$C_6$ alkoxy, $S(O)_q$ C$_1$-C$_6$alkyl, S(O)$_2$NH$_2$, S(O)$_2$NHC$_1$-C$_6$alkyl, S(O)$_2$N(C$_1$-C$_6$alkyl)$_2$, C(O)NH$_2$, C(O)NHC$_1$-C$_6$alkyl, C(O)N(C$_1$-C$_6$alkyl)$_2$, hydroxy, cyano, or 5 or 6 member heteroaryl having one ring heteroatom selected from N, O or S and 0, 1 or 2 additional ring nitrogen atoms which heteroaryl is further substituted with 0, 1 or 2 C$_1$-C$_6$alkyl; or A is C(O)OR$^9$ or C(O)NR$^9$R$^{10}$; or A is optionally substituted 9 or 10 member aromatic or partially unsaturated bicycle having 0, 1 or 2 ring nitrogen atoms and 0 or 1 additional ring heteroatoms selected from N, O or S, which bicycle is substituted with 0, 1 or 2 substituents independently selected from the group consisting of halogen, cyano, C$_1$-C$_6$alkyl, C$_2$-C$_6$alkenyl, C$_2$-C$_6$alkynyl, haloC$_1$-C$_6$alkyl, C$_1$-C$_6$alkoxy, haloC$_1$-C$_6$alkoxy, C(O)NH$_2$, C(O)OH or C(O)NHC$_1$-C$_6$alkyl;

R$^4$ is independently selected at each occurrence from hydrogen or C$_1$-C$_4$alkyl; or N(R$^A$)$_2$, taken in combination, forms a 4 to 7 member azacycle which is optionally substituted with 0, 1, or 2 C$_1$-C$_4$alkyl;

R$^7$ is hydrogen, C$_1$-C$_4$alkyl or amino;

R$^8$ is hydrogen or C$_1$-C$_4$alkyl; or

CR$^7$R$^8$, taken in combination form a 3 to 6 member cycloalkandiyl group;

R$^9$ is hydrogen, C$_1$-C$_6$alkyl, C$_3$-C$_6$cycloalkyl, hydroxyC$_1$-C$_6$alkyl, C$_1$-C$_4$alkoxyC$_1$-C$_6$alkyl, haloC$_1$-C$_6$alkyl, cyano C$_1$-C$_6$alkyl or —(CH$_2$)$_r$R$^{9A}$ wherein r is 0 or 1 and R$^{9A}$ is phenyl, 4 to 7 member heterocycle having one ring heteroatoms selected from N, O or S, which ring sulfur may be optionally oxidized, and 0 or 1 additional ring N atoms or 5 or 6 member heteroaryl having one ring heteroatom selected from N, O or S and 0, 1, or 2 additional ring N atoms, which phenyl, heterocycle or heteroaryl is optionally substituted with 0, 1 or 2 halogen, C$_1$-C$_4$alkyl or C(O)C$_1$-C$_4$alkyl;

R$^{10}$ is hydrogen, C$_1$-C$_6$alkyl, C$_2$-C$_6$alkenyl, C$_2$-C$_6$alkynyl, halo C$_1$-C$_6$alkyl, C$_3$-C$_7$cycloalkyl or saturated, partially unsaturated or aromatic 5 or 6 member heterocycle having 1 or 2 ring heteroatoms independently selected from N, O and S, which sulfur is optionally oxidized, and which heterocycle is optionally substituted with 1 or 2 substituents independently selected from C$_1$-C$_6$alkyl and halogen, which heterocycle has 1 or 2 ring hetero atoms selected from N, O or S, which sulfur may be optionally oxidized, and wherein each alkyl or cycloalkyl is optionally substituted with cyano, halogen, hydroxy, C$_1$-C$_6$alkoxy, S(O)$_q$C$_1$-C$_6$alkyl, 4 to 6 member heterocycle having 1 or 2 ring heteroatoms selected from N, O or S or 5 or 6 member heteroaryl having 1 ring heteroatom selected from N, O or S and 0, 1 or 2 additional ring nitrogen atoms and where each heterocycle or heteroaryl is optionally substituted with 0, 1, or 2 C$_1$-C$_4$alkyl; or NR$^9$R$^{10}$, taken in combination, form a monocyclic or bicyclic 4 to 10 member saturated or partially unsaturated heterocycle having one or two ring nitrogen atoms and 0 or 1 additional ring heteroatom selected from N, O or S, which ring sulfur may be optionally oxidized, which heterocycle is optionally substituted with 0, 1 or 2 substitutents selected from halogen, oxo, hydroxy, cyano, C$_1$-C$_6$alkyl, C$_3$-C$_6$cycloalkyl, haloC$_1$-C$_6$alkyl, hydroxyC$_1$-C$_6$alkyl, cyanoC$_1$-C$_6$alkyl, C$_1$-C$_6$alkoxy, haloC$_1$-C$_6$alkoxy, C$_1$-C$_6$alkoxyC$_1$-C$_4$alkyl, S(O)$_q$C$_1$-C$_6$alkyl, C$_1$-C$_6$alkylS(O)$_q$ C$_1$-C$_6$alkyl CO$_2$H, C(O)C$_1$-C$_6$alkyl, C(O)OC$_1$-C$_6$alkyl, C(O)C$_3$-C$_6$cycloalkyl, N(R$^{15}$)C(O)C$_1$-C$_6$alkyl or C(O)N(R$^{15}$)$_2$, phenyl, 4 to 6 member heterocycle having 1 or 2 ring heteroatoms selected from N, O or S or a 5 or 6 member heteroaryl having 1 ring heteroatom selected from N, O or S and 0, 1 or 2 additional ring nitrogen atoms and where each heterocycle or heteroaryl is optionally substituted with 0, 1, or 2 C$_1$-C$_4$alkyl;

q is 0, 1 or 2;

Z$^1$ is N or CR$^{11}$;

Z$^2$ is N or CR$^{12}$;

Z$^3$ is N or CR$^{13}$;

Z$^4$ is N or CR$^{14}$,

Z$^5$ and Z$^6$ are each independently N or C;

wherein 0, 1 or 2 of Z$^1$, Z$^2$, Z$^3$, Z$^4$, Z$^5$ and Z$^6$ are N;

each of R$^{11}$, R$^{12}$, R$^{13}$ and R$^{14}$ is independently selected from the group consisting of hydrogen, halogen, C$_1$-C$_6$alkyl, C$_2$-C$_6$alkenyl, C$_2$-C$_6$alkynyl, C$_1$-C$_6$alkoxy, haloC$_1$-C$_6$alkyl, haloC$_1$-C$_6$alkoxy, C$_3$-C$_7$cycloalkyl, cyano, SO$_2$C$_1$-C$_6$alkyl, phenyl, and saturated, partially unsaturated or aromatic 5 or 6 member heterocycle having 1 or 2 ring heteroatoms independently selected from N, O and S, which heterocycle is optionally substituted with 1 or 2 substituents independently selected from C$_1$-C$_6$alkyl and halogen; and R$^{15}$ is selected at each occurrence from hydrogen or C$_1$-C$_4$alkyl or N(R$^{15}$)$_2$ taken in combination form a 4 to 7 member azacycle optionally substituted with 0, 1 or 2 C$_1$-C$_4$alkyl; with the proviso that compounds of Formula I do not include 1-[7-fluoro-6-methoxy-1-[[2-(trifluoromethyl)phenyl]methyl]-1H-benzimidazol-2-yl]-3-piperidinamine.

In a second embodiment of the invention, compounds and salts according to Formula I are provided which are generally represented by the structure:

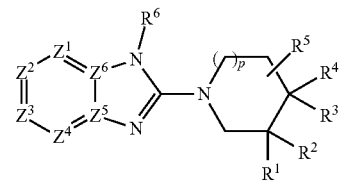

(I)

Wherein p is 0 or 1;

when p is 0, then R$^1$ is hydrogen, C$_1$-C$_6$alkyl, halogen or hydroxy; R$^2$ is amino or aminoC$_1$-C$_4$alkyl; R$^3$ is hydrogen; and R$^4$ is hydrogen, C$_1$-C$_6$alkyl or phenyl; or when p is 0, then R$^1$ and R$^3$, taken in combination, form a fused C$_3$-C$_6$cycloalkyl ring or a fused 4 to 6 member heterocycle ring having 1 or 2 ring heteroatoms independently selected from N, O or S, which cycloalkyl or heterocycle is optionally substituted with amino; R$^2$ is hydrogen, C$_1$-C$_6$alkyl or aminoC$_1$-C$_4$alkyl; and R$^4$ is hydrogen; or when p is 1, then R$^1$ is NHR$^{1a}$; R$^{1a}$ is hydrogen, C$_1$-C$_4$alkyl, C$_3$-C$_7$cycloalkyl, hydroxyC$_1$-C$_4$alkyl, or 4 to 6 member heterocycloalkyl having one ring heteroatom selected from N, O or S; R$^2$ is hydrogen, C$_1$-C$_4$alkyl, hydroxyC$_1$-C$_4$alkyl or C(O)NH$_2$; R$^3$ is hydrogen, halogen, C$_1$-C$_4$alkyl, C$_1$-C$_4$alkoxy or hydroxy; and R$^4$ is hydrogen, C$_1$-C$_4$alkyl or halogen; or when p is 0 or 1, then C(NHR$^{1a}$)R$^2$, taken in combination, form a spirocyclic 4 to 6 member heterocycloalkyl; R$^3$ is hydrogen, halogen C$_1$-C$_4$alkyl, C$_1$-C$_4$alkoxy, or hydroxy; and R$^4$ is hydrogen or halogen; or when p is 1, then R$^1$ and R$^3$, taken in combination, form a fused 4 to 6 member heterocycle or a fused 3 to 7 member carbocycle, which heterocycle comprises a ring nitrogen atom and optionally 0 or 1 additional ring heteroatoms selected from N, O and S, and which carbocycle is substituted with amino; and $R^2$ is hydrogen; and $R^4$ is hydrogen, halogen or hydroxy;

$R^5$ represents 1 or 2 substituents independently selected from hydrogen, halogen, hydroxy, amino, $C_1$-$C_6$alkyl or $C_1$-$C_6$alkoxy;

$R^6$ is —$(CR^7R^8)$-A; or $R^6$ is a 4 to 7 member lactam which is optionally substituted with one or two substituents independently selected from the group consisting of hydroxy, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, hydroxy$C_1$-$C_6$alkyl, $C_1$-$C_6$alkoxy$C_1$-$C_6$alkyl, phenyl or 5 or 6 member heteroaryl having one ring heteroatom selected from N, O or S and 0 or 1 additional ring nitrogen atom, wherein the heteroaryl or phenyl group is optionally substituted with 0, 1 or 2 $C_1$-$C_6$alkyl or halogen; or $R^6$ is a partially unsaturated 9 or 10 member bicyclic carbocycle, which is optionally substituted with 1 or 2 substituents independently selected from halogen, cyano, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, $C(O)NH_2$ and $C(O)NHC_1$-$C_6$alkyl;

A is 5 or 6 member heteroaryl, which heteroaryl comprises one ring heteroatom selected from N, O or S and 0, 1 or 2 additional ring nitrogen atoms, which heteroaryl is optionally substituted with 0, 1, 2, 3 or 4 groups independently selected from halogen, cyano, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, $C(O)NH_2$, $C(O)NHC_1$-$C_6$alkyl, phenyl or 5 or 6 member heteroaryl having one ring heteroatom selected from N, O or S and 0, 1 or 2 additional ring nitrogen atoms, wherein the optional heteroaryl or phenyl substituent is further substituted with 0, 1 or 2 $C_1$-$C_6$alkyl; or A is phenyl substituted with 1, 2 or 3 substituents independently selected from halogen, $C_1$-$C_6$alkyl, $C_2$-$C_6$alkenyl, $C_2$-$C_6$alkynyl, halo$C_1$-$C_6$alkyl, cyano$C_1$-$C_6$alkyl, $C_1$-$C_6$alkoxy, halo$C_1$-$C_6$alkoxy, cyano$C_1$-$C_6$ alkoxy, $S(O)_q$ $C_1$-$C_6$alkyl, $S(O)_2NH_2$, $S(O)_2NHC_1$-$C_6$alkyl, $S(O)_2N(C_1$-$C_6$alkyl$)_2$, $C(O)NH_2$, $C(O)NHC_1$-$C_6$alkyl, $C(O)N(C_1$-$C_6$alkyl$)_2$, hydroxy, cyano, or 5 or 6 member heteroaryl having one ring heteroatom selected from N, O or S and 0, 1 or 2 additional ring nitrogen atoms which heteroaryl is further substituted with 0, 1 or 2 $C_1$-$C_6$alkyl; or A is $C(O)OR^9$ or $C(O)NR^9R^{10}$; or A is optionally substituted 9 or 10 member aromatic or partially unsaturated bicycle having 0, 1 or 2 ring nitrogen atoms and 0 or 1 additional ring heteroatoms selected from N, O or S, which bicycle is substituted with 0, 1 or 2 substituents independently selected from the group consisting of halogen, cyano, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, $C(O)NH_2$, $C(O)OH$ or $C(O)NHC_1$-$C_6$alkyl;

$R^7$ is hydrogen, $C_1$-$C_4$alkyl or amino;

$R^8$ is hydrogen or $C_1$-$C_4$alkyl; or $CR^7R^8$, taken in combination form a 3 to 6 member cycloalkandiyl group;

$R^9$ is hydrogen, $C_1$-$C_6$alkyl, hydroxy$C_1$-$C_6$alkyl, halo$C_1$-$C_6$alkyl or cyano $C_1$-$C_6$alkyl;

$R^{10}$ is hydrogen, $C_1$-$C_6$alkyl, $C_2$-$C_6$alkenyl, $C_2$-$C_6$alkynyl, halo $C_1$-$C_6$alkyl, $C_3$-$C_7$cycloalkyl or 4 to 7 member heterocycle, which heterocycle has 1 or 2 ring hetero atoms selected from N, O or S, which sulfur may be optionally oxidized, and wherein each alkyl or cycloalkyl is optionally substituted with cyano, halogen, hydroxy, $C_1$-$C_6$alkoxy, $S(O)_q C_1$-$C_6$alkyl, 4 to 6 member heterocycle having 1 or 2 ring heteroatoms selected from N, O or S or 5 or 6 member heteroaryl having 1 ring heteroatom selected from N, O or S and 0, 1 or 2 additional ring nitrogen atoms; or $NR^9R^{10}$, taken in combination, form a monocyclic or bicyclic 4 to 9 member heterocycle having one ring nitrogen atom and 0 or 1 additional ring heteroatom selected from N, O or S, which ring sulfur may be optionally oxidized, which heterocycle is optionally substituted with 0, 1 or 2 substitutents selected from halogen, oxo, hydroxy, cyano, $C_1$-$C_6$alkyl, halo $C_1$-$C_6$alkyl, hydroxy$C_1$-$C_6$alkyl, $C_1$-$C_6$alkoxy, $S(O)_q C_1$-$C_6$alkyl, $CO_2H$, $C(O)C_1$-$C_6$alkyl, or $C(O)NH_2$;

q is 0, 1 or 2;

$Z^1$ is N or $CR^{11}$;
$Z^2$ is N or $CR^{12}$;
$Z^3$ is N or $CR^{13}$;
$Z^4$ is N or $CR^{14}$,
$Z^5$ and $Z^6$ are each independently N or C;
wherein 0, 1 or 2 of $Z^1$, $Z^2$, $Z^3$, $Z^4$, $Z^5$ and $Z^6$ are N;

each of $R^{11}$, $R^{12}$, $R^{13}$ and $R^{14}$ is independently selected from the group consisting of hydrogen, halogen, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, $C_3$-$C_7$cycloalkyl, cyano, $SO_2C_1$-$C_6$alkyl, phenyl, and saturated, partially unsaturated or aromatic 5 or 6 member heterocycle having 1 or 2 ring heteroatoms independently selected from N, O and S, which heterocycle is optionally substituted with 1 or 2 substituents independently selected from $C_1$-$C_6$alkyl and halogen; and with the proviso that compounds of Formula I do not include 1-[7-fluoro-6-methoxy-1-[[2-(trifluoromethyl)phenyl]methyl]-1H-benzimidazol-2-yl]-3-piperidinamine.

The proviso is presented in the first embodiment to specifically exclude and disclaim the identified compound which is indexed as CAS Number 1014407-24-9.

In certain aspects of the first or second embodiment, compounds of Formula I include compounds of Formula Ia:

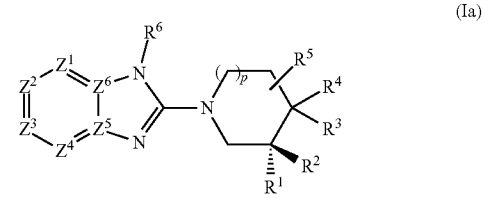

(Ia)

Where variables p, $R^1$, $R^2$, $R^3$, $R^4$, $R^5$, $R^6$, $Z^1$, $Z^2$, $Z^3$, $Z^4$, $Z_5$ and $Z^6$ are as defined in the first or second embodiment.

In a third embodiment, the invention provides compounds of the first or second embodiment in which p is 0; $R^1$ is hydrogen, $C_1$-$C_6$alkyl, halogen or hydroxy; $R^2$ is amino$C_1$-$C_4$alkyl; and $R^3$ and $R^4$ are hydrogen.

In a fourth embodiment, the invention provides compounds of the first or second embodiment in which p is 0; $R^1$ and $R^3$, taken in combination, form a fused $C_3$-$C_6$cycloalkyl ring or a fused 4 to 6 member azacycle ring, which cycloalkyl or azacycle is optionally substituted with amino; and $R^2$ and $R^4$ are hydrogen.

In a fifth embodiment, the invention provides compounds of the fourth embodiment in which $R^1$ and $R^3$ taken in combination, form a fused pyrrolidine; and $R^2$ and $R^4$ are hydrogen.

In a sixth embodiment, the invention provides compounds of the first or second embodiment in which p is 1, $R^1$ is $NHR^{1a}$; $R^{1a}$ is hydrogen, $C_1$-$C_4$alkyl, $C_3$-$C_7$cycloalkyl or 4 to 6 member heterocycloalkyl having one ring heteroatom selected from N, O or S; $R^2$ is hydrogen or $C_1$-$C_4$alkyl; $R^3$ is hydrogen, halogen, $C_1$-$C_4$alkyl, $C_1$-$C_4$alkoxy, or hydroxy; and $R^4$ is hydrogen, halogen or $C_1$-$C_4$alkyl.

In a seventh embodiment, the invention provides compounds of the sixth embodiment in which $R^1$ is $NHR^{1a}$; $R^{1a}$ is hydrogen, methyl, ethyl, propyl, isopropyl or cyclopropyl; $R^2$ is hydrogen or methyl; $R^3$ is hydrogen, halogen, methyl, ethyl, methoxy, ethoxy, or hydroxy; and $R^4$ is hydrogen, halogen, methyl or ethyl. In certain aspects of the seventh embodiment, compounds are provided in which $R^{1a}$ is hydrogen or methyl; $R^2$ is hydrogen, $R^3$ is hydrogen, fluorine, methyl or hydroxy; and $R^4$ is hydrogen, halogen, methyl or eethyl.

In an eighth embodiment, the invention provides compounds of the sixth or seventh embodiment in which $R^1$ is $NH_2$; $R^2$ is hydrogen; $R^3$ is hydrogen, fluorine, methyl, or hydroxy; and $R^4$ is hydrogen, fluorine or methyl.

In a ninth embodiment, the invention provides compounds of the first or second embodiment in which p is 1; $CR^1R^2$, taken in combination, form a spirocyclic 4 to 6 member heterocycloalkyl; $R^3$ is hydrogen, halogen or $C_1$-$C_4$alkyl, $C_1$-$C_4$alkoxy, hydroxy; and $R^4$ is hydrogen or halogen.

In a tenth embodiment, the invention provides compounds of the first or second embodiment in which p is 1; $R^1$ and $R^3$, taken in combination, form a fused 4 or 5 member carbocycle substituted with amino; and $R^2$ and $R^4$ are hydrogen.

In an eleventh embodiment, the invention provides compounds of any one of the first to tenth embodiment in which $R^5$ represents 1 or 2 substitutents independently selected from hydrogen, halogen, hydroxy, $C_1$-$C_4$alkyl.

In a twelfth embodiment, the invention provides compounds of the eleventh embodiment in which $R^5$ represent hydrogen.

In a thirteenth embodiment, the invention provides compounds of any one of the first to twelfth embodiment in which wherein $R^6$ is —$(CR^7R^8)$-A.

In a fourteenth embodiment, the invention provides compounds of the thirteenth embodiment in which $R^7$ is hydrogen, methyl or ethyl; $R^8$ is hydrogen; or $CR^7R^8$, taken in combination form a cyclopropandiyl group.

In a fifteenth embodiment, the invention provides compounds of the thirteenth or fourteenth embodiment in which $R^7$ is hydrogen or methyl; and $R^8$ is hydrogen.

In a sixteenth embodiment, the invention provides compounds of any one of the thirteenth to fifteenth embodiment in which A is 5 or 6 member heteroaryl, which heteroaryl comprises one ring heteroatom selected from N, O or S and 0, 1 or 2 additional ring nitrogen atoms, which heteroaryl is optionally substituted with 0, 1, or 2 groups independently selected from halogen, cyano, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, C(O)$NH_2$, C(O)NH$C_1$-$C_6$alkyl, phenyl or 5 or 6 member heteroaryl having one ring heteroatom selected from N, O or S and 0, 1 or 2 additional ring nitrogen atoms, wherein the optional heteroaryl or phenyl substituent is further substituted with 0, 1 or 2 $C_1$-$C_6$alkyl.

In a seventeenth embodiment, the invention provides compounds of the sixteenth embodiment in which A is pyridin-2-yl, pyridin-3-yl, pyrimidin-2-yl, or pyrazin-2-yl, each of which is substituted with 1 to 3 groups independently selected from the group consisting of halogen, cyano, $C_1$-$C_4$alkyl, halo$C_1$-$C_4$alkyl, $C_1$-$C_4$alkoxy, halo$C_1$-$C_4$alkoxy, C(O)$NH_2$, C(O)NH$C_1$-$C_4$alkyl, phenyl or 5 member heteroaryl having one ring heteroatom selected from N, O or S and 0, 1 or 2 additional ring nitrogen atoms, wherein the optional heteroaryl or phenyl substituent is further substituted with 0, 1 or 2 $C_1$-$C_6$alkyl.

In an eighteenth embodiment, the invention provides compounds of any one of the thirteenth to fifteenth embodiment in which A is phenyl substituted with 1, 2 or 3 substituents independently selected from halogen, $C_1$-$C_6$alkyl, halo$C_1$-$C_6$alkyl, $C_1$-$C_6$alkoxy, halo$C_1$-$C_6$alkoxy, hydroxy, cyano, or 5 or 6 member heteroaryl having one ring heteroatom selected from N, O or S and 0, 1 or 2 additional ring nitrogen atoms which heteroaryl is further substituted with 0, 1 or 2 $C_1$-$C_6$alkyl.

In a nineteenth embodiment, the invention provides compounds of the eighteenth embodiment in which A is phenyl substituted with one substituent selected from the group consisting of halogen, $C_1$-$C_4$alkyl, halo$C_1$-$C_4$alkyl, $C_1$-$C_4$alkoxy, halo$C_1$-$C_4$alkoxy, hydroxy, cyano, or 5 member heteroaryl having one ring heteroatom selected from N, O or S and 0, 1 or 2 additional ring nitrogen atoms, and wherein the phenyl group is further optionally substituted with halogen, $C_1$-$C_4$alkyl, $C_1$-$C_4$alkoxy, halo$C_1$-$C_4$alkyl or halo$C_1$-$C_4$alkoxy.

In a twentieth embodiment, the invention provides compounds of the eighteenth or nineteenth embodiment in which A is phenyl substituted with 1 or 2 substituents independently selected from halogen, $C_1$-$C_3$alkyl, halo$C_1$-$C_4$alkyl, $C_1$-$C_4$alkoxy, halo$C_1$-$C_4$alkoxy, hydroxy or cyano.

In a twenty-first embodiment, the invention provides compounds of any one of the thirteenth to fifteenth embodiment in which A is C(O)$NR^9R^{10}$;

$R^9$ is hydrogen, or $C_1$-$C_4$alkyl;

$R^{10}$ is $C_1$-$C_4$alkyl, halo$C_1$-$C_4$alkyl, $C_3$-$C_7$cycloalkyl or 4 to 7 member heterocycle, which heterocycle has 1 or 2 ring hetero atoms selected from N, O or S, which sulfur may be optionally oxidized, and wherein each alkyl or cycloalkyl is optionally substituted with cyano, halogen, hydroxy, $C_1$-$C_6$alkoxy, S(O)$_q$$C_1$-$C_6$alkyl; or $NR^9R^{10}$, taken in combination, form a monocyclic or bicyclic 4 to 9 member azacycle having one ring nitrogen atom and 0 or 1 additional ring heteroatom selected from N, O or S, which ring sulfur may be optionally oxidized, which azacycle is optionally substituted with 0, 1 or 2 substituents selected from halogen, oxo, hydroxy, cyano, $C_1$-$C_6$alkyl, halo $C_1$-$C_6$alkyl, hydroxy$C_1$-$C_6$alkyl, $C_1$-$C_6$alkoxy, S(O)$_2$$C_1$-$C_6$alkyl, $CO_2H$, C(O)$C_1$-$C_6$alkyl, or C(O)$NH_2$.

In a twenty second embodiment, the invention provides compounds of the twenty first embodiment in which $R^9$ is hydrogen, methyl or ethyl; and $R^{10}$ is $C_1$-$C_4$alkyl or halo$C_1$-$C_4$alkyl wherein each alkyl is optionally substituted with cyano, halogen, hydroxy, $C_1$-$C_6$alkoxy or S(O)$_q$$C_1$-$C_6$alkyl.

In a twenty third embodiment, the invention provides compounds of the twenty first embodiment in which $NR^9R^{10}$, taken in combination, form a 4 to 6 member monocyclic azacycle or a 7 to 9 member bicyclic azacycle, each of which having one ring nitrogen atom and 0 or 1 additional ring heteroatom selected from N, O or S, which ring sulfur may be optionally oxidized, wherein each azacycle is optionally substituted with 0, 1 or 2 substitutents selected from halogen, oxo, hydroxy, cyano, $C_1$-$C_6$alkyl, halo $C_1$-$C_6$alkyl, hydroxy$C_1$-$C_6$alkyl, $C_1$-$C_6$alkoxy, S(O)$_2$$C_1$-$C_6$alkyl, $CO_2H$, C(O)$C_1$-$C_6$alkyl, or C(O)$NH_2$.

In a twenty fourth embodiment, the invention provides compounds of the twenty third embodiment in which the 4 to 6 member monocyclic azacycle is selected from the group consisting of:

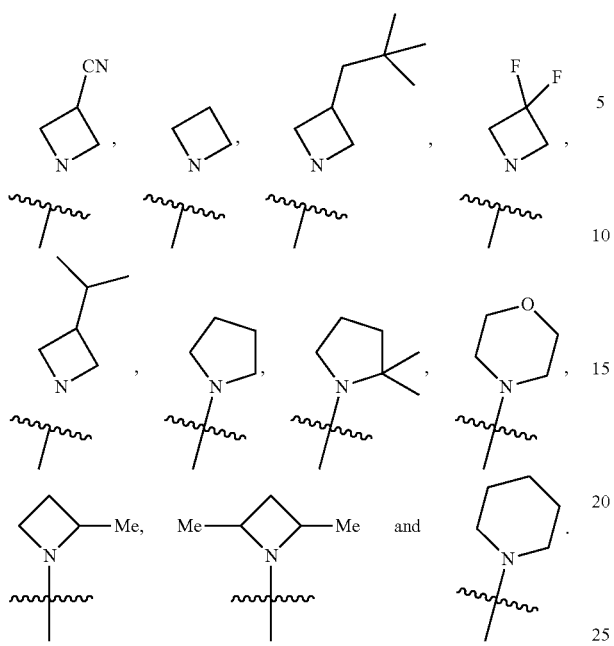

In a twenty fifth embodiment, the invention provides compounds of the twenty third embodiment in which the 7 to 9 member bicyclic azacyle is selected from the group consisting of:

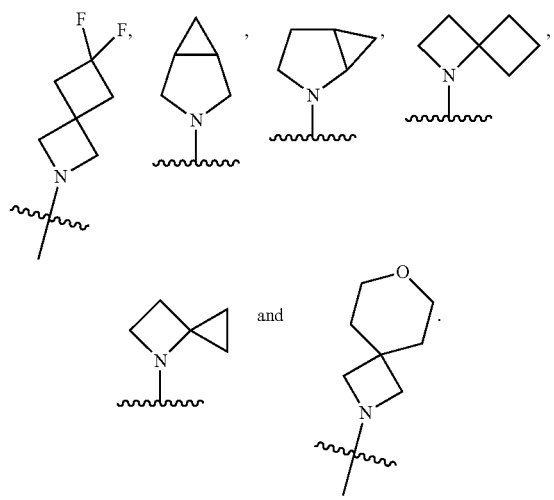

In a twenty sixth embodiment, the invention provides compounds of any one of the first to twelfth embodiment in which $R^6$ is a 2-oxo-pyrollidin-3-yl or 2-oxo-piperidin-3-yl each of which is substituted at nitrogen with $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, hydroxy$C_1$-$C_6$alkyl, $C_1$-$C_6$alkoxy$C_1$-$C_6$alkyl, phenyl or 5 or 6 member heteroaryl having one ring heteroatom selected from N, O or S and 0 or 1 additional ring nitrogen atom, wherein the heteroaryl or phenyl group is optionally substituted with 0, 1 or 2 $C_1$-$C_6$alkyl or halogen.

In a twenty seventh embodiment, the invention provides compounds of the twenty sixth embodiment in which $R^6$ is

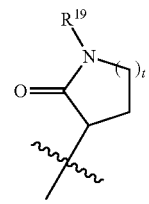

Wherein t is 1 or 2; and
$R^{19}$ is $C_1$-$C_6$alkyl, phenyl substituted with 0, 1 or 2 halogen.

In a twenty eighth embodiment, the invention provides compounds of any one of the first to twenty seventh embodiment in which $Z^1$ is $CR^{11}$;
$Z^2$ is $CR^{12}$;
$Z^3$ is $CR^{13}$;
$Z^4$ is N or $CR^{14}$,
$Z^5$ and $Z^6$ are each C;
$R^{11}$ is hydrogen, halogen, cyano or $C_1$-$C_4$alkyl;
$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, halo$C_1$-$C_4$alkoxy, $C_3$-$C_6$cycloalkyl or 5 member saturated, partially unsaturated or aromatic 5 or 6 member heterocycle having 1 or 2 ring heteroatoms independently selected from N, O and S; and
$R^{14}$ is hydrogen, halogen, cyano or $C_1$-$C_4$alkyl.

In certain aspects of the twenty eighth embodiment, compounds are provided in which $R^{11}$ is hydrogen.

In certain other aspects of the twenty eighth embodiment, compounds are provided in which $R^{14}$ is hydrogen, fluorine, chlorine, methyl or cyano. In certain aspects of the twenty eighth embodiment, compounds are provided in which $R^{12}$ and $R^{13}$ are each independently selected from the group consisting of hydrogen, fluorine, chlorine, cyano, $C_1$-$C_4$alkyl, halo$C_1$-$C_4$alkyl, $C_1$-$C_4$alkoxy, and halo$C_1$-$C_4$alkoxy.

In yet other aspects of the twenty eighth embodiment, compounds are provided in which $R^{11}$ is hydrogen; $R^{14}$ is hydrogen, fluorine, chlorine, methyl or cyano; and $R^{12}$ and $R^{13}$ are each independently selected from the group consisting of hydrogen, fluorine, chlorine, cyano, methyl, ethyl, methoxy, ethoxy, fluoromethyl, difluoromethyl, trifluoromethyl, fluoromethoxy, difluoromethoxy, and trifluoromethoxy.

In a twenty ninth embodiment, the invention provides compounds of the first or second embodiment which include compounds of Formula II:

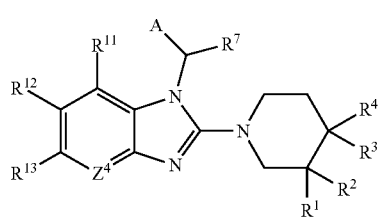

(II)

Wherein
$R^1$ is $NHR^{1a}$;
$R^{1a}$ is hydrogen, $C_1$-$C_4$alkyl, $C_3$-$C_7$cycloalkyl or 4 to 6 member heterocycloalkyl having one ring heteroatom selected from N, O or S;

$R^2$ is hydrogen or $C_1$-$C_4$alkyl;

$R^3$ is hydrogen, halogen, $C_1$-$C_4$alkyl, $C_1$-$C_4$alkoxy, or hydroxy;

$R^4$ is hydrogen or halogen;

$R^1$ is hydrogen, methyl or ethyl;

A is $C(O)NR^9R^{10}$; or

A is 5 or 6 member heteroaryl, which heteroaryl comprises one ring heteroatom selected from N, O or S and 0, 1 or 2 additional ring nitrogen atoms, which heteroaryl is optionally substituted with 0, 1, or 2 groups independently selected from halogen, cyano, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, $C(O)NH_2$, $C(O)NHC_1$-$C_6$alkyl, phenyl or 5 or 6 member heteroaryl having one ring heteroatom selected from N, O or S and 0, 1 or 2 additional ring nitrogen atoms, wherein the optional heteroaryl or phenyl substituent is further substituted with 0, 1 or 2 $C_1$-$C_6$alkyl; or A is phenyl substituted with one substituent selected from the group consisting of halogen, $C_1$-$C_4$alkyl, halo$C_1$-$C_4$alkyl, $C_1$-$C_4$alkoxy, halo$C_1$-$C_4$alkoxy, hydroxy, cyano, or 5 member heteroaryl having one ring heteroatom selected from N, O or S and 0, 1 or 2 additional ring nitrogen atoms, and wherein the phenyl group is further optionally substituted with halogen, $C_1$-$C_4$alkyl, $C_1$-$C_4$alkoxy, halo$C_1$-$C_4$alkyl or halo$C_1$-$C_4$alkoxy.

$R^9$ is hydrogen, or $C_1$-$C_4$alkyl;

$R^{10}$ is $C_1$-$C_4$alkyl, halo$C_1$-$C_4$alkyl, $C_3$-$C_7$cycloalkyl or 4 to 7 member heterocycle, which heterocycle has 1 or 2 ring hetero atoms selected from N, O or S, which sulfur may be optionally oxidized, and wherein each alkyl or cycloalkyl is optionally substituted with cyano, halogen, hydroxy, $C_1$-$C_6$alkoxy, $S(O)_qC_1$-$C_6$alkyl; or $NR^9R^{10}$, taken in combination, form a monocyclic or bicyclic 4 to 9 member azacycle having one ring nitrogen atom and 0 or 1 additional ring heteroatom selected from N, O or S, which ring sulfur may be optionally oxidized, which azacycle is optionally substituted with 0, 1 or 2 substitutents selected from halogen, oxo, hydroxy, cyano, $C_1$-$C_6$alkyl, halo $C_1$-$C_6$alkyl, hydroxy$C_1$-$C_6$alkyl, $C_1$-$C_6$alkoxy, $S(O)_2$ $C_1$-$C_6$alkyl, $CO_2H$, $C(O)C_1$-$C_6$alkyl, or $C(O)NH_2$;

$Z^4$ is $CR^{14}$ or N;

$R^{11}$ is hydrogen, halogen, cyano or $C_1$-$C_4$alkyl;

$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, halo$C_1$-$C_4$alkoxy, $C_3$-$C_6$cycloalkyl or 5 member saturated, partially unsaturated or aromatic 5 or 6 member heterocycle having 1 or 2 ring heteroatoms independently selected from N, O and S; and $R^{14}$ is hydrogen, halogen, cyano or $C_1$-$C_4$alkyl.

In certain aspects of the twenty ninth embodiment, compounds of Formula (II) include compounds of Formula (IIa):

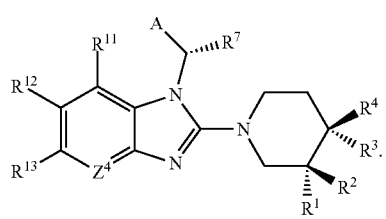

(IIa)

In a thirtieth embodiment, the invention provides compounds of the twenty ninth embodiment which include compounds of Formula III:

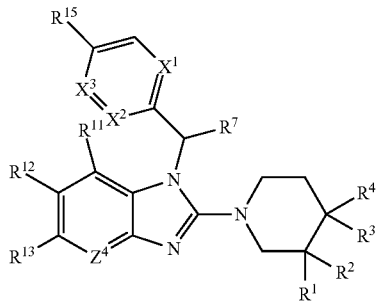

(III)

Wherein $X^1$ is $CR^{16}$ or N;

$X^2$ is $CR^{17}$ or N;

$X^3$ is $CR^{18}$ or N;

$Z^4$ is N or $CR^{14}$;

$R^1$ is $NHR^{1a}$;

$R^{1a}$ is hydrogen or $C_1$-$C_4$alkyl;

$R^2$ is hydrogen or $C_1$-$C_4$alkyl;

$R^3$ is hydrogen or halogen;

$R^4$ is hydrogen or halogen;

$R^7$ is hydrogen, methyl or ethyl;

$R^{11}$ is hydrogen, halogen, cyano or $C_1$-$C_4$alkyl;

$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, or halo$C_1$-$C_4$alkoxy;

$R^{14}$ is hydrogen, halogen, cyano or $C_1$-$C_4$alkyl;

$R^{15}$ is hydrogen, halogen, cyano, $C_1$-$C_4$alkyl, $C_1$-$C_4$alkoxy, halo$C_1$-$C_4$alkyl, halo$C_1$-$C_4$alkoxy, $C(O)NH_2$, $C(O)NH(C_1$-$C_4$alkyl) or 5 member heteroaryl having one ring heteroatom selected from N, O or S and 0, 1 or 2 additional ring nitrogen atoms;

$R^{16}$ is hydrogen, halogen, cyano, $C_1$-$C_4$alkyl, $C_1$-$C_4$alkoxy, halo$C_1$-$C_4$alkyl or halo$C_1$-$C_4$alkoxy;

$R^{17}$ is hydrogen or halogen; and $R^{18}$ is hydrogen, halogen, cyano, $C_1$-$C_4$alkyl, $C_1$-$C_4$alkoxy, halo$C_1$-$C_4$alkyl or halo$C_1$-$C_4$alkoxy, wherein at least one of $R^{15}$, $R^{16}$, $R^{17}$ or $R^{18}$ is not hydrogen.

In certain aspects of the thirtieth embodiment, compounds of Formula (III) include compounds of Formula (IIIa):

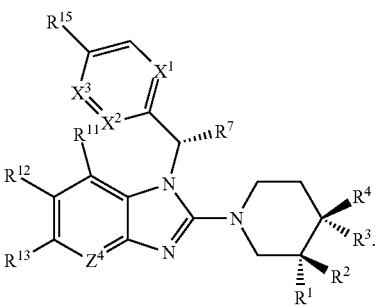

(IIIa)

In certain other aspects of the thirtieth embodiment, compounds of Formula (III) include compounds of Formula (IIIb):

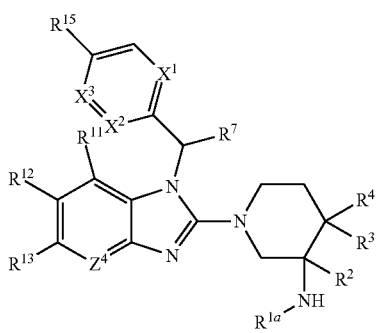

(IIIb)

In certain other aspects of the thirtieth embodiment, compounds of Formula (IIIb) include compounds of Formula (IIIc):

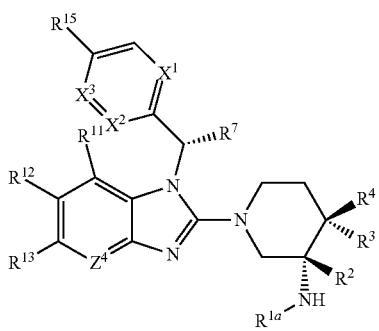

(IIIc)

In a thirty first embodiment, the invention provides compounds of the twenty ninth or thirtieth embodiment in which $R^2$ is hydrogen, $R^7$ is hydrogen or methyl; and $Z^4$ is $CR^{14}$.

In a thirty second embodiment, the invention provides compounds of the twenty ninth embodiment which include compounds of Formula (IV):

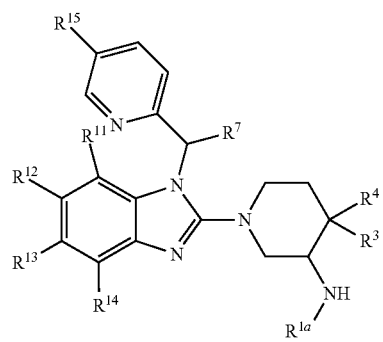

(IV)

Wherein:
$R^{1a}$ is hydrogen or $C_1$-$C_4$alkyl;
$R^3$ is hydrogen or halogen;
$R^4$ is hydrogen or halogen;
$R^7$ is hydrogen, methyl or ethyl;
$R^{11}$ is hydrogen, halogen, cyano or $C_1$-$C_4$alkyl;
$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, or halo$C_1$-$C_4$alkoxy;

$R^{14}$ is hydrogen, halogen, cyano or $C_1$-$C_4$alkyl; and
$R^{15}$ is hydrogen, halogen, cyano, $C_1$-$C_4$alkyl, $C_1$-$C_4$alkoxy, halo$C_1$-$C_4$alkyl, halo$C_1$-$C_4$alkoxy, $C(O)NH_2$, or $C(O)NH(C_1$-$C_4$alkyl).

In certain aspects of the thirty second embodiment, compounds of Formula (IV) include compounds of Formula (IVa):

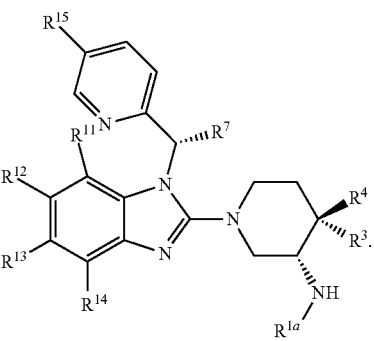

(IVa)

In a thirty third embodiment, the invention provides compounds of the twenty ninth embodiment which include compounds of Formula (V):

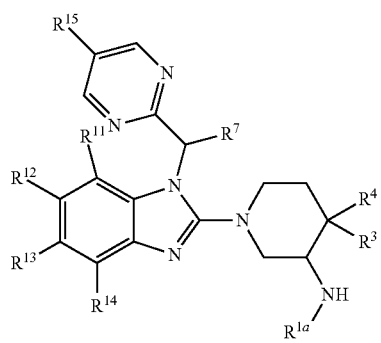

(V)

Wherein:
$R^{1a}$ is hydrogen or $C_1$-$C_4$alkyl;
$R^3$ is hydrogen or halogen;
$R^4$ is hydrogen or halogen;
$R^7$ is hydrogen, methyl or ethyl;
$R^{11}$ is hydrogen, halogen, cyano or $C_1$-$C_4$alkyl;
$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, or halo$C_1$-$C_4$alkoxy;
$R^{14}$ is hydrogen, halogen, cyano or $C_1$-$C_4$alkyl; and
$R^{15}$ is hydrogen, halogen, cyano, $C_1$-$C_4$alkyl, $C_1$-$C_4$alkoxy, halo$C_1$-$C_4$alkyl, halo$C_1$-$C_4$alkoxy, $C(O)NH_2$, or $C(O)NH(C_1$-$C_4$alkyl).

In certain aspects of the thirty third embodiment, compounds of Formula (V) include compounds of Formula (Va):

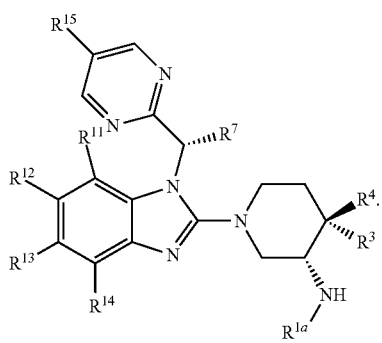

(Va)

In a thirty fourth embodiment, the invention provides compounds of the twenty ninth embodiment which include compounds of Formula (VI):

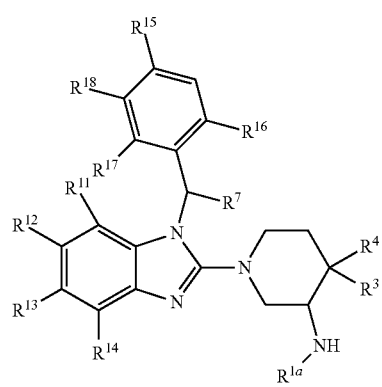

(VI)

Wherein $R^{1a}$ is hydrogen or $C_1$-$C_4$alkyl;

$R^3$ is hydrogen or halogen;

$R^4$ is hydrogen or halogen;

$R^7$ is hydrogen, methyl or ethyl;

$R^{11}$ is hydrogen, halogen, cyano or $C_1$-$C_4$alkyl;

$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, or halo$C_1$-$C_4$alkoxy;

$R^{14}$ is hydrogen, halogen, cyano or $C_1$-$C_4$alkyl;

$R^{15}$ is hydrogen, halogen, cyano, $C_1$-$C_4$alkyl, $C_1$-$C_4$alkoxy, halo$C_1$-$C_4$alkyl, halo$C_1$-$C_4$alkoxy, C(O)NH$_2$, C(O)NH($C_1$-$C_4$alkyl) or 5 member heteroaryl having one ring heteroatom selected from N, O or S and 0, 1 or 2 additional ring nitrogen atoms;

$R^{16}$ is hydrogen, halogen, cyano, $C_1$-$C_4$alkyl, $C_1$-$C_4$alkoxy, halo$C_1$-$C_4$alkyl or halo$C_1$-$C_4$alkoxy;

$R^{17}$ is hydrogen or halogen; and $R^{18}$ is hydrogen, halogen, cyano, $C_1$-$C_4$alkyl, $C_1$-$C_4$alkoxy, halo$C_1$-$C_4$alkyl or halo$C_1$-$C_4$alkoxy, wherein at least one of $R^{15}$, $R^{16}$, $R^{17}$ or $R^{18}$ is not hydrogen.

In certain aspects of the thirty fourth embodiment, compounds of Formula (VI) include compounds of Formula (VIa):

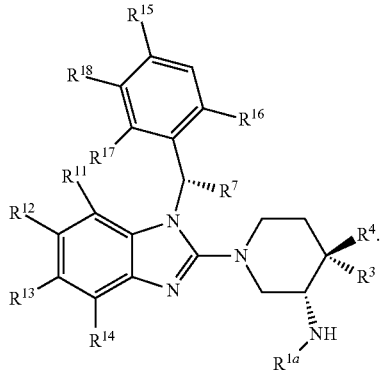

(VIa)

In a thirty fifth embodiment, the invention provides compounds of the twenty ninth embodiment which include compounds of Formula (VII):

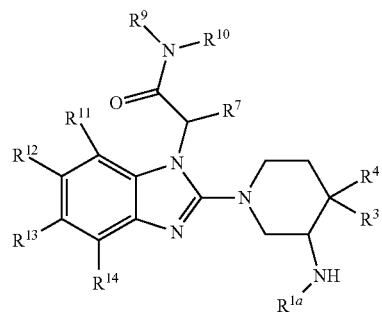

(VII)

Wherein $R^{1a}$ is hydrogen or $C_1$-$C_4$alkyl;

$R^3$ is hydrogen or halogen;

$R^4$ is hydrogen or halogen;

$R^7$ is hydrogen, methyl or ethyl;

$R^9$ is hydrogen, methyl or ethyl;

$R^{10}$ is $C_1$-$C_4$alkyl or halo$C_1$-$C_4$alkyl wherein each alkyl is optionally substituted with cyano, halogen, hydroxy, $C_1$-$C_6$alkoxy or S(O)$_q$$C_1$-$C_6$alkyl; or NR$^9$R$^{10}$, taken in combination, form a 4 to 6 member monocyclic azacycle or a 7 to 9 member bicyclic azacycle, each of which having one ring nitrogen atom and 0 or 1 additional ring heteroatom selected from N, O or S, which ring sulfur may be optionally oxidized, wherein each azacycle is optionally substituted with 0, 1 or 2 substitutents selected from halogen, oxo, hydroxy, cyano, $C_1$-$C_6$alkyl, halo $C_1$-$C_6$alkyl, hydroxy$C_1$-$C_6$alkyl, $C_1$-$C_6$alkoxy, S(O)$_2$ $C_1$-$C_6$alkyl, CO$_2$H, C(O)$C_1$-$C_6$alkyl, or C(O)NH$_2$;

$R^{11}$ is hydrogen, halogen, cyano or $C_1$-$C_4$alkyl;

$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, or halo$C_1$-$C_4$alkoxy; and $R^{14}$ is hydrogen, halogen, cyano or $C_1$-$C_4$alkyl.

In certain aspects of the thirty fifth embodiment, compounds of Formula (VII) include compounds of Formula (VIIa):

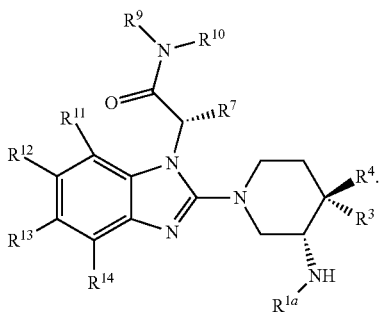

(VIIa)

In a thirty sixth embodiment, the invention provides compounds of any one of the twenty ninth to thirty fifth embodiment in which $R^{11}$ is hydrogen.

In a thirty seventh embodiment, the invention provides compounds of any one of the thirty first to thirty fifth embodiment in which $R^{1a}$ is hydrogen or methyl; $R^3$ is hydrogen or fluorine; and $R^4$ is hydrogen or fluorine.

In a thirty eighth embodiment, the invention provides compounds of the first or second embodiment in which the compound is recited in the below Table A.

Table A (S)-6-((2-(3-aminopiperidin-1-yl)-6-chloro-1H-benzo[d]imidazol-1-yl)methyl)nicotinonitrile;

(S)-6-((2-(3-aminopiperidin-1-yl)-5-chloro-1H-benzo[d]imidazol-1-yl)methyl)nicotinonitrile;

(S)-6-((2-(3-aminopiperidin-1-yl)-4-chloro-1H-benzo[d]imidazol-1-yl)methyl)nicotinonitrile;

6-((2-((3R,4R)-3-amino-4-fluoropiperidin-1-yl)-4-chloro-1H-benzo[d]imidazol-1-yl)methyl)nicotinonitrile;

6-((2-((3R,4S)-3-amino-4-fluoropiperidin-1-yl)-4-chloro-1H-benzo[d]imidazol-1-yl)methyl)nicotinonitrile;

6-((2-((3R,4R)-3-amino-4-fluoropiperidin-1-yl)-6-chloro-1H-benzo[d]imidazol-1-yl)methyl)nicotinonitrile;

6-((2-((3R,4R)-3-amino-4-fluoropiperidin-1-yl)-5-chloro-1H-benzo[d]imidazol-1-yl)methyl)nicotinonitrile;

6-((2-((3R,4S)-3-amino-4-fluoropiperidin-1-yl)-6-chloro-1H-benzo[d]imidazol-1-yl)methyl)nicotinonitrile;

6-((2-((3R,4S)-3-amino-4-fluoropiperidin-1-yl)-5-chloro-1H-benzo[d]imidazol-1-yl)methyl)nicotinonitrile;

(R)-6-((2-(3-amino-4,4-difluoropiperidin-1-yl)-4-chloro-1H-benzo[d]imidazol-1-yl)methyl)nicotinonitrile;

2-((3R,4R)-3-amino-4-fluoropiperidin-1-yl)-1-((5-cyanopyridin-2-yl)methyl)-1H-benzo[d]imidazole-4-carbonitrile;

(R)-6-((2-(3-amino-4,4-difluoropiperidin-1-yl)-6-chloro-1H-benzo[d]imidazol-1-yl)methyl)nicotinonitrile;

(R)-6-((2-(3-amino-4,4-difluoropiperidin-1-yl)-5-chloro-1H-benzo[d]imidazol-1-yl)methyl)nicotinonitrile;

6-((2-((3R,4R)-3-amino-4-fluoropiperidin-1-yl)-6-(trifluoromethyl)-1H-benzo[d]imidazol-1-yl)methyl)nicotinonitrile;

6-((2-((3R,4R)-3-amino-4-fluoropiperidin-1-yl)-5-(trifluoromethyl)-1H-benzo[d]imidazol-1-yl)methyl)nicotinonitrile;

6-((2-((3S,4S)-3-amino-4-fluoropiperidin-1-yl)-1H-benzo[d]imidazol-1-yl)methyl)nicotinonitrile;

(S)-6-((2-(5-amino-3,3-difluoropiperidin-1-yl)-1H-benzo[d]imidazol-1-yl)methyl)nicotinonitrile;

2-((3R,4R)-3-amino-4-fluoropiperidin-1-yl)-1-((5-cyanopyridin-2-yl)methyl)-6-fluoro-1H-benzo[d]imidazole-4-carbonitrile;

6-((2-((3R,4R)-3-amino-4-fluoropiperidin-1-yl)-6-(trifluoromethoxy)-1H-benzo[d]imidazol-1-yl)methyl)nicotinonitrile;

6-((2-((3R,4R)-3-amino-4-fluoropiperidin-1-yl)-5-(trifluoromethoxy)-1H-benzo[d]imidazol-1-yl)methyl)nicotinonitrile;

6-((2-((3R,4R)-3-amino-4-fluoropiperidin-1-yl)-6-fluoro-5-(trifluoromethyl)-1H-benzo[d]imidazol-1-yl)methyl)nicotinonitrile;

6-((2-((3R,4R)-3-amino-4-fluoropiperidin-1-yl)-5-fluoro-6-(trifluoromethyl)-1H-benzo[d]imidazol-1-yl)methyl)nicotinonitrile;

6-((2-((3aR,7aR)-hexahydro-1H-pyrrolo[2,3-c]pyridin-6(2H)-yl)-1H-benzo[d]imidazol-1-yl)methyl)nicotinonitrile;

6-((2-((3aR,7aS)-hexahydro-1H-pyrrolo[2,3-c]pyridin-6(2H)-yl)-1H-benzo[d]imidazol-1-yl)methyl)nicotinonitrile;

6-((2-((3aS,7aS)-hexahydro-1H-pyrrolo[2,3-c]pyridin-6(2H)-yl)-1H-benzo[d]imidazol-1-yl)methyl)nicotinonitrile;

6-((2-((3aS,7aR)-hexahydro-1H-pyrrolo[2,3-c]pyridin-6(2H)-yl)-1H-benzo[d]imidazol-1-yl)methyl)nicotinonitrile;

(R)-6-((2-(1,6-diazaspiro[3.5]nonan-6-yl)-1H-benzo[d]imidazol-1-yl)methyl)nicotinonitrile;

(S)-6-((2-(1,6-diazaspiro[3.5]nonan-6-yl)-1H-benzo[d]imidazol-1-yl)methyl)nicotinonitrile;

(3R,4R)-1-(1-((5-chloropyridin-2-yl)methyl)-6-(methylsulfonyl)-1H-benzo[d]imidazol-2-yl)-4-fluoropiperidin-3-amine;

(3R,4R)-1-(1-((5-chloropyridin-2-yl)methyl)-5-(methylsulfonyl)-1H-benzo[d]imidazol-2-yl)-4-fluoropiperidin-3-amine;

2-((3R,4R)-3-amino-4-fluoropiperidin-1-yl)-1-((5-chloropyrimidin-2-yl)methyl)-6-fluoro-1H-benzo[d]imidazole-4-carbonitrile;

(3R,4R)-1-(5,7-difluoro-1-((5-fluoropyridin-2-yl)methyl)-1H-benzo[d]imidazol-2-yl)-4-fluoropiperidin-3-amine;

(3R,4R)-1-(4,6-difluoro-1-((5-fluoropyridin-2-yl)methyl)-1H-benzo[d]imidazol-2-yl)-4-fluoropiperidin-3-amine;

(3R,4R)-1-(5,7-difluoro-1-((5-fluoropyrimidin-2-yl)methyl)-1H-benzo[d]imidazol-2-yl)-4-fluoropiperidin-3-amine;

(3R,4R)-1-(4,6-difluoro-1-((5-fluoropyrimidin-2-yl)methyl)-1H-benzo[d]imidazol-2-yl)-4-fluoropiperidin-3-amine;

2-((3R,4S)-3-amino-4-fluoropiperidin-1-yl)-6-fluoro-1-((5-fluoropyrimidin-2-yl)methyl)-1H-benzo[d]imidazole-4-carbonitrile;

2-((3R,4R)-3-amino-4-fluoropiperidin-1-yl)-6-fluoro-1-((5-fluoropyrimidin-2-yl)methyl)-1H-benzo[d]imidazole-4-carbonitrile;

6-((2-((3R,4R)-3-amino-4-fluoropiperidin-1-yl)-1H-benzo[d]imidazol-1-yl)methyl)nicotinonitrile;

(3R,4S)-1-(1-((5-chloropyrimidin-2-yl)methyl)-6-fluoro-1H-benzo[d]imidazol-2-yl)-4-fluoropiperidin-3-amine;

(3R,4S)-1-(1-((5-chloropyrimidin-2-yl)methyl)-5-fluoro-1H-benzo[d]imidazol-2-yl)-4-fluoropiperidin-3-amine;

(R)-2-(3-amino-4,4-difluoropiperidin-1-yl)-1-((5-chloropyrimidin-2-yl)methyl)-1H-benzo[d]imidazole-6-carbonitrile;

(R)-2-(3-amino-4,4-difluoropiperidin-1-yl)-1-((5-chloropyrimidin-2-yl)methyl)-1H-benzo[d]imidazole-5-carbonitrile;

6-((2-((3R,4R)-3-amino-4-fluoropiperidin-1-yl)-5,6-dichloro-1H-benzo[d]imidazol-1-yl)methyl)nicotinonitrile;

tert-butyl ((3R,4R)-1-(1-((5-cyanopyridin-2-yl)methyl)-5,6-dimethyl-1H-benzo[d]imidazol-2-yl)-4-fluoropiperidin-3-yl)carbamate;

(S)-6-((2-(3-aminopiperidin-1-yl)-6-fluoro-1H-benzo[d]imidazol-1-yl)methyl)nicotinonitrile hydrochloride;

(S)-6-((2-(3-aminopiperidin-1-yl)-5-fluoro-1H-benzo[d]imidazol-1-yl)methyl)nicotinonitrile hydrochloride;

6-((2-((3R,4S)-3-amino-4-fluoropiperidin-1-yl)-6-fluoro-1H-benzo[d]imidazol-1-yl)methyl)nicotinonitrile hydrochloride;

6-((2-((3R,4S)-3-amino-4-fluoropiperidin-1-yl)-5-fluoro-1H-benzo[d]imidazol-1-yl)methyl)nicotinonitrile hydrochloride;

6-((2-((3R,4R)-3-amino-4-fluoropiperidin-1-yl)-5-fluoro-1H-benzo[d]imidazol-1-yl)methyl)nicotinonitrile hydrochloride;

6-((2-((3R,4R)-3-amino-4-fluoropiperidin-1-yl)-6-fluoro-1H-benzo[d]imidazol-1-yl)methyl)nicotinonitrile hydrochloride;

(S)-2-(3-aminopiperidin-1-yl)-1-((5-cyanopyridin-2-yl)methyl)-1H-benzo[d]imidazole-6-carbonitrile;

(S)-2-(3-aminopiperidin-1-yl)-1-((5-cyanopyridin-2-yl)methyl)-1H-benzo[d]imidazole-5-carbonitrile;

2-((3R,4R)-3-amino-4-fluoropiperidin-1-yl)-1-((5-cyanopyridin-2-yl)methyl)-1H-benzo[d]imidazole-6-carbonitrile;

2-((3R,4R)-3-amino-4-fluoropiperidin-1-yl)-1-((5-cyanopyridin-2-yl)methyl)-1H-benzo[d]imidazole-5-carbonitrile;

(R)-2-(3-amino-4,4-difluoropiperidin-1-yl)-1-((5-cyanopyridin-2-yl)methyl)-1H-benzo[d]imidazole-6-carbonitrile;

(R)-2-(3-amino-4,4-difluoropiperidin-1-yl)-1-((5-cyanopyridin-2-yl)methyl)-1H-benzo[d]imidazole-5-carbonitrile;

(S)-6-((2-(3-aminopiperidin-1-yl)-4,6-dichloro-1H-benzo[d]imidazol-1-yl)methyl)nicotinonitrile;

6-((2-((3R,4R)-3-amino-4-fluoropiperidin-1-yl)-4,6-dichloro-1H-benzo[d]imidazol-1-yl)methyl)nicotinonitrile;

6-((2-((3R,4S)-3-amino-4-fluoropiperidin-1-yl)-4,6-dichloro-1H-benzo[d]imidazol-1-yl)methyl)nicotinonitrile;

(R)-6-((2-(3-amino-4,4-difluoropiperidin-1-yl)-4,6-dichloro-1H-benzo[d]imidazol-1-yl)methyl)nicotinonitrile;

(S)-6-((2-(3-aminopiperidin-1-yl)-4,6-difluoro-1H-benzo[d]imidazol-1-yl)methyl)nicotinonitrile;

(S)-6-((2-(3-aminopiperidin-1-yl)-5,7-difluoro-1H-benzo[d]imidazol-1-yl)methyl)nicotinonitrile;

6-((2-((3R,4R)-3-amino-4-fluoropiperidin-1-yl)-4,6-difluoro-1H-benzo[d]imidazol-1-yl)methyl)nicotinonitrile;

6-((2-((3R,4R)-3-amino-4-fluoropiperidin-1-yl)-5,7-difluoro-1H-benzo[d]imidazol-1-yl)methyl)nicotinonitrile;

6-((2-((3R,4S)-3-amino-4-fluoropiperidin-1-yl)-4,6-difluoro-1H-benzo[d]imidazol-1-yl)methyl)nicotinonitrile;

6-((2-((3R,4S)-3-amino-4-fluoropiperidin-1-yl)-5,7-difluoro-1H-benzo[d]imidazol-1-yl)methyl)nicotinonitrile;

(R)-6-((2-(3-amino-4,4-difluoropiperidin-1-yl)-5,7-difluoro-1H-benzo[d]imidazol-1-yl)methyl)nicotinonitrile;

2-((3R,4S)-3-amino-4-fluoropiperidin-1-yl)-1-((5-cyanopyridin-2-yl)methyl)-1H-benzo[d]imidazole-6-carbonitrile;

2-((3R,4S)-3-amino-4-fluoropiperidin-1-yl)-1-((5-cyanopyridin-2-yl)methyl)-1H-benzo[d]imidazole-5-carbonitrile;

(S)-6-((2-(3-aminopiperidin-1-yl)-1H-benzo[d]imidazol-1-yl)methyl)nicotinonitrile;

(R)-6-((2-(3-amino-4,4-difluoropiperidin-1-yl)-5-fluoro-1H-benzo[d]imidazol-1-yl)methyl)nicotinonitrile hydrochloride;

6-((2-((3R,4R)-3-amino-4-fluoropiperidin-1-yl)-5,6-difluoro-1H-benzo[d]imidazol-1-yl)methyl)nicotinonitrile;

6-((2-((3R,4S)-3-amino-4-fluoropiperidin-1-yl)-1H-benzo[d]imidazol-1-yl)methyl)nicotinonitrile;

6-((2-((1R,5S)-1-(aminomethyl)-3-azabicyclo[3.1.0]hexan-3-yl)-1H-benzo[d]imidazol-1-yl)methyl)nicotinonitrile hydrochloride;

6-((2-((1S,5R)-1-(aminomethyl)-3-azabicyclo[3.1.0]hexan-3-yl)-1H-benzo[d]imidazol-1-yl)methyl)nicotinonitrile hydrochloride;

6-((2-((3aR,4R,6aS)-4-aminohexahydrocyclopenta[c]pyrrol-2(1H)-yl)-1H-benzo[d]imidazol-1-yl)methyl)nicotinonitrile hydrochloride;

6-((2-((3aS,4S,6aR)-4-aminohexahydrocyclopenta[c]pyrrol-2(1H)-yl)-1H-benzo[d]imidazol-1-yl)methyl)nicotinonitrile hydrochloride;

6-((2-((3aR,4S,6aS)-4-aminohexahydrocyclopenta[c]pyrrol-2(1H)-yl)-1H-benzo[d]imidazol-1-yl)methyl)nicotinonitrile hydrochloride;

6-((2-((3aS,4R,6aR)-4-aminohexahydrocyclopenta[c]pyrrol-2(1H)-yl)-1H-benzo[d]imidazol-1-yl)methyl)nicotinonitrile hydrochloride;

(R)-6-((2-(3-(aminomethyl)pyrrolidin-1-yl)-1H-benzo[d]imidazol-1-yl)methyl)nicotinonitrile hydrochloride;

(S)-6-((2-(3-(aminomethyl)pyrrolidin-1-yl)-1H-benzo[d]imidazol-1-yl)methyl)nicotinonitrile hydrochloride;

6-((2-((3R,4S)-3-amino-4-fluoropiperidin-1-yl)-5,6-dichloro-1H-benzo[d]imidazol-1-yl)methyl)nicotinonitrile hydrochloride;

6-((2-((3R,4S)-3-amino-4-fluoropiperidin-1-yl)-5,6-difluoro-1H-benzo[d]imidazol-1-yl)methyl)nicotinonitrile hydrochloride;

(R)-6-((2-(3-amino-4,4-difluoropiperidin-1-yl)-5,6-difluoro-1H-benzo[d]imidazol-1-yl)methyl)nicotinonitrile hydrochloride;

(R)-1-(1-((5-chloropyridin-2-yl)methyl)-1H-benzo[d]imidazol-2-yl)-4,4-difluoropiperidin-3-amine hydrochloride;

(3R,4S)-1-(1-((5-chloropyridin-2-yl)methyl)-1H-benzo[d]imidazol-2-yl)-4-fluoropiperidin-3-amine hydrochloride;

(R)-6-((2-(3-amino-4,4-difluoropiperidin-1-yl)-4,6-difluoro-1H-benzo[d]imidazol-1-yl)methyl)nicotinonitrile hydrochloride;

(R)-6-((2-(3-amino-4,4-difluoropiperidin-1-yl)-6-fluoro-1H-benzo[d]imidazol-1-yl)methyl)nicotinonitrile;

(R)-6-((2-(3-amino-4,4-difluoropiperidin-1-yl)-4-(trifluoromethyl)-1H-benzo[d]imidazol-1-yl)methyl)nicotinonitrile;

6-((2-((3R,4R)-3-amino-4-fluoropiperidin-1-yl)-4-(trifluoromethyl)-1H-benzo[d]imidazol-1-yl)methyl)nicotinonitrile;

6-((2-((3R,4S)-3-amino-4-fluoropiperidin-1-yl)-4-(trifluoromethyl)-1H-benzo[d]imidazol-1-yl)methyl)nicotinonitrile;

6-((2-((3R,4R)-3-amino-4-fluoropiperidin-1-yl)-6-chloro-3H-imidazo[4,5-b]pyridin-3-yl)methyl)nicotinonitrile;

6-((2-((3R,4R)-3-amino-4-fluoropiperidin-1-yl)-6-chloro-1H-imidazo[4,5-b]pyridin-1-yl)methyl)nicotinonitrile;

6-((2-((3R,4R)-3-amino-4-fluoropiperidin-1-yl)-6-chloro-1H-imidazo[4,5-b]pyridin-1-yl)methyl)-N-(tert-butyl)nicotinamide;

6-((2-((3R,4R)-3-amino-4-hydroxypiperidin-1-yl)-1H-benzo[d]imidazol-1-yl)methyl)nicotinonitrile;

6-((2-((3S,4S)-3-amino-4-hydroxypiperidin-1-yl)-1H-benzo[d]imidazol-1-yl)methyl)nicotinonitrile;

6-((2-(2,6-diazaspiro[3.4]octan-6-yl)-1H-benzo[d]imidazol-1-yl)methyl)nicotinonitrile;

6-((2-((4aR,7aS)-hexahydropyrrolo[3,4-b][1,4]oxazin-6(2H)-yl)-1H-benzo[d]imidazol-1-yl)methyl)nicotinonitrile hydrochloride;

6-((2-((4aS,7aR)-hexahydropyrrolo[3,4-b][1,4]oxazin-6(2H)-yl)-1H-benzo[d]imidazol-1-yl)methyl)nicotinonitrile hydrochloride;

6-((2-((4aR,7aR)-hexahydropyrrolo[3,4-b][1,4]oxazin-6(2H)-yl)-1H-benzo[d]imidazol-1-yl)methyl)nicotinonitrile;

6-((2-((4aS,7aS)-hexahydropyrrolo[3,4-b][1,4]oxazin-6(2H)-yl)-1H-benzo[d]imidazol-1-yl)methyl)nicotinonitrile;

(S)-3-amino-1-(1-((5-cyanopyridin-2-yl)methyl)-1H-benzo[d]imidazol-2-yl)piperidine-3-carboxamide;

(R)-3-amino-1-(1-((5-cyanopyridin-2-yl)methyl)-1H-benzo[d]imidazol-2-yl)piperidine-3-carboxamide;

(S)-6-((2-(3-amino-3-(hydroxymethyl)piperidin-1-yl)-1H-benzo[d]imidazol-1-yl)methyl)nicotinonitrile;

(R)-6-((2-(3-amino-3-(hydroxymethyl)piperidin-1-yl)-1H-benzo[d]imidazol-1-yl)methyl)nicotinonitrile;

6-((2-((3R,4S)-3-amino-4-fluoro-1-piperidinyl)-6-(trifluoromethyl)-1H-benzimidazol-1-yl)methyl)-3-pyridinecarbonitrile;

6-((2-((3R,4S)-3-amino-4-fluoro-1-piperidinyl)-5-(trifluoromethyl)-1H-benzimidazol-1-yl)methyl)-3-pyridinecarbonitrile;

6-((2-((3R)-3-amino-4,4-difluoro-1-piperidinyl)-6-(trifluoromethyl)-1H-benzimidazol-1-yl)methyl)-3-pyridinecarbonitrile;

6-((2-((3R)-3-amino-4,4-difluoro-1-piperidinyl)-5-(trifluoromethyl)-1H-benzimidazol-1-yl)methyl)-3-pyridinecarbonitrile;

6-((2-((3R,4R)-3-amino-4-fluoro-1-piperidinyl)-5-methyl-1H-benzimidazol-1-yl)methyl)-3-pyridinecarbonitrile;

6-((2-((3R,4R)-3-amino-4-fluoro-1-piperidinyl)-6-methyl-1H-benzimidazol-1-yl)methyl)-3-pyridinecarbonitrile;

6-((2-((3R,4R)-3-amino-4-fluoro-1-piperidinyl)-6-chloro-5-methyl-1H-benzimidazol-1-yl)methyl)-3-pyridinecarbonitrile;

6-((2-((3R,4R)-3-amino-4-fluoro-1-piperidinyl)-5-chloro-6-methyl-1H-benzimidazol-1-yl)methyl)-3-pyridinecarbonitrile;

6-((2-((3R,4R)-3-amino-4-fluoro-1-piperidinyl)-6-fluoro-5-methyl-1H-benzimidazol-1-yl)methyl)-3-pyridinecarbonitrile;

6-((2-((3R,4R)-3-amino-4-fluoro-1-piperidinyl)-5-fluoro-6-methyl-1H-benzimidazol-1-yl)methyl)-3-pyridinecarbonitrile;

6-((2-((3S)-3-(methylamino)-1-piperidinyl)-1H-benzimidazol-1-yl)methyl)-3-pyridinecarbonitrile;

6-((2-((3R)-3-(methylamino)-1-piperidinyl)-1H-benzimidazol-1-yl)methyl)-3-pyridinecarbonitrile;

6-((2-((3R,4R)-3-amino-4-fluoro-1-piperidinyl)-6-(difluoromethoxy)-1H-benzimidazol-1-yl)methyl)-3-pyridinecarbonitrile;

6-((2-((3R,4R)-3-amino-4-fluoro-1-piperidinyl)-5-(difluoromethoxy)-1H-benzimidazol-1-yl)methyl)-3-pyridinecarbonitrile;

6-((2-((3R,4R)-3-amino-4-fluoro-1-piperidinyl)-4-methoxy-1H-benzimidazol-1-yl)methyl)-3-pyridinecarbonitrile;

6-((2-((3R,4R)-3-amino-4-fluoro-1-piperidinyl)-4-methyl-1H-benzimidazol-1-yl)methyl)-3-pyridinecarbonitrile;

5-((2-((3R,4S)-3-amino-4-fluoro-1-piperidinyl)-6-(trifluoromethyl)-1H-benzimidazol-1-yl)methyl)-2-pyrazinecarboxamide;

5-((2-((3R,4S)-3-amino-4-fluoro-1-piperidinyl)-5-(trifluoromethyl)-1H-benzimidazol-1-yl)methyl)-2-pyrazinecarboxamide;

6-((2-((3R,4R)-3-amino-4-fluoro-1-piperidinyl)-6-chloro-5-(trifluoromethoxy)-1H-benzimidazol-1-yl)methyl)-3-pyridinecarbonitrile;

6-((2-((3R,4R)-3-amino-4-fluoro-1-piperidinyl)-5-chloro-6-(trifluoromethoxy)-1H-benzimidazol-1-yl)methyl)-3-pyridinecarbonitrile;

6-((2-((3R,4R)-3-amino-4-fluoro-1-piperidinyl)-6-chloro-5-(trifluoromethyl)-1H-benzimidazol-1-yl)methyl)-3-pyridinecarbonitrile;

6-((2-((3R,4R)-3-amino-4-fluoro-1-piperidinyl)-5-chloro-6-(trifluoromethyl)-1H-benzimidazol-1-yl)methyl)-3-pyridinecarbonitrile;

6-((2-((5R)-1,7-diazaspiro[4.5]decan-7-yl)-1H-benzimidazol-1-yl)methyl)-3-pyridinecarbonitrile, 6-((2-((5S)-1,7-diazaspiro[4.5]decan-7-yl)-1H-benzimidazol-1-yl)methyl)-3-pyridinecarbonitrile;

6-((2-((6R)-1,8-diazaspiro[5.5]undecan-8-yl)-1H-benzimidazol-1-yl)methyl)-3-pyridinecarbonitrile;

6-((2-((6S)-1,8-diazaspiro[5.5]undecan-8-yl)-1H-benzimidazol-1-yl)methyl)-3-pyridinecarbonitrile;

6-((2-((4aR,8aR)-hexahydro-2H-pyrido[4,3-b][1,4]oxazin-6(5H)-yl)-1H-benzimidazol-1-yl)methyl)-3-pyridinecarbonitrile;

6-((2-((4aS,8aS)-hexahydro-2H-pyrido[4,3-b][1,4]oxazin-6(5H)-yl)-1H-benzimidazol-1-yl)methyl)-3-pyridinecarbonitrile;

5-((2-((3R,4R)-3-amino-4-fluoro-1-piperidinyl)-5,6-difluoro-1H-benzimidazol-1-yl)methyl)-2-pyrazinecarboxamide;

5-((2-((3R,4R)-3-amino-4-fluoro-1-piperidinyl)-6-(trifluoromethyl)-1H-benzimidazol-1-yl)methyl)-2-pyrazinecarboxamide;

6-((2-((5R)-1,7-diazaspiro[4.5]decan-7-yl)-1H-benzimidazol-1-yl)methyl)-3-pyridinecarbonitrile;

6-((2-((5S)-1,7-diazaspiro[4.5]decan-7-yl)-1H-benzimidazol-1-yl)methyl)-3-pyridinecarbonitrile;

6-((2-((3R)-3-amino-4,4-difluoro-1-piperidinyl)-5-methoxy-1H-benzimidazol-1-yl)methyl)-3-pyridinecarbonitrile;

6-((2-((3R)-3-amino-4,4-difluoro-1-piperidinyl)-6-methoxy-1H-benzimidazol-1-yl)methyl)-3-pyridinecarbonitrile;

6-((2-((3S)-3-(methylamino)-1-piperidinyl)-6-(trifluoromethyl)-1H-benzimidazol-1-yl)methyl)-3-pyridinecarbonitrile;

6-((2-((3S)-3-(methylamino)-1-piperidinyl)-5-(trifluoromethyl)-1H-benzimidazol-1-yl)methyl)-3-pyridinecarbonitrile;

6-((2-((3S)-3-amino-3-methyl-1-piperidinyl)-1H-benzimidazol-1-yl)methyl)-3-pyridinecarbonitrile;

(S)-6-((2-(3-aminopiperidin-1-yl)-6-methoxy-1H-benzo[d]imidazol-1-yl)methyl)nicotinonitrile 2,2,2-trifluoroacetate;

(S)-6-((2-(3-aminopiperidin-1-yl)-5-methoxy-1H-benzo[d]imidazol-1-yl)methyl)nicotinonitrile 2,2,2-trifluoroacetate;

6-((2-((3R,4R)-3-amino-4-fluoropiperidin-1-yl)-4-chloro-6-fluoro-1H-benzo[d]imidazol-1-yl)methyl)nicotinonitrile 2,2,2-trifluoroacetate;

6-((2-((3R,4R)-3-amino-4-fluoropiperidin-1-yl)-5-methoxy-1H-benzo[d]imidazol-1-yl)methyl)nicotinonitrile hydrochloride;

6-((2-((3R,4R)-3-amino-4-fluoropiperidin-1-yl)-6-methoxy-1H-benzo[d]imidazol-1-yl)methyl)nicotinonitrile hydrochloride;

6-((2-((3R,4S)-3-amino-4-fluoropiperidin-1-yl)-6-methoxy-1H-benzo[d]imidazol-1-yl)methyl)nicotinonitrile hydrochloride;

6-((2-((3R,4S)-3-amino-4-fluoropiperidin-1-yl)-5-methoxy-1H-benzo[d]imidazol-1-yl)methyl)nicotinonitrile hydrochloride;

2-((3R,4S)-3-amino-4-fluoropiperidin-1-yl)-1-((5-chloropyrimidin-2-yl)methyl)-6-fluoro-1H-benzo[d]imidazole-4-carbonitrile;

(R)-2-(3-amino-4,4-difluoropiperidin-1-yl)-1-((5-chloropyrimidin-2-yl)methyl)-5-fluoro-1H-benzo[d]imidazole-7-carbonitrile;

(R)-2-(3-amino-4,4-difluoropiperidin-1-yl)-1-((5-chloropyrimidin-2-yl)methyl)-6-fluoro-1H-benzo[d]imidazole-4-carbonitrile;

6-((2-((3R,4R)-3-amino-4-hydroxypiperidin-1-yl)-6-chloro-1H-benzo[d]imidazol-1-yl)methyl)nicotinonitrile;

6-((2-((3R,4S)-3-amino-4-hydroxypiperidin-1-yl)-6-chloro-1H-benzo[d]imidazol-1-yl)methyl)nicotinonitrile;

(R)-4-((2-(3-amino-4,4-difluoropiperidin-1-yl)-1H-benzo[d]imidazol-1-yl)methyl)benzonitrile;

4-((2-((3R,4R)-3-amino-4-hydroxypiperidin-1-yl)-1H-benzo[d]imidazol-1-yl)methyl)benzonitrile compound with 4-((2-((3S,4S)-3-amino-4-hydroxypiperidin-1-yl)-1H-benzo[d]imidazol-1-yl)methyl)benzonitrile (1:1) dihydrochloride;

4-((2-((3R,4R)-3-amino-4-fluoro-1-piperidinyl)-5,7-difluoro-1H-benzimidazol-1-yl)methyl)benzonitrile;

4-((2-((3R,4R)-3-amino-4-fluoro-1-piperidinyl)-4,6-difluoro-1H-benzimidazol-1-yl)methyl)benzonitrile;

2-((3R,4R)-3-amino-4-fluoro-1-piperidinyl)-1-(4-cyanobenzyl)-1H-benzimidazole-6-carbonitrile;

2-((3R,4R)-3-amino-4-fluoro-1-piperidinyl)-1-(4-cyanobenzyl)-1H-benzimidazole-5-carbonitrile;

2-((3R)-3-amino-4,4-difluoro-1-piperidinyl)-1-(4-cyanobenzyl)-1H-benzimidazole-6-carbonitrile;

2-((3R)-3-amino-4,4-difluoro-1-piperidinyl)-1-(4-cyanobenzyl)-1H-benzimidazole-5-carbonitrile;

(R)-4-((2-(3-aminopiperidin-1-yl)-1H-benzo[d]imidazol-1-yl)methyl)benzonitrile;

4-((2-((3R,4R)-3-amino-4-methylpiperidin-1-yl)-1H-benzo[d]imidazol-1-yl)methyl)benzonitrile;

4-((2-(3-(aminomethyl)-3-methylpyrrolidin-1-yl)-1H-benzo[d]imidazol-1-yl)methyl)benzonitrile;

4-((2-((3S,4R)-3-amino-4-phenylpyrrolidin-1-yl)-1H-benzo[d]imidazol-1-yl)methyl)benzonitrile & 4-((2-((3R,4S)-3-amino-4-phenylpyrrolidin-1-yl)-1H-benzo[d]imidazol-1-yl)methyl)benzonitrile;

(S)-4-((2-(3-aminopyrrolidin-1-yl)-1H-benzo[d]imidazol-1-yl)methyl)benzonitrile;

(S)-4-((2-(3-aminopiperidin-1-yl)-1H-benzo[d]imidazol-1-yl)methyl)benzonitrile;

4-((2-(6-amino-2-azaspiro[4.4]nonan-2-yl)-1H-benzo[d]imidazol-1-yl)methyl)benzonitrile;

4-((2-(4-aminohexahydrocyclopenta[c]pyrrol-2(1H)-yl)-1H-benzo[d]imidazol-1-yl)methyl)benzonitrile;

4-((2-((3S,4S)-3-amino-4-fluoropiperidin-1-yl)-1H-benzo[d]imidazol-1-yl)methyl)benzonitrile;

4-((2-((3S,4R)-3-amino-4-fluoropiperidin-1-yl)-1H-benzo[d]imidazol-1-yl)methyl)benzonitrile;

4-((2-((3R,4S)-3-amino-4-fluoropiperidin-1-yl)-1H-benzo[d]imidazol-1-yl)methyl)benzonitrile;

4-((2-((3R,4R)-3-amino-4-fluoropiperidin-1-yl)-1H-benzo[d]imidazol-1-yl)methyl)benzonitrile;

(R)-4-((2-(3-(aminomethyl)-3-fluoropyrrolidin-1-yl)-1H-benzo[d]imidazol-1-yl)methyl)benzonitrile 2,2,2-trifluoroacetate;

(S)-4-((2-(3-(aminomethyl)-3-fluoropyrrolidin-1-yl)-1H-benzo[d]imidazol-1-yl)methyl)benzonitrile 2,2,2-trifluoroacetate;

(R)-4-((2-(3-(aminomethyl)-3-hydroxypyrrolidin-1-yl)-1H-benzo[d]imidazol-1-yl)methyl)benzonitrile 2,2,2-trifluoroacetate;

(S)-4-((2-(3-(aminomethyl)-3-hydroxypyrrolidin-1-yl)-1H-benzo[d]imidazol-1-yl)methyl)benzonitrile 2,2,2-trifluoroacetate;

(S)-4-((2-(3-(aminomethyl)pyrrolidin-1-yl)-1H-benzo[d]imidazol-1-yl)methyl)benzonitrile;

(R)-4-((2-(3-(aminomethyl)pyrrolidin-1-yl)-1H-benzo[d]imidazol-1-yl)methyl)benzonitrile;

4-((2-((3S,4S)-3-amino-4-methylpiperidin-1-yl)-1H-benzo[d]imidazol-1-yl)methyl)benzonitrile 2,2,2-trifluoroacetate;

4-((2-((3S,4R)-3-amino-4-methylpiperidin-1-yl)-1H-benzo[d]imidazol-1-yl)methyl)benzonitrile 2,2,2-trifluoroacetate;

4-((2-((3R,4S)-3-amino-4-methylpiperidin-1-yl)-1H-benzo[d]imidazol-1-yl)methyl)benzonitrile 2,2,2-trifluoroacetate;

4-((2-((1S,5R)-1-(aminomethyl)-3-azabicyclo[3.1.0]hexan-3-yl)-1H-benzo[d]imidazol-1-yl)methyl)benzonitrile;

4-((2-((1R,5S)-1-(aminomethyl)-3-azabicyclo[3.1.0]hexan-3-yl)-1H-benzo[d]imidazol-1-yl)methyl)benzonitrile;

(R)-4-((2-(3-aminopiperidin-1-yl)-6-methoxy-1H-benzo[d]imidazol-1-yl)methyl)benzonitrile;

(R)-4-((2-(3-aminopiperidin-1-yl)-5-methoxy-1H-benzo[d]imidazol-1-yl)methyl)benzonitrile;

2-((3R,4R)-3-amino-4-fluoropiperidin-1-yl)-1-((5-chloropyrimidin-2-yl)methyl)-1H-benzo[d]imidazole-6-carbonitrile;

(3R,4R)-4-fluoro-1-(1-((5-fluoropyrimidin-2-yl)methyl)-1H-benzo[d]imidazol-2-yl)piperidin-3-amine;

(3R,4R)-4-fluoro-1-(1-((5-fluoropyrimidin-2-yl)methyl)-1H-benzo[d]imidazol-2-yl)piperidin-3-amine;

2-((3R,4R)-3-amino-4-fluoropiperidin-1-yl)-1-((5-fluoropyridin-2-yl)methyl)-1H-benzo[d]imidazole-6-carbonitrile;

2-((3R,4R)-3-amino-4-fluoropiperidin-1-yl)-1-((5-fluoropyridin-2-yl)methyl)-1H-benzo[d]imidazole-5-carbonitrile;

(3R,4R)-1-(1-((5-bromopyrimidin-2-yl)methyl)-1H-benzo[d]imidazol-2-yl)-4-fluoropiperidin-3-amine;

(3R,4R)-4-fluoro-1-(1-((5-(trifluoromethyl)pyrimidin-2-yl)methyl)-1H-benzo[d]imidazol-2-yl)piperidin-3-amine;

(3R,4R)-4-fluoro-1-(1-((5-methoxypyrimidin-2-yl)methyl)-1H-benzo[d]imidazol-2-yl)piperidin-3-amine;

(3R,4R)-1-(1-((5-chloropyrimidin-2-yl)methyl)-1H-benzo[d]imidazol-2-yl)-4-fluoropiperidin-3-amine;

2-((3R,4R)-3-amino-4-fluoropiperidin-1-yl)-1-((5-fluoropyrimidin-2-yl)methyl)-1H-benzo[d]imidazole-6-carbonitrile;

2-((3R,4R)-3-amino-4-fluoropiperidin-1-yl)-1-((5-fluoropyrimidin-2-yl)methyl)-1H-benzo[d]imidazole-5-carbonitrile;

2-((3R,4R)-3-amino-4-fluoropiperidin-1-yl)-1-((5-cyanopyrimidin-2-yl)methyl)-1H-benzo[d]imidazole-5-carbonitrile;

2-((3R,4R)-3-amino-4-fluoropiperidin-1-yl)-1-((5-chloropyrimidin-2-yl)methyl)-1H-benzo[d]imidazole-5-carbonitrile;

2-((3R,4R)-3-amino-4-fluoropiperidin-1-yl)-1-((5-bromopyrimidin-2-yl)methyl)-1H-benzo[d]imidazole-6-carbonitrile;

2-((3R,4R)-3-amino-4-fluoropiperidin-1-yl)-1-((5-bromopyrimidin-2-yl)methyl)-1H-benzo[d]imidazole-5-carbonitrile;

5-((2-((3R,4R)-3-amino-4-fluoropiperidin-1-yl)-1H-benzo[d]imidazol-1-yl)methyl)pyrazine-2-carbonitrile;

2-((3R,4S)-3-amino-4-fluoropiperidin-1-yl)-1-((5-chloropyrimidin-2-yl)methyl)-1H-benzo[d]imidazole-6-carbonitrile;

2-((3R,4S)-3-amino-4-fluoropiperidin-1-yl)-1-((5-chloropyrimidin-2-yl)methyl)-1H-benzo[d]imidazole-5-carbonitrile;

(3R,4R)-3-amino-1-(1-((5-chloropyrimidin-2-yl)methyl)-6-fluoro-1H-benzo[d]imidazol-2-yl)piperidin-4-ol;

(3R,4R)-3-amino-1-(1-((5-chloropyrimidin-2-yl)methyl)-5-fluoro-1H-benzo[d]imidazol-2-yl)piperidin-4-ol;

6-((2-((3R,4R)-3-amino-4-hydroxypiperidin-1-yl)-6-fluoro-1H-benzo[d]imidazol-1-yl)methyl)nicotinonitrile;

6-((2-((3R,4R)-3-amino-4-hydroxypiperidin-1-yl)-5-fluoro-1H-benzo[d]imidazol-1-yl)methyl)nicotinonitrile;

(S)-1-(1-((5-chloropyridin-2-yl)methyl)-1H-benzo[d]imidazol-2-yl)piperidin-3-amine;

(S)-5-((2-(3-aminopiperidin-1-yl)-1H-benzo[d]imidazol-1-yl)methyl)picolinonitrile;

(3R,4R)-1-(1-((5-chloropyridin-2-yl)methyl)-1H-benzo[d]imidazol-2-yl)-4-fluoropiperidin-3-amine hydrochloride;

(R)-6-((2-(3-amino-4,4-difluoropiperidin-1-yl)-1H-benzo[d]imidazol-1-yl)methyl)nicotinonitrile hydrochloride;

2-((3R,4R)-3-amino-4-fluoropiperidin-1-yl)-1-((5-chloropyridin-2-yl)methyl)-1H-benzo[d]imidazole-6-carbonitrile hydrochloride;

2-((3R,4R)-3-amino-4-fluoropiperidin-1-yl)-1-((5-chloropyridin-2-yl)methyl)-1H-benzo[d]imidazole-5-carbonitrile hydrochloride;

(3R,4R)-1-(1-((R)-1-(5-chloropyridin-2-yl)ethyl)-1H-benzo[d]imidazol-2-yl)-4-fluoropiperidin-3-amine hydrochloride;

(3R,4R)-1-(1-((S)-1-(5-chloropyridin-2-yl)ethyl)-1H-benzo[d]imidazol-2-yl)-4-fluoropiperidin-3-amine hydrochloride;

(3R,4R)-1-(1-((R)-1-(5-chloropyridin-2-yl)ethyl)-5,6-difluoro-1H-benzo[d]imidazol-2-yl)-4-fluoropiperidin-3-amine hydrochloride;

(3R,4R)-1-(1-((S)-1-(5-chloropyridin-2-yl)ethyl)-5,6-difluoro-1H-benzo[d]imidazol-2-yl)-4-fluoropiperidin-3-amine hydrochloride;

(3R,4R)-1-(5-chloro-1-((R)-1-(5-chloropyridin-2-yl)ethyl)-1H-benzo[d]imidazol-2-yl)-4-fluoropiperidin-3-amine hydrochloride;

(3R,4R)-1-(5-chloro-1-((S)-1-(5-chloropyridin-2-yl)ethyl)-1H-benzo[d]imidazol-2-yl)-4-fluoropiperidin-3-amine hydrochloride;

(3R,4R)-1-(6-chloro-1-((R)-1-(5-chloropyridin-2-yl)ethyl)-1H-benzo[d]imidazol-2-yl)-4-fluoropiperidin-3-amine hydrochloride;

(3R,4R)-1-(6-chloro-1-((S)-1-(5-chloropyridin-2-yl)ethyl)-1H-benzo[d]imidazol-2-yl)-4-fluoropiperidin-3-amine hydrochloride;

2-((3R,4R)-3-amino-4-fluoropiperidin-1-yl)-1-((R)-1-(5-cyanopyridin-2-yl)ethyl)-1H-benzo[d]imidazole-6-carbonitrile hydrochloride;

2-((3R,4R)-3-amino-4-fluoropiperidin-1-yl)-1-((R)-1-(5-cyanopyridin-2-yl)ethyl)-1H-benzo[d]imidazole-5-carbonitrile hydrochloride;

2-((3R,4R)-3-amino-4-fluoropiperidin-1-yl)-1-((S)-1-(5-cyanopyridin-2-yl)ethyl)-1H-benzo[d]imidazole-6-carbonitrile hydrochloride;

2-((3R,4R)-3-amino-4-fluoropiperidin-1-yl)-1-((S)-1-(5-cyanopyridin-2-yl)ethyl)-1H-benzo[d]imidazole-5-carbonitrile hydrochloride;

(3R,4R)-1-(1-((5-chloropyridin-2-yl)methyl)-5,6-difluoro-1H-benzo[d]imidazol-2-yl)-4-fluoropiperidin-3-amine hydrochloride;

(3R,4R)-1-(5,6-difluoro-1-((5-fluoropyridin-2-yl)methyl)-1H-benzo[d]imidazol-2-yl)-4-fluoropiperidin-3-amine hydrochloride;

(R)-1-(1-((5-chloropyridin-2-yl)methyl)-5,7-difluoro-1H-benzo[d]imidazol-2-yl)-4,4-difluoropiperidin-3-amine hydrochloride;

(R)-1-(1-((5-chloropyridin-2-yl)methyl)-4,6-difluoro-1H-benzo[d]imidazol-2-yl)-4,4-difluoropiperidin-3-amine hydrochloride;

(R)-1-(2-((3R,4R)-3-amino-4-fluoropiperidin-1-yl)-1H-benzo[d]imidazol-1-yl)-2,3-dihydro-1H-indene-5-carbonitrile hydrochloride;

(S)-1-(2-((3R,4R)-3-amino-4-fluoropiperidin-1-yl)-1H-benzo[d]imidazol-1-yl)-2,3-dihydro-1H-indene-5-carbonitrile hydrochloride;

(R)-5-((2-(3-amino-4,4-difluoropiperidin-1-yl)-6-chloro-1H-benzo[d]imidazol-1-yl)methyl)pyrazine-2-carbonitrile;

(R)-5-((2-(3-amino-4,4-difluoropiperidin-1-yl)-5-chloro-1H-benzo[d]imidazol-1-yl)methyl)pyrazine-2-carbonitrile;

2-(2-((3R,4R)-3-amino-4-fluoropiperidin-1-yl)-5,6-difluoro-1H-benzo[d]imidazol-1-yl)-N-isopropylacetamide;

2-(2-((3R,4R)-3-amino-4-fluoropiperidin-1-yl)-5,6-difluoro-1H-benzo[d]imidazol-1-yl)-1-(azetidin-1-yl)ethanone;

2-(2-((3R,4R)-3-amino-4-fluoropiperidin-1-yl)-5,6-difluoro-1H-benzo[d]imidazol-1-yl)-N-(2-cyanopropyl)-N-ethylacetamide;

3-(2-((3R,4R)-3-amino-4-fluoropiperidin-1-yl)-5,6-difluoro-1H-benzo[d]imidazol-1-yl)-1-methylpyrrolidin-2-one;

3-(2-((3R,4R)-3-amino-4-fluoropiperidin-1-yl)-5,6-difluoro-1H-benzo[d]imidazol-1-yl)-1-phenylpiperidin-2-one;

3-(2-((3R,4R)-3-amino-4-fluoropiperidin-1-yl)-5,6-difluoro-1H-benzo[d]imidazol-1-yl)-1-(4-chlorophenyl)pyrrolidin-2-one;

2-((3R,4R)-3-amino-4-fluoropiperidin-1-yl)-1-((5-methoxypyrimidin-2-yl)methyl)-1H-benzo[d]imidazole-5-carbonitrile hydrochloride;

2-((3R,4R)-3-amino-4-fluoropiperidin-1-yl)-1-((5-methoxypyrimidin-2-yl)methyl)-1H-benzo[d]imidazole-6-carbonitrile hydrochloride;

2-((3R,4R)-3-amino-4-fluoropiperidin-1-yl)-1-((6-(trifluoromethyl)pyridin-3-yl)methyl)-1H-benzo[d]imidazole-6-carbonitrile hydrochloride;

2-((3R,4R)-3-amino-4-fluoropiperidin-1-yl)-1-((6-(trifluoromethyl)pyridin-3-yl)methyl)-1H-benzo[d]imidazole-5-carbonitrile hydrochloride;

(S)-3-(2-((3R,4R)-3-amino-4-fluoropiperidin-1-yl)-5,6-difluoro-1H-benzo[d]imidazol-1-yl)-1-methylpyrrolidin-2-one;

(R)-3-(2-((3R,4R)-3-amino-4-fluoropiperidin-1-yl)-5,6-difluoro-1H-benzo[d]imidazol-1-yl)-1-methylpyrrolidin-2-one;
(S)-3-(2-((3R,4R)-3-amino-4-fluoropiperidin-1-yl)-5,6-difluoro-1H-benzo[d]imidazol-1-yl)-1-(4-chlorophenyl)pyrrolidin-2-one;
(R)-3-(2-((3R,4R)-3-amino-4-fluoropiperidin-1-yl)-5,6-difluoro-1H-benzo[d]imidazol-1-yl)-1-(4-chlorophenyl)pyrrolidin-2-one;
2-((3R,4R)-3-amino-4-fluoro-1-piperidinyl)-1-((5-cyano-2-pyrazinyl)methyl)-1H-benzimidazole-6-carbonitrile;
2-((3R,4R)-3-amino-4-fluoro-1-piperidinyl)-1-((5-cyano-2-pyrazinyl)methyl)-1H-benzimidazole-5-carbonitrile;
5-((2-((3R,4R)-3-amino-4-fluoro-1-piperidinyl)-4,6-difluoro-1H-benzimidazol-1-yl)methyl)-2-pyrazinecarbonitrile;
5-((2-((3R,4R)-3-amino-4-fluoro-1-piperidinyl)-5,7-difluoro-1H-benzimidazol-1-yl)methyl)-2-pyrazinecarbonitrile;
(3S)-1-(1-((5-fluoro-2-pyridinyl)methyl)-1H-benzimidazol-2-yl)-N-methyl-3-piperidinamine;
(3S)-1-(1-((5-chloro-2-pyridinyl)methyl)-1H-benzimidazol-2-yl)-N-methyl-3-piperidinamine;
6-((1R)-1-(2-((3S)-3-(methylamino)-1-piperidinyl)-1H-benzimidazol-1-yl)ethyl)-3-pyridinecarbonitrile;
6-((1S)-1-(2-((3S)-3-(methylamino)-1-piperidinyl)-1H-benzimidazol-1-yl)ethyl)-3-pyridinecarbonitrile;
(3R,4R)-1-(1-((5-chloro-2-pyrimidinyl)methyl)-5,7-difluoro-1H-benzimidazol-2-yl)-4-fluoro-3-piperidinamine;
(3R,4R)-1-(1-((5-chloro-2-pyrimidinyl)methyl)-4,6-difluoro-1H-benzimidazol-2-yl)-4-fluoro-3-piperidinamine;
(3R,4R)-1-(5,6-difluoro-1-((1-methyl-1H-indazol-4-yl)methyl)-1H-benzimidazol-2-yl)-4-fluoro-3-piperidinamine;
(3R,4R)-1-(5,6-difluoro-1-(5-quinolinylmethyl)-1H-benzimidazol-2-yl)-4-fluoro-3-piperidinamine;
(3R,4R)-1-(5,6-difluoro-1-((1R)-1-(8-quinolinyl)ethyl)-1H-benzimidazol-2-yl)-4-fluoro-3-piperidinamine;
(3R,4R)-1-(5,6-difluoro-1-((1S)-1-(8-quinolinyl)ethyl)-1H-benzimidazol-2-yl)-4-fluoro-3-piperidinamine;
(3R,4R)-1-(1-((3-(3-chlorophenyl)-1,2-oxazol-5-yl)methyl)-5,6-difluoro-1H-benzimidazol-2-yl)-4-fluoro-3-piperidinamine;
(3R,4R)-1-(5,6-difluoro-1-((1-methyl-1H-indazol-7-yl)methyl)-1H-benzimidazol-2-yl)-4-fluoro-3-piperidinamine;
(3R,4R)-1-(1-(2,6-dichlorobenzyl)-5,6-difluoro-1H-benzimidazol-2-yl)-4-fluoro-3-piperidinamine;
1-(1-azetidinyl)-2-(2-((3S)-3-(methylamino)-1-piperidinyl)-1H-benzimidazol-1-yl)ethanone;
6-((1R)-1-(4,6-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile;
6-((1R)-1-(4,6-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile;
6-((1S)-1-(4,6-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile;
6-((1S)-1-(4,6-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile;
6-((1R)-1-(5,7-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile;
6-((1R)-1-(5,7-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile;
6-((1S)-1-(5,7-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile;
6-((1S)-1-(5,7-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile;
2-(2-((3R,4R)-3-amino-4-fluoro-1-piperidinyl)-5,6-difluoro-1H-benzimidazol-1-yl)-N-methylacetamide;
2-(2-((3R,4R)-3-amino-4-fluoro-1-piperidinyl)-5,6-difluoro-1H-benzimidazol-1-yl)-1-(4-morpholinyl)ethanone;
2-(2-((3R,4R)-3-amino-4-fluoro-1-piperidinyl)-5,6-difluoro-1H-benzimidazol-1-yl)-1-(1-pyrrolidinyl)ethanone;
2-(2-((3R,4R)-3-amino-4-fluoro-1-piperidinyl)-5,6-difluoro-1H-benzimidazol-1-yl)-N,N-dimethylacetamide;
(2R)-2-(2-((3R,4R)-3-amino-4-fluoro-1-piperidinyl)-5,6-difluoro-1H-benzimidazol-1-yl)-N,N-dimethylpropanamide;
(2S)-2-(2-((3R,4R)-3-amino-4-fluoro-1-piperidinyl)-5,6-difluoro-1H-benzimidazol-1-yl)-N,N-dimethylpropanamide;
2-(2-((3R,4R)-3-amino-4-fluoro-1-piperidinyl)-5,6-difluoro-1H-benzimidazol-1-yl)-1-(1-piperidinyl)ethanone;
2-(2-((3R,4R)-3-amino-4-fluoro-1-piperidinyl)-5,6-difluoro-1H-benzimidazol-1-yl)-N-ethylacetamide;
1-((5-chloro-2-pyrimidinyl)methyl)-2-((3R,4R)-4-fluoro-3-(methylamino)-1-piperidinyl)-1H-benzimidazole-6-carbonitrile;
1-((5-chloro-2-pyrimidinyl)methyl)-2-((3R,4R)-4-fluoro-3-(methylamino)-1-piperidinyl)-1H-benzimidazole-5-carbonitrile;
2-(2-((3R,4R)-3-amino-4-fluoro-1-piperidinyl)-6-chloro-1H-benzimidazol-1-yl)-1-(1-azetidinyl)ethanone;
2-(2-((3R,4R)-3-amino-4-fluoro-1-piperidinyl)-5-chloro-1H-benzimidazol-1-yl)-1-(1-azetidinyl)ethanone;
2-((3R,4S)-3-amino-4-fluoro-1-piperidinyl)-1-(2-(1-azetidinyl)-2-oxoethyl)-1H-benzimidazole-6-carbonitrile;
2-((3R,4S)-3-amino-4-fluoro-1-piperidinyl)-1-(2-(1-azetidinyl)-2-oxoethyl)-1H-benzimidazole-5-carbonitrile;
(3R,4R)-1-(1-((5-chloropyrimidin-2-yl)methyl)-6-fluoro-1H-benzo[d]imidazol-2-yl)-4-fluoropiperidin-3-amine;
(3R,4R)-1-(1-((5-chloropyrimidin-2-yl)methyl)-5-fluoro-1H-benzo[d]imidazol-2-yl)-4-fluoropiperidin-3-amine;
(R)-6-((2-(3-aminopiperidin-1-yl)-1H-benzo[d]imidazol-1-yl)methyl)nicotinonitrile;
(R)-5-((2-(3-aminopiperidin-1-yl)-1H-benzo[d]imidazol-1-yl)methyl)picolinonitrile 2,2,2-trifluoroacetate;
(R)-1-(1-(isoquinolin-7-ylmethyl)-1H-benzo[d]imidazol-2-yl)piperidin-3-amine;
(R)-1-(1-((1-methyl-1H-indazol-7-yl)methyl)-1H-benzo[d]imidazol-2-yl)piperidin-3-amine;
6-((R)-1-(2-((S)-3-aminopiperidin-1-yl)-1H-benzo[d]imidazol-1-yl)ethyl)nicotinonitrile hydrochloride;
6-((S)-1-(2-((S)-3-aminopiperidin-1-yl)-1H-benzo[d]imidazol-1-yl)ethyl)nicotinonitrile hydrochloride;
6-((R)-1-(2-((3R,4R)-3-amino-4-fluoropiperidin-1-yl)-1H-benzo[d]imidazol-1-yl)ethyl)nicotinonitrile hydrochloride;
6-((S)-1-(2-((3R,4R)-3-amino-4-fluoropiperidin-1-yl)-1H-benzo[d]imidazol-1-yl)ethyl)nicotinonitrile hydrochloride;
6-((R)-1-(2-((S)-3-aminopiperidin-1-yl)-1H-benzo[d]imidazol-1-yl)propyl)nicotinonitrile hydrochloride;

6-((S)-1-(2-((S)-3-aminopiperidin-1-yl)-1H-benzo[d]imidazol-1-yl)propyl)nicotinonitrile hydrochloride;
(3R,4R)-1-(5,6-difluoro-1-((5-fluoropyrimidin-2-yl)methyl)-1H-benzo[d]imidazol-2-yl)-4-fluoropiperidin-3-amine;
3-(1-(2-((3R,4R)-3-amino-4-fluoropiperidin-1-yl)-5,6-difluoro-1H-benzo[d]imidazol-1-yl)ethyl)benzonitrile;
(3R,4R)-1-(5,6-difluoro-1-((5-fluoropyrimidin-2-yl)methyl)-1H-benzo[d]imidazol-2-yl)-4-fluoropiperidin-3-amine;
(3R,4S)-1-(5,6-difluoro-1-((5-fluoropyridin-2-yl)methyl)-1H-benzo[d]imidazol-2-yl)-4-fluoropiperidin-3-amine;
(3R,4S)-4-fluoro-1-(1-((5-fluoropyrimidin-2-yl)methyl)-6-(trifluoromethyl)-1H-benzo[d]imidazol-2-yl)piperidin-3-amine;
(3R,4S)-4-fluoro-1-(1-((5-fluoropyrimidin-2-yl)methyl)-5-(trifluoromethyl)-1H-benzo[d]imidazol-2-yl)piperidin-3-amine;
(R)-1-(5,6-difluoro-1-((5-fluoropyridin-2-yl)methyl)-1H-benzo[d]imidazol-2-yl)-4,4-difluoropiperidin-3-amine;
2-(2-((3R,4S)-3-amino-4-fluoropiperidin-1-yl)-6-(trifluoromethyl)-1H-benzo[d]imidazol-1-yl)-1-(azetidin-1-yl)ethan-1-one;
2-(2-((3R,4S)-3-amino-4-fluoropiperidin-1-yl)-5-(trifluoromethyl)-1H-benzo[d]imidazol-1-yl)-1-(azetidin-1-yl)ethan-1-one;
2-(2-((3R,4R)-3-amino-4-fluoropiperidin-1-yl)-5,6-difluoro-1H-benzo[d]imidazol-1-yl)-1-(2,2-dimethylpyrrolidin-1-yl)ethan-1-one;
6-((2-((3R,4S)-3-amino-4-hydroxypiperidin-1-yl)-6-fluoro-1H-benzo[d]imidazol-1-yl)methyl)nicotinonitrile;
6-((2-((3R,4S)-3-amino-4-hydroxypiperidin-1-yl)-5-fluoro-1H-benzo[d]imidazol-1-yl)methyl)nicotinonitrile;
4-((R)-1-(2-((S)-3-aminopiperidin-1-yl)-1H-benzo[d]imidazol-1-yl)ethyl)benzonitrile hydrochloride;
4-((S)-1-(2-((S)-3-aminopiperidin-1-yl)-1H-benzo[d]imidazol-1-yl)ethyl)benzonitrile hydrochloride;
(S)-4-((2-(3-aminopiperidin-1-yl)-1H-benzo[d]imidazol-1-yl)methyl)-3-fluorobenzonitrile hydrochloride;
(S)-1-(1-(4-chlorobenzyl)-1H-benzo[d]imidazol-2-yl)piperidin-3-amine hydrochloride;
4-((R)-1-(2-((3R,4S)-3-amino-4-fluoropiperidin-1-yl)-1H-benzo[d]imidazol-1-yl)ethyl)benzonitrile hydrochloride;
4-((S)-1-(2-((3R,4S)-3-amino-4-fluoropiperidin-1-yl)-1H-benzo[d]imidazol-1-yl)ethyl)benzonitrile hydrochloride;
4-((R)-1-(2-((3R,4R)-3-amino-4-fluoropiperidin-1-yl)-1H-benzo[d]imidazol-1-yl)ethyl)benzonitrile hydrochloride;
4-((S)-1-(2-((3R,4R)-3-amino-4-fluoropiperidin-1-yl)-1H-benzo[d]imidazol-1-yl)ethyl)benzonitrile hydrochloride;
(S)-4-((2-(3-aminopiperidin-1-yl)-1H-benzo[d]imidazol-1-yl)methyl)-3-chlorobenzonitrile hydrochloride;
(3R,4R)-1-(1-((1R)-1-(2,4-dichlorophenyl)ethyl)-5,6-difluoro-1H-benzimidazol-2-yl)-4-fluoro-3-piperidinamine;
(3R,4R)-1-(1-((1S)-1-(2,4-dichlorophenyl)ethyl)-5,6-difluoro-1H-benzimidazol-2-yl)-4-fluoro-3-piperidinamine;
(3R,4R)-1-(1-((1R)-1-(2-chlorophenyl)ethyl)-5,6-difluoro-1H-benzimidazol-2-yl)-4-fluoro-3-piperidinamine;
(3R,4R)-1-(1-((1S)-1-(2-chlorophenyl)ethyl)-5,6-difluoro-1H-benzimidazol-2-yl)-4-fluoro-3-piperidinamine;
(3R,4R)-1-(1-((1R)-1-(3-chlorophenyl)ethyl)-5,6-difluoro-1H-benzimidazol-2-yl)-4-fluoro-3-piperidinamine;
(3R,4R)-1-(1-((1S)-1-(3-chlorophenyl)ethyl)-5,6-difluoro-1H-benzimidazol-2-yl)-4-fluoro-3-piperidinamine;
(3R,4R)-1-(1-((1R)-1-(2,5-dichlorophenyl)ethyl)-5,6-difluoro-1H-benzimidazol-2-yl)-4-fluoro-3-piperidinamine;
(3R,4R)-1-(1-((1S)-1-(2,5-dichlorophenyl)ethyl)-5,6-difluoro-1H-benzimidazol-2-yl)-4-fluoro-3-piperidinamine;
(3R,4R)-1-(1-((1R)-1-(2,4-difluorophenyl)ethyl)-5,6-difluoro-1H-benzimidazol-2-yl)-4-fluoro-3-piperidinamine;
(3R,4R)-1-(1-((1S)-1-(2,4-difluorophenyl)ethyl)-5,6-difluoro-1H-benzimidazol-2-yl)-4-fluoro-3-piperidinamine;
(3R,4R)-1-(1-((1R)-1-(3,4-dichlorophenyl)ethyl)-5,6-difluoro-1H-benzimidazol-2-yl)-4-fluoro-3-piperidinamine;
(3R,4R)-1-(1-((1S)-1-(3,4-dichlorophenyl)ethyl)-5,6-difluoro-1H-benzimidazol-2-yl)-4-fluoro-3-piperidinamine;
(3R,4R)-1-(1-((1R)-1-(2,5-difluorophenyl)ethyl)-5,6-difluoro-1H-benzimidazol-2-yl)-4-fluoro-3-piperidinamine;
(3R,4R)-1-(1-((1S)-1-(2,5-difluorophenyl)ethyl)-5,6-difluoro-1H-benzimidazol-2-yl)-4-fluoro-3-piperidinamine;
(3R,4R)-1-(5,6-difluoro-1-((1R)-1-(4-(trifluoromethyl)phenyl)ethyl)-1H-benzimidazol-2-yl)-4-fluoro-3-piperidinamine;
(3R,4R)-1-(5,6-difluoro-1-((1R)-1-(4-(trifluoromethoxy)phenyl)ethyl)-1H-benzimidazol-2-yl)-4-fluoro-3-piperidinamine;
(3R,4R)-1-(1-(5-chloro-2-(trifluoromethoxy)benzyl)-5,6-difluoro-1H-benzimidazol-2-yl)-4-fluoro-3-piperidinamine;
(3R,4R)-1-(5,6-difluoro-1-(4-(1H-1,2,4-triazol-1-yl)benzyl)-1H-benzimidazol-2-yl)-4-fluoro-3-piperidinamine;
2-((2-((3R,4R)-3-amino-4-fluoro-1-piperidinyl)-5,6-difluoro-1H-benzimidazol-1-yl)methyl)-5-chlorobenzonitrile;
(3R,4R)-1-(1-(2,4-dichlorobenzyl)-5,6-difluoro-1H-benzimidazol-2-yl)-4-fluoro-3-piperidinamine;
4-((2-((3R,4R)-3-amino-4-fluoro-1-piperidinyl)-5,6-difluoro-1H-benzimidazol-1-yl)methyl)-3-(difluoromethoxy)benzonitrile;
(3R,4R)-1-(1-(2,5-dichlorobenzyl)-5,6-difluoro-1H-benzimidazol-2-yl)-4-fluoro-3-piperidinamine;
(3R,4R)-1-(1-(4-(1,1-difluoroethyl)benzyl)-5,6-difluoro-1H-benzimidazol-2-yl)-4-fluoro-3-piperidinamine;
4-((2-((3R,4R)-3-amino-4-fluoro-1-piperidinyl)-5,6-difluoro-1H-benzimidazol-1-yl)methyl)-2-methylbenzonitrile;
4-((2-((3R,4R)-3-amino-4-fluoro-1-piperidinyl)-5,6-difluoro-1H-benzimidazol-1-yl)methyl)-2-chlorobenzonitrile;
2-((2-((3R,4R)-3-amino-4-fluoro-1-piperidinyl)-5,6-difluoro-1H-benzimidazol-1-yl)methyl)-4-chlorobenzonitrile;
(3R,4R)-1-(1-(2-(difluoromethoxy)benzyl)-5,6-difluoro-1H-benzimidazol-2-yl)-4-fluoro-3-piperidinamine;
(3R,4R)-1-(1-(3-chloro-4-fluorobenzyl)-5,6-difluoro-1H-benzimidazol-2-yl)-4-fluoro-3-piperidinamine;
(3R,4R)-1-(1-(4-chloro-2-methoxybenzyl)-5,6-difluoro-1H-benzimidazol-2-yl)-4-fluoro-3-piperidinamine;
(3R,4R)-1-(1-(2,4-difluorobenzyl)-5,6-difluoro-1H-benzimidazol-2-yl)-4-fluoro-3-piperidinamine;
(3R,4R)-1-(5,6-difluoro-1-(2-(trifluoromethyl)benzyl)-1H-benzimidazol-2-yl)-4-fluoro-3-piperidinamine;
2-((2-((3R,4R)-3-amino-4-fluoro-1-piperidinyl)-5,6-difluoro-1H-benzimidazol-1-yl)methyl)benzonitrile;
(3R,4R)-1-(1-(2-chlorobenzyl)-5,6-difluoro-1H-benzimidazol-2-yl)-4-fluoro-3-piperidinamine;
(3R,4R)-1-(1-(2-chloro-4-fluorobenzyl)-5,6-difluoro-1H-benzimidazol-2-yl)-4-fluoro-3-piperidinamine;
(3R,4R)-1-(5,6-difluoro-1-(4-fluoro-2-(trifluoromethyl)benzyl)-1H-benzimidazol-2-yl)-4-fluoro-3-piperidinamine;
(3R,4R)-1-(1-(3,4-difluorobenzyl)-5,6-difluoro-1H-benzimidazol-2-yl)-4-fluoro-3-piperidinamine;
(3R,4R)-1-(1-(4-chloro-2-fluorobenzyl)-5,6-difluoro-1H-benzimidazol-2-yl)-4-fluoro-3-piperidinamine;

(3R,4R)-1-(1-(3,4-dichlorobenzyl)-5,6-difluoro-1H-benz-imidazol-2-yl)-4-fluoro-3-piperidinamine;
(3R,4R)-1-(1-(4-chloro-3-fluorobenzyl)-5,6-difluoro-1H-benzimidazol-2-yl)-4-fluoro-3-piperidinamine;
(3R,4R)-1-(5,6-difluoro-1-(4-(trifluoromethyl)benzyl)-1H-benzimidazol-2-yl)-4-fluoro-3-piperidinamine;
(3R,4R)-1-(5,6-difluoro-1-(4-(trifluoromethoxy)benzyl)-1H-benzimidazol-2-yl)-4-fluoro-3-piperidinamine;
(3R,4R)-1-(1-(4-(difluoromethyl)benzyl)-5,6-difluoro-1H-benzimidazol-2-yl)-4-fluoro-3-piperidinamine;
(3R,4R)-1-(5,6-difluoro-1-(3-(trifluoromethoxy)benzyl)-1H-benzimidazol-2-yl)-4-fluoro-3-piperidinamine;
(3R,4R)-1-(5,6-difluoro-1-(3-(trifluoromethyl)benzyl)-1H-benzimidazol-2-yl)-4-fluoro-3-piperidinamine;
3-((2-((3R,4R)-3-amino-4-fluoro-1-piperidinyl)-5,6-difluoro-1H-benzimidazol-1-yl)methyl)benzonitrile;
(3R,4R)-1-(1-(3-chlorobenzyl)-5,6-difluoro-1H-benzimidazol-2-yl)-4-fluoro-3-piperidinamine;
(S)-1-(1-(4-fluorobenzyl)-1H-benzo[d]imidazol-2-yl)piperidin-3-amine;
(S)-1-(1-(4-(1,2,4-oxadiazol-3-yl)benzyl)-1H-benzo[d]imidazol-2-yl)piperidin-3-amine;
(R)-1-(1-(4-(methylsulfonyl)benzyl)-1H-benzo[d]imidazol-2-yl)piperidin-3-amine;
(R)-1-(1-(4-(1H-1,2,4-triazol-1-yl)benzyl)-1H-benzo[d]imidazol-2-yl)piperidin-3-amine;
(R)-2-((2-(3-aminopiperidin-1-yl)-1H-benzo[d]imidazol-1-yl)methyl)benzonitrile;
(R)-1-(1-(2,6-dichlorobenzyl)-1H-benzo[d]imidazol-2-yl)piperidin-3-amine;
(R)-1-(1-(2-chlorobenzyl)-1H-benzo[d]imidazol-2-yl)piperidin-3-amine;
(R)-1-(1-(4-(trifluoromethyl)benzyl)-1H-benzo[d]imidazol-2-yl)piperidin-3-amine;
(R)-1-(1-(4-(trifluoromethoxy)benzyl)-1H-benzo[d]imidazol-2-yl)piperidin-3-amine;
(R)-1-(1-(4-chlorobenzyl)-1H-benzo[d]imidazol-2-yl)piperidin-3-amine;
(R)-1-(1-(3-chlorobenzyl)-1H-benzo[d]imidazol-2-yl)piperidin-3-amine;
(R)-1-(1-(4-(1,1-difluoroethyl)benzyl)-1H-benzo[d]imidazol-2-yl)piperidin-3-amine;
(R)-2-(4-((2-(3-aminopiperidin-1-yl)-1H-benzo[d]imidazol-1-yl)methyl)phenyl)-2-methylpropanenitrile;
(R)-1-(1-(4-(difluoromethyl)benzyl)-1H-benzo[d]imidazol-2-yl)piperidin-3-amine;
(R)-4-((2-(3-aminopiperidin-1-yl)-1H-benzo[d]imidazol-1-yl)methyl)-N-methylbenzamide;
(R)-4-((2-(3-aminopiperidin-1-yl)-1H-benzo[d]imidazol-1-yl)methyl)-3-fluorobenzonitrile;
(R)-2-(4-((2-(3-aminopiperidin-1-yl)-1H-benzo[d]imidazol-1-yl)methyl)phenoxy)acetonitrile;
(R)-4-((2-(3-aminopiperidin-1-yl)-1H-benzo[d]imidazol-1-yl)methyl)-N,N-dimethylbenzenesulfonamide;
(R)-1-(1-(4-methylbenzyl)-1H-benzo[d]imidazol-2-yl)piperidin-3-amine;
(R)-1-(1-(4-fluorobenzyl)-1H-benzo[d]imidazol-2-yl)piperidin-3-amine;
(R)-1-(1-((1-methyl-1H-indazol-7-yl)methyl)-1H-benzo[d]imidazol-2-yl)piperidin-3-amine;
(R)-1-(1-(2,4-difluorobenzyl)-1H-benzo[d]imidazol-2-yl)piperidin-3-amine;
(R)-1-(1-(3,4-difluorobenzyl)-1H-benzo[d]imidazol-2-yl)piperidin-3-amine;
(R)-1-(1-(4-chloro-3-fluorobenzyl)-1H-benzo[d]imidazol-2-yl)piperidin-3-amine;
(R)-1-(1-((3-(3-chlorophenyl)isoxazol-5-yl)methyl)-1H-benzo[d]imidazol-2-yl)piperidin-3-amine;
(R)-1-(1-(3-chloro-4-methoxybenzyl)-1H-benzo[d]imidazol-2-yl)piperidin-3-amine;
(R)-4-((2-(3-aminopiperidin-1-yl)-1H-benzo[d]imidazol-1-yl)methyl)-3-chlorobenzonitrile;
(R)-1-(1-(2,4-dichlorobenzyl)-1H-benzo[d]imidazol-2-yl)piperidin-3-amine;
(R)-4-((2-(3-aminopiperidin-1-yl)-1H-benzo[d]imidazol-1-yl)methyl)-3-methoxybenzonitrile;
(R)-2-((2-(3-aminopiperidin-1-yl)-1H-benzo[d]imidazol-1-yl)methyl)-5-chlorobenzonitrile;
4-((R)-1-(2-((R)-3-aminopiperidin-1-yl)-1H-benzo[d]imidazol-1-yl)ethyl)benzonitrile;
4-(1-(2-((S)-3-aminopiperidin-1-yl)-1H-benzo[d]imidazol-1-yl)ethyl)benzonitrile;
(R)-3-((2-(3-aminopiperidin-1-yl)-1H-benzo[d]imidazol-1-yl)methyl)benzonitrile;
4-((2-((3R,4S)-3-amino-4-fluoropiperidin-1-yl)-6-chloro-1H-benzo[d]imidazol-1-yl)methyl)benzonitrile hydrochloride;
(S)-4-((2-(3-aminopiperidin-1-yl)-6-methoxy-1H-benzo[d]imidazol-1-yl)methyl)benzonitrile hydrochloride;
4-((2-((3R,4S)-3-amino-4-fluoropiperidin-1-yl)-6-methoxy-1H-benzo[d]imidazol-1-yl)methyl)benzonitrile;
(S)-4-((2-(3-aminopiperidin-1-yl)-5-methoxy-3H-imidazo[4,5-b]pyridin-3-yl)methyl)benzonitrile hydrochloride;
(R)-4-((2-(3-amino-4,4-difluoropiperidin-1-yl)-6-chloro-1H-benzo[d]imidazol-1-yl)methyl)benzonitrile;
(R)-4-((2-(3-amino-4,4-difluoropiperidin-1-yl)-6-methoxy-1H-benzo[d]imidazol-1-yl)methyl)benzonitrile;
(R)-4-((2-(3-amino-4,4-difluoropiperidin-1-yl)-4-chloro-1H-benzo[d]imidazol-1-yl)methyl)benzonitrile;
4-((2-((3R,4R)-3-amino-4-fluoropiperidin-1-yl)-4-chloro-1H-benzo[d]imidazol-1-yl)methyl)benzonitrile;
4-((2-((3R,4S)-3-amino-4-fluoropiperidin-1-yl)-4-chloro-1H-benzo[d]imidazol-1-yl)methyl)benzonitrile;
(R)-4-((2-(3-amino-4,4-difluoropiperidin-1-yl)-4-methoxy-1H-benzo[d]imidazol-1-yl)methyl)benzonitrile;
4-((2-((3R,4R)-3-amino-4-fluoropiperidin-1-yl)-4-methoxy-1H-benzo[d]imidazol-1-yl)methyl)benzonitrile;
4-((2-((3R,4R)-3-amino-4-fluoropiperidin-1-yl)-1H-imidazo[4,5-c]pyridin-1-yl)methyl)benzonitrile;
4-((2-((3R,4R)-3-amino-4-fluoropiperidin-1-yl)-3H-imidazo[4,5-c]pyridin-3-yl)methyl)benzonitrile;
4-((2-((3R,4R)-3-amino-4-fluoro-1-piperidinyl)-6-ethoxy-1H-benzimidazol-1-yl)methyl)benzonitrile;
4-((2-((3R,4S)-3-amino-4-fluoropiperidin-1-yl)-1H-imidazo[4,5-b]pyridin-1-yl)methyl)benzonitrile;
4-((2-((3R)-3-amino-4,4-difluoro-1-piperidinyl)-6-fluoro-1H-benzimidazol-1-yl)methyl)benzonitrile;
4-((2-((3R,4R)-3-amino-4-fluoropiperidin-1-yl)-1H-imidazo[4,5-b]pyridin-1-yl)methyl)benzonitrile;
(S)-4-((2-(3-aminopiperidin-1-yl)-4-chloro-1H-benzo[d]imidazol-1-yl)methyl)benzonitrile 2,2,2-trifluoroacetate;
(S)-4-((2-(3-aminopiperidin-1-yl)-3H-imidazo[4,5-b]pyridin-3-yl)methyl)benzonitrile hydrochloride;
4-((2-((3R,4R)-3-amino-4-fluoropiperidin-1-yl)-6-chloro-1H-benzo[d]imidazol-1-yl)methyl)benzonitrile hydrochloride;
(S)-4-((2-(3-aminopiperidin-1-yl)-6-chloro-1H-benzo[d]imidazol-1-yl)methyl)benzonitrile;
(S)-4-((2-(3-aminopiperidin-1-yl)-5-chloro-1H-benzo[d]imidazol-1-yl)methyl)benzonitrile;
(R)-1-(2-((S)-3-aminopiperidin-1-yl)-1H-benzo[d]imidazol-1-yl)-2,3-dihydro-1H-indene-5-carbonitrile;

(S)-1-(2-((S)-3-aminopiperidin-1-yl)-1H-benzo[d]imidazol-1-yl)-2,3-dihydro-1H-indene-5-carbonitrile;

(3R,4R)-4-fluoro-1-(1-((5-methoxypyridin-2-yl)methyl)-1H-benzo[d]imidazol-2-yl)piperidin-3-amine;

1-(2-(2-((3R,4R)-3-amino-4-fluoropiperidin-1-yl)-5,6-difluoro-1H-benzo[d]imidazol-1-yl)acetyl)azetidine-3-carbonitrile;

2-(2-((3R,4R)-3-amino-4-fluoropiperidin-1-yl)-5,6-difluoro-1H-benzo[d]imidazol-1-yl)-1-(3-(tert-butoxy)azetidin-1-yl)ethan-1-one;

2-(2-((3R,4R)-3-amino-4-fluoropiperidin-1-yl)-5,6-difluoro-1H-benzo[d]imidazol-1-yl)-1-(3,3-difluoroazetidin-1-yl)ethanone;

2-(2-((3R,4R)-3-amino-4-fluoropiperidin-1-yl)-5,6-difluoro-1H-benzo[d]imidazol-1-yl)-1-(3-isopropylazetidin-1-yl)ethanone;

2-(2-((3R,4R)-3-amino-4-fluoropiperidin-1-yl)-5,6-difluoro-1H-benzo[d]imidazol-1-yl)-1-(6,6-difluoro-2-azaspiro[3.3]heptan-2-yl)ethanone;

2-(2-((3R,4R)-3-amino-4-fluoropiperidin-1-yl)-5,6-difluoro-1H-benzo[d]imidazol-1-yl)-1-(7-oxa-2-azaspiro[3.5]nonan-2-yl)ethanone;

(R)-6-((2-(4,4-difluoro-3-(methylamino)piperidin-1-yl)-6-fluoro-1H-benzo[d]imidazol-1-yl)methyl)nicotinonitrile;

(R)-6-((2-(4,4-difluoro-3-((2-hydroxyethyl)amino)piperidin-1-yl)-6-fluoro-1H-benzo[d]imidazol-1-yl)methyl)nicotinonitrile;

(S)-6-((2-(3-aminopiperidin-1-yl)-1H-benzo[d]imidazol-1-yl)methyl)nicotinic acid;

(S)-6-((2-(3-aminopiperidin-1-yl)-1H-benzo[d]imidazol-1-yl)methyl)nicotinamide;

6-((2-((3R,4R)-3-amino-4-fluoropiperidin-1-yl)-1H-benzo[d]imidazol-1-yl)methyl)nicotinamide;

2-(2-((3R,4R)-3-amino-4-fluoropiperidin-1-yl)-5,6-difluoro-1H-benzo[d]imidazol-1-yl)acetic acid;

6-((R)-1-(4,6-difluoro-2-((3R,4R)-4-fluoro-3-(methylamino)piperidin-1-yl)-1H-benzo[d]imidazol-1-yl)ethyl)nicotinonitrile;

6-((S)-1-(4,6-difluoro-2-((3R,4R)-4-fluoro-3-(methylamino)piperidin-1-yl)-1H-benzo[d]imidazol-1-yl)ethyl)nicotinonitrile;

6-((R)-1-(5,7-difluoro-2-((3R,4R)-4-fluoro-3-(methylamino)piperidin-1-yl)-1H-benzo[d]imidazol-1-yl)ethyl)nicotinonitrile; and 6-((S)-1-(5,7-difluoro-2-((3R,4R)-4-fluoro-3-(methylamino)piperidin-1-yl)-1H-benzo[d]imidazol-1-yl)ethyl)nicotinonitrile.

In another aspect of the thirty eighth embodiment, the invention provides compounds of the first embodiment in which the compound is recited in the below Table A-1:

Table A-1

2-((2-((3R,4R)-3-amino-4-fluoropiperidin-1-yl)-6-fluoro-1H-benzo[d]imidazol-1-yl)methyl)pyrimidine-5-carbonitrile;

2-((2-((3R,4R)-3-amino-4-fluoropiperidin-1-yl)-5-fluoro-1H-benzo[d]imidazol-1-yl)methyl)pyrimidine-5-carbonitrile;

(3R,4R)-4-fluoro-1-(6-fluoro-1-((5-methoxypyrimidin-2-yl)methyl)-1H-benzo[d]imidazol-2-yl)piperidin-3-amine;

2-(2-((3R,4R)-3-amino-4-fluoropiperidin-1-yl)-6-fluoro-1H-benzo[d]imidazol-1-yl)-N-methyl-N-(2,2,2-trifluoroethyl)acetamide;

(3R,4R)-4-fluoro-1-(5-fluoro-1-((5-methoxypyrimidin-2-yl)methyl)-1H-benzo[d]imidazol-2-yl)piperidin-3-amine;

2-(2-((3R,4R)-3-amino-4-fluoropiperidin-1-yl)-4-cyano-6-fluoro-1H-benzo[d]imidazol-1-yl)-N-methyl-N-(2,2,2-trifluoroethyl)acetamide;

2-(2-((3R,4R)-3-amino-4-fluoropiperidin-1-yl)-6-methoxy-1H-benzo[d]imidazol-1-yl)-N,N-dimethylacetamide;

2-(2-((3R,4R)-3-amino-4-fluoropiperidin-1-yl)-5-methoxy-1H-benzo[d]imidazol-1-yl)-N-methyl-N-(2,2,2-trifluoroethyl)acetamide;

2-(2-((3R,4R)-3-amino-4-fluoropiperidin-1-yl)-5-methoxy-1H-benzo[d]imidazol-1-yl)-N,N-dimethylacetamide;

6-((2-((3R,4R)-3-amino-4-methoxypiperidin-1-yl)-6-fluoro-1H-benzo[d]imidazol-1-yl)methyl)nicotinonitrile;

6-((2-((3R,4R)-3-amino-4-fluoropiperidin-1-yl)-6-fluoro-4-methoxy-1H-benzo[d]imidazol-1-yl)methyl)nicotinonitrile;

6-((2-((3R,4R)-3-amino-4-fluoropiperidin-1-yl)-5-(trifluoromethyl)-3H-imidazo[4,5-b]pyridin-3-yl)methyl)nicotinonitrile;

(3R,4R)-1-(1-((5-chloropyrimidin-2-yl)methyl)-6-fluoro-1H-benzo[d]imidazol-2-yl)-4-methoxypiperidin-3-amine;

2-(2-((3R,4R)-3-amino-4-fluoropiperidin-1-yl)-6-bromo-1H-benzo[d]imidazol-1-yl)-1-(azetidin-1-yl)ethan-1-one;

(3R,4R)-1-(1-((5-chloropyrimidin-2-yl)methyl)-6-fluoro-1H-benzo[d]imidazol-2-yl)-4-methoxypiperidin-3-amine;

2-(2-((3R,4R)-3-amino-4-fluoropiperidin-1-yl)-6-fluoro-1H-benzo[d]imidazol-1-yl)-N-methyl-N-(2,2,2-trifluoroethyl)acetamide;

6-((2-((3R,4R)-3-amino-4-fluoropiperidin-1-yl)-5-(trifluoromethyl)-1H-imidazo[4,5-b]pyridin-1-yl)methyl)nicotinonitrile;

2-(2-((3R,4R)-3-amino-4-fluoropiperidin-1-yl)-6-(trifluoromethyl)-1H-benzo[d]imidazol-1-yl)-1-morpholinoethan-1-one;

2-(2-((3R,4R)-3-amino-4-fluoropiperidin-1-yl)-5-fluoro-1H-benzo[d]imidazol-1-yl)-N-methyl-N-(2,2,2-trifluoroethyl)acetamide;

2-(2-((3R,4S)-3-amino-4-fluoropiperidin-1-yl)-6-chloro-1H-benzo[d]imidazol-1-yl)-N,N-dimethylacetamide;

2-(2-((3R,4S)-3-amino-4-fluoropiperidin-1-yl)-6-fluoro-1H-benzo[d]imidazol-1-yl)-N-methyl-N-(2,2,2-trifluoroethyl)acetamide;

6-((2-((3R,4S)-3-amino-4-methoxypiperidin-1-yl)-6-fluoro-1H-benzo[d]imidazol-1-yl)methyl)nicotinonitrile;

2-(2-((3R,4S)-3-amino-4-fluoropiperidin-1-yl)-6-(trifluoromethyl)-1H-benzo[d]imidazol-1-yl)-1-morpholinoethan-1-one;

(R)-2-(2-(3-amino-4,4-difluoropiperidin-1-yl)-6-fluoro-1H-benzo[d]imidazol-1-yl)-N-methyl-N-(2,2,2-trifluoroethyl)acetamide;

2-(2-((3R,4S)-3-amino-4-fluoropiperidin-1-yl)-6-fluoro-1H-benzo[d]imidazol-1-yl)-N-methyl-N-(2,2,2-trifluoroethyl)acetamide;

(3R,4S)-1-(1-((5-chloropyrimidin-2-yl)methyl)-6-fluoro-1H-benzo[d]imidazol-2-yl)-4-methoxypiperidin-3-amine;

2-(2-((3R,4R)-3-amino-4-fluoropiperidin-1-yl)-6-(trifluoromethoxy)-1H-benzo[d]imidazol-1-yl)-N,N-dimethylacetamide;

2-(6-fluoro-2-((3R,4R)-4-fluoro-3-(methylamino)piperidin-1-yl)-1H-benzo[d]imidazol-1-yl)-N-methyl-N-(2,2,2-trifluoroethyl)acetamide;

2-(2-((3R,4R)-3-amino-4-fluoropiperidin-1-yl)-5-bromo-1H-benzo[d]imidazol-1-yl)-1-(azetidin-1-yl)ethan-1-one;

2-(2-((3R,4S)-3-amino-4-fluoropiperidin-1-yl)-5-chloro-1H-benzo[d]imidazol-1-yl)-N,N-dimethylacetamide;

2-(6-fluoro-2-(1,7-diazaspiro[4.5]decan-7-yl)-1H-benzo[d]imidazol-1-yl)-N-methyl-N-(2,2,2-trifluoroethyl)acetamide;

2-(2-((3R,4R)-3-amino-4-fluoropiperidin-1-yl)-5-(trifluoromethyl)-1H-benzo[d]imidazol-1-yl)-1-morpholinoethan-1-one;

2-(2-((3R,4R)-3-amino-4-fluoropiperidin-1-yl)-5-(trifluoromethoxy)-1H-benzo[d]imidazol-1-yl)-N,N-dimethylacetamide;

2-(2-((3R,4R)-3-amino-4-fluoropiperidin-1-yl)-5-(trifluoromethoxy)-1H-benzo[d]imidazol-1-yl)-1-morpholinoethan-1-one;

6-((2-((3R,4R)-3-amino-4-fluoropiperidin-1-yl)-5-fluoro-7-methoxy-1H-benzo[d]imidazol-1-yl)methyl)nicotinonitrile;

(3R,4S)-1-(1-((5-chloropyrimidin-2-yl)methyl)-5-fluoro-1H-benzo[d]imidazol-2-yl)-4-methoxypiperidin-3-amine;

2-(2-((3R,4S)-3-amino-4-fluoropiperidin-1-yl)-5-(trifluoromethyl)-1H-benzo[d]imidazol-1-yl)-1-morpholinoethan-1-one;

2-(5-fluoro-2-((3R,4R)-4-fluoro-3-(methylamino)piperidin-1-yl)-1H-benzo[d]imidazol-1-yl)-N-methyl-N-(2,2,2-trifluoroethyl)acetamide;

2-(2-(3-amino-4-methylpyrrolidin-1-yl)-6-fluoro-1H-benzo[d]imidazol-1-yl)-N-methyl-N-(2,2,2-trifluoroethyl)acetamide;

2-(2-((3R,4R)-3-amino-4-hydroxypiperidin-1-yl)-6-fluoro-1H-benzo[d]imidazol-1-yl)-N-methyl-N-(2,2,2-trifluoroethyl)acetamide;

(R)-2-(2-(3-amino-4,4-difluoropiperidin-1-yl)-5-fluoro-1H-benzo[d]imidazol-1-yl)-N-methyl-N-(2,2,2-trifluoroethyl)acetamide;

2-(2-((3R,4R)-3-amino-4-methoxypiperidin-1-yl)-5-fluoro-1H-benzo[d]imidazol-1-yl)-N-methyl-N-(2,2,2-trifluoroethyl)acetamide;

2-(2-((3R)-3-amino-4-hydroxypiperidin-1-yl)-5-fluoro-1H-benzo[d]imidazol-1-yl)-N-methyl-N-(2,2,2-trifluoroethyl)acetamide;

2-(2-((3R,4R)-3-amino-4-methoxypiperidin-1-yl)-6-fluoro-1H-benzo[d]imidazol-1-yl)-N-methyl-N-(2,2,2-trifluoroethyl)acetamide;

2-(2-(3-(aminomethyl)-3-fluoropyrrolidin-1-yl)-6-fluoro-1H-benzo[d]imidazol-1-yl)-N-methyl-N-(2,2,2-trifluoroethyl)acetamide;

2-(2-(3-(aminomethyl)-3-fluoropyrrolidin-1-yl)-5-fluoro-1H-benzo[d]imidazol-1-yl)-N-methyl-N-(2,2,2-trifluoroethyl)acetamide;

2-(6-fluoro-2-((4aR,8aR)-hexahydro-2H-pyrido[4,3-b][1,4]oxazin-6(5H)-yl)-1H-benzo[d]imidazol-1-yl)-N-methyl-N-(2,2,2-trifluoroethyl)acetamide;

(S)-2-(2-(3-aminopyrrolidin-1-yl)-6-fluoro-1H-benzo[d]imidazol-1-yl)-N-methyl-N-(2,2,2-trifluoroethyl)acetamide;

(R)-2-(2-(3-aminopyrrolidin-1-yl)-6-fluoro-1H-benzo[d]imidazol-1-yl)-N-methyl-N-(2,2,2-trifluoroethyl)acetamide;

(S)-2-(2-(3-(aminomethyl)pyrrolidin-1-yl)-6-fluoro-1H-benzo[d]imidazol-1-yl)-N-methyl-N-(2,2,2-trifluoroethyl)acetamide;

2-(6-fluoro-2-((4aR,8aR)-hexahydro-2H-pyrido[4,3-b][1,4]oxazin-6(5H)-yl)-1H-benzo[d]imidazol-1-yl)-N-methyl-N-(2,2,2-trifluoroethyl)acetamide;

2-(5-fluoro-2-((4aS,8aS)-hexahydro-2H-pyrido[4,3-b][1,4]oxazin-6(5H)-yl)-1H-benzo[d]imidazol-1-yl)-N-methyl-N-(2,2,2-trifluoroethyl)acetamide;

(3R,4R)-3-amino-1-(1-((5-chloropyrimidin-2-yl)methyl)-5-fluoro-1H-benzo[d]imidazol-2-yl)piperidin-4-ol;

2-(2-((3R,4R)-3-amino-4-fluoropiperidin-1-yl)-6-chloro-1H-benzo[d]imidazol-1-yl)-1-morpholinoethanone;

(3R,4R)-3-amino-1-(1-((5-chloropyrimidin-2-yl)methyl)-6-fluoro-1H-benzo[d]imidazol-2-yl)piperidin-4-ol;

(2-((3R,4R)-3-amino-4-fluoropiperidin-1-yl)-5-chloro-1H-benzo[d]imidazol-1-yl)-1-morpholinoethanone;

(3R,4R)-1-(1-((R)-1-(5-chloropyrimidin-2-yl)ethyl)-5,6-difluoro-1H-benzo[d]imidazol-2-yl)-4-fluoropiperidin-3-amine;

6-((2-((3R,4R)-3-amino-4-fluoropiperidin-1-yl)-6-(trifluoromethyl)-1H-imidazo[4,5-b]pyridin-1-yl)methyl)nicotinonitrile;

2-(2-((3R,4R)-3-amino-4-fluoropiperidin-1-yl)-5,6-difluoro-1H-benzo[d]imidazol-1-yl)-N-methyl-N-(2,2,2-trifluoroethyl)acetamide;

2-(2-((3R,4R)-3-amino-4-fluoropiperidin-1-yl)-5,6-difluoro-1H-benzo[d]imidazol-1-yl)-N-methyl-N-(thiazol-2-yl)acetamide;

2-(2-((3R,4R)-3-amino-4-fluoropiperidin-1-yl)-6-chloro-1H-benzo[d]imidazol-1-yl)-N,N-dimethylacetamide;

2-(2-((3R,4R)-3-amino-4-fluoropiperidin-1-yl)-6-fluoro-1H-benzo[d]imidazol-1-yl)-1-(azetidin-1-yl)ethan-1-one;

2-(2-((3R,4R)-3-amino-4-fluoropiperidin-1-yl)-5,6-difluoro-1H-benzo[d]imidazol-1-yl)-1-(3-(trifluoromethyl)piperidin-1-yl)ethan-1-one;

2-(2-((3R,4R)-3-amino-4-fluoropiperidin-1-yl)-5,6-difluoro-1H-benzo[d]imidazol-1-yl)-1-(6,7-dihydrothieno[3,2-c]pyridin-5(4H)-yl)ethan-1-one;

2-(2-((3R,4R)-3-amino-4-fluoropiperidin-1-yl)-5-chloro-1H-benzo[d]imidazol-1-yl)-N,N-dimethylacetamide;

2-(2-((3R,4R)-3-amino-4-fluoropiperidin-1-yl)-5,6-difluoro-1H-benzo[d]imidazol-1-yl)-1-(2-methylmorpholino)ethan-1-one;

(3R,4R)-1-(1-((R)-1-(5-chloropyrimidin-2-yl)ethyl)-5,6-difluoro-1H-benzo[d]imidazol-2-yl)-4-fluoropiperidin-3-amine;

2-(2-((3R,4R)-3-amino-4-fluoropiperidin-1-yl)-5-fluoro-7-methoxy-1H-benzo[d]imidazol-1-yl)-N-methyl-N-(2,2,2-trifluoroethyl)acetamide;

2-(2-((3R,4R)-3-amino-4-fluoropiperidin-1-yl)-5,6-difluoro-1H-benzo[d]imidazol-1-yl)-1-(azocan-1-yl)ethan-1-one;

2-(2-((3R,4R)-3-amino-4-fluoropiperidin-1-yl)-5,6-difluoro-1H-benzo[d]imidazol-1-yl)-1-(4-(pyrazin-2-yl)piperazin-1-yl)ethan-1-one;

methyl-1-(2-(2-((3R,4R)-3-amino-4-fluoropiperidin-1-yl)-5,6-difluoro-1H-benzo[d]imidazol-1-yl)acetyl)piperidine-4-carboxylate;

2-(2-((3R,4R)-3-amino-4-fluoropiperidin-1-yl)-5,6-difluoro-1H-benzo[d]imidazol-1-yl)-1-(2-ethylmorpholino)ethan-1-one;

2-(2-((3R,4R)-3-amino-4-fluoropiperidin-1-yl)-5-fluoro-1H-benzo[d]imidazol-1-yl)-1-(azetidin-1-yl)ethan-1-one;

2-(2-((3R,4R)-3-amino-4-fluoropiperidin-1-yl)-5,6-difluoro-1H-benzo[d]imidazol-1-yl)-N-(1,1-dioxido-2,3-dihydrothiophen-3-yl)-N-phenylacetamide;

2-(2-((3R,4R)-3-amino-4-fluoropiperidin-1-yl)-5,6-difluoro-1H-benzo[d]imidazol-1-yl)-1-(4-methylpiperidin-1-yl)ethan-1-one;

(3R,4R)-4-fluoro-1-(6-fluoro-1-((4-methoxypyridin-2-yl)methyl)-1H-benzo[d]imidazol-2-yl)piperidin-3-amine;

2-(2-((3R,4R)-3-amino-4-fluoropiperidin-1-yl)-5,6-difluoro-1H-benzo[d]imidazol-1-yl)-1-(2-ethylmorpholino)ethan-1-one;

6-((2-((3R,4R)-3-amino-4-fluoropiperidin-1-yl)-6-(trifluoromethyl)-3H-imidazo[4,5-b]pyridin-3-yl)methyl)nicotinonitrile;

2-(2-((3R,4R)-3-amino-4-fluoropiperidin-1-yl)-1H-benzo[d]imidazol-1-yl)-1-(azetidin-1-yl)ethan-1-one;

1-(2-(2-((3R,4R)-3-amino-4-fluoropiperidin-1-yl)-5,6-difluoro-1H-benzo[d]imidazol-1-yl)acetyl)piperidine-2-carboxamide;

2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-(thiophen-2-ylmethyl)acetamide;

2-(2-((3R,4R)-3-amino-4-fluoropiperidin-1-yl)-5,6-difluoro-1H-benzo[d]imidazol-1-yl)-1-(octahydroisoquinolin-2(1H)-yl)ethan-1-one;

(3R,4R)-4-fluoro-1-(5-fluoro-1-((4-methoxypyridin-2-yl)methyl)-1H-benzo[d]imidazol-2-yl)piperidin-3-amine;

2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-methylacetamide;

2-(2-((3R,4R)-3-amino-4-fluoropiperidin-1-yl)-5,6-difluoro-1H-benzo[d]imidazol-1-yl)-N-cyclopropyl-N-(1,1-dioxidotetrahydrothiophen-3-yl)acetamide;

2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-ethylacetamide;

4-(2-(2-((3R,4R)-3-amino-4-fluoropiperidin-1-yl)-5,6-difluoro-1H-benzo[d]imidazol-1-yl)acetyl)piperazin-2-one;

2-(2-((3R,4R)-3-amino-4-fluoropiperidin-1-yl)-5,6-difluoro-1H-benzo[d]imidazol-1-yl)-1-(4-(pyrrolidine-1-carbonyl)piperidin-1-yl)ethan-1-one;

1-(2-(2-((3R,4R)-3-amino-4-fluoropiperidin-1-yl)-5,6-difluoro-1H-benzo[d]imidazol-1-yl)acetyl)piperidine-3-carboxamide;

2-(2-((3R,4R)-3-amino-4-fluoropiperidin-1-yl)-5,6-difluoro-1H-benzo[d]imidazol-1-yl)-1-(4-(cyclopropanecarbonyl)piperazin-1-yl)ethan-1-one;

1-(2-(2-((3R,4R)-3-amino-4-fluoropiperidin-1-yl)-5,6-difluoro-1H-benzo[d]imidazol-1-yl)acetyl)piperidine-4-carboxamide;

2-(2-((3R,4R)-3-amino-4-fluoropiperidin-1-yl)-5,6-difluoro-1H-benzo[d]imidazol-1-yl)-N-(2-cyanopropan-2-yl)-N-methylacetamide;

1-(2-(2-((3R,4R)-3-amino-4-fluoropiperidin-1-yl)-5,6-difluoro-1H-benzo[d]imidazol-1-yl)acetyl)-N-methylpiperidine-4-carboxamide;

N-(1-(2-(2-((3R,4R)-3-amino-4-fluoropiperidin-1-yl)-5,6-difluoro-1H-benzo[d]imidazol-1-yl)acetyl)piperidin-3-yl)acetamide;

2-(2-((3R,4R)-3-amino-4-fluoropiperidin-1-yl)-5,6-difluoro-1H-benzo[d]imidazol-1-yl)-1-(4-(piperidine-1-carbonyl)piperidin-1-yl)ethan-1-one;

2-(2-((3R,4R)-3-amino-4-fluoropiperidin-1-yl)-5,6-difluoro-1H-benzo[d]imidazol-1-yl)-1-(4-(azepane-1-carbonyl)piperidin-1-yl)ethan-1-one;

2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-(2-methoxyethyl)acetamide;

2-(2-((3R,4R)-3-amino-4-fluoropiperidin-1-yl)-5,6-difluoro-1H-benzo[d]imidazol-1-yl)-1-(4-(3-methylpiperidine-1-carbonyl)piperidin-1-yl)ethan-1-one;

1-(4-acetylpiperazin-1-yl)-2-(2-((3R,4R)-3-amino-4-fluoropiperidin-1-yl)-5,6-difluoro-1H-benzo[d]imidazol-1-yl)ethan-1-one;

2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-((tetrahydrofuran-2-yl)methyl)acetamide;

1-(2-(2-((3R,4R)-3-amino-4-fluoropiperidin-1-yl)-5,6-difluoro-1H-benzo[d]imidazol-1-yl)acetyl)-N-isopropyl-N-methylpiperidine-4-carboxamide;

2-(2-((3R,4R)-3-amino-4-methoxypiperidin-1-yl)-6-fluoro-1H-benzo[d]imidazol-1-yl)-N-methyl-N-(2,2,2-trifluoroethyl)acetamide;

2-(2-((3R,4R)-3-amino-4-fluoropiperidin-1-yl)-5-fluoro-7-methoxy-1H-benzo[d]imidazol-1-yl)-N-methyl-N-(2,2,2-trifluoroethyl)acetamide;

2-(2-((3R,4R)-3-amino-4-fluoropiperidin-1-yl)-6-fluoro-4-methoxy-1H-benzo[d]imidazol-1-yl)-1-morpholinoethan-1-one;

2-(2-((3R,4R)-3-amino-4-fluoropiperidin-1-yl)-5-fluoro-7-methoxy-1H-benzo[d]imidazol-1-yl)-1-morpholinoethan-1-one;

(R)-3-(2-((3R,4R)-3-amino-4-fluoropiperidin-1-yl)-5,6-difluoro-1H-benzo[d]imidazol-1-yl)-1-cyclopropylpyrrolidin-2-one;

(S)-3-(2-((3R,4R)-3-amino-4-fluoropiperidin-1-yl)-5,6-difluoro-1H-benzo[d]imidazol-1-yl)-1-(tetrahydro-2H-pyran-4-yl)pyrrolidin-2-one;

(S)-3-(2-((3R,4R)-3-amino-4-fluoropiperidin-1-yl)-5,6-difluoro-1H-benzo[d]imidazol-1-yl)-1-cyclopropylpyrrolidin-2-one;

(R)-3-(2-((3R,4R)-3-amino-4-fluoropiperidin-1-yl)-5,6-difluoro-1H-benzo[d]imidazol-1-yl)-1-(tetrahydro-2H-pyran-4-yl)pyrrolidin-2-one;

(3R,4R)-1-(5,6-difluoro-1-((5-methylthiazol-2-yl)methyl)-1H-benzo[d]imidazol-2-yl)-4-fluoropiperidin-3-amine;

(3R,4R)-1-(4,6-difluoro-1-((5-methyl-1,3,4-thiadiazol-2-yl)methyl)-1H-benzo[d]imidazol-2-yl)-4-fluoropiperidin-3-amine;

(3R,4R)-1-(5,6-difluoro-1-((5-methyl-1,3,4-thiadiazol-2-yl)methyl)-1H-benzo[d]imidazol-2-yl)-4-fluoropiperidin-3-amine;

2-(2-((3R,4R)-3-amino-4-fluoropiperidin-1-yl)-6-(trifluoromethyl)-1H-benzo[d]imidazol-1-yl)-N-methyl-N-(2,2,2-trifluoroethyl)acetamide;

(3R,4R)-1-(1-((5-chloropyrimidin-2-yl)methyl)-6-fluoro-1H-imidazo[4,5-b]pyridin-2-yl)-4-fluoropiperidin-3-amine;

(3R,4R)-1-(4,6-difluoro-1-((5-(methylsulfonyl)pyridin-2-yl)methyl)-1H-benzo[d]imidazol-2-yl)-4-fluoropiperidin-3-amine;

(3R,4R)-1-(1-((5-(difluoromethyl)-1,3,4-thiadiazol-2-yl)methyl)-4,6-difluoro-1H-benzo[d]imidazol-2-yl)-4-fluoropiperidin-3-amine;

2-(2-((3R,4R)-3-amino-4-fluoropiperidin-1-yl)-4,6-difluoro-1H-benzo[d]imidazol-1-yl)-N-methyl-N-(2,2,2-trifluoroethyl)acetamide;

2-(2-((3R,4R)-3-amino-4-fluoropiperidin-1-yl)-6-chloro-1H-benzo[d]imidazol-1-yl)-N-methyl-N-(2,2,2-trifluoroethyl)acetamide;

(3R,4R)-1-(1-((5-(difluoromethyl)-1,3,4-thiadiazol-2-yl)methyl)-5,6-difluoro-1H-benzo[d]imidazol-2-yl)-4-fluoropiperidin-3-amine;

(3R,4R)-4-fluoro-1-(6-fluoro-1-((5-methyl-1,3,4-thiadiazol-2-yl)methyl)-1H-benzo[d]imidazol-2-yl)piperidin-3-amine;

(3R,4R)-1-(5,6-difluoro-1-((5-(methylsulfonyl)pyridin-2-yl)methyl)-1H-benzo[d]imidazol-2-yl)-4-fluoropiperidin-3-amine;

2-(2-((3R,4R)-3-amino-4-fluoropiperidin-1-yl)-6-(trifluoromethyl)-1H-benzo[d]imidazol-1-yl)-N,N-dimethylacetamide;

(3R,4R)-1-(5,6-difluoro-1-((5-methylisoxazol-3-yl)methyl)-1H-benzo[d]imidazol-2-yl)-4-fluoropiperidin-3-amine;

2-(2-((3R,4R)-3-amino-4-fluoropiperidin-1-yl)-4,6-difluoro-1H-benzo[d]imidazol-1-yl)-N,N-dimethylacetamide;

2-(2-((3R,4R)-3-amino-4-fluoropiperidin-1-yl)-6-fluoro-1H-benzo[d]imidazol-1-yl)-N,N-dimethylacetamide;

(3R,4R)-1-(5,6-difluoro-1-((5-methyloxazol-2-yl)methyl)-1H-benzo[d]imidazol-2-yl)-4-fluoropiperidin-3-amine;

(3R,4R)-1-(5,6-difluoro-1-((4-methylthiazol-2-yl)methyl)-1H-benzo[d]imidazol-2-yl)-4-fluoropiperidin-3-amine;

(3R,4R)-4-fluoro-1-(6-fluoro-1-((3-(trifluoromethyl)-1,2,4-oxadiazol-5-yl)methyl)-1H-benzo[d]imidazol-2-yl)piperidin-3-amine;

2-(2-((3R,4R)-3-amino-4-fluoropiperidin-1-yl)-5-chloro-1H-benzo[d]imidazol-1-yl)-N-methyl-N-(2,2,2-trifluoroethyl)acetamide;

(3R,4R)-1-(5,6-difluoro-1-((5-methyl-1,3,4-oxadiazol-2-yl)methyl)-1H-benzo[d]imidazol-2-yl)-4-fluoropiperidin-3-amine;

(3R,4R)-1-(5,6-difluoro-1-((5-methyl-1,2,4-oxadiazol-3-yl)methyl)-1H-benzo[d]imidazol-2-yl)-4-fluoropiperidin-3-amine;

(3R,4R)-1-(1-((5-(difluoromethyl)-1,3,4-thiadiazol-2-yl)methyl)-6-fluoro-1H-benzo[d]imidazol-2-yl)-4-fluoropiperidin-3-amine;

(3R,4R)-4-fluoro-1-(6-fluoro-1-((5-methyl-1,3,4-thiadiazol-2-yl)methyl)-1H-imidazo[4,5-b]pyridin-2-yl)piperidin-3-amine;

(3R,4R)-1-(1-((4,5-dimethyloxazol-2-yl)methyl)-5,6-difluoro-1H-benzo[d]imidazol-2-yl)-4-fluoropiperidin-3-amine;

2-(2-((3R,4R)-3-amino-4-fluoropiperidin-1-yl)-5-fluoro-1H-benzo[d]imidazol-1-yl)-N,N-dimethylacetamide;

(3R,4R)-1-(1-((5-ethyl-1,2,4-oxadiazol-3-yl)methyl)-5,6-difluoro-1H-benzo[d]imidazol-2-yl)-4-fluoropiperidin-3-amine;

(3R,4R)-1-(1-((5-cyclopropyl-1,2,4-oxadiazol-3-yl)methyl)-5,6-difluoro-1H-benzo[d]imidazol-2-yl)-4-fluoropiperidin-3-amine;

(3R,4R)-1-(5,6-difluoro-1-((3-methylisoxazol-5-yl)methyl)-1H-benzo[d]imidazol-2-yl)-4-fluoropiperidin-3-amine;

2-(2-((3R,4R)-3-amino-4-fluoropiperidin-1-yl)-5-(trifluoromethyl)-1H-benzo[d]imidazol-1-yl)-N-methyl-N-(2,2,2-trifluoroethyl)acetamide;

(3R,4R)-1-(1-((5-cyclopropyl-1,3,4-oxadiazol-2-yl)methyl)-5,6-difluoro-1H-benzo[d]imidazol-2-yl)-4-fluoropiperidin-3-amine;

(3R,4R)-4-fluoro-1-(5-fluoro-1-((5-methyl-1,3,4-thiadiazol-2-yl)methyl)-1H-benzo[d]imidazol-2-yl)piperidin-3-amine;

(3R,4R)-1-(3-((5-chloropyrimidin-2-yl)methyl)-6-fluoro-3H-imidazo[4,5-b]pyridin-2-yl)-4-fluoropiperidin-3-amine;

(3R,4R)-4-fluoro-1-(5-fluoro-1-((3-(trifluoromethyl)-1,2,4-oxadiazol-5-yl)methyl)-1H-benzo[d]imidazol-2-yl)piperidin-3-amine;

(3R,4R)-4-fluoro-1-(6-fluoro-1-((4-methyl-2-phenylthiazol-5-yl)methyl)-1H-benzo[d]imidazol-2-yl)piperidin-3-amine;

(3R,4R)-1-(1-((4,5-dimethyl-4H-1,2,4-triazol-3-yl)methyl)-5,6-difluoro-1H-benzo[d]imidazol-2-yl)-4-fluoropiperidin-3-amine;

(3R,4R)-1-(1-((5-(difluoromethyl)-1,3,4-thiadiazol-2-yl)methyl)-5-fluoro-1H-benzo[d]imidazol-2-yl)-4-fluoropiperidin-3-amine;

(R)-4,4-difluoro-1-(6-fluoro-1-((5-methyl-1,3,4-thiadiazol-2-yl)methyl)-1H-benzo[d]imidazol-2-yl)piperidin-3-amine;

(3R,4R)-1-(1-((2,4-dimethylthiazol-5-yl)methyl)-6-fluoro-1H-benzo[d]imidazol-2-yl)-4-fluoropiperidin-3-amine;

(3R,4R)-4-fluoro-1-(6-fluoro-3-((5-methyl-1,3,4-thiadiazol-2-yl)methyl)-3H-imidazo[4,5-b]pyridin-2-yl)piperidin-3-amine;

2-(2-((3R,4R)-3-amino-4-fluoropiperidin-1-yl)-5,7-difluoro-1H-benzo[d]imidazol-1-yl)-N-methyl-N-(2,2,2-trifluoroethyl)acetamide;

2-(2-((3R,4R)-3-amino-4-fluoropiperidin-1-yl)-5-(trifluoromethyl)-1H-benzo[d]imidazol-1-yl)-N,N-dimethylacetamide;

(3R,4R)-4-fluoro-1-(5-fluoro-1-((4-methyl-2-phenylthiazol-5-yl)methyl)-1H-benzo[d]imidazol-2-yl)piperidin-3-amine;

2-(2-((3R,4R)-3-amino-4-fluoropiperidin-1-yl)-5,7-difluoro-1H-benzo[d]imidazol-1-yl)-N,N-dimethylacetamide;

(3R,4R)-1-(5,7-difluoro-1-((5-(methylsulfonyl)pyridin-2-yl)methyl)-1H-benzo[d]imidazol-2-yl)-4-fluoropiperidin-3-amine;

(3R,4R)-1-(1-((2,4-dimethylthiazol-5-yl)methyl)-5-fluoro-1H-benzo[d]imidazol-2-yl)-4-fluoropiperidin-3-amine;

(R)-4,4-difluoro-1-(5-fluoro-1-((5-methyl-1,3,4-thiadiazol-2-yl)methyl)-1H-benzo[d]imidazol-2-yl)piperidin-3-amine;

(3R,4R)-1-(1-((5-(difluoromethyl)-1,3,4-thiadiazol-2-yl)methyl)-5,7-difluoro-1H-benzo[d]imidazol-2-yl)-4-fluoropiperidin-3-amine;

(3R,4R)-1-(5,7-difluoro-1-((5-methyl-1,3,4-thiadiazol-2-yl)methyl)-1H-benzo[d]imidazol-2-yl)-4-fluoropiperidin-3-amine;

2-(2-((3R,4R)-3-amino-4-fluoropiperidin-1-yl)-5,6-difluoro-1H-benzo[d]imidazol-1-yl)-1-(2-methylazetidin-1-yl)ethanone;

2-(2-((3R,4R)-3-amino-4-fluoropiperidin-1-yl)-5,6-difluoro-1H-benzo[d]imidazol-1-yl)-N-(2,2-difluoroethyl)-N-methylacetamide;

2-(2-((3R,4R)-3-amino-4-fluoropiperidin-1-yl)-5,6-difluoro-1H-benzo[d]imidazol-1-yl)-N-cyclopropyl-N-methylacetamide;

2-(2-((3R,4R)-3-amino-4-fluoropiperidin-1-yl)-5,6-difluoro-1H-benzo[d]imidazol-1-yl)-N—((R)-1-cyanoethyl)-N-methylacetamide;

2-(2-((3R,4R)-3-amino-4-fluoropiperidin-1-yl)-5,6-difluoro-1H-benzo[d]imidazol-1-yl)-N-methyl-N—((R)-1-(pyridin-2-yl)ethyl)acetamide;

2-(2-((3R,4R)-3-amino-4-fluoropiperidin-1-yl)-5,6-difluoro-1H-benzo[d]imidazol-1-yl)-N-ethyl-N-methylacetamide;

2-(2-((3R,4R)-3-amino-4-fluoropiperidin-1-yl)-5,6-difluoro-1H-benzo[d]imidazol-1-yl)-N-(2-fluoroethyl)-N-methylacetamide;

2-(2-((3R,4R)-3-amino-4-fluoropiperidin-1-yl)-5,6-difluoro-1H-benzo[d]imidazol-1-yl)-1-((1R,5S)-3-azabicyclo[3.1.0]hexan-3-yl)ethanone;

2-(2-((3R,4R)-3-amino-4-fluoropiperidin-1-yl)-5,6-difluoro-1H-benzo[d]imidazol-1-yl)-N-methyl-N-(1-(pyridin-2-yl)ethyl)acetamide;

2-(2-((3R,4R)-3-amino-4-fluoropiperidin-1-yl)-5,6-difluoro-1H-benzo[d]imidazol-1-yl)-1-(2-azabicyclo[3.1.0]hexan-2-yl)ethanone;

2-(2-((3R,4R)-3-amino-4-fluoropiperidin-1-yl)-5,6-difluoro-1H-benzo[d]imidazol-1-yl)-N—((S)-1-cyanoethyl)-N-methylacetamide;

2-(2-((3R,4R)-3-amino-4-fluoropiperidin-1-yl)-5,6-difluoro-1H-benzo[d]imidazol-1-yl)-N-methyl-N-(tetrahydrofuran-3-yl)acetamide;

2-(2-((3R,4R)-3-amino-4-fluoropiperidin-1-yl)-5,6-difluoro-1H-benzo[d]imidazol-1-yl)-N-(1-cyanopropan-2-yl)-N-methylacetamide;

2-(2-((3R,4R)-3-amino-4-fluoropiperidin-1-yl)-5,6-difluoro-1H-benzo[d]imidazol-1-yl)-N-methyl-N-(1-(pyridin-4-yl)ethyl)acetamide;

2-(2-((3R,4R)-3-amino-4-fluoropiperidin-1-yl)-5,6-difluoro-1H-benzo[d]imidazol-1-yl)-N-methyl-N-(1,1,1-trifluoropropan-2-yl)acetamide;

2-(2-((3R,4R)-3-amino-4-fluoropiperidin-1-yl)-5,6-difluoro-1H-benzo[d]imidazol-1-yl)-N-(cyanomethyl)-N-methylacetamide;

2-(2-((3R,4R)-3-amino-4-fluoropiperidin-1-yl)-5,6-difluoro-1H-benzo[d]imidazol-1-yl)-N-methyl-N-propylacetamide;

2-(2-((3R,4R)-3-amino-4-fluoropiperidin-1-yl)-5,6-difluoro-1H-benzo[d]imidazol-1-yl)-N-cyclopropyl-N-(2-hydroxyethyl)acetamide;

1-(2-(2-((3R,4R)-3-amino-4-fluoropiperidin-1-yl)-5,6-difluoro-1H-benzo[d]imidazol-1-yl)acetyl)-3-fluoropyrrolidine-3-carbonitrile;

2-(2-((3R,4R)-3-amino-4-fluoropiperidin-1-yl)-5,6-difluoro-1H-benzo[d]imidazol-1-yl)-1-(2-oxa-5-azabicyclo[2.2.1]heptan-5-yl)ethanone;

2-(2-((3R,4R)-3-amino-4-fluoropiperidin-1-yl)-5,6-difluoro-1H-benzo[d]imidazol-1-yl)-1-(hexahydropyrano[4,3-b][1,4]oxazin-4(7H)-yl)ethanone;

2-(2-((3R,4R)-3-amino-4-fluoropiperidin-1-yl)-5,6-difluoro-1H-benzo[d]imidazol-1-yl)-N-(2-cyanopropyl)-N-methylacetamide;

-(2-((3R,4R)-3-amino-4-fluoropiperidin-1-yl)-5,6-difluoro-1H-benzo[d]imidazol-1-yl)-N-methyl-N-(3,3,3-trifluoropropyl)acetamide;

2-(2-((3R,4R)-3-amino-4-fluoropiperidin-1-yl)-5,6-difluoro-1H-benzo[d]imidazol-1-yl)-1-((1R,5S)-6,6-difluoro-3-azabicyclo[3.1.0]hexan-3-yl)ethanone;

2-(2-((3R,4R)-3-amino-4-fluoropiperidin-1-yl)-5,6-difluoro-1H-benzo[d]imidazol-1-yl)-1-(4-(pyrimidin-2-yl)piperazin-1-yl)ethanone;

2-(2-((3R,4R)-3-amino-4-fluoropiperidin-1-yl)-5,6-difluoro-1H-benzo[d]imidazol-1-yl)-1-(2-isopropylazetidin-1-yl)ethanone;

2-(2-((3R,4R)-3-amino-4-fluoropiperidin-1-yl)-5,6-difluoro-1H-benzo[d]imidazol-1-yl)-1-(3-(difluoromethoxy)pyrrolidin-1-yl)ethanone;

4-(2-(2-((3R,4R)-3-amino-4-fluoropiperidin-1-yl)-5,6-difluoro-1H-benzo[d]imidazol-1-yl)acetyl)morpholine-2-carbonitrile;

2-(2-((3R,4R)-3-amino-4-fluoropiperidin-1-yl)-5,6-difluoro-1H-benzo[d]imidazol-1-yl)-1-(3-hydroxypiperidin-1-yl)ethanone;

1-(2-(2-((3R,4R)-3-amino-4-fluoropiperidin-1-yl)-5,6-difluoro-1H-benzo[d]imidazol-1-yl)acetyl)-4-methylpiperidine-4-carbonitrile;

2-(2-((3R,4R)-3-amino-4-fluoropiperidin-1-yl)-5,6-difluoro-1H-benzo[d]imidazol-1-yl)-1-(3,4-dihydro-1,8-naphthyridin-1(2H)-yl)ethanone;

2-(2-((3R,4R)-3-amino-4-fluoropiperidin-1-yl)-5,6-difluoro-1H-benzo[d]imidazol-1-yl)-N-cyclopropyl-N-(2,2-difluoroethyl)acetamide;

2-(2-((3R,4R)-3-amino-4-fluoropiperidin-1-yl)-5,6-difluoro-1H-benzo[d]imidazol-1-yl)-1-(5H-pyrrolo[3,4-b]pyridin-6(7H)-yl)ethanone;

2-(2-((3R,4R)-3-amino-4-fluoropiperidin-1-yl)-5,6-difluoro-1H-benzo[d]imidazol-1-yl)-N-methyl-N-((tetrahydrofuran-3-yl)methyl)acetamide;

-(2-((3R,4R)-3-amino-4-fluoropiperidin-1-yl)-5,6-difluoro-1H-benzo[d]imidazol-1-yl)-N-(2,2-difluoroethyl)-N-methylacetamide;

2-(2-((3R,4R)-3-amino-4-fluoropiperidin-1-yl)-5,6-difluoro-1H-benzo[d]imidazol-1-yl)-N-methyl-N-(2,2,2-trifluoroethyl)acetamide;

(R)-1-(2-(2-((3R,4R)-3-amino-4-fluoropiperidin-1-yl)-5,6-difluoro-1H-benzo[d]imidazol-1-yl)acetyl)pyrrolidine-2-carbonitrile;

2-(2-((3R,4R)-3-amino-4-fluoropiperidin-1-yl)-5,6-difluoro-1H-benzo[d]imidazol-1-yl)-N-((1r,4R)-4-hydroxycyclohexyl)-N-methylacetamide;

2-(2-((3R,4R)-3-amino-4-fluoropiperidin-1-yl)-5,6-difluoro-1H-benzo[d]imidazol-1-yl)-N-methyl-N—((S)-1-(pyridin-2-yl)ethyl)acetamide;

2-(2-((3R,4R)-3-amino-4-fluoropiperidin-1-yl)-5,6-difluoro-1H-benzo[d]imidazol-1-yl)-1-(octahydro-1H-pyrano[4,3-b]pyridin-1-yl)ethanone;

2-(2-((3R,4R)-3-amino-4-fluoropiperidin-1-yl)-5,6-difluoro-1H-benzo[d]imidazol-1-yl)-1-(4-hydroxypiperidin-1-yl)ethanone;

1-(3-(1H-1,2,4-triazol-1-yl)azetidin-1-yl)-2-(2-((3R,4R)-3-amino-4-fluoropiperidin-1-yl)-5,6-difluoro-1H-benzo[d]imidazol-1-yl)ethanone;

7-(2-(2-((3R,4R)-3-amino-4-fluoropiperidin-1-yl)-5,6-difluoro-1H-benzo[d]imidazol-1-yl)acetyl)hexahydroimidazo[1,5-a]pyrazin-3(2H)-one;

2-(2-((3R,4R)-3-amino-4-fluoropiperidin-1-yl)-5,6-difluoro-1H-benzo[d]imidazol-1-yl)-N-(2-cyanoethyl)-N-((tetrahydrofuran-3-yl)methyl)acetamide;

4-(2-(2-((3R,4R)-3-amino-4-fluoropiperidin-1-yl)-5,6-difluoro-1H-benzo[d]imidazol-1-yl)acetyl)-N-methylmorpholine-2-carboxamide;

2-(2-((3R,4R)-3-amino-4-fluoropiperidin-1-yl)-5,6-difluoro-1H-benzo[d]imidazol-1-yl)-1-(3-((methylsulfonyl)methyl)pyrrolidin-1-yl)ethanone;

2-(2-((3R,4R)-3-amino-4-fluoropiperidin-1-yl)-5,6-difluoro-1H-benzo[d]imidazol-1-yl)-1-(5,6-dihydro-[1,2,4]triazolo[1,5-a]pyrazin-7(8H)-yl)ethanone;

2-(2-((3R,4R)-3-amino-4-fluoropiperidin-1-yl)-5,6-difluoro-1H-benzo[d]imidazol-1-yl)-1-(2-(methoxymethyl)morpholino)ethanone;

2-(2-((3R,4R)-3-amino-4-fluoropiperidin-1-yl)-5,6-difluoro-1H-benzo[d]imidazol-1-yl)-1-(3-hydroxy-3-methylpyrrolidin-1-yl)ethanone;

2-(2-((3R,4R)-3-amino-4-fluoropiperidin-1-yl)-5,6-difluoro-1H-benzo[d]imidazol-1-yl)-1-(4-(methylsulfonyl)piperazin-1-yl)ethanone;

N-((1-acetylpyrrolidin-3-yl)methyl)-2-(2-((3R,4R)-3-amino-4-fluoropiperidin-1-yl)-5,6-difluoro-1H-benzo[d]imidazol-1-yl)-N-ethylacetamide;

2-(2-((3R,4R)-3-amino-4-fluoropiperidin-1-yl)-5,6-difluoro-1H-benzo[d]imidazol-1-yl)-N-(1,1-dioxidotetrahydro-2H-thiopyran-4-yl)-N-methylacetamide;

2-(2-((3R,4R)-3-amino-4-fluoropiperidin-1-yl)-5,6-difluoro-1H-benzo[d]imidazol-1-yl)-N-((1,1-dioxidotetrahydrothiophen-3-yl)methyl)-N-methylacetamide;

2-(1-(2-(2-((3R,4R)-3-amino-4-fluoropiperidin-1-yl)-5,6-difluoro-1H-benzo[d]imidazol-1-yl)acetyl)piperidin-4-yl)-2-methylpropanenitrile;

1-(2-(2-((3R,4R)-3-amino-4-fluoropiperidin-1-yl)-5,6-difluoro-1H-benzo[d]imidazol-1-yl)acetyl)-N-methylpiperidine-3-carboxamide;

2-(2-((3R,4R)-3-amino-4-fluoropiperidin-1-yl)-5,6-difluoro-1H-benzo[d]imidazol-1-yl)-N-(2-hydroxyethyl)-N-(pyridin-3-ylmethyl)acetamide;

2-(2-((3R,4R)-3-amino-4-fluoropiperidin-1-yl)-5,6-difluoro-1H-benzo[d]imidazol-1-yl)-N-(2-cyanoethyl)-N-(tetrahydro-2H-pyran-4-yl)acetamide;

1-(2-(2-((3R,4R)-3-amino-4-fluoropiperidin-1-yl)-5,6-difluoro-1H-benzo[d]imidazol-1-yl)acetyl)-N,N-dimethylpiperidine-3-carboxamide;

1-(2-(2-((3R,4R)-3-amino-4-fluoropiperidin-1-yl)-5,6-difluoro-1H-benzo[d]imidazol-1-yl)acetyl)-4-(methoxymethyl)piperidine-4-carbonitrile;

7-(2-(2-((3R,4R)-3-amino-4-fluoropiperidin-1-yl)-5,6-difluoro-1H-benzo[d]imidazol-1-yl)acetyl)tetrahydro-1H-oxazolo[3,4-a]pyrazin-3(5H)-one;

2-(2-((3R,4R)-3-amino-4-fluoropiperidin-1-yl)-6-fluoro-1H-benzo[d]imidazol-1-yl)-N-(thiazol-2-yl)acetamide;

2-(2-((3R,4R)-3-amino-4-fluoropiperidin-1-yl)-6-fluoro-1H-benzo[d]imidazol-1-yl)-N-(2,2,2-trifluoroethyl)acetamide;

2-(2-((3R,4R)-3-amino-4-fluoropiperidin-1-yl)-6-fluoro-1H-benzo[d]imidazol-1-yl)-N-cyclopropyl-N-(2,2,2-trifluoroethyl)acetamide;

2-(2-((3R,4R)-3-amino-4-fluoropiperidin-1-yl)-6-fluoro-1H-benzo[d]imidazol-1-yl)-N-(2-methoxyethyl)-N-methylacetamide;

2-(2-((3R,4R)-3-amino-4-fluoropiperidin-1-yl)-6-fluoro-1H-benzo[d]imidazol-1-yl)-N-methyl-N—((S)-tetrahydrofuran-3-yl)acetamide;

2-(2-((3R,4R)-3-amino-4-fluoropiperidin-1-yl)-6-fluoro-1H-benzo[d]imidazol-1-yl)-N-methyl-N—((R)-tetrahydrofuran-3-yl)acetamide;

2-(2-((3R,4R)-3-amino-4-fluoropiperidin-1-yl)-6-fluoro-1H-benzo[d]imidazol-1-yl)-N—((S)-1-(pyridin-2-yl)ethyl)acetamide;

2-(2-((3R,4R)-3-amino-4-fluoropiperidin-1-yl)-6-fluoro-1H-benzo[d]imidazol-1-yl)-N—((S)-tetrahydrofuran-3-yl)-N-(2,2,2-trifluoroethyl)acetamide;

2-(2-((3R,4R)-3-amino-4-fluoropiperidin-1-yl)-6-fluoro-1H-benzo[d]imidazol-1-yl)-N-cyclobutylacetamide;

2-(2-((3R,4R)-3-amino-4-fluoropiperidin-1-yl)-6-fluoro-1H-benzo[d]imidazol-1-yl)-N—((S)-1-cyanopropan-2-yl)acetamide;

2-(2-((3R,4R)-3-amino-4-fluoropiperidin-1-yl)-6-fluoro-1H-benzo[d]imidazol-1-yl)-N—((R)-1-cyanopropan-2-yl)acetamide;

2-(2-((3R,4R)-3-amino-4-fluoropiperidin-1-yl)-6-fluoro-1H-benzo[d]imidazol-1-yl)-N-ethyl-N-(2-methoxyethyl)acetamide;

2-(2-((3R,4R)-3-amino-4-fluoropiperidin-1-yl)-6-fluoro-1H-benzo[d]imidazol-1-yl)-N—((R)-tetrahydrofuran-3-yl)-N-(2,2,2-trifluoroethyl)acetamide;

2-(2-((3R,4R)-3-amino-4-fluoropiperidin-1-yl)-6-fluoro-1H-benzo[d]imidazol-1-yl)-N-(3,3,3-trifluoropropyl)acetamide;

2-(2-((3R,4R)-3-amino-4-fluoropiperidin-1-yl)-6-fluoro-1H-benzo[d]imidazol-1-yl)-N—((R)-1-(pyridin-2-yl)ethyl)acetamide;

2-(2-((3R,4R)-3-amino-4-fluoropiperidin-1-yl)-6-fluoro-1H-benzo[d]imidazol-1-yl)-N—((S)-tetrahydrofuran-3-yl)acetamide;

2-(2-((3R,4R)-3-amino-4-fluoropiperidin-1-yl)-6-fluoro-1H-benzo[d]imidazol-1-yl)-N—((R)-tetrahydrofuran-3-yl)acetamide;

2-(2-((3R,4R)-3-amino-4-fluoropiperidin-1-yl)-6-fluoro-1H-benzo[d]imidazol-1-yl)-1-(2-methylazetidin-1-yl)ethan-1-one;

2-(2-((3R,4R)-3-amino-4-fluoropiperidin-1-yl)-6-fluoro-1H-benzo[d]imidazol-1-yl)-1-((S)-3-methylmorpholino)ethan-1-one;

2-(2-((3R,4R)-3-amino-4-fluoropiperidin-1-yl)-6-fluoro-1H-benzo[d]imidazol-1-yl)-1-((R)-2-methylpyrrolidin-1-yl)ethan-1-one;

2-(2-((3R,4R)-3-amino-4-fluoropiperidin-1-yl)-6-fluoro-1H-benzo[d]imidazol-1-yl)-1-((R)-3-(methoxymethyl)morpholino)ethan-1-one;

2-(2-((3R,4R)-3-amino-4-fluoropiperidin-1-yl)-6-fluoro-1H-benzo[d]imidazol-1-yl)-1-((R)-3-methylmorpholino)ethan-1-one;

2-(2-((3R,4R)-3-amino-4-fluoropiperidin-1-yl)-6-fluoro-1H-benzo[d]imidazol-1-yl)-1-((S)-2-methylpyrrolidin-1-yl)ethan-1-one;

2-(2-((3R,4R)-3-amino-4-fluoropiperidin-1-yl)-6-fluoro-1H-benzo[d]imidazol-1-yl)-1-(3,5-dimethylmorpholino)ethan-1-one;

2-(2-((3R,4R)-3-amino-4-fluoropiperidin-1-yl)-6-fluoro-1H-benzo[d]imidazol-1-yl)-1-(3-ethylmorpholino)ethan-1-one;

2-(2-((3R,4R)-3-amino-4-fluoropiperidin-1-yl)-6-fluoro-1H-benzo[d]imidazol-1-yl)-1-((S)-3-cyclopropylmorpholino)ethan-1-one;

2-(2-((3R,4R)-3-amino-4-fluoropiperidin-1-yl)-6-fluoro-1H-benzo[d]imidazol-1-yl)-1-((R)-3-(hydroxymethyl)morpholino)ethan-1-one; and 2-(2-((3R,4R)-3-amino-4-fluoropiperidin-1-yl)-6-fluoro-1H-benzo[d]imidazol-1-yl)-1-(3,3-dimethylmorpholino)ethan-1-one.

In a thirty ninth embodiment, the invention provides compounds of the first or second embodiment in which the compound is recited in the below Table B:

Table B 6-((2-((3R,4S)-3-amino-4-fluoropiperidin-1-yl)-6-chloro-1H-benzo[d]imidazol-1-yl)methyl)nicotinonitrile;

2-((3R,4R)-3-amino-4-fluoropiperidin-1-yl)-1-((5-cyanopyridin-2-yl)methyl)-1H-benzo[d]imidazole-4-carbonitrile;

6-((2-((3R,4R)-3-amino-4-fluoropiperidin-1-yl)-5-(trifluoromethyl)-1H-benzo[d]imidazol-1-yl)methyl)nicotinonitrile;

6-((2-((3R,4R)-3-amino-4-fluoropiperidin-1-yl)-6-(trifluoromethoxy)-1H-benzo[d]imidazol-1-yl)methyl)nicotinonitrile;

2-((3R,4R)-3-amino-4-fluoropiperidin-1-yl)-1-((5-chloropyrimidin-2-yl)methyl)-6-fluoro-1H-benzo[d]imidazole-4-carbonitrile;

(3R,4R)-1-(4,6-difluoro-1-((5-fluoropyridin-2-yl)methyl)-1H-benzo[d]imidazol-2-yl)-4-fluoropiperidin-3-amine;

(3R,4R)-1-(4,6-difluoro-1-((5-fluoropyrimidin-2-yl)methyl)-1H-benzo[d]imidazol-2-yl)-4-fluoropiperidin-3-amine;

2-((3R,4R)-3-amino-4-fluoropiperidin-1-yl)-6-fluoro-1-((5-fluoropyrimidin-2-yl)methyl)-1H-benzo[d]imidazole-4-carbonitrile;

6-((2-((3R,4R)-3-amino-4-fluoropiperidin-1-yl)-1H-benzo[d]imidazol-1-yl)methyl)nicotinonitrile;

6-((2-((3R,4S)-3-amino-4-fluoropiperidin-1-yl)-5-fluoro-1H-benzo[d]imidazol-1-yl)methyl)nicotinonitrile hydrochloride;

6-((2-((3R,4R)-3-amino-4-fluoropiperidin-1-yl)-5-fluoro-1H-benzo[d]imidazol-1-yl)methyl)nicotinonitrile hydrochloride;

6-((2-((3R,4R)-3-amino-4-fluoropiperidin-1-yl)-4,6-difluoro-1H-benzo[d]imidazol-1-yl)methyl)nicotinonitrile;

(R)-6-((2-(3-amino-4,4-difluoropiperidin-1-yl)-4,6-difluoro-1H-benzo[d]imidazol-1-yl)methyl)nicotinonitrile hydrochloride;

(R)-6-((2-(3-amino-4,4-difluoropiperidin-1-yl)-6-fluoro-1H-benzo[d]imidazol-1-yl)methyl)nicotinonitrile;

6-((2-((3R,4R)-3-amino-4-fluoropiperidin-1-yl)-6-chloro-1H-imidazo[4,5-b]pyridin-1-yl)methyl)nicotinonitrile;

6-((2-((3R)-3-amino-4,4-difluoro-1-piperidinyl)-6-(trifluoromethyl)-1H-benzimidazol-1-yl)methyl)-3-pyridinecarbonitrile;

6-((2-((3R,4R)-3-amino-4-fluoro-1-piperidinyl)-5-(difluoromethoxy)-1H-benzimidazol-1-yl)methyl)-3-pyridinecarbonitrile;

6-((2-((3R,4R)-3-amino-4-fluoro-1-piperidinyl)-4-methoxy-1H-benzimidazol-1-yl)methyl)-3-pyridinecarbonitrile;

6-((2-((3R)-3-amino-4,4-difluoro-1-piperidinyl)-6-methoxy-1H-benzimidazol-1-yl)methyl)-3-pyridinecarbonitrile;

6-((2-((3R,4S)-3-amino-4-fluoropiperidin-1-yl)-6-methoxy-1H-benzo[d]imidazol-1-yl)methyl)nicotinonitrile hydrochloride;

2-((3R,4S)-3-amino-4-fluoropiperidin-1-yl)-1-((5-chloropyrimidin-2-yl)methyl)-6-fluoro-1H-benzo[d]imidazole-4-carbonitrile;

(R)-2-(3-amino-4,4-difluoropiperidin-1-yl)-1-((5-chloropyrimidin-2-yl)methyl)-6-fluoro-1H-benzo[d]imidazole-4-carbonitrile;

4-((2-((3R,4R)-3-amino-4-fluoro-1-piperidinyl)-4,6-difluoro-1H-benzimidazol-1-yl)methyl)benzonitrile;

4-((2-((3S,4S)-3-amino-4-fluoropiperidin-1-yl)-1H-benzo[d]imidazol-1-yl)methyl)benzonitrile;

4-((2-((3R,4R)-3-amino-4-fluoropiperidin-1-yl)-1H-benzo[d]imidazol-1-yl)methyl)benzonitrile;

(R)-4-((2-(3-aminopiperidin-1-yl)-6-methoxy-1H-benzo[d]imidazol-1-yl)methyl)benzonitrile;

2-((3R,4R)-3-amino-4-fluoropiperidin-1-yl)-1-((5-chloropyrimidin-2-yl)methyl)-1H-benzo[d]imidazole-6-carbonitrile;

(3R,4R)-4-fluoro-1-(1-((5-fluoropyrimidin-2-yl)methyl)-1H-benzo[d]imidazol-2-yl)piperidin-3-amine;

2-((3R,4R)-3-amino-4-fluoropiperidin-1-yl)-1-((5-fluoropyrimidin-2-yl)methyl)-1H-benzo[d]imidazole-6-carbonitrile;

2-((3R,4S)-3-amino-4-fluoropiperidin-1-yl)-1-((5-chloropyrimidin-2-yl)methyl)-1H-benzo[d]imidazole-6-carbonitrile;

(3R,4R)-3-amino-1-(1-((5-chloropyrimidin-2-yl)methyl)-6-fluoro-1H-benzo[d]imidazol-2-yl)piperidin-4-ol;

(R)-1-(1-((5-chloropyridin-2-yl)methyl)-4,6-difluoro-1H-benzo[d]imidazol-2-yl)-4,4-difluoropiperidin-3-amine hydrochloride;

(3R,4R)-1-(1-((5-chloro-2-pyrimidinyl)methyl)-4,6-difluoro-1H-benzimidazol-2-yl)-4-fluoro-3-piperidinamine;

2-(2-((3R,4R)-3-amino-4-fluoro-1-piperidinyl)-5,6-difluoro-1H-benzimidazol-1-yl)-1-(1-piperidinyl)ethanone;

2-(2-((3R,4R)-3-amino-4-fluoro-1-piperidinyl)-6-chloro-1H-benzimidazol-1-yl)-1-(1-azetidinyl)ethanone;

(3R,4R)-1-(1-((5-chloropyrimidin-2-yl)methyl)-6-fluoro-1H-benzo[d]imidazol-2-yl)-4-fluoropiperidin-3-amine;

(3R,4R)-1-(1-((5-chloropyrimidin-2-yl)methyl)-5-fluoro-1H-benzo[d]imidazol-2-yl)-4-fluoropiperidin-3-amine;

(3R,4R)-1-(5,6-difluoro-1-((5-fluoropyrimidin-2-yl)methyl)-1H-benzo[d]imidazol-2-yl)-4-fluoropiperidin-3-amine;

(3R,4S)-4-fluoro-1-(1-((5-fluoropyrimidin-2-yl)methyl)-6-(trifluoromethyl)-1H-benzo[d]imidazol-2-yl)piperidin-3-amine; and 4-((2-((3R,4R)-3-amino-4-fluoropiperidin-1-yl)-6-chloro-1H-benzo[d]imidazol-1-yl)methyl)benzonitrile hydrochloride.

In a fortieth embodiment, the invention provides compounds of the first or second embodiment in which the compound is recited in the below Table C:

Table C 6-((2-((3R,4S)-3-amino-4-fluoropiperidin-1-yl)-6-chloro-1H-benzo[d]imidazol-1-yl)methyl)nicotinonitrile;

6-((2-((3R,4R)-3-amino-4-fluoropiperidin-1-yl)-6-(trifluoromethoxy)-1H-benzo[d]imidazol-1-yl)methyl)nicotinonitrile;

2-((3R,4R)-3-amino-4-fluoropiperidin-1-yl)-1-((5-chloropyrimidin-2-yl)methyl)-6-fluoro-1H-benzo[d]imidazole-4-carbonitrile;

(3R,4R)-1-(4,6-difluoro-1-((5-fluoropyridin-2-yl)methyl)-1H-benzo[d]imidazol-2-yl)-4-fluoropiperidin-3-amine;

(3R,4R)-1-(4,6-difluoro-1-((5-fluoropyrimidin-2-yl)methyl)-1H-benzo[d]imidazol-2-yl)-4-fluoropiperidin-3-amine;

6-((2-((3R,4R)-3-amino-4-fluoropiperidin-1-yl)-1H-benzo[d]imidazol-1-yl)methyl)nicotinonitrile;

6-((2-((3R,4R)-3-amino-4-fluoropiperidin-1-yl)-5-fluoro-1H-benzo[d]imidazol-1-yl)methyl)nicotinonitrile hydrochloride;

6-((2-((3R,4R)-3-amino-4-fluoropiperidin-1-yl)-4,6-difluoro-1H-benzo[d]imidazol-1-yl)methyl)nicotinonitrile;

(R)-6-((2-(3-amino-4,4-difluoropiperidin-1-yl)-4,6-difluoro-1H-benzo[d]imidazol-1-yl)methyl)nicotinonitrile hydrochloride;

(R)-6-((2-(3-amino-4,4-difluoropiperidin-1-yl)-6-fluoro-1H-benzo[d]imidazol-1-yl)methyl)nicotinonitrile;

6-((2-((3R,4R)-3-amino-4-fluoro-1-piperidinyl)-4-methoxy-1H-benzimidazol-1-yl)methyl)-3-pyridinecarbonitrile;

6-((2-((3R)-3-amino-4,4-difluoro-1-piperidinyl)-6-methoxy-1H-benzimidazol-1-yl)methyl)-3-pyridinecarbonitrile;

2-((3R,4S)-3-amino-4-fluoropiperidin-1-yl)-1-((5-chloropyrimidin-2-yl)methyl)-6-fluoro-1H-benzo[d]imidazole-4-carbonitrile;

(R)-2-(3-amino-4,4-difluoropiperidin-1-yl)-1-((5-chloropyrimidin-2-yl)methyl)-6-fluoro-1H-benzo[d]imidazole-4-carbonitrile;

2-((3R,4R)-3-amino-4-fluoropiperidin-1-yl)-1-((5-chloropyrimidin-2-yl)methyl)-1H-benzo[d]imidazole-6-carbonitrile;

(3R,4R)-4-fluoro-1-(1-((5-fluoropyrimidin-2-yl)methyl)-1H-benzo[d]imidazol-2-yl)piperidin-3-amine;

2-((3R,4S)-3-amino-4-fluoropiperidin-1-yl)-1-((5-chloropyrimidin-2-yl)methyl)-1H-benzo[d]imidazole-6-carbonitrile;

(R)-1-(1-((5-chloropyridin-2-yl)methyl)-4,6-difluoro-1H-benzo[d]imidazol-2-yl)-4,4-difluoropiperidin-3-amine hydrochloride;

(3R,4R)-1-(1-((5-chloro-2-pyrimidinyl)methyl)-4,6-difluoro-1H-benzimidazol-2-yl)-4-fluoro-3-piperidinamine; and (3R,4R)-1-(1-((5-chloropyrimidin-2-yl)methyl)-6-fluoro-1H-benzo[d]imidazol-2-yl)-4-fluoropiperidin-3-amine.

In a forty first embodiment, the invention provides compounds of the first or second embodiment in which the compound is recited in the below Table D:

Table D
6-((2-((3R,4S)-3-amino-4-fluoropiperidin-1-yl)-6-chloro-1H-benzo[d]imidazol-1-yl)methyl)nicotinonitrile;
2-((3R,4R)-3-amino-4-fluoropiperidin-1-yl)-1-((5-chloropyrimidin-2-yl)methyl)-6-fluoro-1H-benzo[d]imidazole-4-carbonitrile;
(3R,4R)-1-(4,6-difluoro-1-((5-fluoropyrimidin-2-yl)methyl)-1H-benzo[d]imidazol-2-yl)-4-fluoropiperidin-3-amine;
6-((2-((3R,4R)-3-amino-4-fluoropiperidin-1-yl)-1H-benzo[d]imidazol-1-yl)methyl)nicotinonitrile;
(R)-6-((2-(3-amino-4,4-difluoropiperidin-1-yl)-4,6-difluoro-1H-benzo[d]imidazol-1-yl)methyl)nicotinonitrile hydrochloride;
(R)-6-((2-(3-amino-4,4-difluoropiperidin-1-yl)-6-fluoro-1H-benzo[d]imidazol-1-yl)methyl)nicotinonitrile;
6-((2-((3R,4R)-3-amino-4-fluoro-1-piperidinyl)-4-methoxy-1H-benzimidazol-1-yl)methyl)-3-pyridinecarbonitrile;
2-((3R,4R)-3-amino-4-fluoropiperidin-1-yl)-1-((5-chloropyrimidin-2-yl)methyl)-1H-benzo[d]imidazole-6-carbonitrile;
(3R,4R)-4-fluoro-1-(1-((5-fluoropyrimidin-2-yl)methyl)-1H-benzo[d]imidazol-2-yl)piperidin-3-amine; and
(3R,4R)-1-(1-((5-chloropyrimidin-2-yl)methyl)-6-fluoro-1H-benzo[d]imidazol-2-yl)-4-fluoropiperidin-3-amine.

In a further embodiment, each of the compounds disclosed herein are provided in the form of a pharmaceutically acceptable salt.

In a forty second embodiment, the invention provides 6-((2-((3R,4S)-3-amino-4-fluoropiperidin-1-yl)-6-chloro-1H-benzo[d]imidazol-1-yl)methyl)nicotinonitrile. In certain aspects of the forty second embodiment, the invention provides a pharmaceutically acceptable salt of 6-((2-((3R,4S)-3-amino-4-fluoropiperidin-1-yl)-6-chloro-1H-benzo[d]imidazol-1-yl)methyl)nicotinonitrile.

In a forty third embodiment, the invention provides 2-((3R,4R)-3-amino-4-fluoropiperidin-1-yl)-1-((5-chloropyrimidin-2-yl)methyl)-6-fluoro-1H-benzo[d]imidazole-4-carbonitrile. In certain aspects of the forty third embodiment, the invention provides a pharmaceutically acceptable salt of 2-((3R,4R)-3-amino-4-fluoropiperidin-1-yl)-1-((5-chloropyrimidin-2-yl)methyl)-6-fluoro-1H-benzo[d]imidazole-4-carbonitrile.

In a forty fourth embodiment, the invention provides (3R,4R)-1-(4,6-difluoro-1-((5-fluoropyrimidin-2-yl)methyl)-1H-benzo[d]imidazol-2-yl)-4-fluoropiperidin-3-amine. In certain aspects of the forty fourth embodiment, the invention provides a pharmaceutically acceptable salt of (3R,4R)-1-(4,6-difluoro-1-((5-fluoropyrimidin-2-yl)methyl)-1H-benzo[d]imidazol-2-yl)-4-fluoropiperidin-3-amine.

In a forty fifth embodiment, the invention provides 6-((2-((3R,4R)-3-amino-4-fluoropiperidin-1-yl)-1H-benzo[d]imidazol-1-yl)methyl)nicotinonitrile. In certain aspects of the forty fifth embodiment embodiment, the invention provides a pharmaceutically acceptable salt of 6-((2-((3R,4R)-3-amino-4-fluoropiperidin-1-yl)-1H-benzo[d]imidazol-1-yl)methyl)nicotinonitrile.

In a forty sixth embodiment, the invention provides (R)-6-((2-(3-amino-4,4-difluoropiperidin-1-yl)-4,6-difluoro-1H-benzo[d]imidazol-1-yl)methyl)nicotinonitrile. In certain aspects of the forty sixth embodiment, the invention provides a pharmaceutically acceptable salt of (R)-6-((2-(3-amino-4,4-difluoropiperidin-1-yl)-4,6-difluoro-1H-benzo[d]imidazol-1-yl)methyl)nicotinonitrile. The hydrochloride salt is a particularly preferred aspect of the forty sixth embodiment, e.g., (R)-6-((2-(3-amino-4,4-difluoropiperidin-1-yl)-6-fluoro-1H-benzo[d]imidazol-1-yl)methyl)nicotinonitrile hydrochloride.

In a forty seventh embodiment, the invention provides (R)-6-((2-(3-amino-4,4-difluoropiperidin-1-yl)-6-fluoro-1H-benzo[d]imidazol-1-yl)methyl)nicotinonitrile. In certain aspects of the forty seventh embodiment, the invention provides a pharmaceutically acceptable salt of (R)-6-((2-(3-amino-4,4-difluoropiperidin-1-yl)-6-fluoro-1H-benzo[d]imidazol-1-yl)methyl)nicotinonitrile.

In a forty eighth embodiment, the invention provides 6-((2-((3R,4R)-3-amino-4-fluoro-1-piperidinyl)-4-methoxy-1H-benzimidazol-1-yl)methyl)-3-pyridinecarbonitrile. In certain aspects of the forty eighth embodiment, the invention provides a pharmaceutically acceptable salt of 6-((2-((3R,4R)-3-amino-4-fluoro-1-piperidinyl)-4-methoxy-1H-benzimidazol-1-yl)methyl)-3-pyridinecarbonitrile.

In a forty ninth embodiment, the invention provides 2-((3R,4R)-3-amino-4-fluoropiperidin-1-yl)-1-((5-chloropyrimidin-2-yl)methyl)-1H-benzo[d]imidazole-6-carbonitrile. In certain aspects of the forty ninth embodiment, the invention provides a pharmaceutically acceptable salt of (2-((3R,4R)-3-amino-4-fluoropiperidin-1-yl)-1-((5-chloropyrimidin-2-yl)methyl)-1H-benzo[d]imidazole-6-carbonitrile.

In a fiftieth embodiment, the invention provides (3R,4R)-4-fluoro-1-(1-((5-fluoropyrimidin-2-yl)methyl)-1H-benzo[d]imidazol-2-yl)piperidin-3-amine. In certain aspects of the fiftieth embodiment, the invention provides a pharmaceutically acceptable salt of (3R,4R)-4-fluoro-1-(1-((5-fluoropyrimidin-2-yl)methyl)-1H-benzo[d]imidazol-2-yl)piperidin-3-amine.

In a fifty first embodiment, the invention provides (3R,4R)-1-(1-((5-chloropyrimidin-2-yl)methyl)-6-fluoro-1H-benzo[d]imidazol-2-yl)-4-fluoropiperidin-3-amine. In certain aspects of the fifty first embodiment, the invention provides a pharmaceutically acceptable salt of (3R,4R)-1-(1-((5-chloropyrimidin-2-yl)methyl)-6-fluoro-1H-benzo[d]imidazol-2-yl)-4-fluoropiperidin-3-amine.

In a further aspect of each of the forty second to fifty first embodiment, each of the compounds and pharmaceutically acceptable salts provided therein may be used in the preparation of a medicament for use in treating a disease mediated by TRPC6 activity. In certain aspects, the compounds provided in the forty second to fifty first embodiment, or pharmaceutically acceptable salt thereof, may be used in the manufacture of a medicament for the treatment of a disease or disorder selected from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor or muscular dystrophy. In still other aspects, the compounds of the forty second to fifty first embodiment, or pharmaceutically acceptable salt thereof may be used in the preparation of a medicament for the treatment of nephrotic syndrome, membranous nephropathy and acute renal failure.

In a fifty second embodiment, a method of treating disease or disorder in a patient in need of therapy is provided, the method comprises the step of administering a pharmaceutically acceptable composition comprising a compound of any one of the forty second to fifty first embodiments, or a pharmaceutically acceptable salt thereof, wherein the disease or disorder is selected from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor or muscular dystrophy. In certain aspects of the fifty first embodiment the disease or disorder is selected from nephrotic syndrome, membranous nephropathy and acute renal failure.

In a further embodiment, the invention provides methods of making a compound of formula IIIb or a subformulae thereof.

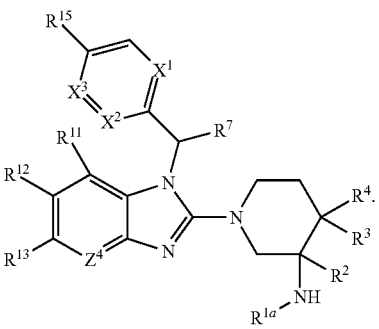
(IIIb)

The method comprising the synthetic steps of (a) Alkylating a halogenated benzimidazole having the formula:

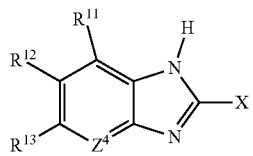

with an electrophilic moiety having the formula:

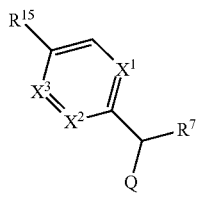

under basic conditions to provide an alkylated halogenated benzimidazole compound having the formula:

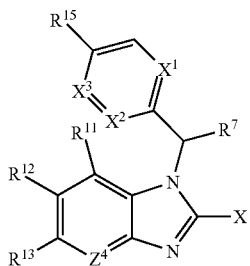

wherein X is chlorine, bromine or iodine and Q is chlorine, bromine, iodine, $C_1$-$C_6$alkylsulfonate or optionally substituted phenylsulfonate;

(b) Coupling the alkylated halogenated benzimidazole generated in step (a) with a protected piperidine having the formula:

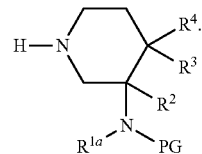

wherein PG is an amide protecting group stable to nucleophilic aromatic substitution (such as an alkoxycarbonyl protecting group) under conditions conducive to nucleophilic aromatic substitution to generate an alkylated 2-(piperidin-1-yl)benzimidazole compound having the formula:

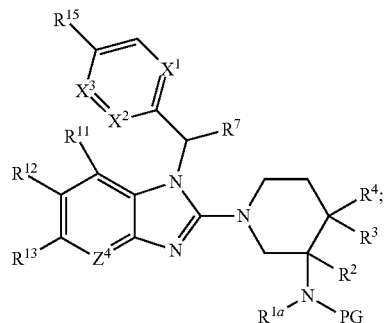

(c) removing PG from the alkylated 2-(piperidin-1-yl) benzimidazole compound formed in step (b) to generate the compound of Formula (IIIb), wherein variables $X^1$, $X^2$, $X^3$, $Z^4$, $R^{1a}$, $R^2$, $R^3$, $R^4$, $R^7$, $R^{11}$, $R^{12}$, $R^{13}$ and $R^{15}$ have the definitions provided in the thirtieth embodiment In preferred aspects of the synthetic method, the basic conditions of step (a) comprise contacting the halogenated benzimidazole with the electrophilic moiety in the presence of a carbonate base, such as potassium carbonate or more preferably cesium carbonate.

In a further embodiment, the invention provides methods of making compounds of formula IIIb or a subformulae thereof.

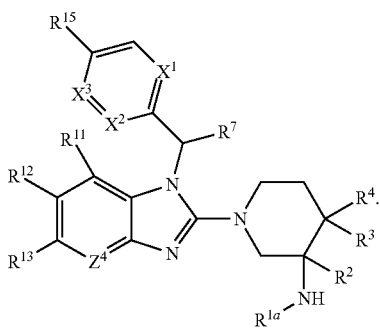
(IIIb)

The method comprising the synthetic steps of (a) Coupling a halogenated benzimidazole having the formula:

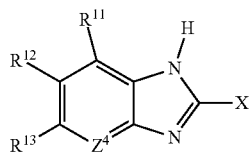

with a protected piperidine having the formula:

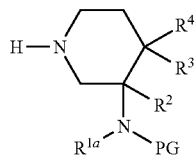

under conditions conducive to nucleophilic aromatic substitution to generate a 2-(piperidin-1-yl)benzimidazole compound having the formula:

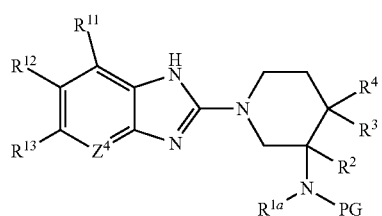

wherein X is chlorine, bromine or iodine and PG is an amide protecting group stable to nucleophilic aromatic substitution such as an alkoxycarbonyl protecting group;

(b) Alkylating the 2-(piperidin-1-yl)benzimidazole compound generated in step (a) with an electrophilic moiety having the structure

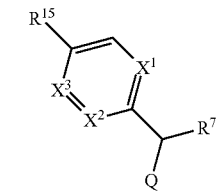

under basic conditions to provide an alkylated 2-(piperidin-1-yl)benzimidazole compound having the formula:

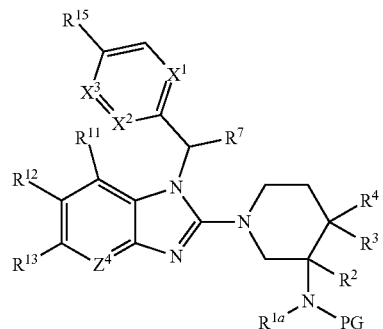

wherein Q is chlorine, bromine, iodine, $C_1$-$C_6$alkylsulfonate or optionally substituted phenylsulfonate;

(c) removing PG from the alkylated 2-(piperidin-1-yl) benzimidazole compound generated in step (b) to generate the compound of Formula (IIIb), wherein variables $X^1$, $X^2$, $X^3$, $Z^4$, $R^{1a}$, $R^2$, $R^3$, $R^4$, $R^7$, $R^{11}$, $R^{12}$, $R^{13}$ and $R^{15}$ have the definitions provided in the thirtieth embodiment.

In a further embodiment, the invention provides methods of making compounds of formula IIIb or a subformulae thereof.

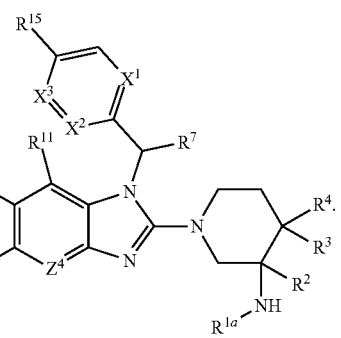
(IIIb)

The method comprising the synthetic steps of (a) Coupling a brominated isothiocyanate compound having the formula

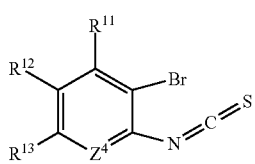

with a protected piperidine compound having the formula:

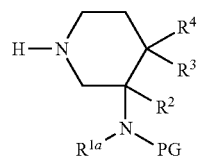

under conditions conducive to thiourea formation to generate a N,N'-disubstituted thiourea compound having the formula

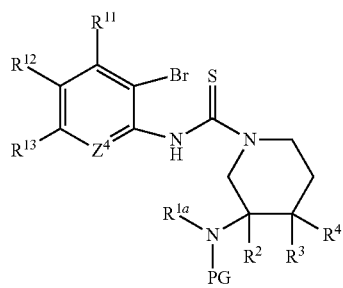

wherein PG is an amide protecting group such as an alkoxycarbonyl protecting group;

(b) Condensing the N,N'-disubstituted thiourea compound generated in step (a) with an amine compound having the formula

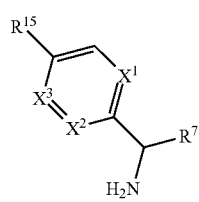

under conditions suitable to guanidine formation to provide a N,N',N"-trisubstituted guanidine compound having the formula:

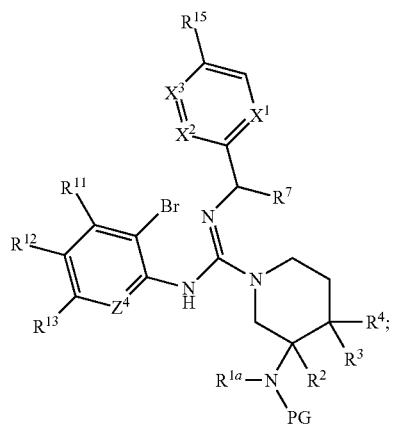

(c) Intramolecular cyclization of the N,N',N"-trisubstituted guanidine compound generated in step (b) in presence of a transition metal catalyst to form an alkylated 2-(piperidin-1-yl)benzimidazole compound having the formula:

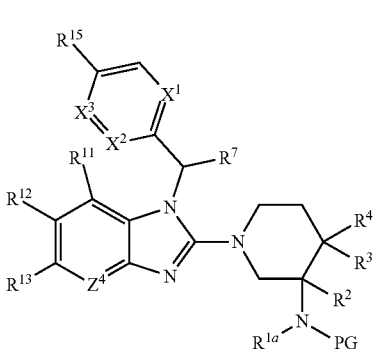

(d) removing PG from the alkylated 2-(piperidin-1-yl) benzimidazole compound generated in step (c) to provide a compound of Formula (IIIb), wherein variables $X^1$, $X^2$, $X^3$, $Z^4$, $R^{1a}$, $R^2$, $R^3$, $R^4$, $R^7$, $R^{11}$, $R^{12}$, $R^{13}$ and $R^{15}$ have the definitions provided in the thirtieth embodiment.

In a further embodiment, the invention provides methods of making compounds of formula IIId or a subformulae thereof.

(IIId)

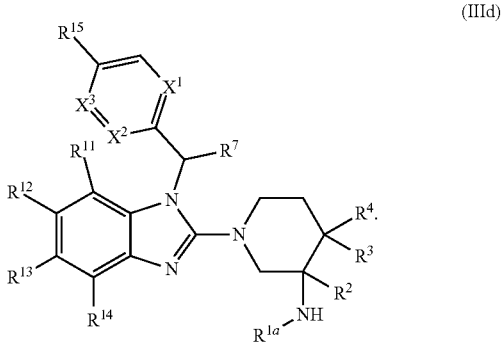

The method comprising the synthetic steps of a) coupling an optionally substituted ortho-fluoro nitrobenzene compound having the formula:

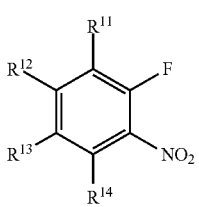

with a primary amine having the formula:

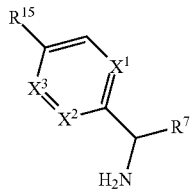

under conditions suitable for nucleophilic aromatic substitution to provide a secondary amine amine having the formula:

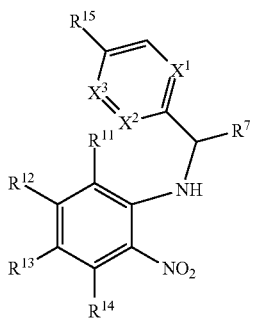

b) generating an alkylated-2-chlorobenzimidazole compound having the formula:

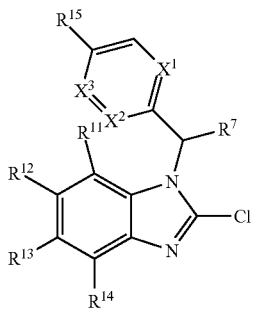

by reduction of the nitro substitutent in the secondary amine compounds generated in step (a) to form in situ a dianiline compound, cyclizing said dianiline with a carbonyl source and clorination (with a chlorine source such as e.g., P(O)Cl₃) to generate the alkylated-2-chlorobenzimidazole compound:

c) coupling the alkylated-2-chlorobenzimidazole compound generated in step (b) with a protected piperidine having the formula:

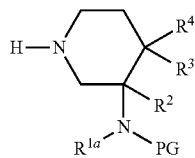

under conditions suitable for nucleophilic aromatic substitution to generate an alkylated 2-(piperidin-1-yl)benzimidazole compound having the formula:

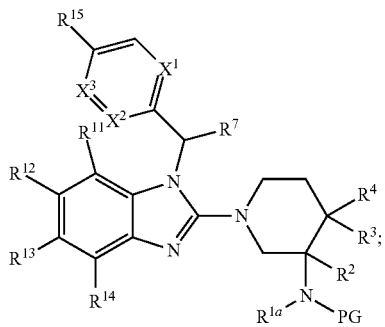

d) removing the PG from the alkylated 2-(piperidin-1-yl)benzimidazole compound generated in step (c), to generate the compound of Formula (IIId), wherein variables $X^1$, $X^2$, $X^3$, $R^{1a}$, $R^2$, $R^3$, $R^4$, $R^7$, $R^{11}$, $R^{12}$, $R^{13}$, $R^{14}$ and $R^{15}$ have the definitions provided in the thirtieth embodiment.

In a further embodiment, the invention provides methods of making compounds of formula VII or a subformulae thereof.

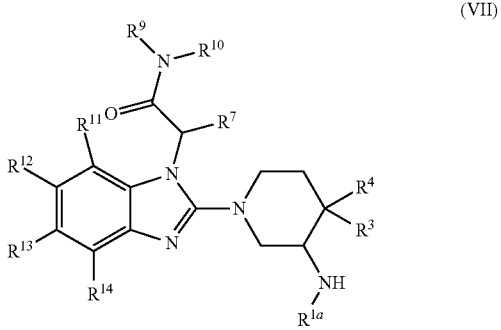

(VII)

(a) Coupling a halogenated benzimidazole having the formula:

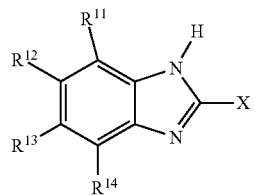

with a protected piperidine having the formula

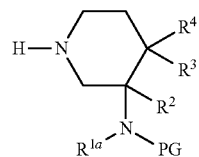

under conditions conducive to nucleophilic aromatic substitution to generate a 2-(piperidin-1-yl)benzimidazole compound having the formula

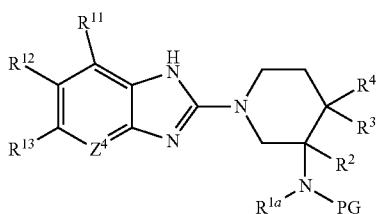

wherein X is chlorine, bromine or iodine and PG is an amide protecting group stable to nucleophilic aromatic substitution such as an alkoxycarbonyl protecting group;

(b) Alkylating the 2-(piperidin-1-yl)benzimidazole compound generated in step (a) with a halo ester,

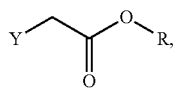

wherein Y is X is chlorine, bromine or iodine and R is $C_1$-$C_6$alkyl, to generate an substituted 1-acetyl-2-(piperidin-1-yl)benzimidazole compound having the formula:

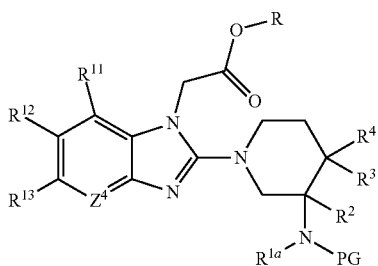

(c) Saponification of the substituted 1-acetyl-2-(piperidin-1-yl)benzimidazole compound generated in step (b) to provide a free acid followed by amination with an amine, $HNR^9R^{10}$, under conditions conducive to amide bond formation to provide a 1-[(2-piperidin-1-yl)benzimidazole)] acetamide compound;

(d) removing PG from the 1-[(2-piperidin-1-yl)benzimidazole)]acetamide compound generated in step (c) to generate the compound of Formula (VII), wherein variables $X^1$, $X^2$, $X^3$, $Z^4$, $R^{1a}$, $R^2$, $R^3$, $R^4$, $R^7$, $R^{11}$, $R^{12}$, $R^{13}$ and $R^{15}$ have the definitions provided in the thirty fourth embodiment.

In another embodiment, pharmaceutical compositions are provided which comprise one or more pharmaceutically acceptable carriers and a therapeutically effective amount of a compound of any one of formulae I or a subformulae thereof. In some aspects, the composition is formulated in a form selected from the group consisting of an injectable fluid, an aerosol, a tablet, a pill, a capsule, a syrup, a cream, a gel and a transdermal patch.

In another embodiment, combinations, in particular pharmaceutical combinations, are provided which comprise a therapeutically effective amount of the compound any one of formulae I or a subformulae thereof.

In another embodiment, methods of modulating TRPC protein activity in a subject are provided which methods comprise administering to the subject a therapeutically effective amount of Formula I or a subformulae thereof. In preferred aspects of the embodiment, methods of inhibiting TRPC6 activity in a subject are provided, which methods comprise administering to the subject a therapeutically effective amount of a compound of Formula I or subformulae thereof. In certain aspects of the embodiment, method of inhibiting TRPC6 activity in a subject are provided, which methods comprise administering to the subject a therapeutically effective amount of a compound of Formula I or subformulae thereof.

In yet other embodiments, methods of treating a disorder or a disease in a subject mediated by TRPC protein activity are provided, in particular methods of treating a disease or disorder mediated by TRPC6 protein activity are provided. The methods comprise administering to the subject a therapeutically effective amount of the compound of Formula I or a subformulae thereof.

In another embodiment, methods of treating or preventing a disease or disorder are provided where the disease or disorder is selected from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor or muscular dystrophy which method comprises the step of administering to a subject in need of therapy a therapeutically effective amount of a compound or salt of Formula I or a subformulae thereof. In certain aspects of this embodiment, the method comprises treating a disease or disorder selected from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor or muscular dystrophy. In certain instances, the treatment methods and/or the prevention methods are suitable for the treatment and or prevention nephrotic syndrome, membranous nephropathy, and acute renal failure.

In another aspect, the invention provides for the use of compounds of Formula I or a subformulae thereof for use in the preparation of a medicament or for use in the manufacture of a medicament for the treatment of a disorder or disease in a subject mediated by TRPC protein activity. In certain other aspects, the invention provides for the use of a compound according to formula I or a subformulae thereof in the treatment of nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor or muscular dystrophy. In certain instances, the invention provides for the use of compounds of Formula I or a subformulae thereof for use in the preparation of a medicament or for use in the manufacture of a medicament or the treatment of a disease or disorder in a subject selected from nephrotic syndrome, membranous nephropathy, and acute renal failure.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 20 carbon atoms, 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. Unless otherwise provided, alkylene refers to moieties having 1 to 20 carbon atoms, 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, which is substituted with one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "hydroxy alkyl" refers to an alkyl as defined herein which is substituted with one or more hydroxy groups. The term "hydroxy cycloalkyl-alkyl" refers to an alkyl group that is substituted with a cycloalkyl group, as defined herein, and further substituted with a hydroxy group. The hydroxy group can be on the alkyl group, the cycloalkyl group, or on each of the alkyl and cycloalkyl groups.

The term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl, each of which may optionally be substituted with 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S-nitro, cyano, carboxy, alkyl-O—C(O)—, carbamoyl, alkyl-S(O)—, sulfonyl, sulfonamido, phenyl, and heterocyclyl.

As used herein, the term "heterocycle," "heterocyclyl," "heterocycloalkyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran, dihydrofuran, 1, 4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, azetidine, thiazolidine, morpholine, and the like.

As used herein, the term "azacycle" refers to a heterocycle which comprises at least one ring nitrogen atoms and which may optionally comprise 0, 1 or 2 additional ring heteroatoms selected from N, O or S.

As used herein, the term "cycloalkyl" refers to saturated or partially unsaturated monocyclic, bicyclic or tricyclic hydrocarbon groups of 3-12 carbon atoms. For the avoidance of doubt, cycloalkyl is not intended to include aromatic groups such as naphthylene or phenyl. Unless otherwise provided, cycloalkyl refers to cyclic hydrocarbon groups having between 3 and 9 ring carbon atoms or between 3 and 7 ring carbon atoms, each of which can be optionally substituted with one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. The term "hydroxy cycloalkyl" refers specifically to a cycloalkyl group substituted with one or more hydroxy groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "cycloalkoxy" refers to cycloalkyl-O— and cycloalkyl-alkyl-O, wherein cycloalkyl and alkyl are defined herein above. Representative examples of cycloalkoxy include, but are not limited to, cyclopropyloxy, cyclobutyloxy, cyclopentyloxy, 1-methylcyclopropyloxy, cyclopropylmethoxy, 1-methylcyclobutyloxy and the like. Typically, cycloalkoxy groups have about 3-7, more preferably about 3-6 carbon atoms.

Divalent substituents are represented with a "diyl" suffix. Thus a divalent alkyl linker is referred to as an alkandiyl group and a divalent cycloalkane group is referred to as a cycloalkandiyl (e.g., cyclopropandiyl).

As used herein, the term "heteroaryl" refers to a 5-14 membered monocyclic- or bicyclic- or tricyclic-aromatic ring system, having 1 to 8 heteroatoms selected from N, O and S. In certain preferred aspects, the heteroaryl is a 5-10 membered ring system (e.g., 5-7 membered monocycle or an 8-10 membered bicycle) or a 5-7 membered ring system. Exemplary monocyclic heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, and 5-pyrimidinyl. Exemplary bicyclic heteroaryl groups include 1-, 3-, 4-, 5-, 6-, 7-, or 8-isoquinolinyl, 2-, 3-, 4-, 5-, 6-, 7-, or 8-quinolinyl, 1-, 3-, 4-, 5-, 6-, 7-, or 8-isoquinolinyl, 1-, 2-, 4-, 5-, 6-, 7-, or 8-benzimidazolyl and 1-, 2-, 3-, 4-, 5-, 6-, 7-, or 8-indolyl.

The term "heteroaryl" also refers to a group in which a heteroaromatic ring is fused to one or more aryl, cycloaliphatic, or heterocyclyl rings, where the radical or point of attachment is on the heteroaromatic ring.

The terms "bicycle" and "bicyclyl" refers to a ring system having two fused rings each of which rings may be carbocyclic or heterocyclic and each of which rings may be saturated, unsaturated or aromatic.

As used herein, the term "halogen" or "halo" refers to fluoro, chloro, bromo, and iodo.

As used herein, the term "optionally substituted" unless otherwise specified refers to a group that is unsubstituted or is substituted with one or more, typically 1, 2, 3 or 4, suitable non-hydrogen substituents. If the identity of the "optional substituent" is not clearly defined in context of the optionally substituted group, then each optional substituent is independently selected from the group consisting of: alkyl, hydroxy, halogen, oxo, amino, alkylamino, dialkylamino, alkoxy, cycloalkyl, $CO_2H$, heterocycloalkyloxy (which denotes a heterocyclic group bonded through an oxygen bridge), —$CO_2$alkyl, mercapto, nitro, cyano, sulfamoyl, sulfonamide, aryl, —OC(O)alkyl, —OC(O)aryl, aryl-S—, aryloxy; alkylthio, formyl (i.e., HC(O)—), —C(O)$NH_2$, aralkyl (alkyl substituted with aryl), aryl and aryl substituted with alkyl, cycloalkyl, alkoxy, hydroxy, amino, alkyl-C(O)—NH—, alkylamino, dialkylamino or halogen. It is understood that where a group is indicated to be optionally substituted, the disclosure includes embodiments in which the group is unsubstituted as well as embodiments in which the group is substituted.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The use of "rel" indicates that the diastereomeric orientation is known but the absolute stereochemistry is not. In cases where the absolute stereochemistry has not been determined the optical rotation and/or chiral chromatography conditions will indicate which isomer is present.

"Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line or retention time on chiral chromatography separation. Certain of the compounds described herein contain one or more asymmetric centers or axes and may thus give rise to enantiomers, diastereomers, and other stereoisomeric forms that may be defined, in terms of absolute stereochemistry, as (R)- or (S)-, or with the (+) or (−) sign. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

It is understood that for any compound provided herein, including any compound of Formula (I), or any embodiment thereof, or any compound of Table A, B, or C, or a salt of any of the foregoing, the compound may exist in any stereochemical form, such as a single enantiomer, diastereomer, or tautomer or a mixture of one or more enantiomers, diastereomers, and tautomers in any ratio.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, benzenesuflonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper. In certain other embodiments, the salts are selected from ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds as disclosed herein in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds as disclosed herein in $C_1$-$C_4$alkyl sufonic acid, benzenesulfonic acid or mono-, di- or tri-$C_1$-$C_4$alkyl substituted benzene sulfonic acid addition salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{124}$I, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and salts thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has at least 50% deuterium incorporation at each designated deuterium atom, 60% deuterium incorporation, at least 75% deuterium incorporation, at least 90% deuterium incorporation, at least 95% deuterium incorporation, at least 99% deuterium incorporation, or at least 99.5% deuterium incorporation.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (i) mediated by TRPC6 activity, or (ii) associated with TRPC6 activity; or (2) inhibiting the activity of TRPC6. In another non-limiting embodiment, the term "a therapeutically effective amount" refers to the amount of the compound of the present invention that, when administered to a cell, or a tissue, or a non-cellular biological material, or a medium, is effective to at least partially inhibit TRPC6 activity.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevent," "preventing" or "prevention" of any disease or disorder refers in one embodiment, to delay or avoidance of onset of the disease or disorder (i.e., slowing or preventing the onset of the disease or disorder in a patient susceptible to development of the disease or disorder).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)— or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) or supercritical fluid chromatography (SFC) using a chiral adsorbent.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Intermediates and final products can be worked up and/or purified according to standard methods, e.g. using chromatographic methods, distribution methods, (re-) crystallization, and the like.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any process steps disclosed herein can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Typically, the pharmaceutical compositions are tablets or gelatin capsules comprising the active ingredient together with one or more of: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners. Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin. Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives. As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds disclosed herein in free form or in pharmaceutically acceptable salt form, exhibit valuable pharmacological properties, e.g. TRPC protein modulating properties and more particularly inhibition of TRPC6 protein activity, e.g. as indicated in in vitro and in vivo tests as provided in the next sections and are therefore indicated for therapy.

The present invention provides methods of treating a disease or disorder associated with TRPC6 protein activity by administering to a subject in need thereof an effective amount of a compound disclosed herein. In certain aspects, the disease or disorder suitable for therapy by administration of the compound of the invention include, but are not limited to, nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor or muscular dystrophy. In certain instances, the patient is suffering from nephrotic syndrome, membranous nephropathy, and acute renal failure.

In a specific embodiment, the present invention provides a method of treating or preventing renal disease by administering to a subject in need thereof an effective amount of a compound disclosed herein. In certain embodiments, patients who are currently asymptomatic but are at risk of developing renal disease are suitable for administration with a compound of the invention. The methods of treating or preventing renal disease include, but are not limited to, methods of treating or preventing nephrotic syndrome, membranous nephropathy, acute renal failure, sepsis, chronic renal failure and diabetic nephropathy.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by in vitro & in vivo methods, such as those described in the examples below.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound disclosed herein and at least one other therapeutic agent as a combined preparation for simultaneous, separate or sequential use in therapy. In one embodiment, the therapy is the treatment of a disease or condition mediated by TRPC protein activity. In preferred aspects, the therapy is a treatment for nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor, or muscular dystrophy.

Products provided as a combined preparation include a composition comprising the compound disclosed herein and the other therapeutic agent(s) together in the same pharmaceutical composition, or the compound disclosed herein and the other therapeutic agent(s) in separate form, e.g. in the form of a kit.

In one embodiment, the invention provides a pharmaceutical composition comprising a compound as disclosed herein and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers.

Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound as disclosed herein for treating a disease or condition mediated by TRPC protein activity wherein the medicament is prepared for administration with another therapeutic agent. The invention also provides the use of another therapeutic agent for treating a disease or condition mediated by the TRPC protein activity, wherein the medicament is administered with a compound as disclosed herein. In another aspect, the invention provides the use of a compound as disclosed herein for treating a disease or disorder selected from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor, or muscular dystrophy wherein the medicament is prepared for administration with another therapeutic agent. The invention also provides the use of another therapeutic agent for treating a disease or disorder selected from nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor, or muscular dystrophy, wherein the medicament is administered with a compound as disclosed herein.

The invention also provides a compound as disclosed herein for use in a method of treating a disease or condition mediated by TRPC protein activity wherein the compound is prepared for administration with another therapeutic agent. The invention also provides another therapeutic agent for use in a method of treating a disease or condition mediated by TRPC protein activity, wherein the other therapeutic agent is prepared for administration with a compound as disclosed herein. The invention also provides a compound as disclosed herein for use in a method of treating a disease or condition mediated by TRPC protein activity, wherein the compound is administered with another therapeutic agent. The invention also provides another therapeutic agent for use in a method of treating a disease or condition mediated by TRPC protein activity, wherein the other therapeutic agent is administered with a compound as disclosed herein.

The invention also provides the use of a compound as disclosed herein for treating a disease or condition mediated by TRPC protein activity wherein the patient has previously (e.g. within 24 hours) been treated with another therapeutic agent. The invention also provides the use of another therapeutic agent for treating a disease or condition mediated by TRPC protein activity wherein the patient has previously (e.g. within 24 hours) been treated with a compound as disclosed herein.

The pharmaceutical compositions can be administered alone or in combination with other molecules known to have a beneficial effect in treatment of kidney disease or more particularly in the treatment of FSGS, nephrotic syndrome, minimal change diseases or diabetic kidney disease. A combination therapy regimen may be additive, or it may produce synergistic results (e.g., improvement in kidney function which is more than expected for the combined use of the two agents). In some embodiments, the present invention provide a combination therapy for preventing and/or treating kidney disease or more particularly FSGS, nephrotic syndrome or minimal change diseases with a compound of the invention and a second therapeutic agent selected from the group consisting of ACE/ARB (such as captopril, llisinopril or losartan), steroid therapy (such as prednisone), immunomodulators (such as mycophenolate mofetil, tacrolimus or cyclosporine A), adrenocorticotropic hormone analogs (such acthar gel), anti-CD20 antibodies (such as rituximab), calcium channel blockers (such as amlodipine), diuretics (such as hydrochlorothiazide), anti-platelet agents (such as dipyridamole), anticoagulants (such as heparin), DPP-4 inhibitors (such as sitagliptin), SGLT2 inhibitors (such as dapagliflozin), anti-hyperlipidemia (such as rosuvastatin), anemia therapy (darbepoetin alfa), or anti-hyperuricemia (febxostat).

In one embodiment, the invention provides a method of inhibiting the activity of a TRPC protein, or more preferably inhibiting the activity of TRPC6 protein, in a subject, wherein the method comprises administering to the subject a therapeutically effective amount of the compound according to the definition of Formula (I). The invention further provides methods of inhibiting the activity of a TRPC protein, or more preferably inhibiting the activity of TRPC6 protein in a subject by administering a compound as disclosed herein, wherein the method comprises administering to the subject a therapeutically effective amount of the compound as disclosed herein.

In one embodiment, the invention provides a compound as disclosed herein, for use as a medicament.

In one embodiment, the invention provides the use of a compound as disclosed herein for the treatment of a disorder or disease in a subject characterized by the activity of a TRPC protein, or more preferably the activity of TRPC6 protein. In particular, the invention provides the use of a compound as disclosed herein for the treatment of a disorder or disease mediated by the activity of a TRPC protein, or more preferably the activity of TRPC6 protein, e.g., nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), zheart failure, stroke, malignant tumor, or muscular dystrophy. In certain preferred aspects, the invention provides for the use of a compound as disclosed herein for the treatment of a disorder or disease mediated by the activity of TRPC6 protein selected from nephrotic syndrome, membranous nephropathy and acute renal failure.

In one embodiment, the invention provides the use of a compound as disclosed herein in the manufacture of a medicament for the treatment of a disorder or disease in a subject characterized by activity of a TRPC protein, or more preferably the activity of TRPC6 protein. More particularly in the manufacture of a medicament for the treatment of a disease or disorder in a subject characterized by activity of a TRPC protein, or more preferably the activity of TRPC6 protein, e.g., nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor, or muscular dystrophy. In certain preferred aspects, the invention provides the use of a compound as disclosed herein in the manufacture of a medicament for the treatment of nephrotic syndrome, membranous nephropathy and acute renal failure.

In one embodiment, the invention provides the use of a compound as disclosed herein for the treatment of a disorder or disease in a subject characterized by activity of a TRPC protein, or more preferably the activity of TRPC6 protein. More particularly, the invention provides uses of the compounds provided herein in the treatment of a disease or disorder characterized by activity of a TRPC protein, or more preferably the activity of TRPC6 protein, e.g., nephrotic syndrome, minimal change disease, focal segmental glomerulosclerosis, collapsing glomerulopathy, membranous nephropathy, membranoproliferative glomerulonephritis, IGA nephropathy, acute renal failure, chronic renal failure, diabetic nephropathy, sepsis, pulmonary hypertension, acute lung disorder, acute respiratory distress syndrome (ARDS), heart failure, stroke, malignant tumor, or muscular dystrophy. In certain embodiments, the uses of the compounds provided herein is for the treatment of a disease or disorder is selected from nephrotic syndrome, membranous nephropathy and acute renal failure.

In a specific embodiment, the present invention provides use of the compounds of the invention for treating or preventing nephrotic syndrome, membranous nephropathy, acute renal failure, sepsis, chronic renal failure, diabetic nephropathy, pulmonary hypertension, acute lung disorder, acute respiratory distress syndrome (ARDS), heart failure, stroke, malignant tumor or muscular dystrophy. In certain embodiments, patients who are currently asymptomatic but are at risk of developing a symptomatic nephrotic syndrome, membranous nephropathy, acute renal failure, sepsis, chronic renal failure, diabetic nephropathy, pulmonary hypertension, acute lung disorder, acute respiratory distress syndrome (ARDS), heart failure, stroke, malignant tumor or muscular dystrophy are suitable for administration with a compound of the invention. The use in treating or preventing nephrotic syndrome, membranous nephropathy, acute renal failure, sepsis, chronic renal failure, diabetic nephropathy, pulmonary hypertension, acute lung disorder, acute respiratory distress syndrome (ARDS), heart failure, stroke, malignant tumor or muscular dystrophyinclude, but are not limited to, uses in treating or preventing one or more symptoms or aspects of nephrotic syndrome, membranous nephropathy, acute renal failure, sepsis, chronic renal failure, diabetic nephropathy, pulmonary hypertension, acute lung disorder, acute respiratory distress syndrome (ARDS), heart failure, stroke, malignant tumor or muscular dystrophy.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

The following examples are intended to illustrate the invention and are not to be construed as being limitations thereon. Temperatures are given in degrees centigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Biotage. Mass spectral data was determined by electrospray ionization technique. All examples were purified to >95% purity as determined by high-performance liquid chromatography. Unless otherwise stated, reactions were run at room temperature.

Commercially available materials were purchased from Sigma Aldrich, HDH Pharma, Pharmablock, Alfa Aesar, Enovation Chemicals, and Combi-Blocks.

Compound names, i.e., IUPAC names, for compounds described in the instant application were generated using ChemDraw compound naming software.

The following abbreviations are used:
CDI—1,1'-carbonyldiimidazole
DCM—dichloromethane
DMSO—dimethyl sulfoxide
DMF—N,N-dimethylformamide
THF—tetrahydrofuran
Et$_2$O—diethyl ether
EtOAc—ethyl acetate
EtOH—ethyl alcohol
Ms—mesylate
MeCN—acetonitrile
MeOH—methyl alcohol
SFC—supercritical fluid chromatography
TFA—trifluoroacetic acid
tmp—2,2,6,6-tetramethylpiperidine
h—hour
min—min
rt—room temperature (22-25° C.)
mL milliliters
μL microliters
g grams
μg micrograms
mg milligrams
μmoL micromolars

GENERAL METHOD OF PREPARATION

The compounds described herein are prepared using techniques known to one skilled in the art through the reaction sequences depicted in schemes 1-6 as well as by other methods. Furthermore, in the following schemes, where specific acids, bases, reagents, coupling agents, solvents, etc. are mentioned, it is understood that other suitable acids, bases, reagents, coupling agents, solvents, etc. may be used and are included within the scope of the present invention.

Synthesis of selected compounds of the present invention were prepared as described in Scheme 1. CDI coupling of the desired bis-anline provided the corresponding benzimidazolone. Subjection to refluxing POCl$_3$ delivered the chlorobenzimidazole. These intermediates could be alkylated with a variety of electrophiles, then subjected to SnAr conditions to provide the Boc protected penultimate intermediates. Exposure to a variety of acids effected Boc deprotection to furnish the final products.

Scheme 1

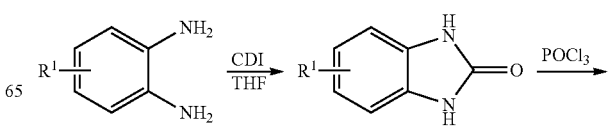

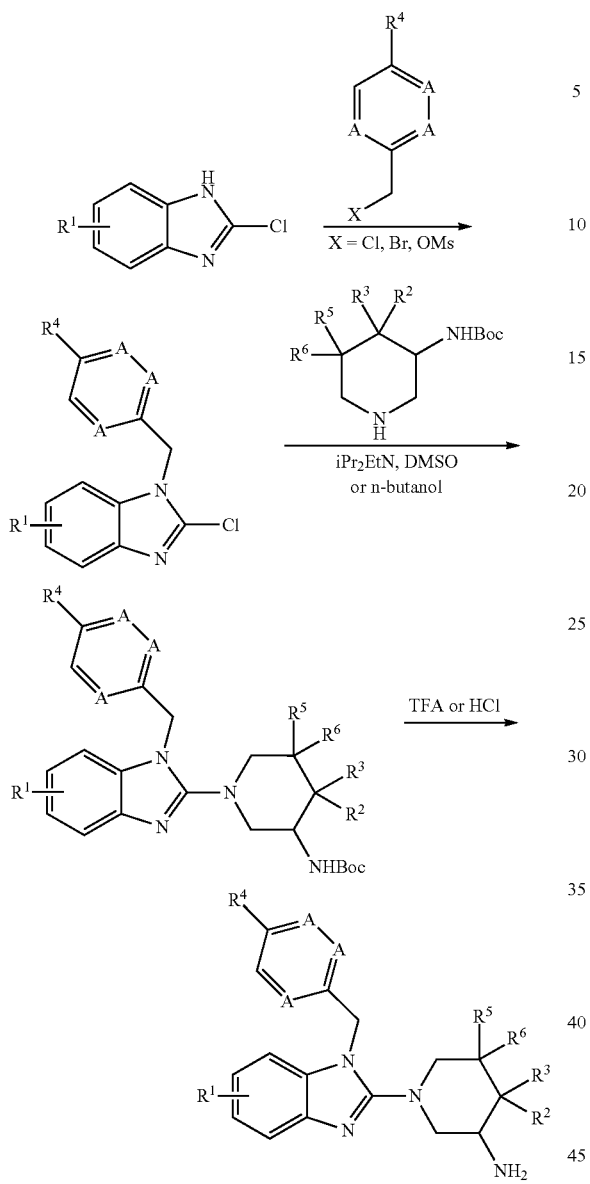

An alternative approach to benzimidazole intermediates which was used to synthesize additional compounds in the present invention is shown in Scheme 2. CDI coupling of the desired bis-aniline provided the corresponding benzimidazolone. Subjection to refluxing POCl₃ delivered the chlorobenzimidazole. These intermediates were heated with base and nucleophile to provide the SnAr products. Alkylation with a variety of electrophiles followed by acidic Boc deprotection furnished the final compounds.

Additionally, examples in this invention could be synthesized by the methods shown in Scheme 3-6.

Scheme 2

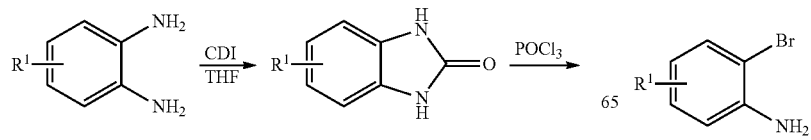

Scheme 3

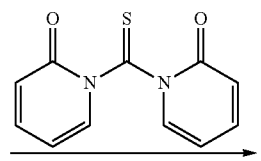

-continued

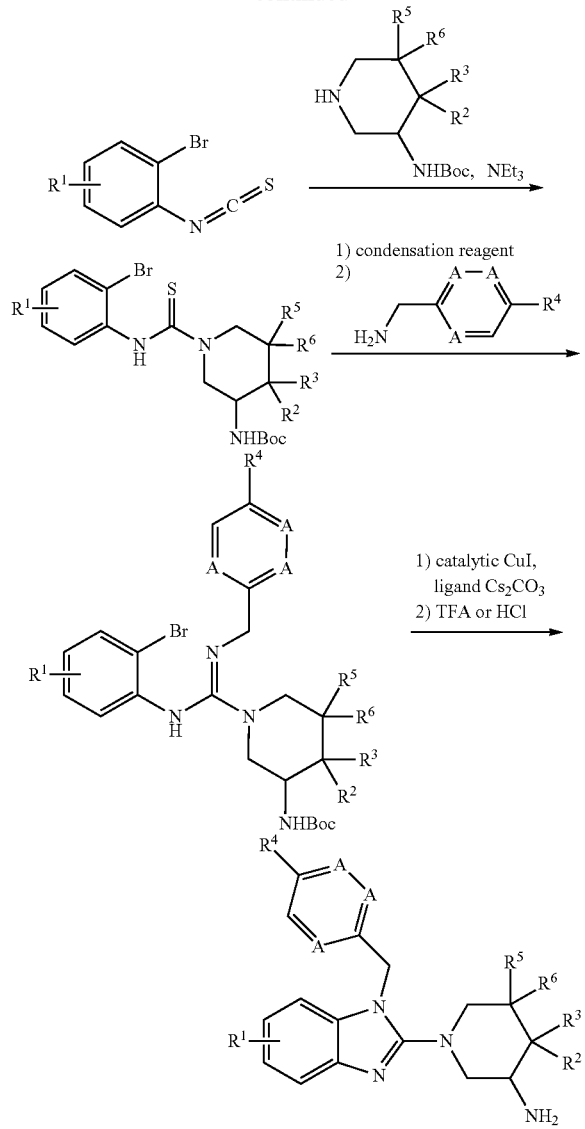

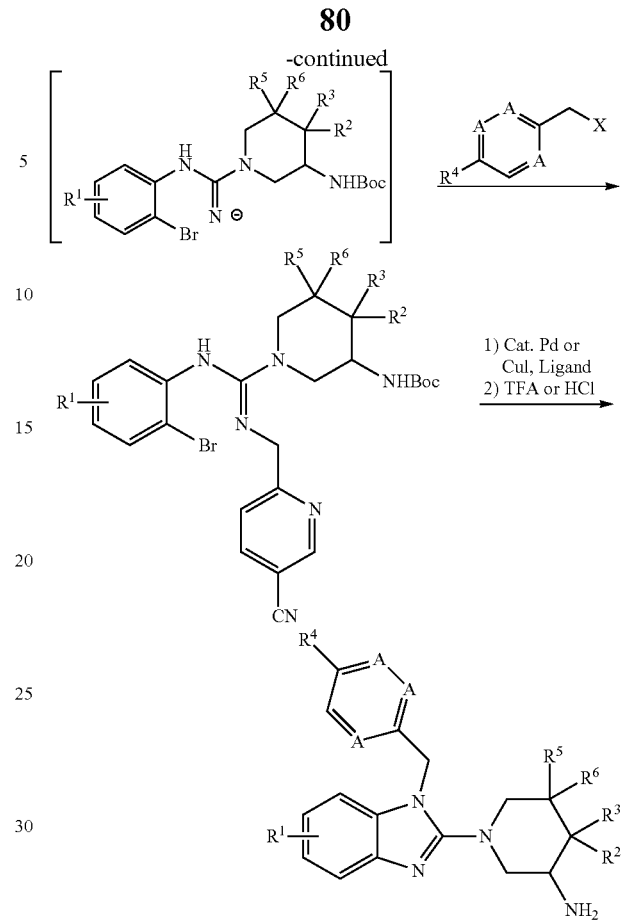

Isothiocyanate formation was accomplished using a variety of reagents. Addition of secondary amines followed by condensation with primary amines provided the corresponding substituted quanidine. Intramolecule cyclizations were accomplished using copper catalysis. Final acidic Boc deprotection furnished the desired compounds.

Subjection of substituted piperidines to cyanogen bromide provided the corresponding peperidine-1-carbonitriles. These were susceptible to nucleophile attack by a variety of anliline nucleophiles, which were then trapped with benzyl electrophiles. The corresponding guanidine underwent intramolecule crosscoupling under palladium and copper catalysis. Final Boc deprotection under acidic conditions furnished the desired compounds.

Scheme 4

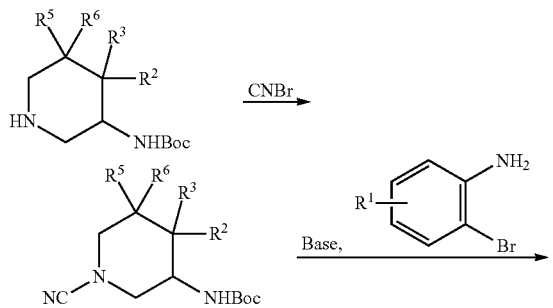

Scheme 5

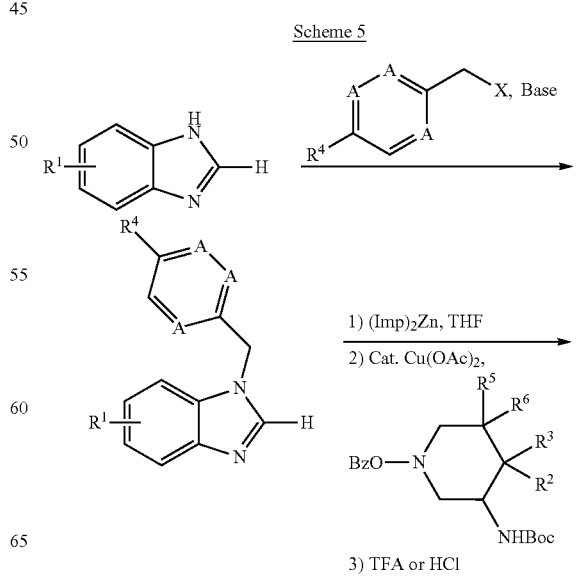

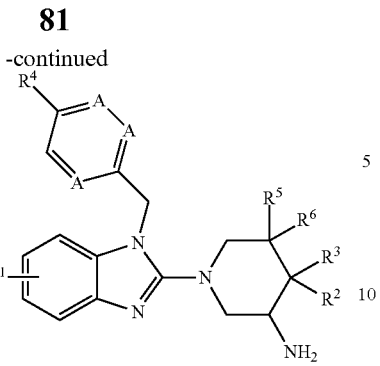

Benzimidazoles were alkylated with a variety of electrophiles and base. These intermediates were subjected to Zn(tmp)$_2$, copper catalysis, and benzoylhydroxylamines to furnish the aminated products. Final subjection to acidic Boc deprotection conditions yielded the desired products.

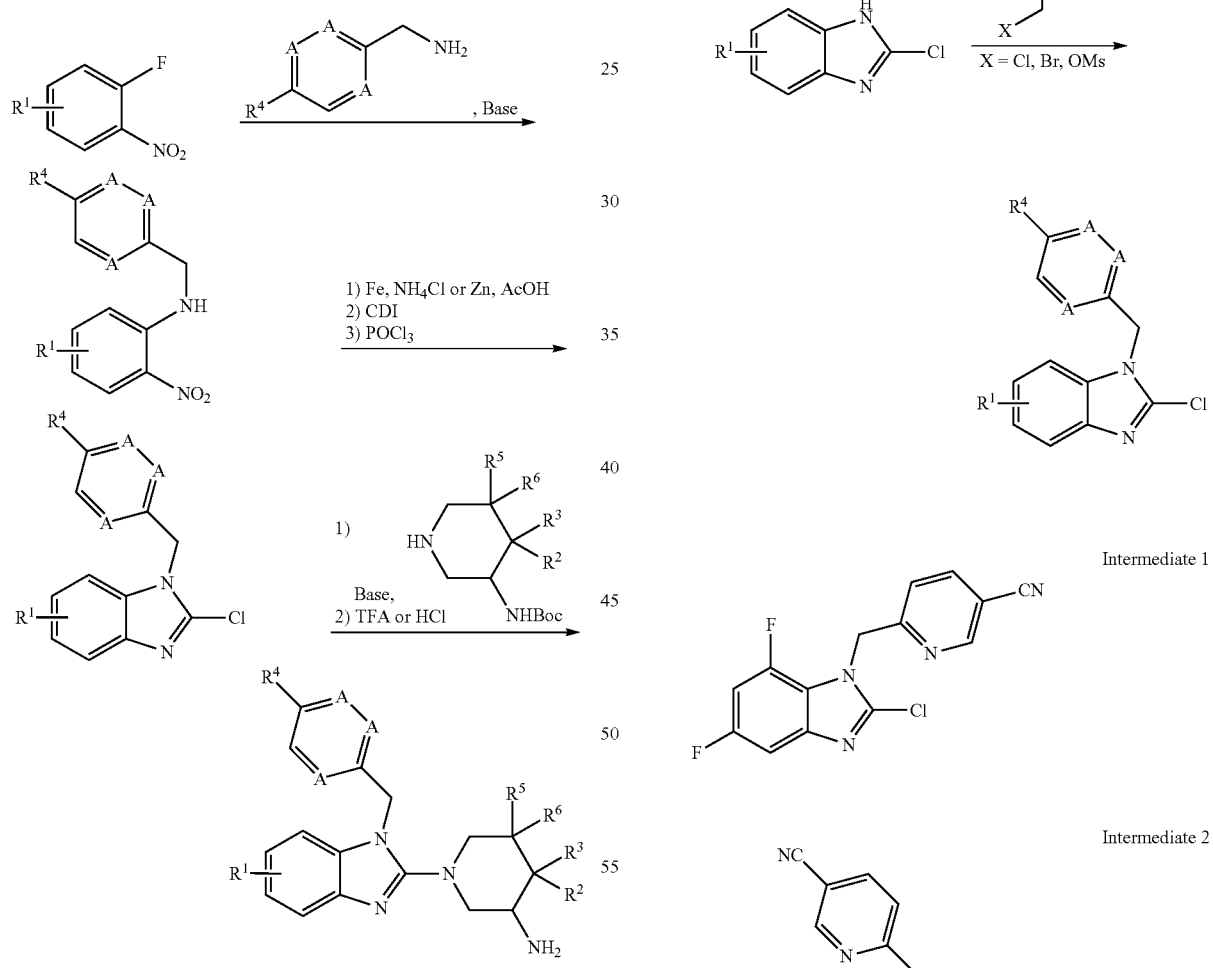

Scheme 6

Scheme 7. General Synthesis of Alkylated Intermediates

SnAr transformations were accomplished on substituted fluoro-nitrobenzenes using primary benzyl amines and base. The corresponding nitro intermediates were reduced with iron or zinc, then subjected to CDI couplings and POCl$_3$ chlorination reactions. These intermediates were resubjected to SnAr conditions then Boc deprotected under acidic conditions to furnish the final compounds.

Intermediate 1

Intermediate 2

Intermediate 1: 6-((2-chloro-5,7-difluoro-1H-benzo[d]imidazol-1-yl)methyl)nicotinonitrile and Intermediate 2: 6-((2-chloro-4,6-difluoro-1H-benzo[d]imidazol-1-yl)methyl)nicotinonitrile

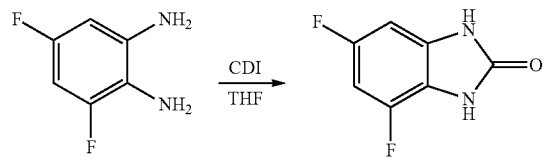

Step 1. 4,6-difluoro-1H-benzo[d]imidazol-2(3H)-one 3,5-difluorobenzene-1,2-diamine (210.0 g, 1.457 mol, 1.0 equiv) and CDI (236.0 g, 1.457 mol, 1.0 equiv) were dissolved in anhydrous THF (2.5 L, 11.9 mL/g) and stirred for 12 h at room temperature. LCMS indicated completion of the reaction. Reaction mixture was diluted with water (6.0 L) and extracted with ethyl acetate (2×6.0 L). The combined organic layer was dried over sodium sulphate, filtered and concentrated under reduced pressure to provide crude 4,6-difluoro-1H-benzo[d]imidazol-2(3H)-one as black solid which was used for next step without further purification. $^1$H NMR (400 MHz, DMSO-$d_6$): δ 11.20 (s, 1H), 11.05 (s, 1H), 6.85 (td, J=10.7, 2.2 Hz, 1H), 6.69 (dd, J=8.6, 2.2 Hz, 1H). MS (ESI, pos. ion) m/z: 171.0 [M+1]

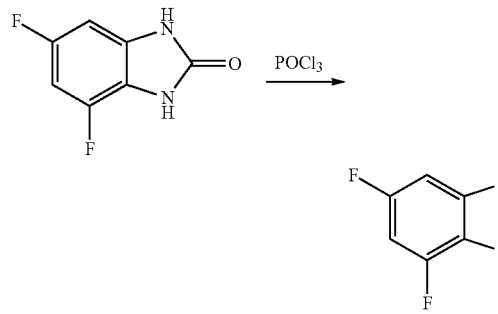

Step 2. 2-chloro-4,6-difluoro-1H-benzo[d]imidazole 4,6-difluoro-1H-benzo[d]imidazol-2(3H)-one (180.0 g, 1.058 mol, 1.0 equiv) was suspended in POCl$_3$ (2.0 L) and heated under stirring at 110° C. for 2 h, at which time LCMS indicated completion of the reaction. Excess POCl$_3$ was removed via vacuum distillation and the remaining residue was diluted with acetonitrile (1.0 L) and sat. aq. sodium bicarbonate solution (1.0 L), then extracted with ethyl acetate (2×4.0 L). The combined organic layer was dried over sodium sulfate, filtered and concentrated under reduced pressure to provide 2-chloro-4,6-difluoro-1H-benzo[d]imidazole as brown solid which was used for next reaction without further purification. $^1$H NMR (400 MHz, DMSO-$d_6$): 13.40 (bs, 1H), 7.31-7.03 (m, 2H). MS (ESI, pos. ion) m/z: 189.0 [M+1].

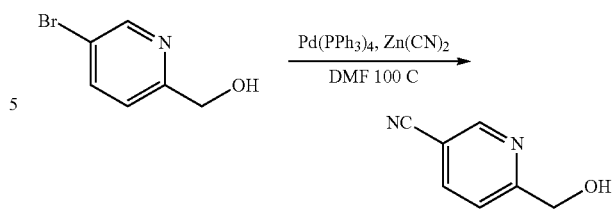

Step 3. 6-(hydroxymethyl)nicotinonitrile (5-bromopyridin-2-yl)methanol (75.0 g, 399.0 mmol, 1.0 equiv), zinc cyanide (141.0 g, 1.197 mol, 3.0 equiv) and tetrakis(triphenylphosphine)palladium(0) (46.1 g, 39.9 mmol, 0.1 equiv) were dissolved in N,N-dimethylformamide (750.0 mL, 10.0 mL/g) and degassed with nitrogen for 30 minutes. The reaction mixture was heated at 110° C. for 2 h. LCMS indicated formation of the product. After completion of the reaction, the mixture was allowed to cool to room temperature, diluted with water (700 mL) and extracted with ethyl acetate (3×700 mL). The combined organic layers were dried over sodium sulfate, filtered and concentrated under reduced pressure. The crude material was adsorbed onto a plug of silica gel (230-400 mesh) and purified through a Biotage Isolera-one pre-packed silica gel column, eluting with a gradient of 40% ethyl acetate in hexane to provide 6-(hydroxymethyl)nicotinonitrile as white solid. $^1$H NMR (400 MHz, DMSO-$d_6$) δ 8.93 (dt, J=1.8, 0.8 Hz, 1H), 8.32-8.28 (m, 1H), 7.66 (dt, J=8.3, 0.9 Hz, 1H), 5.68 (td, J=5.9, 0.8 Hz, 1H), 4.64 (d, J=5.8 Hz, 2H). MS (ESI, pos. ion) m/z: 135.0 [M+1]

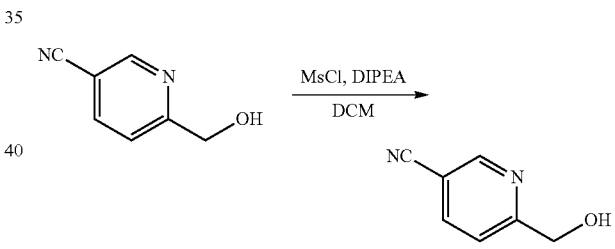

X = Cl X = OMs

Step 4. 6-(chloromethyl)nicotinonitrile and (5-cyanopyridin-2-yl)methyl methanesulfonate 6-(hydroxymethyl)nicotinonitrile (25.0 g, 186.0 mmol, 1.0 equiv) was dissolved in dichloromethane (360.0 mL, 14.4 mL/g) and cooled to 0° C. N,N-diisopropylethylamine (48.8 mL, 280.0 mmol, 1.5 equiv) was added, followed by dropwise addition of methanesulfonyl chloride (16.0 g, 205.0 mmol, 1.1 equiv) over 15 minutes. The reaction mixture was allowed to warm to room temperature and stirred for 45 min. LCMS indicated formation of the product. The reaction mixture was diluted with water (500 mL) and extracted with DCM (2×250 mL). The combined organic layers were dried over sodium sulfate, filtered and concentrated under reduced pressure to get crude material which was adsorbed into a plug of silica gel (230-400 mesh) and purified by chromatography through a Biotage Isolera-one pre-packed silica gel column, eluting with a gradient of 15% ethyl acetate in hexane to afford 6-(chloromethyl)nicotinonitrile (VI) as yellowish solid. $^1$H NMR (400 MHz, DMSO-$d_6$) δ 9.03 (dd, J=2.2, 1.0 Hz, 1H), 8.38 (dd, J=8.1, 2.2 Hz, 1H), 7.77 (dd, J=8.1, 0.9 Hz, 1H), 4.88 (s, 2H). Further elution of the column with a gradient of 50% ethyl acetate in hexane provided 5-cyanopyridin-2-yl)methyl methanesulfonate as brown solid. $^1$H NMR (400 MHz, DMSO-$d_6$) δ 9.06 (dt, J=2.1, 1.0 Hz, 1H), 8.41 (dt, J=8.2, 1.7 Hz, 1H), 7.73 (dd, J=8.2, 1.0 Hz, 1H), 5.42 (d, J=1.1 Hz, 2H), 3.34 (s, 3H). MS (ESI, pos. ion) m/z: 213.2 [M+1]. Both compounds were competent electrophiles in the alkylation (step 5).

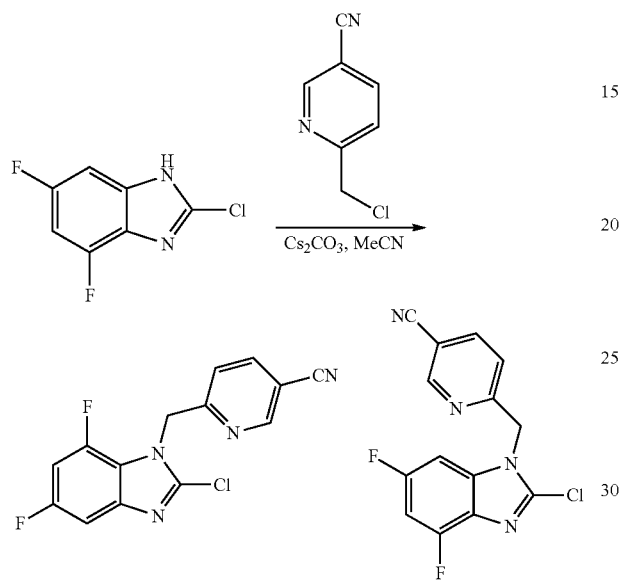

Step 5. 6-((2-chloro-4,6-difluoro-1H-benzo[d]imidazol-1-yl)methyl)nicotinonitrile and 6-((2-chloro-5,7-difluoro-1H-benzo[d]imidazol-1-yl)methyl)nicotinonitrile 2-chloro-4,6-difluoro-1H-benzo[d]imidazole (50.0 g, 265.0 mmol, 1.0 equiv) and 6-(chloromethyl)nicotinonitrile (40.5 g, 265.0 mmol, 1.0 equiv) was dissolved in acetonitrile (500.0 mL, 10.0 mL/g) at room temperature. Cesium carbonate (138.0 g, 427.0 mmol, 1.6 equiv) was added and the mixture was stirred at room temperature for 12 h. The reaction mixture was diluted with water (200 mL) and extracted with ethyl acetate (2×200 mL). The combined organic layers were dried over sodium sulfate, filtered and concentrate under reduced pressure. The crude material was adsorbed onto a plug of silica gel (60-120 mesh) and purified by column chromatography, eluting with a gradient of 25% ethyl acetate in hexane to provide 6-((2-chloro-4,6-difluoro-1H-benzo[d]imidazol-1-yl)methyl)nicotinonitrile and 6-((2-chloro-5,7-difluoro-1H-benzo[d]imidazol-1-yl)methyl) nicotinonitrile as a mixture of isomers (light yellow solid). In some instances, the mixture of isomers was carried forward without separation and in others the isomers were separated at this stage.

Step 6. Separation of 6-((2-chloro-5,7-difluoro-1H-benzo[d]imidazol-1-yl)methyl)nicotinonitrile (Intermediate 1) and 6-((2-chloro-4,6-difluoro-1H-benzo[d]imidazol-1-yl)methyl)nicotinonitrile (Intermediate 2)

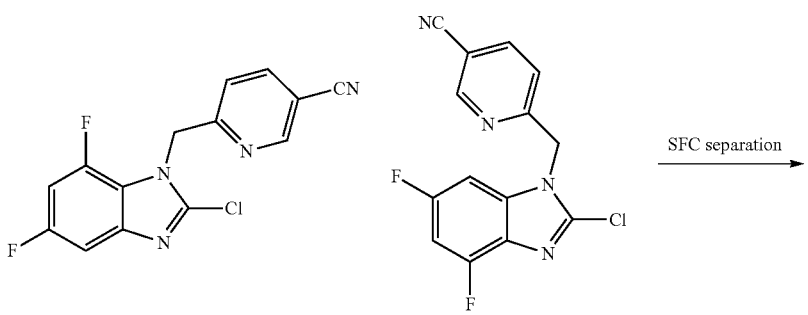

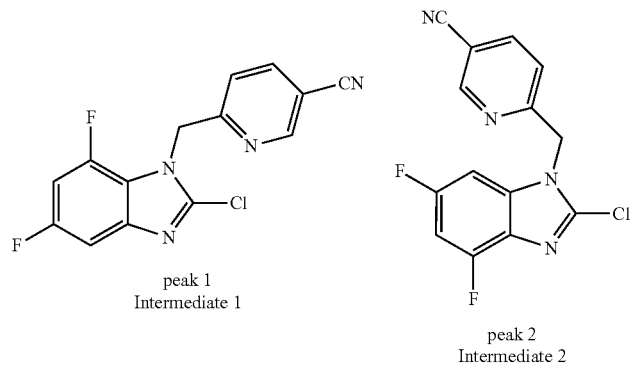

peak 1
Intermediate 1 peak 2
Intermediate 2

1.0 g sample was dissolved in 20 mL Methanol, Column Lux C4 (250×50 mm, 5 μm), Mobile phase: 70:30 (A:B), A: Liquid CO2, B: Methanol, Flow Rate: 120 mL/min, Wave length: 220 nm, Sample load: 100 mg/injection, Inlet pressure: 200-210 bar, Cycle time: 3.5, Run time: 10. In total, (51.0 g mixture of isomers) was separated by SFC to get 6-((2-chloro-5,7-difluoro-1H-benzo[d]imidazol-1-yl)methyl)nicotinonitrile (Intermediate 1, peak 1) and 6-((2-chloro-4,6-difluoro-1H-benzo[d]imidazol-1-yl)methyl)nicotinonitrile (Intermediate 2, peak 2) as yellow solids. Peak 1: $^1$H NMR (400 MHz, DMSO-d$_6$): δ 8.90 (d, J=2.0 Hz, 1H), 8.37 (dd, J=8.2, 2.1 Hz, 1H), 7.70 (d, J=8.2 Hz, 1H), 7.42 (dd, J=9.0, 2.2 Hz, 1H), 7.22 (ddd, J=11.9, 10.3, 2.2 Hz, 1H), 5.79 (s, 2H). MS (ESI, pos. ion) m/z: 304.0 [M+1]. Peak 2: $^1$H NMR (400 MHz, DMSO-d$_6$): δ 8.91 (t, J=3.0 Hz, 1H), 8.37 (ddd, J=8.2, 4.4, 2.1 Hz, 1H), 7.67 (dd, J=8.4, 4.2 Hz, 1H), 7.49 (dt, J=8.7, 3.0 Hz, 1H), 7.20 (tdd, J=10.7, 4.5, 2.1 Hz, 1H), 5.79 (d, J=3.8 Hz, 2H). MS (ESI, pos. ion) m/z: 304.0 [M+1].

The following intermediates were synthesized using a sequence analogous to that used to synthesize Intermediates 1 and 2 and general Scheme 7 above:

TABLE 1

Alkylated Intermediates

| Int # | Structure | Compound Name | 1H NMR | MS MH+ | Separation Conditions |
|---|---|---|---|---|---|
| 1 | 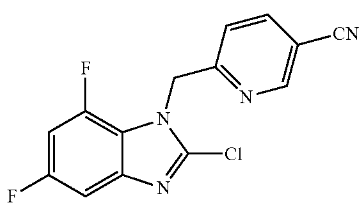 [SMILES: N#Cc1ccc(Cn2c(Cl)nc3cc(F)cc(F)c32)nc1] | 6-((2-chloro-5,7-difluoro-1H-benzo[d]imidazol-1-yl)methyl)nicotinonitrile | $^1$H NMR (400 MHz, DMSO-d6): δ 8.90 (d, J = 2.0 Hz, 1H), 8.37 (dd, J = 8.2, 2.1 Hz, 1H), 7.70 (d, J = 8.2 Hz, 1H), 7.42 (dd, J = 9.0, 2.2 Hz, 1H), 7.22 (ddd, J = 11.9, 10.3, 2.2 Hz, 1H), 5.79 (s, 2H) | 304.0 | Column Lux C4, 30% MeOH, peak 1 |
| 2 | 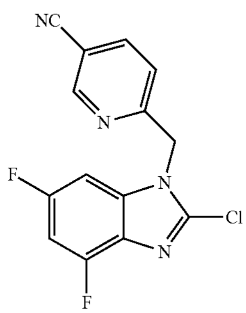 [SMILES: N#Cc1ccc(Cn2c(Cl)nc3c(F)cc(F)cc32)nc1] | 6-((2-Chloro-4,6-difluoro-1H-benzo[d]imidazol-1-yl)methyl)nicotinonitrile | $^1$H NMR (400 MHz, DMSO-d6): δ 8.91 (t, J = 3.0 Hz, 1H), 8.37 (ddd, J = 8.2, 4,4, 2.1 Hz, 1H), 7.67 (dd, J = 8.4, 4.2 Hz, 1H), 7.49 (dt, J = 8.7, 3.0 Hz, 1H), 7.20 (tdd, J = 10.7, 4.5, 2.1 Hz, 1H), 5.79 (d, J = 3.8 Hz, 2H) | 304.0 | Column Lux C4, 30% MeOH, peak 2 |
| 3 | 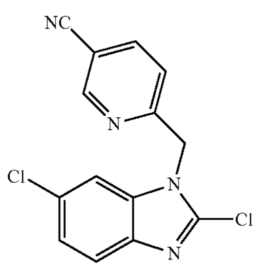 [SMILES: N#Cc1ccc(Cn2c(Cl)nc3ccc(Cl)cc32)nc1] | 6-((2,6-dichloro-1H-benzo[d]imidazol-1-yl)methyl)nicotinonitrile | $^1$H NMR (400 MHz, DMSO-d$_6$): δ 8.90 (dd, J = 2.1, 0.9 Hz, 1H), 8.36 (dd, J = 8.2, 2.2 Hz, 1H 7.80 (d, J = 2.1 Hz, 1H), 7.68-7.60 (m, 2H), 7.29 (dd, J = 8.6, 2.1 Hz, 1H), 5.79 (s, 2H) | 303.0 | YMC Amyose SA, Methanol THF (70:30) 40%; peak 1 |
| 4 | 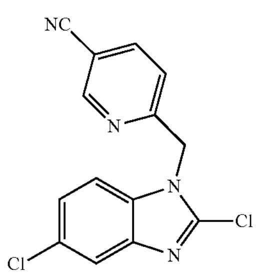 [SMILES: N#Cc1ccc(Cn2c(Cl)nc3cc(Cl)ccc32)nc1] | 6-((2,5-dichloro-1H-benzo[d]imidazol-1-yl)methyl)nicotinonitrile | 1H NMR (400 MHz, DMSO-d6): δ 8.90 (d, J = 2.1 Hz, 1H), 8.35 (dd, J = 8.2, 2.1 Hz, 1H), 7.74 (d, J = 2.0 Hz, 1H), 7.66-7.55 (m, 2H), 7.33 (dd, J = 8.7, 2.1 Hz, 1H), 5.79 (s, 2H) | 303.0 | YMC Amyose SA, Methanol THF (70:30) 40%; peak 2 |

TABLE 1-continued

| | | Alkylated Intermediates | | | |
|---|---|---|---|---|---|
| Int # | Structure | Compound Name | 1H NMR | MS MH+ | Separation Conditions |
| 5 | | 6-((2-chloro-6-fluoro-1H-benzo[d]imidazol-1-yl)methyl)nicotinonitrile | 1H NMR (400 MHz, DMSO-d6): δ 8.93-8.86 (m, 1H), 8.34 (dd, J = 8.2, 2.1 Hz, 1H), 7.67-7.58 (m, 2H), 7.54 (dd, J = 9.2, 2.6 Hz, 1H), 7.17-7.06 (m, 1H), 5.75 (s, 2H) | 287.0 | YMC Amyose SA, Methanol THF (70:30) 40%; peak 1 |
| 6 | | 6-((2-chloro-5-fluoro-1H-benzo[d]imidazol-1-yl)methyl)nicotinonitrile | 1H NMR (400 MHz, DMSO-d6): δ 8.90 (d, J = 2.3 Hz, 1H), 8.34 (dt, J = 8.0, 2.3 Hz, 1H), 7.59 (tq, J = 7.5, 2.2 Hz, 2H), 7.48 (dq, J = 9.5, 2.4 Hz, 1H), 7.24-7.05 (m, 1H), 5.77 (s, 2H) | 287.0 | YMC Amyose SA, Methanol THF (70:30) 40%; peak 2 |
| 7 | | 6-((2-chloro-1H-benzo[d]imidazol-1-yl)methyl)nicotinonitrile | 1H NMR (400 MHz, DMSO-d6): δ 8.92 (d, J = 2.1 Hz, 1H), 8.34 (dd, J = 8.1, 2.1 Hz, 1H), 7.67-7.54 (m, 3H), 7.30-7.245 (m, 2H), 5.76 (s, 2H) | 269.2 | — |
| 8 | | 6-((2-chloro-4-(trifluoromethyl)-1H-benzo[d]imidazol-1-yl)methyl)nicotinonitrile | — | 337.2 | — |
| 9$^a$ | | 6-((2,6-dichloro-1H-imidazo[4,5-b]pyridin-1-yl)methyl)nicotinonitrile | — | 304.0 | Separated at final product |

TABLE 1-continued

| | | Alkylated Intermediates | | | |
|---|---|---|---|---|---|
| Int # | Structure | Compound Name | 1H NMR | MS MH+ | Separation Conditions |
| 10 | | 2-chloro-1-((5-cyanopyridin-2-yl)methyl)-1H-benzo[d]imidazole-4-carbonitrile | — | 294.0 | — |
| 11 | | 2-chloro-1-((5-cyanopyridin-2-yl)methyl)-6-fluoro-1H-benzo[d]imidazole-4-carbonitrile | — | 312.2 | — |
| 12[a] | | 6-((2-chloro-6-(trifluoromethoxy)-1H-benzo[d]imidazol-1-yl)methyl)nicotinonitrile | — | 353.2 | Separated at final product |
| 13[a] | | 2-chloro-1-((5-chloropyridin-2-yl)methyl)-6-(methylsulfonyl)-1H-benzo[d]imidazole | — | 357.8 | Separated at final product |
| 14 | | 2-chloro-1-((5-chloropyrimidin-2-yl)methyl)-6-fluoro-1H-benzo[d]imidazole-4-carbonitrile | — | 323.8 | — |

TABLE 1-continued

Alkylated Intermediates

| Int # | Structure | Compound Name | 1H NMR | MS MH+ | Separation Conditions |
|---|---|---|---|---|---|
| 15[a] | 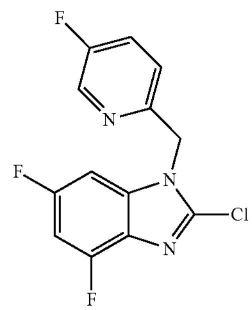 [SMILES: Fc1ccc(Cn2c(Cl)nc3c(F)cc(F)cc32)nc1] | 2-chloro-4,6-difluoro-1-((5-fluoropyridin-2-yl)methyl)-1H-benzo[d]imidazole | — | 298.0 | Separated at final product |
| 16[a] | 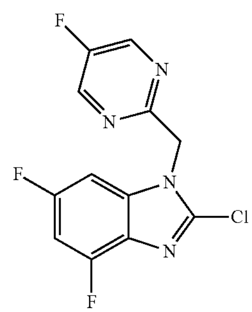 [SMILES: Fc1cnc(Cn2c(Cl)nc3c(F)cc(F)cc32)nc1] | 2-chloro-4,6-difluoro-1-((5-fluoropyrimidin-2-yl)methyl)-1H-benzo[d]imidazole | — | 299.0 | Separated at final product |
| 17[a] | 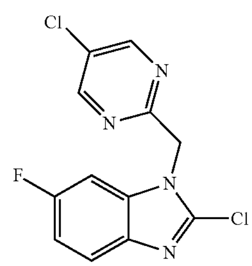 [SMILES: Fc1ccc2nc(Cl)n(Cc3ncc(Cl)cn3)c2c1] | 2-chloro-1-((5-chloropyrimidin-2-yl)methyl)-6-fluoro-1H-benzo[d]imidazole | — | 297.0 | Separated at final product |
| 18 | 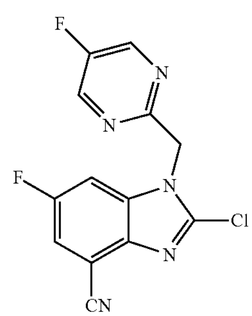 [SMILES: N#Cc1cc(F)cc2c1nc(Cl)n2Cc1ncc(F)cn1] | 2-chloro-6-fluoro-1-((5-fluoropyrimidin-2-yl)methyl)-1H-benzo[d]imidazole-4-carbonitrile | — | 306.2 | — |
| 19[a] | 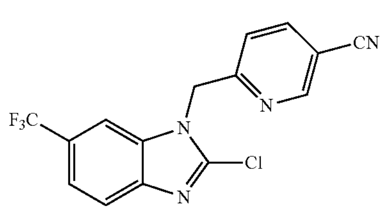 [SMILES: N#Cc1ccc(Cn2c(Cl)nc3ccc(C(F)(F)F)cc32)nc1] | 6-((2-chloro-6-(trifluoromethyl)-1H-benzo[d]imidazol-1-yl)methyl)nicotinonitrile | — | 337.0 | Separated at final product |

TABLE 1-continued

| | | Alkylated Intermediates | | | |
|---|---|---|---|---|---|
| Int # | Structure | Compound Name | 1H NMR | MS MH+ | Separation Conditions |
| 20[a] | | 6-((2,5-dichloro-6-methyl-1H-benzo[d]imidazol-1-yl)methyl)nicotinonitrile | — | 317.0 | Separated at final product |
| 21[a] | | 6-((2-chloro-6-(difluoromethoxy)-1H-benzo[d]imidazol-1-yl)methyl)nicotinonitrile | — | 335.0 | Separated at final product |
| 22 | | 6-((2-chloro-4-methoxy-1H-benzo[d]imidazol-1-yl)methyl)nicotinonitrile | — | 299.2 | Separated at final product |
| 23 | | 6-((2-chloro-4-methyl-1H-benzo[d]imidazol-1-yl)methyl)nicotinonitrile | — | 283.2 | — |
| 24[a] | | 6-((2-chloro-6-methoxy-1H-benzo[d]imidazol-1-yl)methyl)nicotinonitrile | — | 299.2 | Separated at final product |

TABLE 1-continued

| | Alkylated Intermediates | | | | |
|---|---|---|---|---|---|
| Int # | Structure | Compound Name | 1H NMR | MS MH+ | Separation Conditions |
| 25[a] | | 6-((2-chloro-6-fluoro-5-(trifluoromethyl)-1H-benzo[d]imidazol-1-yl)methyl)nicotinonitrile | — | 355.0 | Separated at final product |
| 26[a] | | 6-((2,6-dichloro-5-(trifluoromethyl)-1H-benzo[d]imidazol-1-yl)methyl)nicotinonitrile | — | 371.0 | Separated at final product |
| 27[a] | | 6-((2,6-dichloro-5-(trifluoromethoxy)-1H-benzo[d]imidazol-1-yl)methyl)nicotinonitrile | — | 387.0 | Separated at final product |
| 28 | | 6-((2,5,6-trichloro-1H-benzo[d]imidazol-1-yl)methyl)nicotinonitrile | — | 337.0 | — |
| 29 | | 6-((2-chloro-5,6-difluoro-1H-benzo[d]imidazol-1-yl)methyl)nicotinonitrile | — | 305.1 | — |

TABLE 1-continued

Alkylated Intermediates

| Int # | Structure | Compound Name | 1H NMR | MS MH+ | Separation Conditions |
|---|---|---|---|---|---|
| 30 | 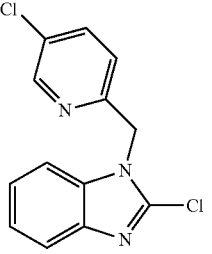 [SMILES: Clc1ccc(Cn2c(Cl)nc3ccccc32)nc1] | 2-chloro-1-((5-chloropyridin-2-yl)methyl)-1H-benzo[d]imidazole | — | 278.2 | — |
| 31[a] | 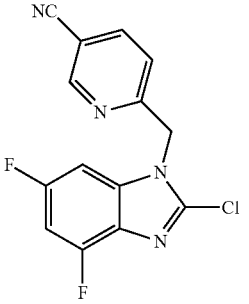 | 6-((2-chloro-4,6-difluoro-1H-benzo[d]imidazol-1-yl)methyl)nicotinonitrile | — | 305.2 | Separated at final product |
| 32 | 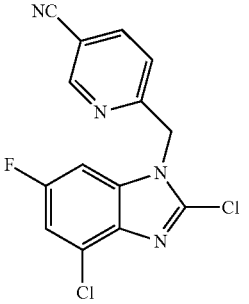 | 6-((2,4-dichloro-6-fluoro-1H-benzo[d]imidazol-1-yl)methyl)nicotinonitrile | — | 321.0 | — |
| 33[a] | 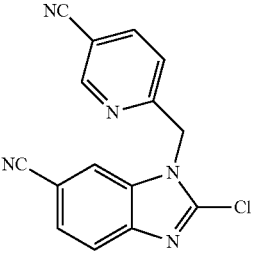 [SMILES: N#Cc1ccc(Cn2c(Cl)nc3ccc(C#N)cc32)nc1] | 2-chloro-1-((5-cyanopyridin-2-yl)methyl)-1H-benzo[d]imidazole-6-carbonitrile | — | 294.0 | Separated at final product |
| 34[a] | 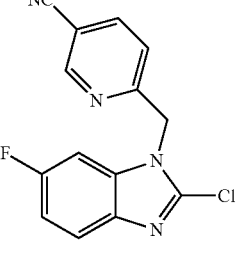 | 6-((2-chloro-6-fluoro-1H-benzo[d]imidazol-1-yl)methyl)nicotinonitrile | — | 287.0 | Separated at final product |

TABLE 1-continued

| | | Alkylated Intermediates | | | |
|---|---|---|---|---|---|
| Int # | Structure | Compound Name | 1H NMR | MS MH+ | Separation Conditions |
| 35 | | 6-((2-chloro-5,6-dimethyl-1H-benzo[d]imidazol-1-yl)methyl)nicotinonitrile | — | 297.0 | — |
| 36 | | 6-((2,4,6-trichloro-1H-benzo[d]imidazol-1-yl)methyl)nicotinonitrile | — | 336.8 | — |
| 37[a] | | 6-((2,6-dichloro-1H-benzo[d]imidazol-1-yl)methyl)nicotinonitrile | — | 304.0 | Separated at final product |
| 38 | | 6-((2,4-dichloro-1H-benzo[d]imidazol-1-yl)methyl)nicotinonitrile | — | 304.2 | — |
| 39[a] | | 2-chloro-1-((5-cyanopyridin-2-yl)methyl)-1H-benzo[d]imidazole-6-carbonitrile | — | 294.2 | Separated at final product |
| 40[a] | | 6-((2-chloro-6-methyl-1H-benzo[d]imidazol-1-yl)methyl)nicotinonitrile | — | 283.2 | Separated at final product |

TABLE 1-continued

| | Alkylated Intermediates | | | | |
|---|---|---|---|---|---|
| Int # | Structure | Compound Name | 1H NMR | MS MH+ | Separation Conditions |
| 41[a] | | 6-((2-chloro-5-fluoro-6-methyl-1H-benzo[d]imidazol-1-yl)methyl)nicotinonitrile | — | 301.2 | Separated at final product |
| 42[a] | | 5-((2-chloro-6-(trifluoromethyl)-1H-benzo[d]imidazol-1-yl)methyl)pyrazine-2-carbonitrile | — | 338.2 | Separated at final product |
| 43 | | 5-((2-chloro-5,6-difluoro-1H-benzo[d]imidazol-1-yl)methyl)pyrazine-2-carbonitrile | — | 306.2 | — |
| 44[a] | | 4-((2-chloro-1H-benzo[d]imidazol-1-yl)methyl)benzonitrile | — | 268.2 | — |
| 45[a] | | 4-((2-chloro-4,6-difluoro-1H-benzo[d]imidazol-1-yl)methyl)benzonitrile | — | 304.2 | Separated at final product |
| 46[a] | | 2-chloro-1-(4-cyanobenzyl)-1H-benzo[d]imidazole-6-carbonitrile | — | 293.2 | Separated at final product |

TABLE 1-continued

Alkylated Intermediates

| Int # | Structure | Compound Name | 1H NMR | MS MH+ | Separation Conditions |
|---|---|---|---|---|---|
| 47[a] | 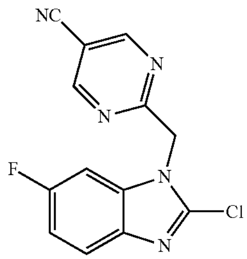 | 2-((2-chloro-6-fluoro-1H-benzo[d]imidazol-1-yl)methyl)pyrimidine-5-carbonitrile | — | 288.2 | Separated at final product |
| 48[a] | 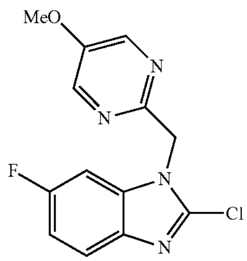 [SMILES: COc1cnc(Cn2c(Cl)nc3ccc(F)cc32)nc1] | 2-chloro-6-fluoro-1-((5-methoxypyrimidin-2-yl)methyl)-1H-benzo[d]imidazole | — | 293.2 | Separated at final product |
| 49[a] | 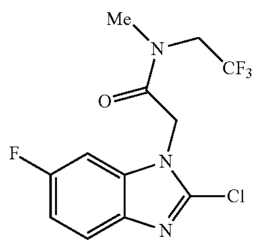 [SMILES: CN(CC(F)(F)F)C(=O)Cn1c(Cl)nc2ccc(F)cc21] | 2-(2-chloro-6-fluoro-1H-benzo[d]imidazol-1-yl)-N-methyl-N-(2,2,2-trifluoroethyl)acetamide | — | 324.2 | Separated at final product |
| 50[a] | 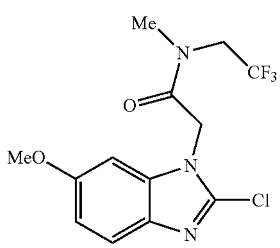 [SMILES: COc1ccc2nc(Cl)n(CC(=O)N(C)CC(F)(F)F)c2c1] | 2-(2-chloro-6-methoxy-1H-benzo[d]imidazol-1-yl)-N-methyl-N-(2,2,2-trifluoroethyl)acetamide | — | 336.0 | Separated at final product |
| 51[a] | 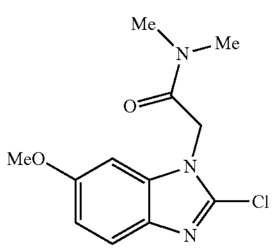 [SMILES: COc1ccc2nc(Cl)n(CC(=O)N(C)C)c2c1] | 2-(2-chloro-6-methoxy-1H-benzo[d]imidazol-1-yl)-N,N-dimethylacetamide | — | 268.2 | Separated at final product |
| 52 | 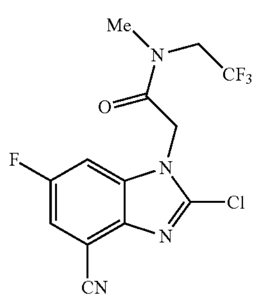 [SMILES: CN(CC(F)(F)F)C(=O)Cn1c(Cl)nc2c(C#N)cc(F)cc21] | 2-(2-chloro-4-cyano-6-fluoro-1H-benzo[d]imidazol-1-yl)-N-methyl-N-(2,2,2-trifluoroethyl)acetamide | — | 349.2 | — |

TABLE 1-continued

| | | Alkylated Intermediates | | | |
|---|---|---|---|---|---|
| Int # | Structure | Compound Name | 1H NMR | MS MH+ | Separation Conditions |
| 53[a] | | 2-(2-chloro-6-fluoro-4-methoxy-1H-benzo[d]imidazol-1-yl)-N-methyl-N-(2,2,2-trifluoroethyl)acetamide | — | 354.2 | Separated at final product |
| 54[a] | | 6-((2-chloro-5-(trifluoromethyl)-3H-imidazo[4,5-b]pyridin-3-yl)methyl)nicotinonitrile | — | 338.2 | Separated at final product |
| 55[a] | | 1-(azetidin-1-yl)-2-(6-bromo-2-chloro-1H-benzo[d]imidazol-1-yl)ethanone | — | 329.2 | Separated at final product |
| 56[a] | | 2-(2-chloro-6-(trifluoromethyl)-1H-benzo[d]imidazol-1-yl)-1-morpholinoethanone | — | 348.2 | Separated at final product |
| 57[a] | | 2-(2,6-dichloro-1H-benzo[d]imidazol-1-yl)-N,N-dimethylacetamide | — | 273.0 | Separated at final product |

TABLE 1-continued

Alkylated Intermediates

| Int # | Structure | Compound Name | 1H NMR | MS MH+ | Separation Conditions |
|---|---|---|---|---|---|
| 58[a] | 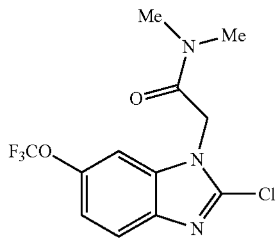 [SMILES: CN(C)C(=O)Cn1c(Cl)nc2ccc(OC(F)(F)F)cc21] | 2-(2-chloro-6-(trifluoromethoxy)-1H-benzo[d]imidazol-1-yl)-N,N-dimethylacetamide | — | 322.2 | Separated at final product |
| 59[a] | 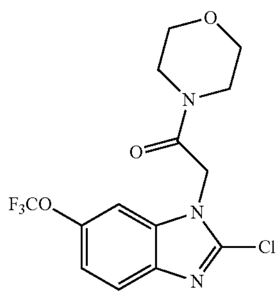 [SMILES: O=C(Cn1c(Cl)nc2ccc(OC(F)(F)F)cc21)N1CCOCC1] | 2-(2-chloro-6-(trifluoromethoxy)-1H-benzo[d]imidazol-1-yl)-1-morpholinoethanone | — | 264.2 | Separated at final product |

[a]Mixture of isomers formed through non-selective benzylation that were separated at final product or penultimate intermediate

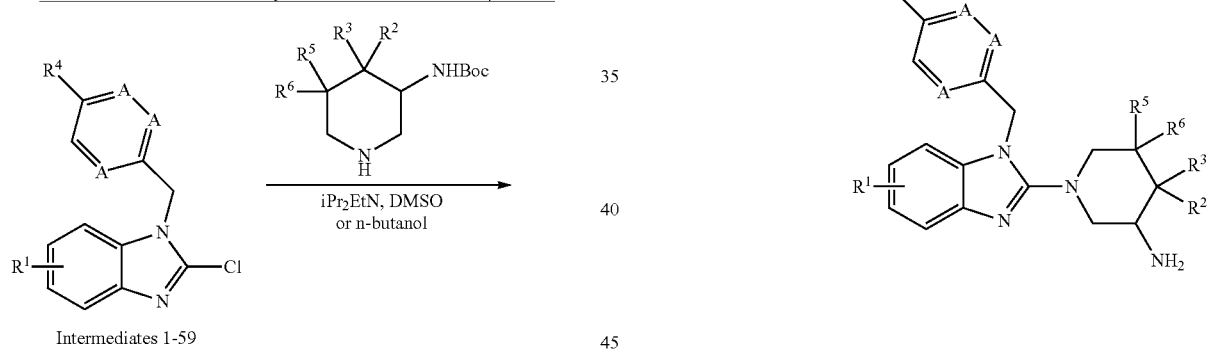

Scheme 8. Advancement of alkylated intermediates to final products

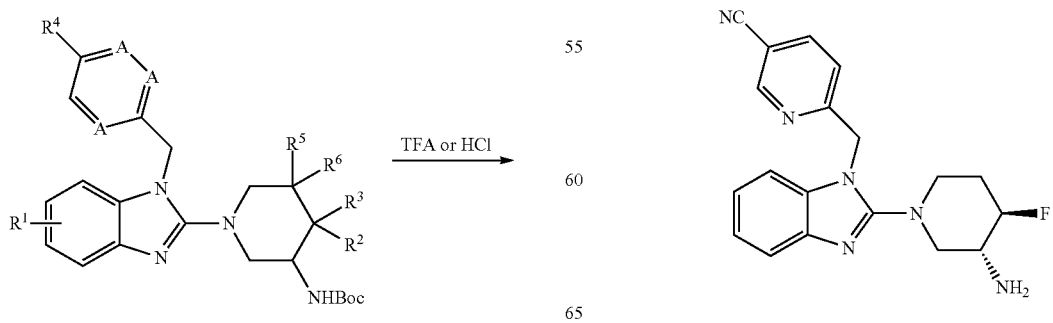

Example 38: 6-((2-((3R,4R)-3-amino-4-fluoropiperidin-1-yl)-1H-benzo[d]imidazol-1-yl)methyl)nicotinonitrile

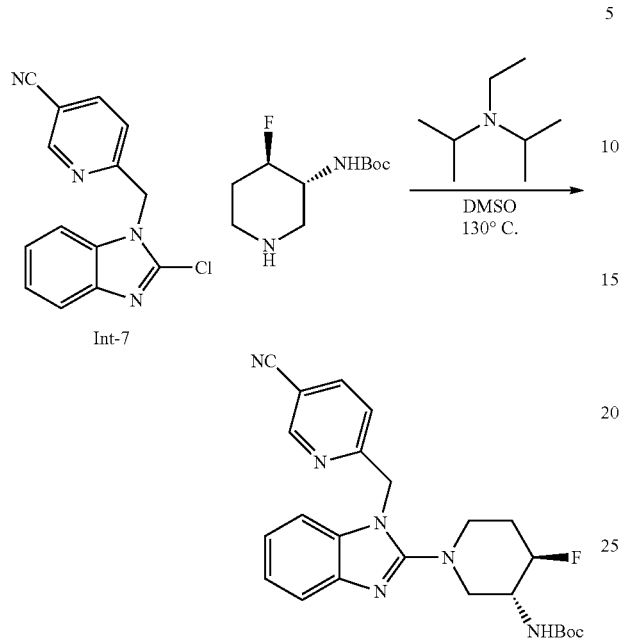

Int-7

Step 1. tert-butyl ((3R,4R)-1-(1-((5-cyanopyridin-2-yl)methyl)-1H-benzo[d]imidazol-2-yl)-4-fluoropiperidin-3-yl)carbamate 1,1'-dimethyltriethylamine (1.300 ml, 7.44 mmol), tert-butyl ((3R,4R)-4-fluoropiperidin-3-yl)carbamate (0.975 g, 4.47 mmol), 6-((2-chloro-1H-benzo[d]imidazol-1-yl)methyl)nicotinonitrile (Intermediate 7, 1 g, 3.72 mmol), and dimethyl sulfoxide (7.44 ml) were combined in a flask and heated to 130° C. for 36 hours. The mixture was cooled, poured into water, then extracted with EtOAc (3×). The organics were combined, dried over Na2SO4, filtered, and concentrated. The crude material was loaded onto an 80 g RediSep ISCO cartridge, eluting with 10-50% EtOAc in heptanes to provide tert-butyl ((3R,4R)-1-(1-((5-cyanopyridin-2-yl)methyl)-1H-benzo[d]imidazol-2-yl)-4-fluoropiperidin-3-yl)carbamate as a light orange foam. MS (ESI, pos. ion) m/z: 451.2 [M+1]

Note: n-butanol is a competent substitute for DMSO. Difluorinated piperidines required heating to 150 C.

Boc Deprotection Procedure with TFA (Procedure B)

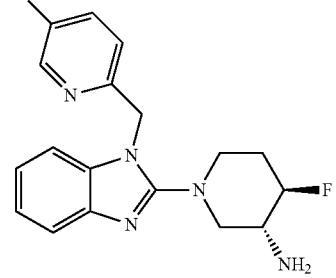

Step 2. 6-((2-((3R,4R)-3-amino-4-fluoropiperidin-1-yl)-1H-benzo[d]imidazol-1-yl)methyl)nicotinonitrile (Example 43)

Tert-butyl ((3R,4R)-1-(1-((5-cyanopyridin-2-yl)methyl)-1H-benzo[d]imidazol-2-yl)-4-fluoropiperidin-3-yl)carbamate (1.31 g, 2.91 mmol, 1 equiv) was dissolved in DCM (10 mL) and slowly dripped into a flask of cooled (0 C) TFA (~10 mL). After 1 hour, deprotection was complete. The mixture was poured onto an SCX column (pre-wetted with MeOH), flushed with MeOH, then eluted with methanolic ammonia. The methanolic ammonia was concentrated, and the light orange oil redissolved in MeCN/water, frozen, and lyophilized to provide the title compound as a light yellow solid. $^1$H NMR (500 MHz, MeOD) δ 8.81-8.92 (m, 1H), 8.23 (dd, J=8.30, 2.08 Hz, 1H), 7.49-7.66 (m, 2H), 7.17-7.39 (m, 3H), 5.64 (s, 2H), 4.69-4.86 (m, 1H), 3.92-4.06 (m, 1H), 3.61-3.79 (m, 2H), 3.20-3.32 (m, 2H), 2.24-2.41 (m, 1H), 1.92-2.14 (m, 1H). (ESI, pos. ion) m/z: 351.2 [M+1]

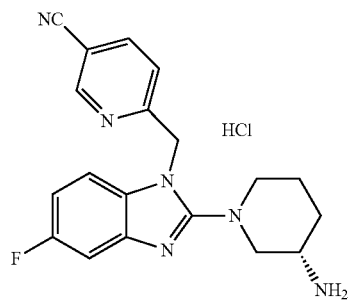 [SMILES: N#Cc1ccc(Cn2c(N3CCC[C@H](N)C3)nc3cc(F)ccc32)nc1 ; Cl]

Example 45: 6-((2-((3R,4R)-3-amino-4-fluoropiperidin-1-yl)-1H-benzo[d]imidazol-1-yl)methyl)nicotinonitrile hydrochloride

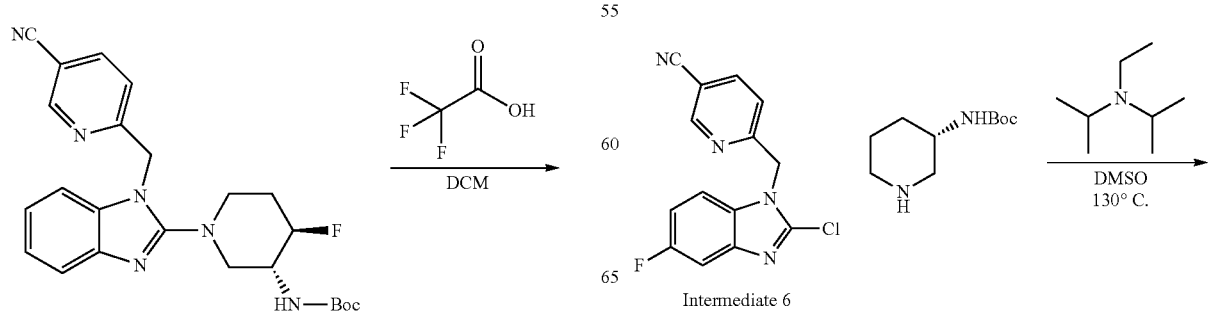

Intermediate 6

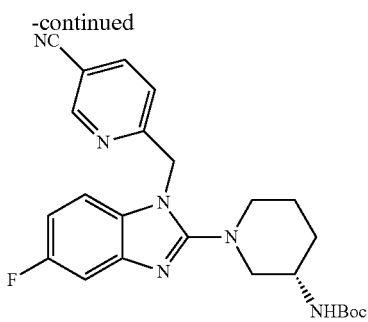

Step 1. (S)-tert-butyl (1-(1-((5-cyanopyridin-2-yl)methyl)-5-fluoro-1H-benzo[d]imidazol-2-yl)piperidin-3-yl)carbamate To a suspension of 6-((2-chloro-6-fluoro-1H-benzo[d]imidazol-1-yl)methyl)nicotinonitrile (150 mg, 0.523 mmol) and hunig's base (137 µL, 0.785 mmol) in 1-butanol (2093 µL) was added (S)-tert-butyl piperidin-3-ylcarbamate (115 mg, 0.576 mmol). The reaction was stirred at 130° C. overnight. After 24 hours, the reaction mixture was concentrated and purified by column chromatography, eluting with 20-100% ethyl acetate in heptane, to provide the title compound as an off white solid. (ESI, pos. ion) m/z: 451.2 [M+1] Boc Deprotection with HCl (Procedure A)

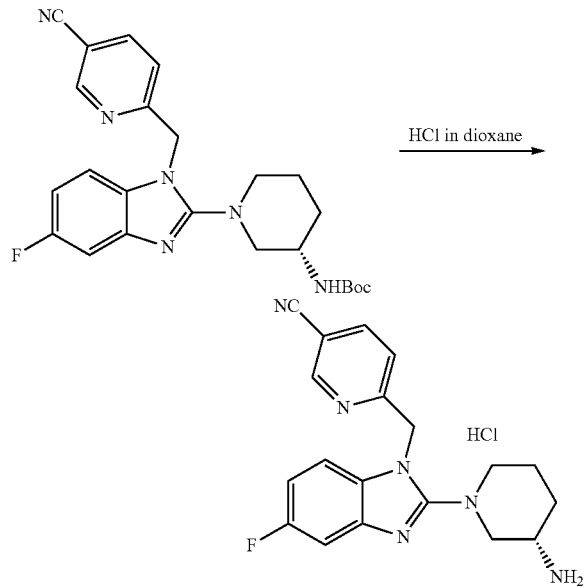

(S)-6-((2-(3-aminopiperidin-1-yl)-5-fluoro-1H-benzo[d]imidazol-1-yl)methyl)nicotinonitrile hydrochloride (Example 51)

Step 2. (S)-tert-butyl (1-(1-((5-cyanopyridin-2-yl)methyl)-5-fluoro-1H-benzo[d]imidazol-2-yl)piperidin-3-yl)carbamate (77 mg) was dissolved in dioxane (2 mL), and 4 N HCl in dioxane (585 µL, 2.340 mmol) was added. The reaction was stirred at ambient temperature. After 16 hours, LC/MS analysis showed the reaction was complete. The reaction mixture was concentrated in vacuo to provide the title compound as an off white solid. $^1$H NMR (400 MHz, d$_6$-DMSO) δ 8.94 (s, 1H), 8.48 (br s, 2H), 8.40 (dd, J=2.18, 8.19 Hz, 1H), 7.77 (d, J=8.19 Hz, 1H), 7.40 (dd, J=2.85, 8.66 Hz, 2H), 7.14 (dt, J=2.38, 9.33 Hz, 1H), 5.65-5.84 (m, 2H), 3.89 (br d, J=10.57 Hz, 1H), 3.28-3.52 (m, 3H), 3.18 (br t, J=9.80 Hz, 1H), 1.94-2.02 (m, 1H), 1.81-1.93 (m, 1H), 1.47-1.72 (m, 2H). (ESI, pos. ion) m/z: 351.0 [M+1].

Note: The HCl salt was sometimes converted to a free base form using an aqueous work up or using ion exchange chromatography. Isolation of salt or free base is specified in table.

The following compounds were made in a manner analogous to that outlined above:

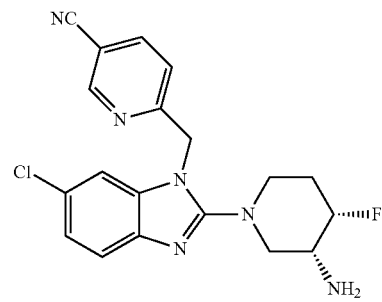 [SMILES: N#Cc1ccc(Cn2c(N3CC[C@H](F)[C@H](N)C3)nc3ccc(Cl)cc32)nc1]

Example 8: 6-((2-((3R,4S)-3-amino-4-fluoropiperidin-1-yl)-6-chloro-1H-benzo[d]imidazol-1-yl)methyl)nicotinonitrile 6-((2-((3R,4S)-3-amino-4-fluoropiperidin-1-yl)-6-chloro-1H-benzo[d]imidazol-1-yl)methyl)nicotinonitrile was synthesized on a 1 mmol scale following a procedure analogous to sequence outlined above using the TFA Boc deprotection (procedure B). It was separated at the Boc intermediate: Chiralcel OD-H, 25% IPA, peak 1. $^1$H NMR (500 MHz, MeOD) δ 8.86 (d, J=1.30 Hz, 1H), 8.14-8.20 (m, 1H), 7.47 (d, J=8.56 Hz, 1H), 7.44 (d, J=8.30 Hz, 1H), 7.23 (d, J=2.08 Hz, 1H), 7.19 (dd, J=1.95, 8.43 Hz, 1H), 5.53 (s, 2H), 4.33-4.50 (m, 1H), 3.53-3.61 (m, 1H), 3.43-3.50 (m, 1H), 3.02-3.20 (m, 2H), 2.95 (dd, J=8.69, 12.33 Hz, 1H), 2.12-2.24 (m, 1H), 1.82-1.94 (m, 1H). (ESI, pos. ion) m/z: 387.2 [M+1].

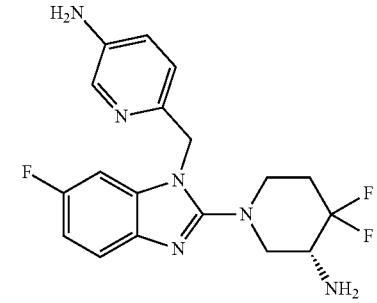 [SMILES: Nc1ccc(Cn2c(N3CCC(F)(F)[C@H](N)C3)nc3ccc(F)cc32)nc1]

Example 93: (R)-6-((2-(3-amino-4,4-difluoropiperidin-1-yl)-6-fluoro-1H-benzo[d]imidazol-1-yl)methyl)nicotinonitrile (R)-6-((2-(3-amino-4,4-difluoropiperidin-1-yl)-6-fluoro-1H-benzo[d]imidazol-1-yl)methyl)nicotinonitrile was synthesized on a 1.9 mmol scale following a procedure analogous to the sequence outlines above, using the TFA Boc deprotection (procedure B). It was separated at the chlorobenzimidazole intermediate (YMC Amyose SA, Methanol THF (70:30) 40%; peak 1). ¹H NMR (500 MHz, MeOD) δ 8.84 (d, J=1.82 Hz, 1H), 8.15 (dd, J=2.08, 8.30 Hz, 1H), 7.40-7.52 (m, 2H), 6.91-7.00 (m, 2H), 5.47-5.62 (m, 2H), 3.34-3.54 (m, 2H), 3.08-3.28 (m, 3H), 2.21-2.36 (m, 1H), 2.00-2.21 (m, 1H). (ESI, pos. ion) m/z: 351.0 [M+1].

The examples in Table 2 were synthesized using a sequence analogous to that used to synthesize Examples 38, 45, 8, and 88 and general Scheme 8 above:

TABLE 2

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 1 | 37 | 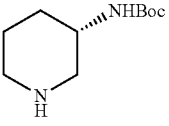 | B | 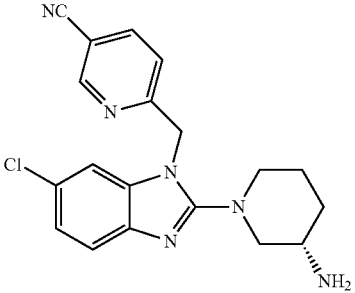 | (S)-6-((2-(3-aminopiperidin-1-yl)-6-chloro-1H-benzo[d]imidazol-1-yl)methyl)nicotinonitrile | 367.0 |
| 2 | 37 | 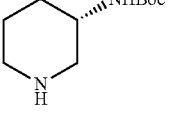 | B | 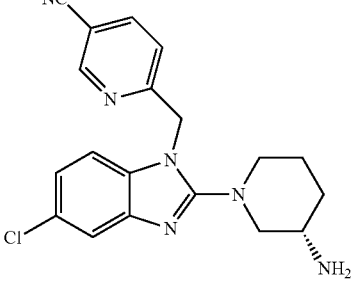 | (S)-6-((2-(3-aminopiperidin-1-yl)-5-chloro-1H-benzo[d]imidazol-1-yl)methyl)nicotinonitrile | 367.0 |
| 3 | 38 | 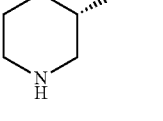 | B | 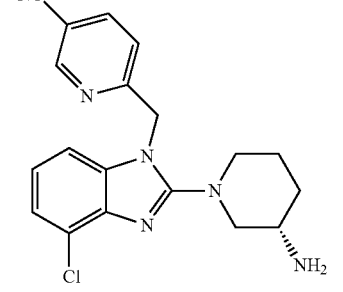 | (S)-6-((2-(3-aminopiperidin-1-yl)-4-chloro-1H-benzo[d]imidazol-1-yl)methyl)nicotinonitrile | 367.0 |
| 4 | 38 | 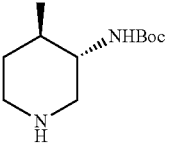 | B | 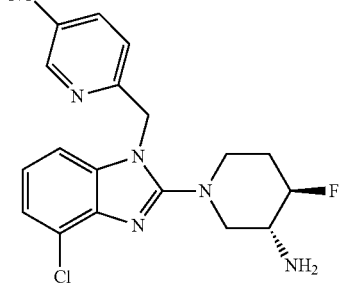 | 6-((2-((3R,4R)-3-amino-4-fluoropiperidin-1-yl)-4-chloro-1H-benzo[d]imidazol-1-yl)methyl)nicotinonitrile | 385.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 5 | 38 | (structure with F, NHBoc) | B | (structure) | 6-((2-((3R,4S)-3-amino-4-fluoropiperidin-1-yl)-4-chloro-1H-benzo[d]imidazol-1-yl)methyl)nicotinonitrile | 385.0 |
| 6 | 37 | (structure with F, NHBoc) | B | (structure) | 6-((2-((3R,4R)-3-amino-4-fluoropiperidin-1-yl)-6-chloro-1H-benzo[d]imidazol-1-yl)methyl)nicotinonitrile | 385.0 |
| 7 | 37 | (structure with F, NHBoc) | B | (structure) | 6-((2-((3R,4R)-3-amino-4-fluoropiperidin-1-yl)-5-chloro-1H-benzo[d]imidazol-1-yl)methyl)nicotinonitrile | 385.0 |
| 8 | 37 | (structure with F, NHBoc) | B | (structure) | 6-((2-((3R,4S)-3-amino-4-fluoropiperidin-1-yl)-6-chloro-1H-benzo[d]imidazol-1-yl)methyl)nicotinonitrile | 385.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 9 | 37 | 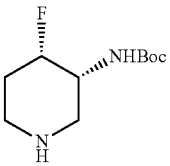 [SMILES: CC(C)(C)OC(=O)N[C@@H]1CNCC[C@@H]1F] | B | 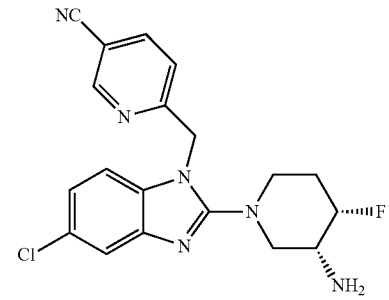 [SMILES: N#Cc1ccc(Cn2c(N3CC[C@H](F)[C@H](N)C3)nc3cc(Cl)ccc32)nc1] | 6-((2-((3R,4S)-3-amino-4-fluoropiperidin-1-yl)-5-chloro-1H-benzo[d]imidazol-1-yl)methyl)nicotinonitrile | 385.0 |
| 10 | 38 | 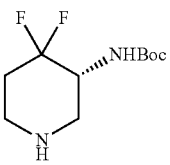 [SMILES: CC(C)(C)OC(=O)N[C@@H]1CNCCC1(F)F] | B | 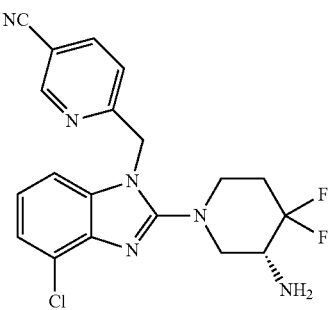 [SMILES: N#Cc1ccc(Cn2c(N3CCC(F)(F)[C@H](N)C3)nc3c(Cl)cccc32)nc1] | (R)-6-((2-(3-amino-4,4-difluoropiperidin-1-yl)-4-chloro-1H-benzo[d]imidazol-1-yl)methyl)nicotinonitrile | 403.0 |
| 11 | 10 | 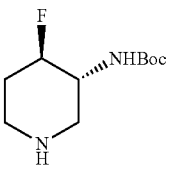 [SMILES: CC(C)(C)OC(=O)N[C@@H]1CNCC[C@H]1F] | B | 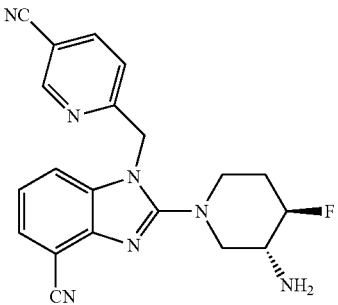 [SMILES: N#Cc1ccc(Cn2c(N3CC[C@@H](F)[C@H](N)C3)nc3c(C#N)cccc32)nc1] | 2-((3R,4R)-3-amino-4-fluoropiperidin-1-yl)-1-((5-cyanopyridin-2-yl)methyl)-1H-benzo[d]imidazole-4-carbonitrile | 376.0 |
| 12 | 37 | 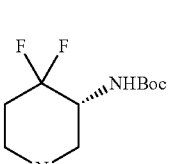 | B | 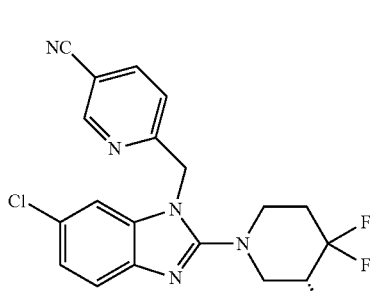 | (R)-6-((2-(3-amino-4,4-difluoropiperidin-1-yl)-6-chloro-1H-benzo[d]imidazol-1-yl)methyl)nicotinonitrile | 403.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 13 | 37 | (4,4-difluoro-3-NHBoc-piperidine) | B | 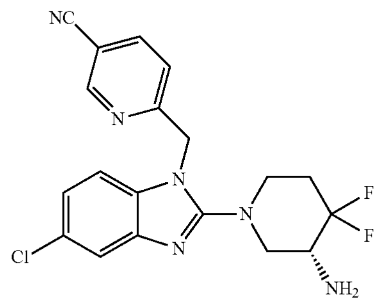 [SMILES: N#Cc1ccc(Cn2c(N3CCC(F)(F)[C@H](N)C3)nc3cc(Cl)ccc32)nc1] | (R)-6-((2-(3-amino-4,4-difluoropiperidin-1-yl)-5-chloro-1H-benzo[d]imidazol-1-yl)methyl)nicotinonitrile | 403.0 |
| 14 | 19 | (4-fluoro-3-NHBoc-piperidine) | B | 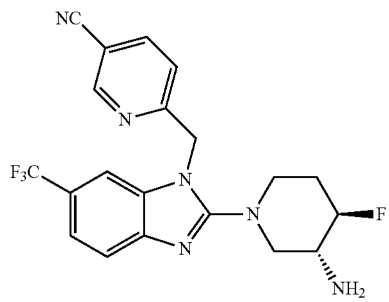 [SMILES: N#Cc1ccc(Cn2c(N3CC[C@@H](F)[C@H](N)C3)nc3ccc(C(F)(F)F)cc32)nc1] | 6-((2-((3R,4R)-3-amino-4-fluoropiperidin-1-yl)-6-(trifluoromethyl)-1H-benzo[d]imidazol-1-yl)methyl)nicotinonitrile | 419.0 |
| 15 | 19 | (4-fluoro-3-NHBoc-piperidine) | B | 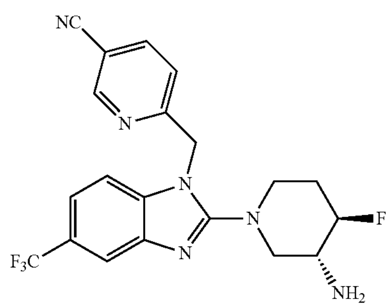 [SMILES: N#Cc1ccc(Cn2c(N3CC[C@@H](F)[C@H](N)C3)nc3cc(C(F)(F)F)ccc32)nc1] | 6-((2-((3R,4R)-3-amino-4-fluoropiperidin-1-yl)-5-(trifluoromethyl)-1H-benzo[d]imidazol-1-yl)methyl)nicotinonitrile | 419.0 |
| 16 | 7 | (4-fluoro-3-NHBoc-piperidine) | B | 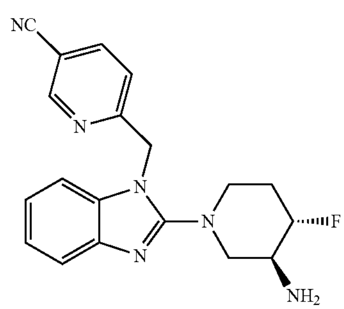 [SMILES: N#Cc1ccc(Cn2c(N3CC[C@H](F)[C@@H](N)C3)nc3ccccc32)nc1] | 6-((2-((3S,4S)-3-amino-4-fluoropiperidin-1-yl)-1H-benzo[d]imidazol-1-yl)methyl)nicotinonitrile | 351.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 17 | 7 | 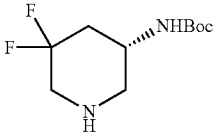 | B | 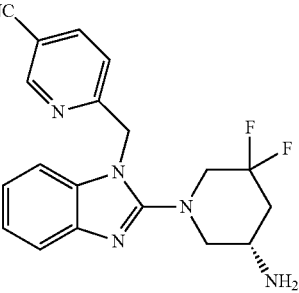 | (S)-6-((2-(5-amino-3,3-difluoropiperidin-1-yl)-1H-benzo[d]imidazol-1-yl)methyl)nicotinonitrile | 369.2 |
| 18 | 11 | 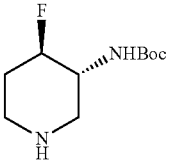 [SMILES: CC(C)(C)OC(=O)N[C@@H]1CNCC[C@H]1F] | B | 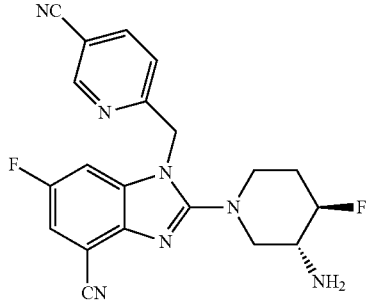 [SMILES: N#Cc1ccc(Cn2c(N3CC[C@@H](F)[C@H](N)C3)nc3c(C#N)cc(F)cc32)nc1] | 2-((3R,4R)-3-amino-4-fluoropiperidin-1-yl)-1-((5-cyanopyridin-2-yl)methyl)-6-fluoro-1H-benzo[d]imidazole-4-carbonitrile | 394.4 |
| 19 | 12 | 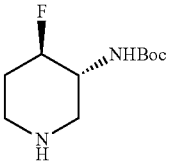 [SMILES: CC(C)(C)OC(=O)N[C@@H]1CNCC[C@H]1F] | B | 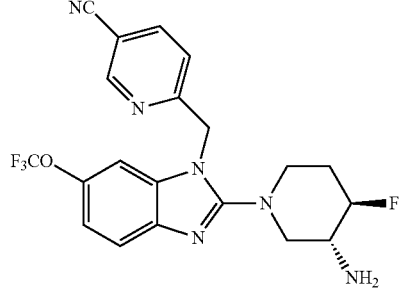 [SMILES: N#Cc1ccc(Cn2c(N3CC[C@@H](F)[C@H](N)C3)nc3ccc(OC(F)(F)F)cc32)nc1] | 6-((2-((3R,4R)-3-amino-4-fluoropiperidin-1-yl)-6-(trifluoromethoxy)-1H-benzo[d]imidazol-1-yl)methyl)nicotinonitrile | 435.4 |
| 20 | 12 | 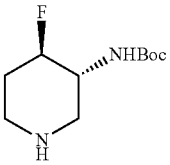 [SMILES: CC(C)(C)OC(=O)N[C@@H]1CNCC[C@H]1F] | B | 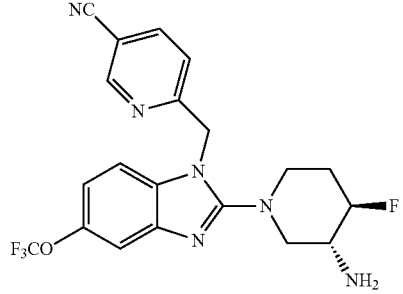 [SMILES: N#Cc1ccc(Cn2c(N3CC[C@@H](F)[C@H](N)C3)nc3cc(OC(F)(F)F)ccc32)nc1] | 6-((2-((3R,4R)-3-amino-4-fluoropiperidin-1-yl)-5-(trifluoromethoxy)-1H-benzo[d]imidazol-1-yl)methyl)nicotinonitrile | 435.4 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 21 | 25 | (structure with F, NHBoc) | B | (structure) | 6-((2-((3R,4R)-3-amino-4-fluoropiperidin-1-yl)-6-fluoro-5-(trifluoromethyl)-1H-benzo[d]imidazol-1-yl)methyl)nicotinonitrile | 437.0 |
| 22 | 25 | (structure with F, NHBoc) | B | (structure) | 6-((2-((3R,4R)-3-amino-4-fluoropiperidin-1-yl)-5-fluoro-6-(trifluoromethyl)-1H-benzo[d]imidazol-1-yl)methyl)nicotinonitrile | 437.0 |
| 23 | 7 | (structure N-Boc) | B | (structure) | 6-((2-((3aS,7aR)-hexahydro-1H-pyrrolo[2,3-c]pyridin-6(2H)-yl)-1H-benzo[d]imidazol-1-yl)methyl)nicotinonitrile | 359.2 |
| 24 | 7 | (structure N-Boc) | B | (structure) | 6-((2-((3aS,7aS)-hexahydro-1H-pyrrolo[2,3-c]pyridin-6(2H)-yl)-1H-benzo[d]imidazol-1-yl)methyl)nicotinonitrile | 359.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 25 | 7 | 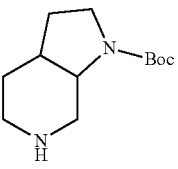 [SMILES: CC(C)(C)OC(=O)N1CCC2CCNCC21] | B | 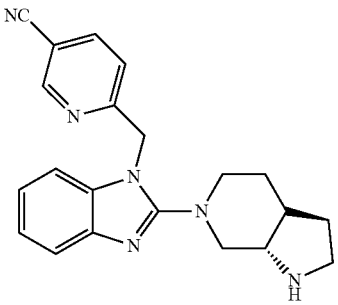 | 6-((2-((3aS,7aS)-hexahydro-1H-pyrrolo[2,3-c]pyridin-6(2H)-yl)-1H-benzo[d]imidazol-1-yl)methyl)nicotinonitrile | 359.2 |
| 26 | 7 | 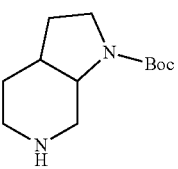 [SMILES: CC(C)(C)OC(=O)N1CCC2CCNCC21] | B | 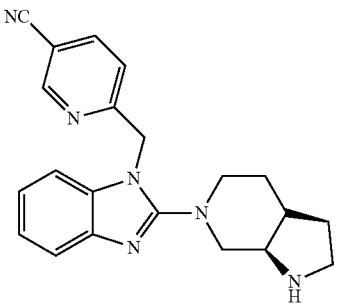 | 6-((2-((3aS,7aR)-hexahydro-1H-pyrrolo[2,3-c]pyridin-6(2H)-yl)-1H-benzo[d]imidazol-1-yl)methyl)nicotinonitrile | 359.2 |
| 27 | 7 | 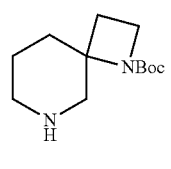 [SMILES: CC(C)(C)OC(=O)N1CCC12CCCNC2] | B | 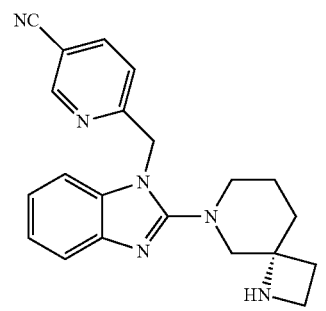 [SMILES: N#Cc1ccc(Cn2c(N3CCC[C@@]4(CCN4)C3)nc3ccccc32)nc1] | (R)-6-((2-(1,6-diazaspiro[3.5]nonan-6-yl)-1H-benzo[d]imidazol-1-yl)methyl)nicotinonitrile | 359.2 |
| 28 | 7 | 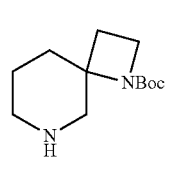 [SMILES: CC(C)(C)OC(=O)N1CCC12CCCNC2] | B | 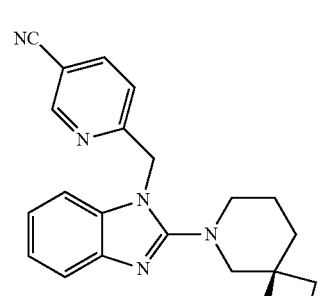 | (S)-6-((2-(1,6-diazaspiro[3.5]nonan-6-yl)-1H-benzo[d]imidazol-1-yl)methyl)nicotinonitrile | 359.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 29 | 13 | (3R,4R)-4-fluoro-3-NHBoc-piperidine | B | 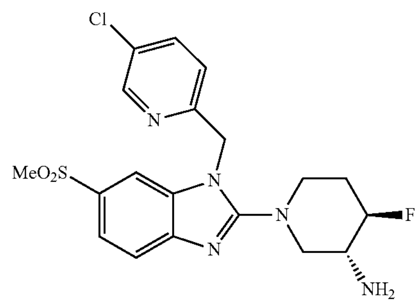 [SMILES: CS(=O)(=O)c1ccc2nc(N3CC[C@@H](F)[C@H](N)C3)n(Cc3ccc(Cl)cn3)c2c1] | (3R,4R)-1-(1-((5-chloropyridin-2-yl)methyl)-6-(methylsulfonyl)-1H-benzo[d]imidazol-2-yl)-4-fluoropiperidin-3-amine | 438.0 |
| 30 | 13 | (3R,4R)-4-fluoro-3-NHBoc-piperidine | B | 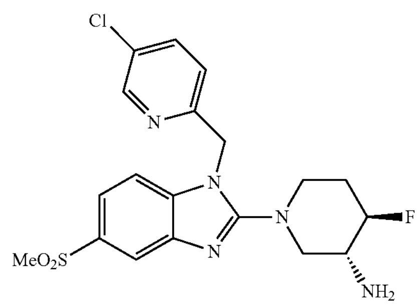 [SMILES: CS(=O)(=O)c1ccc2c(c1)nc(N1CC[C@@H](F)[C@H](N)C1)n2Cc1ccc(Cl)cn1] | (3R,4R)-1-(1-((5-chloropyridin-2-yl)methyl)-5-(methylsulfonyl)-1H-benzo[d]imidazol-2-yl)-4-fluoropiperidin-3-amine | 438.0 |
| 31 | 14 | (3R,4R)-4-fluoro-3-NHBoc-piperidine | B | 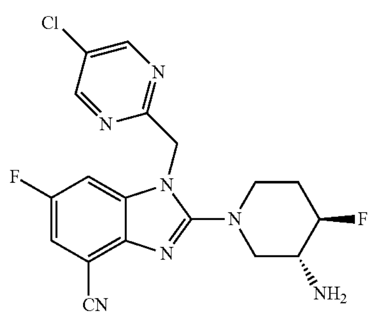 [SMILES: N#Cc1cc(F)cc2c1nc(N1CC[C@@H](F)[C@H](N)C1)n2Cc1ncc(Cl)cn1] | 2-((3R,4R)-3-amino-4-fluoropiperidin-1-yl)-1-((5-chloropyrimidin-2-yl)methyl)-6-fluoro-1H-benzo[d]imidazole-4-carbonitrile | 404.0 |
| 32 | 15 | (3R,4R)-4-fluoro-3-NHBoc-piperidine | B | 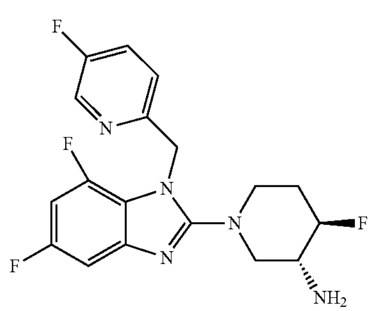 | (3R,4R)-1-(5,7-difluoro-1-((5-fluoropyridin-2-yl)methyl)-1H-benzo[d]imidazol-2-yl)-4-fluoropiperidin-3-amine | 380.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 33 | 15 | | B | 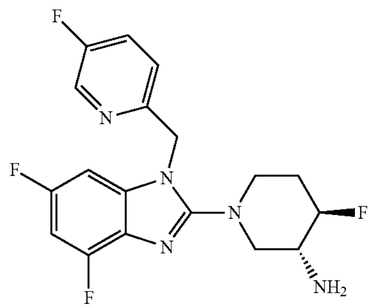 [SMILES: N[C@@H]1CN(c2nc3c(F)cc(F)cc3n2Cc2ccc(F)cn2)CC[C@H]1F] | (3R,4R)-1-(4,6-difluoro-1-((5-fluoropyridin-2-yl)methyl)-1H-benzo[d]imidazol-2-yl)-4-fluoropiperidin-3-amine | 380.0 |
| 34 | 16 | | B | 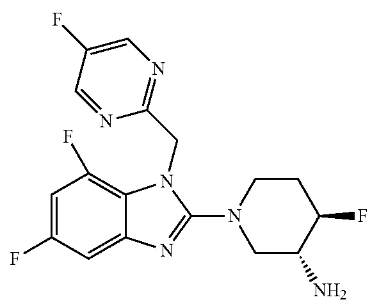 [SMILES: N[C@@H]1CN(c2nc3cc(F)cc(F)c3n2Cc2ncc(F)cn2)CC[C@H]1F] | (3R,4R)-1-(5,7-difluoro-1-((5-fluoropyrimidin-2-yl)methyl)-1H-benzo[d]imidazol-2-yl)-4-fluoropiperidin-3-amine | 381.2 |
| 35 | 16 | | B | 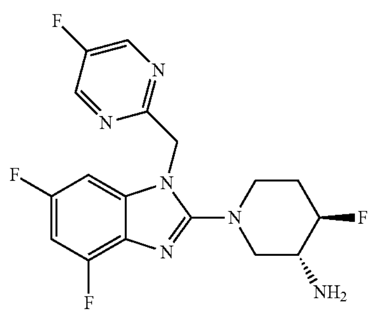 [SMILES: N[C@@H]1CN(c2nc3c(F)cc(F)cc3n2Cc2ncc(F)cn2)CC[C@H]1F] | (3R,4R)-1-(4,6-difluoro-1-((5-fluoropyrimidin-2-yl)methyl)-1H-benzo[d]imidazol-2-yl)-4-fluoropiperidin-3-amine | 381.2 |
| 36 | 18 | | B | 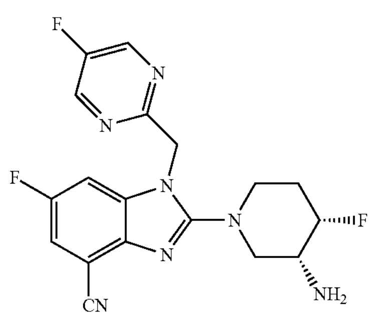 [SMILES: N#Cc1cc(F)cc2c1nc(N1CC[C@H](F)[C@H](N)C1)n2Cc1ncc(F)cn1] | 2-((3R,4S)-3-amino-4-fluoropiperidin-1-yl)-6-fluoro-1-((5-fluoropyrimidin-2-yl)methyl)-1H-benzo[d]imidazole-4-carbonitrile | 338.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 37 | 18 | (4-F, 3-NHBoc piperidine) | B | 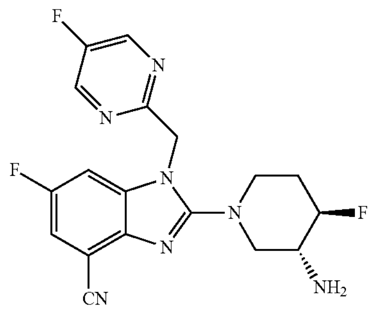 [SMILES: N#Cc1cc(F)cc2c1nc(N1CC[C@@H](F)[C@H](N)C1)n2Cc1ncc(F)cn1] | 2-((3R,4R)-3-amino-4-fluoropiperidin-1-yl)-6-fluoro-1-((5-fluoropyrimidin-2-yl)methyl)-1H-benzo[d]imidazole-4-carbonitrile | 338.0 |
| 38 | 7 | (4-F, 3-NHBoc piperidine) | B | 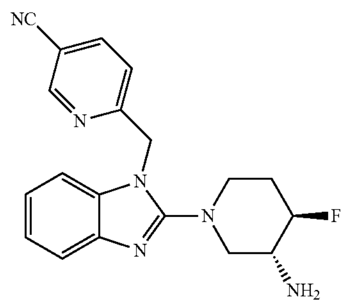 | 6-((2-((3R,4R)-3-amino-4-fluoropiperidin-1-yl)-1H-benzo[d]imidazol-1-yl)methyl)nicotinonitrile | 351.2 |
| 39 | 17 | (4-F, 3-NHBoc piperidine) | B | 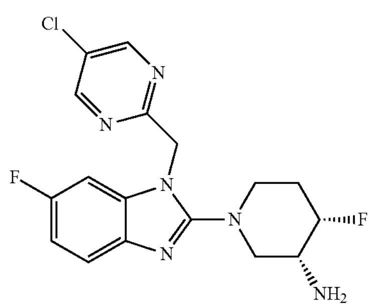 [SMILES: N[C@@H]1CN(c2nc3ccc(F)cc3n2Cc2ncc(Cl)cn2)CC[C@@H]1F] | (3R,4S)-1-(1-((5-chloropyrimidin-2-yl)methyl)-6-fluoro-1H-benzo[d]imidazol-2-yl)-4-fluoropiperidin-3-amine | 379.2 |
| 40 | 17 | (4-F, 3-NHBoc piperidine) | B | 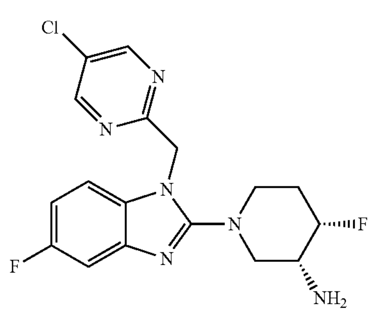 [SMILES: N[C@@H]1CN(c2nc3cc(F)ccc3n2Cc2ncc(Cl)cn2)CC[C@@H]1F] | (3R,4S)-1-(1-((5-chloropyrimidin-2-yl)methyl)-5-fluoro-1H-benzo[d]imidazol-2-yl)-4-fluoropiperidin-3-amine | 379.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 41 | 39 | (structure) | B | (structure) | (R)-2-(3-amino-4,4-difluoropiperidin-1-yl)-1-((5-chloropyrimidin-2-yl)methyl)-1H-benzo[d]imidazole-6-carbonitrile | 404.2 |
| 42 | 39 | (structure) | B | (structure) | (R)-2-(3-amino-4,4-difluoropiperidin-1-yl)-1-((5-chloropyrimidin-2-yl)methyl)-1H-benzo[d]imidazole-5-carbonitrile | 404.2 |
| 43 | 28 | (structure) | B | (structure) | 6-((2-((3R,4R)-3-amino-4-fluoropiperidin-1-yl)-5,6-dichloro-1H-benzo[d]imidazol-1-yl)methyl)nicotinonitrile | 419.0 |
| 44 | 35 | (structure) | B | (structure) | tert-butyl ((3R,4R)-1-(1-((5-cyanopyridin-2-yl)methyl)-5,6-dimethyl-1H-benzo[d]imidazol-2-yl)-4-fluoropiperidin-3-yl)carbamate | 379.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 45 | 34 | piperidine-3-NHBoc | A | 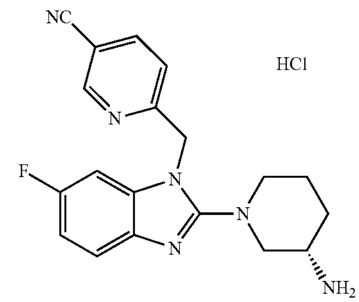 [SMILES: N#Cc1ccc(Cn2c(N3CCC[C@H](N)C3)nc3ccc(F)cc32)nc1 ; Cl] | (S)-6-((2-(3-aminopiperidin-1-yl)-6-fluoro-1H-benzo[d]imidazol-1-yl)methyl)nicotinonitrile hydrochloride | 351.0 |
| 46 | 34 | piperidine-3-NHBoc | A | 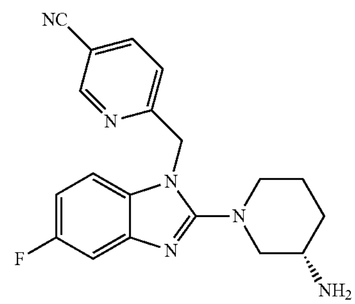 [SMILES: N#Cc1ccc(Cn2c(N3CCC[C@H](N)C3)nc3cc(F)ccc32)nc1] | (S)-6-((2-(3-aminopiperidin-1-yl)-5-fluoro-1H-benzo[d]imidazol-1-yl)methyl)nicotinonitrile hydrochloride | 351.0 |
| 47 | 34 | 4-F-piperidine-3-NHBoc | A | 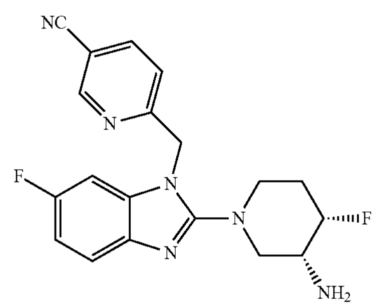 | 6-((2-((3R,4S)-3-amino-4-fluoropiperidin-1-yl)-6-fluoro-1H-benzo[d]imidazol-1-yl)methyl)nicotinonitrile hydrochloride | 369.0 |
| 48 | 34 | 4-F-piperidine-3-NHBoc | A | 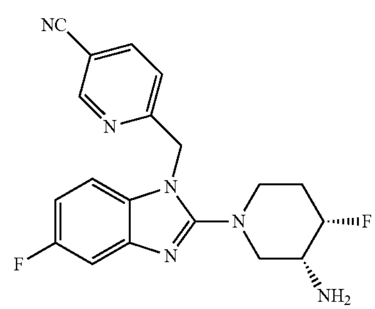 | 6-((2-((3R,4S)-3-amino-4-fluoropiperidin-1-yl)-5-fluoro-1H-benzo[d]imidazol-1-yl)methyl)nicotinonitrile hydrochloride | 369.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 49 | 34 | | A | 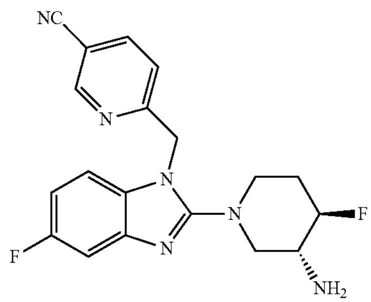 [SMILES: N#Cc1ccc(Cn2c(N3CC[C@@H](F)[C@H](N)C3)nc3cc(F)ccc32)nc1] | 6-((2-((3R,4R)-3-amino-4-fluoropiperidin-1-yl)-5-fluoro-1H-benzo[d]imidazol-1-yl)methyl)nicotinonitrile hydrochloride | 369.0 |
| 50 | 5 | | A | 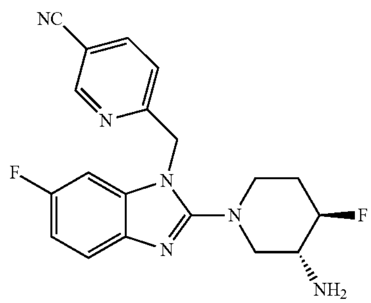 [SMILES: N#Cc1ccc(Cn2c(N3CC[C@@H](F)[C@H](N)C3)nc3ccc(F)cc32)nc1] | 6-((2-((3R,4R)-3-amino-4-fluoropiperidin-1-yl)-5-fluoro-1H-benzo[d]imidazol-1-yl)methyl)nicotinonitrile hydrochloride | 369.0 |
| 51 | 33 | | B | 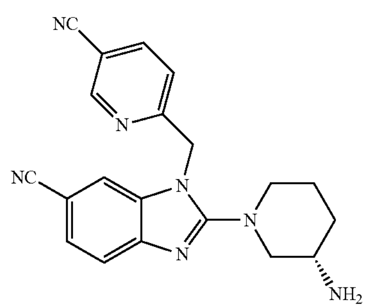 [SMILES: N#Cc1ccc(Cn2c(N3CCC[C@H](N)C3)nc3ccc(C#N)cc32)nc1] | (S)-2-(3-aminopiperidin-1-yl)-1-((5-cyanopyridin-2-yl)methyl)-1H-benzo[d]imidazole-6-carbonitrile | 358.0 |
| 52 | 33 | | B | 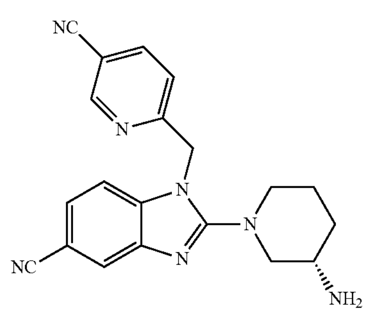 [SMILES: N#Cc1ccc(Cn2c(N3CCC[C@H](N)C3)nc3cc(C#N)ccc32)nc1] | (S)-2-(3-aminopiperidin-1-yl)-1-((5-cyanopyridin-2-yl)methyl)-1H-benzo[d]imidazole-5-carbonitrile | 358.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 53 | 33 | | B | 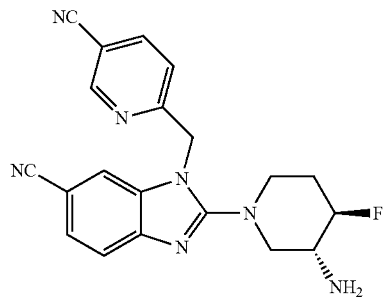 [SMILES: N#Cc1ccc(Cn2c(N3CC[C@@H](F)[C@H](N)C3)nc3ccc(C#N)cc32)nc1] | 2-((3R,4R)-3-amino-4-fluoropiperidin-1-yl)-1-((5-cyanopyridin-2-yl)methyl)-1H-benzo[d]imidazole-6-carbonitrile | 376.0 |
| 54 | 33 | | B | 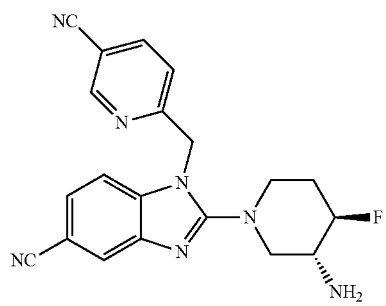 [SMILES: N#Cc1ccc(Cn2c(N3CC[C@@H](F)[C@H](N)C3)nc3cc(C#N)ccc32)nc1] | 2-((3R,4R)-3-amino-4-fluoropiperidin-1-yl)-1-((5-cyanopyridin-2-yl)methyl)-1H-benzo[d]imidazole-5-carbonitrile | 376.0 |
| 55 | 33 | | B | 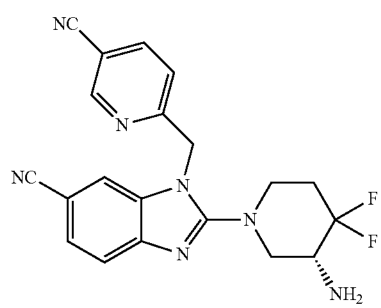 | (R)-2-(3-amino-4,4-difluoropiperidin-1-yl)-1-((5-cyanopyridin-2-yl)methyl)-1H-benzo[d]imidazole-6-carbonitrile | 394.0 |
| 56 | 33 | | B | 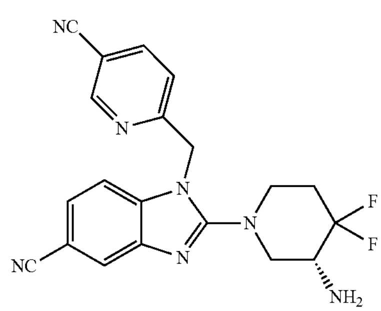 [SMILES: N#Cc1ccc(Cn2c(N3CCC(F)(F)[C@H](N)C3)nc3cc(C#N)ccc32)nc1] | (R)-2-(3-amino-4,4-difluoropiperidin-1-yl)-1-((5-cyanopyridin-2-yl)methyl)-1H-benzo[d]imidazole-5-carbonitrile | 394.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 57 | 36 | 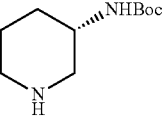 | B | 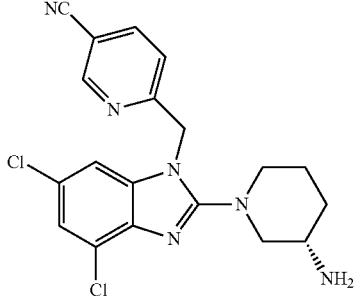 [SMILES: N#Cc1ccc(Cn2c(N3CCC[C@H](N)C3)nc3c(Cl)cc(Cl)cc32)nc1] | (S)-6-((2-(3-aminopiperidin-1-yl)-4,6-dichloro-1H-benzo[d]imidazol-1-yl)methyl)nicotinonitrile | 401.0 |
| 58 | 36 | 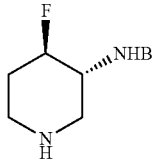 | B | 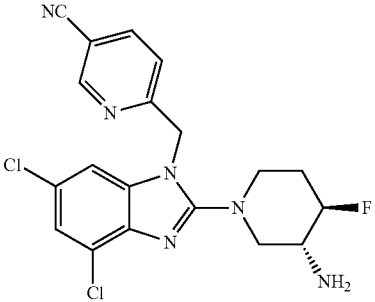 [SMILES: N#Cc1ccc(Cn2c(N3CC[C@@H](F)[C@H](N)C3)nc3c(Cl)cc(Cl)cc32)nc1] | 6-((2-((3R,4R)-3-amino-4-fluoropiperidin-1-yl)-4,6-dichloro-1H-benzo[d]imidazol-1-yl)methyl)nicotinonitrile | 419.0 |
| 59 | 36 | 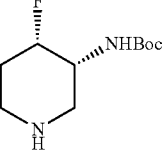 | B | 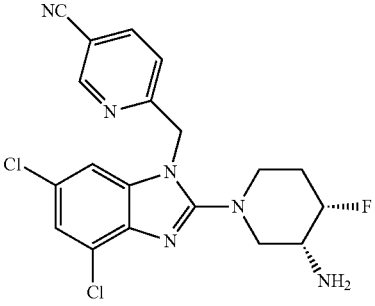 [SMILES: N#Cc1ccc(Cn2c(N3CC[C@H](F)[C@H](N)C3)nc3c(Cl)cc(Cl)cc32)nc1] | 6-((2-((3R,4S)-3-amino-4-fluoropiperidin-1-yl)-4,6-dichloro-1H-benzo[d]imidazol-1-yl)methyl)nicotinonitrile | 419.0 |
| 60 | 36 | 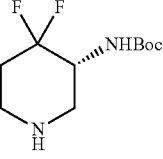 [SMILES: CC(C)(C)OC(=O)N[C@@H]1CNCCC1(F)F] | B | 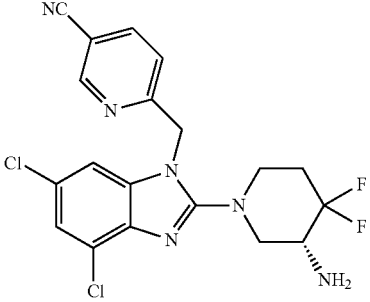 [SMILES: N#Cc1ccc(Cn2c(N3CCC(F)(F)[C@H](N)C3)nc3c(Cl)cc(Cl)cc32)nc1] | (R)-6-((2-(3-amino-4,4-difluoropiperidin-1-yl)-4,6-dichloro-1H-benzo[d]imidazol-1-yl)methyl)nicotinonitrile | 437.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 61 | 31 | 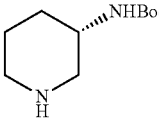 | B | 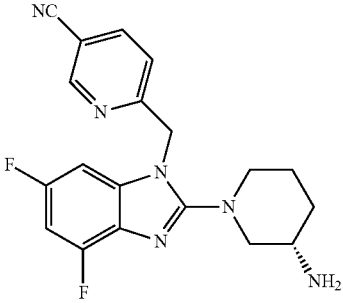 [SMILES: N#Cc1ccc(Cn2c(N3CCC[C@H](N)C3)nc3c(F)cc(F)cc32)nc1] | (S)-6-((2-(3-aminopiperidin-1-yl)-4,6-difluoro-1H-benzo[d]imidazol-1-yl)methyl)nicotinonitrile | 369.0 |
| 62 | 31 | 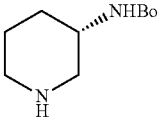 | B | 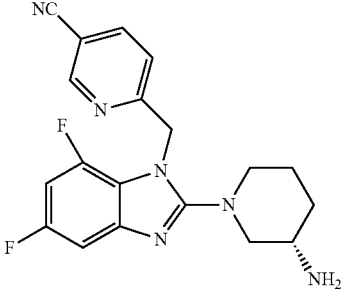 [SMILES: N#Cc1ccc(Cn2c(N3CCC[C@H](N)C3)nc3cc(F)cc(F)c32)nc1] | (S)-6-((2-(3-aminopiperidin-yl)-5,7-difluoro-1H-benzo[d]imidazol-1-yl)methyl)nicotinonitrile | 369.0 |
| 63 | 31 | 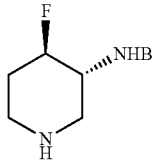 | B | 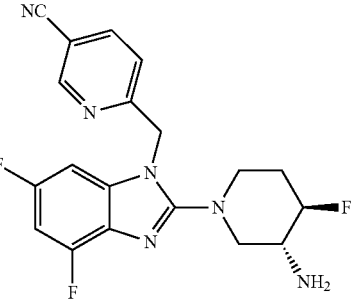 | 6-((2-((3R,4R)-3-amino-4-fluoropiperidin-1-yl)-4,6-difluoro-1H-benzo[d]imidazol-1-yl)methyl)nicotinonitrile | 387.0 |
| 64 | 31 | 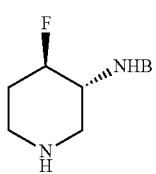 | B | 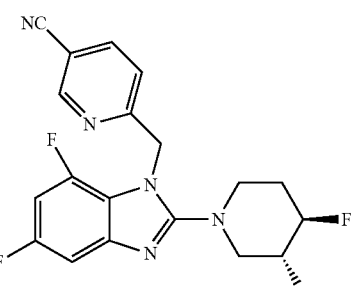 | 6-((2-((3R,4R)-3-amino-4-fluoropiperidin-1-yl)-5,7-difluoro-1H-benzo[d]imidazol-1-yl)methyl)nicotinonitrile | 387.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 65 | 31 | (3R,4S)-4-F,3-NHBoc piperidine | B | 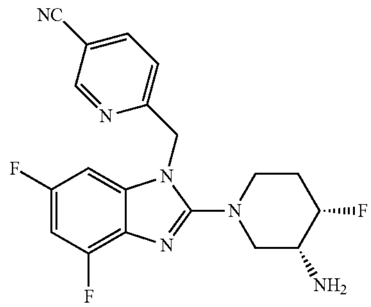 [SMILES: N#Cc1ccc(Cn2c(N3CC[C@H](F)[C@H](N)C3)nc3c(F)cc(F)cc32)nc1] | 6-((2-((3R,4S)-3-amino-4-fluoropiperidin-1-yl)-4,6-difluoro-1H-benzo[d]imidazol-1-yl)methyl)nicotinonitrile | 387.0 |
| 66 | 31 | (3R,4S)-4-F,3-NHBoc piperidine | B | 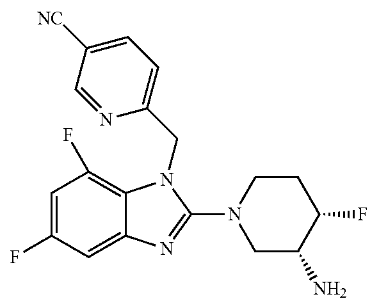 [SMILES: N#Cc1ccc(Cn2c(N3CC[C@H](F)[C@H](N)C3)nc3cc(F)cc(F)c32)nc1] | 6-((2-((3R,4S)-3-amino-4-fluoropiperidin-1-yl)-5,7-difluoro-1H-benzo[d]imidazol-1-yl)methyl)nicotinonitrile | 387.0 |
| 67 | 31 | 4,4-diF,3-NHBoc piperidine | B | 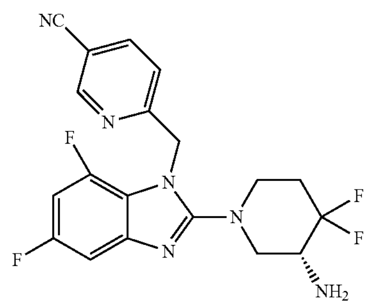 [SMILES: N#Cc1ccc(Cn2c(N3CCC(F)(F)[C@H](N)C3)nc3cc(F)cc(F)c32)nc1] | (R)-6-((2-(3-amino-4,4-difluoropiperidin-1-yl)-5,7-difluoro-1H-benzo[d]imidazol-1-yl)methyl)nicotinonitrile | 405.0 |
| 68 | 33 | (3R,4S)-4-F,3-NHBoc piperidine | B | 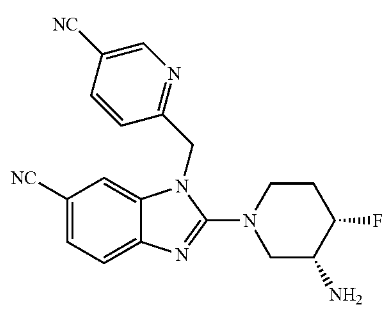 [SMILES: N#Cc1ccc(Cn2c(N3CC[C@H](F)[C@H](N)C3)nc3ccc(C#N)cc32)nc1] | 2-((3R,4S)-3-amino-4-fluoropiperidin-1-yl)-1-((5-cyanopyridin-2-yl)methyl)-1H-benzo[d]imidazole-6-carbonitrile | 376.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 69 | 33 | (4S,3R)-4-fluoro-3-NHBoc-piperidine | B | 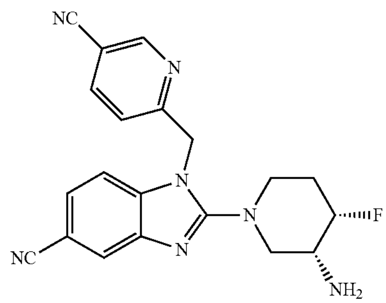 [SMILES: N#Cc1ccc(Cn2c(N3CC[C@H](F)[C@H](N)C3)nc3cc(C#N)ccc32)nc1] | 2-((3R,4S)-3-amino-4-fluoropiperidin-1-yl)-1-((5-cyanopyridin-2-yl)methyl)-1H-benzo[d]imidazole-5-carbonitrile | 376.0 |
| 70 | 7 | (3S)-3-NHBoc-piperidine | A | 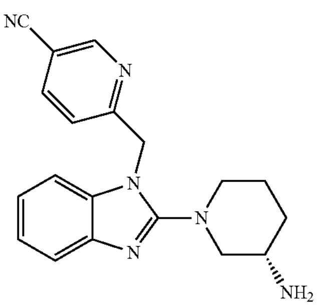 [SMILES: N#Cc1ccc(Cn2c(N3CCC[C@H](N)C3)nc3ccccc32)nc1] | (S)-6-((2-(3-aminopiperidin-1-yl)-1H-benzo[d]imidazol-1-yl)methyl)nicotinonitrile | 333.0 |
| 71 | 34 | 4,4-difluoro-3-NHBoc-piperidine | A | 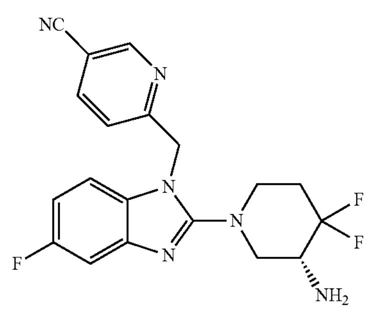 [SMILES: N#Cc1ccc(Cn2c(N3CCC(F)(F)[C@H](N)C3)nc3cc(F)ccc32)nc1] | (R)-6-((2-(3-amino-4,4-difluoropiperidin-1-yl)-5-fluoro-1H-benzo[d]imidazol-1-yl)methyl)nicotinonitrile hydrochloride | 387.0 |
| 72 | 29 | (3R,4R)-4-fluoro-3-NHB-piperidine | B | 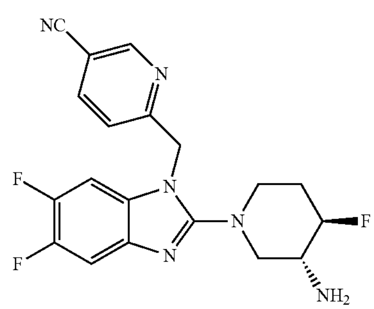 [SMILES: N#Cc1ccc(Cn2c(N3CC[C@@H](F)[C@H](N)C3)nc3cc(F)c(F)cc32)nc1] | 6-((2-((3R,4R)-3-amino-4-fluoropiperidin-1-yl)-5,6-difluoro-1H-benzo[d]imidazol-1-yl)methyl)nicotinonitrile | 387.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 73 | 7 | | A | 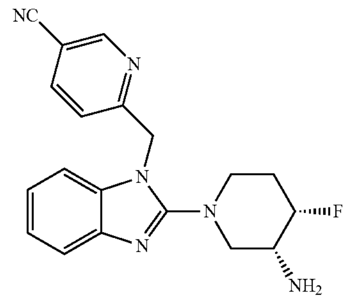 [SMILES: N#Cc1ccc(Cn2c(N3CC[C@H](F)[C@H](N)C3)nc3ccccc32)nc1] | 6-((2-((3R,4S)-3-amino-4-fluoropiperidin-1-yl)-1H-benzo[d]imidazol-1-yl)methyl)nicotinonitrile | 351.0 |
| 74 | 7 | | A | 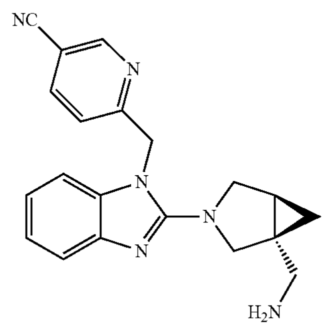 | 6-((2-((1R,5S)-1-(aminomethyl)-3-azabicyclo[3.1.0]hexan-3-yl)-1H-benzo[d]imidazol-1-yl)methyl)nicotinonitrile hydrochloride | 345.2 |
| 75 | 7 | | A | 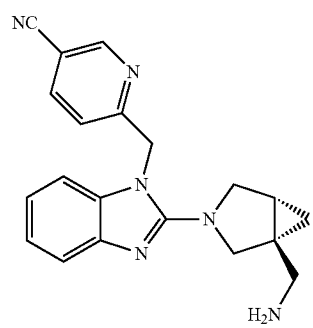 | 6-((2-((1S,5R)-1-(aminomethyl)-3-azabicyclo[3.1.0]hexan-3-yl)-1H-benzo[d]imidazol-1-yl)methyl)nicotinonitrile hydrochloride | 345.2 |
| 76 | 7 | | A | 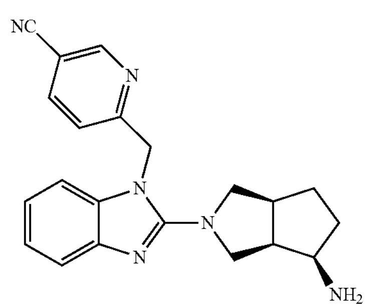 [SMILES: N#Cc1ccc(Cn2c(N3C[C@H]4CC[C@H](N)[C@H]4C3)nc3ccccc32)nc1 ; Cl] | 6-((2-((3aR,4R,6aS)-4-aminohexahydrocyclopenta[c]pyrrol-2(1H)-yl)-1H-benzo[d]imidazol-1-yl)methyl)nicotinonitrile hydrochloride | 359.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 77 | 7 | (structure) | A | (structure) | 6-((2-((3aS,4S,6aR)-4-aminohexahydrocyclopenta[c]pyrrol-2(1H)-yl)-1H-benzo[d]imidazol-1-yl)methyl)nicotinonitrile hydrochloride | 359.0 |
| 78 | 7 | (structure) | A | (structure) | 6-((2-((3aR,4S,6aS)-4-aminohexahydrocyclopenta[c]pyrrol-2(1H)-yl)-1H-benzo[d]imidazol-1-yl)methyl)nicotinonitrile hydrochloride | 359.2 |
| 79 | 7 | (structure) | A | (structure) | 6-((2-((3aS,4R,6aR)-4-aminohexahydrocyclopenta[c]pyrrol-2(1H)-yl)-1H-benzo[d]imidazol-1-yl)methyl)nicotinonitrile hydrochloride | 359.2 |
| 80 | 7 | (structure) | A | (structure) | (R)-6-((2-(3-(aminomethyl)pyrrolidin-1-yl)-1H-benzo[d]imidazol-1-yl)methyl)nicotinonitrile hydrochloride | 333.2 |
| 81 | 7 | (structure) | A | (structure) | (S)-6-((2-(3-(aminomethyl)pyrrolidin-1-yl)-1H-benzo[d]imidazol-1-yl)methyl)nicotinonitrile hydrochloride | 333.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 82 | 28 | | B | 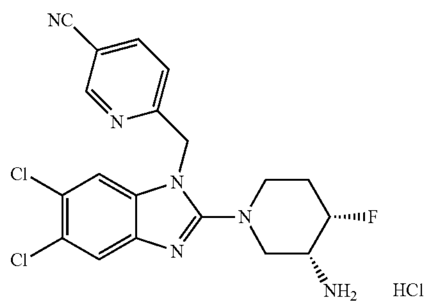 [SMILES: N#Cc1ccc(Cn2c(N3CC[C@H](F)[C@H](N)C3)nc3cc(Cl)c(Cl)cc32)nc1 ; Cl] | 6-((2-((3R,4S)-3-amino-4-fluoropiperidin-1-yl)-5,6-dichloro-1H-benzo[d]imidazol-1-yl)methyl)nicotinonitrile hydrochloride | 419.2 |
| 83 | 29 | | B | 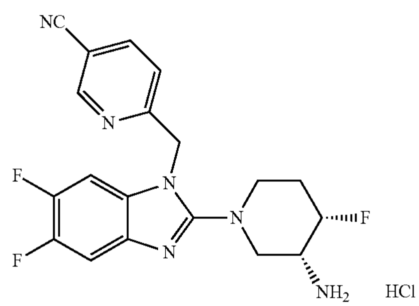 [SMILES: N#Cc1ccc(Cn2c(N3CC[C@H](F)[C@H](N)C3)nc3cc(F)c(F)cc32)nc1 ; Cl] | 6-((2-((3R,4S)-3-amino-4-fluoropiperidin-1-yl)-5,6-difluoro-1H-benzo[d]imidazol-1-yl)methyl)nicotinonitrile hydrochloride | 387.2 |
| 84 | 29 | | B | 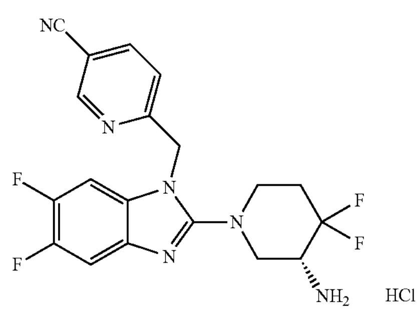 [SMILES: N#Cc1ccc(Cn2c(N3CCC(F)(F)[C@H](N)C3)nc3cc(F)c(F)cc32)nc1 ; Cl] | (R)-6-((2-(3-amino-4,4-difluoropiperidin-1-yl)-5,6-difluoro-1H-benzo[d]imidazol-1-yl)methyl)nicotinonitrile hydrochloride | 405.2 |
| 85 | 30 | | B | 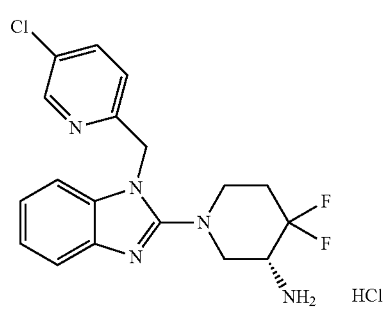 [SMILES: N[C@@H]1CN(c2nc3ccccc3n2Cc2ccc(Cl)cn2)CCC1(F)F ; Cl] | (R)-1-(1-((5-chloropyridin-2-yl)methyl)-1H-benzo[d]imidazol-2-yl)-4,4-difluoropiperidin-3-amine hydrochloride | 378.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 86 | 30 | | B | 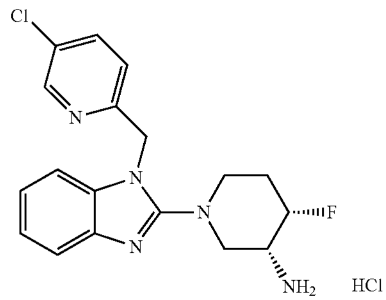 [SMILES: N[C@@H]1CN(c2nc3ccccc3n2Cc2ccc(Cl)cn2)CC[C@@H]1F ; Cl] | (3R,4S)-1-(1-((5-chloropyridin-2-yl)methyl)-1H-benzo[d]imidazol-2-yl)-4-fluoropiperidin-3-amine hydrochloride | 360.2 |
| 87 | 31 | | B | 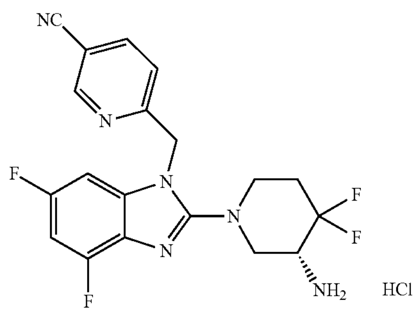 [SMILES: N#Cc1ccc(Cn2c(N3CCC(F)(F)[C@H](N)C3)nc3c(F)cc(F)cc32)nc1 ; Cl] | (R)-6-((2-(3-amino-4,4-difluoropiperidin-1-yl)-4,6-difluoro-1H-benzo[d]imidazol-1-yl)methyl)nicotinonitrile hydrochloride | 405.2 |
| 88 | 5 | | B | 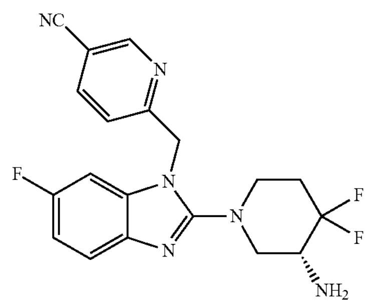 [SMILES: N#Cc1ccc(Cn2c(N3CCC(F)(F)[C@H](N)C3)nc3ccc(F)cc32)nc1] | (R)-6-((2-(3-amino-4,4-difluoropiperidin-1-yl)-6-fluoro-1H-benzo[d]imidazol-1-yl)methyl)nicotinonitrile | 387.2 |
| 89 | 8 | | A | 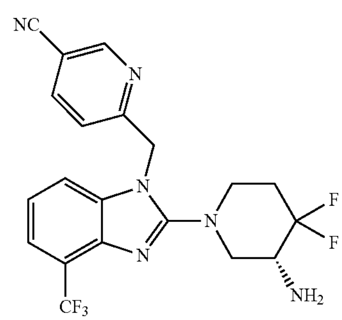 [SMILES: N#Cc1ccc(Cn2c(N3CCC(F)(F)[C@H](N)C3)nc3c(C(F)(F)F)cccc32)nc1] | (R)-6-((2-(3-amino-4,4-difluoropiperidin-1-yl)-4-(trifluoromethyl)-1H-benzo[d]imidazol-1-yl)methyl)nicotinonitrile | 437.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 90 | 8 | (4S,3R) 4-F, 3-NHBoc piperidine | A | 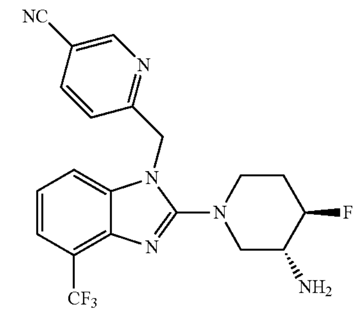 [SMILES: N#Cc1ccc(Cn2c(N3CC[C@@H](F)[C@H](N)C3)nc3c(C(F)(F)F)cccc32)nc1] | 6-((2-((3R,4R)-3-amino-4-fluoropiperidin-1-yl)-4-(trifluoromethyl)-1H-benzo[d]imidazol-1-yl)methyl)nicotinonitrile | 419.2 |
| 91 | 8 | (4R,3R) 4-F, 3-NHBoc piperidine | A | 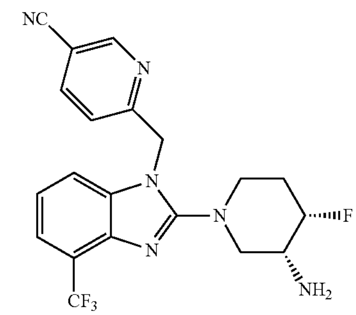 [SMILES: N#Cc1ccc(Cn2c(N3CC[C@H](F)[C@H](N)C3)nc3c(C(F)(F)F)cccc32)nc1] | 6-((2-((3R,4S)-3-amino-4-fluoropiperidin-1-yl)-4-(trifluoromethyl)-1H-benzo[d]imidazol-1-yl)methyl)nicotinonitrile | 419.2 |
| 92 | 9 | (4S,3R) 4-F, 3-NHBoc piperidine | A | 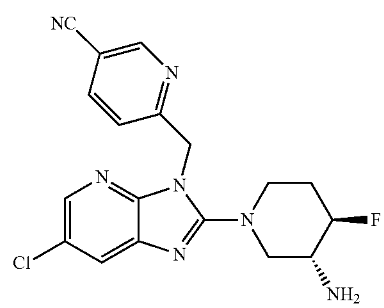 [SMILES: N#Cc1ccc(Cn2c(N3CC[C@@H](F)[C@H](N)C3)nc3cc(Cl)cnc32)nc1] | 6-((2-((3R,4R)-3-amino-4-fluoropiperidin-1-yl)-6-chloro-3H-imidazo[4,5-b]pyridin-3-yl)methyl)nicotinonitrile | 386.2 |
| 93 | 9 | (4S,3R) 4-F, 3-NHBoc piperidine | A | 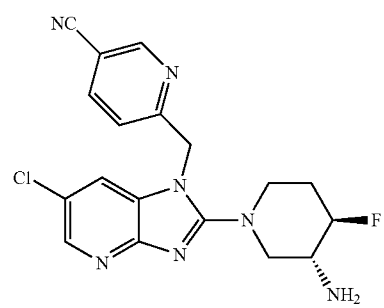 [SMILES: N#Cc1ccc(Cn2c(N3CC[C@@H](F)[C@H](N)C3)nc3ncc(Cl)cc32)nc1] | 6-((2-((3R,4R)-3-amino-4-fluoropiperidin-1-yl)-6-chloro-1H-imidazo[4,5-b]pyridin-1-yl)methyl)nicotinonitrile | 386.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 94 | 9 | (4-fluoro-3-NHBoc piperidine) | A[b] | 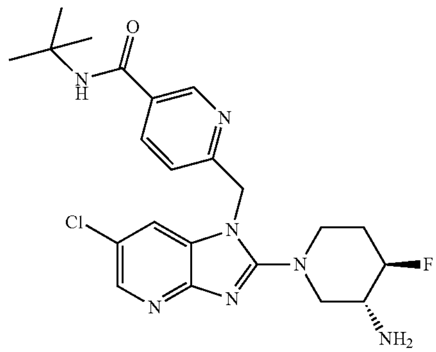 [SMILES: CC(C)(C)NC(=O)c1ccc(Cn2c(N3CC[C@@H](F)[C@H](N)C3)nc3ncc(Cl)cc32)nc1] | 6-((2-((3R,4R)-3-amino-4-fluoropiperidin-1-yl)-6-chloro-1H-imidazo[4,5-b]pyridin-1-yl)methyl)-N-(tert-butyl)nicotinamide | 460.2 |
| 95 | 7 | (4-OH-3-NHBoc piperidine) | A | 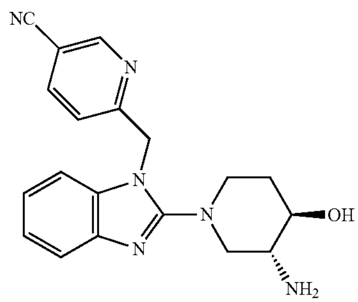 [SMILES: N#Cc1ccc(Cn2c(N3CC[C@@H](O)[C@H](N)C3)nc3ccccc32)nc1] | 6-((2-((3R,4R)-3-amino-4-hydroxypiperidin-1-yl)-1H-benzo[d]imidazol-1-yl)methyl)nicotinonitrile | 349.2 |
| 96 | 7 | (4-OH-3-NHBoc piperidine) | A | 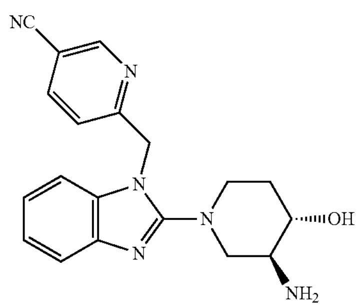 [SMILES: N#Cc1ccc(Cn2c(N3CC[C@H](O)[C@@H](N)C3)nc3ccccc32)nc1] | 6-((2-((3S,4S)-3-amino-4-hydroxypiperidin-1-yl)-1H-benzo[d]imidazol-1-yl)methyl)nicotinonitrile | 349.2 |
| 97 | 7 | (NBoc diazaspiro) | A | 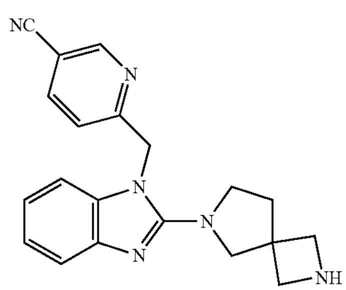 [SMILES: N#Cc1ccc(Cn2c(N3CCC4(CNC4)C3)nc3ccccc32)nc1] | 6-((2-(2,6-diazaspiro[3.4]octan-6-yl)-1H-benzo[d]imidazol-1-yl)methyl)nicotinonitrile | 345.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 98 | 7 | (structure) | A | (structure) | 6-((2-((4aR,7aS)-hexahydropyrrolo[3,4-b][1,4]oxazin-6(2H)-yl)-1H-benzo[d]imidazol-1-yl)methyl)nicotinonitrile hydrochloride | 361.2 |
| 99 | 7 | (structure) | A | (structure) | 6-((2-((4aS,7aR)-hexahydropyrrolo[3,4-b][1,4]oxazin-6(2H)-yl)-1H-benzo[d]imidazol-1-yl)methyl)nicotinonitrile hydrochloride | 361.2 |
| 100 | 7 | (structure) | A | (structure) | 6-((2-((4aR,7aR)-hexahydropyrrolo[3,4-b][1,4]oxazin-6(2H)-yl)-1H-benzo[d]imidazol-1-yl)methyl)nicotinonitrile | 361.2 |
| 101 | 7 | (structure) | A | (structure) | 6-((2-((4aS,7aS)-hexahydropyrrolo[3,4-b][1,4]oxazin-6(2H)-yl)-1H-benzo[d]imidazol-1-yl)methyl)nicotinonitrile | 361.2 |
| 102 | 7 | (structure) | — | (structure) | (S)-3-amino-1-(1-((5-cyanopyridin-2-yl)methyl)-1H-benzo[d]imidazol-2-yl)piperidine-3-carboxamide | 376.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 103 | 7 | | — | 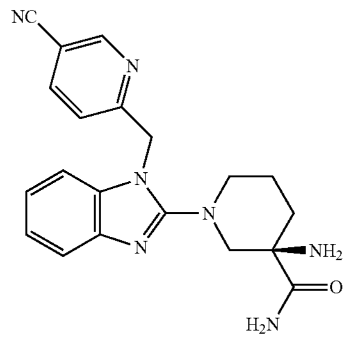 [SMILES: N#Cc1ccc(Cn2c(N3CCC[C@](N)(C(N)=O)C3)nc3ccccc32)nc1] | (R)-3-amino-1-(1-((5-cyanopyridin-2-yl)methyl)-1H-benzo[d]imidazol-2-yl)piperidine-3-carboxamide | 376.2 |
| 104 | 7 | | A | 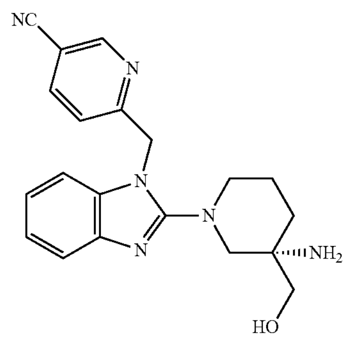 [SMILES: N#Cc1ccc(Cn2c(N3CCC[C@@](N)(CO)C3)nc3ccccc32)nc1] | (S)-6-((2-(3-amino-3-(hydroxymethyl)piperidin-1-yl)-1H-benzo[d]imidazol-1-yl)methyl)nicotinonitrile | 363.2 |
| 105 | 7 | | A | 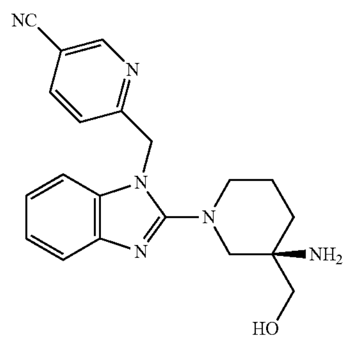 [SMILES: N#Cc1ccc(Cn2c(N3CCC[C@](N)(CO)C3)nc3ccccc32)nc1] | (R)-6-((2-(3-amino-3-(hydroxymethyl)piperidin-1-yl)-1H-benzo[d]imidazol-1-yl)methyl)nicotinonitrile | 363.2 |
| 106 | 19 | | B | 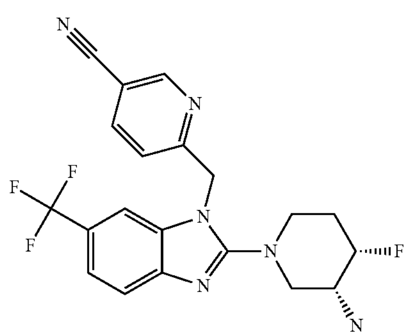 [SMILES: N#Cc1ccc(Cn2c(N3CC[C@H](F)[C@H](N)C3)nc3ccc(C(F)(F)F)cc32)nc1] | 6-((2-((3R,4S)-3-amino-4-fluoro-1-piperidinyl)-6-(trifluoromethyl)-1H-benzimidazol-1-yl)methyl)-3-pyridinecarbonitrile | 419.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 107 | 19 | | B | 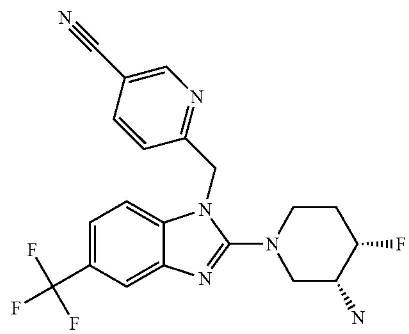 [SMILES: N#Cc1ccc(Cn2c(N3CC[C@H](F)[C@H](N)C3)nc3cc(C(F)(F)F)ccc32)nc1] | 6-((2-((3R,4S)-3-amino-4-fluoro-1-piperidinyl)-5-(trifluoromethyl)-1H-benzimidazol-1-yl)methyl)-3-pyridinecarbonitrile | 419.2 |
| 108 | 19 | | B | 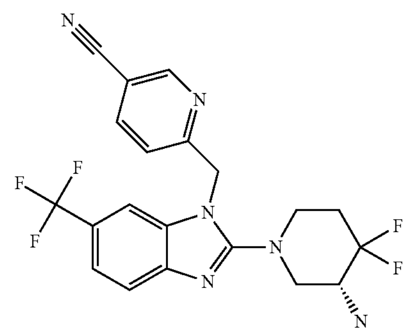 [SMILES: N#Cc1ccc(Cn2c(N3CCC(F)(F)[C@H](N)C3)nc3ccc(C(F)(F)F)cc32)nc1] | 6-((2-((3R)-3-amino-4,4-difluoro-1-piperidinyl)-6-(trifluoromethyl)-1H-benzimidazol-1-yl)methyl)-3-pyridinecarbonitrile | 437.2 |
| 109 | 19 | | B | 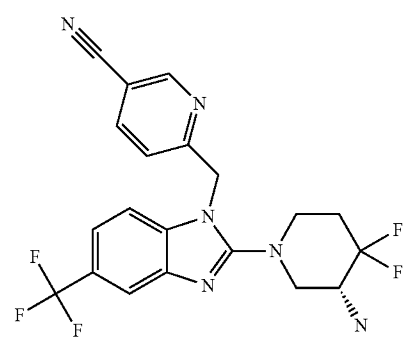 [SMILES: N#Cc1ccc(Cn2c(N3CCC(F)(F)[C@H](N)C3)nc3cc(C(F)(F)F)ccc32)nc1] | 6-((2-((3R)-3-amino-4,4-difluoro-1-piperidinyl)-5-(trifluoromethyl)-1H-benzimidazol-1-yl)methyl)-3-pyridinecarbonitrile | 437.2 |
| 110 | 40 | | B | 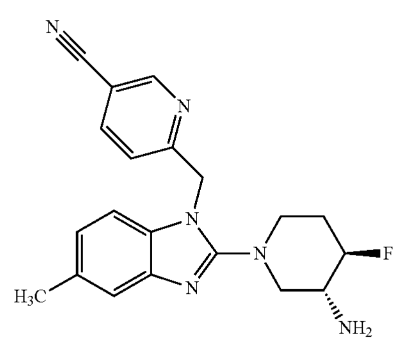 [SMILES: Cc1ccc2c(c1)nc(N1CC[C@@H](F)[C@H](N)C1)n2Cc1ccc(C#N)cn1] | 6-((2-((3R,4R)-3-amino-4-fluoro-1-piperidinyl)-5-methyl-1H-benzimidazol-1-yl)methyl)-3-pyridinecarbonitrile | 365.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 111 | 40 | 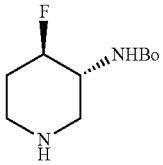 | B | 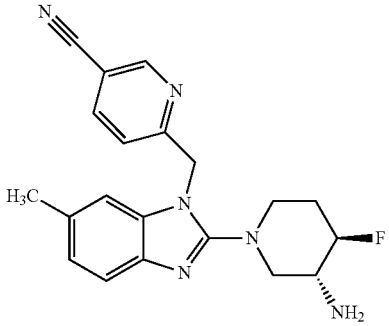 [SMILES: Cc1ccc2nc(N3CC[C@@H](F)[C@H](N)C3)n(Cc3ccc(C#N)cn3)c2c1] | 6-((2-((3R,4R)-3-amino-4-fluoro-1-piperidinyl)-6-methyl-1H-benzimidazol-1-yl)methyl)-3-pyridinecarbonitrile | 365.2 |
| 112 | 20 | 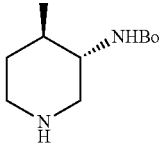 | B | 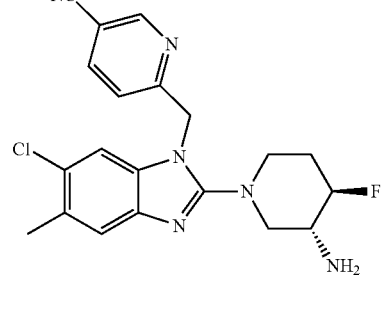 | 6-((2-((3R,4R)-3-amino-4-fluoro-1-piperidinyl)-6-chloro-5-methyl-1H-benzimidazol-1-yl)methyl)-3-pyridinecarbonitrile | 399.1 |
| 113 | 20 | 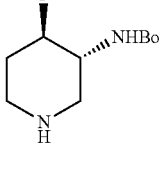 | B | 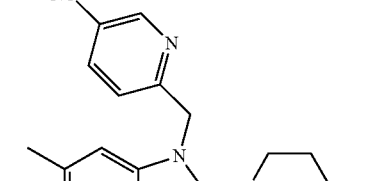 | 6-((2-((3R,4R)-3-amino-4-fluoro-1-piperidinyl)-5-chloro-6-methyl-1H-benzimidazol-1-yl)methyl)-3-pyridinecarbonitrile | 399.1 |
| 114 | 41 | 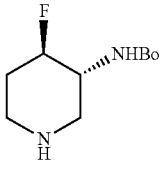 | B | 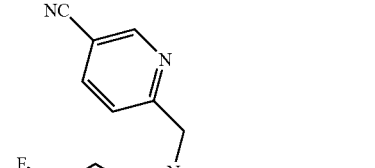 | 6-((2-((3R,4R)-3-amino-4-fluoro-1-piperidinyl)-6-fluoro-5-methyl-1H-benzimidazol-1-yl)methyl)-3-pyridinecarbonitrile | 383.1 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 115 | 41 | (4-fluoro-3-NHBoc piperidine) | B | 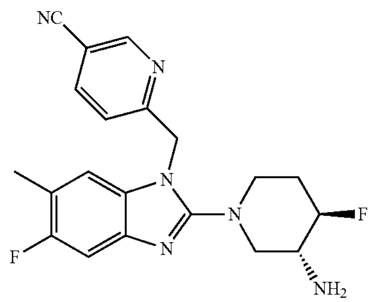 | 6-((2-((3R,4R)-3-amino-4-fluoro-1-piperidinyl)-5-fluoro-6-methyl-1H-benzimidazol-1-yl)methyl)-3-pyridinecarbonitrile | 383.1 |
| 116 | 7 | (3-N(Me)Boc piperidine) | B | 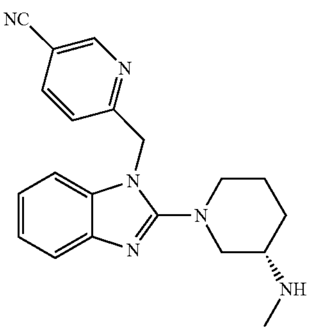 [SMILES: CN[C@H]1CCCN(c2nc3ccccc3n2Cc2ccc(C#N)cn2)C1] | 6-((2-((3S)-3-(methylamino)-1-piperidinyl)-1H-benzimidazol-1-yl)methyl)-3-pyridinecarbonitrile | 347.2 |
| 117 | 7 | (3-N(Me)Boc piperidine) | B | 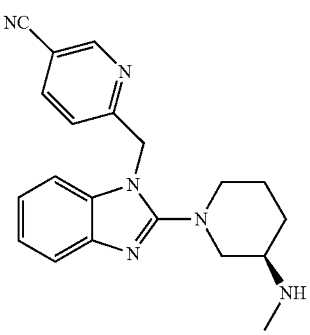 [SMILES: CN[C@@H]1CCCN(c2nc3ccccc3n2Cc2ccc(C#N)cn2)C1] | 6-((2-((3R)-3-(methylamino)-1-piperidinyl)-1H-benzimidazol-1-yl)methyl)-3-pyridinecarbonitrile | 347.2 |
| 118 | 21 | (4-fluoro-3-NHBoc piperidine) | B | 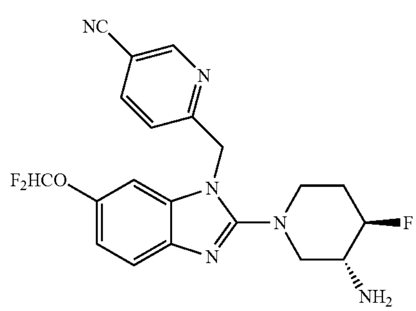 [SMILES: N#Cc1ccc(Cn2c(N3CC[C@@H](F)[C@H](N)C3)nc3ccc(OC(F)F)cc32)nc1] | 6-((2-((3R,4R)-3-amino-4-fluoro-1-piperidinyl)-6-(difluoromethoxy)-1H-benzimidazol-1-yl)methyl)-3-pyridinecarbonitrile | 417.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 119 | 21 | | B | 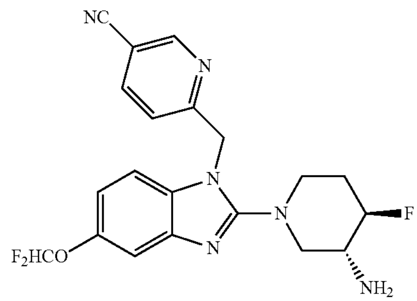 [SMILES: N#Cc1ccc(Cn2c(N3CC[C@@H](F)[C@H](N)C3)nc3cc(OC(F)F)ccc32)nc1] | 6-((2-((3R,4R)-3-amino-4-fluoro-1-piperidinyl)-5-(difluoromethoxy)-1H-benzimidazol-1-yl)methyl)-3-pyridinecarbonitrile | 417.2 |
| 120 | 22 | | B | 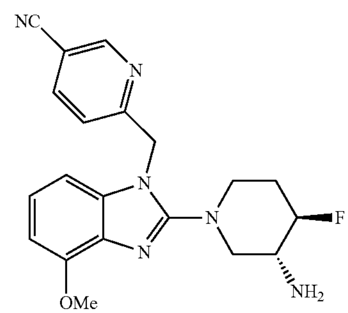 [SMILES: COc1cccc2c1nc(N1CC[C@@H](F)[C@H](N)C1)n2Cc1ccc(C#N)cn1] | 6-((2-((3R,4R)-3-amino-4-fluoro-1-piperidinyl)-4-methoxy-1H-benzimidazol-1-yl)methyl)-3-pyridinecarbonitrile | 381.2 |
| 121 | 23 | | B | 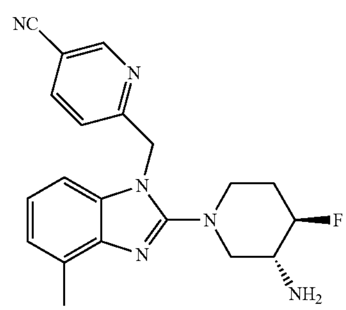 [SMILES: Cc1cccc2c1nc(N1CC[C@@H](F)[C@H](N)C1)n2Cc1ccc(C#N)cn1] | 6-((2-((3R,4R)-3-amino-4-fluoro-1-piperidinyl)-4-methyl-1H-benzimidazol-1-yl)methyl)-3-pyridinecarbonitrile | 365.2 |
| 122 a | 42 | | B | 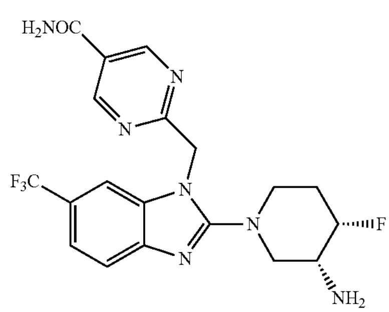 [SMILES: NC(=O)c1cnc(Cn2c(N3CC[C@H](F)[C@H](N)C3)nc3ccc(C(F)(F)F)cc32)nc1] | 5-((2-((3R,4S)-3-amino-4-fluoro-1-piperidinyl)-6-(trifluoromethyl)-1H-benzimidazol-1-yl)methyl)-2-pyrazinecarboxamide | 438.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 123 a | 42 | (3R,4S)-4-fluoro-3-NHBoc piperidine | B | 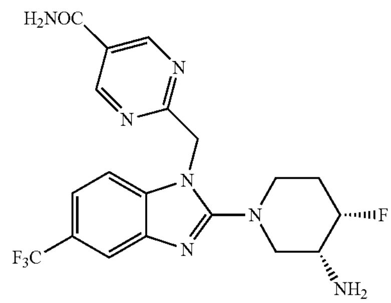 [SMILES: NC(=O)c1cnc(Cn2c(N3CC[C@H](F)[C@H](N)C3)nc3cc(C(F)(F)F)ccc32)nc1] | 5-((2-((3R,4S)-3-amino-4-fluoro-1-piperidinyl)-5-(trifluoromethyl)-1H-benzimidazol-1-yl)methyl)-2-pyrazinecarboxamide | 438.2 |
| 124 | 27 | (3R,4R)-4-fluoro-3-NHBoc piperidine | B | 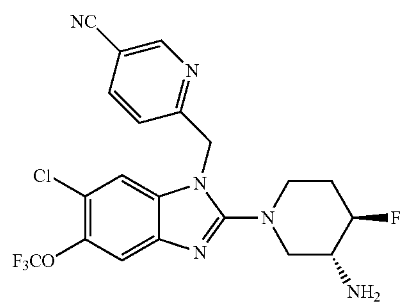 [SMILES: N#Cc1ccc(Cn2c(N3CC[C@@H](F)[C@H](N)C3)nc3cc(OC(F)(F)F)c(Cl)cc32)nc1] | 6-((2-((3R,4R)-3-amino-4-fluoro-1-piperidinyl)-6-chloro-5-(trifluoromethoxy)-1H-benzimidazol-1-yl)methyl)-3-pyridinecarbonitrile | 469.2 |
| 125 | 27 | (3R,4R)-4-fluoro-3-NHBoc piperidine | B | 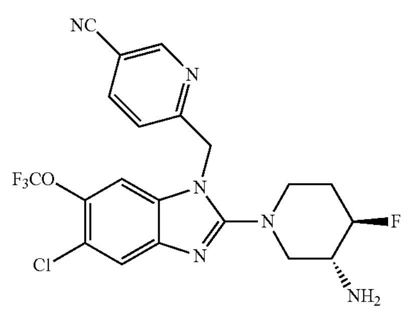 [SMILES: N#Cc1ccc(Cn2c(N3CC[C@@H](F)[C@H](N)C3)nc3cc(Cl)c(OC(F)(F)F)cc32)nc1] | 6-((2-((3R,4R)-3-amino-4-fluoro-1-piperidinyl)-5-chloro-6-(trifluoromethoxy)-1H-benzimidazol-1-yl)methyl)-3-pyridinecarbonitrile | 469.2 |
| 126 | 26 | (3R,4R)-4-fluoro-3-NHBoc piperidine | B | 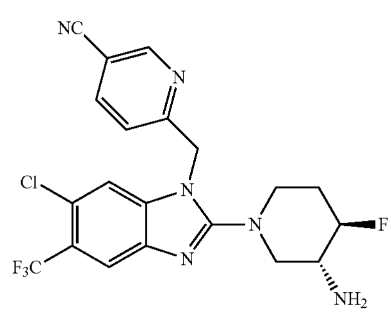 | 6-((2-((3R,4R)-3-amino-4-fluoro-1-piperidinyl)-6-chloro-5-(trifluoromethyl)-1H-benzimidazol-1-yl)methyl)-3-pyridinecarbonitrile | 453.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 127 | 26 | 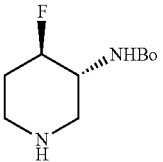 | B | 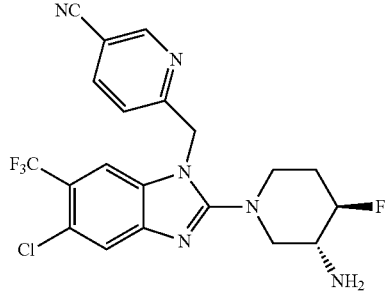 | 6-((2-((3R,4R)-3-amino-4-fluoro-1-piperidinyl)-5-chloro-6-(trifluoromethyl)-1H-benzimidazol-1-yl)methyl)-3-pyridinecarbonitrile | 453.2 |
| 128 | 7 | 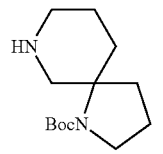 | B | 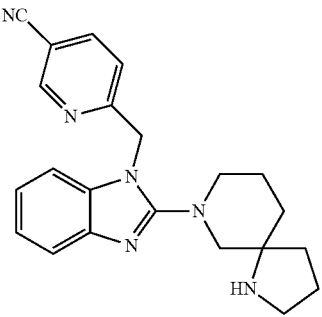 | 6-((2-((5R)-1,7-diazaspiro[4.5.]decan-7-yl)-1H-benzimidazol-1-yl)methyl)-3-pyridinecarbonitrile, 6-((2-((5S)-1,7-diazaspiro[4.5]decan-7-yl)-1H-benzimidazol-1-yl)methyl)-3-pyridinecarbonitrile | 373.2 |
| 129 | 7 | 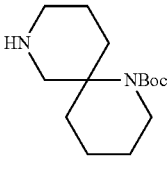 | B | 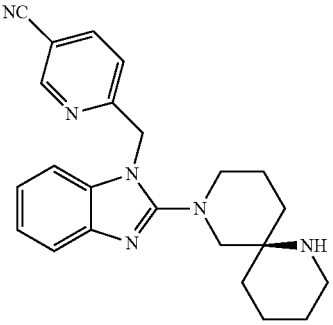 [SMILES: N#Cc1ccc(Cn2c(N3CCC[C@]4(CCCCN4)C3)nc3ccccc32)nc1] | 6-((2-((6R)-1,8-diazaspiro[5.5]undecan-8-yl)-1H-benzimidazol-1-yl)methyl)-3-pyridinecarbonitrile | 387.2 |
| 130 | 7 | 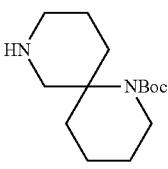 | B | 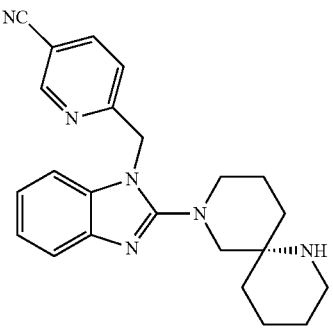 [SMILES: N#Cc1ccc(Cn2c(N3CCC[C@@]4(CCCCN4)C3)nc3ccccc32)nc1] | 6-((2-((6S)-1,8-diazaspiro[5.5]undecan-8-yl)-1H-benzimidazol-1-yl)methyl)-3-pyridinecarbonitrile | 387.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 131 | 7 | | B | 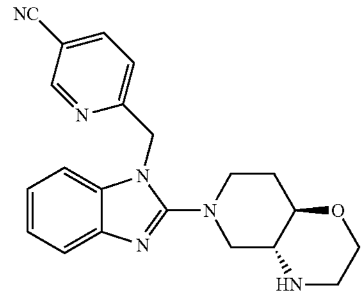 [SMILES: N#Cc1ccc(Cn2c(N3CC[C@H]4OCCN[C@@H]4C3)nc3ccccc32)nc1] | 6-((2-((4aR,8aR)-hexahydro-2H-pyrido[4,3-b][1,4]oxazin-6(5H)-yl)-1H-benzimidazol-1-yl)methyl)-3-pyridinecarbonitrile | 375.2 |
| 132 | 7 | | B | 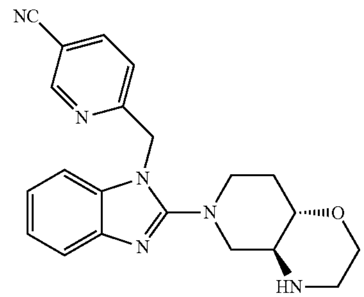 [SMILES: N#Cc1ccc(Cn2c(N3CC[C@@H]4OCCN[C@H]4C3)nc3ccccc32)nc1] | 6-((2-((4aS,8aS)-hexahydro-2H-pyrido[4,3-b][1,4]oxazin-6(5H)-yl)-1H-benzimidazol-1-yl)methyl)-3-pyridinecarbonitrile | 375.2 |
| 133 a | 43 | | B | 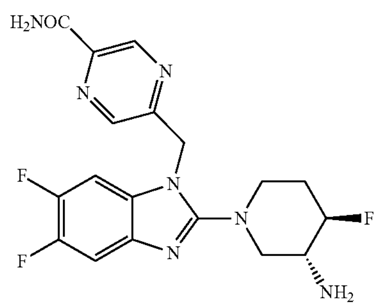 [SMILES: NC(=O)c1cnc(Cn2c(N3CC[C@@H](F)[C@H](N)C3)nc3cc(F)c(F)cc32)cn1] | 5-((2-((3R,4R)-3-amino-4-fluoro-1-piperidinyl)-5,6-difluoro-1H-benzimidazol-1-yl)methyl)-2-pyrazinecarboxamide | 406.2 |
| 134 a | 42 | | B | 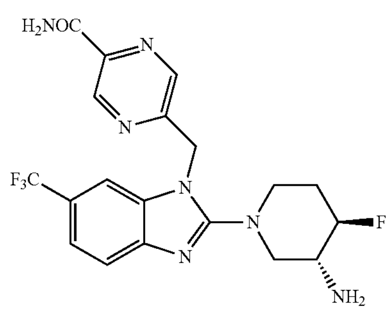 | 5-((2-((3R,4R)-3-amino-4-fluoro-1-piperidinyl)-6-(trifluoromethyl)-1H-benzimidazol-1-yl)methyl)-2-pyrazinecarboxamide | 438.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 135 | 7 | 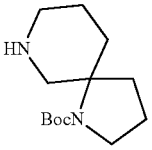 | B | 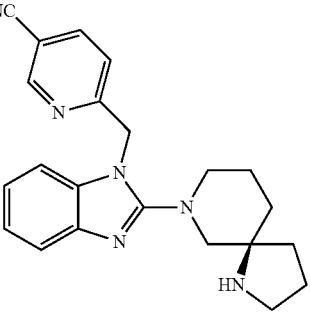 | 6-((2-((5R)-1,7-diazaspiro[4.5]decan-7-yl)-1H-benzimidazol-1-yl)methyl)-3-pyridinecarbonitrile | 373.2 |
| 136 | 7 | 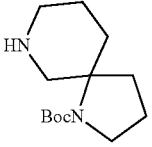 [SMILES: CC(C)(C)OC(=O)N1CCCC12CCCNC2] | B | 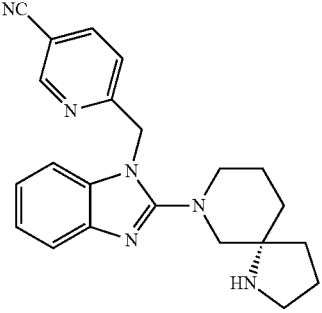 [SMILES: N#Cc1ccc(Cn2c(N3CCC[C@@]4(CCCN4)C3)nc3ccccc32)nc1] | 6-((2-((5S)-1,7-diazaspiro[4.5]decan-7-yl)-1H-benzimidazol-1-yl)methyl)-3-pyridinecarbonitrile | 373.2 |
| 137 | 24 | 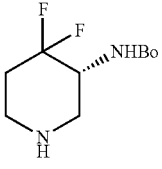 | B | 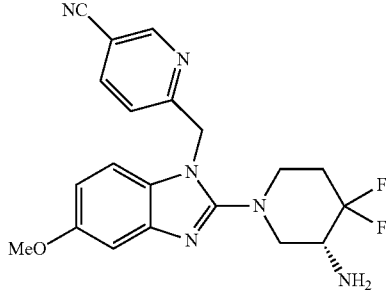 [SMILES: COc1ccc2c(c1)nc(N1CCC(F)(F)[C@H](N)C1)n2Cc1ccc(C#N)cn1] | 6-((2-((3R)-3-amino-4,4-difluoro-1-piperidinyl)-5-methoxy-1H-benzimidazol-1-yl)methyl)-3-pyridinecarbonitrile | 399.2 |
| 138 | 24 | 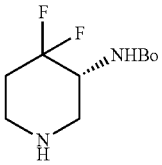 | B | 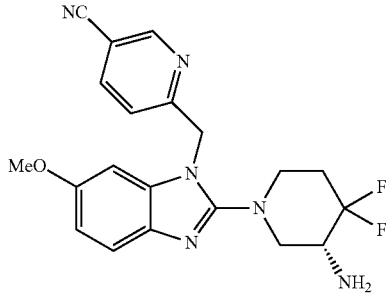 [SMILES: COc1ccc2nc(N3CCC(F)(F)[C@H](N)C3)n(Cc3ccc(C#N)cn3)c2c1] | 6-((2-((3R)-3-amino-4,4-difluoro-1-piperidinyl)-6-methoxy-1H-benzimidazol-1-yl)methyl)-3-pyridinecarbonitrile | 399.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 139 | 19 | 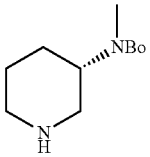 | B | 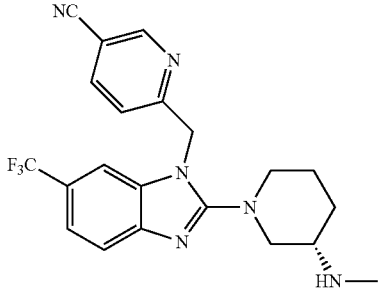 [SMILES: CN[C@H]1CCCN(c2nc3ccc(C(F)(F)F)cc3n2Cc2ccc(C#N)cn2)C1] | 6-((2-((3S)-3-(methylamino)-1-piperidinyl)-6-(trifluoromethyl)-1H-benzimidazol-1-yl)methyl)-3-pyridinecarbonitrile | 415.2 |
| 140 | 19 | 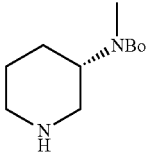 | B | 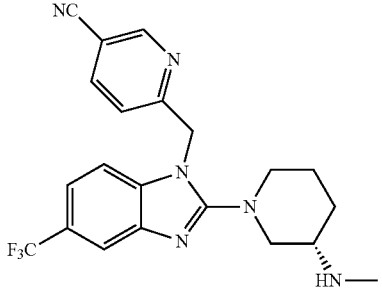 [SMILES: CN[C@H]1CCCN(c2nc3cc(C(F)(F)F)ccc3n2Cc2ccc(C#N)cn2)C1] | 6-((2-((3S)-3-(methylamino)-1-piperidinyl)-5-(trifluoromethyl)-1H-benzimidazol-1-yl)methyl)-3-pyridinecarbonitrile | 415.2 |
| 141 | 7 | 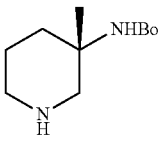 | B | 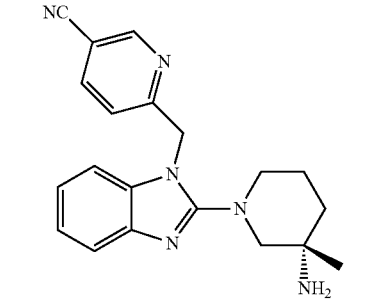 [SMILES: C[C@]1(N)CCCN(c2nc3ccccc3n2Cc2ccc(C#N)cn2)C1] | 6-((2-((3S)-3-amino-3-methyl-1-piperidinyl)-1H-benzimidazol-1-yl)methyl)-3-pyridinecarbonitrile | 347.2 |
| 142 | 24 | 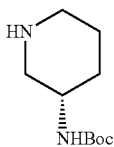 | B | 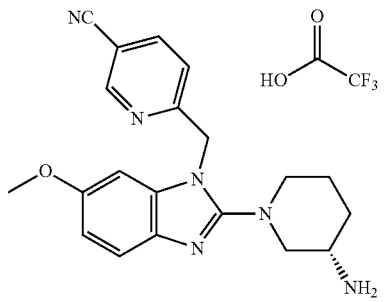 [SMILES: COc1ccc2nc(N3CCC[C@H](N)C3)n(Cc3ccc(C#N)cn3)c2c1 ; O=C(O)C(F)(F)F] | (S)-6-((2-(3-aminopiperidin-1-yl)-6-methoxy-1H-benzo[d]imidazol-1-yl)methyl)nicotinonitrile 2,2,2-trifluoroacetate | 363.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 143 | 24 | (3S)-3-NHBoc-piperidine | B | 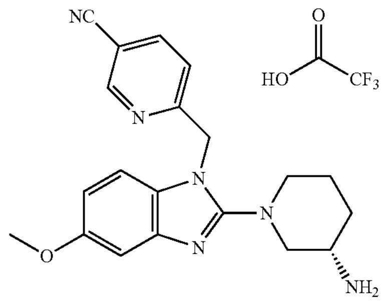 [SMILES: COc1ccc2c(c1)nc(N1CCC[C@H](N)C1)n2Cc1ccc(C#N)cn1 ; O=C(O)C(F)(F)F] | (S)-6-((2-(3-aminopiperidin-1-yl)-5-methoxy-1H-benzo[d]imidazol-1-yl)methyl)nicotinonitrile 2,2,2-trifluoroacetate | 363.2 |
| 144 | 32 | (3R,4R)-4-fluoro-3-NHBoc-piperidine | B | 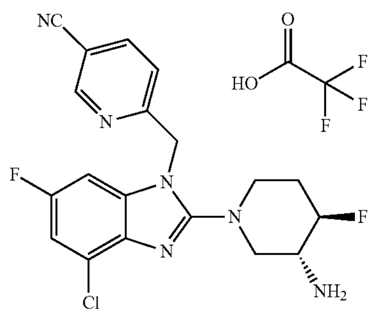 [SMILES: N#Cc1ccc(Cn2c(N3CC[C@@H](F)[C@H](N)C3)nc3c(Cl)cc(F)cc32)nc1 ; O=C(O)C(F)(F)F] | 6-((2-((3R,4R)-3-amino-4-fluoropiperidin-1-yl)-4-chloro-6-fluoro-1H-benzo[d]imidazol-1-yl)methyl)nicotinonitrile 2,2,2-trifluoroacetate | 403.0 |
| 145 | 24 | (3R,4R)-4-fluoro-3-NHBoc-piperidine | A | 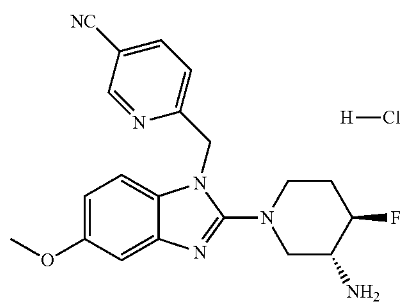 [SMILES: COc1ccc2c(c1)nc(N1CC[C@@H](F)[C@H](N)C1)n2Cc1ccc(C#N)cn1 ; Cl] | 6-((2-((3R,4R)-3-amino-4-fluoropiperidin-1-yl)-5-methoxy-1H-benzo[d]imidazol-1-yl)methyl)nicotinonitrile hydrochloride | 381.0 |
| 146 | 24 | (3R,4R)-4-fluoro-3-NHBoc-piperidine | A | 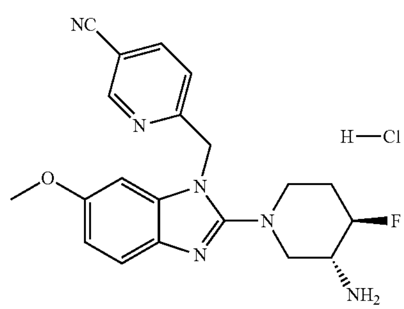 | 6-((2-((3R,4R)-3-amino-4-fluoropiperidin-1-yl)-6-methoxy-1H-benzo[d]imidazol-1-yl)methyl)nicotinonitrile hydrochloride | 381.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 147 | 24 | | A | 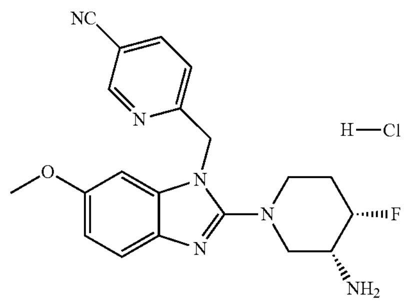 | 6-((2-((3R,4S)-3-amino-4-fluoropiperidin-1-yl)-6-methoxy-1H-benzo[d]imidazol-1-yl)methyl)nicotinonitrile hydrochloride | 381.0 |
| 148 | 24 | | A | 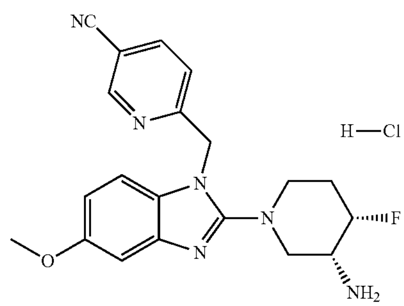 | 6-((2-((3R,4S)-3-amino-4-fluoropiperidin-1-yl)-5-methoxy-1H-benzo[d]imidazol-1-yl)methyl)nicotinonitrile hydrochloride | 381.0 |
| 149 | 14 | | B | 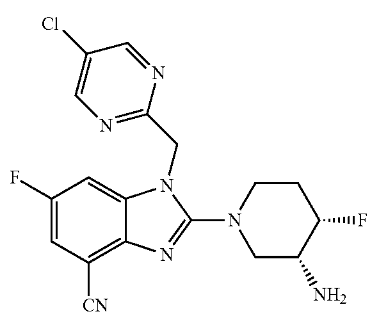 [SMILES: N#Cc1cc(F)cc2c1nc(N1CC[C@H](F)[C@H](N)C1)n2Cc1ncc(Cl)cn1] | 2-((3R,4S)-3-amino-4-fluoropiperidin-1-yl)-1-((5-chloropyrimidin-2-yl)methyl)-6-fluoro-1H-benzo[d]imidazole-4-carbonitrile | 404.0 |
| 150 | 14 | | B | 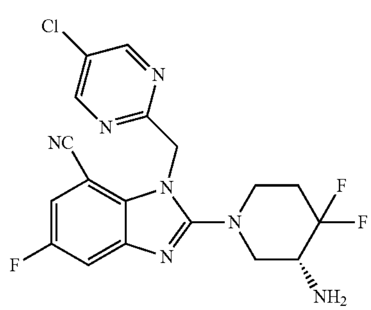 [SMILES: N#Cc1cc(F)cc2nc(N3CCC(F)(F)[C@H](N)C3)n(Cc3ncc(Cl)cn3)c12] | (R)-2-(3-amino-4,4-difluoropiperidin-1-yl)-1-((5-chloropyrimidin-2-yl)methyl)-5-fluoro-1H-benzo[d]imidazole-7-carbonitrile | 422.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 151 | 14 | | B | 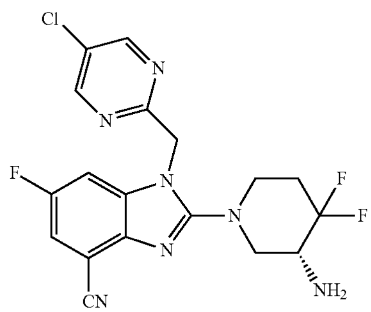 [SMILES: N#Cc1cc(F)cc2c1nc(N1CCC(F)(F)[C@H](N)C1)n2Cc1ncc(Cl)cn1] | (R)-2-(3-amino-4,4-difluoropiperidin-1-yl)-1-((5-chloropyrimidin-2-yl)methyl)-6-fluoro-1H-benzo[d]imidazole-4-carbonitrile | 422.0 |
| 152 | 3 | | B | 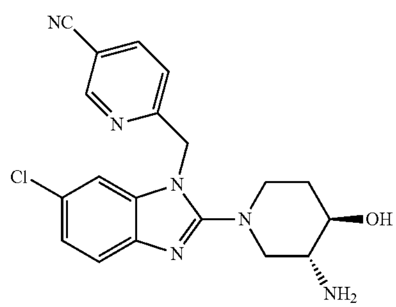 [SMILES: N#Cc1ccc(Cn2c(N3CC[C@@H](O)[C@H](N)C3)nc3ccc(Cl)cc32)nc1] | 6-((2-((3R,4R)-3-amino-4-hydroxypiperidin-1-yl)-6-chloro-1H-benzo[d]imidazol-1-yl)methyl)nicotinonitrile | 383.2 |
| 153 | 3 | | B | 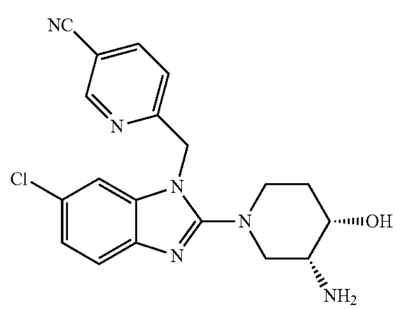 [SMILES: N#Cc1ccc(Cn2c(N3CC[C@H](O)[C@H](N)C3)nc3ccc(Cl)cc32)nc1] | 6-((2-((3R,4S)-3-amino-4-hydroxypiperidin-1-yl)-6-chloro-1H-benzo[d]imidazol-1-yl)methyl)nicotinonitrile | 383.2 |
| 154 | 44 | | B | 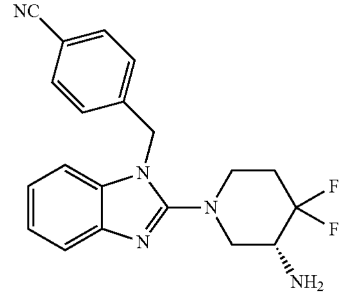 [SMILES: N#Cc1ccc(Cn2c(N3CCC(F)(F)[C@H](N)C3)nc3ccccc32)cc1] | (R)-4-((2-(3-amino-4,4-difluoropiperidin-1-yl)-1H-benzo[d]imidazol-1-yl)methyl)benzonitrile | 368.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 155 | 44 | OH, NHBoc piperidine, racemic | A | benzimidazole structure with HCl, OH, NH2 (both enantiomers shown) | 4-((2-((3R,4R)-3-amino-4-hydroxypiperidin-1-yl)-1H-benzo[d]imidazol-1-yl)methyl)benzonitrile compound with 4-((2-((3S,4S)-3-amino-4-hydroxypiperidin-1-yl)-1H-benzo[d]imidazol-1-yl)methyl)benzonitrile (1:1) dihydrochloride | 346.2 |
| 156 | 45 | F, NHBoc piperidine | B | 5,7-difluorobenzimidazole structure | 4-((2-(3R,4R)-3-amino-4-fluoro-1-piperidinyl)-5,7-difluoro-1H-benzimidazol-1-yl)methyl)benzonitrile | 386.2 |
| 157 | 45 | F, NHBoc piperidine | B | 4,6-difluorobenzimidazole structure | 4-((2-((3R,4R)-3-amino-4-fluoro-1-piperidinyl)-4,6-difluoro-1H-benzimidazol-1-yl)methyl)benzonitrile | 386.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 158 | 46 | | B | 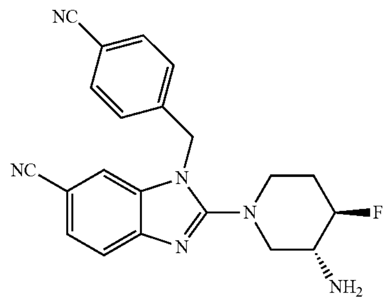 [SMILES: N#Cc1ccc(Cn2c(N3CC[C@@H](F)[C@H](N)C3)nc3ccc(C#N)cc32)cc1] | 2-((3R,4R)-3-amino-4-fluoro-1-piperidinyl)-1-(4-cyanobenzyl)-1H-benzimidazole-6-carbonitrile | 375.2 |
| 159 | 46 | | B | 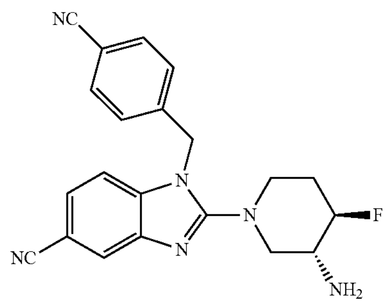 [SMILES: N#Cc1ccc(Cn2c(N3CC[C@@H](F)[C@H](N)C3)nc3cc(C#N)ccc32)cc1] | 2-((3R,4R)-3-amino-4-fluoro-1-piperidinyl)-1-(4-cyanobenzyl)-1H-benzimidazole-5-carbonitrile | 375.2 |
| 160 | 46 | | B | 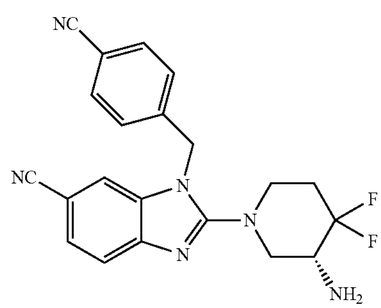 [SMILES: N#Cc1ccc(Cn2c(N3CCC(F)(F)[C@H](N)C3)nc3ccc(C#N)cc32)cc1] | 2-((3R)-3-amino-4,4-difluoro-1-piperidinyl)-1-(4-cyanobenzyl)-1H-benzimidazole-6-carbonitrile | 393.3 |
| 161 | 46 | | B | 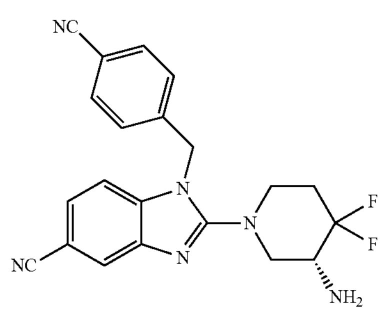 | 2-((3R)-3-amino-4,4-difluoro-1-piperidinyl)-1-(4-cyanobenzyl)-1H-benzimidazole-5-carbonitrile | 393.3 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 162 | 44 | 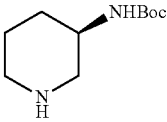 [SMILES: CC(C)(C)OC(=O)N[C@@H]1CCCNC1] | A | 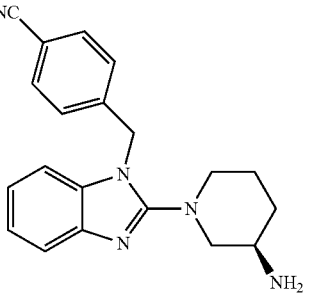 | (R)-4-((2-(3-aminopiperidin-1-yl)-1H-benzo[d]imidazol-1-yl)methyl)benzonitrile | 332.2 |
| 163 | 44 | 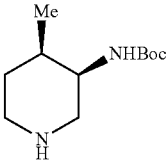 [SMILES: C[C@@H]1CCNC[C@@H]1NC(=O)OC(C)(C)C] | A | 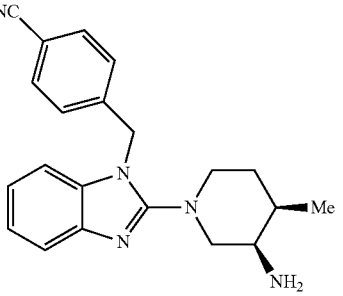 | 4-((2-((3R,4R)-3-amino-4-methylpiperidin-1-yl)-1H-benzo[d]imidazol-1-yl)methyl)benzonitrile | 346.0 |
| 164 c | 44 | 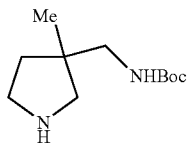 | A | 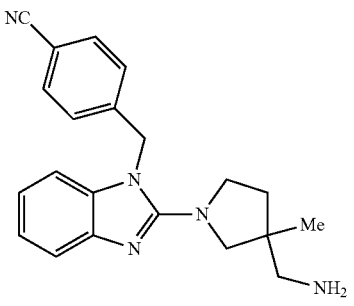 [SMILES: CC1(CN)CCN(c2nc3ccccc3n2Cc2ccc(C#N)cc2)C1] | 4-((2-(3-(aminomethyl)-3-methylpyrrolidin-1-yl)-1H-benzo[d]imidazol-1-yl)methyl)benzonitrile | 346.2 |
| 165 | 44 | Racemic 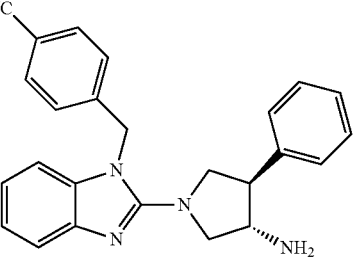 | A | | 4-((2-((3S,4R)-3-amino-4-phenylpyrrolidin-1-yl)-1H-benzo[d]imidazol-1-yl)methyl)benzonitrile & 4-((2-((3R,4S)-3-amino-4-phenylpyrrolidin-1-yl)-1H-benzo[d]imidazol-1-yl)methyl)benzonitrile | 394.2 |

… 197 198

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 166 | 44 | 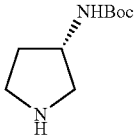 | A | 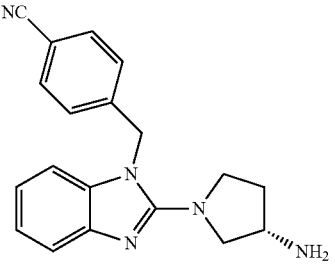 [SMILES: N#Cc1ccc(Cn2c(N3CC[C@H](N)C3)nc3ccccc32)cc1] | (S)-4-((2-(3-aminopyrrolidin-1-yl)-1H-benzo[d]imidazol-1-yl)methyl)benzonitrile | 318.2 |
| 167 | 44 | 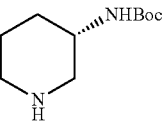 [SMILES: CC(C)(C)OC(=O)N[C@H]1CCCNC1] | A | 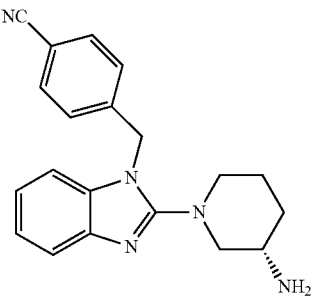 [SMILES: N#Cc1ccc(Cn2c(N3CCC[C@H](N)C3)nc3ccccc32)cc1] | (S)-4-((2-(3-aminopiperidin-1-yl)-1H-benzo[d]imidazol-1-yl)methyl)benzonitrile | 332.2 |
| 168 | 44 | 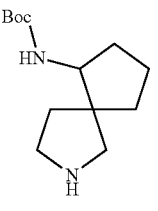 [SMILES: CC(C)(C)OC(=O)NC1CCCC12CCNC2] | A | 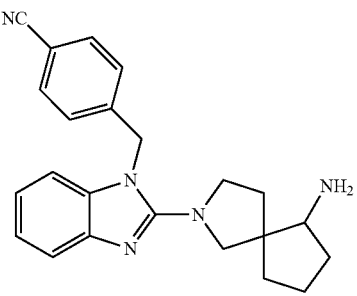 [SMILES: N#Cc1ccc(Cn2c(N3CCC4(CCCC4N)C3)nc3ccccc32)cc1] | 4-((2-(6-amino-2-azaspiro[4.4]nonan-2-yl)-1H-benzo[d]imidazol-1-yl)methyl)benzonitrile | 32.0 |
| 169 | 44 | 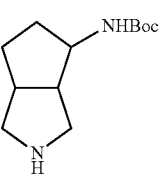 [SMILES: CC(C)(C)OC(=O)NC1CCC2CNCC21] | A | 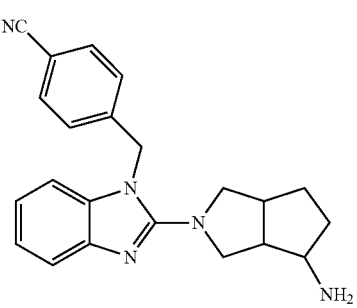 [SMILES: N#Cc1ccc(Cn2c(N3CC4CCC(N)C4C3)nc3ccccc32)cc1] | 4-((2-(4-aminohexahydrocyclopenta[c]pyrrol-2(1H)-yl)-1H-benzo[d]imidazol-1-yl)methyl)benzonitrile | 358.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 170 | 44 | | A | 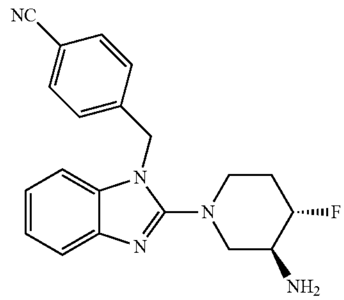 [SMILES: N#Cc1ccc(Cn2c(N3CC[C@H](F)[C@@H](N)C3)nc3ccccc32)cc1] | 4-((2-((3S,4S)-3-amino-4-fluoropiperidin-1-yl)-1H-benzo[d]imidazol-1-yl)methyl)benzonitrile | 350.2 |
| 171 | 44 | | A | 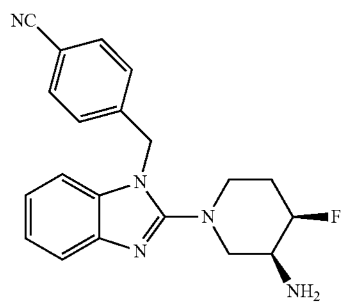 [SMILES: N#Cc1ccc(Cn2c(N3CC[C@@H](F)[C@@H](N)C3)nc3ccccc32)cc1] | 4-((2-((3S,4R)-3-amino-4-fluoropiperidin-1-yl)-1H-benzo[d]imidazol-1-yl)methyl)benzonitrile | 350.2 |
| 172 | 44 | | A | 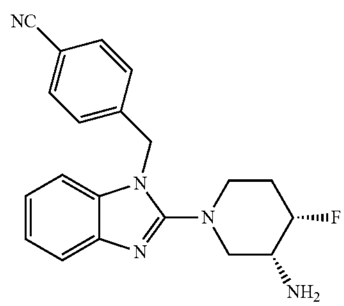 [SMILES: N#Cc1ccc(Cn2c(N3CC[C@H](F)[C@H](N)C3)nc3ccccc32)cc1] | 4-((2-((3R,4S)-3-amino-4-fluoropiperidin-1-yl)-1H-benzo[d]imidazol-1-yl)methyl)benzonitrile | 350.2 |
| 173 | 44 | | A | 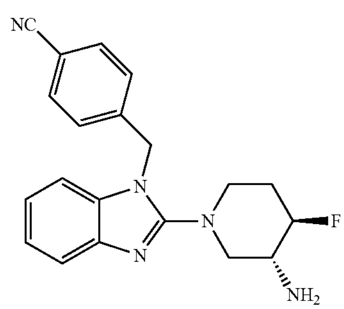 [SMILES: N#Cc1ccc(Cn2c(N3CC[C@@H](F)[C@H](N)C3)nc3ccccc32)cc1] | 4-((2-((3R,4R)-3-amino-4-fluoropiperidin-1-yl)-1H-benzo[d]imidazol-1-yl)methyl)benzonitrile | 350.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 174 | 44 | (3-fluoropyrrolidin-3-yl)methyl-NHBoc | B | 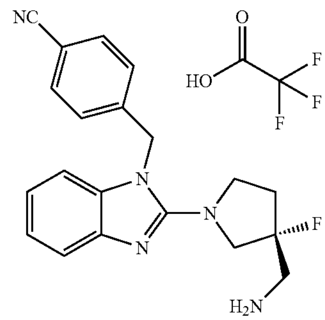 [SMILES: N#Cc1ccc(Cn2c(N3CC[C@@](F)(CN)C3)nc3ccccc32)cc1 ; O=C(O)C(F)(F)F] | (R)-4-((2-(3-(aminomethyl)-3-fluoropyrrolidin-1-yl)-1H-benzo[d]imidazol-1-yl)methyl)benzonitrile 2,2,2-trifluoroacetate | 350.0 |
| 175 | 44 | (3-fluoropyrrolidin-3-yl)methyl-NHBoc | B | 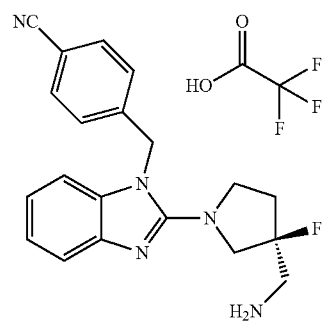 [SMILES: N#Cc1ccc(Cn2c(N3CC[C@](F)(CN)C3)nc3ccccc32)cc1 ; O=C(O)C(F)(F)F] | (S)-4-((2-(3-(aminomethyl)-3-fluoropyrrolidin-1-yl)-1H-benzo[d]imidazol-1-yl)methyl)benzonitrile 2,2,2-trifluoroacetate | 350.0 |
| 176 | 44 | (3-hydroxypyrrolidin-3-yl)methyl-NHBoc | B | 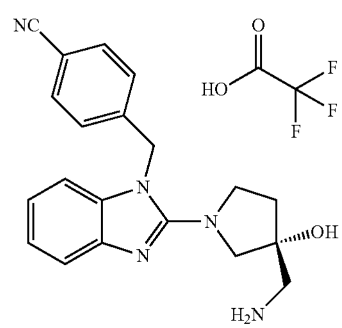 [SMILES: N#Cc1ccc(Cn2c(N3CC[C@@](O)(CN)C3)nc3ccccc32)cc1 ; O=C(O)C(F)(F)F] | (R)-4-((2-(3-(aminomethyl)-3-hydroxypyrrolidin-1-yl)-1H-benzo[d]imidazol-1-yl)methyl)benzonitrile 2,2,2-trifluoroacetate | 348.2 |
| 177 | 44 | (3-hydroxypyrrolidin-3-yl)methyl-NHBoc | B | 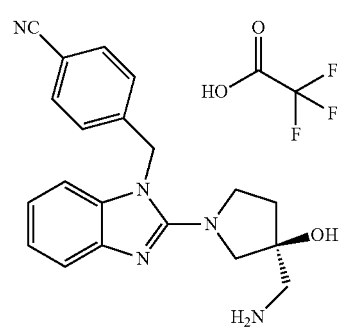 [SMILES: N#Cc1ccc(Cn2c(N3CC[C@](O)(CN)C3)nc3ccccc32)cc1 ; O=C(O)C(F)(F)F] | (S)-4-((2-(3-(aminomethyl)-3-hydroxypyrrolidin-1-yl)-1H-benzo[d]imidazol-1-yl)methyl)benzonitrile 2,2,2-trifluoroacetate | 348.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 178 | 44 | (pyrrolidin-3-yl)methyl-NHBoc | A | 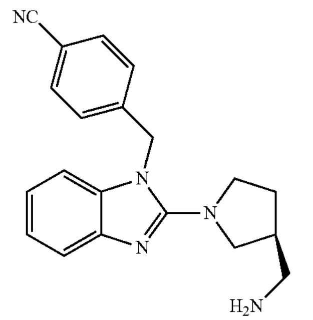 [SMILES: N#Cc1ccc(Cn2c(N3CC[C@@H](CN)C3)nc3ccccc32)cc1] | (S)-4-((2-(3-(aminomethyl)pyrrolidin-1-yl)-1H-benzo[d]imidazol-1-yl)methyl)benzonitrile Molecular Weight: 331.41 | 332.2 |
| 179 | 44 | (pyrrolidin-3-yl)methyl-NHBoc | A | 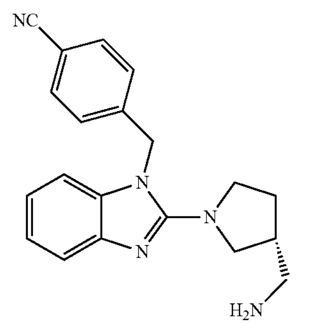 [SMILES: N#Cc1ccc(Cn2c(N3CC[C@H](CN)C3)nc3ccccc32)cc1] | (R)-4-((2-(3-(aminomethyl)pyrrolidin-1-yl)-1H-benzo[d]imidazol-1-yl)methyl)benzonitrile Molecular Weight: 331.41 | 332.2 |
| 180 | 44 | 4-Me-3-NHBoc-piperidine | B | 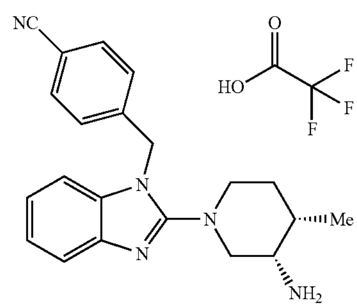 [SMILES: C[C@H]1CCN(c2nc3ccccc3n2Cc2ccc(C#N)cc2)C[C@H]1N ; O=C(O)C(F)(F)F] | 4-((2-((3S,4S)-3-amino-4-methylpiperidin-1-yl)-1H-benzo[d]imidazol-1-yl)methyl)benzonitrile 2,2,2-trifluoroacetate | 346.2 |
| 181 | 44 | 4-Me-3-NHBoc-piperidine | B | 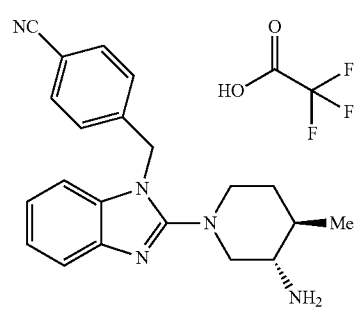 [SMILES: C[C@@H]1CCN(c2nc3ccccc3n2Cc2ccc(C#N)cc2)C[C@H]1N ; O=C(O)C(F)(F)F] | 4-((2-((3S,4R)-3-amino-4-methylpiperidin-1-yl)-1H-benzo[d]imidazol-1-yl)methyl)benzonitrile 2,2,2-trifluoroacetate | 346.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 182 | 44 | 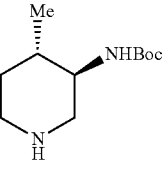 [SMILES: C[C@H]1CCNC[C@@H]1NC(=O)OC(C)(C)C] | B | 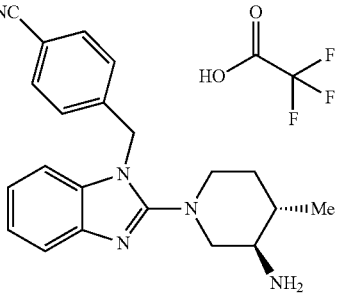 | 4-((2-((3R,4S)-3-amino-4-methylpiperidin-1-yl)-1H-benzo[d]imidazol-1-yl)methyl)benzonitrile 2,2,2-trifluoroacetate | 346.2 |
| 183 | 44 | 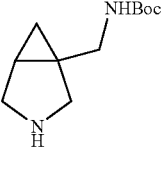 | A | 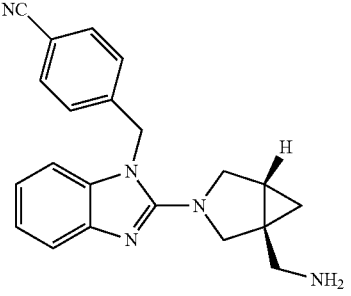 [SMILES: N#Cc1ccc(Cn2c(N3C[C@@H]4C[C@]4(CN)C3)nc3ccccc32)cc1] | 4-((2-((1S,5R)-1-(aminomethyl)-3-azabicyclo[3.1.0]hexan-3-yl)-1H-benzo[d]imidazol-1-yl)methyl)benzonitrile | 344.2 |
| 184 | 44 | 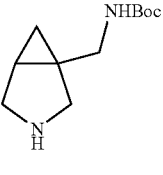 [SMILES: CC(C)(C)OC(=O)NCC12CNCC1C2] | A | 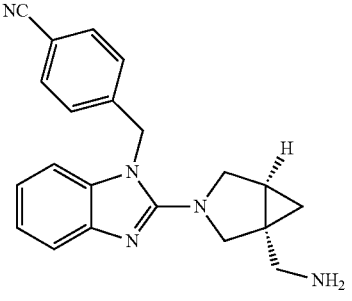 [SMILES: N#Cc1ccc(Cn2c(N3C[C@H]4C[C@@]4(CN)C3)nc3ccccc32)cc1] | 4-((2-((1R,5S)-1-(aminomethyl)-3-azabicyclo[3.1.0]hexan-3-yl)-1H-benzo[d]imidazol-1-yl)methyl)benzonitrile | 344.2 |
| 185 | 44 | 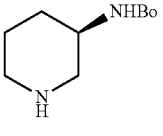 | A | 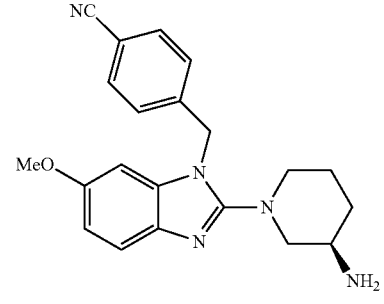 [SMILES: COc1ccc2nc(N3CCC[C@@H](N)C3)n(Cc3ccc(C#N)cc3)c2c1] | (R)-4-((2-(3-aminopiperidin-1-yl)-6-methoxy-1H-benzo[d]imidazol-1-yl)methyl)benzonitrile | 362.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 186 | 44 | 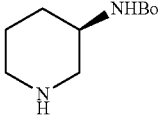 | A | 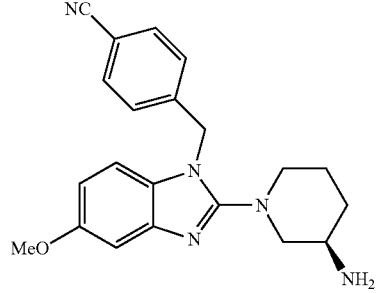 [SMILES: COc1ccc2c(c1)nc(N1CCC[C@@H](N)C1)n2Cc1ccc(C#N)cc1] | (R)-4-((2-(3-aminopiperidin-1-yl)-5-methoxy-1H-benzo[d]imidazol-1-yl)methyl)benzonitrile | 362.2 |
| 442 | 47 | 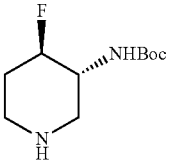 [SMILES: CC(C)(C)OC(=O)N[C@@H]1CNCC[C@H]1F] | B | 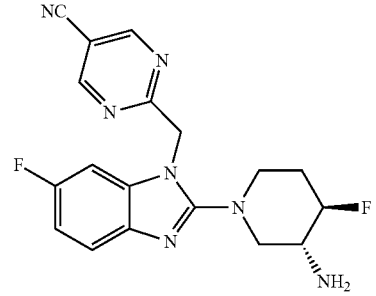 | 2-((2-((3R,4R)-3-amino-4-fluoropiperidin-1-yl)-6-fluoro-1H-benzo[d]imidazol-1-yl)methyl)pyrimidine-5-carbonitrile | 370.2 |
| 443 | 47 | 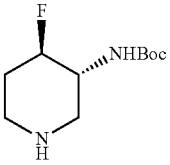 [SMILES: CC(C)(C)OC(=O)N[C@@H]1CNCC[C@H]1F] | B | 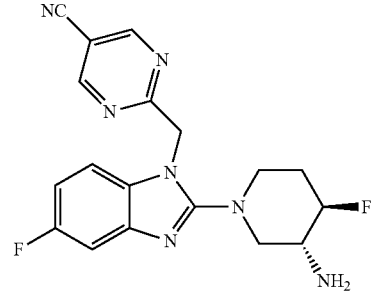 | 2-((2-((3R,4R)-3-amino-4-fluoropiperidin-1-yl)-5-fluoro-1H-benzo[d]imidazol-1-yl)methyl)pyrimidine-5-carbonitrile | 370.2 |
| 444 | 48 | 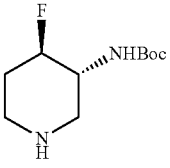 [SMILES: CC(C)(C)OC(=O)N[C@@H]1CNCC[C@H]1F] | B | 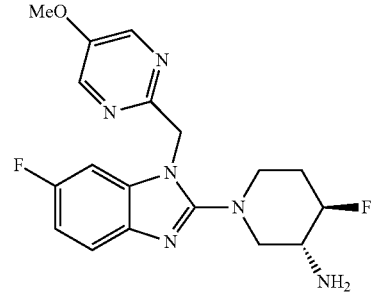 [SMILES: COc1cnc(Cn2c(N3CC[C@@H](F)[C@H](N)C3)nc3ccc(F)cc32)nc1] | (3R,4R)-4-fluoro-1-(6-fluoro-1-((5-methoxypyrimidin-2-yl)methyl)-1H-benzo[d]imidazol-2-yl)piperidin-3-amine | 375.4 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 445 | 49 | (3R,4R)-4-fluoro-3-NHBoc-piperidine | B | 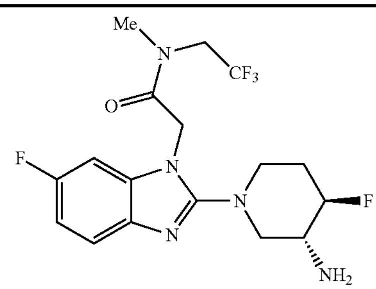 | 2-(2-((3R,4R)-3-amino-4-fluoropiperidin-1-yl)-6-fluoro-1H-benzo[d]imidazol-1-yl)-N-methyl-N-(2,2,2-trifluoroethyl)acetamide | 406.2 |
| 446 | 48 | (3R,4R)-4-fluoro-3-NHBoc-piperidine | B | 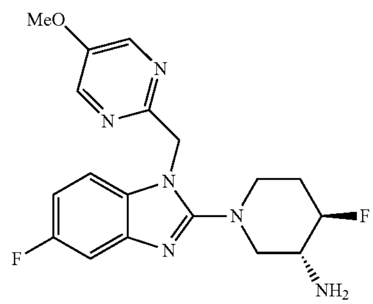 [SMILES: COc1cnc(Cn2c(N3CC[C@@H](F)[C@H](N)C3)nc3cc(F)ccc32)nc1] | (3R,4R)-4-fluoro-1-(5-fluoro-1-((5-methoxypyrimidin-2-yl)methyl)-1H-benzo[d]imidazol-2-yl)piperidin-3-amine | 375.2 |
| 447 | 52 | (3R,4R)-4-fluoro-3-NHBoc-piperidine | B | 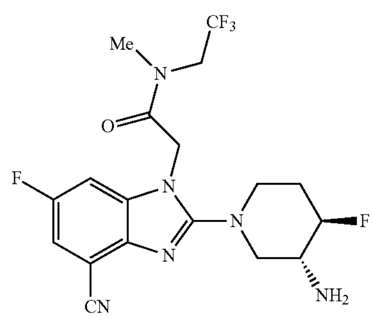 [SMILES: CN(CC(F)(F)F)C(=O)Cn1c(N2CC[C@@H](F)[C@H](N)C2)nc2c(C#N)cc(F)cc21] | 2-(2-((3R,4R)-3-amino-4-fluoropiperidin-1-yl)-4-cyano-6-fluoro-1H-benzo[d]imidazol-1-yl)-N-methyl-N-(2,2,2-trifluoroethyl)acetamide | 431.2 |
| 448 | 51 | (3R,4R)-4-fluoro-3-NHBoc-piperidine | B | 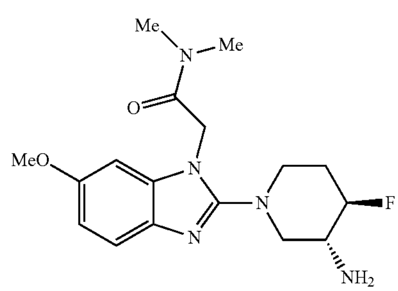 [SMILES: COc1ccc2nc(N3CC[C@@H](F)[C@H](N)C3)n(CC(=O)N(C)C)c2c1] | 2-(2-((3R,4R)-3-amino-4-fluoropiperidin-1-yl)-6-methoxy-1H-benzo[d]imidazol-1-yl)-N,N-dimethylacetamide | 350.2 |
| 449 | 50 | (3R,4R)-4-fluoro-3-NHBoc-piperidine | B | 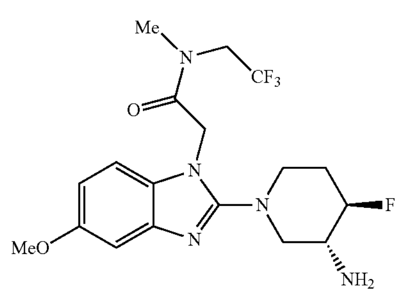 [SMILES: COc1ccc2c(c1)nc(N1CC[C@@H](F)[C@H](N)C1)n2CC(=O)N(C)CC(F)(F)F] | 2-(2-((3R,4R)-3-amino-4-fluoropiperidin-1-yl)-5-methoxy-1H-benzo[d]imidazol-1-yl)-N-methyl-N-(2,2,2-trifluoroethyl)acetamide | 418.0 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 450 | 51 | | B | 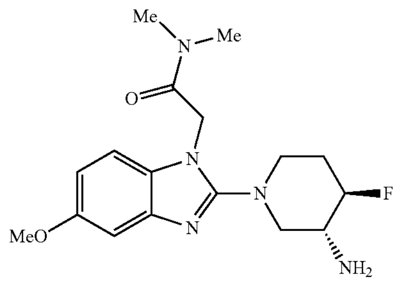 [SMILES: COc1ccc2c(c1)nc(N1CC[C@@H](F)[C@H](N)C1)n2CC(=O)N(C)C] | 2-(2-((3R,4R)-3-amino-4-fluoropiperidin-1-yl)-5-methoxy-1H-benzo[d]imidazol-1-yl)-N,N-dimethylacetamide | 350.2 |
| 451 | 5 | | B | 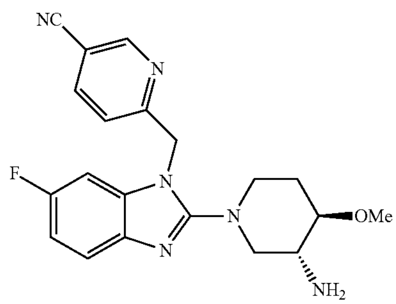 | 6-((2-((3R,4R)-3-amino-4-methoxypiperidin-1-yl)-benzo[d]imidazol-1-yl)methyl)nicotinonitrile | 381.2 |
| 452 | 53 | | B | 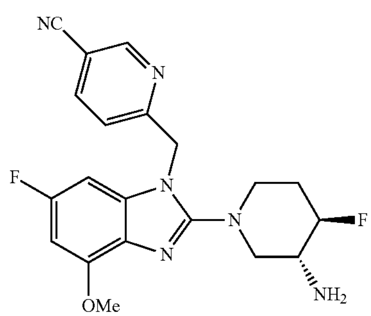 [SMILES: COc1cc(F)cc2c1nc(N1CC[C@@H](F)[C@H](N)C1)n2Cc1ccc(C#N)cn1] | 6-((2-((3R,4R)-3-amino-4-fluoropiperidin-1-yl)-6-fluoro-4-methoxy-1H-benzo[d]imidazol-1-yl)methyl)nicotinonitrile | 399.2 |
| 453 | 54 | | B | 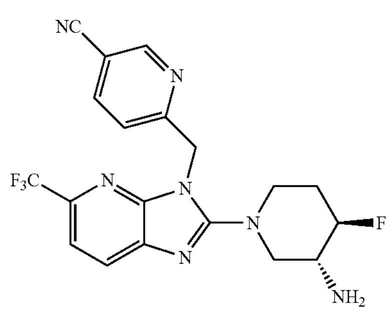 [SMILES: N#Cc1ccc(Cn2c(N3CC[C@@H](F)[C@H](N)C3)nc3ccc(C(F)(F)F)nc32)nc1] | 6-((2-((3R,4R)-3-amino-4-fluoropiperidin-1-yl)-5-(trifluoromethyl)-3H-imidazo[4,5-b]pyridin-3-yl)methyl)nicotinonitrile | 420.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 454 | 17 | | B | 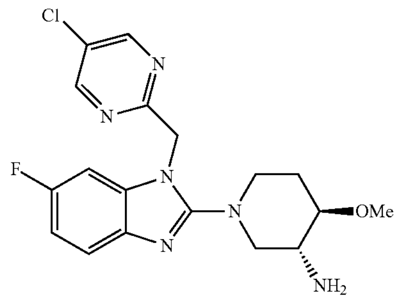 [SMILES: CO[C@@H]1CCN(c2nc3ccc(F)cc3n2Cc2ncc(Cl)cn2)C[C@H]1N] | (3R,4R)-1-(1-((5-chloropyrimidin-2-yl)methyl)-6-fluoro-1H-benzo[d]imidazol-2-yl)-4-methoxypiperidin-3-amine | 391.2 |
| 455 | 55 | | B | 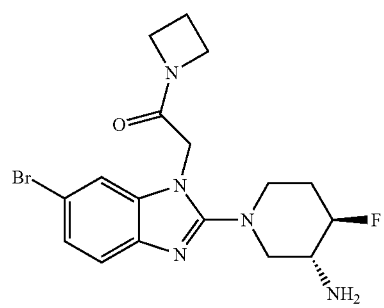 [SMILES: N[C@@H]1CN(c2nc3ccc(Br)cc3n2CC(=O)N2CCC2)CC[C@H]1F] | 2-(2-((3R,4R)-3-amino-4-fluoropiperidin-1-yl)-6-bromo-1H-benzo[d]imidazol-1-yl)-1-(azetidin-1-yl)ethan-1-one | 412.0 |
| 456 | 17 | | B | 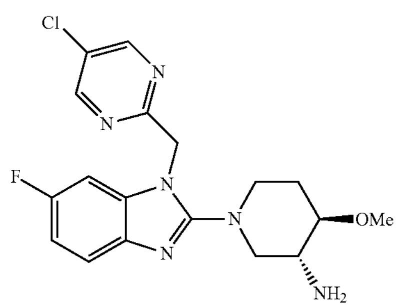 [SMILES: CO[C@@H]1CCN(c2nc3ccc(F)cc3n2Cc2ncc(Cl)cn2)C[C@H]1N] | (3R,4R)-1-(1-((5-chloropyrimidin-2-yl)methyl)-6-fluoro-1H-benzo[d]imidazol-2-yl)-4-methoxypiperidin-3-amine | 391.2 |
| 457 | 49 | | B | 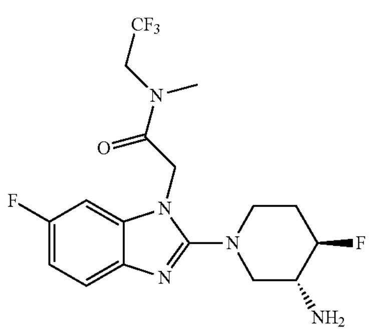 [SMILES: CN(CC(F)(F)F)C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-N-methyl-N-(2,2,2-trifluoroethyl)acetamide | 406.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 458 | 54 | 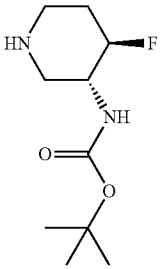 | B | 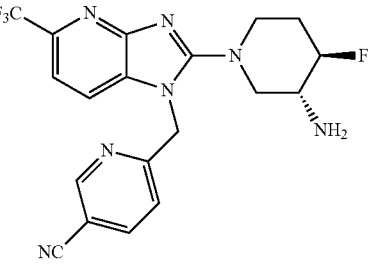 | 6-((2-((3R,4R)-3-amino-4-fluoropiperidin-1-yl)-5-(trifluoromethyl)-1H-imidazo[4,5-b]pyridin-1-yl)methyl)nicotinonitrile | 420.2 |
| 459 | 56 | 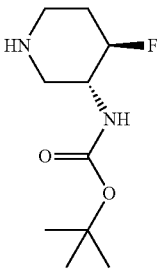 | B | 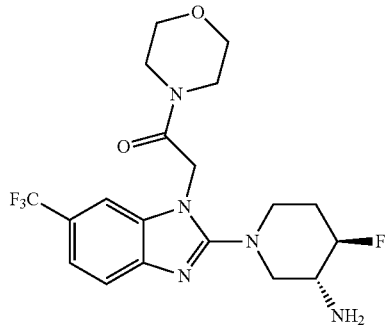 [SMILES: N[C@@H]1CN(c2nc3ccc(C(F)(F)F)cc3n2CC(=O)N2CCOCC2)CC[C@H]1F] | 2-(2-((3R,4R)-3-amino-4-fluoropiperidin-1-yl)-6-(trifluoromethyl)-1H-benzo[d]imidazol-1-yl)-1-morpholinoethan-1-one | 430.2 |
| 460 | 49 | 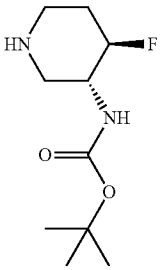 | B | 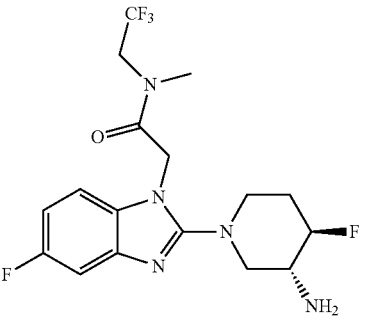 [SMILES: CN(CC(F)(F)F)C(=O)Cn1c(N2CC[C@@H](F)[C@H](N)C2)nc2cc(F)ccc21] | 2-(2-((3R,4R)-3-amino-4-fluoropiperidin-1-yl)-5-fluoro-1H-benzo[d]imidazol-1-yl)-N-methyl-N-(2,2,2-trifluoroethyl)acetamide | 406.2 |
| 461 | 57 | 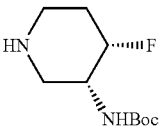 | B | 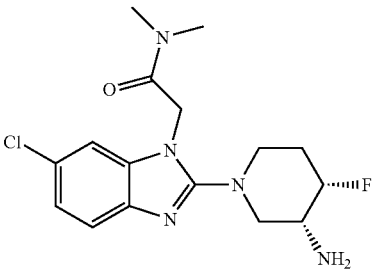 [SMILES: CN(C)C(=O)Cn1c(N2CC[C@H](F)[C@H](N)C2)nc2ccc(Cl)cc21] | 2-(2-((3R,4S)-3-amino-4-fluoropiperidin-1-yl)-6-chloro-1H-benzo[d]imidazol-1-yl)-N,N-dimethylacetamide | 354.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 462 | 49 | | B | 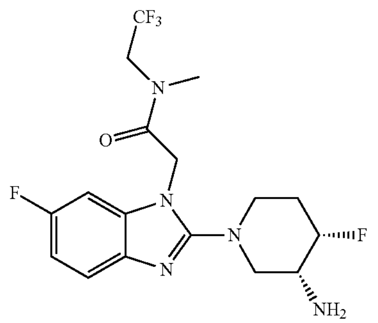 [SMILES: CN(CC(F)(F)F)C(=O)Cn1c(N2CC[C@H](F)[C@H](N)C2)nc2ccc(F)cc21] | 2-(2-((3R,4S)-3-amino-4-fluoropiperidin-1-yl)-6-fluoro-1H-benzo[d]imidazol-1-yl)-N-methyl-N-(2,2,2-trifluoroethyl)acetamide | 406.2 |
| 463 | 17 | HCl | B | 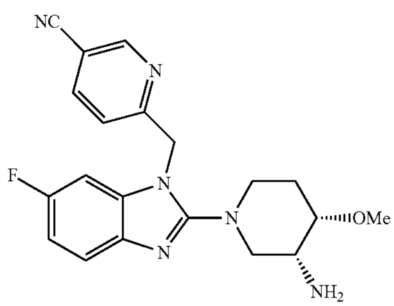 | 6-((2-((3R,4S)-3-amino-4-methoxypiperidin-1-yl)-6-fluoro-1H-benzo[d]imidazol-1-yl)methyl)nicotinonitrile | 381.2 |
| 464 | 56 | | B | 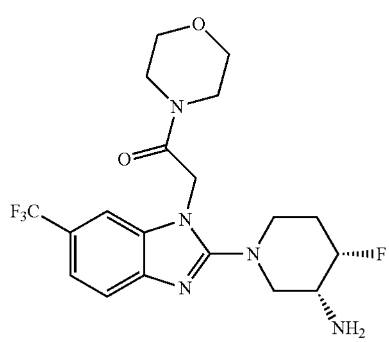 [SMILES: N[C@@H]1CN(c2nc3ccc(C(F)(F)F)cc3n2CC(=O)N2CCOCC2)CC[C@@H]1F] | 2-(2-((3R,4S)-3-amino-4-fluoropiperidin-1-yl)-6-(trifluoromethyl)-1H-benzo[d]imidazol-1-yl)-1-morpholinoethan-1-one | 430.2 |
| 465 | 49 | | B | 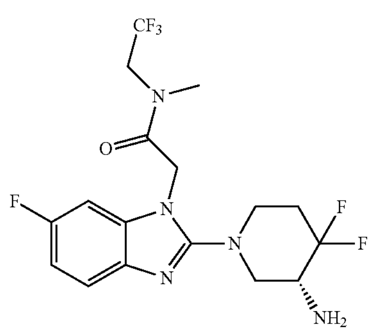 [SMILES: CN(CC(F)(F)F)C(=O)Cn1c(N2CCC(F)(F)[C@H](N)C2)nc2ccc(F)cc21] | (R)-2-(2-(3-amino-4,4-difluoropiperidin-1-yl)-6-fluoro-1H-benzo[d]imidazol-1-yl)-N-methyl-N-(2,2,2-trifluoroethyl)acetamide | 424.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 466 | 49 | | B | 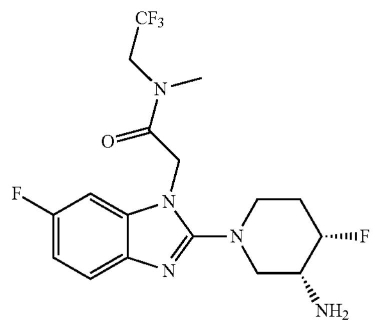 [SMILES: CN(CC(F)(F)F)C(=O)Cn1c(N2CC[C@H](F)[C@H](N)C2)nc2ccc(F)cc21] | 2-(2-((3R,4S)-3-amino-4-fluoropiperidin-1-yl)-6-fluoro-1H-benzo[d]imidazol-1-yl)-N-methyl-N-(2,2,2-trifluoroethyl)acetamide | 406.2 |
| 467 | 17 | | B | 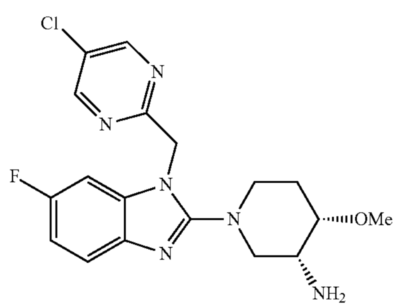 [SMILES: CO[C@H]1CCN(c2nc3ccc(F)cc3n2Cc2ncc(Cl)cn2)C[C@H]1N] | (3R,4S)-1-(1-((5-chloropyrimidin-2-yl)methyl)-6-fluoro-1H-benzo[d]imidazol-2-yl)-4-methoxypiperidin-3-amine | 391.2 |
| 468 | 58 | | B | 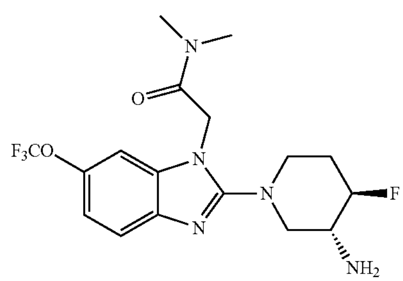 [SMILES: CN(C)C(=O)Cn1c(N2CC[C@@H](F)[C@H](N)C2)nc2ccc(OC(F)(F)F)cc21] | 2-(2-((3R,4R)-3-amino-4-fluoropiperidin-1-yl)-6-(trifluoromethoxy)-1H-benzo[d]imidazol-1-yl)-N,N-dimethylacetamide | 404.2 |
| 469 | 49 | | B | 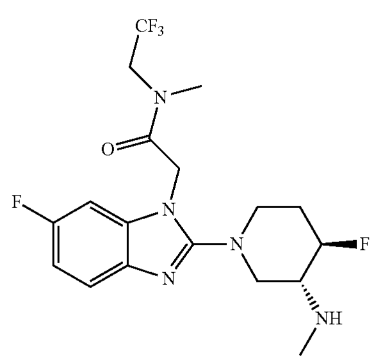 [SMILES: CN[C@@H]1CN(c2nc3ccc(F)cc3n2CC(=O)N(C)CC(F)(F)F)CC[C@H]1F] | 2-(6-fluoro-2-((3R,4R)-4-fluoro-3-(methylamino)piperidin-1-yl)-1H-benzo[d]imidazol-1-yl)-N-methyl-N-(2,2,2-trifluoroethyl)acetamide | 420.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 470 | 55 | 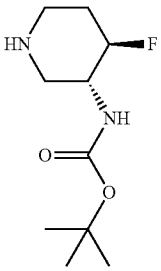 | B | 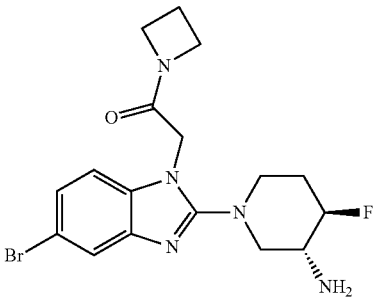 [SMILES: N[C@@H]1CN(c2nc3cc(Br)ccc3n2CC(=O)N2CCC2)CC[C@H]1F] | 2-(2-((3R,4R)-3-amino-4-fluoropiperidin-1-yl)-5-bromo-1H-benzo[d]imidazol-1-yl)-1-(azetidin-1-yl)ethan-1-one | 410.0 |
| 471 | 57 | 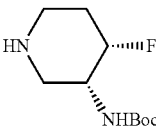 | B | 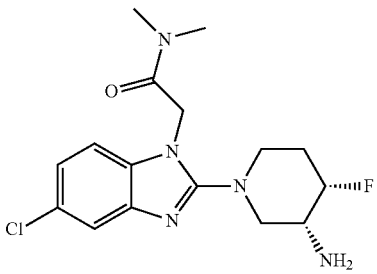 [SMILES: CN(C)C(=O)Cn1c(N2CC[C@H](F)[C@H](N)C2)nc2cc(Cl)ccc21] | 2-(2-((3R,4S)-3-amino-4-fluoropiperidin-1-yl)-5-chloro-1H-benzo[d]imidazol-1-yl)-N,N-dimethylacetamide | 354.2 |
| 472 | 49 | 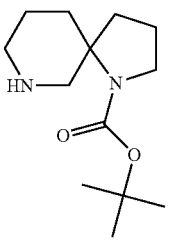 [SMILES: CC(C)(C)OC(=O)N1CCCC12CCCNC2] | B | 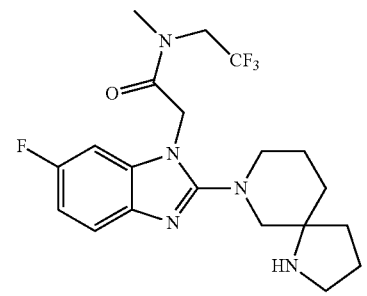 [SMILES: CN(CC(F)(F)F)C(=O)Cn1c(N2CCCC3(CCCN3)C2)nc2ccc(F)cc21] | 2-(6-fluoro-2-(1,7-diazaspiro[4.5]decan-7-yl)-1H-benzo[d]imidazol-1-yl)-N-methyl-N-(2,2,2-trifluoroethyl)acetamide | 428.2 |
| 473 | 56 | 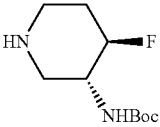 | B | 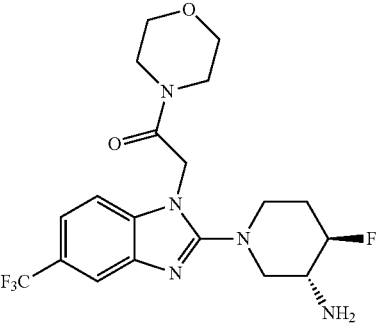 [SMILES: N[C@@H]1CN(c2nc3cc(C(F)(F)F)ccc3n2CC(=O)N2CCOCC2)CC[C@H]1F] | 2-(2-((3R,4R)-3-amino-4-fluoropiperidin-1-yl)-5-(trifluoromethyl)-1H-benzo[d]imidazol-1-yl)-1-morpholinoethan-1-one | 430.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 474 | 58 | | B | 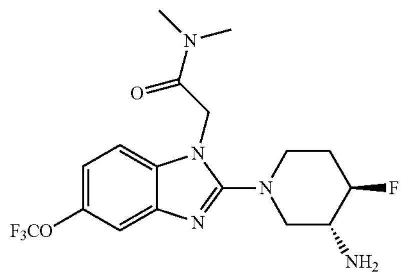 [SMILES: CN(C)C(=O)Cn1c(N2CC[C@@H](F)[C@H](N)C2)nc2cc(OC(F)(F)F)ccc21] | 2-(2-((3R,4R)-3-amino-4-fluoropiperidin-1-yl)-5-(trifluoromethoxy)-1H-benzo[d]imidazol-1-yl)-N,N-dimethylacetamide | 404.2 |
| 475 | 59 | | B | 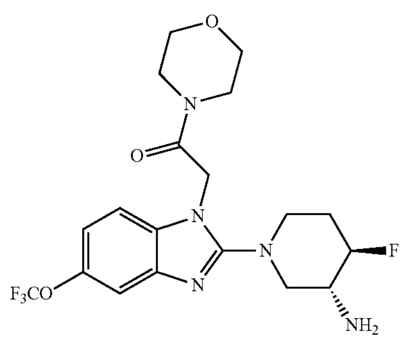 [SMILES: N[C@@H]1CN(c2nc3cc(OC(F)(F)F)ccc3n2CC(=O)N2CCOCC2)CC[C@H]1F] | 2-(2-((3R,4R)-3-amino-4-fluoropiperidin-1-yl)-5-(trifluoromethoxy)-1H-benzo[d]imidazol-1-yl)-1-morpholinoethan-1-one | 446.2 |
| 476 | 53 | | B | 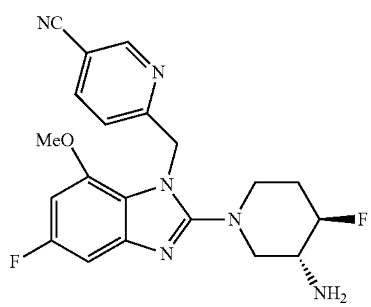 [SMILES: COc1cc(F)cc2nc(N3CC[C@@H](F)[C@H](N)C3)n(Cc3ccc(C#N)cn3)c12] | 6-((2-((3R,4R)-3-amino-4-fluoropiperidin-1-yl)-5-fluoro-7-methoxy-1H-benzo[d]imidazol-1-yl)methyl)nicotinonitrile | 399.2 |
| 477 | 17 | HCl | B | 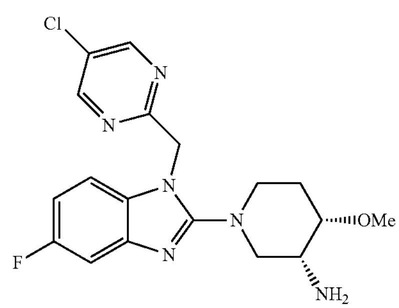 [SMILES: CO[C@H]1CCN(c2nc3cc(F)ccc3n2Cc2ncc(Cl)cn2)C[C@H]1N] | (3R,4S)-1-(1-((5-chloropyrimidin-2-yl)methyl)-5-fluoro-1H-benzo[d]imidazol-2-yl)-4-methoxypiperidin-3-amine | 3912 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 478 | 56 | | B | 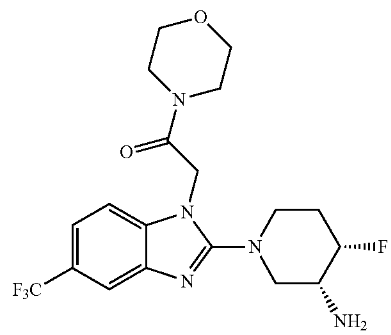 [SMILES: N[C@@H]1CN(c2nc3cc(C(F)(F)F)ccc3n2CC(=O)N2CCOCC2)CC[C@@H]1F] | 2-(2-((3R,4S)-3-amino-4-fluoropiperidin-1-yl)-5-(trifluoromethyl)-1H-benzo[d]imidazol-1-yl)-1-morpholinoethan-1-one | 430.2 |
| 479 | 49 | | B | 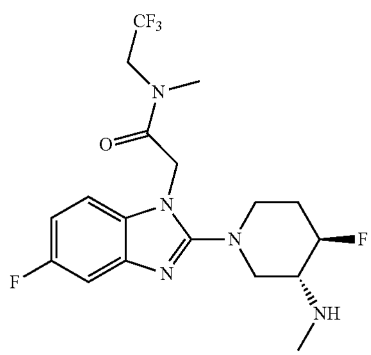 [SMILES: CN[C@@H]1CN(c2nc3cc(F)ccc3n2CC(=O)N(C)CC(F)(F)F)CC[C@H]1F] | 2-(5-fluoro-2-((3R,4R)-4-fluoro-3-(methylamino)piperidin-1-yl)-1H-benzo[d]imidazol-1-yl)-N-methyl-N-(2,2,2-trifluoroethyl)acetamide | 420.2 |
| 480 | 49 | | B | 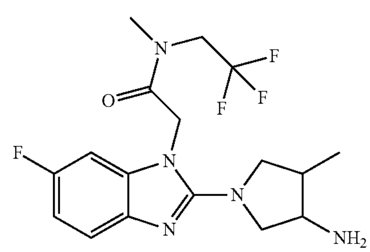 [SMILES: CC1CN(c2nc3ccc(F)cc3n2CC(=O)N(C)CC(F)(F)F)CC1N] | 2-(2-(3-amino-4-methylpyrrolidin-1-yl)-6-fluoro-1H-benzo[d]imidazol-1-yl)-N-methyl-N-(2,2,2-trifluoroethyl)acetamide | 388.2 |
| 481 | 49 | | B | 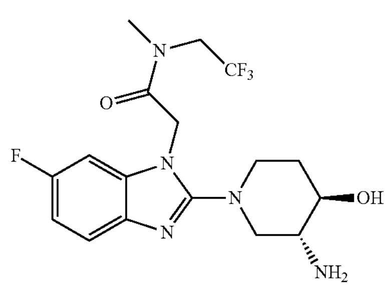 [SMILES: CN(CC(F)(F)F)C(=O)Cn1c(N2CC[C@@H](O)[C@H](N)C2)nc2ccc(F)cc21] | 2-(2-((3R,4R)-3-amino-4-hydroxypiperidin-1-yl)-6-fluoro-1H-benzo[d]imidazol-1-yl)-N-methyl-N-(2,2,2-trifluoroethyl)acetamide | 404.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 482 | 49 | | B | 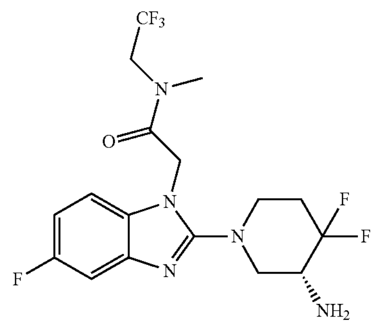 [SMILES: CN(CC(F)(F)F)C(=O)Cn1c(N2CCC(F)(F)[C@H](N)C2)nc2cc(F)ccc21] | (R)-2-(2-(3-amino-4,4-difluoropiperidin-1-yl)-5-fluoro-1H-benzo[d]imidazol-1-yl)-N-methyl-N-(2,2,2-trifluoroethyl)acetamide | 424.2 |
| 483 | 49 | | B | 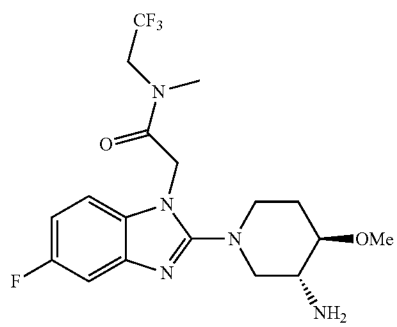 [SMILES: CO[C@@H]1CCN(c2nc3cc(F)ccc3n2CC(=O)N(C)CC(F)(F)F)C[C@H]1N] | 2-(2-((3R,4R)-3-amino-4-methoxypiperidin-1-yl)-5-fluoro-1H-benzo[d]imidazol-1-yl)-N-methyl-N-(2,2,2-trifluoroethyl)acetamide | 418.2 |
| 484 | 49 | | B | 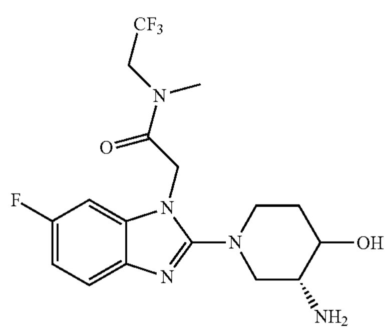 [SMILES: CN(CC(F)(F)F)C(=O)Cn1c(N2CCC(O)[C@H](N)C2)nc2ccc(F)cc21] | 2-(2-((3R)-3-amino-4-hydroxypiperidin-1-yl)-5-fluoro-1H-benzo[d]imidazol-1-yl)-N-methyl-N-(2,2,2-trifluoroethyl)acetamide | 404.2 |
| 485 | 49 | | B | 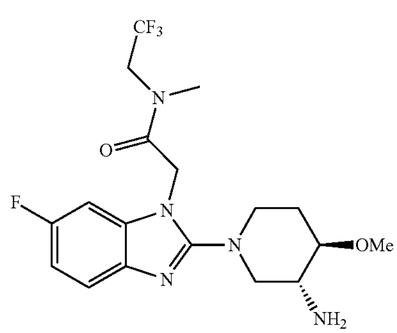 [SMILES: CO[C@@H]1CCN(c2nc3ccc(F)cc3n2CC(=O)N(C)CC(F)(F)F)C[C@H]1N] | 2-(2-((3R,4R)-3-amino-4-methoxypiperidin-1-yl)-6-fluoro-1H-benzo[d]imidazol-1-yl)-N-methyl-N-(2,2,2-trifluoroethyl)acetamide | 418.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 486 | 49 | | B | 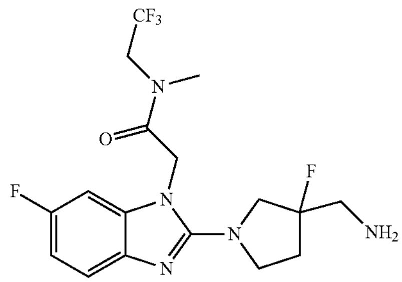 [SMILES: CN(CC(F)(F)F)C(=O)Cn1c(N2CCC(F)(CN)C2)nc2ccc(F)cc21] | 2-(2-(3-(aminomethyl)-3-fluoropyrrolidin-1-yl)-6-fluoro-1H-benzo[d]imidazol-1-yl)-N-methyl-N-(2,2,2-trifluoroethyl)acetamide | 406.2 |
| 487 | 49 | | B | 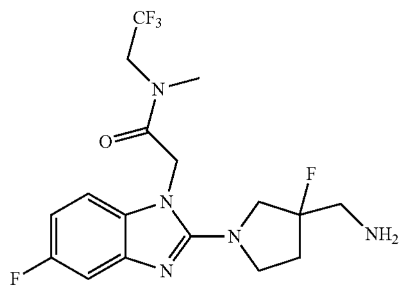 [SMILES: CN(CC(F)(F)F)C(=O)Cn1c(N2CCC(F)(CN)C2)nc2cc(F)ccc21] | 2-(2-(3-(aminomethyl)-3-fluoropyrrolidin-1-yl)-5-fluoro-1H-benzo[d]imidazol-1-yl)-N-methyl-N-(2,2,2-trifluoroethyl)acetamide | 406.2 |
| 488 | 49 | | B | 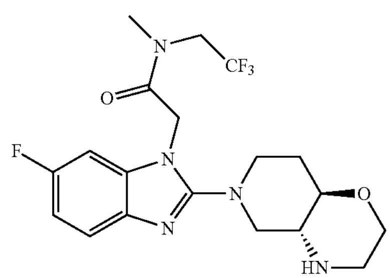 [SMILES: CN(CC(F)(F)F)C(=O)Cn1c(N2CC[C@H]3OCCN[C@@H]3C2)nc2ccc(F)cc21] | 2-(6-fluoro-2-((4aR,8aR)-hexahydro-2H-pyrido[4,3-b][1,4]oxazin-6(5H)-yl)-1H-benzo[d]imidazol-1-yl)-N-methyl-N-(2,2,2-trifluoroethyl)acetamide | 430.2 |
| 489 | 49 | | B | 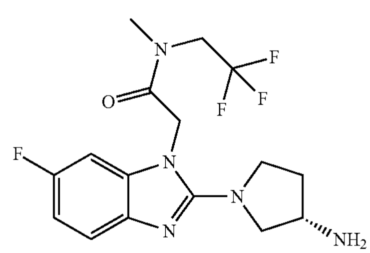 [SMILES: CN(CC(F)(F)F)C(=O)Cn1c(N2CC[C@H](N)C2)nc2ccc(F)cc21] | (S)-2-(2-(3-aminopyrrolidin-1-yl)-6-fluoro-1H-benzo[d]imidazol-1-yl)-N-methyl-N-(2,2,2-trifluoroethyl)acetamide | 374.2 |
| 490 | 49 | | B | 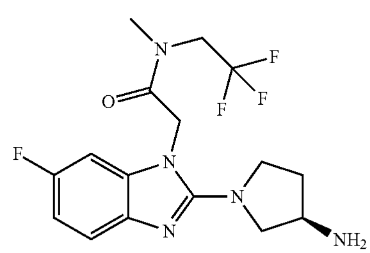 | (R)-2-(2-(3-aminopyrrolidin-1-yl)-6-fluoro-1H-benzo[d]imidazol-1-yl)-N-methyl-N-(2,2,2-trifluoroethyl)acetamide | 374.2 |

TABLE 2-continued

Compounds made following Scheme 8
Boc Deprotection procedure: A = HCl procedure, B = TFA procedure

| Ex. # | Alkylated Intermediate | Amine | Boc Deprotection Procedure | Structure | Compound Name | MS MH+ |
|---|---|---|---|---|---|---|
| 491 | 49 | (pyrrolidine with CH2NHBoc) | B | (structure) | (S)-2-(2-(3-(aminomethyl)pyrrolidin-1-yl)-6-fluoro-1H-benzo[d]imidazol-1-yl)-N-methyl-N-(2,2,2-trifluoroethyl)acetamide | 388.2 |
| 492 | 49 | (BocN-hexahydropyrido[4,3-b][1,4]oxazine, 4aR,8aR) | B | (structure) | 2-(6-fluoro-2-((4aR,8aR)-hexahydro-2H-pyrido[4,3-b][1,4]oxazin-6(5H)-yl)-1H-benzo[d]imidazol-1-yl)-N-methyl-N-(2,2,2-trifluoroethyl)acetamide | 430.2 |
| 493 | 49 | (BocN-hexahydropyrido[4,3-b][1,4]oxazine, 4aS,8aS) | B | (structure) | 2-(5-fluoro-2-((4aS,8aS)-hexahydro-2H-pyrido[4,3-b][1,4]oxazin-6(5H)-yl)-1H-benzo[d]imidazol-1-yl)-N-methyl-N-(2,2,2-trifluoroethyl)acetamide | 430.2 | a hydroysis of nitrite occurred during SnAr
b Ritter reactivity observed during Boc deprotection
c unspecified sterochemistry designates mixtures of enantiomers or diastereomers

TABLE 3

Characterization data for compounds made following Scheme 8.
The column "Separation Stage" indicates after which process step regioisomers formed due to asymmetric benzimidazole substitution at R¹ in Scheme 8 were separated during the preparation of the tabulated final compound (I = after preparation of the alkylated intermediate 1-59 (where at least one R¹ is not hydrogen); B prior to boc deprotection; or F = final compound).

| Ex. #. | Freq., Solvent | ¹HNMR Data (δ ppm) | Separation Stage | SFC Isomer Separation Conditions |
|---|---|---|---|---|
| 1 | 400 MHz d₄-MeOH | 8.85 (dd, J = 0.83, 2.07 Hz, 1H), 8.12-8.16 (m, 1H), 7.44 (d, J = 8.50 Hz, 1H), 7.37 (dd, J = 0.62, 8.29 Hz, 1H), 7.20 (d, J = 1.66 Hz, 1H), 7.12-7.16 (m, 1H), 5.48 (s, 2H), 3.50 (br s, 1H), 2.97-3.03 (m, 1H), 2.89-2.96 (m, 1H), 2.78-2.86 (m, 1H), 1.92-2.01 (m, 1H), 1.81 (dt, J = 3.94, 8.71 Hz, 1H), 1.57-1.72 (m, 1H), 1.31-1.42 (m, 1H) | B | Chiralpak AD-H, 20% MeOH, Peak 1 |
| 2 | 500 MHz d₄- | 8.81-8.86 (m, 1H), 8.11-8.17 (m, 1H), 7.44-7.48 (m, 1H), 7.36 (d, J = 8.04 Hz, 1H), 7.06-7.10 (m, | B | Chiralpak AD-H, 20% |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
|  | MeOH | 2H), 5.49 (s, 2H), 3.52 (br dd, J = 1.69, 11.81 Hz, 1H), 2.97-3.06 (m, 1H), 2.90-2.96 (m, 1H), 2.80-2.88 (m, 1H), 1.92-2.01 (m, 1H), 1.82 (br dd, J = 4.28, 9.47 Hz, 1H), 1.58-1.71 (m, 1H), 1.29-1.41 (m, 1H) |  | MeOH, Peak 2 |
| 3 | 500 MHz d₄-MeOH | 8.75-8.80 (m, 1H), 8.06 (d, J = 8.30 Hz, 1H), 7.23-7.31 (m, 1H), 7.11 (d, J = 7.27 Hz, 1H), 6.94-7.05 (m, 2H), 5.44 (s, 2H), 3.48 (br d, J = 10.12 Hz, 1H), 3.24-3.30 (m, 1H), 3.23-3.28 (m, 1H), 2.94-3.04 (m, 1H), 2.77-2.90 (m, 2H), 1.83-1.96 (m, 1H), 1.71-1.81 (m, 1H), 1.51-1.65 (m, 1H), 1.19-1.35 (m, 1H) | — | — |
| 4 | 500 MHz d₄-MeOH | 8.83 (s, 1H), 8.11-8.16 (m, 1H), 7.39 (d, J = 8.30 Hz, 1H), 7.18 (d, J = 7.01 Hz, 1H), 7.02-7.11 (m, 2H), 5.53 (s, 2H), 4.33-4.52 (m, 1H), 3.59-3.66 (m, 1H), 3.50 (br d, J = 12.46 Hz, 1H), 3.14-3.22 (m, 1H), 3.09 (dq, J = 4.02, 8.69 Hz, 1H), 2.95-3.05 (m, 1H), 2.07-2.22 (m, 1H), 1.76-1.94 (m, 1H) | — | — |
| 5 | 500 MHz d₄-MeOH | 8.83 (s, 1H), 8.10-8.15 (m, 1H), 7.37 (d, J = 8.04 Hz, 1H), 7.17 (d, J = 7.01 Hz, 1H), 7.01-7.09 (m, 2H), 5.52 (s, 2H), 3.43 (dd, J = 4.15, 12.20 Hz, 1H), 3.20-3.35 (m, 2H), 3.18-3.35 (m, 1H), 3.04-3.17 (m, 1H), 2.10 (ddd, J = 4.93, 9.80, 14.34 Hz, 1H), 1.88-2.04 (m, 1H) | — | — |
| 6 | 500 MHz d₄-MeOH | 8.86 (d, J = 1.30 Hz, 1H), 8.14-8.20 (m, 1H), 7.47 (d, J = 8.56 Hz, 1H), 7.44 (d, J = 8.30 Hz, 1H), 7.23 (d, J = 2.08 Hz, 1H), 7.19 (dd, J = 1.95, 8.43 Hz, 1H), 5.53 (s, 2H), 4.33-4.50 (m, 1H), 3.53-3.61 (m, 1H), 3.43-3.50 (m, 1H), 3.02-3.20 (m, 2H), 2.95 (dd, J = 8.69, 12.33 Hz, 1H), 2.12-2.24 (m, 1H), 1.82-1.94 (m, 1H) | B | Chiralcel OD-H, 25% IPA, peak 1 |
| 7 | 500 MHz d₄-MeOH | 8.86 (d, J = 1.30 Hz, 1H), 8.13-8.20 (m, 1H), 7.49 (s, 1H), 7.42 (d, J = 8.30 Hz, 1H), 7.12 (s, 2H), 5.54 (s, 2H), 4.43 (s, 1H), 3.57-3.63 (m, 1H), 3.45-3.55 (m, 1H), 3.12-3.20 (m, 1H), 3.03-3.12 (m, 1H), 2.97 (dd, J = 8.82, 12.46 Hz, 1H), 2.12-2.24 (m, 1H), 1.80-1.96 (m, 1H) | B | Chiralcel OD-H, 25% IPA, peak 2 |
| 8 | 500 MHz d₄-MeOH | 8.86 (d, J = 1.82 Hz, 1H), 8.14-8.19 (m, 1H), 7.47 (d, J = 8.56 Hz, 1H), 7.43 (d, J = 8.04 Hz, 1H), 7.22 (s, 1H), 7.13-7.20 (m, 1H), 5.53 (s, 2H), 4.75-4.81 (m, 1H), 3.37-3.43 (m, 1H), 3.01-3.29 (m, 4H), 2.08-2.20 (m, 1H), 1.88-2.03 (m, 1H) | B | Chiralcel OD-H, 25% IPA, peak 1 |
| 9 | 500 MHz d₄-MeOH | 8.86 (d, J = 1.30 Hz, 1H), 8.14-8.19 (m, 1H), 7.49 (s, 1H), 7.41 (d, J = 8.04 Hz, 1H), 7.12 (s, 2H), 5.53 (s, 2H), 3.37-3.49 (m, 2H), 3.28 (dd, J = 3.37, 8.04 Hz, 2H), 3.03-3.21 (m, 2H), 2.09-2.18 (m, 1H), 1.89-2.05 (m, 1H) | B | Chiralcel OD-H, 25% IPA, peak 2 |
| 10 | 500 MHz d₄-MeOH | 8.84 (s, 1H), 8.16 (d, J = 8.04 Hz, 1H), 7.42-7.47 (m, 1H), 7.19-7.23 (m, 1H), 7.05-7.12 (m, 2H), 5.58 (s, 2H), 3.59 (br d, J = 11.42 Hz, 1H), 3.45-3.53 (m, 1H), 3.37 (ddd, J = 3.11, 9.54, 12.78 Hz, 1H), 3.16-3.30 (m, 2H), 2.30 (tdd, J = 4.70, 9.67, 14.66 Hz, 1H), 2.06-2.22 (m, 1H) | — | — |
| 11 | 500 MHz d₄-MeOH | 8.80-8.84 (m, 1H), 8.14-8.19 (m, 1H), 7.45-7.51 (m, 2H), 7.41 (d, J = 8.04 Hz, 1H), 7.17 (t, J = 7.91 Hz, 1H), 5.54-5.60 (m, 2H), 4.35-4.53 (m, 1H), 3.70-3.76 (m, 1H), 3.50-3.64 (m, 1H), 3.19-3.26 (m, 1H), 3.14 (dq, J = 4.15, 8.82 Hz, 1H), 2.98-3.08 (m, 1H), 2.11-2.23 (m, 1H), 1.80-1.95 (m, 1H) | — | — |
| 12 | 500 MHz d₄-MeOH | 8.85 (d, J = 1.56 Hz, 1H), 8.15-8.20 (m, 1H), 7.48 (d, J = 8.56 Hz, 2H), 7.23 (d, J = 1.56 Hz, 1H), 7.19 (dd, J = 1.82, 8.56 Hz, 1H), 5.56 (s, 2H), 3.53 (br d, J = 12.20 Hz, 1H), 3.40-3.48 (m, 1H), 3.28-3.32 (m, 1H), 3.12-3.27 (m, 2H), 2.23-2.37 (m, 1H), 2.06-2.21 (m, 1H) | F | Chiralcel OD-H, 25% MeOH, peak 1 |
| 13 | 500 MHz d₄- | 8.85 (d, J = 1.04 Hz, 1H), 8.15-8.19 (m, 1H), 7.50 (s, 1H), 7.46 (d, J = 8.04 Hz, 1H), 7.07-7.15 (m, | F | Chiralcel OD-H, 25% |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
|  | MeOH | 2H), 5.54-5.59 (m, 2H), 3.56 (br d, J = 12.20 Hz, 1H), 3.40-3.50 (m, 1H), 3.34-3.39 (m, 1H), 3.13-3.29 (m, 2H), 2.24-2.39 (m, 1H), 2.06-2.22 (m, 1H) |  | MeOH, peak 2 |
| 14 | 500 MHz d₄-MeOH | 8.85 (d, J = 1.82 Hz, 1H), 8.15-8.20 (m, 1H), 7.64 (d, J = 8.30 Hz, 1H), 7.44-7.54 (m, 3H), 5.59-5.64 (m, 2H), 4.36-4.54 (m, 1H), 3.60-3.71 (m, 1H), 3.48-3.56 (m, 1H), 3.14-3.22 (m, 1H), 3.06-3.13 (m, 1H), 2.95-3.03 (m, 1H), 2.12-2.23 (m, 1H), 1.81-1.97 (m, 1H) | B | Chiralcel OD-H, 15% IPA, peak 1 |
| 15 | 500 MHz d₄-MeOH | 8.82-8.87 (m, 1H), 8.15-8.21 (m, 1H), 7.78 (s, 1H), 7.48 (d, J = 8.30 Hz, 1H), 7.41 (d, J = 8.56 Hz, 1H), 7.31 (d, J = 8.30 Hz, 1H), 5.55-5.64 (m, 2H), 4.35-4.54 (m, 1H), 3.60-3.69 (m, 1H), 3.50-3.59 (m, 1H), 3.15-3.22 (m, 1H), 3.06-3.15 (m, 1H), 3.01 (dd, J = 8.82, 12.46 Hz, 1H), 2.13-2.27 (m, 1H), 1.83-1.97 (m, 1H) | B | Chiralcel OD-H, 15% IPA, peak 2 |
| 16 | 500 MHz d₄-MeOH | 8.86 (d, J = 1.30 Hz, 1H), 8.11-8.18 (m, 1H), 7.53 (d, J = 7.79 Hz, 1H), 7.37 (d, J = 8.04 Hz, 1H), 7.18-7.25 (m, 1H), 7.11-7.17 (m, 2H), 5.51-5.57 (m, 2H), 4.37-4.53 (m, 1H), 3.57-3.65 (m, 1H), 3.40-3.54 (m, 1H), 3.09-3.21 (m, 2H), 2.99 (dd, J = 8.95, 12.33 Hz, 1H), 2.19 (Tt, J = 4.28. 13.62 Hz, 1H), 1.81-1.98 (m, 1H) | — | — |
| 17 | 500 MHz d₄-MeOH | 8.90 (d, J = 1.30 Hz, 1H), 8.08-8.16 (m, 1H), 7.33-7.38 (m, 1H), 7.25 (d, J = 8.04 Hz, 1H), 7.06-7.11 (m, 2H), 6.96-7.02 (m, 1H), 5.45 (s, 2H), 4.14-4.23 (m, 1H), 3.26 (br d, J = 13.23 Hz, 1H), 3.04-3.16 (m, 1H), 2.83-2.94 (m, 1H), 2.49-2.60 (m, 2H), 2.43-2.46 (m, 1H), 1.99-2.13 (m, 1H), 1.48-1.57 (m, 1H), 1.38 (qd, J = 7.28, 15.02 Hz, 1H) | — | — |
| 18 | 500 MHz d₄-MeOH | 8.83 (dd, J = 1.56, 16.35 Hz, 1H), 8.18-8.25 (m, 1H), 7.50-7.61 (m, 1H), 7.27-7.37 (m, 2H), 5.56 (d, J = 3.11 Hz, 2H), 3.04-3.26 (m, 3H), 2.99 (br d, J = 8.04 Hz, 2H), 2.11-2.26 (m, 1H), 1.84-2.01 (m, 2H) | — | — |
| 19 | 500 MHz d₄-MeOH | 8.84 (s, 1H), 8.13-8.21 (m, 1H), 7.52-7.58 (m, 1H), 7.43-7.50 (m, 1H), 7.06-7.18 (m, 2H), 5.50-5.61 (m, 2H), 4.39-4.58 (m, 1H), 3.64 (br d, J = 12.46 Hz, 1H), 3.45-3.56 (m, 1H), 3.11-3.22 (m, 2H), 3.01 (dd, J = 9.21, 12.33 Hz, 1H), 2.12-2.25 (m, 1H), 1.83-1.97 (m, 1H) | B | Chiralpak AD-H, 15% MeOH, peak 1 |
| 20 | 500 MHz d₄-MeOH | 8.85 (d, J = 1.30 Hz, 1H), 8.11-8.21 (m, 1H), 7.45 (d, J = 8.30 Hz, 1H), 7.40 (s, 1H), 7.17-7.24 (m, 1H), 7.01-7.08 (m, 1H), 5.51-5.60 (m, 2H), 4.37-4.54 (m, 1H), 3.61-3.68 (m, 1H), 3.45-3.57 (m, 1H), 3.05-3.23 (m, 2H), 3.00 (dd, J = 9.08, 12.46 Hz, 1H), 2.13-2.27 (m, 1H), 1.90 (ddd, J = 3.63, 9.60, 13.23 Hz, 1H) | B | Chiralpak AD-H, 15% MeOH, peak 2 |
| 21 | 500 MHz d₄-MeOH | 8.84 (d, J = 2.08 Hz, 1H), 8.16-8.22 (m, 1H), 7.46-7.54 (m, 2H), 7.35 (d, J = 11.16 Hz, 1H), 5.57-5.61 (m, 2H), 4.36-4.53 (m, 1H), 3.64-3.72 (m, 1H), 3.49-3.59 (m, 1H), 3.15-3.24 (m, 1H), 3.07-3.15 (m, 1H), 3.02 (dd, J = 8.95, 12.59 Hz, 1H), 2.18 (br dd, J = 4.80, 9.21 Hz, 1H), 1.82-1.92 (m, 1H) | B | Phenomenex Lux Cellulose-2, 15% MeOH, peak 1 |
| 22 | 500 MHz d₄-MeOH | 8.83 (d, J = 1.30 Hz, 1H), 8.16-8.21 (m, 1H), 7.73 (d, J = 6.23 Hz, 1H), 7.52 (d, J = 8.30 Hz, 1H), 7.21 (d, J = 10.38 Hz, 1H), 5.58 (s, 2H), 4.34-4.53 (m, 1H), 3.63 (br dd, J = 1.56, 12.46 Hz, 1H), 3.49 (br s, 1H), 3.05-3.22 (m, 2H), 2.99 (dd, J = 8.82, 12.46 Hz, 1H), 2.11-2.26 (m, 1H), 1.89 (ddd, J = 3.63, 9.67, 13.43 Hz, 1H) | B | Phenomenex Lux Cellulose-2, 15% MeOH, peak 2 |
| 23 | 500 MHz d₄-MeOH | 8.85 (s, 1H), 8.06-8.13 (m, 1H), 7.51 (d, J = 7.79 Hz, 1H), 7.29 (d, J = 8.30 Hz, 1H), 7.05-7.22 (m, 3H), 5.49 (s, 2H), 3.30-3.36 (m, 2H), 3.10-3.23 (m, 3H), 2.94-3.09 (m, 1H), 2.38 (qd, J = 6.47, 12.52 Hz, 1H), 1.88-2.03 (m, 2H), 1.66-1.88 (m, 2H) | B | Chiralpak AD-H, 30% IPA, peak 1 |
| 24 | 500 MHz d₄- | 8.85 (s, 1H), 8.18-8.23 (m, 1H), 7.50-7.59 (m, 2H), 7.27-7.33 (m, 1H), 7.21-7.26 (m, 2H), 5.61 | B | Chiralpak AD-H, 30% |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. #. | Freq., Solvent | $^1$HNMR Data (δ ppm) | Separation Stage | SFC Isomer Separation Conditions |
|---|---|---|---|---|
|  | MeOH | (s, 2H), 4.00 (br dd, J = 2.47, 12.85 Hz, 1H), 3.80-3.91 (m, 1H), 3.37-3.56 (m, 4H), 3.25 (br d, J = 2.34 Hz, 3H), 2.13-2.28 (m, 3H), 1.88-2.07 (m, 3H), 1.69-1.83 (m, 1H) |  | IPA, peak 2 |
| 25 | 500 MHz d$_4$-MeOH | 8.85 (s, 1H), 8.06-8.13 (m, 1H), 7.51 (d, J = 7.79 Hz, 1H), 7.29 (d, J = 8.30 Hz, 1H), 7.05-7.22 (m, 3H), 5.49 (s, 2H), 3.30-3.36 (m, 2H), 3.10-3.23 (m, 3H), 2.94-3.09 (m, 1H), 2.38 (qd, J = 6.47, 12.52 Hz, 1H), 1.88-2.03 (m, 2H), 1.66-1.88 (m, 2H) | B | Chiralpak AD-H, 30% IPA, peak 3 |
| 26 | 500 MHz d$_4$-MeOH | 8.85 (s, 1H), 8.18-8.23 (m, 1H), 7.50-7.59 (m, 2H), 7.27-7.33 (m, 1H), 7.21-7.26 (m, 2H), 5.61 (s, 2H), 4.00 (br dd, J = 2.47, 12.85 Hz, 1H), 3.80-3.91 (m, 1H), 3.37-3.56 (m, 4H), 3.25 (br d, J = 2.34 Hz, 3H), 2.13-2.28 (m, 3H), 1.88-2.07 (m, 3H), 1.69-1.83 (m, 1H) | B | Chiralpak AD-H, 30% IPA, peak 4 |
| 27 | 400 MHz d$_4$-MeOH | 8.83 (dd, J = 0.62, 2.07 Hz, 1H), 8.08 (dd, J = 2.07, 8.09 Hz, 1H), 7.49-7.54 (m, 1H), 7.32 (d, J = 8.29 Hz, 1H), 7.07-7.19 (m, 3H), 5.45-5.52 (m, 2H), 3.38-3.45 (m, 2H), 2.99-3.17 (m, 2H), 1.94-2.14 (m, 2H), 1.57-1.86 (m, 4H) | B | Chiralpak IC, 40% MeOH, peak 1 |
| 28 | 400 MHz d$_4$-MeOH | 8.83 (dd, J = 0.83, 2.07 Hz, 1H), 8.06-8.11 (m, 1H), 7.49-7.55 (m, 1H), 7.32 (d, J = 8.29 Hz, 1H), 7.05-7.19 (m, 3H), 5.47-5.52 (m, 2H), 3.37-3.46 (m, 2H), 3.01-3.18 (m, 2H), 1.96-2.18 (m, 2H), 1.56-1.84 (m, 4H) | B | Chiralpak IC, 40% MeOH, peak 2 |
| 29 | 500 MHz d$_4$-MeOH | 8.49 (d, J = 2.34 Hz, 1H), 7.83-7.87 (m, 1H), 7.75-7.79 (m, 2H), 7.66 (d, J = 8.30 Hz, 1H), 7.36 (d, J = 8.56 Hz, 1H), 5.52 (s, 2H), 4.42-4.59 (m, 1H), 3.77 (dtd, J = 1.69, 4.27, 12.62 Hz, 1H), 3.56-3.67 (m, 1H), 3.18-3.26 (m, 2H), 3.09 (s, 3H), 3.02-3.08 (m, 1H), 2.15-2.26 (m, 1H), 1.84-1.96 (m, 1H) | B | Chiralcel OD-H, 25% MeOH, peak 1 |
| 30 | 500 MHz d$_4$-MeOH | 8.48 (d, J = 2.34 Hz, 1H), 8.04-8.08 (m, 1H), 7.83-7.88 (m, 1H), 7.69 (dd, J = 1.82, 8.56 Hz, 1H), 7.37 (dd, J = 4.02, 8.43 Hz, 2H), 5.48-5.53 (m, 2H), 4.47-4.65 (m, 1H), 3.79 (dtd, J = 1.69, 4.27, 12.62 Hz, 1H), 3.58-3.67 (m, 1H), 3.33-3.38 (m, 1H), 3.17-3.25 (m, 1H), 3.07-3.14 (m, 4H), 2.18-2.29 (m, 1H), 1.87-2.03 (m, 1H) | B | Chiralcel OD-H, 25% MeOH, peak 1 |
| 31 | 400 MHz d$_4$-MeOH | 8.77-8.82 (m, 2H), 7.35-7.43 (m, 1H), 7.28-7.32 (m, 1H), 5.54 (s, 2H), 4.38-4.60 (m, 1H), 3.76 (dtd, J = 1.97, 4.31, 12.62 Hz, 1H), 3.56-3.68 (m, 1H), 3.16-3.26 (m, 2H), 2.97-3.10 (m, 1H), 2.12-2.26 (m, 1H), 1.79-1.98 (m, 1H) | — | — |
| 32 | 400 MHz d$_4$-MeOH | 8.37 (d, J = 2.90 Hz, 1H), 7.57-7.64 (m, 1H), 7.33 (dd, J = 4.35, 8.71 Hz, 1H), 7.05 (dd, J = 2.07, 8.91 Hz, 1H), 6.73 (ddd, J = 2.18, 9.85, 11.61 Hz, 1H), 5.49 (s, 2H), 4.39-4.60 (m, 1H), 3.70 (dtd, J = 1.76, 4.28, 12.49 Hz, 1H), 3.49-3.61 (m, 1H), 3.11-3.31 (m, 2H), 3.04 (dd, J = 9.12, 12.44 Hz, 1H), 2.13-2.28 (m, 1H), 1.83-2.04 (m, 1H) | B | Regis Whelk-O, 20% MeOH, peak 2 |
| 33 | 400 MHz d$_4$-MeOH | 8.41 (d, J = 2.90 Hz, 1H), 7.57-7.64 (m, 1H), 7.35 (dd, J = 4.15, 8.71 Hz, 1H), 6.71-6.85 (m, 2H), 5.41 (s, 2H), 4.32-4.54 (m, 1H), 3.61 (dtd, J = 1.66, 4.17, 12.39 Hz, 1H), 3.43-3.53 (m, 1H), 3.06-3.20 (m, 2H), 2.97 (dd, J = 8.60, 12.34 Hz, 1H), 2.11-2.25 (m, 1H), 1.80-1.97 (m, 1H) | B | Regis Whelk-O, 20% MeOH, peak 1 |
| 34 | 400 MHz d$_4$-MeOH | 8.66-8.74 (m, 2H), 6.86-6.92 (m, 1H), 6.72-6.82 (m, 1H), 5.51 (s, 2H), 4.36-4.59 (m, 1H), 3.64 (dtd, J = 1.87, 4.28, 12.39 Hz, 1H), 3.47-3.57 (m, 1H), 3.09-3.22 (m, 2H), 2.99 (dd, J = 8.91, 12.44 Hz, 1H), 2.07-2.26 (m, 1H), 1.75-1.99 (m, 1H) | B | Regis Whelk-O, 15% MeOH, peak 2 |
| 35 | 400 MHz d$_4$-MeOH | 8.67-8.72 (m, 2H), 7.03-7.08 (m, 1H), 6.68-6.77 (m, 1H), 5.62 (d, J = 0.83 Hz, 2H), 4.44-4.65 (m, 1H), 3.69 (dtd, J = 1.76, 4.35, 12.54 Hz, 1H), 3.44-3.58 (m, 1H), 3.24-3.32 (m, 1H), 3.12-3.19 (m, 1H), 3.05 (dd, J = 9.43, 12.54 Hz, 1H), 2.17-2.27 (m, 1H), 1.84-2.01 (m, 1H) | B | Regis Whelk-O, 15% MeOH, peak 1 |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
| 36 | 500 MHz d₄-MeOH | 8.73 (s, 2H), 7.39-7.44 (m, 1H), 7.35 (dd, J = 2.34, 9.34 Hz, 1H), 5.57 (d, J = 4.15 Hz, 2H), 5.00-5.16 (m, 1H), 3.72-3.85 (m, 2H), 3.46-3.54 (m, 2H), 3.35-3.44 (m, 1H), 1.98-2.19 (m, 2H) | — | — |
| 37 | 500 MHz d₄-MeOH | 8.72 (s, 2H), 7.37-7.41 (m, 1H), 7.31 (dd, J = 2.47, 9.47 Hz, 1H), 5.55 (s, 2H), 4.41-4.60 (m, 1H), 3.78 (dtd, J = 1.82, 4.25, 12.78 Hz, 1H), 3.56-3.70 (m, 1H), 3.16-3.29 (m, 2H), 3.07 (dd, J = 9.34, 12.72 Hz, 1H), 2.14-2.24 (m, 1H), 1.83-1.96 (m, 1H) | — | — |
| 38 | 500 MHz d₄-MeOH | 8.81-8.92 (m, 1 H), 8.23 (dd, J = 8.30, 2.08 Hz, 1 H), 7.49-7.66 (m, 2H), 7.17-7.39 (m, 3H), 5.64 (s, 2H), 4.69-4.86 (m, 1H), 3.92-4.06 (m, 1H), 3.61-3.79 (m, 2H), 3.20-3.32 (m, 2H), 2.24-2.41 (m, 1H), 1.92-2.14 (m, 1H) | — | — |
| 39 | 500 MHz d₄-MeOH | 8.74-8.81 (m, 2 H), 7.39-7.51 (m, 1 H), 7.00 (dd, J = 8.95, 2.47 Hz, 1 H), 6.94 (ddd, J = 9.86, 8.82, 2.60 Hz, 1 H), 5.51 (s, 2 H), 4.98 (dt, J = 5.26, 2.43 Hz, 1 H), 3.48 (dd, J = 11.94, 3.89 Hz, 1 H), 3.19-3.41 (m, 5 H), 1.92-2.21 (m, 2 H) | B | Chiralpak IC, 20% IPA, peak 1 |
| 40 | 500 MHz d₄-MeOH | 8.78 (s, 2 H), 7.04-7.25 (m, 2 H), 6.80-6.96 (m, 1 H), 5.45-5.61 (m, 2 H), 3.42-3.58 (m, 1 H), 3.17-3.40 (m, 5 H), 1.88-2.23 (m, 2 H) | B | Chiralpak IC, 20% IPA, peak 2 |
| 41 | 500 MHz d₄-MeOH | 8.81 (s, 2H), 7.67-7.71 (m, 1H), 7.61 (d, J = 8.30 Hz, 1H), 7.49-7.53 (m, 1H), 5.61 (s, 2H), 3.69-3.77 (m, 1H), 3.58-3.66 (m, 1H), 3.43-3.53 (m, 1H), 3.36-3.43 (m, 1H), 3.23-3.30 (m, 1H), 2.14-2.41 (m, 2H) | B | Chiralpak OJ, 15% MeOH, peak 2 |
| 42 | 500 MHz d₄-MeOH | 8.79 (s, 2H), 7.80-7.86 (m, 1H), 7.42-7.48 (m, 1H), 7.37 (d, J = 8.30 Hz, 1H), 5.61 (s, 2H), 3.66-3.74 (m, 1H), 3.55-3.63 (m, 1H), 3.34-3.53 (m, 3H), 3.22-3.30 (m, 1H), 2.29-2.41 (m, 1H), 2.07-2.27 (m, 1H) | B | Chiralpak OJ, 15% MeOH, peak 1 |
| 43 | 400 MHz d₆-DMSO | 8.93 (d, J = 1.35 Hz, 1H), 8.32 (dd, J = 2.18, 8.19 Hz, 1H), 7.67 (s, 1H), 7.54 (s, 1H), 7.52-7.56 (m, 1H), 7.49 (d, J = 7.92 Hz, 1H), 5.56 (s, 2H), 4.22-4.48 (m, 1H), 3.36-3.45 (m, 2H), 2.97-3.09 (m, 1H), 2.72-2.94 (m, 2H), 1.97-2.11 (m, 1H), 1.61-1.77 (m, 1H) | — | — |
| 44 | 400 MHz d₆-DMSO | 8.96 (s, 1H), 8.27 (dd, J = 2.18, 8.19 Hz, 1H), 7.27 (d, J = 7.98 Hz, 1H), 7.23 (s, 1H), 6.92 (s, 1H), 5.44 (s, 2H), 4.21-4.48 (m, 1H), 3.35 (br s, 3H), 2.86-3.03 (m, 2H), 2.74 (dd, J = 8.60, 12.44 Hz, 1H), 2.24 (s, 3H), 2.20 (s, 3H), 1.93-2.12 (m, 1H), 1.87 (br s, 1H), 1.64-1.82 (m, 1H) | — | — |
| 45 | 400 MHz d₆-DMSO | 8.92-8.95 (m, 1H), 8.36-8.50 (m, 3H), 7.76 (d, J = 8.09 Hz, 1H), 7.53-7.60 (m, 1H), 7.35-7.43 (m, 1H), 7.18 (t, J = 9.23 Hz, 1H), 5.65-5.84 (m, 2H), 3.86 (br d, J = 10.47 Hz, 1H), 3.26-3.52 (m, 3H), 3.15 (br t, J = 9.90 Hz, 1H), 1.82-2.01 (m, 2H), 1.40-1.69 (m, 2H) | B | Chiralcel OD-H, 15% IPA Peak 1 |
| 46 | 400 MHz d₆-DMSO | 8.94 (s, 1H), 8.48 (br s, 2H), 8.40 (dd, J = 2.18, 8.19 Hz, 1H), 7.77 (d, J = 8.19 Hz, 1H), 7.40 (dd, J = 2.85, 8.66 Hz, 2H), 7.14 (dt, J = 2.38, 9.33 Hz, 1H), 5.65-5.84 (m, 2H), 3.89 (br d, J = 10.57 Hz, 1H), 3.28-3.52 (m, 3H), 3.18 (br t, J = 9.80 Hz, 1H), 1.94-2.02 (m, 1H), 1.81-1.93 (m, 1H), 1.47-1.72 (m, 2H) | B | Chiralcel OD-H, 15% IPA Peak 2 |
| 47 | 400 MHz d₆-DMSO | 8.93 (s, 1H), 8.71 (br s, 2H), 8.38 (dd, J = 1.75, 8.24 Hz, 1H), 7.73 (d, J = 8.17 Hz, 1H), 7.57 (dd, J = 4.54, 8.69 Hz, 1H), 7.36 (br d, J = 8.30 Hz, 1H), 7.16 (t, J = 8.68 Hz, 1H), 5.65-5.82 (m, 2H), 5.06-5.24 (m, 1H), 3.79 (br d, J = 12.07 Hz, 1H), 3.62-3.74 (m, 1H), 3.36-3.52 (m, 3H), 3.24-3.33 (m, 1H), 2.09-2.20 (m, 1H), 1.88-2.09 (m, 1H) | B | Chiralcel OD-H, 15% IPA Peak 1 |
| 48 | 400 MHz d₆-DMSO | 8.94 (s, 1H), 8.66 (br s, 3H), 8.37 (dd, J = 1.82, 8.17 Hz, 1H), 7.67 (d, J = 8.17 Hz, 1H), 7.37 (dd, J = 2.14, 9.02 Hz, 1H), 7.31 (br dd, J = 4.41, 8.69 Hz, 1H), 7.07 (t, J = 8.71 Hz, 1H), 5.60-5.78 (m, | B | Chiralcel OD-H, 15% IPA Peak 2 |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. #. | Freq., Solvent | $^1$HNMR Data (δ ppm) | Separation Stage | SFC Isomer Separation Conditions |
|---|---|---|---|---|
| | | 2H), 5.05-5.24 (m, 1H), 3.62-3.78 (m, 2H), 3.36-3.51 (m, 2H), 3.22-3.31 (m, 1H), 2.09-2.18 (m, 1H), 1.93-2.07 (m, 1H) | | |
| 49 | 400 MHz d$_6$-DMSO | 8.90-8.96 (m, 1H), 8.87 (br s, 2H), 8.40 (dd, J = 1.95, 8.17 Hz, 1H), 7.76 (d, J = 8.30 Hz, 1H), 7.58 (dd, J = 4.54, 8.69 Hz, 1H), 7.39 (br d, J = 7.40 Hz, 1H), 7.18 (t, J = 8.78 Hz, 1H), 5.68-5.84 (m, 2H), 4.86-5.05 (m, 1H), 4.04 (br d, J = 12.46 Hz, 1H), 3.59-3.73 (m, 1H), 3.33-3.53 (m, 2H), 3.22 (br t, J = 11.42 Hz, 1H), 2.22-2.32 (m, 1H), 1.75-1.92 (m, 1H) | B | Chiralcel OD-H, 15% IPA Peak 1 |
| 50 | 400 MHz d$_6$-DMSO | 8.94 (s, 1H), 8.90 (br s, 2H), 8.39 (dd, J = 1.62, 8.24 Hz, 1H), 7.76 (d, J = 8.17 Hz, 1H), 7.35-7.45 (m, 2H), 7.13 (t, J = 8.77 Hz, 1H), 5.68-5.84 (m, 2H), 4.87-5.07 (m, 1H), 4.07 (br d, J = 12.72 Hz, 1H), 3.60-3.73 (m, 1H), 3.36-3.53 (m, 2H), 3.25 (br t, J = 11.55 Hz, 1H), 2.23-2.32 (m, 1H), 1.78-1.91 (m, 1H) | B | Chiralcel OD-H, 15% IPA Peak 2 |
| 51 | 400 MHz d$_6$-DMSO | 8.94 (d, J = 1.45 Hz, 1H), 8.32 (dd, J = 2.18, 8.19 Hz, 1H), 7.72 (d, J = 0.93 Hz, 1H), 7.45-7.55 (m, 3H), 5.56 (s, 2H), 3.48 (br d, J = 11.71 Hz, 1H), 3.34-3.42 (m, 1H), 2.84-2.95 (m, 1H), 2.61-2.78 (m, 2H), 1.74-1.83 (m, 1H), 1.59-1.72 (m, 1H), 1.40-1.58 (m, 1H), 1.03-1.29 (m, 1H) | B | Chiralpak AD-H, 20% methanol Peak 1 |
| 52 | 400 MHz d$_6$-DMSO | 8.93 (d, J = 1.35 Hz, 1H), 8.32 (dd, J = 2.18, 8.19 Hz, 1H), 7.89 (d, J = 1.14 Hz, 1H), 7.47-7.54 (m, 1H), 7.42 (d, J = 1.45 Hz, 1H), 7.32 (d, J = 8.29 Hz, 1H), 5.57 (s, 2H), 3.38-3.50 (m, 1H), 3.29-3.37 (m, 1H), 2.87 (br s, 1H), 2.78 (br s, 1H), 2.66 (br dd, J = 9.07, 11.87 Hz, 1H), 1.74-1.85 (m, 1H), 1.62-1.74 (m, 1H), 1.43-1.57 (m, 1H), 1.11-1.31 (m, 1H) | B | Chiralpak AD-H, 20% methanol Peak 2 |
| 53 | 400 MHz d$_6$-DMSO | 8.93 (dd, J = 0.73, 2.07 Hz, 1H), 8.33 (dd, J = 2.07, 8.19 Hz, 1H), 7.74 (d, J = 0.93 Hz, 1H), 7.48-7.58 (m, 3H), 5.61 (s, 2H), 4.25-4.48 (m, 1H), 3.38-3.57 (m, 2H), 3.03-3.16 (m, 1H), 2.80-2.92 (m, 2H), 1.97-2.13 (m, 1H), 1.61-1.80 (m, 3H) | B | Chiralpak AD-H, 25% methanol Peak 1 |
| 54 | 400 MHz d$_6$-DMSO | 8.92 (s, 1H), 8.33 (dd, J = 2.12, 8.14 Hz, 1H), 7.91 (d, J = 1.14 Hz, 1H), 7.54 (d, J = 8.29 Hz, 1H), 7.45 (dd, J = 1.50, 8.24 Hz, 1H), 7.33 (d, J = 8.29 Hz, 1H), 5.61 (s, 2H), 4.25-4.48 (m, 1H), 3.36-3.52 (m, 3H), 3.07 (br s, 1H), 2.79-2.95 (m, 2H), 1.96-2.18 (m, 1H), 1.65-1.80 (m, 2H) | B | Chiralpak AD-H, 25% methanol Peak 2 |
| 55 | 400 MHz CDCl$_3$ | 8.88 (d, J = 1.35 Hz, 1H), 8.00 (dd, J = 2.13, 8.14 Hz, 1H), 7.64 (d, J = 8.19 Hz, 1H), 7.45-7.54 (m, 1H), 7.28 (d, J = 1.04 Hz, 1H), 7.21-7.26 (m, 1H), 5.36-5.47 (m, 2H), 3.43-3.63 (m, 3H), 3.14-3.33 (m, 2H), 2.27-2.40 (m, 1H), 2.10-2.24 (m, 1H), 1.75 (br s, 2H) | B | Chiralpak AD-H, 20% IPA Peak 1 |
| 56 | 400 MHz CDCl$_3$ | 8.89 (d, J = 1.35 Hz, 1H), 7.99 (dd, J = 2.07, 8.09 Hz, 1H), 7.92 (d, J = 0.93 Hz, 1H), 7.42 (dd, J = 1.45, 8.29 Hz, 1H), 7.20 (d, J = 8.19 Hz, 1H), 7.06 (d, J = 8.19 Hz, 1H), 5.40-5.54 (m, 2H), 3.40-3.62 (m, 3H), 3.17-3.35 (m, 2H), 2.29-2.42 (m, 1H), 2.01-2.26 (m, 1H), 1.95 (br s, 2H) | B | Chiralpak AD-H, 20% IPA Peak 2 |
| 57 | 400 MHz d$_6$-DMSO | 8.93 (s, 1H), 8.31 (br d, J = 8.19 Hz, 1H), 7.48 (d, J = 8.19 Hz, 1H), 7.35 (s, 1H), 7.24 (s, 1H), 5.53 (s, 2H), 3.39 (br d, J = 11.09 Hz, 2H), 3.29 (br d, J = 12.44 Hz, 2H), 2.84 (br t, J = 10.37 Hz, 1H), 2.57-2.78 (m, 2H), 1.77 (br dd, J = 3.89, 8.55 Hz, 1H), 1.65 (br dd, J = 4.20, 9.38 Hz, 1H), 1.40-1.61 (m, 1H), 1.05-1.21 (m, 1H) | — | — |
| 58 | 400 MHz d$_6$-DMSO | 8.93 (s, 1H), 8.32 (d, J = 8.19 Hz, 1H), 7.52 (d, J = 8.19 Hz, 1H), 7.36 (s, 1H), 7.26 (s, 1H), 5.58 (s, 2H), 4.24-4.47 (m, 1H), 3.34-3.52 (m, 3H), 2.98-3.10 (m, 1H), 2.78-2.95 (m, 2H), 2.05 (br t, J = 12.70 Hz, 1H), 1.84-1.99 (m, 1H), 1.64-1.83 (m, 1H) | — | — |
| 59 | 400 MHz d$_6$- | 8.93 (s, 1H), 8.32 (d, J = 8.29 Hz, 1H), 7.52 (d, J = 8.09 Hz, 1H), 7.35 (s, 1H), 7.26 (s, 1H), 5.57 (s, | — | — |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | $^1$HNMR Data (δ ppm) | Separation Stage | SFC Isomer Separation Conditions |
|---|---|---|---|---|
| | DMSO | 2H), 4.64-4.86 (m, 2H), 3.17-3.38 (m, 2H), 3.05-3.17 (m, 1H), 2.93-3.02 (m, 1H), 2.82-2.93 (m, 1H), 1.92-2.04 (m, 1H), 1.79 (br s, 1H) | | |
| 60 | 400 MHz d$_6$-DMSO | 8.89-8.96 (m, 1H), 8.33 (d, J = 7.79 Hz, 1H), 7.56 (d, J = 8.29 Hz, 1H), 7.32-7.40 (m, 1H), 7.28 (s, 1H), 5.54-5.66 (m, 2H), 3.34-3.46 (m, 2H), 3.15-3.26 (m, 1H), 2.96-3.14 (m, 2H), 2.16-2.31 (m, 1H), 1.87-2.08 (m, 2H), 1.78-1.87 (m, 1H) | — | — |
| 61 | 400 MHz d$_6$-DMSO | 8.94 (s, 1H), 8.31 (dd, J = 2.07, 8.19 Hz, 1H), 7.44 (d, J = 8.29 Hz, 1H), 7.02 (d, J = 8.78 Hz, 1H), 6.95 (t, J = 10.39 Hz, 1H), 5.50 (s, 2H), 3.33 (br d, J = 11.82 Hz, 2H), 3.23 (br d, J = 12.23 Hz, 2H), 2.66-2.87 (m, 2H), 2.54-2.63 (m, 1H), 1.73-1.90 (m, 1H), 1.60-1.72 (m, 1H), 1.41-1.58 (m, 1H), 1.16 (br s, 1H) | B | Regis Whelk-O s, s, 30% methanol Peak 2 |
| 62 | 400 MHz d$_6$-DMSO | 8.93 (s, 1H), 8.31 (dd, J = 1.97, 8.19 Hz, 1H), 7.48 (d, J = 8.29 Hz, 1H), 7.14 (dd, J = 1.92, 9.28 Hz, 1H), 6.85 (t, J = 10.74 Hz, 1H), 5.50 (s, 2H), 3.34-3.44 (m, 4H), 2.73-2.91 (m, 2H), 2.63 (dd, J = 9.07, 11.87 Hz, 1H), 1.74-1.86 (m, 1H), 1.62-1.74 (m, 1H), 1.43-1.60 (m, 1H), 1.11-1.28 (m, 1H) | B | Regis Whelk-O s, s, 30% methanol Peak 1 |
| 63 | 400 MHz d$_6$-DMSO | 8.93 (s, 1H), 8.32 (dd, J = 2, 02, 8.24 Hz, 1H), 7.50 (d, J = 8.19 Hz, 1H), 7.03 (d, J = 8.98 Hz, 1H), 6.98 (t, J = 10.69 Hz, 1H), 5.55 (s, 2H), 4.33-4.59 (m, 1H), 3.69-4.05 (m, 2H), 3.31-3.50 (m, 2H), 2.96-3.09 (m, 2H), 2.83 (dd, J = 9.02, 12.54 Hz, 1H), 2.02-2.12 (m, 1H), 1.67-1.79 (m, 1H) | B | Chiralcel OJ-H, 15% methanol Peak 2 |
| 64 | 400 MHz d$_6$-DMSO | 8.92 (s, 1H), 8.32 (dd, J = 1.76, 8.19 Hz, 1H), 7.52 (d, J = 8.29 Hz, 1H), 7.16 (dd, J = 1.92, 9.28 Hz, 1H), 6.87 (t, J = 10.73 Hz, 1H), 5.55 (s, 2H), 4.26-4.49 (m, 1H), 3.36-3.45 (m, 2H), 3.02-3.10 (m, 1H), 2.88-2.99 (m, 1H), 2.82 (dd, J = 8.60, 12.44 Hz, 1H), 1.92-2.15 (m, 1H), 1.66-1.86 (m, 3H) | B | Chiralcel OJ-H, 15% methanol Peak 1 |
| 65 | 400 MHz d$_6$-DMSO | 8.94 (s, 1H), 8.31 (dd, J = 1, 97, 8.19 Hz, 1H), 7.48 (d, J = 8.19 Hz, 1H), 7.02 (d, J = 8.08 Hz, 1H), 6.96 (t, J = 10.40 Hz, 1H), 5.49-5.58 (m, 2H), 4.63-4.83 (m, 1H), 3.04-3.26 (m, 3H), 2.84-2.97 (m, 2H), 1.75-2.01 (m, 2H), 1.65 (br s, 2H) | B | Phenomenex Lux Cellulose-2, 20% methanol Peak 2 |
| 66 | 400 MHz d$_6$-DMSO | 8.92 (s, 1H), 8.31 (dd, J = 1.87, 8.19 Hz, 1H), 7.51 (d, J = 8.19 Hz, 1H), 7.16 (dd, J = 1.92, 9.28 Hz, 1H), 6.86 (t, J = 10.73 Hz, 1H), 5.49-5.59 (m, 2H), 4.81 (br s, 1H), 3.10-3.29 (m, 3H), 2.90-3.02 (m, 2H), 1.81-2.03 (m, 2H), 1.63 (br s, 2H) | B | Phenomenex Lux Cellulose-2, 20% methanol Peak 1 |
| 67 | 400 MHz d$_6$-DMSO | 8.92 (s, 1H), 8.32 (dd, J = 1.97, 8.19 Hz, 1H), 7.55 (d, J = 8.19 Hz, 1H), 7.19 (dd, J = 1.81, 9.28 Hz, 1H), 6.89 (t, J = 10.66 Hz, 1H), 5.59 (s, 2H), 3.33-3.56 (m, 2H), 3.10-3.26 (m, 2H), 2.98-3.10 (m, 1H), 2.21-2.32 (m, 1H), 2.00-2.14 (m, 1H), 1.78 (br s, 2H) | B | Phenomenex Lux Cellulose-2, 20% methanol Peak 1 |
| 68 | 400 MHz d$_6$-DMSO | 8.93 (s, 1H), 8.33 (dd, J = 2.18, 8.19 Hz, 1H), 7.74 (d, J = 1.04 Hz, 1H), 7.48-7.58 (m, 3H), 5.61 (s, 2H), 4.25-4.47 (m, 1H), 3.38-3.57 (m, 2H), 3.04-3.17 (m, 1H), 2.80-2.92 (m, 2H), 1.99-2.12 (m, 1H), 1.60-1.79 (m, 3H) | B | Chiralpak AD-H, 25% methanol Peak 1 |
| 69 | 400 MHz d$_6$-DMSO | 8.92 (s, 1H), 8.33 (dd, J = 2.18, 8.19 Hz, 1H), 7.91 (d, J = 1.14 Hz, 1H), 7.54 (d, J = 8.19 Hz, 1H), 7.45 (dd, J = 1.45, 8.29 Hz, 1H), 7.33 (d, J = 8.29 Hz, 1H), 5.62 (s, 2H), 4.27-4.48 (m, 1H), 3.36-3.56 (m, 2H), 3.01-3.14 (m, 1H), 2.79-2.96 (m, 2H), 1.96-2.22 (m, 2H), 1.81-1.96 (m, 1H), 1.66-1.81 (m, 1H) | B | Chiralpak AD-H, 25% methanol Peak 2 |
| 70 | 400 MHz d$_6$-DMSO | 8.96 (d, J = 1.45 Hz, 1H), 8.28 (dd, J = 2.18, 8.19 Hz, 1H), 7.43 (d, J = 7.67 Hz, 1H), 7.32 (d, J = 8.29 Hz, 1H), 6.98-7.13 (m, 3H), 5.47 (s, 2H), 3.35 (br dd, J = 3.42, 11.71 Hz, 2H), 3.14-3.30 (m, 1H), 2.67-2.89 (m, 2H), 2.58 (dd, J = 9.02, 11.71 Hz, | — | — |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | $^1$HNMR Data (δ ppm) | Separation Stage | SFC Isomer Separation Conditions |
|---|---|---|---|---|
| | | 1H), 1.73-1.87 (m, 1H), 1.60-1.72 (m, 1H), 1.42-1.60 (m, 2H), 1.08-1.22 (m, 1H) | | |
| 71 | 400 MHz d$_6$-DMSO | 9.06 (br s, 3H), 8.88-9.00 (m, 1H), 8.37 (dd, J = 2.18, 8.19 Hz, 1H), 7.67 (d, J = 8.19 Hz, 1H), 7.38 (dd, J = 2.44, 9.17 Hz, 1H), 7.27 (dd, J = 4.56, 8.81 Hz, 1H), 7.05 (t, J = 9.27 Hz, 1H), 5.61-5.87 (m, 2H), 3.96-4.12 (m, 1H), 3.90 (br d, J = 12.85 Hz, 1H), 3.42-3.54 (m, 2H), 3.23-3.34 (m, 1H), 2.45-2.60 (m, 1H), 2.20-2.37 (m, 1H) | B | Chiralcel OD-H, 15% IPA Peak 2 |
| 72 | 400 MHz d$_6$-DMSO | 8.94 (d, J = 1.45 Hz, 1H), 8.31 (dd, J = 2.18, 8.19 Hz, 1H), 7.50 (t, J = 9.11 Hz, 1H), 7.45 (d, J = 8.50 Hz, 1H), 7.36 (dd, J = 7.36, 10.78 Hz, 1H), 5.52 (s, 2H), 4.23-4.46 (m, 1H), 3.22-3.45 (m, 3H), 2.81-3.05 (m, 2H), 2.76 (dd, J = 8.60, 12.44 Hz, 1H), 1.87-2.12 (m, 1H), 1.63-1.87 (m, 3H) | — | — |
| 73 | 400 MHz d$_6$-DMSO | 8.96 (dd, J = 0.73, 2.07 Hz, 1H), 8.29 (dd, J = 2.18, 8.19 Hz, 1H), 7.45 (d, J = 7.54 Hz, 1H), 7.37 (d, J = 8.29 Hz, 1H), 7.00-7.13 (m, 3H), 5.51 (s, 2H), 4.63-4.84 (m, 1H), 3.06-3.26 (m, 3H), 2.88-3.00 (m, 2H), 1.79-2.03 (m, 2H), 1.59 (br s, 2H) | — | — |
| 74 | 400 MHz d$_6$-DMSO | 8.90 (d, J = 1.45 Hz, 1H), 8.37-8.43 (m, 1H), 8.34 (br s, 2H), 7.85 (d, J = 8.19 Hz, 1H), 7.46-7.54 (m, 2H), 7.22-7.34 (m, 2H), 5.93 (s, 2H), 3.83-4.11 (m, 4H), 3.60-3.75 (m, 1H), 2.95-3.15 (m, 2H), 1.91 (td, J = 4.13, 8.22 Hz, 1H), 1.03 (dd, J = 5.29, 7.77 Hz, 1H), 0.52 (t, J = 4.87 Hz, 1H) | B | Chiralpak AD-H, 30% isopropanol Peak 1 |
| 75 | 400 MHz d$_6$-DMSO | 8.90 (d, J = 1.97 Hz, 1H), 8.39 (s, 1H), 8.34 (br s, 3H), 7.86 (d, J = 8.29 Hz, 1H), 7.47-7.53 (m, 2H), 7.22-7.34 (m, 2H), 5.93 (s, 2H), 4.04-4.13 (m, 1H), 3.83-4.02 (m, 3H), 3.63-3.73 (m, 1H), 2.95-3.20 (m, 2H), 1.91 (td, J = 4.09, 8.19 Hz, 1H), 0.98-1.07 (m, 1H), 0.52 (t, J = 4.87 Hz, 1H) | B | Chiralpak AD-H, 30% isopropanol Peak 2 |
| 76 | 400 MHz d$_6$-DMSO | 8.89-8.97 (m, 1H), 8.50 (br s, 2H), 8.41 (dd, J = 2.13, 8.24 Hz, 1H), 7.91 (d, J = 8.29 Hz, 1H), 7.49 (d, J = 8.71 Hz, 2H), 7.23-7.34 (m, 2H), 5.88-6.16 (m, 2H), 4.21 (br dd, J = 6.22, 10.88 Hz, 1H), 3.87 (br dd, J = 7.26, 10.26 Hz, 1H), 3.42-3.77 (m, 3H), 2.97-3.16 (m, 1H), 2.82-2.94 (m, 1H), 1.71-2.04 (m, 3H), 1.42-1.64 (m, 1H) | B | Phenomenex Lux Cellulose-2, 25% isopropanol w/0.2% DEA Peak 1 |
| 77 | 400 MHz d$_6$-DMSO | 8.92 (d, J = 1.45 Hz, 1H), 8.47 (br d, J = 1.35 Hz, 3H), 8.41 (dd, J = 2.07, 8.19 Hz, 1H), 7.89 (br d, J = 8.09 Hz, 1H), 7.49 (d, J = 8.09 Hz, 2H), 7.23-7.34 (m, 2H), 5.86-6.14 (m, 2H), 4.10-4.29 (m, 1H), 3.75-4.02 (m, 1H), 3.54-3.73 (m, 3H), 2.97-3.07 (m, 1H), 2.82-2.92 (m, 1H), 1.74-1.99 (m, 3H), 1.41-1.65 (m, 1H) | B | Phenomenex Lux Cellulose-2, 25% isopropanol w/0.2% DEA Peak 4 |
| 78 | 400 MHz d$_4$-methanol | 8.82 (s, 1H), 8.20-8.29 (m, 1H), 7.79 (d, J = 8.19 Hz, 1H), 7.28-7.50 (m, 4H), 5.90 (s, 2H), 3.92-4.12 (m, 3H), 3.69-3.76 (m, 1H), 3.55-3.63 (m, 1H), 3.02-3.17 (m, 1H), 2.89-2.96 (m, 2H), 2.28-2.38 (m, 1H), 2.18 (dtd, J = 5.34, 7.78, 13.31 Hz, 1H), 1.73-1.85 (m, 1H), 1.60-1.72 (m, 1H) | B | Phenomenex Lux Cellulose-2, 25% isopropanol w/0.2% DEA Peak 2 |
| 79 | 400 MHz d$_4$-methanol | 8.82 (d, J = 1.45 Hz, 1H), 8.26 (dd, J = 2.07, 8.19 Hz, 1H), 7.78 (d, J = 8.09 Hz, 1H), 7.29-7.50 (m, 4H), 5.85-5.93 (m, 2H), 4.05-4.12 (m, 1H), 3.91-4.01 (m, 2H), 3.55-3.77 (m, 2H), 3.01-3.18 (m, 1H), 2.92 (ddt, J = 4.28, 4.51, 8.41 Hz, 1H), 2.28-2.37 (m, 1H), 2.13-2.23 (m, 1H), 1.74-1.85 (m, 1H), 1.58-1.71 (m, 1H), 1.43 (s, 1H) | B | Phenomenex Lux Cellulose-2, 25% isopropanol w/0.2% DEA Peak 3 |
| 80 | 400 MHz d$_6$-DMSO | 8.91 (d, J = 1.45 Hz, 1H), 8.40 (dd, J = 2.18, 8.19 Hz, 1H), 8.28 (br s, 3H), 7.82 (d, J = 8.09 Hz, 1H), 7.48 (dd, J = 3.21, 7.77 Hz, 2H), 7.28-7.33 (m, 1H), 7.25 (d, J = 7.37 Hz, 1H), 5.94 (d, J = 3.73 Hz, 2H), 3.87-3.94 (m, 1H), 3.64-3.86 (m, 3H), 2.88 (br t, J = 6.27 Hz, 2H), 2.61-2.70 (m, 1H), 2.16 (br d, J = 6.22 Hz, 1H), 1.82-1.91 (m, 1H) | B | Chiralpak IC, 40% isopropanol w/0.2% DEA Peak 1 |

TABLE 3-continued

Characterization data for compounds made following Scheme 8.
The column "Separation Stage" indicates after which process step
regioisomers formed due to asymmetric benzimidazole substitution at R[1]
in Scheme 8 were separated during the preparation of the tabulated final
compound (I = after preparation of the alkylated intermediate 1-59
(where at least one R[1] is not hydrogen); B prior to boc
deprotection; or F = final compound).

| Ex. #. | Freq., Solvent | $^1$HNMR Data (δ ppm) | Separation Stage | SFC Isomer Separation Conditions |
|---|---|---|---|---|
| 81 | 400 MHz d$_6$-DMSO | 8.91 (d, J = 1.45 Hz, 1H), 8.36-8.43 (m, 1H), 8.33 (br s, 2H), 7.82 (d, J = 8.19 Hz, 1H), 7.49 (dd, J = 3.84, 7.67 Hz, 2H), 7.21-7.36 (m, 2H), 5.89-5.97 (m, 2H), 3.65-3.93 (m, 5H), 3.47-3.51 (m, 1H), 2.79-2.96 (m, 2H), 2.61-2.72 (m, 1H), 2.12-2.21 (m, 1H), 1.82-1.92 (m, 1H) | B | Chiralpak IC, 40% isopropanol w/0.2% DEA Peak 2 |
| 82 | 500 MHz DMSO-d$_6$ | 8.92 (s, 1H), 8.54 (br s, 2H), 8.33 (br d, J = 7.79 Hz, 1H), 7.72 (s, 1H), 7.57 (br s, 2H), 5.62 (q, J = 17.82 Hz, 2H), 5.01-5.20 (m, 1H), 3.59-3.63 (m, 1H), 3.20-3.31 (m, 2H), 3.08 (br t, J = 10.96 Hz, 1H), 2.08 (br s, 1H), 1.86-2.03 (m, 1H) | B | — |
| 83 | 400 MHz DMSO-d$_6$ | 8.93 (s, 1H), 8.40 (br s, 2H), 8.33 (dd, J = 1.66, 8.09 Hz, 1H), 7.48-7.57 (m, 2H), 7.38 (dd, J = 7.46, 10.26 Hz, 1H), 5.50-5.63 (m, 2H), 5.00-5.20 (m, 1H), 3.50 (br s, 1H), 3.24-3.33 (m, 1H), 3.15-3.23 (m, 1H), 3.02-3.14 (m, 1H), 1.87-2.12 (m, 2H) | B | — |
| 84 | 400 MHz DMSO-d$_6$ | 8.90-8.97 (m, 1H), 8.86 (br s, 2H), 8.34 (br d, J = 8.29 Hz, 1H), 7.53-7.63 (m, 2H), 7.40 (dd, J = 7.31, 10.52 Hz, 1H), 5.54-5.73 (m, 2H), 3.92-4.21 (m, 2H), 3.65-3.78 (m, 2H), 3.33 (br d, J = 7.05 Hz, 1H), 3.09-3.21 (m, 1H), 2.15-2.32 (m, 1H) | B | — |
| 85 | 500 MHz, DMSO-d$_6$ | 8.86-8.99 (m, 2H), 8.56 (d, J = 2.21 Hz, 1H), 7.99 (br d, J = 8.04 Hz, 1H), 7.47-7.59 (m, 2H), 7.25 (br s, 2H), 7.15-7.23 (m, 1H), 5.50-5.67 (m, 2H), 4.06-4.14 (m, 1H), 3.78-3.95 (m, 3H), 3.25-3.39 (m, 1H), 2.25-2.35 (m, 1H) | B | — |
| 86 | 500 MHz, DMSO-d$_6$ | 8.55 (d, J = 2.21 Hz, 1H), 8.47 (br s, 2H), 7.96 (dd, J = 2.34, 8.43 Hz, 1H), 7.50 (d, J = 7.78 Hz, 1H), 7.40 (br d, J = 7.40 Hz, 1H), 7.09-7.22 (m, 3H), 5.43-5.58 (m, 2H), 5.04-5.22 (m, 1H), 3.72-3.84 (m, 2H), 3.62-3.69 (m, 2H), 3.36-3.43 (m, 2H), 3.19-3.28 (m, 1H), 2.04-2.16 (m, 1H) | B | — |
| 87 | 500 MHz, DMSO-d$_6$ | 8.93 (d, J = 1.95 Hz, 1H), 8.81 (br s, 2H), 8.34 (dd, J = 2.08, 8.17 Hz, 1H), 7.59 (d, J = 8.17 Hz, 1H), 6.98-7.06 (m, 2H), 5.56-5.75 (m, 2H), 4.00 (dt, J = 3.63, 5.51 Hz, 1H), 3.73 (br d, J = 12.33 Hz, 1H), 3.38 (br d, J = 12.33 Hz, 1H), 3.27-3.34 (m, 1H), 3.10-3.19 (m, 1H), 2.37-2.44 (m, 1H), 2.16-2.33 (m, 1H) | B | — |
| 88 | 500 MHz d$_4$-MeOH | 8.84 (d, J = 1.82 Hz, 1H), 8.15 (dd, J = 2.08, 8.30 Hz, 1H), 7.40-7.52 (m, 2H), 6.91-7.00 (m, 2H), 5.47-5.62 (m, 2H), 3.34-3.54 (m, 2H), 3.08-3.28 (m, 3H), 2.21-2.36 (m, 1H), 2.00-2.21 (m, 1H) | I | YMC Amyose SA, Methanol THF (70:30) 40%; peak 1 |
| 89 | 500 MHz d$_6$-DMSO | 8.94 (d, J = 1.56 Hz, 1H), 8.33 (dd, J = 1.95, 8.17 Hz, 1H), 7.57 (d, J = 8.56 Hz, 1H), 7.43 (t, J = 7.27 Hz, 2H), 7.18 (t, J = 7.91 Hz, 1H), 5.58-5.69 (m, 2H), 3.34-3.28 (m, 3H), 3.02-3.13 (m, 2H), 2.18-2.33 (m, 1H), 1.97-2.13 (m, 1H) | — | — |
| 90 | 600 MHz d$_6$-DMSO | 8.95 (d, J = 1.56 Hz, 1H), 8.34 (dd, J = 2.02, 8.25 Hz, 1H), 7.54 (d, J = 8.10 Hz, 1H), 7.44 (d, J = 8.10 Hz, 1H), 7.41 (d, J = 7.79 Hz, 1H), 7.16 (t, J = 7.94 Hz, 1H), 5.54-5.67 (m, 2H), 4.26-4.45 (m, 1H), 3.38-3.50 (m, 2H), 3.01-3.10 (m, 1H), 2.79-2.92 (m, 2H), 2.00-2.13 (m, 1H), 1.66-1.80 (m, 1H) | — | — |
| 91 | 600 MHz d$_6$-DMSO | 8.95 (d, J = 1.25 Hz, 1H), 8.33 (dd, J = 2.02, 8.25 Hz, 1H), 7.53 (d, J = 8.41 Hz, 1H), 7.43 (d, J = 8.10 Hz, 1H), 7.40 (d, J = 7.79 Hz, 1H), 7.16 (t, J = 7.79 Hz, 1H), 5.54-5.66 (m, 2H), 4.66-4.84 (m, 1H), 3.30 (br d, J = 3.74 Hz, 1H), 3.25 (td, J = 4.05, 12.77 Hz, 1H), 3.08-3.16 (m, 1H), 2.97-3.05 (m, 1H), 2.83-2.95 (m, 1H), 1.95-2.02 (m, 1H), 1.78-1.94 (m, 1H) | — | — |
| 92 | 500 MHz d$_4$-MeOH | 8.79 (d, J = 1.30 Hz, 1H), 8.15 (dd, J = 2.08, 8.04 Hz, 1H), 8.05 (d, J = 1.82 Hz, 1H), 7.77 (d, J = 2.08 Hz, 1H), 7.54 (d, J = 8.04 Hz, 1H), 5.52-5.64 (m, 2H), 4.30-4.48 (m, 1H), 3.68-3.75 (m, 1H), 3.58- | B | Separated by flash chromatography |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
| | | 3.67 (m, 1H), 3.14-3.23 (m, 1H), 2.94-3.06 (m, 2H), 2.08-2.19 (m, 1H), 1.75-1.87 (m, 1H) | | |
| 93 | 500 MHz $d_4$-MeOH | 8.83 (d, J = 1.30 Hz, 1H), 8.17-8.22 (m, 2H), 7.66 (d, J = 2.34 Hz, 1H), 7.54 (d, J = 8.30 Hz, 1H), 5.54 (s, 2H), 4.32-4.50 (m, 1H), 3.64-3.75 (m, 1H), 3.52-3.64 (m, 1H), 3.15-3.27 (m, 1H), 3.02-3.10 (m, 1H), 2.99 (dd, J = 8.56, 12.20 Hz, 1H), 2.06-2.23 (m, 1H), 1.78-1.92 (m, 1H) | B | Separated by flash chromatography |
| 94 | 500 MHz $d_4$-MeOH | 8.80 (d, J = 1.82 Hz, 1H), 8.19 (d, J = 2.34 Hz, 1H), 8.12 (dd, J = 2.34, 8.04 Hz, 1H), 7.62 (d, J = 2.08 Hz, 1H), 7.41 (d, J = 8.04 Hz, 1H), 5.49 (s, 2H), 4.34-4.50 (m, 1H), 3.70-3.77 (m, 1H), 3.58-3.66 (m, 1H), 3.21 (ddd, J = 2.47, 10.19, 13.04 Hz, 1H), 3.06-3.15 (m, 1H), 2.99-3.05 (m, 1H), 2.10-2.20 (m, 1H), 1.82-1.92 (m, 1H), 1.43 (s, 9H) | B | Separated by flash chromatography |
| 95 | 500 MHz $d_4$-MeOH | 8.86 (d, J = 1.30 Hz, 1H), 8.13 (dd, J = 2.08, 8.30 Hz, 1H), 7.51 (d, J = 7.79 Hz, 1H), 7.31 (d, J = 8.30 Hz, 1H), 7.16-7.22 (m, 1H), 7.09-7.16 (m, 2H), 5.51 (s, 2H), 3.57-3.63 (m, 1H), 3.37-3.51 (m, 2H), 3.01-3.10 (m, 1H), 2.76-2.92 (m, 2H), 1.95-2.03 (m, 1H), 1.57-1.72 (m, 1H) | — | — |
| 96 | 500 MHz $d_4$-MeOH | 8.85 (d, J = 1.56 Hz, 1H), 8.13 (dd, J = 2.08, 8.30 Hz, 1H), 7.51 (d, J = 8.04 Hz, 1H), 7.31 (d, J = 8.56 Hz, 1H), 7.16-7.21 (m, 1H), 7.09-7.15 (m, 2H), 5.51 (s, 2H), 3.56-3.64 (m, 1H), 3.37-3.51 (m, 2H), 3.06 (dt, J = 2.60, 12.07 Hz, 1H), 2.78-2.92 (m, 2H), 1.99 (br dd, J = 2.85, 13.23 Hz, 1H), 1.60-1.71 (m, 1H) | — | — |
| 97 | 500 MHz $d_4$-MeOH | 8.86 (s, 1H), 8.08 (dd, J = 2.08, 8.30 Hz, 1H), 7.37 (d, J = 7.79 Hz, 1H), 7.23 (d, J = 8.04 Hz, 1H), 7.07-7.13 (m, 2H), 7.01 (t, J = 7.53 Hz, 1H), 5.55 (s, 2H), 3.68 (s, 2H), 3.49-3.61 (m, 6H), 2.15 (t, J = 6.88 Hz, 2H) | — | — |
| 98 | 500 MHz $d_4$-MeOH | 8.83 (d, J = 1.30 Hz, 1H), 8.26 (dd, J = 2.08, 8.04 Hz, 1H), 7.80 (d, J = 8.30 Hz, 1H), 7.51 (d, J = 8.04 Hz, 1H), 7.33-7.47 (m, 3H), 5.95 (d, J = 19.72 Hz, 1H), 5.80 (br d, J = 18.68 Hz, 1H), 4.17-4.37 (m, 3H), 3.97-4.10 (m, 2H), 3.80 (br t, J = 8.95 Hz, 1H), 3.68-3.76 (m, 1H), 3.55 (dd, J = 1.95, 13.36 Hz, 1H), 3.32-3.46 (m, 2H) | B | Chiralcel OD-H, 25% MeOH Peak 1 |
| 99 | 500 MHz $d_4$-MeOH | 8.83 (s, 1H), 8.27 (dd, J = 1.82, 8.30 Hz, 1H), 7.80 (d, J = 8.56 Hz, 1H), 7.51 (d, J = 8.04 Hz, 1H), 7.38-7.47 (m, 2H), 7.35 (br d, J = 8.04 Hz, 1H), 5.94 (d, J = 18.68 Hz, 1H), 5.80 (br d, J = 18.68 Hz, 1H), 4.18-4.36 (m, 3H), 3.95-4.06 (m, 2H), 3.80 (br t, J = 8.30 Hz, 1H), 3.67-3.76 (m, 1H), 3.50-3.59 (m, 1H), 3.33-3.47 (m, 2H) | B | Chiralcel OD-H, 25% MeOH Peak 2 |
| 100 | 500 MHz $d_4$-MeOH | 8.87 (d, J = 1.30 Hz, 1H), 8.11 (dd, J = 2.08, 8.04 Hz, 1H), 7.38 (d, J = 7.79 Hz, 1H), 7.28 (d, J = 8.30 Hz, 1H), 7.07-7.16 (m, 2H), 6.99-7.06 (m, 1H), 5.63 (d, J = 18.42 Hz, 1H), 5.48 (d, J = 18.42 Hz, 1H), 3.93 (dd, J = 2.72, 11.81 Hz, 1H), 3.64-3.75 (m, 3H), 3.48-3.63 (m, 2H), 3.43 (dd, J = 8.95, 10.77 Hz, 1H), 2.84-3.00 (m, 3H) | B | Chiralcel OD-H, 20% MeOH Peak 1 |
| 101 | 500 MHz $d_4$-MeOH | 8.87 (d, J = 1.56 Hz, 1H), 8.11 (dd, J = 2.08, 8.30 Hz, 1H), 7.38 (d, J = 8.04 Hz, 1H), 7.28 (d, J = 8.30 Hz, 1H), 7.07-7.16 (m, 2H), 6.99-7.06 (m, 1H), 5.63 (d, J = 18.42 Hz, 1H), 5.48 (d, J = 18.68 Hz, 1H), 3.93 (dd, J = 2.60, 11.94 Hz, 1H), 3.64-3.74 (m, 3H), 3.47-3.62 (m, 2H), 3.43 (dd, J = 8.95, 10.77 Hz, 1H), 2.85-2.99 (m, 3H) | B | Chiralcel OD-H, 20% MeOH Peak 2 |
| 102 | 500 MHz $d_4$-MeOH | 8.79-8.88 (m, 1H), 8.12 (dd, J = 2.21, 8.17 Hz, 1H), 7.50 (d, J = 7.79 Hz, 1H), 7.38 (d, J = 8.30 Hz, 1H), 7.06-7.21 (m, 3H), 5.48-5.65 (m, 2H), 3.46 (d, J = 11.94 Hz, 1H), 3.35-3.42 (m, 1H), 3.17-3.23 (m, 1H), 3.03-3.12 (m, 1H), 2.12 (ddd, J = 4.41, 11.35, 13.30 Hz, 1H), 1.89-2.01 (m, 1H), 1.70-1.80 (m, 1H), 1.59-1.68 (m, 1H) | F | Chiralpak AD-H, 60% MeOH w/ 0.2% DEA Peak 1 |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | $^1$HNMR Data (δ ppm) | Separation Stage | SFC Isomer Separation Conditions |
|---|---|---|---|---|
| 103 | 500 MHz d$_4$-MeOH | 8.85 (d, J = 1.56 Hz, 1H), 8.13 (dd, J = 2.08, 8.30 Hz, 1H), 7.51 (d, J = 7.79 Hz, 1H), 7.39 (d, J = 8.04 Hz, 1H), 7.08-7.22 (m, 3H), 5.51-5.66 (m, 2H), 3.47 (d, J = 12.20 Hz, 1H), 3.37-3.43 (m, 1H), 3.21 (br d, J = 12.20 Hz, 1H), 3.04-3.11 (m, 1H), 2.07-2.18 (m, 1H), 1.90-2.01 (m, 1H), 1.72-1.81 (m, 1H), 1.58-1.70 (m, 1H) | F | Chiralpak AD-H, 60% MeOH w/ 0.2% DEA Peak 2 |
| 104 | 500 MHz d$_4$-MeOH | 8.86 (d, J = 1.56 Hz, 1H), 8.12 (dd, J = 2.08, 8.30 Hz, 1H), 7.51 (d, J = 7.78 Hz, 1H), 7.32 (d, J = 8.30 Hz, 1H), 7.06-7.23 (m, 3H), 5.48-5.62 (m, 2H), 3.54 (d, J = 10.90 Hz, 1H), 3.37 (d, J = 10.90 Hz, 1H), 3.24-3.28 (m, 1H), 3.08-3.22 (m, 2H), 3.04 (br d, J = 11.94 Hz, 1H), 1.79-1.90 (m, 1H), 1.66-1.77 (m, 1H), 1.61 (ddd, J = 4.28, 9.02. 13.43 Hz, 1H), 1.44-1.54 (m, 1H) | B | Chiralcel OD-H, 25% iPrOH w/ 0.2% DEA Peak 1 |
| 105 | 500 MHz d$_4$-MeOH | 8.86 (d, J = 1.30 Hz, 1H), 8.12 (dd, J = 2.08, 8.04 Hz, 1H), 7.51 (d, J = 7.78 Hz, 1H), 7.33 (d, J = 8.04 Hz, 1H), 7.07-7.22 (m, 3H), 5.51-5.62 (m, 2H), 3.54 (d, J = 11.16 Hz, 1H), 3.37 (d, J = 11.16 Hz, 1H), 3.24-3.28 (m, 1H), 3.09-3.22 (m, 2H), 3.01-3.08 (m, 1H), 1.79-1.90 (m, 1H), 1.67-1.77 (m, 1H), 1.62 (ddd, J = 4.41, 9.02, 13.56 Hz, 1H), 1.46-1.56 (m, 1H) | B | Chiralcel OD-H, 25% iPrOH w/ 0.2% DEA Peak 2 |
| 106 | 600 MHz DMSO-d$_6$ | 8.94 (d, J = 1.48 Hz, 1H), 8.33 (dd, J = 2.10, 8.17 Hz, 1H), 7.58-7.63 (m, 2H), 7.51 (d, J = 8.25 Hz, 1H), 7.42 (d, J = 8.21 Hz, 1H), 5.61-5.68 (m, 2H), 4.75-4.83 (m, 1H), 4.68-4.73 (m, 1H), 3.28-3.32 (m, 3H), 3.24 (td, J = 4.03, 12.81 Hz, 1H), 3.05-3.19 (m, 2H), 2.86-3.04 (m, 3H), 2.57-2.65 (m, 1H), 2.33-2.48 (m, 1H), 1.92-2.01 (m, 1H), 1.77-1.91 (m, 1H) | B | SFC: Chiralcel OD-H, 15% methanol. |
| 107 | 600 MHz DMSO-d$_6$ | 9.00 (d, J = 1.32 Hz, 1H), 8.39 (dd, J = 2.10, 8.25 Hz, 1H), 7.84 (s, 1H), 7.58 (d, J = 8.17 Hz, 1H), 7.37-7.45 (m, 2H), 5.63-5.72 (m, 2H), 4.83-4.90 (m, 1H), 4.76-4.81 (m, 1H), 3.33-3.37 (m, 2H), 3.30 (td, J = 3.99, 12.65 Hz, 1H), 3.13-3.25 (m, 2H), 2.95-3.11 (m, 2H), 2.01-2.09 (m, 1H), 1.87-2.00 (m, 1H) | B | SFC: Chiralcel OD-H, 15% methanol. |
| 108 | 600 MHz DMSO-d$_6$ | 8.94 (d, J = 1.40 Hz, 1H), 8.34 (dd, J = 2.14, 8.21 Hz, 1H), 7.62 (s, 1H), 7.63 (d, J = 6.89 Hz, 1H), 7.56 (d, J = 8.17 Hz, 1H), 7.44 (d, J = 8.47 Hz, 1H), 5.65-5.73 (m, 2H), 3.18-3.26 (m, 1H), 2.98-3.12 (m, 2H), 2.17-2.29 (m, 1H), 1.89-2.07 (m, 1H), 1.79 (br s, 2H) | B | SFC: Chiralcel OD-H, 15% methanol. |
| 109 | 600 MHz DMSO-d$_6$ | 8.94 (dd, J = 0.66, 2.06 Hz, 1H), 8.34 (dd, J = 2.14, 8.21 Hz, 1H), 7.80 (s, 1H), 7.56 (d, J = 8.17 Hz, 1H), 7.38 (dd, J = 1.21, 8.45 Hz, 1H), 7.33 (d, J = 8.41 Hz, 1H), 5.58-5.69 (m, 2H), 3.37-3.44 (m, 1H), 3.20-3.30 (m, 1H), 3.07-3.18 (m, 1H), 2.99-3.06 (m, 1H), 2.21-2.31 (m, 1H), 1.96-2.11 (m, 2H), 1.92 (br s, 1H) | B | SFC: Chiralcel OD-H, 15% methanol. |
| 110 | 600 MHz DMSO-d$_6$ | 8.94 (d, J = 1.48 Hz, 1H), 8.49 (br s, 3H), 8.36 (dd, J = 2.06, 8.21 Hz, 1H), 7.55 (br d, J = 8.10 Hz, 1H), 7.33 (s, 1H), 7.10 (d, J = 8.25 Hz, 1H), 6.99 (br d, J = 8.17 Hz, 1H), 5.55-5.63 (m, 2H), 4.69-4.81 (m, 1H), 4.24-4.38 (m, 1H), 3.81 (br d, J = 12.38 Hz, 1H), 3.61 (br s, 1H), 3.54 (br d, J = 12.69 Hz, 1H), 3.10-3.21 (m, 2H), 2.51-2.54 (m, 9H), 2.37 (s, 3H), 2.21 (br t, J = 9.81 Hz, 1H), 1.82-1.90 (m, 1H) | B | SFC: Phenomenex Lux Cellulose-2, 25% methanol. |
| 111 | 600 MHz DMSO-d$_6$ | 8.40 (br s, 1H), 8.27 (dd, J = 2.06, 8.21 Hz, 1H), 7.47 (br d, J = 8.17 Hz, 1H), 6.94-6.98 (m, 1H), 5.44-5.54 (m, 1H), 4.76 (dt, J = 4.94, 9.17 Hz, 1H), 3.90-4.72 (m, 3H), 3.69 (br d, J = 12.61 Hz, 1H), 3.52 (br s, 1H), 3.42 (br d, J = 12.38 Hz, 1H), 2.98-3.12 (m, 1H), 2.42-2.52 (m, 5H), 2.23 (s, 2H), 2.11 (br t, J = 9.81 Hz, 1H), 1.72-1.81 (m, 1H) | B | SFC: Phenomenex Lux Cellulose-2, 25% methanol. |
| 112 | 600 MHz DMSO- | 8.95 (dd, J = 0.70, 2.02 Hz, 1H), 8.31 (dd, J = 2.14, 8.21 Hz, 1H), 7.41 (s, 1H), 7.41 (d, J = 6.67 Hz, | B | SFC: Phenomenex |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
| | d₆ | 1H), 7.29 (s, 1H), 5.43-5.54 (m, 2H), 4.34-4.43 (m, 1H), 4.26-4.34 (m, 1H), 3.25-3.38 (m, 11H), 2.96-3.05 (m, 1H), 2.85-2.91 (m, 1H), 2.76 (dd, J = 8.60, 12.50 Hz, 1H), 2.34 (s, 3H), 1.94-2.08 (m, 2H), 1.65-1.83 (m, 1H) | | Lux Cellulose-2, 20% methanol |
| 113 | 600 MHz DMSO-d₆ | 8.96 (s, 1H), 8.31 (dd, J = 2.14, 8.21 Hz, 1H), 7.38-7.53 (m, 2H), 7.15 (s, 1H), 5.38-5.53 (m, 2H), 4.25-4.43 (m, 1H), 3.38-3.40 (m, 1H), 3.29-3.34 (m, 1H), 2.97-3.05 (m, 1H), 2.84-2.92 (m, 1H), 2.76 (dd, J = 8.56, 12.53 Hz, 1H), 2.30 (s, 3H), 1.98-2.09 (m, 1H), 1.63-1.80 (m, 3H) | B | SFC: Phenomenex Lux Cellulose-2, 20% methanol |
| 114 | 600 MHz DMSO-d₆ | 8.95 (s, 1H), 8.30 (dd, J = 2.14, 8.21 Hz, 1H), 7.37 (d, J = 8.33 Hz, 1H), 7.31 (d, J = 6.93 Hz, 1H), 7.03 (d, J = 9.89 Hz, 1H), 5.44-5.52 (m, 2H), 4.35-4.41 (m, 1H), 4.26-4.34 (m, 1H), 3.19-3.33 (m, 1H), 2.93-3.02 (m, 1H), 2.78-2.93 (m, 1H), 2.74 (dd, J = 8.64, 12.46 Hz, 1H), 2.25 (d, J = 1.48 Hz, 3H), 2.10-2.23 (m, 1H), 1.95-2.09 (m, 2H), 1.66-1.83 (m, 1H) | B | SFC: Phenomenex Lux Cellulose-2, 20% methanol. |
| 115 | 600 MHz DMSO-d₆ | 8.92-8.98 (m, 1H), 8.30 (d, J = 7.92 Hz, 1H), 7.31-7.44 (m, 2H), 7.22 (d, J = 10.43 Hz, 1H), 7.03 (d, J = 7.01 Hz, 1H), 5.36-5.51 (m, 2H), 4.35-4.41 (m, 1H), 4.26-4.34 (m, 1H), 3.26-3.44 (m, 1H), 2.85-3.02 (m, 1H), 2.69-2.81 (m, 2H), 2.23-2.27 (m, 1H), 2.21 (d, J = 1.56 Hz, 3H), 1.92-2.08 (m, 1H), 1.60-1.92 (m, 1H) | B | SFC: Phenomenex Lux Cellulose-2, 20% methanol. |
| 116 | 600 MHz DMSO-d₆ | 8.98 (d, J = 1.63 Hz, 1H), 8.31 (dd, J = 2.14, 8.21 Hz, 1H), 7.44 (d, J = 7.63 Hz, 1H), 7.38 (d, J = 8.25 Hz, 1H), 7.07-7.15 (m, 2H), 6.94-7.04 (m, 1H), 5.44-5.50 (m, 2H), 3.38-3.48 (m, 1H), 3.23-3.32 (m, 1H), 2.82-2.91 (m, 1H), 2.52-2.62 (m, 1H), 2.43-2.49 (m, 1H), 2.11 (s, 3H), 1.80-1.88 (m, 1H), 1.68 (td, J = 3.67, 13.14 Hz, 1H), 1.50-1.61 (m, 1H), 1.11-1.23 (m, 1H) | B | — |
| 117 | 600 MHz DMSO-d₆ | 8.96 (s, 1H), 8.34 (dd, J = 2.14, 8.21 Hz, 1H), 7.52 (d, J = 7.98 Hz, 2H), 7.27 (s, 1H), 7.15-7.20 (m, 1H), 7.12 (d, J = 7.93 Hz, 1H), 7.10 (s, 1H), 5.62 (d, J = 17.75 Hz, 1H), 5.55 (d, J = 17.75 Hz, 1H), 3.68 (br d, J = 11.83 Hz, 1H), 3.34 (br s, 1H), 3.19-3.28 (m, 2H), 3.01 (br t, J = 9.42 Hz, 1H), 2.51-2.61 (m, 3H), 1.98-2.06 (m, 1H), 1.83 (dt, J = 2.88, 6.50 Hz, 1H), 1.53-1.67 (m, 2H) | — | — |
| 118 | 600 MHz DMSO-d₆ | 8.94 (s, 1H), 8.33 (dd, J = 2.14, 8.21 Hz, 1H), 7.47 (dd, J = 2.18, 8.33 Hz, 2H), 7.05-7.09 (m, 2H), 6.95 (d, J = 8.98 Hz, 1H), 5.51-5.58 (m, 2H), 4.47-4.56 (dt, J = 4.59, 8.68 Hz, 1H), 3.43-3.57 (m, 1H), 3.37-3.43 (m, 1H), 3.10-3.23 (m, 1H), 2.96-3.03 (m, 1H), 2.87 (dd, J = 9.26, 12.61 Hz, 1H), 2.05-2.12 (m, 1H), 1.70-1.79 (m, 1H) | B | SFC: Chiralcel OD-H, 15% methanol. |
| 119 | 600 MHz DMSO-d₆ | 8.95 (s, 1H), 8.32 (dd, J = 2.14, 8.21 Hz, 1H), 7.45 (d, J = 8.33 Hz, 1H), 7.22-7.30 (m, 1H), 7.10-7.18 (m, 1H), 6.87 (dd, J = 2.34, 8.56 Hz, 1H), 5.50-5.57 (m, 2H), 4.43 (dt, J = 4.59, 8.25 Hz, 1H), 3.40-3.49 (m, 1H), 3.37-3.40 (m, 1H), 2.91-3.07 (m, 1H), 2.81 (dd, J = 8.80, 12.53 Hz, 1H), 2.57-2.65 (m, 1H), 2.01-2.11 (m, 1H), 1.68-1.78 (m, 1H) | B | SFC: Chiralcel OD-H, 15% methanol. |
| 120 | 600 MHz DMSO-d₆ | 8.95 (d, J = 1.95 Hz, 1H), 8.29 (dd, J = 2.10, 8.25 Hz, 1H), 7.33 (d, J = 8.25 Hz, 1H), 6.96 (t, J = 8.02 Hz, 1H), 6.73 (d, J = 8.02 Hz, 1H), 6.67 (d, J = 8.08 Hz, 1H), 5.44-5.53 (m, 2H), 4.28-4.34 (m, 1H), 3.89 (s, 3H), 3.24-3.42 (m, 1H), 2.85-3.01 (m, 2H), 2.75 (dd, J = 8.64, 12.46 Hz, 1H), 1.98-2.16 (m, 1H), 1.95 (br s, 1H), 1.69-1.86 (m, 1H) | — | — |
| 121 | 600 MHz DMSO-d₆ | 8.94 (s, 1H), 8.30 (dd, J = 1.95, 8.17 Hz, 1H), 7.43 (d, J = 8.25 Hz, 1H), 6.91-7.03 (m, 3H), 5.48-5.57 (m, 2H), 4.86-4.78(m, 1H), 3.64-3.78 (m, 1H), 3.48-3.63 (m, 1H), 3.06-3.17 (m, 1H), 2.99 (br t, J = 11.44 Hz, 1H), 2.46-2.49 (m, 1H), 2.14-2.23 (m, 1H), 1.82-1.91 (m, 1H) | — | — |

TABLE 3-continued

Characterization data for compounds made following Scheme 8.
The column "Separation Stage" indicates after which process step
regioisomers formed due to asymmetric benzimidazole substitution at R¹
in Scheme 8 were separated during the preparation of the tabulated final
compound (I = after preparation of the alkylated intermediate 1-59
(where at least one R¹ is not hydrogen); B prior to boc
deprotection; or F = final compound).

| Ex. #. | Freq., Solvent | ¹HNMR Data (δ ppm) | Separation Stage | SFC Isomer Separation Conditions |
|---|---|---|---|---|
| 122 | 600 MHz DMSO-d₆ | 9.03 (d, J = 1.40 Hz, 1H), 8.71-8.78 (m, 1H), 8.28 (br s, 1H), 7.86 (br s, 1H), 7.67 (s, 1H), 7.60 (d, J = 8.33 Hz, 1H), 7.42 (d, J = 8.47 Hz, 1H), 5.64-5.77 (m, 2H), 4.75-71 (m, 1H), 3.30-3.31 (m, 2H), 3.07-3.17 (m, 1H), 2.86-3.02 (m, 1H), 2.28-2.45 (m, 1H), 1.93-2.12 (m, 1H), 1.78-1.93 (m, 1H) | B | SFC: Chiralpak AD-H, 25% methanol |
| 123 | 600 MHz DMSO-d₆ | 9.03 (d, J = 1.32 Hz, 1H), 8.75 (d, J = 1.32 Hz, 1H), 8.27 (s, 1H), 7.86 (br s, 1H), 7.77 (s, 1H), 7.34-7.41 (m, 2H), 5.68 (d, J = 1.79 Hz, 2H), 4.77-4.72 (m, 1H), 3.22-3.32 (m, 1H), 3.09-3.20 (m, 1H), 2.89-3.04 (m, 2H), 1.95-2.05 (m, 1H), 1.80-1.94 (m, 1H), 1.76 (br s, 1H) | B | SFC: Chiralpak AD-H, 25% methanol |
| 124 | 600 MHz DMSO-d₆ | 8.92 (s, 1H), 8.33 (dd, J = 2.14, 8.21 Hz, 1H), 7.70 (s, 1H), 7.52 (d, J = 8.47 Hz, 1H), 7.49 (s, 1H), 5.60 (s, 2H), 4.35-4.35 (m, 1H), 3.38-3.51 (m, 1H), 2.98-3.08 (m, 1H), 2.82-2.90 (m, 1H), 2.78 (dd, J = 8.64, 12.53 Hz, 1H), 2.00-2.09 (m, 1H), 1.77 (br s, 1H), 1.63-1.74 (m, 1H) | B | SFC: Chiralpak AD-H, 25% methanol |
| 125 | 600 MHz DMSO-d₆ | 8.94 (s, 1H), 8.33 (dd, J = 2.14, 8.21 Hz, 1H), 7.62 (s, 1H), 7.57 (s, 1H), 7.55 (d, J = 8.35 Hz, 1H), 5.54-5.63 (m, 2H), 4.39-4.27 (m, 1H), 3.37-3.46 (m, 2H), 2.98-3.09 (m, 1H), 2.82-2.91 (m, 1H), 2.78 (dd, J = 8.60, 12.57 Hz, 1H), 1.98-2.09 (m, 1H), 1.63-1.80 (m, 1H) | B | SFC: Chiralpak AD-H, 25% methanol |
| 126 | 600 MHz DMSO-d₆ | 8.93 (s, 1H), 8.34 (dd, J = 2.14, 8.21 Hz, 1H), 7.75 (s, 1H), 7.72 (s, 1H), 7.55 (d, J = 8.25 Hz, 1H), 5.63-5.71 (m, 2H), 4.37-4.28(m, 1H), 3.36-3.51 (m, 2H), 3.04-3.11 (m, 1H), 2.79-2.88 (m, 2H), 2.00-2.08 (m, 1H), 1.62-1.78 (m, 1H) | B | SFC: Chiralcel OJ-H, 10% methanol |
| 127 | 600 MHz DMSO-d₆ | ¹H NMR (600 MHz, DMSO-d₆) δ 8.93 (d, J = 1.40 Hz, 1H), 8.34 (dd, J = 2.10, 8.17 Hz, 1H), 7.88 (s, 1H), 7.63 (s, 1H), 7.57 (d, J = 8.17 Hz, 1H), 5.60-5.67 (m, 2H), 4.37-4.42-4.29 (m, 1H), 3.36-3.45 (m, 1H), 3.14-3.29 (m, 1H), 3.00-3.09 (m, 1H), 2.77-2.89 (m, 2H), 1.95-2.08 (m, 1H), 1.64-1.81 (m, 1H) | B | SFC: Chiralcel OJ-H, 10% methanol. |
| 128 | 600 MHz DMSO-d₆ | 8.90-8.99 (m, 1H), 8.26-8.35 (m, 1H), 7.52-7.44 (d, J = 7.66 Hz, 1H), 7.33 (d, J = 8.30 Hz, 1H), 7.23-7.29 (m, 1H), 7.00-7.19 (m, 1H), 6.99-7.19 (m, 1H), 5.76-5.42 (m, 2H), 2.98-3.15 (m, 2H), 2.72-2.91 (m, 2H), 2.69-2.65 (s, 1H), 2.22-2.39 (m, 1H), 1.71 (br d, J = 6.36 Hz, 1H), 1.69 (br d, J = 5.19 Hz, 1H), 1.42-1.62 (m, 6H), 1.38 (s, 1H). | — | — |
| 129 | 600 MHz DMSO-d₆ | 8.97 (s, 1H), 8.30 (dd, J = 2.14, 8.21 Hz, 1H), 7.45 (d, J = 7.79 Hz, 1H), 7.33 (d, J = 8.17 Hz, 1H), 7.18 (d, J = 7.79 Hz, 1H), 7.00-7.14 (m, 2H), 5.47-5.60 (m, 2H), 3.12-3.27 (m, 1H), 3.06 (br d, J = 11.99 Hz, 1H), 2.88-3.01 (m, 2H), 2.56-2.64 (m, 1H), 2.51-2.56 (m, 1H), 1.64-1.73 (m, 2H), 1.46-1.59 (m, 1H), 1.21-1.41 (m, 7H) | B | SFC: Phenomenex Lux Cellulose-2, 30% methanol |
| 130 | 600 MHz DMSO-d₆ | 8.97 (d, J = 1.71 Hz, 1H), 8.30 (dd, J = 2.14, 8.21 Hz, 1H), 7.45 (d, J = 7.55 Hz, 1H), 7.33 (d, J = 8.17 Hz, 1H), 7.18 (d, J = 7.86 Hz, 1H), 7.02-7.12 (m, 2H), 5.47-5.58 (m, 2H), 3.12-3.26 (m, 1H), 3.06 (br d, J = 12.07 Hz, 1H), 2.87-3.01 (m, 2H), 2.56-2.63 (m, 1H), 2.52-2.55 (m, 1H), 1.63-1.73 (m, 2H), 1.46-1.58 (m, 1H), 1.21-1.41 (m, 7H) | B | SFC: Phenomenex Lux Cellulose-2, 30% methanol |
| 131 | 600 MHz DMSO-d₆ | 8.96 (s, 1H), 8.29 (dd, J = 2.14, 8.21 Hz, 1H), 7.44 (d, J = 7.71 Hz, 1H), 7.35 (d, J = 8.25 Hz, 1H), 7.06-7.12 (m, 2H), 6.93-7.04 (m, 1H), 5.41-5.51 (m, 2H), 4.10 (br s, 1H), 3.75 (td, J = 2.88, 10.98 Hz, 1H), 3.69 (q, J = 3.58 Hz, 1H), 3.37-3.49 (m, 1H), 3.01-3.21 (m, 2H), 2.80-2.94 (m, 2H), 2.43-2.49 (m, 1H), 1.81 (br s, 1H), 1.67-1.79 (m, 1H) | B | SFC: Phenomenex Lux Cellulose-2, 30% methanol. |
| 132 | 600 MHz DMSO-d₆ | 8.96 (s, 1H), 8.29 (dd, J = 2.14, 8.21 Hz, 1H), 7.45 (d, J = 7.97 Hz, 1H), 7.37 (d, J = 8.25 Hz, 1H), 7.07-7.13 (m, 2H), 6.98-7.06 (m, 1H), 5.44-5.52 (m, 2H), 4.11 (br s, 1H), 3.80 (td, J = 2.86, 11.25 Hz, | B | SFC: Phenomenex Lux Cellulose-2, |

TABLE 3-continued

Characterization data for compounds made following Scheme 8.
The column "Separation Stage" indicates after which process step
regioisomers formed due to asymmetric benzimidazole substitution at R$^1$
in Scheme 8 were separated during the preparation of the tabulated final
compound (I = after preparation of the alkylated intermediate 1-59
(where at least one R$^1$ is not hydrogen); B prior to boc
deprotection; or F = final compound).

| Ex. #. | Freq., Solvent | $^1$HNMR Data (δ ppm) | Separation Stage | SFC Isomer Separation Conditions |
|---|---|---|---|---|
| | | 1H), 3.74 (br d, J = 3.11 Hz, 1H), 3.44-3.54 (m, 1H), 3.14-3.21 (m, 2H), 2.94-3.12 (m, 2H), 2.51-2.62 (m, 1H), 1.83 (br s, 1H), 1.69-1.80 (m, 1H) | | 30% methanol. |
| 133 | 600 MHz DMSO-d$_6$ | 9.04 (s, 1H), 8.70 (s, 1H), 7.85 (m, 1H), 7.52 (dd, J = 7.47, 10.98 Hz, 1H), 7.50 (br dd, J = 7.32, 10.35 Hz, 1H), 7.10-7.25 (m, 1H), 5.57 (s, 2H), 4.45-4.60 (m, 1H), 3.62-3.70 (m, 1H), 3.36-3.46 (m, 1H), 2.97 (br t, J = 11.21 Hz, 1H), 2.75 (br dd, J = 10.12, 12.30 Hz, 1H), 2.33-2.46 (m, 1H), 2.10-2.20 (m, 1H), 1.78-1.86 (m, 1H) | — | — |
| 134 | 600 MHz DMSO-d$_6$ | 9.03 (d, J = 1.37 Hz, 1H), 8.74-8.75 (dd, J = 1.37, 5.87 Hz, 1H), 8.25 (br d, J = 3.97 Hz, 1H), 7.83 (br s, 1H), 7.5-7.68 (s, 1H), 7.60 (d, J = 8.32 Hz, 1H), 7.36-7.44 (m, 2H), 5.72 (s, 1H), 5.68 (s, 1H), 4.36-4.45 (m, 1H), 3.38-3.54 (m, 2H), 3.02-3.13 (m, 1H), 2.80-2.95 (m, 2H), 1.99-2.16 (m, 1H), 1.67-1.78 (m, 1H) | — | — |
| 135 | 600 MHz DMSO-d$_6$ | 8.98 (d, J = 1.56 Hz, 1H), 8.30 (dd, J = 2.14, 8.21 Hz, 1H), 7.44 (d, J = 7.79 Hz, 1H), 7.33 (d, J = 8.25 Hz, 1H), 7.15 (d, J = 7.86 Hz, 1H), 7.10 (t, J = 7.76 Hz, 1H), 7.03 (t, J = 7.58 Hz, 1H), 5.54-5.60 (m, 1H), 5.44-5.52 (m, 1H), 3.15-3.27 (m, 1H), 3.04-3.13 (m, 2H), 2.75-2.89 (m, 3H), 2.56-2.64 (m, 1H), 1.65-1.76 (m, 1H), 1.54-1.63 (m, 2H), 1.42-1.52 (m, 4H), 1.27-1.41 (m, 1H) | B | SFC: Phenomenex Lux Cellulose-2, 40% methanol |
| 136 | 600 MHz DMSO-d$_6$ | 8.98 (dd, J = 0.74, 2.06 Hz, 1H), 8.30 (dd, J = 2.14, 8.21 Hz, 1H), 7.44 (d, J = 7.55 Hz, 1H), 7.33 (d, J = 8.33 Hz, 1H), 7.15 (d, J = 7.86 Hz, 1H), 7.10 (dt, J = 1.17, 7.59 Hz, 1H), 7.00-7.06 (m, 1H), 5.57 (d, J = 17.91 Hz, 1H), 5.48 (d, J = 17.91 Hz, 1H), 3.15-3.27 (m, 1H), 3.02-3.14 (m, 2H), 2.75-2.90 (m, 3H), 2.56-2.64 (m, 1H), 1.65-1.76 (m, 1H), 1.54-1.63 (m, 2H), 1.42-1.52 (m, 4H), 1.27-1.40 (m, 1H) | B | SFC: Phenomenex Lux Cellulose-2, 40% methanol. |
| 137 | 600 MHz DMSO-d$_6$ | 8.96 (d, J = 1.48 Hz, 1H), 8.29 (dd, J = 2.14, 8.21 Hz, 1H), 7.38 (d, J = 8.17 Hz, 1H), 7.05 (s, 1H), 7.01 (d, J = 8.55 Hz, 1H), 6.67 (dd, J = 2.41, 8.72 Hz, 1H), 5.46-5.55 (m, 2H), 3.73 (s, 1H), 3.08-3.24 (m, 2H), 2.97 (br dd, J = 9.03, 11.29 Hz, 1H), 2.52-2.57 (m, 1H), 2.19-2.28 (m, 1H), 1.93-2.09 (m, 1H), 1.83 (br s, 1H) | B | SFC: Chiralcel OJ-H, 15% methanol |
| 138 | 600 MHz DMSO-d$_6$ | 8.96 (d, J = 1.63 Hz, 1H), 8.29 (dd, J = 2.10, 8.17 Hz, 1H), 7.39 (d, J = 8.10 Hz, 1H), 7.36 (d, J = 8.52 Hz, 1H), 6.78 (s, 1H), 6.74 (d, J = 8.78 Hz, 1H), 5.53 (s, 2H), 3.66-3.69 (m, 1H), 3.05-3.17 (m, 2H), 2.90-2.96 (m, 1H), 2.17-2.26 (m, 1H), 1.97-2.07 (m, 1H), 1.75 (br s, 1H) | B | SFC: Chiralcel OJ-H, 15% methanol |
| 139 | 600 MHz DMSO-d$_6$ | 8.95 (d, J = 1.95 Hz, 1H), 8.30-8.35 (m, 1H), 7.60 (s, 1H), 7.59 (d, J = 10.87 Hz, 1H), 7.50 (d, J = 8.17 Hz, 1H), 7.42 (dd, J = 1.32, 8.33 Hz, 1H), 5.56-5.63 (m, 2H), 3.49 (br dd, J = 3.23, 12.03 Hz, 2H), 2.87-2.94 (m, 1H), 2.57-2.69 (m, 1H), 2.42-2.48 (m, 1H), 2.11 (s, 3H), 1.81-1.87 (m, 1H), 1.64-1.71 (m, 1H), 1.48-1.56 (m, 1H), 1.15-1.28 (m, 1H) | B | SFC: Chiralcel OD-H, 15% methanol w/ 0.2% DEA |
| 140 | 600 MHz DMSO-d$_6$ | 8.95 (d, J = 1.63 Hz, 1H), 8.33 (dd, J = 2.10, 8.25 Hz, 1H), 7.75 (s, 1H), 7.50 (d, J = 8.25 Hz, 1H), 7.29-7.40 (m, 2H), 5.51-5.60 (m, 2H), 3.48 (br dd, J = 3.23, 12.03 Hz, 2H), 2.86-2.95 (m, 1H), 2.62 (dd, J = 9.03, 12.07 Hz, 1H), 2.43-2.48 (m, 1H), 2.09-2.13 (m, 3H), 1.81-1.88 (m, 1H), 1.69 (td, J = 3.79, 13.29 Hz, 1H), 1.51-1.59 (m, 1H), 1.16-1.28 (m, 1H) | B | SFC: Chiralcel OD-H, 15% methanol w/ 0.2% DEA |
| 141 | 600 MHz DMSO-d$_s$ | 8.97 (s, 1H), 8.28 (dd, J = 2.02, 8.17 Hz, 1H), 7.43 (d, J = 7.79 Hz, 1H), 7.32 (d, J = 8.25 Hz, 1H), 7.16 (d, J = 7.79 Hz, 1H), 7.09 (t, J = 7.24 Hz, 1H), 7.02 (t, J = 7.28 Hz, 1H), 5.47-5.57 (m, 2H), 3.08-3.25 (m, 2H), 2.96 (br t, J = 8.95 Hz, 1H), 2.77-2.89 (m, 2H), 1.73 (tdd, J = 4.41, 8.78, 13.23 Hz, 1H), 1.55 (td, J = 3.37, 6.50 Hz, 2H), 1.29-1.48 (m, 2H), 0.93 (s, 1H) | — | — |
| 142 | 500 MHz DMSO- | 8.95 (s, 1H), 8.36 (br d, J = 8.19 Hz, 1H), 8.10 (br s, 3H), 7.56 (d, J = 8.19 Hz, 1H), 7.15 (d, J = 8.81 Hz, | B | SFC: Chiralpak IC, |

TABLE 3-continued

Characterization data for compounds made following Scheme 8.
The column "Separation Stage" indicates after which process step
regioisomers formed due to asymmetric benzimidazole substitution at R¹
in Scheme 8 were separated during the preparation of the tabulated final
compound (I = after preparation of the alkylated intermediate 1-59
(where at least one R¹ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
| | d₆ | 1H), 7.07 (s, 1H), 6.81 (br d, J = 8.91 Hz, 1H), 5.52-5.65 (m, 2H), 3.77 (s, 3H), 3.58-3.75 (m, 1H), 3.34 (br d, J = 13.27 Hz, 2H), 3.21 (br dd, J = 8.71, 12.13 Hz, 1H), 3.07 (br t, J = 9.23 Hz, 1H), 1.96 (br s, 1H), 1.83 (br s, 1H), 1.58 (br s, 2H) | | 40% isopropanol |
| 143 | 500 MHz DMSO-d₆ | 8.95 (s, 1H), 8.35 (d, J = 8.09 Hz, 1H), 8.02 (br s, 3H), 7.52 (d, J = 8.29 Hz, 1H), 7.42 (d, J = 8.50 Hz, 1H), 6.83-6.89 (m, 2H), 5.51-5.66 (m, 2H), 3.48-3.67 (m, 1H), 3.34 (br s, 1H), 3.26 (br d, J = 13.48 Hz, 1H), 3.15 (br dd, J = 8.34, 12.39 Hz, 1H), 2.94-3.07 (m, 1H), 1.94 (br s, 1H), 1.81 (br s, 1H), 1.56 (br s, 2H) | B | SFC: Chiralpak IC, 40% isopropanol |
| 144 | 500 MHz DMSO-d₆ | 8.91 (d, J = 1.45 Hz, 1H), 8.41 (br s, 3H), 8.33 (dd, J = 2.07, 8.19 Hz, 1H), 7.55 (d, J = 8.29 Hz, 1H), 7.15-7.21 (m, 2H), 5.40-5.64 (2, 2H), 4.72-4.84 (dt, J = 5.03, 9.36 Hz, 1H), 3.69-3.78 (m, 1H), 3.51 (br s, 1H), 3.43 (br d, J = 12.54 Hz, 1H), 2.94-3.12 (m, 2H), 2.12-2.22 (m, 1H), 1.73-1.88 (m, 1H) | — | — |
| 145 | 500 MHz DMSO-d₆ | 8.94 (d, J = 1.55 Hz, 1H), 8.75 (br s, 3H), 8.37 (dd, J = 2.07, 8.19 Hz, 1H), 7.66 (br d, J = 7.15 Hz, 1H), 7.21 (br d, J = 8.71 Hz, 1H), 7.08 (d, J = 2.28 Hz, 1H), 6.84 (br d, J = 8.40 Hz, 1H), 5.60-5.76 (m, 2H), 4.86-4.98 (m, 1H), 3.95 (br d, J = 6.95 Hz, 1H), 3.59-3.79 (m, 1H), 3.28-3.52 (m, 1H), 3.00-3.27 (m, 2H), 2.19-2.31 (m, 1H), 1.79-1.91 (m, 1H) | B | SFC: Chiralpak AD-H, 20% methanol |
| 146 | 500 MHz DMSO-d₆ | 8.94 (d, J = 1.45 Hz, 1H), 8.74 (br s, 3H), 8.35 (dd, J = 2.07, 8.19 Hz, 1H), 7.60 (br d, J = 7.98 Hz, 1H), 7.40-7.47 (m, J = 8.71 Hz, 1H), 6.93 (br s, 1H), 6.81-6.90 (m, J = 8.60 Hz, 1H), 5.59-5.76 (m, 2H), 4.81-5.01 (m, 1H), 3.86 (br d, J = 11.30 Hz, 1H), 3.59-3.79 (m, 1H), 3.33-3.55 (m, 1H), 3.05-3.32 (m, 2H), 2.17-2.33 (m, 1H), 1.70-1.88 (m, 1H) | B | SFC: Chiralpak AD-H, 20% methanol |
| 147 | 500 MHz CDCl₃ | 8.87 (s, 2H), 8.05 (d, J = 8.19 Hz, 2H), 7.65 (d, J = 8.19 Hz, 2H), 5.84 (q, J = 6.57 Hz, 2H), 3.08 (s, 6H), 1.78 (d, J = 6.63 Hz, 6H), 1.62 (br s, 3H), 1.44 (br s, 2H) | B | SFC: Chiralcel OD-H, 20% methanol |
| 148 | 500 MHz DMSO-d₆ | 8.97 (s, 1H), 8.59 (br s, 3H), 8.33 (dd, J = 1.95, 8.17 Hz, 1H), 7.48 (br d, J = 7.91 Hz, 1H), 7.30-7.44 (m, 1H), 7.04-7.11 (m, 2H), 6.73 (d, J = 9.04 Hz, 1H), 5.50-5.63 (m, 2H), 5.10-5.20 (br s, 1H), 3.70-3.80 (m, 1H), 3.44-3.65 (m, 2H), 3.10-3.29 (m, 2H), 1.93-2.16 (m, 2H). | B | SFC: Chiralcel OD-H, 20% methanol |
| 149 | 500 MHz DMSO-d₆ | 8.92 (s, 2H), 7.59 (d, J = 8.89 Hz, 1H), 7.52 (d, J = 9.41 Hz, 1H), 5.60 (d, J = 2.02 Hz, 2H), 4.73-4.84 (m, 1H), 3.37-3.49 (m, 1H), 3.11-3.17 (m, 1H), 2.97-3.08 (m, 2H), 2.51-2.55 (m, 1H), 1.93-2.03 (m, 1H), 1.78-1.91 (m, 1H). | — | — |
| 150 | 500 MHz DMSO-d₆ | 8.91 (s, 2H), 7.55-7.63 (m, 2H), 5.59-5.69 (m, 2H), 3.87-4.10 (m, 1H), 3.47 (br d, J = 13.23 Hz, 1H), 3.32-3.42 (m, 1H), 3.12-3.20 (m, 2H), 2.36 (br d, J = 1.69 Hz, 1H), 2.26 (br s, 1H). | B | 0.1% NH4OH in ACN and water as mobile phase |
| 151 | 500 MHz DMSO-d₆ | 8.89 (s, 2H), 7.52-7.64 (m, 2H), 5.55-5.74 (m, 2H), 3.83-3.95 (m, 1H), 3.32-3.50 (m, 2H), 3.10-3.22 (m, 2H), 2.36-2.44 (m, 1H), 2.11-2.33 (m, 1H) | B | 0.1% NH4OH in ACN and water as mobile phase |
| 152 | 500 MHz MeOD | 8.82-8.86 (m, 1H), 8.11-8.20 (m, 1H), 7.37-7.46 (m, 2H), 7.21 (d, J = 1.82 Hz, 1H), 7.16 (dd, J = 1.82, 8.30 Hz, 1H), 5.49 (s, 2H), 3.58-3.63 (m, 1H), 3.42-3.53 (m, 2H), 3.05 (dt, J = 2.34, 12.07 Hz, 1H), 2.80-2.91 (m, 2H), 1.95-2.02 (m, 1H), 1.59-1.70 (m, 1H) | I | YMC Amyose SA, Methanol THF (70:30) 40%; peak 1 |
| 153 | 500 MHz MeOD | 8.84 (br s, 1H), 8.07-8.20 (m, 1H), 7.37-7.50 (m, 2H), 7.06-7.27 (m, 2H), 5.52 (br s, 2H), 3.93 (br s, 1H), 3.34-3.43 (m, 2H), 3.01-3.16 (m, 2H), 1.85 (br d, J = 3.37 Hz, 2H) | I | YMC Amyose SA, Methanol THF (70:30) 40%; peak 1 |
| 154 | 400 MHz d₆- | 7.77-7.83 (m, J = 7.98 Hz, 2H), 7.48 (d, J = 7.67 Hz, 1H), 7.29-7.36 (m, J = 7.98 Hz, 2H), 7.03-7.19 (m, | — | — |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
|  | DMSO | 3H), 5.47 (s, 2H), 3.35-3.41 (m, 1H), 3.26-3.30 (m, 1H), 3.11-3.24 (m, 2H), 2.94-3.05 (m, 1H), 2.19-2.34 (m, 1H), 2.01-2.16 (m, 1H), 1.76 (br s, 2H) |  |  |
| 155 | 400 MHz d₆-DMSO | 8.54 (br d, J = 3.01 Hz, 2H), 7.86 (d, J = 8.29 Hz, 2H), 7.60 (d, J = 7.52 Hz, 1H), 7.44-7.53 (m, J = 8.19 Hz, 2H), 7.23-7.39 (m, 3H), 5.66 (br d, J = 9.95 Hz, 2H), 4.04 (br d, J = 9.95 Hz, 1H), 3.72-3.80 (m, 1H), 3.57-3.64 (m, 1H), 3.31-3.53 (m, 2H), 3.01-3.29 (m, 2H), 1.96-2.08 (m, 1H), 1.47-1.64 (m, 1H) | — | — |
| 156 | 600 MHz DMSO-d₆ | 7.79-7.84 (m, J = 8.41 Hz, 2H), 7.26-7.32 (m, J = 8.41 Hz, 2H), 7.18 (dd, J = 2.18, 9.26 Hz, 1H), 6.91 (t, J = 10.35 Hz, 1H), 5.43 (s, 2H), 4.39-4.38 (m, 1H), 3.39-3.51 (m, 1H), 3.36-3.14-3.28 (m, 1H), 3.04-3.13 (m, 1H), 2.92-3.03 (m, 1H), 2.84 (dd, J = 8.60, 12.65 Hz, 1H), 1.94-2.13 (m, 1H), 1.74-1.91 (m, 1H) | B | SFC: Chiralcel OD-H, 15% methanol. |
| 157 | 600 MHz DMSO-d₆ | δ 7.79-7.84 (m, 2H), 7.28-7.33 (m, J = 8.49 Hz, 2H), 7.08 (dd, J = 2.22, 8.84 Hz, 1H), 6.99 (dt, J = 2.18, 10.59 Hz, 1H), 5.41-5.48 (m, 2H), 4.28-4.36 (m, 1H), 3.37-3.43 (m, 1H), 2.99-3.06 (m, 1H), 2.93 (tdd, J = 4.16, 7.88, 14.31 Hz, 1H), 2.79 (dd, J = 8.60, 12.50 Hz, 1H), 2.01-2.13 (m, 1H), 1.66-1.80 (m, 1H) | B | SFC: Chiralcel OJ-H, 15% methanol |
| 158 | 600 MHz DMSO-d₆ | 7.81-7.84 (m, J = 8.25 Hz, 2H), 7.78 (s, 1H), 7.43-7.58 (m, 2H), 7.28-7.33 (m, 2H), 5.51 (s, 2H), 4.39-4.36 (m, 1H), 3.49-3.54 (m, 1H), 3.40-3.48 (m, 1H), 3.03-3.17 (m, 1H), 2.73-2.94 (m, 1H), 1.93-2.11 (m, 1H), 1.82 (br s, 1H), 1.63-1.79 (m, 1H), | B | SFC: Chiralpak AD-H, 25% methanol |
| 159 | 600 MHz DMSO-d₆ | 7.94 (s, 1H), 7.78-7.84 (m, J = 8.25 Hz, 2H), 7.47 (dd, J = 1.01, 8.25 Hz, 1H), 7.36 (d, J = 8.33 Hz, 1H), 7.26-7.32 (m, J = 8.17 Hz, 2H), 5.47-5.56 (m, 2H), 4.42-4.34 (dt, J = 4.32, 8.19 Hz, 1H), 3.44-3.52 (m, 1H), 3.38-3.43 (m, 1H), 3.15-3.28 (m, 1H), 3.04-3.14 (m, 1H), 2.80-2.97 (m, 2H), 2.03-2.12 (m, 1H), 1.70-1.88 (m, 1H) | B | SFC: Chiralpak AD-H, 25% methanol |
| 160 | 600 MHz DMSO-d₆ | 7.76-7.85 (m, 3H), 7.46-7.65 (m, 2H), 7.29-7.38 (m, 2H), 5.54 (s, 2H), 3.85-4.05 (m, 1H), 3.35-3.46 (m, 1H), 3.21-3.35 (m, 1H), 3.03-3.20 (m, 1H), 2.54-2.79 (m, 1H), 2.18-2.32 (m, 1H), 1.98-2.14 (m, 1H), | B | SFC: Chiralpak AD-H, 25% methanol |
| 161 | 600 MHz DMSO-d₆ | 7.96 (d, J = 1.17 Hz, 1H), 7.81 (d, J = 8.43 Hz, 2H), 7.48 (dd, J = 1.49, 8.24 Hz, 1H), 7.29-7.38 (m, 3H), 5.48-5.57 (m, 2H), 3.34-3.47 (m, 1H), 3.20-3.30 (m, 1H), 3.10-3.19 (m, 1H), 2.96-3.09 (m, 1H), 2.17-2.32 (m, 1H), 1.99-2.15 (m, 1H), 1.79 (br d, J = 19.33 Hz, 1H) | B | SFC: Chiralpak AD-H, 25% methanol |
| 162 | 400 MHz d₆-DMSO | 7.80 (d, J = 8.29 Hz, 2H), 7.43 (d, J = 7.46 Hz, 1H), 7.30 (d, J = 8.29 Hz, 2H), 7.15 (d, J = 7.88 Hz, 1H), 6.98-7.11 (m, 2H), 5.39 (s, 2H), 3.57 (s, 1H), 3.38 (br dd, J = 3.42, 11.82 Hz, 1H), 3.20-3.28 (m, 1H), 2.78-2.91 (m, 2H), 2.63 (dd, J = 9.12, 11.82 Hz, 1H), 2.08-2.28 (m, 1H), 1.78-1.87 (m, 1H), 1.65-1.75 (m, 1H), 1.49-1.63 (m, 1H) | — | — |
| 163 | 500 MHz d₆-DMSO | 7.81 (d, J = 8.30 Hz, 2H), 7.45 (d, J = 7.53 Hz, 1H), 7.32 (d, J = 8.30 Hz, 2H), 7.07-7.18 (m, 2H), 6.98-7.07 (m, 1H), 5.47 (s, 2H), 3.38-3.48 (m, 1H), 3.05-3.17 (m, 2H), 2.79-2.93 (m, 1H), 1.83 (br s, 1H), 1.60-1.74 (m, 1H), 1.41-1.54 (m, 1H), 0.94 (d, J = 6.75 Hz, 3H) | — | — |
| 164 | 600 MHz d₆-DMSO | 7.81 (d, J = 8.10 Hz, 2H), 7.29 (d, J = 7.78 Hz, 1H), 7.25 (d, J = 8.10 Hz, 2H), 7.14 (d, J = 7.79 Hz, 1H), 7.03 (t, J = 7.63 Hz, 1H), 6.93 (t, J = 7.63 Hz, 1H), 5.51 (s, 2H), 3.51-3.59 (m, 2H), 3.42 (d, J = 9.65 Hz, 1H), 3.18 (s, 1H), 3.14 (d, J = 9.65 Hz, 1H), 2.43 (d, J = 4.36 Hz, 1H), 1.77-1.85 (m, 1H), 1.49-1.56 (m, 1H), 0.96 (s, 3H) | — | — |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | $^1$HNMR Data (δ ppm) | Separation Stage | SFC Isomer Separation Conditions |
|---|---|---|---|---|
| 165 | 600 MHz d$_6$-DMSO | 7.82 (d, J = 8.10 Hz, 2H), 7.21-7.37 (m, 8H), 7.17 (d, J = 7.79 Hz, 1H), 7.04-7.08 (m, 1H), 6.95 (t, J = 7.47 Hz, 1H), 5.49-5.58 (m, 2H), 3.94 (dd, J = 7.79, 9.65 Hz, 1H), 3.73 (dd, J = 6.85, 9.34 Hz, 1H), 3.66 (t, J = 9.19 Hz, 1H), 3.42 (q, J = 7.16 Hz, 1H), 3.18 (d, J = 4.67 Hz, 1H), 3.06 (q, J = 7.79 Hz, 1H), 1.72 (br s, 2H) | — | — |
| 166 | 600 MHz d$_6$-DMSO | 7.82 (d, J = 8.10 Hz, 2H), 7.25-7.32 (m, 3H), 7.11 (d, J = 8.10 Hz, 1H), 7.03 (t, J = 7.47 Hz, 1H), 6.92 (t, J = 7.63 Hz, 1H), 5.50 (s, 2H), 3.57-3.66 (m, 2H), 3.44-3.51 (m, 2H), 3.14 (dd, J = 4.83, 9.50 Hz, 1H), 1.95 (qd, J = 6.40, 12.26 Hz, 1H), 1.61 (qd, J = 6.34, 12.42 Hz, 1H) | — | — |
| 167 | 400 MHz d$_6$-DMSO | 7.80 (d, J = 8.29 Hz, 2H), 7.43 (d, J = 7.46 Hz, 1H), 7.30 (d, J = 8.29 Hz, 2H), 7.15 (d, J = 7.88 Hz, 1H), 6.98-7.11 (m, 2H), 5.39 (s, 2H), 3.57 (s, 1H), 3.38 (br dd, J = 3.42, 11.82 Hz, 1H), 3.20-3.28 (m, 1H), 2.78-2.91 (m, 2H), 2.63 (dd, J = 9.12, 11.82 Hz, 1H), 2.08-2.28 (m, 1H), 1.78-1.87 (m, 1H), 1.65-1.75 (m, 1H), 1.49-1.63 (m, 1H) | — | — |
| 168 | 500 MHz d$_6$-DMSO | Mixture of diasteromers: 7.80 (br d, J = 7.79 Hz, 2H), 7.27 (br dd, J = 7.91, 17.52 Hz, 3H), 7.13 (br d, J = 8.04 Hz, 1H), 7.02 (br t, J = 8.04 Hz, 1H), 6.93 (br d, J = 7.53 Hz, 1H), 5.45-5.57 (m, 2H), 3.56-3.79 (m, 1H), 3.09-3.19 (m, 2H), 1.92-2.05 (m, 1H), 1.71-1.90 (m, 2H), 1.15-1.66 (m, 7H) | — | — |
| 169 | 600 MHz DMSO-d$_6$ | Mixture of diasteromers: 1.20-1.38 (m, 2 H), 1.56-1.71 (m, 2 H), 1.88-2.07 (m, 1 H), 2.07-2.24 (m, 1 H), 2.52-2.59 (m, 1 H), 2.62-2.72 (m, 1 H), 2.87 (q, J = 5.45 Hz, 1 H), 3.06 (br d, J = 10.12 Hz, 1 H), 3.12-3.21 (m, 4 H), 3.23-3.31 (m, 2 H), 3.31-3.42 (m, 3 H), 3.43-3.56 (m, 1 H), 3.61 (dd, J = 10.35, 4.59 Hz, 1 H), 5.47-5.55 (m, 2 H), 6.92-7.01 (m, 1 H), 7.06 (t, J = 7.47 Hz, 1 H), 7.11-7.19 (m, 1 H), 7.22-7.31 (m, 2 H), 7.37 (d, J = 7.79 Hz, 1 H), 7.80 (d, J = 7.75 Hz, 2 H) | — | — |
| 170 | 400 MHz MeOD | 8.45 (br s, 3H), 7.83 (d, J = 8.29 Hz, 2H), 7.49-7.58 (m, 1H), 7.36 (d, J = 8.09 Hz, 2H), 7.07-7.25 (m, 3H), 5.49 (s, 2H), 4.71-4.91 (m, 1H), 3.75-3.84 (m, 1H), 3.61-3.73 (m, 1H), 3.36-3.48 (m, 1H), 2.95-3.22 (m, 2H), 2.13-2.25 (m, 1H), 1.72-1.95 (m, 1H) | — | — |
| 171 | 400 MHz MeOD | 8.34 (br d, J = 1.04 Hz, 3H), 7.82 (d, J = 8.29 Hz, 2H), 7.46-7.56 (m, 1H), 7.34 (d, J = 8.29 Hz, 2H), 7.07-7.24 (m, 3H), 5.48 (s, 2H), 5.03-5.21 (m, 1H), 3.76-3.87 (m, 1H), 3.52-3.61 (m, 1H), 3.31-3.42 (m, 1H), 3.07-3.28 (m, 2H), 1.89-2.16 (m, 2H) | — | — |
| 172 | 400 MHz MeOD | 8.37 (br s, 3H), 7.83 (d, J = 8.29 Hz, 2H), 7.48-7.56 (m, 1H), 7.35 (d, J = 8.29 Hz, 2H), 7.08-7.23 (m, 3H), 5.48 (s, 2H), 5.01-5.22 (m, 1H), 3.74-3.91 (m, 1H), 3.57 (br dd, J = 4.04, 12.75 Hz, 1H), 3.40 (br d, J = 11.20 Hz, 1H), 3.08-3.27 (m, 2H), 1.92-2.18 (m, 2H) | — | — |
| 173 | 400 MHz MeOD | 7.75-7.84 (m, 2H), 7.39-7.49 (m, 1H), 7.31 (d, J = 8.50 Hz, 2H), 7.15-7.21 (m, 1H), 7.11 (dt, J = 1.35, 7.52 Hz, 1H), 7.02-7.07 (m, 1H), 5.44 (s, 2H), 4.26-4.48 (m, 1H), 3.33-3.44 (m, 2H), 2.90-3.09 (m, 2H), 2.80 (dd, J = 8.71, 12.44 Hz, 1H), 2.00-2.16 (m, 1H), 1.70-1.87 (m, 2H) | — | — |
| 174 | 400 MHz MeOD | 7.75-7.83 (m, 2H), 7.52-7.58 (m, 1H), 7.33-7.47 (m, 5H), 5.68-5.89 (m, 2H), 4.00-4.23 (m, 4H), 3.42-3.65 (m, 2H), 2.48-2.64 (m, 1H), 2.24-2.47 (m, 1H) | B | Phenomenex Lux Cellulose-2, 25% MeOH, Peak 1 |
| 175 | 400 MHz MeOD | 7.76-7.82 (m, 2H), 7.52-7.57 (m, 1H), 7.32-7.46 (m, 5H), 5.68-5.88 (m, 2H), 4.01-4.17 (m, 4H), 3.44-3.65 (m, 2H), 2.50-2.63 (m, 1H), 2.26-2.47 (m, 1H) | B | Phenomenex Lux Cellulose-2, 25% MeOH, Peak 2 |

TABLE 3-continued

Characterization data for compounds made following Scheme 8.
The column "Separation Stage" indicates after which process step
regioisomers formed due to asymmetric benzimidazole substitution at R[1]
in Scheme 8 were separated during the preparation of the tabulated final
compound (I = after preparation of the alkylated intermediate 1-59
(where at least one R[1] is not hydrogen); B prior to boc
deprotection; or F = final compound).

| Ex. #. | Freq., Solvent | $^1$HNMR Data (δ ppm) | Separation Stage | SFC Isomer Separation Conditions |
|---|---|---|---|---|
| 176 | 400 MHz MeOD | 7.75-7.82 (m, 2H), 7.50-7.55 (m, 1H), 7.39-7.46 (m, 3H), 7.33-7.37 (m, 2H), 5.65-5.86 (m, 2H), 4.08 (dt, J = 7.05, 9.74 Hz, 1H), 3.91-4.01 (m, 2H), 3.78 (dd, J = 1.14, 10.26 Hz, 1H), 3.22 (d, J = 2.28 Hz, 2H), 2.08-2.28 (m, 2H) | B | Chiralpak AD-H, 30% MeOH w/ 0.2% DEA, Peak 1 |
| 177 | 400 MHz MeOD | 7.74-7.83 (m, 2H), 7.50-7.55 (m, 1H), 7.38-7.48 (m, 3H), 7.31-7.38 (m, 2H), 5.66-5.86 (m, 2H), 4.08 (dt, J = 6.95, 9.80 Hz, 1H), 3.89-4.01 (m, 2H), 3.79 (dd, J = 1.14, 10.26 Hz, 1H), 3.23 (d, J = 2.70 Hz, 2H), 2.11-2.33 (m, 2H) | B | Chiralpak AD-H, 30% MeOH w/ 0.2% DEA, Peak 2 |
| 178 | 400 MHz MeOD | 7.66-7.74 (m, 2H), 7.36-7.44 (m, 1H), 7.29 (d, J = 8.71 Hz, 2H), 7.00-7.16 (m, 3H), 5.48-5.55 (m, 2H), 3.68 (dd, J = 7.15, 9.64 Hz, 1H), 3.59 (dd, J = 6.12, 7.98 Hz, 2H), 2.70 (d, J = 7.26 Hz, 2H), 2.31-2.43 (m, 1H), 2.12 (dd, J = 6.01, 12.23 Hz, 1H), 1.70 (dd, J = 8.29, 12.44 Hz, 1H), 1.25-1.34 (m, 1H) | — | — |
| 179 | 400 MHz MeOD | 7.70 (d, J = 8.50 Hz, 2H), 7.36-7.43 (m, 1H), 7.29 (d, J = 8.71 Hz, 2H), 6.99-7.17 (m, 3H), 5.46-5.59 (m, 2H), 3.68 (dd, J = 7.26, 9.54 Hz, 1H), 3.54-3.64 (m, 2H), 2.69 (d, J = 7.26 Hz, 2H), 2.31-2.43 (m, 1H), 2.12 (d, J = 6.01 Hz, 1H), 1.61-1.78 (m, 1H) | — | — |
| 180 | 400 MHz $d_6$-DMSO | 8.39 (br s, 3H), 7.87 (d, J = 8.29 Hz, 2H), 7.53-7.62 (m, 1H), 7.50 (d, J = 8.29 Hz, 2H), 7.27-7.36 (m, 1H), 7.22-7.26 (m, 2H), 5.53-5.75 (m, 2H), 3.86-4.00 (m, 1H), 3.41-3.65 (m, 3H), 3.28-3.36 (m, 1H), 3.00-3.17 (m, 2H), 1.89-2.09 (m, 2H), 1.51 (br dd, J = 3.01, 12.96 Hz, 1H), 1.00 (d, J = 6.63 Hz, 3H) | — | — |
| 181 | 400 MHz $d_6$-DMSO | 8.12-8.25 (m, 3H), 7.83 (d, J = 8.29 Hz, 2H), 7.48-7.56 (m, 1H), 7.35-7.40 (m, 2H), 7.10-7.26 (m, 3H), 5.49 (br d, J = 1.66 Hz, 2H), 3.74-3.87 (m, 1H), 3.39 (br d, J = 12.65 Hz, 1H), 2.92-3.13 (m, 3H), 1.64-1.82 (m, 2H), 1.32-1.47 (m, 1H), 1.04 (d, J = 6.22 Hz, 3H) | — | — |
| 182 | 400 MHz $d_6$-DMSO | 8.12 (br d, J = 1.24 Hz, 3H), 7.83 (d, J = 8.50 Hz, 2H), 7.48-7.58 (m, 1H), 7.31-7.40 (m, 2H), 7.17-7.25 (m, 2H), 7.07-7.17 (m, 1H), 5.47 (d, J = 1.66 Hz, 2H), 3.79 (br d, J = 9.74 Hz, 1H), 3.38 (br d, J = 12.85 Hz, 1H), 2.89-3.18 (m, 3H), 1.58-1.85 (m, 2H), 1.40 (br d, J = 11.40 Hz, 1H), 1.04 (d, J = 6.22 Hz, 3H) | — | — |
| 183 | 400 MHz MeOD | 7.66-7.75 (m, 2H), 7.39-7.47 (m, 1H), 7.27 (d, J = 8.50 Hz, 2H), 7.03-7.20 (m, 3H), 5.44-5.51 (m, 2H), 3.76 (d, J = 9.33 Hz, 1H), 3.52-3.69 (m, 3H), 2.90-3.00 (m, 1H), 2.80 (d, J = 13.48 Hz, 1H), 1.49-1.58 (m, 1H), 0.84-0.95 (m, 1H), 0.69-0.79 (m, 1H), 0.53 (t, J = 4.56 Hz, 1H) | F | Chiralpak AD-H, 20% MeOH w/ 0.2% DEA, Peak 1 |
| 184 | 400 MHz MeOD | 7.65-7.75 (m, 2H), 7.37-7.45 (m, 1H), 7.27 (d, J = 8.29 Hz, 2H), 7.00-7.19 (m, 3H), 5.48 (s, 2H), 3.76 (d, J = 9.33 Hz, 1H), 3.51-3.67 (m, 3H), 2.94 (br d, J = 13.48 Hz, 1H), 2.81 (s, 1H), 1.53 (td, J = 3.81, 7.93 Hz, 1H), 0.74 (dd, J = 5.18, 7.88 Hz, 1H), 0.52 (t, J = 4.35 Hz, 1H) | F | Chiralpak AD-H, 20% MeOH w/ 0.2% DEA, Peak 2 |
| 185 | 400 MHz MeOD | 7.70 (d, J = 8.50 Hz, 2H), 7.38-7.44 (m, 1H), 7.31 (d, J = 8.29 Hz, 2H), 6.82 (dd, J = 2.28, 8.71 Hz, 1H), 6.71 (d, J = 2.28 Hz, 1H), 5.40 (s, 2H), 3.38-3.46 (m, 1H), 3.21 (td, J = 4.17, 11.97 Hz, 1H), 2.88-2.99 (m, 2H), 2.79 (dd, J = 8.91, 11.61 Hz, 1H), 1.90-2.01 (m, 1H), 1.76-1.87 (m, 1H), 1.60-1.73 (m, 1H), 1.28-1.40 (m, 1H) | F | Chiralpak IC, 45% IPA w/ 0.2% DEA, peak 1 |
| 186 | 400 MHz MeOD | 7.69 (d, J = 8.29 Hz, 2H), 7.27-7.34 (m, 2H), 7.07 (d, J = 2.49 Hz, 1H), 7.00 (d, J = 8.71 Hz, 1H), 6.75 (dd, J = 2.49, 8.71 Hz, 1H), 5.37 (s, 2H), 3.42-3.50 (m, 1H), 3.26 (br d, J = 12.23 Hz, 1H), 2.89-3.02 (m, 2H), 2.81 (dd, J = 8.91, 11.61 Hz, 1H), 1.93-2.01 (m, 1H), 1.76-1.86 (m, 1H), 1.59-1.75 (m, 1H), 1.28-1.41 (m, 1H) | F | Chiralpak IC, 45% IPA w/ 0.2% DEA, peak 2 |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | $^1$HNMR Data (δ ppm) | Separation Stage | SFC Isomer Separation Conditions |
|---|---|---|---|---|
| 442 | 500 MHz d$_4$-MeOH | 9.05-9.18 (m, 2H), 7.39-7.56 (m, 1H), 6.86-7.12 (m, 2H), 5.51-5.68 (m, 2H), 4.40-4.67 (m, 1H), 3.60-3.71 (m, 1H), 3.46-3.56 (m, 1H), 3.28 (dd, J = 4.25, 8.40 Hz, 1H), 3.07-3.16 (m, 1H), 3.02 (dd, J = 9.43, 12.34 Hz, 1H), 2.17-2.28 (m, 1H), 1.83-1.98 (m, 1H) | B | Chiralpak OD-H, 15% IPA, Peak 1 |
| 443 | 500 MHz d$_4$-MeOH | 9.06-9.17 (m, 2H), 7.12-7.23 (m, 2H), 6.84-6.93 (m, 1H), 5.57-5.67 (m, 2H), 4.36-4.57 (m, 1H), 3.58-3.69 (m, 1H), 3.48-3.55 (m, 1H), 3.09-3.19 (m, 2H), 2.98 (dd, J = 8.82, 12.46 Hz, 1H), 2.18-2.27 (m, 1H), 1.81-1.96 (m, 1H) | B | Chiralpak OD-H, 15% IPA, Peak 2 |
| 444 | 500 MHz d$_4$-MeOH | 8.47 (s, 2H), 7.39-7.51 (m, 1H), 7.00 (dd, J = 2.34, 8.82 Hz, 1H), 6.95 (ddd, J = 2.47, 8.76, 9.80 Hz, 1H), 5.36-5.51 (m, 2H), 4.60-4.80 (m, 1H), 3.89-3.99 (m, 3H), 3.77-3.89 (m, 1H), 3.61-3.71 (m, 1H), 3.57 (br dd, J = 4.28, 8.95 Hz, 1H), 3.07-3.20 (m, 2H), 2.20-2.36 (m, 1H), 1.91-2.06 (m, 1H) | B | Chiralpak OD-H, 15% MeOH, Peak 1 |
| 445 | 500 MHz d$_4$-MeOH | 7.37-7.42 (m, 1H), 6.71-6.87 (m, 2H), 5.06-5.16 (m, 2H), 4.47-4.61 (m, 1H), 4.14-4.29 (m, 2H), 3.77-3.85 (m, 3H), 3.48-3.55 (m, 1H), 3.02-3.09 (m, 1H), 2.94-3.00 (m, 1H), 2.17-2.25 (m, 1H), 1.91-2.01 (m, 1H) | B | Chiralpak IC, 20% MeOH, Peak 1 |
| 446 | 500 MHz d$_4$-MeOH | 8.39-8.49 (m, 2H), 7.10-7.24 (m, 2H), 6.77-6.93 (m, 1H), 5.34-5.49 (m, 2H), 4.35-4.57 (m, 1H), 3.70 (dtd, J = 1.82, 4.17, 12.42 Hz, 1H), 3.51-3.60 (m, 1H), 3.13-3.23 (m, 2H), 3.01 (dd, J = 8.82, 12.46 Hz, 1H), 2.14-2.28 (m, 1H), 1.78-1.99 (m, 1H) | B | Chiralpak OD-H, 15% MeOH, Peak 2 |
| 447 | 500 MHz d$_4$-MeOH | 7.26-7.43 (m, 2H), 5.07-5.23 (m, 2H), 4.42-4.59 (m, 1H), 4.12-4.24 (m, 1H), 3.61-3.70 (m, 1H), 3.44-3.56 (m, 1H), 3.19-3.27 (m, 1H), 2.99-3.11 (m, 1H), 2.12-2.27 (m, 1H), 1.86-1.99 (m, 1H) | — | — |
| 448 | 500 MHz d$_4$-MeOH | 7.37-7.40 (m, 1H), 6.79-6.87 (m, 2H), 5.03 (s, 2H), 4.47-4.57 (m, 1H), 4.38-4.61 (m, 2H), 3.83 (s, 3H), 3.47-3.57 (m, 2H), 3.23 (s, 3H), 3.05-3.11 (m, 1H), 3.03 (s, 3H), 2.96 (br dd, J = 8.95, 12.07 Hz, 1H), 2.15-2.28 (m, 2H), 1.87-2.08 (m, 3H | B | Chiralpak OD-H, 15% MeOH, Peak 1 |
| 449 | 500 MHz d$_4$-MeOH | 7.37-7.42 (m, 1H), 6.71-6.87 (m, 2H), 5.06-5.16 (m, 2H), 4.47-4.61 (m, 1H), 4.14-4.29 (m, 2H), 3.77-3.85 (m, 3H), 3.48-3.55 (m, 1H), 3.02-3.09 (m, 1H), 2.94-3.00 (m, 1H), 2.17-2.25 (m, 1H), 1.91-2.01 (m, 1H) | B | Chiralpak IC, 15% MeOH, Peak 2 |
| 450 | 500 MHz d$_4$-MeOH | 7.11 (d, J = 8.82 Hz, 1H), 7.05 (d, J = 2.34 Hz, 1H), 6.80-6.85 (m, 1H), 5.01 (s, 2H), 4.44-4.58 (m, 1H), 3.82 (s, 3H), 3.53-3.60 (m, 1H), 3.41-3.47 (m, 2H), 3.21 (s, 3H), 3.07-3.14 (m, 1H), 3.02 (s, 3H), 2.93-2.99 (m, 1H), 2.18-2.28 (m, 1H), 1.91-2.03 (m, 1H) | B | Chiralpak OD-H, 15% MeOH, Peak 2 |
| 451 | 600 MHz DMSO-d$_6$ | 8.95 (d, J = 1.48 Hz, 1H), 8.30 (dd, J = 2.10, 8.25 Hz, 1H), 7.41 (td, J = 4.55, 8.80 Hz, 2H), 7.09 (dd, J = 2.41, 9.19 Hz, 1H), 6.92 (t, J = 9.42 Hz, 1H), 5.49 (s, 2H), 3.40 (br s, 1H), 3.24-3.36 (m, 3H), 3.17 (s, 1H), 2.86-2.98 (m, 2H), 2.60-2.75 (m, 2H), 1.89-2.04 (m, 1H), 1.26-1.43 (m, 1H) | — | — |
| 452 | 600 MHz DMSO-d$_6$ | 8.94 (d, J = 1.40 Hz, 1H), 8.29 (dd, J = 2.14, 8.21 Hz, 1H), 7.37 (d, J = 8.17 Hz, 1H), 6.69 (dd, J = 2.26, 8.88 Hz, 1H), 6.59 (dd, J = 2.22, 12.18 Hz, 1H), 5.48 (s, 2H), 4.25-4.38 (m, 1H), 3.89 (s, 3H), 3.22-3.29 (m, 1H), 2.84-2.98 (m, 2H), 2.62-2.76 (m, 1H), 1.99-2.07 (m, 1H), 1.79 (br s, 1H), 1.64-1.76 (m, 1H) | — | — |
| 453 | 600 MHz DMSO-d$_6$ | 8.90 (s, 1H), 8.34 (dd, J = 2.14, 8.21 Hz, 1H), 7.90 (d, J = 8.10 Hz, 1H), 7.64 (d, J = 8.35 Hz, 1H), 7.61 (d, J = 8.06 Hz, 1H), 5.64 (s, 2H), 4.30-4.44 (m, 1H), 3.59-3.68 (m, 2H), 3.13-3.28 (m, 1H), 2.77-2.90 (m, 2H), 1.99-2.08 (m, 1H), 1.57-1.70 (m, 1H) | B | Chiralpak AD-H, 25% IPA, peak 1 |
| 454 | 600 MHz DMSO-d$_6$ | 8.91 (s, 2H), 7.40 (dd, J = 4.90, 8.64 Hz, 1H), 7.11 (dd, J = 2.49, 9.26 Hz, 1H), 6.91 (ddd, J = 2.57, 8.68, 10.08 Hz, 1H), 5.45-5.52 (m, 2H), 3.27-3.29 (m, | B | Chiralpak AD-H, 25% IPA, peak 1 |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. #. | Freq., Solvent | $^1$HNMR Data (δ ppm) | Separation Stage | SFC Isomer Separation Conditions |
|---|---|---|---|---|
| | | 3H), 2.86-2.97 (m, 2H), 2.61-2.71 (m, 2H), 1.96-2.05 (m, 1H), 1.58 (br s, 2H), 1.31-1.48 (m, 1H) | | |
| 455 | 500 MHz DMSO-d$_6$ | 7.47 (d, J = 1.82 Hz, 1H), 7.35 (d, J = 8.30 Hz, 1H), 7.22 (dd, J = 1.75, 8.37 Hz, 1H), 4.75 (s, 2H), 4.24-4.31 (m, 2H), 3.95 (t, J = 7.66 Hz, 2H), 3.33-3.38 (m, 1H), 2.97-3.06 (m, 2H), 2.80 (dd, J = 8.30, 12.59 Hz, 1H), 2.36 (s, 1H), 2.29 (quin, J = 7.62 Hz, 2H), 2.08-2.17 (m, 1H), 1.74-1.94 (m, 1H) | — | — |
| 456 | 600 MHz DMSO-d$_6$ | 8.91 (s, 2H), 7.22 (dd, J = 2.41, 9.81 Hz, 1H), 7.14 (dd, J = 4.79, 8.68 Hz, 1H), 6.85 (ddd, J = 2.49, 8.70, 9.91 Hz, 1H), 5.49 (d, J = 2.10 Hz, 2H), 3.36-3.43 (m, 2H), 3.28-3.30 (m, 3H), 2.90-2.99 (m, 1H), 2.66-2.72 (m, 2H), 1.98-2.06 (m, 1H), 1.62 (br s, 1H), 1.33-1.42 (m, 1H) | — | — |
| 457 | 600 MHz DMSO-d$_6$ | 7.38-7.43 (m, 1H), 7.12 (dd, J = 2.49, 9.26 Hz, 1H), 6.90-6.96 (m, 1H), 5.07-5.16 (m, 2H), 4.23-4.50 (m, 1H), 4.23 (q, J = 9.45 Hz, 1H), 3.21-3.29 (m, 3H), 2.93-3.01 (m, 3H), 2.72-2.81 (m, 1H), 1.96-2.12 (m, 1H), 1.72-1.90 (m, 3H) | B | Chiralpak AD-H, 25% IPA, peak 1 |
| 458 | 600 MHz DMSO-d$_6$ | 8.93 (dd, J = 0.66, 2.06 Hz, 1H), 8.34 (dd, J = 2.14, 8.21 Hz, 1H), 7.72 (d, J = 8.10 Hz, 1H), 7.61 (d, J = 8.56 Hz, 1H), 7.49 (d, J = 8.10 Hz, 1H), 5.66 (d, J = 1.71 Hz, 2H), 4.32-4.43 (m, 1H), 3.50-3.64 (m, 2H), 3.15-3.28 (m, 1H), 2.85-2.94 (m, 2H), 2.04-2.12 (m, 1H), 1.66-1.77 (m, 1H) | B | Chiralpak AD-H, 25% IPA, peak 1 |
| 459 | 600 MHz DMSO-d$_6$ | 7.66 (s, 1H), 7.57 (d, J = 8.25 Hz, 1H), 7.41 (dd, J = 1.25, 8.33 Hz, 1H), 5.11-5.21 (m, 2H), 4.38-4.49 (m, 1H), 3.64-3.72 (m, 2H), 3.61 (td, J = 4.74, 9.75 Hz, 4H), 3.44-3.53 (m, 2H), 3.34-3.41 (m, 1H), 3.17 (d, J = 4.90 Hz, 1H), 3.09 (ddd, J = 2.84, 9.48, 12.59 Hz, 1H), 2.95-3.05 (m, 1H), 2.86 (dd, J = 8.06, 12.65 Hz, 1H), 2.09-2.19 (m, 1H), 1.75-1.93 (m, 1H) | B | Chiralpak AD-H, 25% IPA, peak 1 |
| 460 | 600 MHz DMSO-d$_6$ | 7.23 (d, J = 9.81 Hz, 1H), 7.16-7.20 (m, 1H), 6.92 (t, J = 8.84 Hz, 1H), 5.08-5.17 (m, 2H), 4.32-4.51 (m, 1H), 4.23 (q, J = 9.55 Hz, 2H), 3.34-3.39 (m, 1H), 3.25-3.30 (m, 4H), 2.93-3.05 (m, 2H), 2.74-2.85 (m, 1H), 2.03-2.13 (m, 1H), 1.71-1.89 (m, 1H) | B | Chiralpak AD-H, 25% IPA, peak 2 |
| 461 | 600 MHz DMSO-d$_6$ | 7.39 (d, J = 8.41 Hz, 1H), 7.33 (d, J = 2.02 Hz, 1H), 7.09 (dd, J = 2.10, 8.41 Hz, 1H), 4.94-5.05 (m, 2H), 4.70-4.84 (m, 1H), 3.14-3.28 (m, 2H), 3.10-3.13 (m, 6H), 2.91-3.06 (m, 2H), 2.89 (s, 1H), 1.87-2.05 (m, 1H), 1.68 (br s, 1H) | B | Chiralpak AD-H, 25% IPA, peak 1 |
| 462 | 600 MHz DMSO-d$_6$ | 8.42 (br s, 2H), 7.44-7.48 (m, 1H), 7.20 (dd, J = 2.37, 9.23 Hz, 1H), 6.99 (t, J = 9.27 Hz, 1H), 5.10-5.21 (m, 2H), 5.04-5.10 (m, 1H), 4.36-4.55 (m, 1H), 4.23 (q, J = 9.52 Hz, 2H), 3.78 (br s, 1H), 3.48 (br dd, J = 4.01, 12.42 Hz, 1H), 3.26-3.34 (m, 1H), 3.02-3.17 (m, 2H), 2.99 (s, 1H), 2.51-2.65 (m, 1H), 1.95-2.12 (m, 2H) | B | Chiralpak AD-H, 25% IPA, peak 1 |
| 463 | 600 MHz DMSO-d$_6$ | 8.95 (d, J = 1.32 Hz, 1H), 8.30 (dd, J = 2.10, 8.17 Hz, 1H), 7.38-7.45 (m, 2H), 7.07 (dd, J = 2.49, 9.19 Hz, 1H), 6.92 (ddd, J = 2.57, 8.66, 10.10 Hz, 1H), 5.47-5.57 (m, 2H), 3.24-3.31 (m, 3H), 3.13-3.23 (m, 2H), 2.99-3.10 (m, 2H), 2.89-2.98 (m, 2H), 1.75-1.89 (m, 1H), 1.53-1.67 (m, 1H). | — | — |
| 464 | 600 MHz DMSO-d$_6$ | 8.44 (br s, 2H), 7.74 (s, 1H), 7.62 (d, J = 8.33 Hz, 1H), 7.46 (d, J = 8.21 Hz, 1H), 5.14-5.24 (m, 2H), 4.88 (dt, J = 4.87, 9.32 Hz, 1H), 4.69-4.83 (m, 1H), 4.42-4.55 (m, 1H), 3.73-3.83 (m, 1H), 3.69 (br d, J = 4.36 Hz, 3H), 3.57-3.65 (m, 4H), 3.37-3.56 (m, 3H), 2.99-3.17 (m, 2H), 2.24 (br t, J = 9.46 Hz, 1H), 1.83-1.92 (m, 1H) | B | Chiralpak AD-H, 25% IPA, peak 1 |
| 465 | 600 MHz DMSO-d$_6$ | 8.73 (br s, 2H), 7.46-7.50 (m, 1H), 7.21-7.23 (m, 1H), 6.98-7.02 (m, 1H), 5.17-5.22 (m, 1H), 4.36-4.53 (m, 1H), 4.13-4.32 (m, 2H), 3.95-4.13 (m, 2H), 3.64 (br d, J = 12.53 Hz, 1H), 3.25-3.34 (m, 3H), 3.09-3.15 (m, 1H), 2.52-2.65 (m, 3H) | B | Chiralpak AD-H, 25% IPA, peak 1 |

TABLE 3-continued

Characterization data for compounds made following Scheme 8.
The column "Separation Stage" indicates after which process step
regioisomers formed due to asymmetric benzimidazole substitution at R¹
in Scheme 8 were separated during the preparation of the tabulated final
compound (I = after preparation of the alkylated intermediate 1-59
(where at least one R¹ is not hydrogen); B prior to boc
deprotection; or F = final compound).

| Ex. # | Freq., Solvent | ¹HNMR Data (δ ppm) | Separation Stage | SFC Isomer Separation Conditions |
|---|---|---|---|---|
| 466 | 600 MHz DMSO-d₆ | 8.38 (br s, 2H), 7.23-7.30 (m, 1H), 6.99 (t, J = 9.27 Hz, 1H), 5.05-5.21 (m, 2H), 4.49 (q, J = 8.93 Hz, 1H), 4.23 (q, J = 9.52 Hz, 2H), 3.79 (br s, 1H), 3.44-3.66 (m, 1H), 3.30-3.37 (m, 1H), 3.28 (s, 2H), 3.06-3.18 (m, 1H), 2.52-2.55 (m, 3H), 1.93-2.11 (m, 1H) | B | Chiralpak AD-H, 25% IPA, peak 1 |
| 467 | 600 MHz DMSO-d₆ | 8.91 (s, 2H), 7.40 (dd, J = 4.87, 8.68 Hz, 1H), 7.07 (dd, J = 2.53, 9.30 Hz, 1H), 6.91 (ddd, J = 2.53, 8.62, 10.10 Hz, 1H), 5.46-5.57 (m, 2H), 3.25-3.31 (m, 3H), 3.12-3.22 (m, 1H), 2.90-3.08 (m, 4H), 1.84 (dtd, J = 3.58, 7.67, 13.31 Hz, 1H), 1.49-1.64 (m, 1H), 1.40 (br s, 1H) | B | Chiralpak AD-H, 25% IPA, peak 1 |
| 468 | 600 MHz DMSO-d⁶ | 7.47 (d, J = 8.56 Hz, 1H), 7.31 (s, 1H), 7.06 (dd, J = 1.21, 8.60 Hz, 1H), 4.97-5.07 (m, 2H), 4.34-4.45 (m, 1H), 3.32 (s, 1H), 3.12 (s, 3H), 2.95-3.09 (m, 2H), 2.89 (s, 3H), 2.76-2.85 (m, 1H), 2.06-2.15 (m, 1H), 1.72-1.89 (m, 2H) | B | SFC: Chiralpak AD-H analytical column, 15% methanol with 0.2% DEA |
| 469 | 600 MHz DMSO-d₆ | 9.07 (br s, 2H), 7.44-7.48 (m, 1H), 7.21 (dd, J = 2.57, 9.26 Hz, 1H), 6.96-7.03 (m, 1H), 5.06-5.19 (m, 2H), 4.92-5.03 (m, 1H), 4.23 (q, J = 9.58 Hz, 2H), 3.56-3.86 (m, 2H), 3.46 (br s, 1H), 3.29 (s, 3H), 3.11 (br dd, J = 9.89, 12.61 Hz, 1H), 2.92-3.04 (m, 1H), 2.68 (br s, 3H), 2.16-2.25 (m, 1H), 1.82-1.95 (m, 1H) | — | — |
| 470 | 600 MHz DMSO-d₆ | 7.58 (d, J = 1.82 Hz, 1H), 7.17-7.24 (m, 2H), 4.70-4.77 (m, 2H), 4.46-4.35 (m, 1H), 4.21-4.29 (m, 2H), 3.94 (t, J = 7.72 Hz, 2H), 3.33-3.41 (m, 2H), 2.97-3.08 (m, 3H), 2.82 (dd, J = 8.30, 12.59 Hz, 1H), 2.28 (quin, J = 7.72 Hz, 2H), 2.14 (ddd, J = 4.61, 8.66, 17.09 Hz, 1H), 1.73-1.88 (m, 1H) | B | SFC: Chiralpak IC, 45% methanol Peak 2 |
| 471 | 600 MHz DMSO-d₆ | 7.44 (d, J = 2.02 Hz, 1H), 7.19 (d, J = 8.49 Hz, 1H), 7.07 (dd, J = 2.02, 8.41 Hz, 1H), 4.93-5.04 (m, 2H), 4.79-4.84 (m, 1H), 4.70-4.76 (m, 1H), 3.10-3.23 (m, 6H), 2.94-3.10 (m, 2H), 2.88 (s, 2H), 1.86-2.05 (m, 1H), 1.75 (br s, 1H) | B | SFC: Chiralpak IC, 30% methanol Peak 2 |
| 472 | 600 MHz DMSO-d₆ | 7.21 (d, J = 9.28 Hz, 1H), 6.96-7.03 (m, 2H), 5.09-5.17 (m, 2H), 4.17-4.40 (m, 1H), 3.39-3.56 (m, 1H), 3.13-3.25 (m, 2H), 3.00 (s, 1H), 2.89 (br t, J = 10.63 Hz, 1H), 2.52-2.55 (m, 2H), 2.35-2.46 (m, 2H), 1.92-2.00 (m, 2H), 1.73-1.86 (m, 1H), 1.19-1.29 (m, 1H), | — | — |
| 473 | 600 MHz DMSO-d₆ | 7.74 (s, 1H), 7.37-7.46 (m, 2H), 5.08-5.18 (m, 2H), 4.36-4.50 (m, 1H), 3.56-3.72 (m, 6H), 3.42-3.54 (m, 2H), 3.35-3.41 (m, 1H), 2.98-3.11 (m, 2H), 2.85 (dd, J = 8.17, 12.61 Hz, 1H), 2.03-2.19 (m, 1H), 1.75-1.91 (m, 1H) | B | SFC: IC, 15% methanol Peak 2 |
| 474 | 600 MHz DMSO-d₆ | 7.39 (s, 1H), 7.26 (d, J = 8.56 Hz, 1H), 7.05 (d, J = 8.79 Hz, 1H), 4.98-5.11 (m, 2H), 3.35-3.41 (m, 1H), 3.11-3.17 (m, 3H), 2.96-3.10 (m, 2H), 2.89 (s, 3H), 2.77-2.86 (m, 1H), 2.07-2.17 (m, 1H), 1.73-1.90 (m, 3H) | B | SFC: Chiralpak AD-H analytical column, 15% methanol with 0.2% DEA. Peak 2 |
| 475 | 600 MHz DMSO-d₆ | 7.40 (s, 1H), 7.29 (d, J = 8.64 Hz, 1H), 7.06 (d, J = 8.63 Hz, 1H), 4.98-5.12 (m, 2H), 4.37-4.48 (m, 1H), 3.56-3.71 (m, 5H), 3.41-3.54 (m, 2H), 3.37-3.41 (m, 1H), 3.12-3.26 (m, 2H), 2.93-3.09 (m, 2H), 2.79-2.90 (m, 1H), 2.05-2.22 (m, 1H), 1.75-1.87 (m, 1H) | B | Chiralcel OD-H column Peak 2 |
| 476 | 600 MHz DMSO-d₆ | 8.90 (s, 1H), 8.27 (dd, J = 2.10, 8.25 Hz, 1H), 7.30 (d, J = 8.33 Hz, 1H), 6.87 (dd, J = 2.18, 9.34 Hz, 1H), 6.57 (dd, J = 2.18, 11.91 Hz, 1H), 5.48-5.56 (m, 2H), 4.37 4.45(m, 1H), 3.55 (s, 3H), 3.38-3.48 (m, 2H), 3.17 (s, 1H), 2.96-3.06 (m, 2H), 2.81 (dd, | B | SFC: Chiralpak AD-H, 25% methanol Peak1 |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. #. | Freq., Solvent | ¹HNMR Data (δ ppm) | Separation Stage | SFC Isomer Separation Conditions |
|---|---|---|---|---|
| | | J = 8.91, 12.57 Hz, 1H), 2.01-2.11 (m, 1H), 1.68-1.80 (m, 1H) | | |
| 477 | 600 MHz DMSO-d₆ | 8.91 (s, 2H), 7.22 (dd, J = 2.49, 9.81 Hz, 1H), 7.10 (dd, J = 4.75, 8.72 Hz, 1H), 6.84 (ddd, J = 2.49, 8.70, 9.91 Hz, 1H), 5.46-5.58 (m, 2H), 3.26-3.31 (m, 3H), 2.98-3.24 (m, 4H), 2.93 (td, J = 3.28, 6.75 Hz, 1H), 1.86 (dtd, J = 3.54, 7.61, 13.38 Hz, 1H), 1.58-1.66 (m, 1H), 1.40 (br s, 1H) | B | SFC: Phenomenex Lux Cellulose-2, 15% methanol. Peak2 |
| 478 | 600 MHz DMSO-d₆ | 8.47 (br s, 2H), 7.78 (s, 1H), 7.44-7.50 (m, 2H), 5.09-5.23 (m, 2H), 4.80-4.88 (m, 1H), 3.72-3.84 (m, 1H), 3.69 (br d, J = 4.52 Hz, 3H), 3.57-3.66 (m, 4H), 3.38-3.53 (m, 2H), 3.13 (br dd, J = 10.32, 12.57 Hz, 1H), 3.05 (br t, J = 11.60 Hz, 1H), 2.24 (br t, J = 9.54 Hz, 1H), 1.85-1.93 (m, 1H), 1.15-1.27 (m, 1H) | B | SFC: Chiralpak IC, 15% methanol. Peak2 |
| 479 | 600 MHz DMSO-d₆ | 7.26-7.29 (m, 1H), 7.25 (t, J = 6.83 Hz, 1H), 6.99 (t, J = 9.32 Hz, 1H), 5.05-5.21 (m, 2H), 4.87-5.01 (m, 1H), 4.23 (q, J = 9.55 Hz, 2H), 3.69-3.79 (m, 1H), 3.58 (dt, J = 4.36, 8.99 Hz, 1H), 3.27-3.30 (m, 3H), 3.06-3.14 (m, 1H), 2.97-3.03 (m, 2H), 2.65 (s, 3H), 2.16-2.25 (m, 1H), 1.81-1.95 (m, 1H) | B | FC using an (2 × Chiralpak IC 2 × 25 cm, 5 μm column), Peak2 |
| 480 | 600 MHz DMSO-d₆ | 8.23-8.31 (br s, 1H), 6.90-7.33 (m, 3H), 5.13-5.26 (m, 2H), 4.11-4.29 (m, 1H), 3.82-3.91 (m, 1H), 3.63 (br d, J = 9.19 Hz, 1H), 3.45-3.59 (m, 1H), 3.36 (td, J = 8.29, 16.43 Hz, 1H), 3.28 (s, 3H), 3.10-3.23 (m, 1H), 2.52-2.55 (m, 1H), 2.34-2.47 (m, 1H), 0.97-1.19 (m, 3H) | — | — |
| 481 | 600 MHz DMSO-d₆ | 7.28-7.59 (m, 1H), 7.05-7.16 (m, 1H), 6.75-6.95 (m, 1H), 4.77-4.93 (m, 1H), 4.08-4.53 (m, 1H), 4.02-4.32 (m, 1H), 3.32-3.32 (m, 2H), 3.21-3.30 (m, 1H), 2.76-2.93 (m, 1H), 2.53-2.70 (m, 1H), 1.68-1.86 (m, 1H), 1.45-1.63 (m, 1H), 1.02-1.18 (m, 1H), −0.05-0.15 (m, 1H) | — | — |
| 482 | 600 MHz DMSO-d₆ | 8.70 (br s, 2H), 7.26-7.32 (m, 1H), 7.02 (ddd, J = 2.53, 8.86, 9.79 Hz, 1H), 5.15-5.24 (m, 1H), 4.12-4.30 (m, 2H), 4.03-4.12 (m, 1H), 3.68 (br d, J = 11.91 Hz, 5H), 3.26-3.40 (m, 3H), 3.11-3.18 (m, 1H), 2.65 (br s, 1H), 2.58-2.63 (m, 1H), 2.52-2.56 (m, 4H) | B | SFC with Chiralcel OD-H, 10% methanol Peak2 |
| 483 | 600 MHz DMSO-d₆ | 8.70 (br s, 2H), 7.26-7.32 (m, 2H), 7.02 (ddd, J = 2.53, 8.86, 9.79 Hz, 1H), 5.15-5.24 (m, 2H), 4.12-4.30 (m, 2H), 4.03-4.12 (m, 2H), 3.68 (br d, J = 11.91 Hz, 2H), 3.26-3.40 (m, 4H), 3.11-3.18 (m, 1H), 2.65 (br s, 1H), 2.58-2.63 (m, 1H). | B | SFC: Chiralpak IC, 25% isopropanol. Peak2 |
| 484 | 600 MHz DMSO-d₆ | 8.14 (br s, 2H), 7.22-7.27 (m, 2H), 7.11-7.19 (m, 1H), 5.03-5.15 (m, 2H), 4.23 (dq, J = 3.35, 9.37 Hz, 1H), 3.58-3.69 (m, 2H), 3.27 (s, 3H), 3.15-3.25 (m, 2H), 2.96-3.03 (m, 2H), 2.85-2.93 (m, 1H), 1.79-2.00 (m, 1H), 1.55-1.61 (m, 1H) | B | SFC: Chiralpak IC, 25% isopropanol. Peak1 |
| 485 | 600 MHz DMSO-d₆ | 8.14 (br s, 2H), 7.23-7.28 (m, 2H), 6.98 (t, J = 9.21 Hz, 1H), 5.03-5.18 (m, 2H), 4.23 (q, J = 9.47 Hz, 2H), 3.63-3.82 (m, 1H), 3.47 (br s, 1H), 3.29-3.42 (m, 1H), 3.28 (s, 2H), 2.97-3.11 (m, 2H), 2.87-2.96 (m, 1H), 2.52-2.55 (m, 4H), 2.14-2.31 (m, 1H), 1.38-1.50 (m, 1H) | B | SFC using an Chiralpak IC 2 × 25 cm, 5 micron, a mobile phase of 25% isopropanol Peak 2 |
| 486 | 600 MHz DMSO-d₆ | 8.23 (br s, 2H), 7.15-7.28 (m, 1H), 6.98-7.14 (m, 2H), 6.78-6.91 (m, 1H), 5.09-5.28 (m, 1H), 4.16-4.29 (m, 1H), 3.50-3.89 (m, 3H), 3.40-3.49 (m, 1H), 3.26-3.30 (m, 2H), 2.54 (s, 2H), 2.15-2.33 (m, 1H) | B | SFC: Chiralpak AD-H analytical column, 25% isopropano Peak1 |
| 487 | 600 MHz DMSO-d₆ | 8.23 (br s, 2H), 7.14-7.28 (m, 1H), 7.12 (br s, 1H), 6.99-7.10 (m, 1H), 5.16-5.29 (m, 1H), 4.16-4.29 (m, 1H), 3.64-3.83 (m, 2H), 3.41 (br s, 2H), 3.37- | B | SFC: Chiralpak AD-H |

TABLE 3-continued

Characterization data for compounds made following Scheme 8.
The column "Separation Stage" indicates after which process step
regioisomers formed due to asymmetric benzimidazole substitution at $R^1$
in Scheme 8 were separated during the preparation of the tabulated final
compound (I = after preparation of the alkylated intermediate 1-59
(where at least one $R^1$ is not hydrogen); B prior to boc
deprotection; or F = final compound).

| Ex. # | Freq., Solvent | $^1$HNMR Data (δ ppm) | Separation Stage | SFC Isomer Separation Conditions |
|---|---|---|---|---|
| | | 3.39 (m, 1H), 3.26-3.29 (m, 2H), 2.52-2.55 (m, 2H), 2.15-2.33 (m, 1H) | | analytical column, 25% isopropano Peak2 |
| 488 | 600 MHz DMSO-$d_6$ | 7.36-7.43 (m, 1H), 7.09 (dd, J = 2.49, 9.34 Hz, 1H), 6.87-6.96 (m, 1H), 5.03-5.09 (m, 2H), 4.17-4.28 (m, 2H), 3.73-3.79 (m, 1H), 3.71 (br d, J = 3.11 Hz, 1H), 3.40-3.49 (m, 2H), 3.23-3.29 (m, 1H), 2.89-3.08 (m, 6H), 2.51-2.57 (m, 1H), 1.72-1.82 (m, 1H) | B | SFC using two Regis Whelk-O s, s 2 × 25 cm, 5 micron columns Peak2 |
| 489 | 600 MHz DMSO-$d_6$ | 7.16-7.21 (m, 1H), 7.05 (dd, J = 2.49, 9.42 Hz, 1H), 6.78-6.84 (m, 1H), 5.07-5.19 (m, 2H), 4.20-4.46 (m, 2H), 3.52-3.65 (m, 2H), 3.40-3.51 (m, 2H), 3.26 (s, 3H), 3.07-3.14 (m, 1H), 1.87-2.00 (m, 1H), 1.62 (qd, J = 6.18, 12.45 Hz, 1H) | — | — |
| 490 | 600 MHz DMSO-$d_6$ | 7.16-7.21 (m, 1H), 7.05 (dd, J = 2.49, 9.42 Hz, 1H), 6.78-6.84 (m, 1H), 5.07-5.19 (m, 2H), 4.16-4.31 (m, 2H), 3.92 (br s, 1H), 3.77 (br s, 1H), 3.44-3.58 (m, 3H), 3.25-3.29 (m, 1H), 2.99 (s, 1H), 2.52-2.55 (m, 1H), 2.28 (qd, J = 7.20, 13.97 Hz, 1H), 2.00 (br d, J = 4.83 Hz) | — | — |
| 491 | 600 MHz DMSO-$d_6$ | 7.17-7.23 (m, 1H), 7.08 (dd, J = 2.49, 9.42 Hz, 1H), 6.79-6.89 (m, 1H), 5.07-5.21 (m, 2H), 4.16-4.41(m, 2H), 3.39-3.58 (m, 2H), 3.14-3.27 (m, 2H), 2.94-3.03 (m, 1H), 2.68 (br d, J = 6.93 Hz, 2H), 2.52-2.57 (m, 1H), 2.27-2.34 (m, 1H), 1.95-2.04 (m, 1H), 1.65 (qd, J = 8.03, 12.28 Hz, 1H) | — | — |
| 492 | 600 MHz DMSO-$d_6$ | 1.79 (br dd, J = 8.64, 3.11 Hz, 1H) 1.84 (br s, 1H) 2.88-2.97 (m, 2H) 2.97-3.13 (m, 4H) 3.17 (s, 1H), 3.24-3.28 (m, 3H) 3.38-3.53 (m, 2H) 3.68-3.80 (m, 2H) 4.17-4.28 (m, 2H) 4.48 (q, J = 8.93 Hz, 1H) 5.00 (s, 1H) 5.07 (s, 1H) 6.87-6.94 (m, 1H) 7.15 (dd, J = 8.68, 4.79 Hz, 1H) 7.18-7.25 (m, 1H) | — | — |
| 493 | 600 MHz DMSO-$d_6$ | 1.65-1.82 (m, 2H) 1.84 (br s, 1H) 2.52-2.56 (m, 1H) 2.90-2.96 (m, 2H) 2.98-3.13 (m, 5H) 3.17 (s, 1H) 3.24-3.28 (m, 3H) 3.38-3.53 (m, 3H) 3.69-3.79 (m, 2H) 4.09 (br s, 1H) 4.16-4.29 (m, 2H) 4.48 (q, J = 9.16 Hz, 1H) 5.00 (s, 1H) 5.07 (s, 2H) 6.88-6.94 (m, 1H) 7.13-7.25 (m, 2H) | — | — |

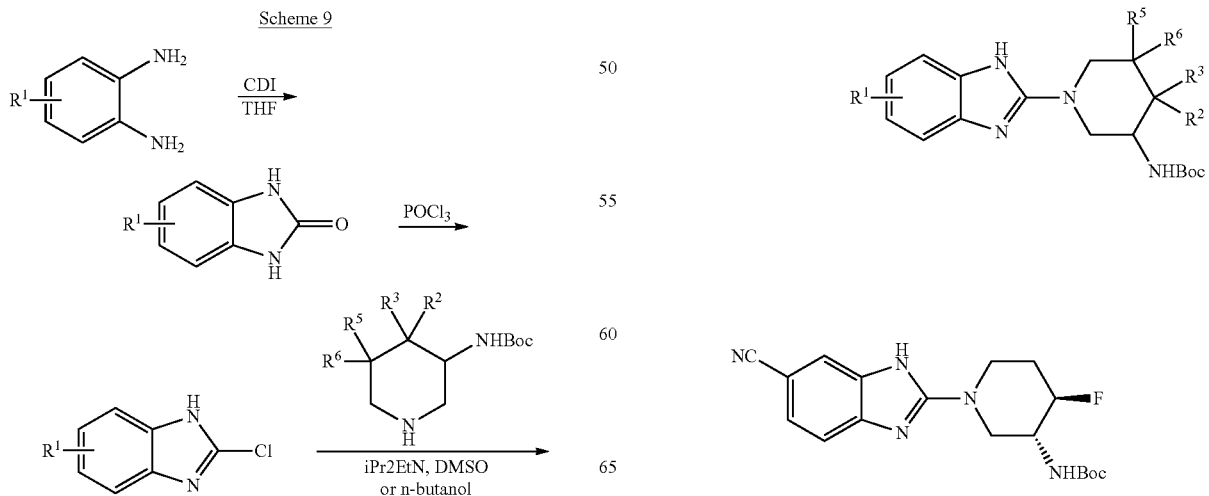

Scheme 9

Intermediate 60: tert-butyl ((3R,4R)-1-(6-cyano-1H-benzo[d]imidazol-2-yl)-4-fluoropiperidin-3-yl)carbamate

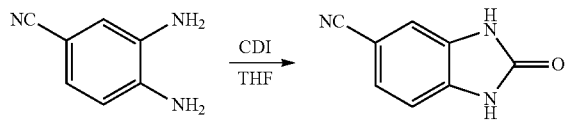

Step 1. 2-oxo-2,3-dihydro-1H-benzo[d]imidazole-5-carbonitrile

To a solution of 1,2-diamino-4-cyanobenzene (1.00 mL, 7.51 mmol) in tetrahydrofuran (5 mL) was added 1,1'-carbonyldiimidazole (1.22 g, 7.51 mmol). The reaction was stirred at ambient temperature for one hour, concentrated, then triturated with water. The brown precipitate was collected by vacuum filtration to provide 2-oxo-2,3-dihydro-1H-benzo[d]imidazole-5-carbonitrile as a brown powder. MS (ESI, pos. ion) m/z: 160.2 [M+1]

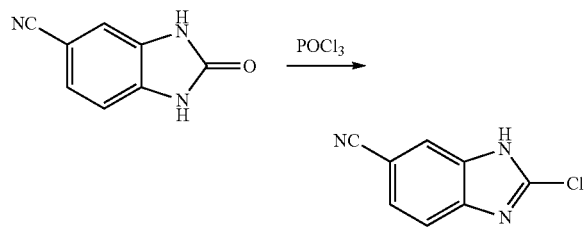

Step 2. 2-chloro-1H-benzo[d]imidazole-6-carbonitrile

To a suspension of 2-oxo-2,3-dihydro-1H-benzo[d]imidazole-5-carbonitrile (XVIII, 1.19 g, 7.48 mmol, 1 equiv) in acetonitrile (5 mL) was added phosphorus(v) oxychloride (1.398 mL, 14.95 mmol). The reaction was stirred at 110° C. for 16 hours, then cooled to room temperature. It was diluted with acetonitrile and then slowly added to a cold, rapidly-stirring beaker of saturated aqueous sodium bicarbonate (50 mL). The mixture was extracted with ethyl acetate; which was dried over anhydrous magnesium sulfate, filtered, and concentrated to provide 2-chloro-1H-benzo[d]imidazole-6-carbonitrile as a tan powder. (ESI, pos. ion) m/z: 178.2 [M+1]

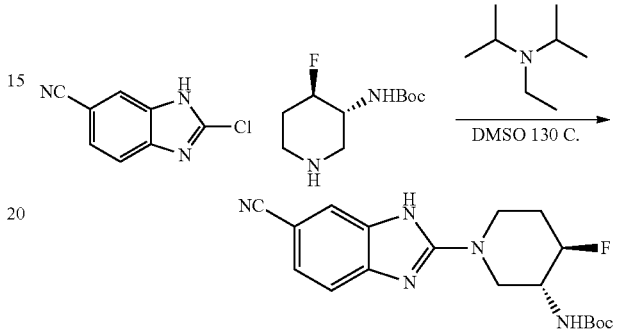

Step 3. tert-butyl ((3R,4R)-1-(6-cyano-1H-benzo[d]imidazol-2-yl)-4-fluoropiperidin-3-yl)carbamate (Intermediate 60)

N,N-diisopropylethylamine (3.93 mL, 22.52 mmol), 2-chloro-1H-benzo[d]imidazole-6-carbonitrile (2 g, 11.26 mmol), tert-butyl ((3R,4R)-4-fluoropiperidin-3-yl)carbamate (2.95 g, 13.51 mmol), and 1-butanol (25 mL) were combined in a flask and heated to 130 C for 48 hours. The mixture was concentrated, then loaded onto a 125 g RediSep ISCO cartridge, eluting with 0-4% MeOH in DCM to provide the title compound as a light brown foam. (ESI, pos. ion) m/z: 360.2 [M+1]

The following intermediates were synthesized using a sequence analogous to that described for intermediate 60 and general scheme 9 above:

TABLE 4

SnAr Intermediates prepared following Scheme 9

| Int # | Structure | Compound Name | MS MH+ |
|---|---|---|---|
| 60 | 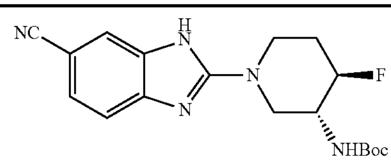 | tert-butyl ((3R,4R)-1-(6-cyano-1H-benzo[d]imidazol-2-yl)-4-fluoropiperidin-3-yl)carbamate | 360.2 |
| 61 | 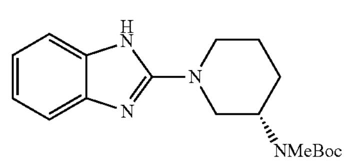 | (S)-tert-butyl (1-(1H-benzo[d]imidazol-2-yl)piperidin-3-yl)(methyl)carbamate | 331.3 |
| 62 | 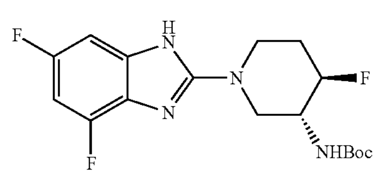 [SMILES: CC(C)(C)OC(=O)N[C@@H]1CN(c2nc3c(F)cc(F)cc3[nH]2)CC[C@H]1F] | tert-butyl ((3R,4R)-1-(4,6-difluoro-1H-benzo[d]imidazol-2-yl)-4-fluoropiperidin-3-yl)carbamate | 371.2 |

TABLE 4-continued

SnAr Intermediates prepared following Scheme 9

| Int # | Structure | Compound Name | MS MH+ |
|---|---|---|---|
| 63 | 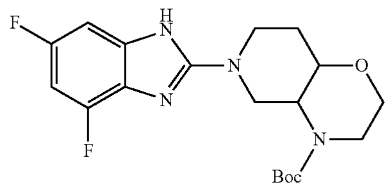 [SMILES: CC(C)(C)OC(=O)N1CCOC2CCN(c3nc4c(F)cc(F)cc4[nH]3)CC21] | tert-butyl 6-(4,6-difluoro-1H-benzo[d]imidazol-2-yl)hexahydro-2H-pyrido[4,3-b][1,4]oxazine-4(3H)-carboxylate | 396.2 |
| 64 | 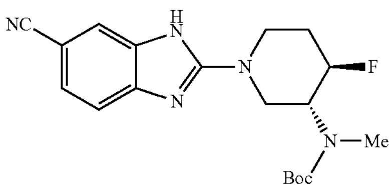 [SMILES: CN(C(=O)OC(C)(C)C)[C@@H]1CN(c2nc3ccc(C#N)cc3[nH]2)CC[C@H]1F] | tert-butyl ((3R,4R)-1-(6-cyano-1H-benzo[d]imidazol-2-yl)-4-fluoropiperidin-3-yl)(methyl)carbamate | 374.2 |
| 65 | 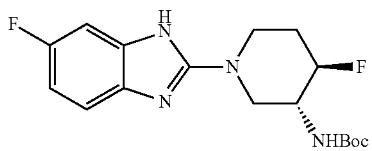 [SMILES: CC(C)(C)OC(=O)N[C@@H]1CN(c2nc3ccc(F)cc3[nH]2)CC[C@H]1F] | tert-butyl ((3R,4R)-4-fluoro-1-(6-fluoro-1H-benzo[d]imidazol-2-yl)piperidin-3-yl)carbamate | 353.2 |
| 66 | 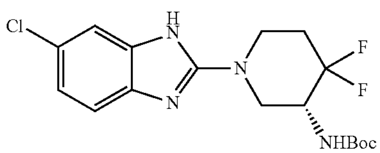 [SMILES: CC(C)(C)OC(=O)N[C@@H]1CN(c2nc3ccc(Cl)cc3[nH]2)CCC1(F)F] | (R)-tert-butyl (1-(6-chloro-1H-benzo[d]imidazol-2-yl)-4,4-difluoropiperidin-3-yl)carbamate | 387.2 |
| 67 | 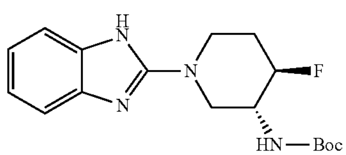 [SMILES: CC(C)(C)OC(=O)N[C@@H]1CN(c2nc3ccccc3[nH]2)CC[C@H]1F] | tert-butyl ((3R,4R)-1-(1H-benzo[d]imidazol-2-yl)-4-fluoropiperidin-3-yl)carbamate | 335.0 |
| 68 | 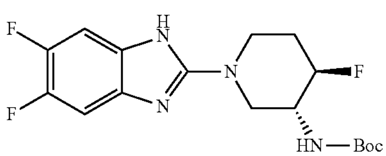 [SMILES: CC(C)(C)OC(=O)N[C@@H]1CN(c2nc3cc(F)c(F)cc3[nH]2)CC[C@H]1F] | tert-butyl ((3R,4R)-1-(5,6-difluoro-1H-benzo[d]imidazol-2-yl)-4-fluoropiperidin-3-yl)carbamate | 371.2 |
| 69 | 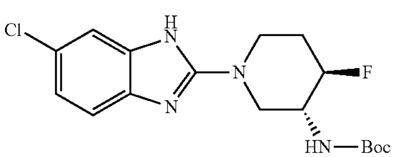 [SMILES: CC(C)(C)OC(=O)N[C@@H]1CN(c2nc3ccc(Cl)cc3[nH]2)CC[C@H]1F] | tert-butyl ((3R,4R)-1-(6-chloro-1H-benzo[d]imidazol-2-yl)-4-fluoropiperidin-3-yl)carbamate | 369.2 |
| 70 | 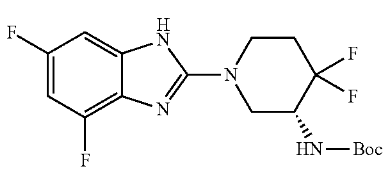 [SMILES: CC(C)(C)OC(=O)N[C@@H]1CN(c2nc3c(F)cc(F)cc3[nH]2)CCC1(F)F] | (R)-tert-butyl (1-(4,6-difluoro-1H-benzo[d]imidazol-2-yl)-4,4-difluoropiperidin-3-yl)carbamate | 389.2 |
| 71 | 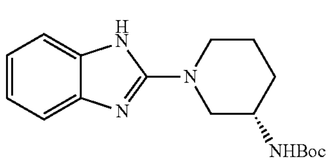 [SMILES: CC(C)(C)OC(=O)N[C@H]1CCCN(c2nc3ccccc3[nH]2)C1] | (S)-tert-butyl (1-(1H-benzo[d]imidazol-2-yl)piperidin-3-yl)carbamate | 317.2 |

TABLE 4-continued

SnAr Intermediates prepared following Scheme 9

| Int # | Structure | Compound Name | MS MH+ |
|---|---|---|---|
| 72 | 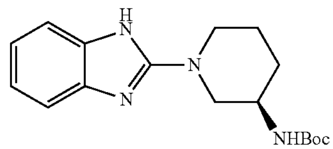 [SMILES: CC(C)(C)OC(=O)N[C@@H]1CCCN(c2nc3ccccc3[nH]2)C1] | (R)-tert-butyl (1-(1H-benzo[d]imidazol-2-yl)piperidin-3-yl)carbamate | 317.2 |
| 73 | 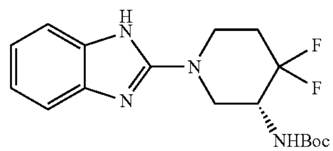 [SMILES: CC(C)(C)OC(=O)N[C@@H]1CN(c2nc3ccccc3[nH]2)CCC1(F)F] | (R)-tert-butyl (1-(1H-benzo[d]imidazol-2-yl)-4,4-difluoropiperidin-3-yl)carbamate | 353.2 |
| 74 | 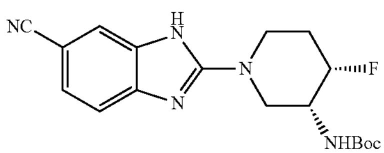 [SMILES: CC(C)(C)OC(=O)N[C@@H]1CN(c2nc3ccc(C#N)cc3[nH]2)CC[C@@H]1F] | tert-butyl ((3R,4S)-1-(6-cyano-1H-benzo[d]imidazol-2-yl)-4-fluoropiperidin-3-yl)carbamate | 360.2 |
| 75 | 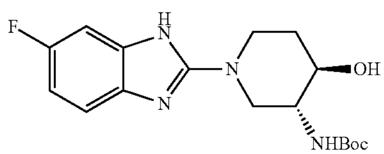 [SMILES: CC(C)(C)OC(=O)N[C@@H]1CN(c2nc3ccc(F)cc3[nH]2)CC[C@H]1O] | tert-butyl ((3R,4R)-1-(6-fluoro-1H-benzo[d]imidazol-2-yl)-4-hydroxypiperidin-3-yl)carbamate | 351.2 |
| 76 | 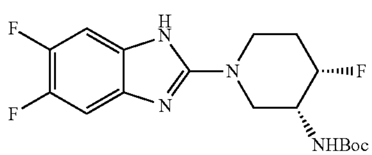 [SMILES: CC(C)(C)OC(=O)N[C@@H]1CN(c2nc3cc(F)c(F)cc3[nH]2)CC[C@@H]1F] | tert-butyl ((3R,4S)-1-(5,6-difluoro-1H-benzo[d]imidazol-2-yl)-4-fluoropiperidin-3-yl)carbamate | 371.0 |
| 77 | 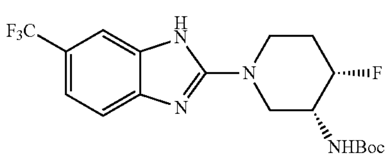 [SMILES: CC(C)(C)OC(=O)N[C@@H]1CN(c2nc3ccc(C(F)(F)F)cc3[nH]2)CC[C@@H]1F] | tert-butyl ((3R,4S)-4-fluoro-1-(6-(trifluoromethyl)-1H-benzo[d]imidazol-2-yl)piperidin-3-yl)carbamate | 403.2 |
| 78 | 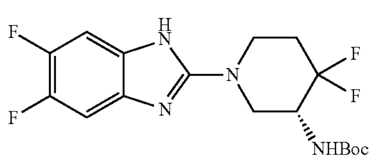 [SMILES: CC(C)(C)OC(=O)N[C@@H]1CN(c2nc3cc(F)c(F)cc3[nH]2)CCC1(F)F] | (R)-tert-butyl (1-(5,6-difluoro-1H-benzo[d]imidazol-2-yl)-4,4-difluoropiperidin-3-yl)carbamate | 389.2 |
| 79 | 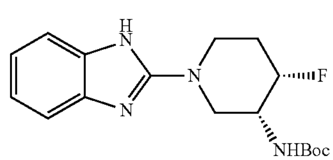 [SMILES: CC(C)(C)OC(=O)N[C@@H]1CN(c2nc3ccccc3[nH]2)CC[C@@H]1F] | tert-butyl ((3R,4S)-1-(1H-benzo[d]imidazol-2-yl)-4-fluoropiperidin-3-yl)carbamate | 335.2 |
| 80 | 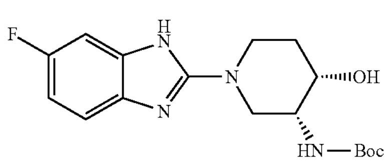 [SMILES: CC(C)(C)OC(=O)N[C@@H]1CN(c2nc3ccc(F)cc3[nH]2)CC[C@@H]1O] | tert-butyl ((3R,4S)-1-(6-fluoro-1H-benzo[d]imidazol-2-yl)-4-hydroxypiperidin-3-yl)carbamate | 351.2 |

TABLE 4-continued

SnAr Intermediates prepared following Scheme 9

| Int # | Structure | Compound Name | MS MH+ |
|---|---|---|---|
| 81 | 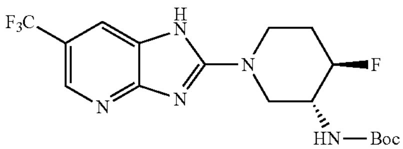 [SMILES: CC(C)(C)OC(=O)N[C@@H]1CN(c2nc3ncc(C(F)(F)F)cc3[nH]2)CC[C@H]1F] | tert-butyl ((3R,4R)-4-fluoro-1-(6-(trifluoromethyl)-1H-imidazo[4,5-b]pyridin-2-yl)piperidin-3-yl)carbamate | 404.2 |
| 82 | 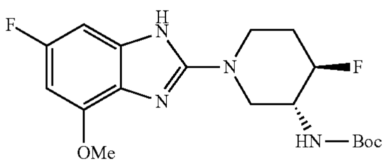 [SMILES: COc1cc(F)cc2[nH]c(N3CC[C@@H](F)[C@H](NC(=O)OC(C)(C)C)C3)nc12] | tert-butyl ((3R,4R)-4-fluoro-1-(6-fluoro-4-methoxy-1H-benzo[d]imidazol-2-yl)piperidin-3-yl)carbamate | 383.2 |
| 83 | 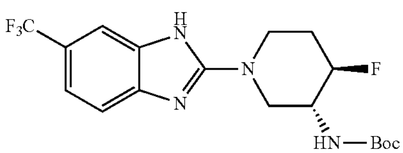 [SMILES: CC(C)(C)OC(=O)N[C@@H]1CN(c2nc3ccc(C(F)(F)F)cc3[nH]2)CC[C@H]1F] | tert-butyl ((3R,4R)-4-fluoro-1-(6-(trifluoromethyl)-1H-benzo[d]imidazo-2-yl)piperidin-3-yl)carbamate | 403.2 |
| 84 | 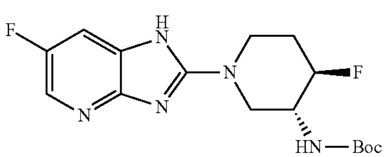 [SMILES: CC(C)(C)OC(=O)N[C@@H]1CN(c2nc3ncc(F)cc3[nH]2)CC[C@H]1F] | tert-butyl ((3R,4R)-4-fluoro-1-(6-fluoro-1H-imidazo[4,5-b]pyridin-2-yl)piperidin-3-yl)carbamate | 354.2 |
| 85 | 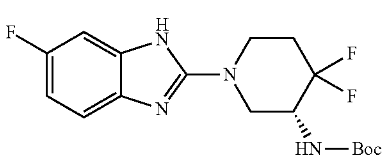 [SMILES: CC(C)(C)OC(=O)N[C@@H]1CN(c2nc3ccc(F)cc3[nH]2)CCC1(F)F] | (R)-tert-butyl (4,4-difluoro-1-(6-fluoro-1H-benzo[d]imidazol-2-yl)piperidin-3-yl)carbamate | 371.2 |

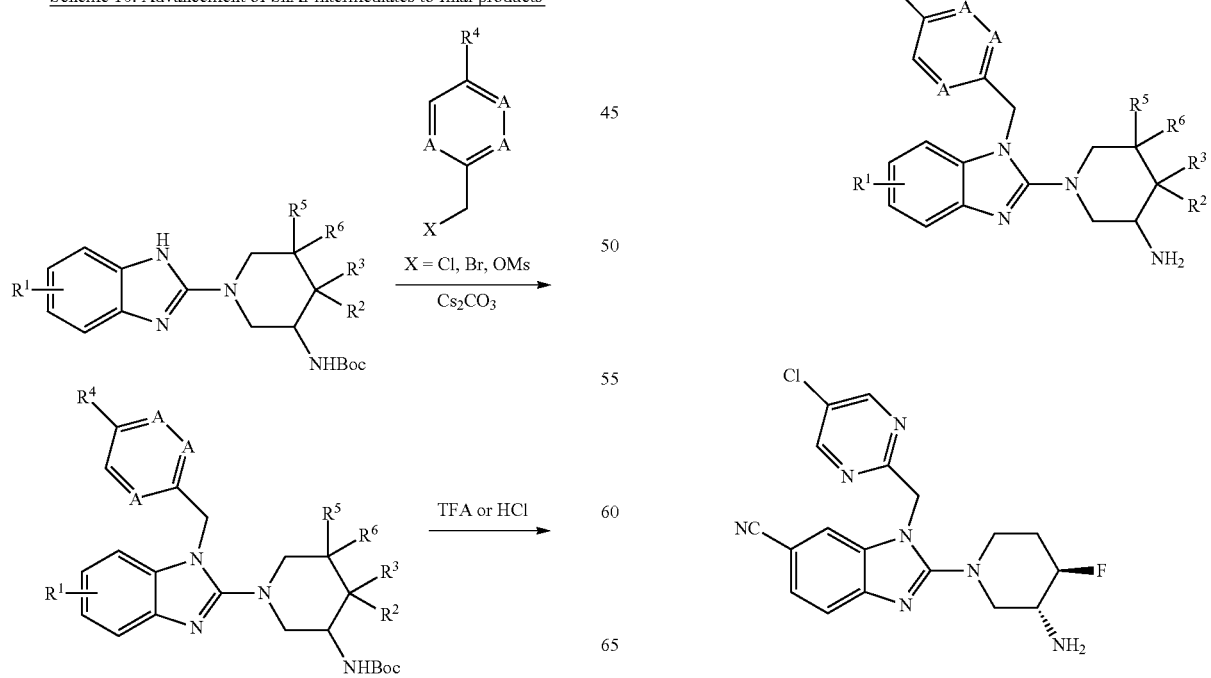

Scheme 10. Advancement of SnAr intermediates to final products

Example 187: 2-((3R,4R)-3-amino-4-fluoropiperidin-1-yl)-1-((5-chloropyrimidin-2-yl)methyl)-1H-benzo[d]imidazole-6-carbonitrile

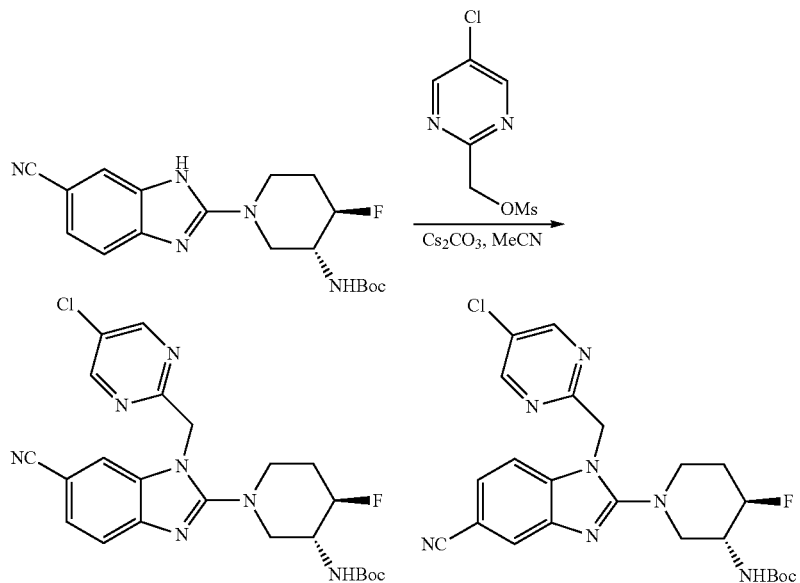

Step 1. tert-butyl ((3R,4R)-1-(1-((5-chloropyrimidin-2-yl)methyl)-6-cyano-1H-benzo[d]imidazol-2-yl)-4-fluoropiperidin-3-yl)carbamate Cesium carbonate (0.707 mg, 2.170 mmol), tert-butyl ((3R,4R)-1-(6-cyano-1H-benzo[d]imidazol-2-yl)-4-fluoropiperidin-3-yl)carbamate (390 mg, 1.085 mmol), (5-chloropyrimidin-2-yl)methyl methanesulfonate (290 mg, 1.302 mmol), and acetonitrile (10 mL) were combined in a vial and stirred overnight. The mixture was poured into water and extracted with DCM (3×). The organics were combined, dried over Na2SO4, filtered, and concentrated. The brown solid was dissolved in DCM, loaded onto a 20 g plug of silica and flushed with EtOAc (~4 column volumes). The EtOAc was concentrated to provide tert-butyl ((3R,4R)-1-(1-((5-chloropyrimidin-2-yl)methyl)-6-cyano-1H-benzo[d]imidazol-2-yl)-4-fluoropiperidin-3-yl)carbamate and tert-butyl ((3R,4R)-1-(1-((5-chloropyrimidin-2-yl)methyl)-5-cyano-1H-benzo[d]imidazol-2-yl)-4-fluoropiperidin-3-yl)carbamate as a mixture of isomers. The isomers were separated using chiral SFC (Chiralcel AD, 25% IPA, peak 1). (ESI, pos. ion) m/z: 486.2 [M+1]

Boc Deprotection Using TFA (Procedure B)

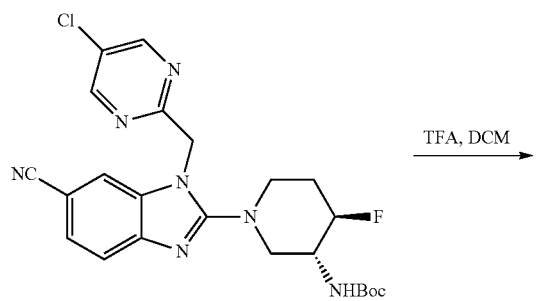

TFA, DCM

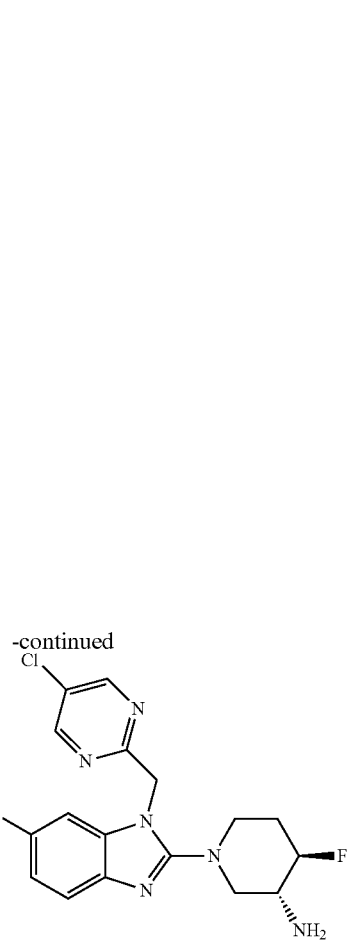

Step 2. 2-((3R,4R)-3-amino-4-fluoropiperidin-1-yl)-1-((5-chloropyrimidin-2-yl)methyl)-1H-benzo[d]imidazole-6-carbonitrile (Example 187)

tert-Butyl ((3R,4R)-1-(1-((5-chloropyrimidin-2-yl)methyl)-6-cyano-1H-benzo[d]imidazol-2-yl)-4-fluoropiperidin-3-yl)carbamate (150 mg, 0.309 mmol) was loaded into a vial. DCM (5 mL), then TFA (2 mL) was added. After 1 hour, the mixture was poured onto an SCX column, prewetted with methanol, flushed with methanol, then eluted with methanolic ammonia. The residue was redissolved in MeCN/H₂O, frozen, and lyophilized to provide the title compound as a white solid. $^1$H NMR (500 MHz, MeOD) δ 8.80 (s, 2H), 7.65-7.69 (m, 1H), 7.54-7.61 (m, 1H), 7.49 (d, J=8.30 Hz, 1H), 5.57 (s, 2H), 4.42-4.60 (m, 1H), 3.72-3.80 (m, 1H), 3.64 (br d, J=13.23 Hz, 1H), 3.15-3.27 (m, 2H), 3.06 (dd, J=9.21, 12.59 Hz, 1H), 2.13-2.27 (m, 1H), 1.80-1.99 (m, 1H). (ESI, pos. ion) m/z: 386.2 [M+1]

Note: In some cases, the free base was redissolved in DCM, and HCl was added to crash out the HCl salt. This is noted in the table as a TFA deprotection, but HCl product.

Alternative Boc Deprotection with HCl (Procedure A)

Step 2. 2-((3R,4R)-3-amino-4-fluoropiperidin-1-yl)-1-((5-methoxypyrimidin-2-yl)methyl)-1H-benzo[d]imidazole-6-carbonitrile hydrochloride (Example 242)

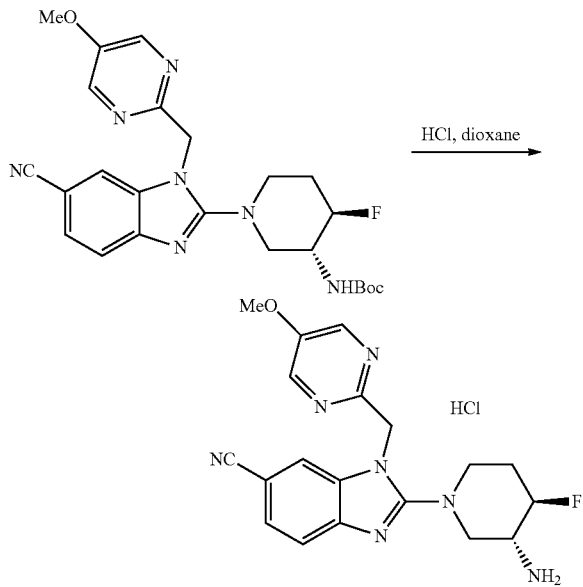

tert-Butyl ((3R,4R)-1-(6-cyano-1-((5-methoxypyrimidin-2-yl)methyl)-1H-benzo[d]imidazol-2-yl)-4-fluoropiperidin-3-yl)carbamate (69 mg) was dissolved in dioxane (2 mL), and 4 N HCl in dioxane (500 uL) was added. The reaction was stirred at ambient temperature overnight, then concentrated in vacuo to provide the title compound as a white solid. $^1$H NMR (500 MHz, MeOD) δ 8.52 (s, 2H), 7.94 (s, 1H), 7.66-7.74 (m, 2H), 5.54-5.67 (m, 2H), 4.77-4.93 (m, 1H), 4.21-4.30 (m, 1H), 4.01 (br d, J=12.98 Hz, 1H), 3.96 (s, 3H), 3.71-3.78 (m, 1H), 3.43-3.50 (m, 2H), 2.32-2.46 (m, 1H), 1.98-2.14 (m, 1H). (ESI, pos. ion) m/z: 382.2 [M+1].

Note: HC salt was sometimes free based using an aqueous work up or using ion exchange chromatography. Isolation of salt or free base is specified in table.

The following compounds were made in a manner analogous to that outlined in Schemes 9 and 10:

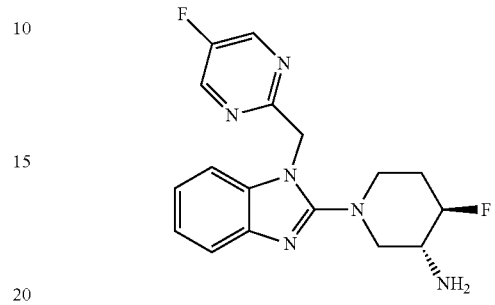

Example 188

(3R,4R)-4-fluoro-1-(1-((5-fluoropyrimidin-2-yl)methyl)-1H-benzo[d]imidazol-2-yl)piperidin-3-amine(3R,4R)-4-fluoro-1-(1-((5-fluoropyrimidin-2-yl)methyl)-1H-benzo[d]imidazol-2-yl)piperidin-3-amine was synthesized on 0.3 mmol scale following a sequence analogous to that described above. The Boc deprotection was accomplished using the TFA procedure. $^1$H NMR (500 MHz, MeOD) δ 8.68-8.74 (s, 2H), 7.47-7.52 (m, 1H), 7.14-7.20 (m, 2H), 7.08-7.13 (m, 1H), 5.53 (s, 2H), 4.34-4.52 (m, 1H), 3.64 (dtd, J=1.95, 4.14, 12.36 Hz, 1H), 3.48-3.57 (m, 1H), 3.04-3.21 (m, 2H), 2.98 (dd, J=8.82, 12.20 Hz, 1H), 2.12-2.25 (m, 1H), 1.82-1.92 (m, 1H). (ESI, pos. ion) m/z: 345.2 [M+1].

The following Examples were synthesized using a sequence analogous to that described for examples 239-240 and general scheme 9-10 above:

TABLE 5

Compounds made following schemes 9-10

| Ex. # | SnAr Intermediate | Electrophile | Boc Deprotection Procedure | Structure | Compound Name | MS MH+ |
|---|---|---|---|---|---|---|
| 187 | 60 | 5-chloropyrimidine with OMs | B | structure with Cl-pyrimidine, NC-benzimidazole, fluoropiperidine-NH2 | (2-((3R,4R)-3-amino-4-fluoropiperidin-1-yl)-1-((5-chloropyrimidin-2-yl)methyl)-1H-benzo[d]imidazole-6-carbonitrile | 386.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 188 | 67 | 5-fluoro-2-(chloromethyl)pyrimidine | B | 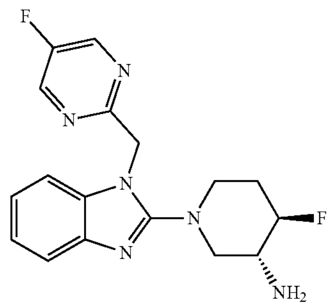 [SMILES: N[C@@H]1CN(c2nc3ccccc3n2Cc2ncc(F)cn2)CC[C@H]1F] | (3R,4R)-4-fluoro-1-(1-((5-fluoropyrimidin-2-yl)methyl)-1H-benzo[d]imidazol-2-yl)piperidin-3-amine | 345.2 |
| 189 | 67 | 5-fluoro-2-(chloromethyl)pyridine | B | 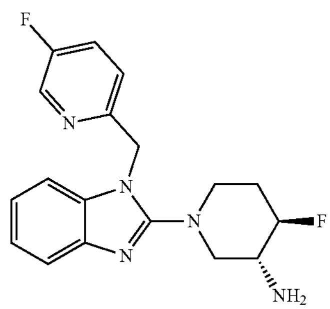 [SMILES: N[C@@H]1CN(c2nc3ccccc3n2Cc2ccc(F)cn2)CC[C@H]1F] | (3R,4R)-4-fluoro-1-(1-((5-fluoropyridin-2-yl)methyl)-1H-benzo[d]imidazol-2-yl)piperidin-3-amine | 344.2 |
| 190 | 60 | 5-fluoro-2-(chloromethyl)pyridine | B | 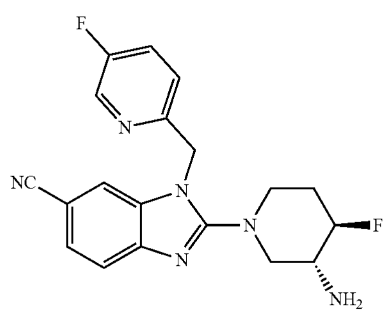 [SMILES: N#Cc1ccc2nc(N3CC[C@@H](F)[C@H](N)C3)n(Cc3ccc(F)cn3)c2c1] | 2-((3R,4R)-3-amino-4-fluoropiperidin-1-yl)-1-((5-fluoropyridin-2-yl)methyl)-1H-benzo[d]imidazole-6-carbonitrile | 369.0 |
| 191 | 60 | 5-fluoro-2-(chloromethyl)pyridine | B | 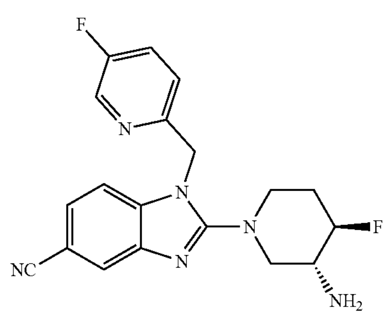 | 2-((3R,4R)-3-amino-4-fluoropiperidin-1-yl)-1-((5-fluoropyridin-2-yl)methyl)-1H-benzo[d]imidazole-5-carbonitrile | 369.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 192 | 67 | 5-bromo-2-(chloromethyl)pyrimidine | B | 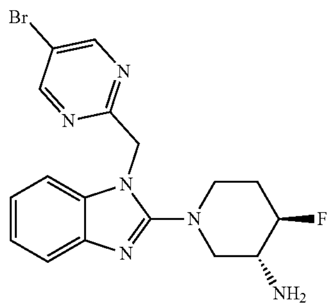 | (3R,4R)-1-(1-((5-bromopyrimidin-2-yl)methyl)-1H-benzo[d]imidazol-2-yl)-4-fluoropiperidin-3-amine | 405.0 |
| 193 | 67 | 2-(chloromethyl)-5-(trifluoromethyl)pyrimidine | B | 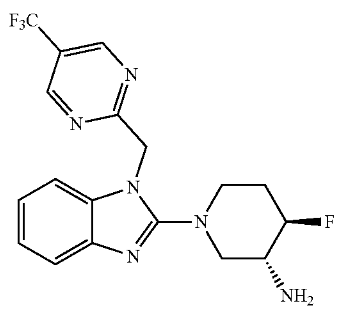 [SMILES: N[C@@H]1CN(c2nc3ccccc3n2Cc2ncc(C(F)(F)F)cn2)CC[C@H]1F] | (3R,4R)-4-fluoro-1-(1-((5-(trifluoromethyl)pyrimidin-2-yl)methyl)-1H-benzo[d]imidazol-2-yl)piperidin-3-amine | 395.2 |
| 194 | 67 | 2-(chloromethyl)-5-methoxypyrimidine | B | 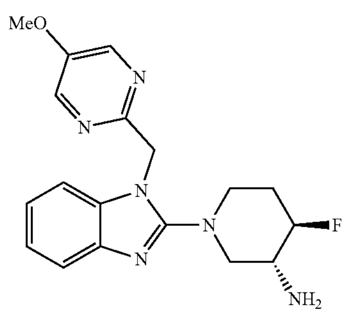 [SMILES: COc1cnc(Cn2c(N3CC[C@@H](F)[C@H](N)C3)nc3ccccc32)nc1] | (3R,4R)-4-fluoro-1-(1-((5-methoxypyrimidin-2-yl)methyl)-1H-benzo[d]imidazol-2-yl)piperidin-3-amine | 357.2 |
| 195 | 67 | (5-chloropyrimidin-2-yl)methyl methanesulfonate | B | 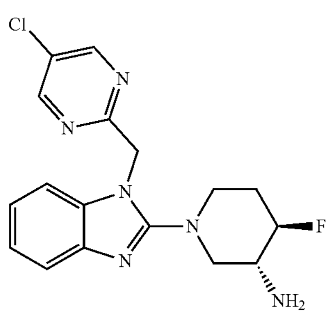 [SMILES: N[C@@H]1CN(c2nc3ccccc3n2Cc2ncc(Cl)cn2)CC[C@H]1F] | (3R,4R)-1-(1-((5-chloropyrimidin-2-yl)methyl)-1H-benzo[d]imidazol-2-yl)-4-fluoropiperidin-3-amine | 361.8 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 196 | 60 | | B | 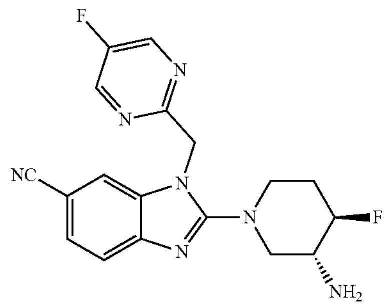 | 2-((3R,4R)-3-amino-4-fluoropiperidin-1-yl)-1-((5-fluoropyrimidin-2-yl)methyl)-1H-benzo[d]imidazole-6-carbonitrile | 370.0 |
| 197 | 60 | | B | 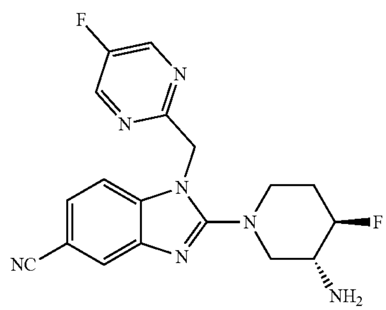 [SMILES: N#Cc1ccc2c(c1)nc(N1CC[C@@H](F)[C@H](N)C1)n2Cc1ncc(F)cn1] | 2-((3R,4R)-3-amino-4-fluoropiperidin-1-yl)-1-((5-fluoropyrimidin-2-yl)methyl)-1H-benzo[d]imidazole-5-carbonitrile | 370.0 |
| 198 | 60 | | B | 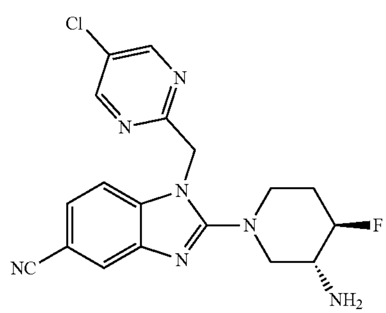 | 2-((3R,4R)-3-amino-4-fluoropiperidin-1-yl)-1-((5-cyanopyrimidin-2-yl)methyl)-1H-benzo[d]imidazole-5-carbonitrile | 386.0 |
| 199 | 73 | | B | 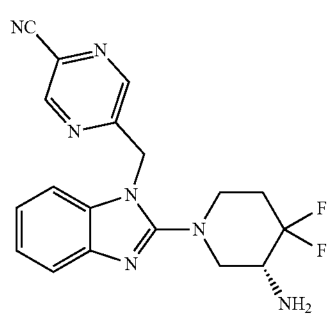 [SMILES: N#Cc1cnc(Cn2c(N3CCC(F)(F)[C@H](N)C3)nc3ccccc32)cn1] | 2-((3R,4R)-3-amino-4-fluoropiperidin-1-yl)-1-((5-chloropyrimidin-2-yl)methyl)-1H-benzo[d]imidazole-5-carbonitrile | 370.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 200 | 60 | 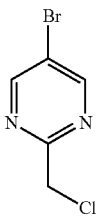 | B | 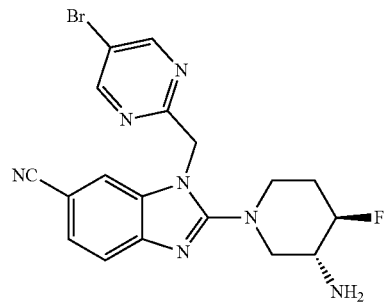 | 2-((3R,4R)-3-amino-4-fluoropiperidin-1-yl)-1-((5-bromopyrimidin-2-yl)methyl)-1H-benzo[d]imidazole-6-carbonitrile | 432.0 |
| 201 | 60 | 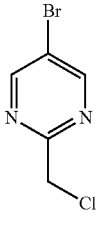 | B | 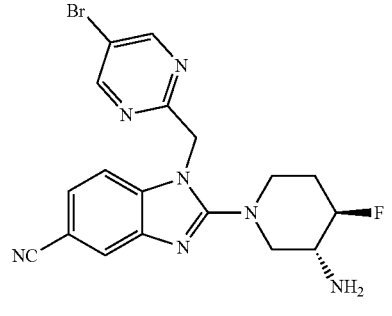 [SMILES: N#Cc1ccc2c(c1)nc(N1CC[C@@H](F)[C@H](N)C1)n2Cc1ncc(Br)cn1] | 2-((3R,4R)-3-amino-4-fluoropiperidin-1-yl)-1-((5-bromopyrimidin-2-yl)methyl)-1H-benzo[d]imidazole-5-carbonitrile | 432.0 |
| 202 | 67 | 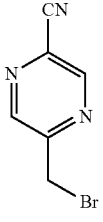 | B | 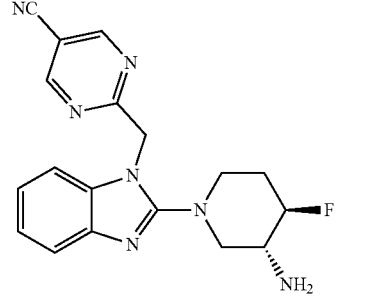 | 5-((2-((3R,4R)-3-amino-4-fluoropiperidin-1-yl)-1H-benzo[d]imidazol-1-yl)methyl)pyrazine-2-carbonitrile | 352.2 |
| 203 | 74 | 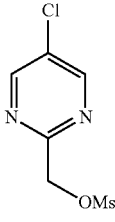 | B | 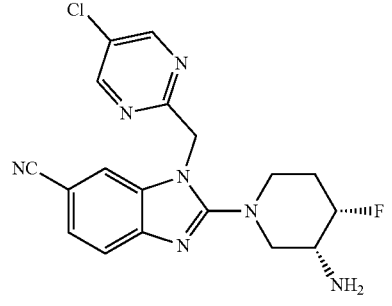 [SMILES: N#Cc1ccc2nc(N3CC[C@H](F)[C@H](N)C3)n(Cc3ncc(Cl)cn3)c2c1] | 2-((3R,4S)-3-amino-4-fluoropiperidin-1-yl)-1-((5-chloropyrimidin-2-yl)methyl)-1H-benzo[d]imidazole-6-carbonitrile | 386.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 204 | 74 | 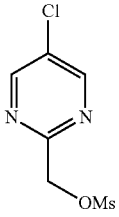 [SMILES: CS(=O)(=O)OCc1ncc(Cl)cn1] | B | 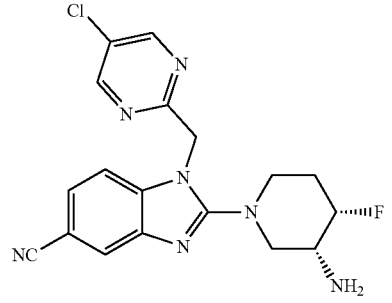 [SMILES: N#Cc1ccc2c(c1)nc(N1CC[C@H](F)[C@H](N)C1)n2Cc1ncc(Cl)cn1] | 2-((3R,4S)-3-amino-4-fluoropiperidin-1-yl)-1-((5-chloropyrimidin-2-yl)methyl)-1H-benzo[d]imidazole-5-carbonitrile | 386.2 |
| 205 | 75 | 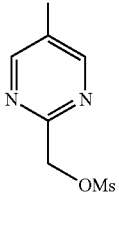 | B | 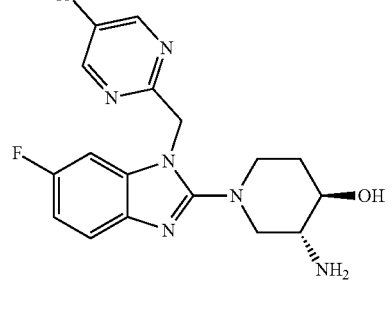 | (3R,4R)-3-amino-1-(1-((5-chloropyrimidin-2-yl)methyl)-6-fluoro-1H-benzo[d]imidazol-2-yl)piperidin-4-ol | 377.0 |
| 206 | 75 | 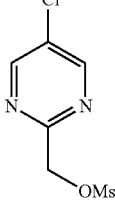 | B | 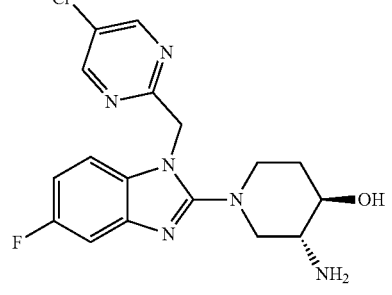 | (3R,4R)-3-amino-1-(1-((5-chloropyrimidin-2-yl)methyl)-5-fluoro-1H-benzo[d]imidazol-2-yl)piperidin-4-ol | 377.0 |
| 207 | 75 | 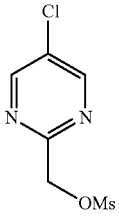 [SMILES: CS(=O)(=O)OCc1ncc(Cl)cn1] | B | 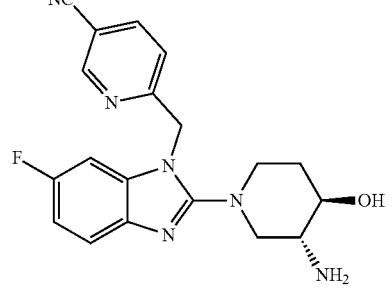 | 6-((2-((3R,4R)-3-amino-4-hydroxypiperidin-1-yl)-6-fluoro-1H-benzo[d]imidazol-1-yl)methyl)nicotinonitrile | 367.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 208 | 75 | 5-chloro-2-(mesyloxymethyl)pyrimidine | B | 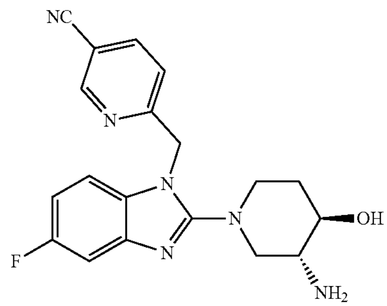 [SMILES: N#Cc1ccc(Cn2c(N3CC[C@@H](O)[C@H](N)C3)nc3cc(F)ccc32)nc1] | 6-((2-((3R,4R)-3-amino-4-hydroxypiperidin-1-yl)-5-fluoro-1H-benzo[d]imidazol-1-yl)methyl)nicotinonitrile | 367.2 |
| 209 | 71 | 2-(bromomethyl)-5-chloropyridine | B | 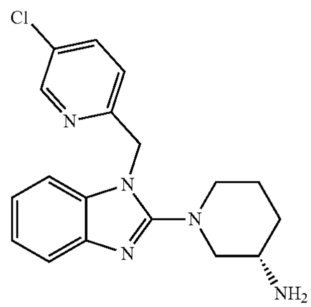 [SMILES: N[C@H]1CCCN(c2nc3ccccc3n2Cc2ccc(Cl)cn2)C1] | (S)-1-(1-((5-chloropyridin-2-yl)methyl)-1H-benzo[d]imidazol-2-yl)piperidin-3-amine | 342.0 |
| 210 | 71 | 5-(bromomethyl)-2-cyanopyridine | B | 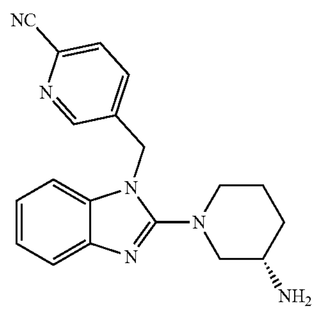 [SMILES: N#Cc1ccc(Cn2c(N3CCC[C@H](N)C3)nc3ccccc32)cn1] | (S)-5-((2-(3-aminopiperidin-1-yl)-1H-benzo[d]imidazol-1-yl)methyl)picolinonitrile | 333.2 |
| 211 | 67 | 2-(bromomethyl)-5-chloropyridine·HBr | A | 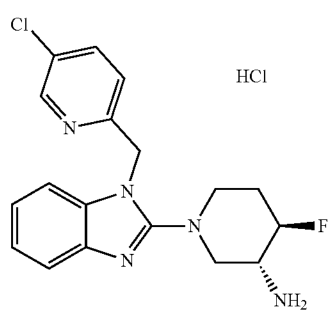 [SMILES: N[C@@H]1CN(c2nc3ccccc3n2Cc2ccc(Cl)cn2)CC[C@H]1F ; Cl] | (3R,4R)-1-(1-((5-chloropyridin-2-yl)methyl)-1H-benzo[d]imidazol-2-yl)-4-fluoropiperidin-3-amine hydrochloride | 360.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 212 | 73 | 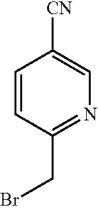 | A | 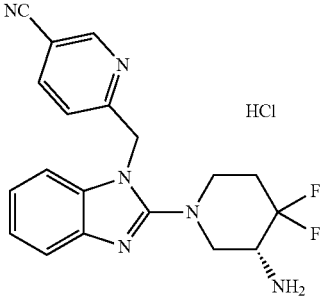 [SMILES: N#Cc1ccc(Cn2c(N3CCC(F)(F)[C@H](N)C3)nc3ccccc32)nc1 ; Cl] | (R)-6-((2-(3-amino-4,4-difluoropiperidin-1-yl)-1H-benzo[d]imidazol-1-yl)methyl)nicotinonitrile hydrochloride | 369.0 |
| 213 | 60 | 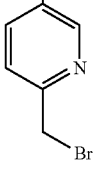 | B$^a$ | 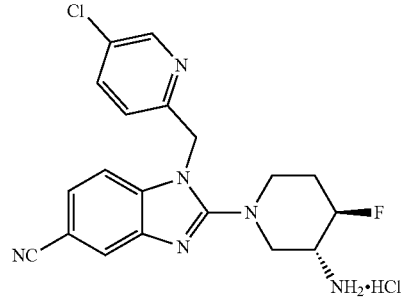 | 2-((3R,4R)-3-amino-4-fluoropiperidin-1-yl)-1-((5-chloropyridin-2-yl)methyl)-1H-benzo[d]imidazole-6-carbonitrile hydrochloride | 385.0 |
| 214 | 60 | 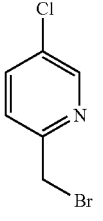 | B$^a$ | 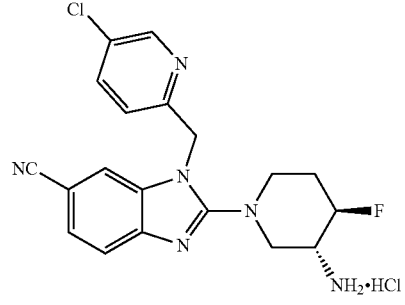 | 2-((3R,4R)-3-amino-4-fluoropiperidin-1-yl)-1-((5-chloropyridin-2-yl)methyl)-1H-benzo[d]imidazole-5-carbonitrile hydrochloride | 385.0 |
| 215 | 67 | 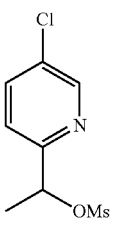 | B$^a$ | 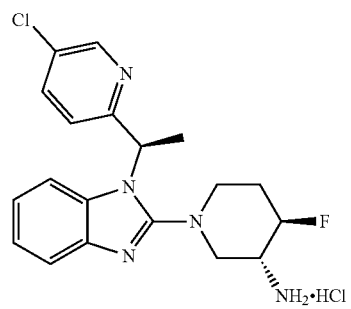 | (3R,4R)-1-(1-((R)-1-(5-chloropyridin-2-yl)ethyl)-1H-benzo[d]imidazol-2-yl)-4-fluoropiperidin-3-amine hydrochloride | 374.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 216 | 67 | 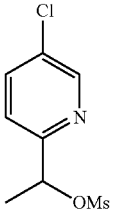 | B[a] | 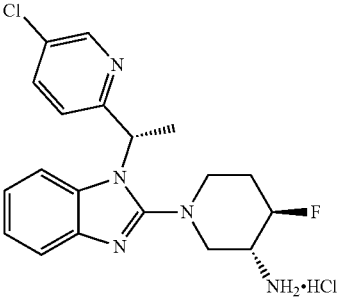 | (3R,4R)-1-(1-((S)-1-(5-chloropyridin-2-yl)ethyl)-1H-benzo[d]imidazol-2-yl)-4-fluoropiperidin-3-amine hydrochloride | 374.2 |
| 217 | 68 | 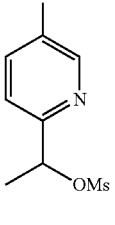 | B[a] | 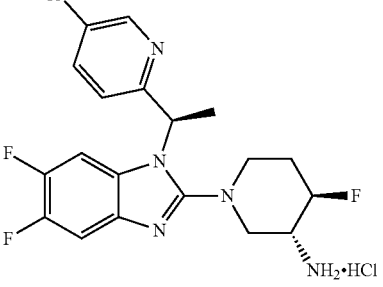 | (3R,4R)-1-(1-((R)-1-(5-chloropyridin-2-yl)ethyl)-5,6-difluoro-1H-benzo[d]imidazol-2-yl)-4-fluoropiperidin-3-amine hydrochloride | 410.2 |
| 218 | 68 | 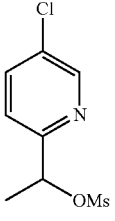 | B[a] | 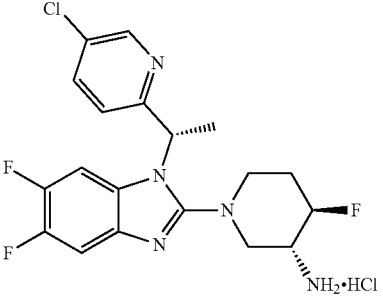 | (3R,4R)-1-(1-((S)-1-(5-chloropyridin-2-yl)ethyl)-5,6-difluoro-1H-benzo[d]imidazol-2-yl)-4-fluoropiperidin-3-amine hydrochloride | 410.2 |
| 219 | 69 | 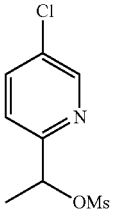 | B[a] | 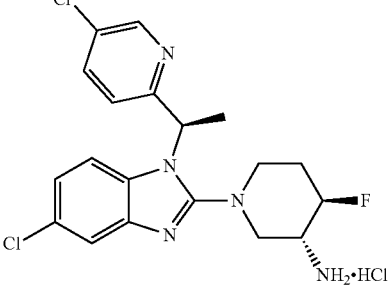 | (3R,4R)-1-(5-chloro-1-((R)-1-(5-chloropyridin-2-yl)ethyl)-1H-benzo[d]imidazol-2-yl)-4-fluoropiperidin-3-amine hydrochloride | 408.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 220 | 69 | 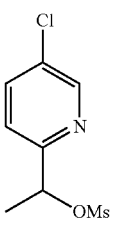 | B<sup>a</sup> | 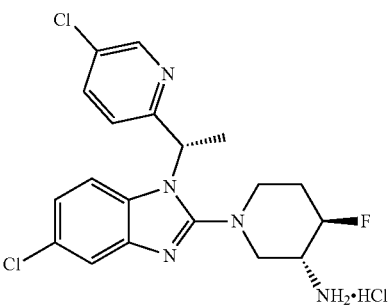 | (3R,4R)-1-(5-chloro-1-((S)-1-(5-chloropyridin-2-yl)ethyl)-1H-benzo[d]imidazol-2-yl)-4-fluoropiperidin-3-amine hydrochloride | 408.0 |
| 221 | 69 | 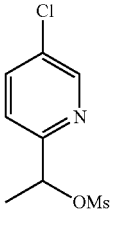 | B<sup>a</sup> | 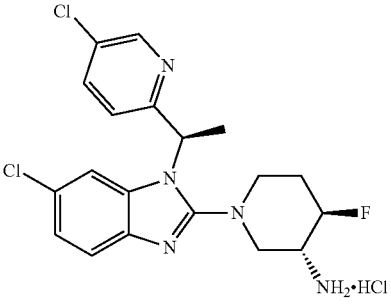 | (3R,4R)-1-(6-chloro-1-((R)-1-(5-chloropyridin-2-yl)ethyl)-1H-benzo[d]imidazol-2-yl)-4-fluoropiperidin-3-amine hydrochloride | 408.0 |
| 222 a | 69 | 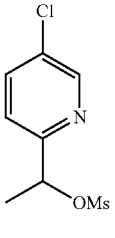 | B<sup>a</sup> | 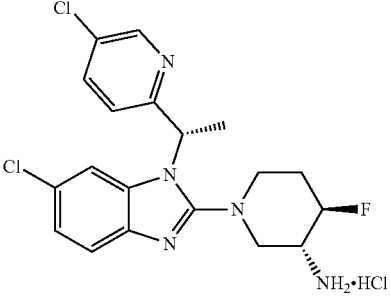 | (3R,4R)-1-(6-chloro-1-((S)-1-(5-chloropyridin-2-yl)ethyl)-1H-benzo[d]imidazol-2-yl)-4-fluoropiperidin-3-amine hydrochloride | 408.0 |
| 223 | 60 | 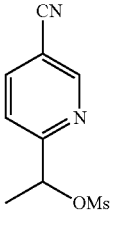 | B<sup>a</sup> | 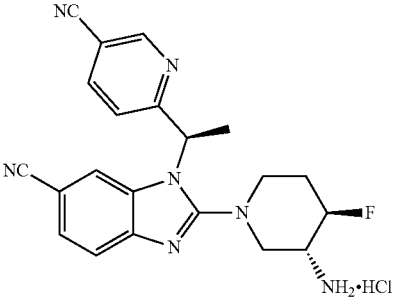 | 2-((3R,4R)-3-amino-4-fluoropiperidin-1-yl)-1-((R)-1-(5-cyanopyridin-2-yl)ethyl)-1H-benzo[d]imidazole-6-carbonitrile hydrochloride | 390.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 224 | 60 | 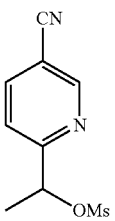 | B<sup>a</sup> | 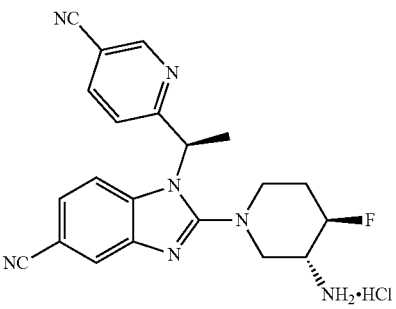 | 2-((3R,4R)-3-amino-4-fluoropiperidin-1-yl)-1-((R)-1-(5-cyanopyridin-2-yl)ethyl)-1H-benzo[d]imidazole-5-carbonitrile hydrochloride | 390.2 |
| 225 | 60 | 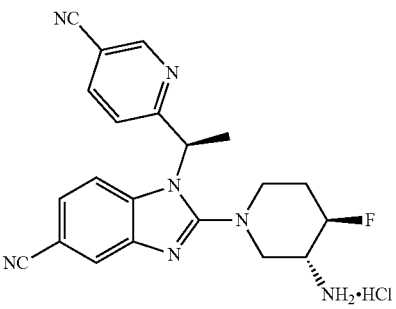 | B<sup>a</sup> | 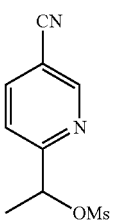 | 2-((3R,4R)-3-amino-4-fluoropiperidin-1-yl)-1-((S)-1-(5-cyanopyridin-2-yl)ethyl)-1H-benzo[d]imidazole-6-carbonitrile hydrochloride | 390.2 |
| 226 | 60 | 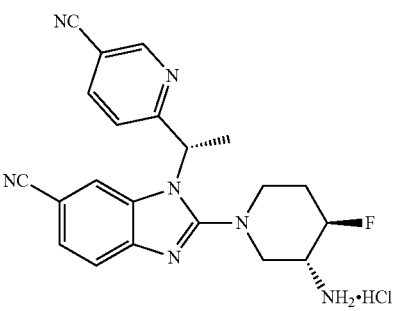 | B<sup>a</sup> | 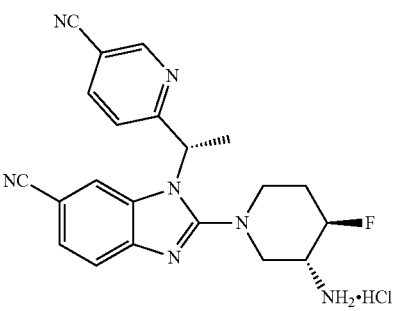 | 2-((3R,4R)-3-amino-4-fluoropiperidin-1-yl)-1-((S)-1-(5-cyanopyridin-2-yl)ethyl)-1H-benzo[d]imidazole-5-carbonitrile hydrochloride | 390.2 |
| 227 | 68 | 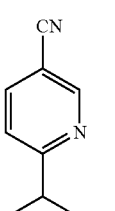 | B<sup>a</sup> | 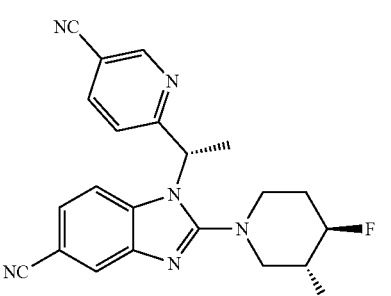 | (3R,4R)-1-(1-((5-chloropyridin-2-yl)methyl)-5,6-difluoro-1H-benzo[d]imidazol-2-yl)-4-fluoropiperidin-3-amine hydrochloride | 396.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 228 | 68 | 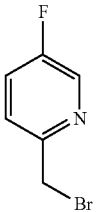 | B$^a$ | 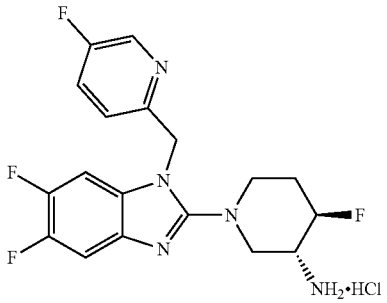 | (3R,4R)-1-(5,6-difluoro-1-((5-fluoropyridin-2-yl)methyl)-1H-benzo[d]imidazol-2-yl)-4-fluoropiperidin-3-amine hydrochloride | 380.2 |
| 229 | 70 | 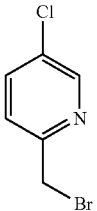 | B$^a$ | 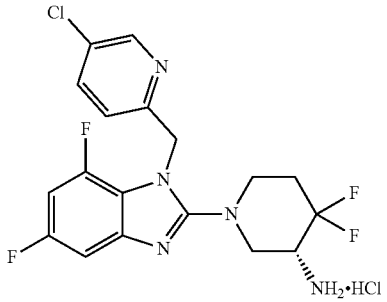 | (R)-1-(1-((5-chloropyridin-2-yl)methyl)-5,7-difluoro-1H-benzo[d]imidazol-2-yl)-4,4-difluoropiperidin-3-amine hydrochloride | 414.2 |
| 230 | 70 | 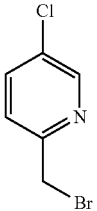 | B$^a$ | 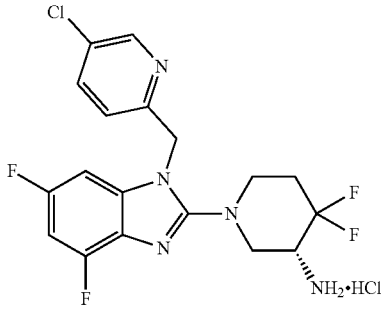 | (R)-1-(1-((5-chloropyridin-2-yl)methyl)-4,6-difluoro-1H-benzo[d]imidazol-2-yl)-4,4-difluoropiperidin-3-amine hydrochloride | 414.2 |
| 231 | 67 | 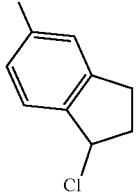 | A | 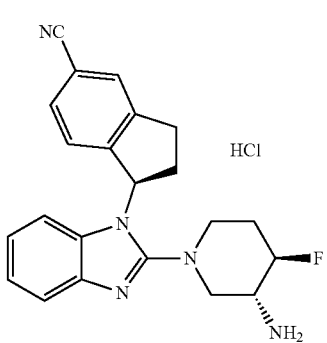 [SMILES: N#Cc1ccc2c(c1)CC[C@H]2n1c(N2CC[C@@H](F)[C@H](N)C2)nc2ccccc21 ; Cl] | (R)-1-(2-((3R,4R)-3-amino-4-fluoropiperidin-1-yl)-1H-benzo[d]imidazol-1-yl)-2,3-dihydro-1H-indene-5-carbonitrile hydrochloride | 376.2 |

TABLE 5-continued

Compounds made following schemes 9-10

| Ex. # | SnAr Inter- mediate | Electrophile | Boc Depro- tection Pro- cedure | Structure | Compound Name | MS MH+ |
|---|---|---|---|---|---|---|
| 232 | 67 | 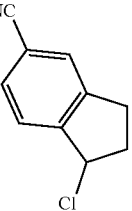 | A | 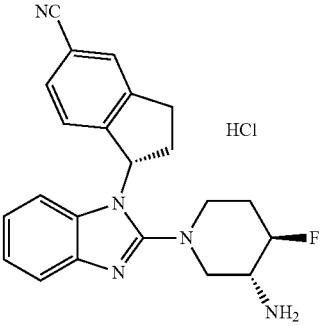 [SMILES: N#Cc1ccc2c(c1)CC[C@@H]2n1c(N2CC[C@@H](F)[C@H](N)C2)nc2ccccc21 ; Cl] | (S)-1-(2-((3R,4R)-3-amino-4-fluoropiperidin-1-yl)-1H-benzo[d]imidazol-1-yl)-2,3-dihydro-1H-indene-5-carbonitrile hydrochloride | 376.2 |
| 233 | 66 | 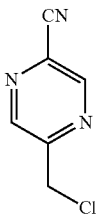 | A | 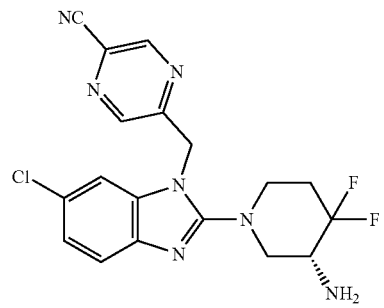 [SMILES: N#Cc1cnc(Cn2c(N3CCC(F)(F)[C@H](N)C3)nc3ccc(Cl)cc32)cn1] | (R)-5-((2-(3-amino-4,4-difluoropiperidin-1-yl)-6-chloro-1H-benzo[d]imidazol-1-yl)methyl)pyrazine-2-carbonitrile | 404.0 |
| 234 | 66 | 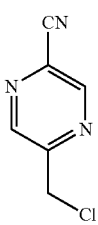 | A | 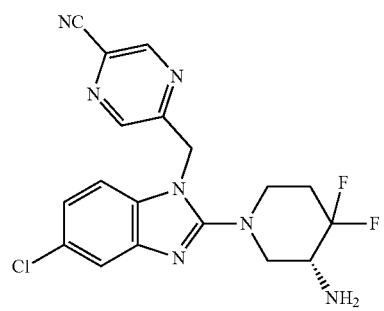 [SMILES: N#Cc1cnc(Cn2c(N3CCC(F)(F)[C@H](N)C3)nc3cc(Cl)ccc32)cn1] | (R)-5-((2-(3-amino-4,4-difluoropiperidin-1-yl)-5-chloro-1H-benzo[d]imidazol-1-yl)methyl)pyrazine-2-carbonitrile | 404.0 |
| 235 | 68 | 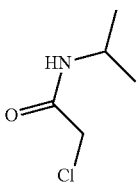 | B | 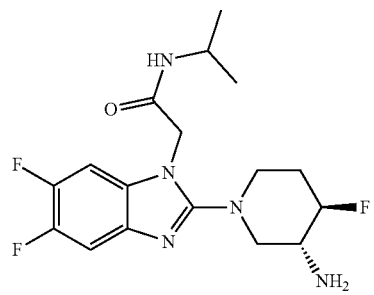 [SMILES: CC(C)NC(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-isopropylacetamide | 370.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 236 | 68 | 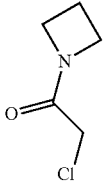 | B | 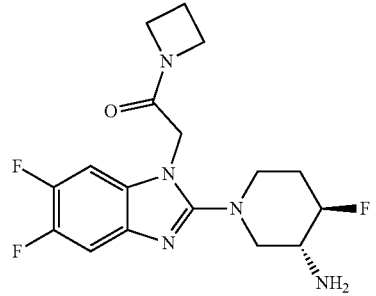 [SMILES: N[C@@H]1CN(c2nc3cc(F)c(F)cc3n2CC(=O)N2CCC2)CC[C@H]1F] | 2-(2-((3R,4R)-3-amino-4-fluoropiperidin-1-yl)-5,6-difluoro-1H-benzo[d]imidazol-1-yl)-1-(azetidin-1-yl)ethanone | 368.2 |
| 237 | 68 | 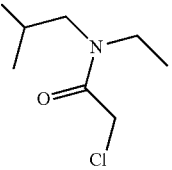 | B | 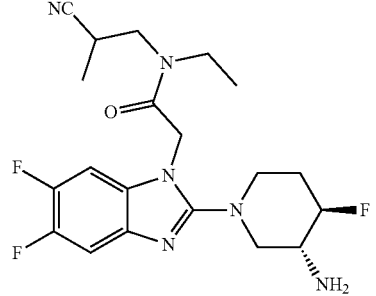 [SMILES: CCN(CC(C)C#N)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-(2-cyanopropyl)-N-ethylacetamide | 423.2 |
| 238 | 68 | 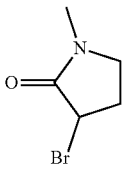 | B | 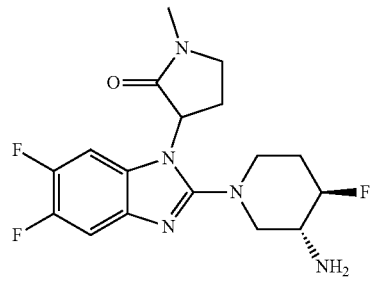 [SMILES: CN1CCC(n2c(N3CC[C@@H](F)[C@H](N)C3)nc3cc(F)c(F)cc32)C1=O] | 3-(2-((3R,4R)-3-amino-4-fluoropiperidin-1-yl)-5,6-difluoro-1H-benzo[d]imidazol-1-yl)-1-methylpyrrolidin-2-one | 368.2 |
| 239 | 68 | 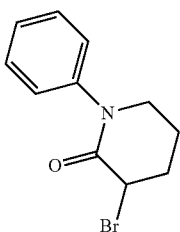 [SMILES: O=C1C(Br)CCCN1c1ccccc1] | B | 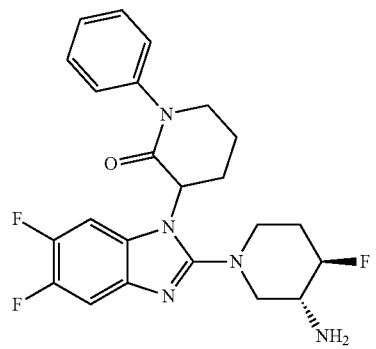 [SMILES: N[C@@H]1CN(c2nc3cc(F)c(F)cc3n2C2CCCN(c3ccccc3)C2=O)CC[C@H]1F] | 3-(2-((3R,4R)-3-amino-4-fluoropiperidin-1-yl)-5,6-difluoro-1H-benzo[d]imidazol-1-yl)-1-phenylpiperidin-2-one | 444.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 240 | 68 | (4-chlorophenyl-3-bromopyrrolidin-2-one) | B | (structure) | 3-(2-((3R,4R)-3-amino-4-fluoropiperidin-1-yl)-5,6-difluoro-1H-benzo[d]imidazol-1-yl)-1-(4-chlorophenyl)pyrrolidin-2-one | 464.2 |
| 241 | 60 | (2-(chloromethyl)-5-methoxypyrimidine) | A | (structure) | 2-((3R,4R)-3-amino-4-fluoropiperidin-1-yl)-1-((5-methoxypyrimidin-2-yl)methyl)-1H-benzo[d]imidazole-5-carbonitrile hydrochloride | 382.2 |
| 242 | 60 | (2-(chloromethyl)-5-methoxypyrimidine) | A | (structure) | 2-((3R,4R)-3-amino-4-fluoropiperidin-1-yl)-1-((5-methoxypyrimidin-2-yl)methyl)-1H-benzo[d]imidazole-6-carbonitrile hydrochloride | 382.2 |
| 243 | 60 | (5-(chloromethyl)-2-(trifluoromethyl)pyridine) | A | (structure) | 2-((3R,4R)-3-amino-4-fluoropiperidin-1-yl)-1-((6-(trifluoromethyl)pyridin-3-yl)methyl)-1H-benzo[d]imidazole-6-carbonitrile hydrochloride | 419.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 244 | 60 | | A | 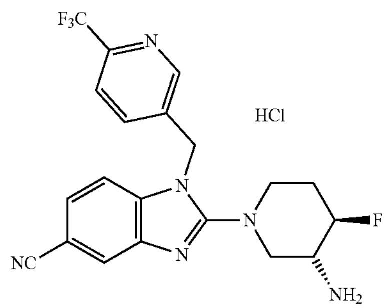 | 2-((3R,4R)-3-amino-4-fluoropiperidin-1-yl)-1-((6-(trifluoromethyl)pyridin-3-yl)methyl)-1H-benzo[d]imidazole-5-carbonitrile hydrochloride | 419.2 |
| 245 | 68 | | B | 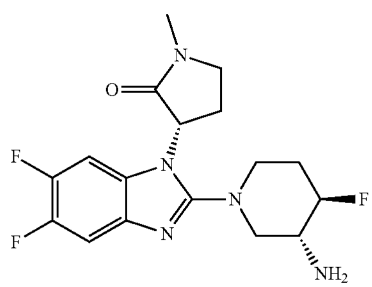 | (S)-3-(2-((3R,4R)-3-amino-4-fluoropiperidin-1-yl)-5,6-difluoro-1H-benzo[d]imidazol-1-yl)-1-methylpyrrolidin-2-one | 368.2 |
| 246 | 68 | | B | 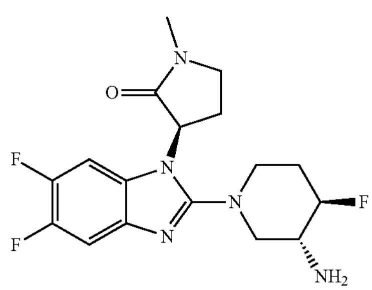 [SMILES: CN1CC[C@@H](n2c(N3CC[C@@H](F)[C@H](N)C3)nc3cc(F)c(F)cc32)C1=O] | (R)-3-(2-((3R,4R)-3-amino-4-fluoropiperidin-1-yl)-5,6-difluoro-1H-benzo[d]imidazol-1-yl)-1-methylpyrrolidin-2-one | 368.2 |
| 247 | 68 | | B | 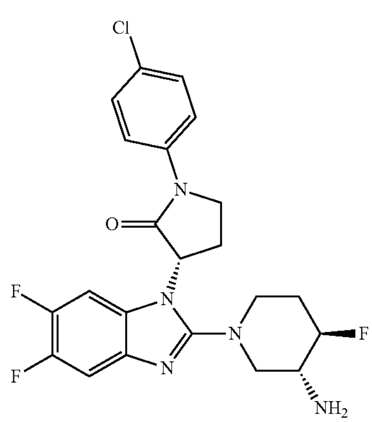 [SMILES: N[C@@H]1CN(c2nc3cc(F)c(F)cc3n2[C@H]2CCN(c3ccc(Cl)cc3)C2=O)CC[C@H]1F] | (S)-3-(2-((3R,4R)-3-amino-4-fluoropiperidin-1-yl)-5,6-difluoro-1H-benzo[d]imidazol-1-yl)-1-(4-chlorophenyl)pyrrolidin-2-one | 464.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 248 | 68 | 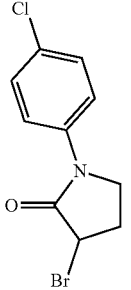 [SMILES: O=C1C(Br)CCN1c1ccc(Cl)cc1] | B | 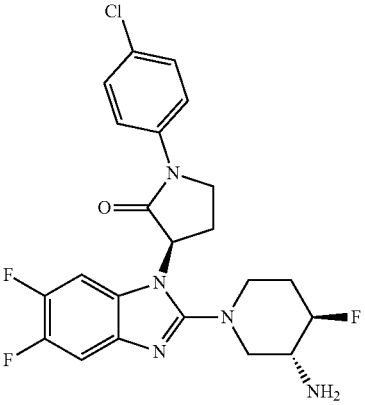 [SMILES: N[C@@H]1CN(c2nc3cc(F)c(F)cc3n2[C@@H]2CCN(c3ccc(Cl)cc3)C2=O)CC[C@H]1F] | (R)-3-(2-((3R,4R)-3-amino-4-fluoropiperidin-1-yl)-5,6-difluoro-1H-benzo[d]imidazol-1-yl)-1-(4-chlorophenyl)pyrrolidin-2-one | 464.2 |
| 249 | 60 | 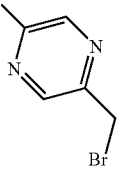 | B | 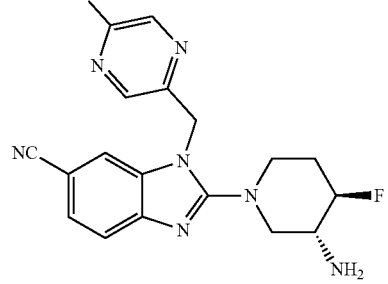 | 2-((3R,4R)-3-amino-4-fluoro-1-piperidinyl)-1-((5-cyano-2-pyrazinyl)methyl)-1H-benzimidazole-6-carbonitrile | 377.2 |
| 250 | 60 | 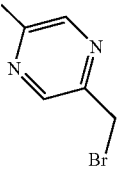 | B | 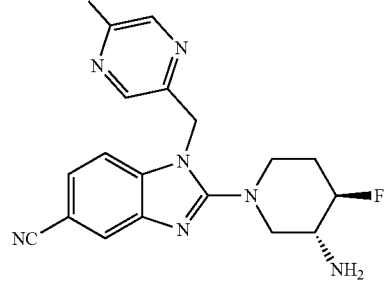 | 2-((3R,4R)-3-amino-4-fluoro-1-piperidinyl)-1-((5-cyano-2-pyrazinyl)methyl)-1H-benzimidazole-5-carbonitrile | 377.2 |
| 251 | 62 | 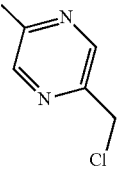 | B | 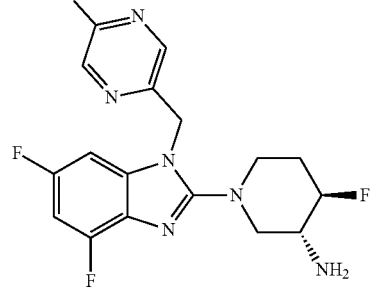 | 5-((2-((3R,4R)-3-amino-4-fluoro-1-piperidinyl)-4,6-difluoro-1H-benzimidazol-1-yl)methyl)-2-pyrazinecarbonitrile | 388.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 252 | 62 | 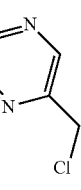 | B | 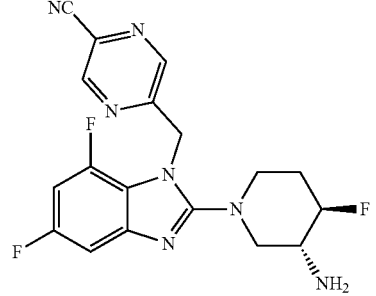 [SMILES: N#Cc1cnc(Cn2c(N3CC[C@@H](F)[C@H](N)C3)nc3cc(F)cc(F)c32)cn1] | 5-((2-((3R,4R)-3-amino-4-fluoro-1-piperidinyl)-5,7-difluoro-1H-benzimidazol-1-yl)methyl)-2-pyrazinecarbonitrile | 388.2 |
| 253 | 61 | HCl 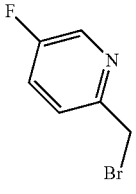 | B | 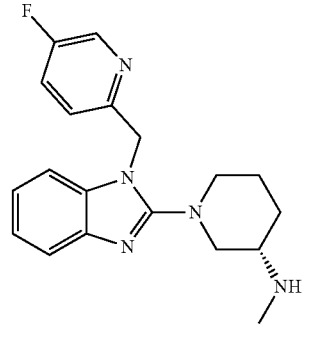 [SMILES: CN[C@H]1CCCN(c2nc3ccccc3n2Cc2ccc(F)cn2)C1] | (3S)-1-(1-((5-fluoro-2-pyridinyl)methyl)-1H-benzimidazol-2-yl)-N-methyl-3-piperidinamine | 340.2 |
| 254 | 61 | 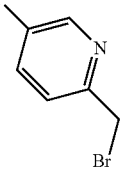 | B | 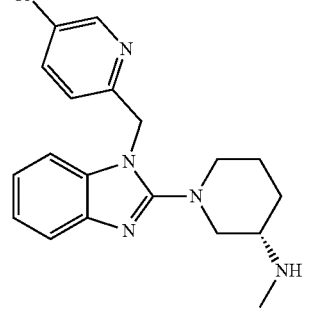 | (3S)-1-(1-((5-chloro-2-pyridinyl)methyl)-1H-benzimidazol-2-yl)-N-methyl-3-piperidinamine | 356.2 |
| 255 | 61 | 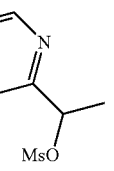 | B | 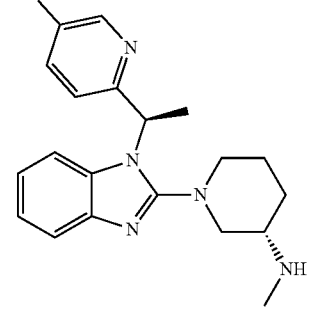 | 6-((1R)-1-(2-((3S)-3-(methylamino)-1-piperidinyl)-1H-benzimidazol-1-yl)ethyl)-3-pyridinecarbonitrile | 361.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 256 | 61 | 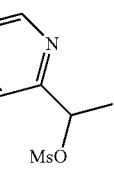 | B | 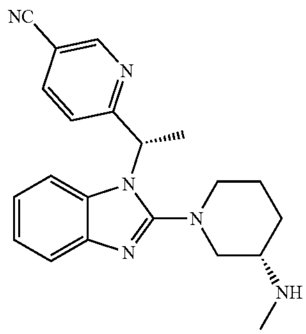 [SMILES: CN[C@H]1CCCN(c2nc3ccccc3n2[C@@H](C)c2ccc(C#N)cn2)C1] | 6-((1S)-1-(2-((3S)-3-(methylamino)-1-piperidinyl)-1H-benzimidazol-1-yl)ethyl)-3-pyridinecarbonitrile | 361.2 |
| 257 | 62 | 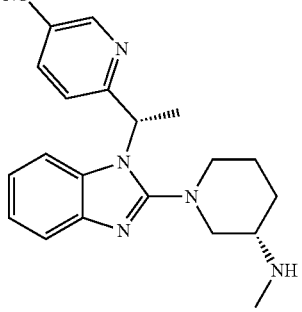 | B | 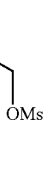 | (3R,4R)-1-(1-((5-chloro-2-pyrimidinyl)methyl)-5,7-difluoro-1H-benzimidazol-2-yl)-4-fluoro-3-piperidinamine | 397.2 |
| 258 | 62 |  | B | 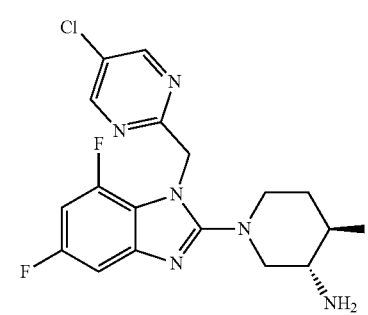 | (3R,4R)-1-(1-((5-chloro-2-pyrimidinyl)methyl)-4,6-difluoro-1H-benzimidazol-2-yl)-4-fluoro-3-piperidinamine | 397.2 |
| 259 | 68 | 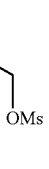 | B | 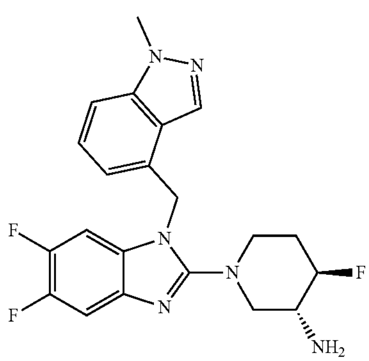 [SMILES: Cn1ncc2c(Cn3c(N4CC[C@@H](F)[C@H](N)C4)nc4cc(F)c(F)cc43)cccc21] | (3R,4R)-1-(5,6-difluoro-1-((1-methyl-1H-indazol-4-yl)methyl)-1H-benzimidazol-2-yl)-4-fluoro-3-piperidinamine | 415.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 260 | 68 | | B | 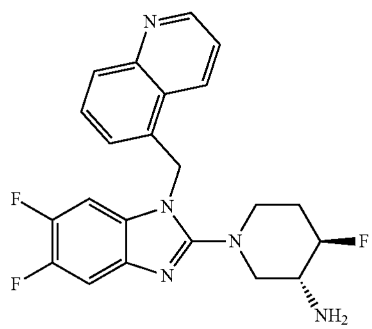 [SMILES: N[C@@H]1CN(c2nc3cc(F)c(F)cc3n2Cc2cccc3ncccc23)CC[C@H]1F] | (3R,4R)-1-(5,6-difluoro-1-(5-quinolinylmethyl)-1H-benzimidazol-2-yl)-4-fluoro-3-piperidinamine | 412.2 |
| 261 | 68 | | B | 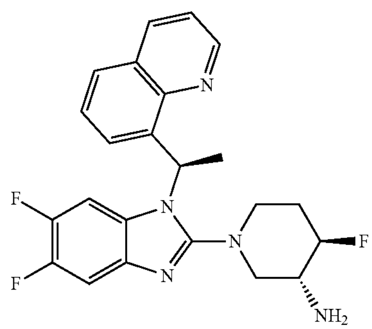 [SMILES: C[C@H](c1cccc2cccnc12)n1c(N2CC[C@@H](F)[C@H](N)C2)nc2cc(F)c(F)cc21] | (3R,4R)-1-(5,6-difluoro-1-((1R)-1-(8-quinolinyl)ethyl)-1H-benzimidazol-2-yl)-4-fluoro-3-piperidinamine | 426.2 |
| 262 | 68 | | B | 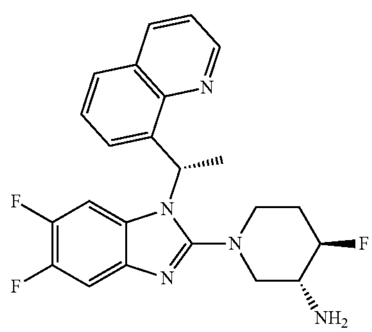 [SMILES: C[C@@H](c1cccc2cccnc12)n1c(N2CC[C@@H](F)[C@H](N)C2)nc2cc(F)c(F)cc21] | (3R,4R)-1-(5,6-difluoro-1-((1S)-1-(8-quinolinyl)ethyl)-1H-benzimidazol-2-yl)-4-fluoro-3-piperidinamine | 426.2 |
| 263 | 68 | | B | 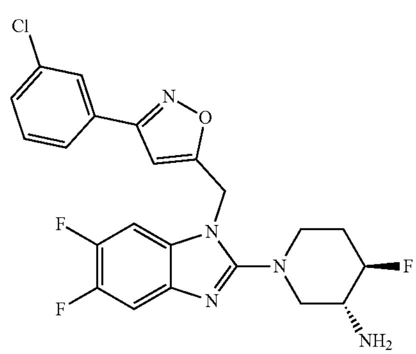 [SMILES: N[C@@H]1CN(c2nc3cc(F)c(F)cc3n2Cc2cc(-c3cccc(Cl)c3)no2)CC[C@H]1F] | (3R,4R)-1-(1-((3-(3-chlorophenyl)-1,2-oxazol-5-yl)methyl)-5,6-difluoro-1H-benzimidazol-2-yl)-4-fluoro-3-piperidinamine | 462.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 264 | 68 | | B | 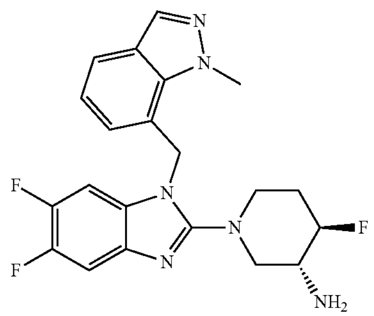 [SMILES: Cn1ncc2cccc(Cn3c(N4CC[C@@H](F)[C@H](N)C4)nc4cc(F)c(F)cc43)c21] | (3R,4R)-1-(5,6-difluoro-1-((1-methyl-1H-indazol-7-yl)methyl)-1H-benzimidazol-2-yl)-4-fluoro-3-piperidinamine | 415.2 |
| 265 | 68 | | B | 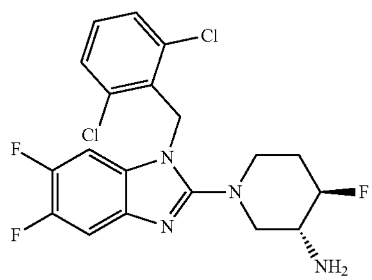 [SMILES: N[C@@H]1CN(c2nc3cc(F)c(F)cc3n2Cc2c(Cl)cccc2Cl)CC[C@H]1F] | (3R,4R)-1-(1-(2,6-dichlorobenzyl)-5,6-difluoro-1H-benzimidazol-2-yl)-4-fluoro-3-piperidinamine | 429.0 |
| 266 | 61 | | B | 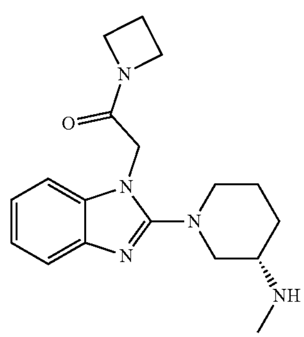 [SMILES: CN[C@H]1CCCN(c2nc3ccccc3n2CC(=O)N2CCC2)C1] | 1-(1-azetidinyl)-2-(2-((3S)-3-(methylamino)-1-piperidinyl)-1H-benzimidazol-1-yl)ethanone | 328.2 |
| 267 | 63 | | B | 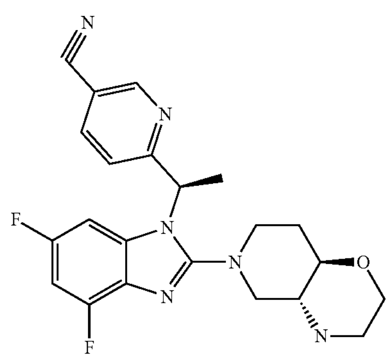 [SMILES: C[C@H](c1ccc(C#N)cn1)n1c(N2CC[C@H]3OCCN[C@@H]3C2)nc2c(F)cc(F)cc21] | 6-((1R)-1-(4,6-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile | 425.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 268 | 63 | (5-CN-pyridin-2-yl)-CH(OMs)CH3 | B | 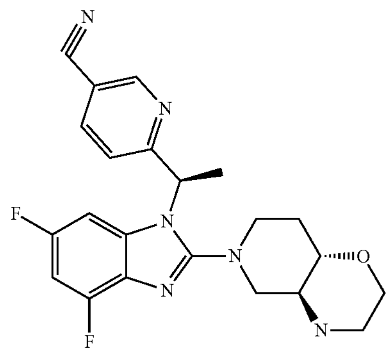 [SMILES: C[C@H](c1ccc(C#N)cn1)n1c(N2CC[C@@H]3OCCN[C@H]3C2)nc2c(F)cc(F)cc21] | 6-((1R)-1-(4,6-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile | 425.2 |
| 269 | 63 | (5-CN-pyridin-2-yl)-CH(OMs)CH3 | B | 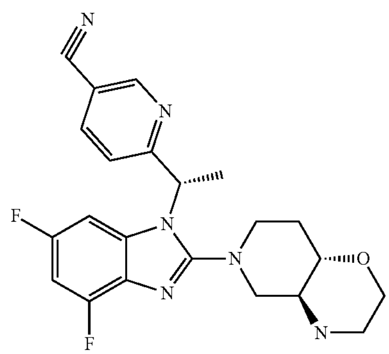 [SMILES: C[C@@H](c1ccc(C#N)cn1)n1c(N2CC[C@@H]3OCCN[C@H]3C2)nc2c(F)cc(F)cc21] | 6-((1S)-1-(4,6-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile | 425.2 |
| 270 | 63 | (5-CN-pyridin-2-yl)-CH(OMs)CH3 | B | 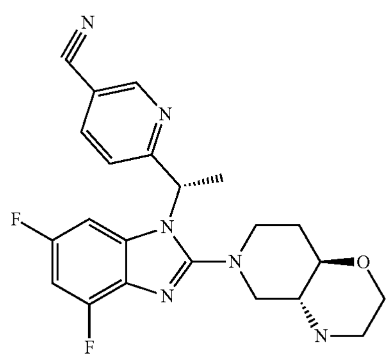 [SMILES: C[C@@H](c1ccc(C#N)cn1)n1c(N2CC[C@H]3OCCN[C@@H]3C2)nc2c(F)cc(F)cc21] | 6-((1S)-1-(4,6-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile | 425.2 |
| 271 | 63 | (5-CN-pyridin-2-yl)-CH(OMs)CH3 | B | 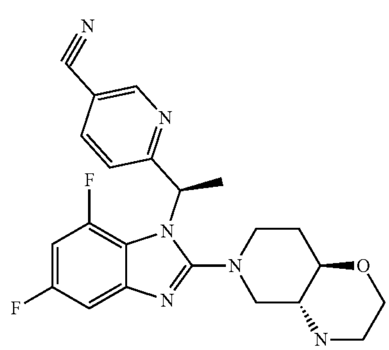 [SMILES: C[C@H](c1ccc(C#N)cn1)n1c(N2CC[C@H]3OCCN[C@@H]3C2)nc2cc(F)cc(F)c21] | 6-((1R)-1-(5,7-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile | 425.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 272 | 63 | | B | 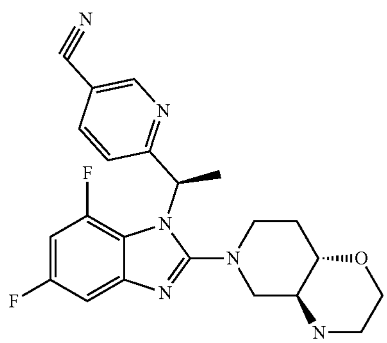 [SMILES: C[C@H](c1ccc(C#N)cn1)n1c(N2CC[C@@H]3OCCN[C@H]3C2)nc2cc(F)cc(F)c21] | 6-((1R)-1-(5,7-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile | 425.2 |
| 273 | 63 | | B | 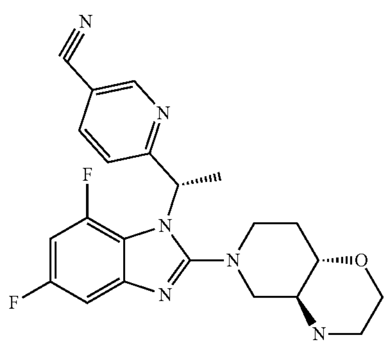 [SMILES: C[C@@H](c1ccc(C#N)cn1)n1c(N2CC[C@@H]3OCCN[C@H]3C2)nc2cc(F)cc(F)c21] | 6-((1S)-1-(5,7-difluoro-2-((4aS,8aS)-hexahydro-2H-pyrido[4,3-b][1,4]oxazin-6(5H)-yl)-1H-benzimidazol-1-yl)ethyl)-3-pyridinecarbonitrile | 425.2 |
| 274 | 63 | | B | 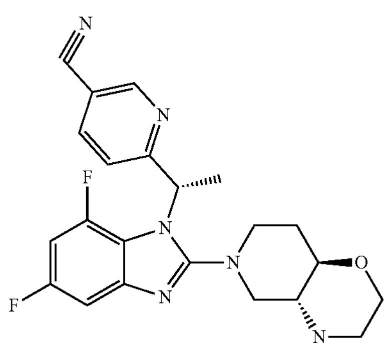 [SMILES: C[C@@H](c1ccc(C#N)cn1)n1c(N2CC[C@H]3OCCN[C@@H]3C2)nc2cc(F)cc(F)c21] | 6-((1S)-1-(5,7-difluoro-2-((4aR,8aR)-hexahydro-2H-pyrido[4,3-b][1,4]oxazin-6(5H)-yl)-1H-benzimidazol-1-yl)ethyl)-3-pyridinecarbonitrile | 425.2 |
| 275 | 68 | | B | 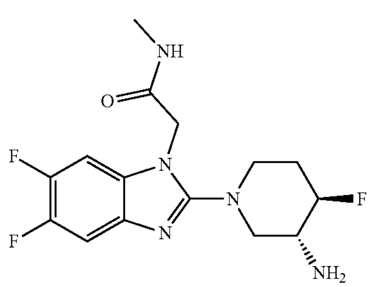 [SMILES: CNC(=O)Cn1c(N2CC[C@@H](F)[C@H](N)C2)nc2cc(F)c(F)cc21] | 2-(2-((3R,4R)-3-amino-4-fluoro-1-piperidinyl)-5,6-difluoro-1H-benzimidazol-1-yl)-N-methylacetamide | 342.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 276 | 68 | | B | 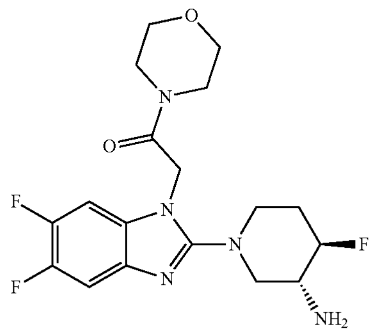 [SMILES: N[C@@H]1CN(c2nc3cc(F)c(F)cc3n2CC(=O)N2CCOCC2)CC[C@H]1F] | 2-(2-((3R,4R)-3-amino-4-fluoro-1-piperidinyl)-5,6-difluoro-1H-benzimidazol-1-yl)-1-(4-morpholinyl)ethanone | 398.2 |
| 277 | 68 | | B | 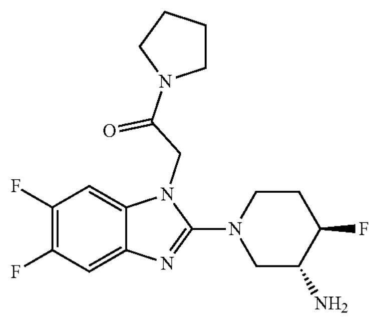 [SMILES: N[C@@H]1CN(c2nc3cc(F)c(F)cc3n2CC(=O)N2CCCC2)CC[C@H]1F] | 2-(2-((3R,4R)-3-amino-4-fluoro-1-piperidinyl)-5,6-difluoro-1H-benzimidazol-1-yl)-1-(1-pyrrolidinyl)ethanone | 382.2 |
| 278 | 68 | | B | 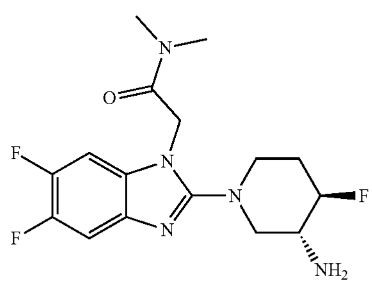 [SMILES: CN(C)C(=O)Cn1c(N2CC[C@@H](F)[C@H](N)C2)nc2cc(F)c(F)cc21] | 2-(2-((3R,4R)-3-amino-4-fluoro-1-piperidinyl)-5,6-difluoro-1H-benzimidazol-1-yl)-N,N-dimethylacetamide | 356.2 |
| 279 | 68 | | B | 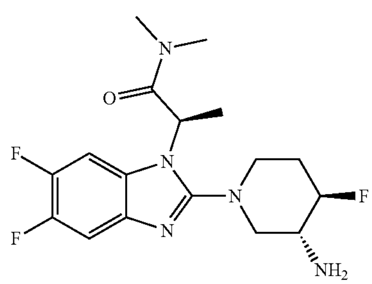 [SMILES: C[C@H](C(=O)N(C)C)n1c(N2CC[C@@H](F)[C@H](N)C2)nc2cc(F)c(F)cc21] | (2R)-2-(2-((3R,4R)-3-amino-4-fluoro-1-piperidinyl)-5,6-difluoro-1H-benzimidazol-1-yl)-N,N-dimethylpropanamide | 370.2 |
| 280 | 68 | | B | 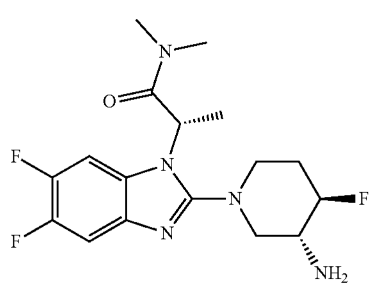 [SMILES: C[C@@H](C(=O)N(C)C)n1c(N2CC[C@@H](F)[C@H](N)C2)nc2cc(F)c(F)cc21] | (2S)-2-(2-((3R,4R)-3-amino-4-fluoro-1-piperidinyl)-5,6-difluoro-1H-benzimidazol-1-yl)-N,N-dimethylpropanamide | 370.2 |

US 11,332,459 B2

335                                                                 336

TABLE 5-continued

Compounds made following schemes 9-10

| Ex. # | SnAr Inter- mediate | Electrophile | Boc Depro- tection Pro- cedure | Structure | Compound Name | MS MH+ |
|---|---|---|---|---|---|---|
| 281 | 68 | 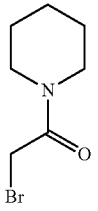 | B | 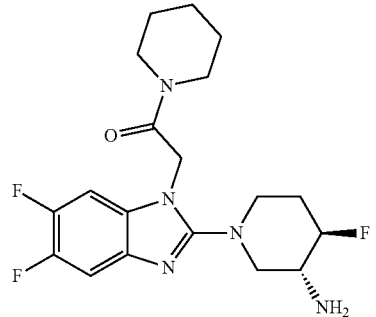 [SMILES: N[C@@H]1CN(c2nc3cc(F)c(F)cc3n2CC(=O)N2CCCCC2)CC[C@H]1F] | 2-(2-((3R,4R)-3-amino-4-fluoro-1-piperidinyl)-5,6-difluoro-1H-benzimidazol-1-yl)-1-(1-piperidinyl)ethanone | 396.2 |
| 282 | 68 | 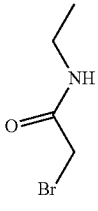 | B | 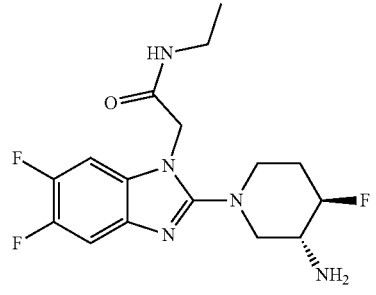 [SMILES: CCNC(=O)Cn1c(N2CC[C@@H](F)[C@H](N)C2)nc2cc(F)c(F)cc21] | 2-(2-((3R,4R)-3-amino-4-fluoro-1-piperidinyl)-5,6-difluoro-1H-benzimidazol-1-yl)-N-ethylacetamide | 356.2 |
| 283 | 64 | 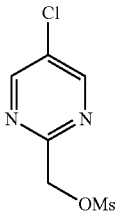 [SMILES: CS(=O)(=O)OCc1ncc(Cl)cn1] | B | 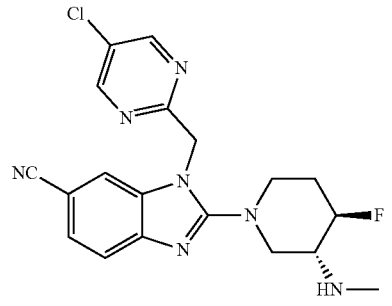 [SMILES: CN[C@@H]1CN(c2nc3ccc(C#N)cc3n2Cc2ncc(Cl)cn2)CC[C@H]1F] | 1-((5-chloro-2-pyrimidinyl)methyl)-2-((3R,4R)-4-fluoro-3-(methylamino)-1-piperidinyl)-1H-benzimidazole-6-carbonitrile | 400.0 |
| 284 | 64 | 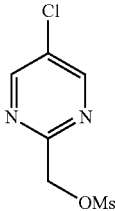 [SMILES: CS(=O)(=O)OCc1ncc(Cl)cn1] | B | 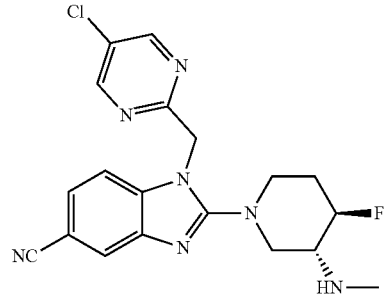 [SMILES: CN[C@@H]1CN(c2nc3cc(C#N)ccc3n2Cc2ncc(Cl)cn2)CC[C@H]1F] | 1-((5-chloro-2-pyrimidinyl)methyl)-2-((3R,4R)-4-fluoro-3-(methylamino)-1-piperidinyl)-1H-benzimidazole-5-carbonitrile | 400.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 285 | 69 | 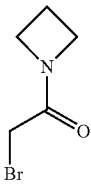 | B | 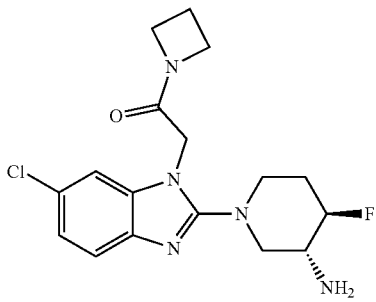 [SMILES: N[C@@H]1CN(c2nc3ccc(Cl)cc3n2CC(=O)N2CCC2)CC[C@H]1F] | 2-(2-((3R,4R)-3-amino-4-fluoro-1-piperidinyl)-6-chloro-1H-benzimidazol-1-yl)-1-(1-azetidinyl)ethanone | 366.2 |
| 286 | 69 | 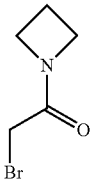 | B | 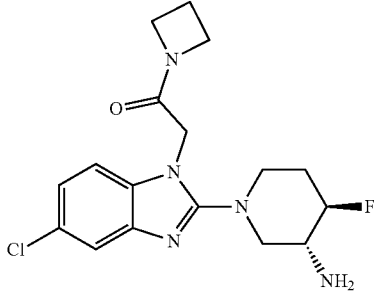 [SMILES: N[C@@H]1CN(c2nc3cc(Cl)ccc3n2CC(=O)N2CCC2)CC[C@H]1F] | 2-(2-((3R,4R)-3-amino-4-fluoro-1-piperidinyl)-5-chloro-1H-benzimidazol-1-yl)-1-(1-azetidinyl)ethanone | 366.2 |
| 287 | 74 | 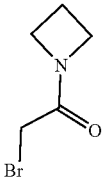 | B | 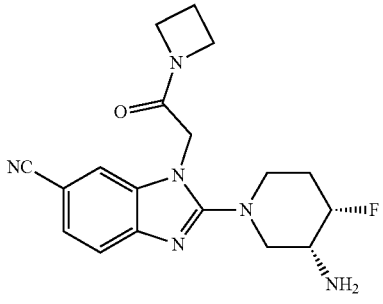 [SMILES: N#Cc1ccc2nc(N3CC[C@H](F)[C@H](N)C3)n(CC(=O)N3CCC3)c2c1] | 2-((3R,4S)-3-amino-4-fluoro-1-piperidinyl)-1-(2-(1-azetidinyl)-2-oxoethyl)-1H-benzimidazole-6-carbonitrile | 357.2 |
| 288 | 74 | 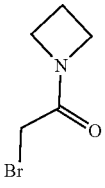 | B | 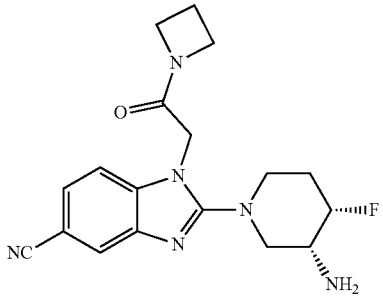 [SMILES: N#Cc1ccc2c(c1)nc(N1CC[C@H](F)[C@H](N)C1)n2CC(=O)N1CCC1] | 2-((3R,4S)-3-amino-4-fluoro-1-piperidinyl)-1-(2-(1-azetidinyl)-2-oxoethyl)-1H-benzimidazole-5-carbonitrile | 357.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 289 | 65 | 5-chloro-2-(methanesulfonyloxymethyl)pyrimidine | B | 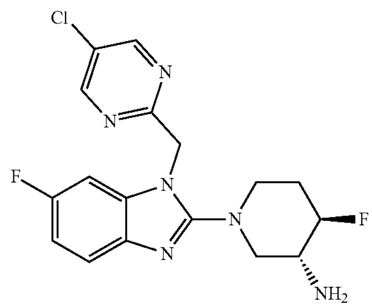 [SMILES: N[C@@H]1CN(c2nc3ccc(F)cc3n2Cc2ncc(Cl)cn2)CC[C@H]1F] | (3R,4R)-1-(1-((5-chloropyrimidin-2-yl)methyl)-6-fluoro-1H-benzo[d]imidazol-2-yl)-4-fluoropiperidin-3-amine | 379.0 |
| 290 | 65 | 5-chloro-2-(methanesulfonyloxymethyl)pyrimidine | B | 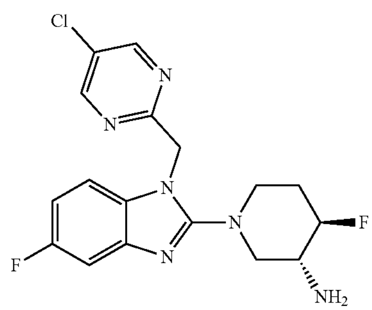 [SMILES: N[C@@H]1CN(c2nc3cc(F)ccc3n2Cc2ncc(Cl)cn2)CC[C@H]1F] | (3R,4R)-1-(1-((5-chloropyrimidin-2-yl)methyl)-5-fluoro-1H-benzo[d]imidazol-2-yl)-4-fluoropiperidin-3-amine | 379.0 |
| 291 | 71 | 6-(bromomethyl)nicotinonitrile | A | 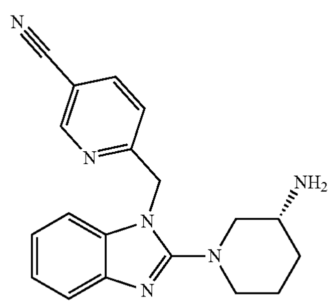 [SMILES: N#Cc1ccc(Cn2c(N3CCC[C@@H](N)C3)nc3ccccc32)nc1] | (R)-6-((2-(3-aminopiperidin-1-yl)-1H-benzo[d]imidazol-1-yl)methyl)nicotinonitrile | 333.2 |
| 292 | 72 | 5-(bromomethyl)picolinonitrile | A | 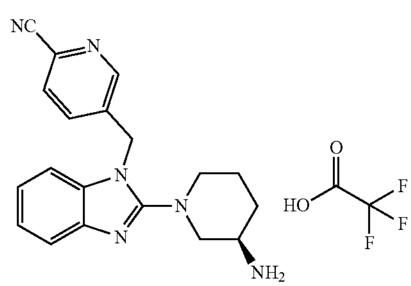 | (R)-5-((2-(3-aminopiperidin-1-yl)-1H-benzo[d]imidazol-1-yl)methyl)picolinonitrile 2,2,2-trifluoroacetate | 333.0 |
| 293 | 72 | | A | 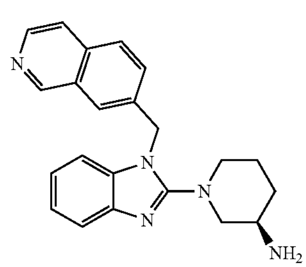 [SMILES: N[C@@H]1CCCN(c2nc3ccccc3n2Cc2ccc3ccncc3c2)C1] | (R)-1-(1-(isoquinolin-7-ylmethyl)-1H-benzo[d]imidazol-2-yl)piperidin-3-amine | 358.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 294 | 72 | 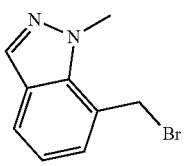 | A | 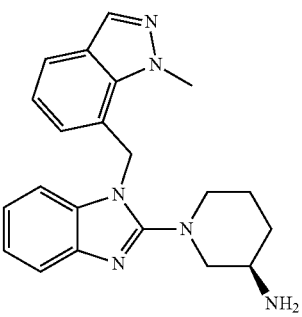 [SMILES: Cn1ncc2cccc(Cn3c(N4CCC[C@@H](N)C4)nc4ccccc43)c21] | (R)-1-(1-((1-methyl-1H-indazol-7-yl)methyl)-1H-benzo[d]imidazol-2-yl)piperidin-3-amine | 361.2 |
| 295 | 71 | 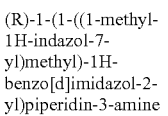 | A | 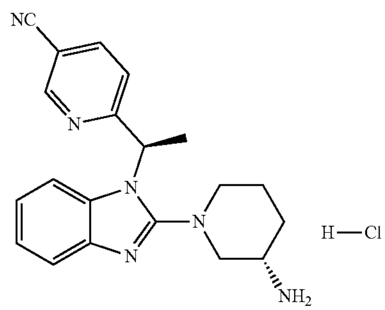 | 6-((R)-1-(2-((S)-3-aminopiperidin-1-yl)-1H-benzo[d]imidazol-1-yl)ethyl)nicotinonitrile hydrochloride | 347.2 |
| 296 | 71 | 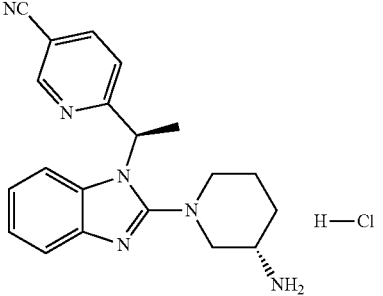 | A | 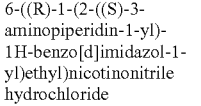 | 6-((S)-1-(2-((S)-3-aminopiperidin-1-yl)-1H-benzo[d]imidazol-1-yl)ethyl)nicotinonitrile hydrochloride | 347.2 |
| 297 | 67 | 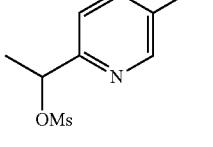 | B | 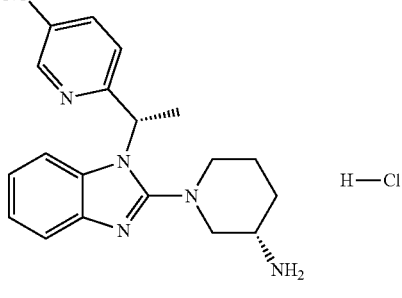 | 6-((R)-1-(2-((3R,4R)-3-amino-4-fluoropiperidin-1-yl)-1H-benzo[d]imidazol-1-yl)ethyl)nicotinonitrile hydrochloride | 365.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 298 | 67 |  | B | 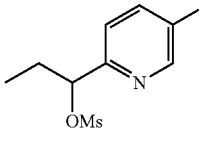 | 6-((S)-1-(2-((3R,4R)-3-amino-4-fluoropiperidin-1-yl)-1H-benzo[d]imidazol-1-yl)ethyl)nicotinonitrile hydrochloride | 365.0 |
| 299 | 71 | 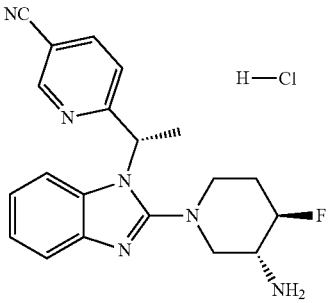 [SMILES: C[C@@H](c1ccc(C#N)cn1)n1c(N2CC[C@@H](F)[C@H](N)C2)nc2ccccc21 ; Cl] | B | 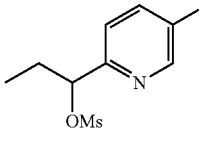 | 6-((R)-1-(2-((S)-3-aminopiperidin-1-yl)-1H-benzo[d]imidazol-1-yl)propyl)nicotinonitrile hydrochloride | 361.2 |
| 300 | 71 | 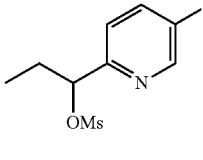 | B | 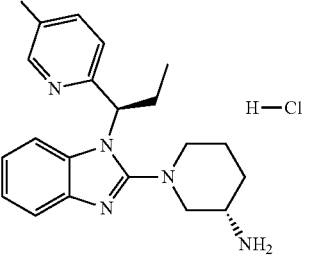 | 6-((S)-1-(2-((S)-3-aminopiperidin-1-yl)-1H-benzo[d]imidazol-1-yl)propyl)nicotinonitrile hydrochloride | 361.2 |
| 301 | 68 | 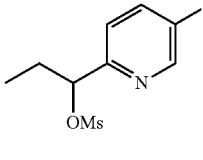 | B | 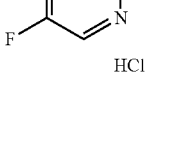 | (3R,4R)-1-(5,6-difluoro-1-((5-fluoropyrimidin-2-yl)methyl)-1H-benzo[d]imidazol-2-yl)-4-fluoropiperidin-3-amine | 381.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 302 | 68 | 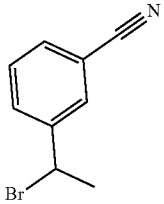 | B | 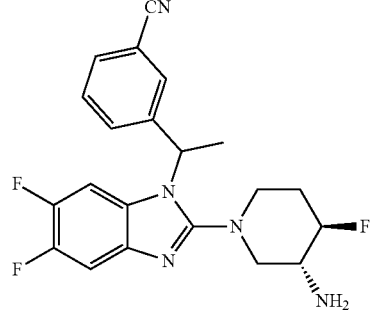 [SMILES: CC(c1cccc(C#N)c1)n1c(N2CC[C@@H](F)[C@H](N)C2)nc2cc(F)c(F)cc21] | 3-(1-(2-((3R,4R)-3-amino-4-fluoropiperidin-1-yl)-5,6-difluoro-1H-benzo[d]imidazol-1-yl)ethyl)benzonitrile | 400.2 |
| 303 | 68 | 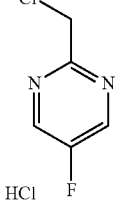 | B | 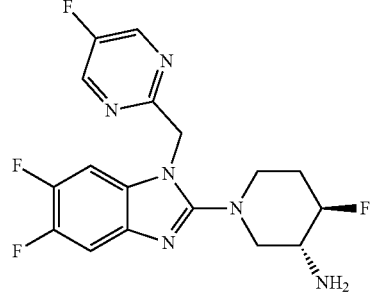 [SMILES: N[C@@H]1CN(c2nc3cc(F)c(F)cc3n2Cc2ncc(F)cn2)CC[C@H]1F] | (3R,4R)-1-(5,6-difluoro-1-((5-fluoropyrimidin-2-yl)methyl)-1H-benzo[d]imidazol-2-yl)-4-fluoropiperidin-3-amine | 381.0 |
| 304 | 76 | 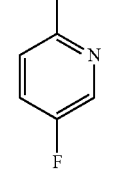 | B | 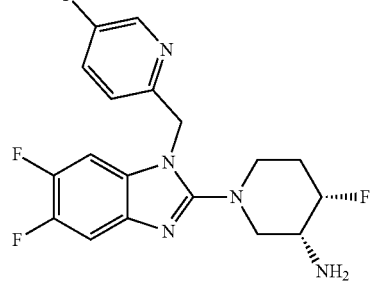 | (3R,4S)-1-(5,6-difluoro-1-((5-fluoropyridin-2-yl)methyl)-1H-benzo[d]imidazol-2-yl)-4-fluoropiperidin-3-amine | 380.2 |
| 305 | 77 | 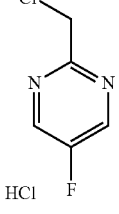 | B | 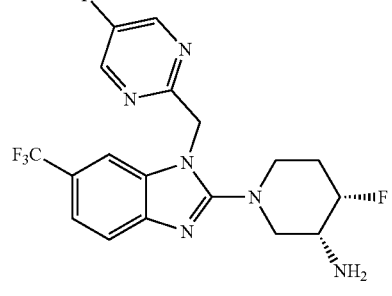 | (3R,4S)-4-fluoro-1-(1-((5-fluoropyrimidin-2-yl)methyl)-6-(trifluoromethyl)-1H-benzo[d]imidazol-2-yl)piperidin-3-amine | 413.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 306 | 77 | 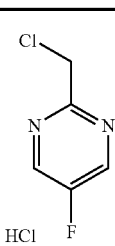 | B | 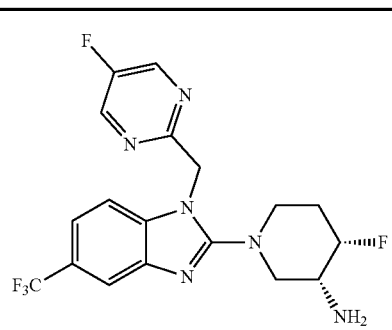 | (3R,4S)-4-fluoro-1-(1-((5-fluoropyrimidin-2-yl)methyl)-5-(trifluoromethyl)-1H-benzo[d]imidazol-2-yl)piperidin-3-amine | 413.2 |
| 307 | 78 | 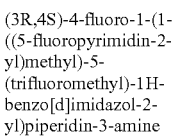 | B | 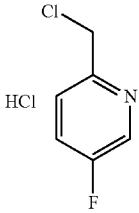 | (R)-1-(5,6-difluoro-1-((5-fluoropyridin-2-yl)methyl)-1H-benzo[d]imidazol-2-yl)-4,4-difluoropiperidin-3-amine | 398.0 |
| 308 | 77 | 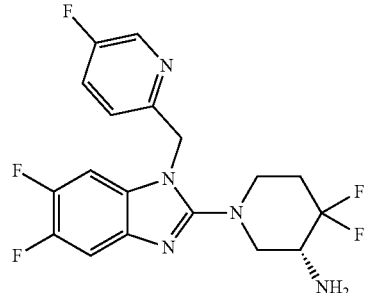 | B | 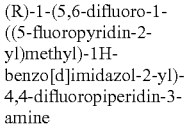 | 2-(2-((3R,4S)-3-amino-4-fluoropiperidin-1-yl)-6-(trifluoromethyl)-1H-benzo[d]imidazol-1-yl)-1-(azetidin-1-yl)ethan-1-one | 400.2 |
| 309 | 77 | 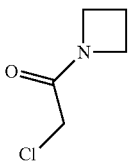 | B | 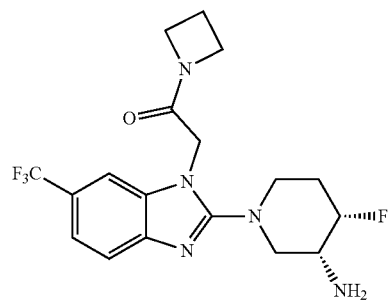 [SMILES: N[C@@H]1CN(c2nc3ccc(C(F)(F)F)cc3n2CC(=O)N2CCC2)CC[C@@H]1F] | 2-(2-((3R,4S)-3-amino-4-fluoropiperidin-1-yl)-5-(trifluoromethyl)-1H-benzo[d]imidazol-1-yl)-1-(azetidin-1-yl)ethan-1-one | 400.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 310 | 68 | 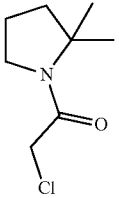 | B | 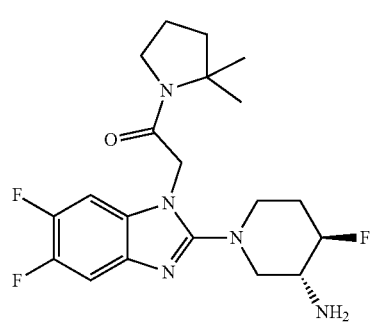 [SMILES: CC1(C)CCCN1C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-1-(2,2-dimethylpyrrolidin-1-yl)ethan-1-one | 410.2 |
| 311 | 80 | 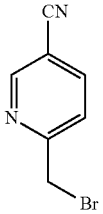 | B | 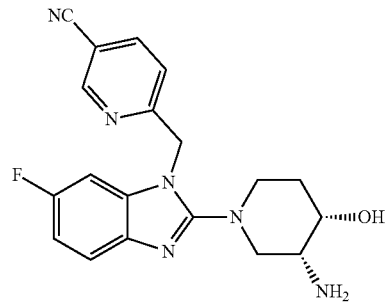 [SMILES: N#Cc1ccc(Cn2c(N3CC[C@H](O)[C@H](N)C3)nc3ccc(F)cc32)nc1] | 6-((2-((3R,4S)-3-amino-4-hydroxypiperidin-1-yl)-6-fluoro-1H-benzo[d]imidazol-1-yl)methyl)nicotinonitrile | 367.2 |
| 312 | 80 | 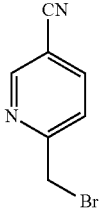 | B | 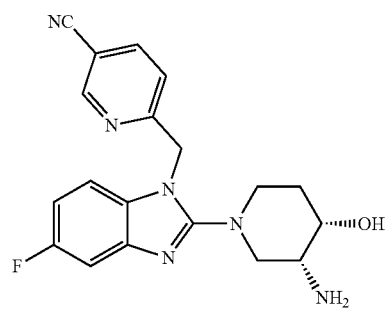 [SMILES: N#Cc1ccc(Cn2c(N3CC[C@H](O)[C@H](N)C3)nc3cc(F)ccc32)nc1] | 6-((2-((3R,4S)-3-amino-4-hydroxypiperidin-1-yl)-5-fluoro-1H-benzo[d]imidazol-1-yl)methyl)nicotinonitrile | 367.2 |
| 313 | 71 | 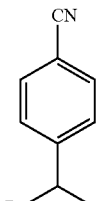 | A | 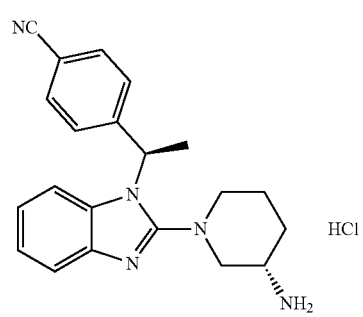 [SMILES: C[C@H](c1ccc(C#N)cc1)n1c(N2CCC[C@H](N)C2)nc2ccccc21 ; Cl] | 4-((R)-1-(2-((S)-3-aminopiperidin-1-yl)-1H-benzo[d]imidazol-1-yl)ethyl)benzonitrile hydrochloride | 346.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 314 | 71 | 4-(1-bromoethyl)benzonitrile | A | 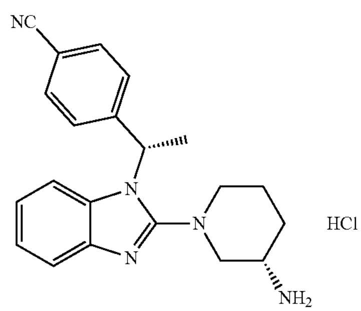 [SMILES: C[C@@H](c1ccc(C#N)cc1)n1c(N2CCC[C@H](N)C2)nc2ccccc21 ; Cl] | 4-((S)-1-(2-((S)-3-aminopiperidin-1-yl)-1H-benzo[d]imidazol-1-yl)ethyl)benzonitrile hydrochloride | 346.2 |
| 315 | 71 | 4-(bromomethyl)-3-fluorobenzonitrile | A | 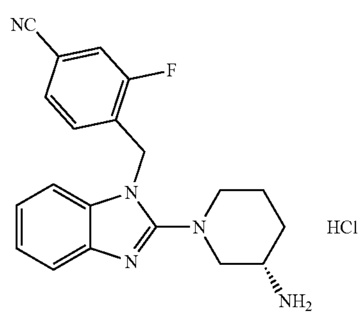 [SMILES: N#Cc1ccc(Cn2c(N3CCC[C@H](N)C3)nc3ccccc32)c(F)c1 ; Cl] | (S)-4-((2-(3-aminopiperidin-1-yl)-1H-benzo[d]imidazol-1-yl)methyl)-3-fluorobenzonitrile hydrochloride | 350.0 |
| 316 | 71 | 4-chlorobenzyl bromide | A | 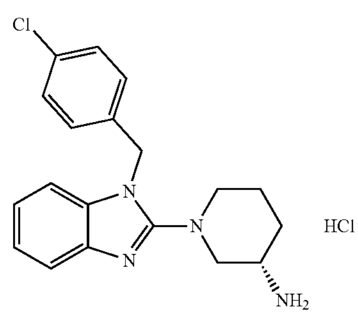 [SMILES: N[C@H]1CCCN(c2nc3ccccc3n2Cc2ccc(Cl)cc2)C1 ; Cl] | (S)-1-(1-(4-chlorobenzyl)-1H-benzo[d]imidazol-2-yl)piperidin-3-amine hydrochloride | 341.0 |
| 317 | 79 | 4-(1-bromoethyl)benzonitrile | A | 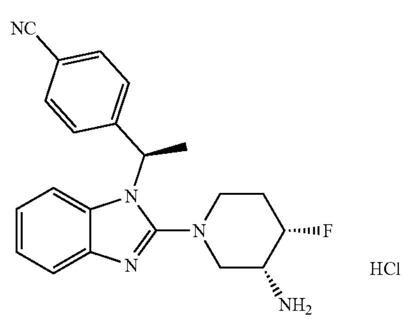 [SMILES: C[C@H](c1ccc(C#N)cc1)n1c(N2CC[C@H](F)[C@H](N)C2)nc2ccccc21 ; Cl] | 4-((R)-1-(2-((3R,4S)-3-amino-4-fluoropiperidin-1-yl)-1H-benzo[d]imidazol-1-yl)ethyl)benzonitrile hydrochloride | 364.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 318 | 79 | 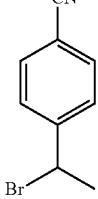 | A | 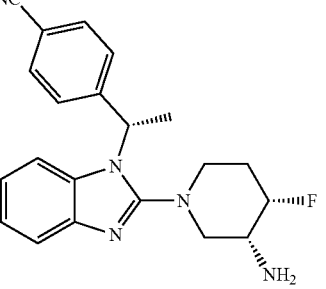 | 4-((S)-1-(2-((3R,4S)-3-amino-4-fluoropiperidin-1-yl)-1H-benzo[d]imidazol-1-yl)ethyl)benzonitrile hydrochloride | 364.0 |
| 319 | 67 | 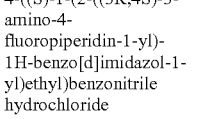 | A | 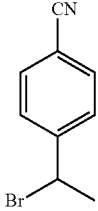 | 4-((R)-1-(2-((3R,4R)-3-amino-4-fluoropiperidin-1-yl)-1H-benzo[d]imidazol-1-yl)ethyl)benzonitrile hydrochloride | 364.2 |
| 320 | 67 | 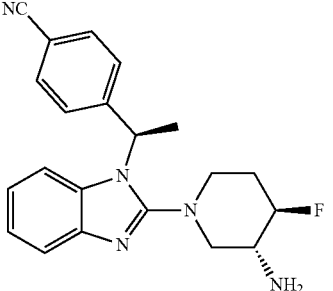 | A | 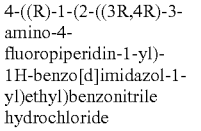 | 4-((S)-1-(2-((3R,4R)-3-amino-4-fluoropiperidin-1-yl)-1H-benzo[d]imidazol-1-yl)ethyl)benzonitrile hydrochloride | 364.2 |
| 321 | 71 | 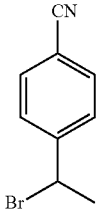 | A | 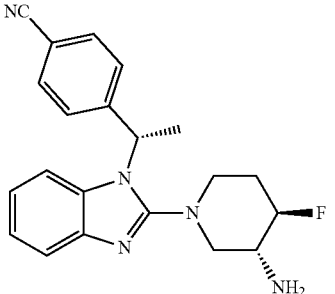 | (S)-4-((2-(3-aminopiperidin-1-yl)-1H-benzo[d]imidazol-1-yl)methyl)-3-chlorobenzonitrile hydrochloride | 366.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 322 | 68 | 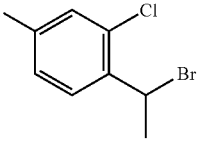 | B | 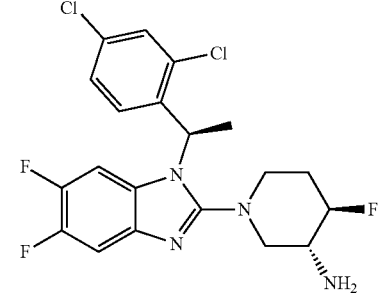 [SMILES: C[C@H](c1ccc(Cl)cc1Cl)n1c(N2CC[C@@H](F)[C@H](N)C2)nc2cc(F)c(F)cc21] | (3R,4R)-1-(1-((1R)-1-(2,4-dichlorophenyl)ethyl)-5,6-difluoro-1H-benzimidazol-2-yl)-4-fluoro-3-piperidinamine | 453.2 |
| 323 | 68 | 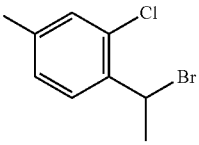 | B | 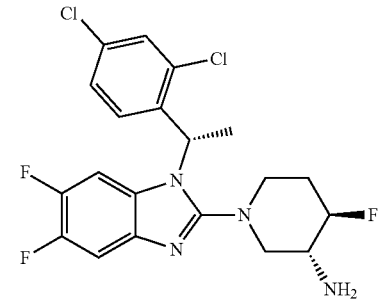 [SMILES: C[C@@H](c1ccc(Cl)cc1Cl)n1c(N2CC[C@@H](F)[C@H](N)C2)nc2cc(F)c(F)cc21] | (3R,4R)-1-(1-((1S)-1-(2,4-dichlorophenyl)ethyl)-5,6-difluoro-1H-benzimidazol-2-yl)-4-fluoro-3-piperidinamine | 453.2 |
| 324 | 68 | 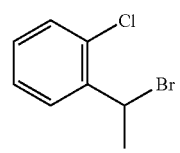 | B | 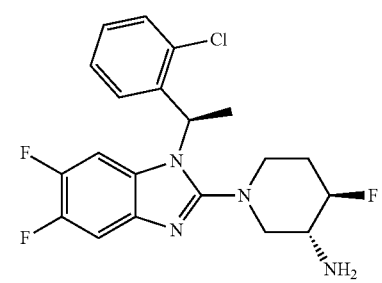 [SMILES: C[C@H](c1ccccc1Cl)n1c(N2CC[C@@H](F)[C@H](N)C2)nc2cc(F)c(F)cc21] | (3R,4R)-1-(1-((1R)-1-(2-chlorophenyl)ethyl)-5,6-difluoro-1H-benzimidazol-2-yl)-4-fluoro-3-piperidinamine | 409.2 |
| 325 | 68 | 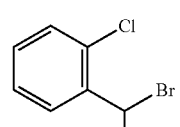 | B | 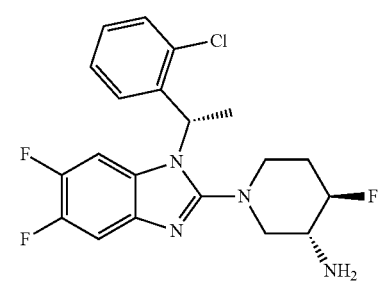 [SMILES: C[C@@H](c1ccccc1Cl)n1c(N2CC[C@@H](F)[C@H](N)C2)nc2cc(F)c(F)cc21] | (3R,4R)-1-(1-((1S)-1-(2-chlorophenyl)ethyl)-5,6-difluoro-1H-benzimidazol-2-yl)-4-fluoro-3-piperidinamine | 409.2 |
| 326 | 68 | 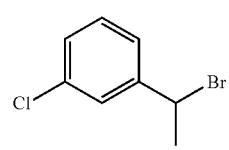 | B | 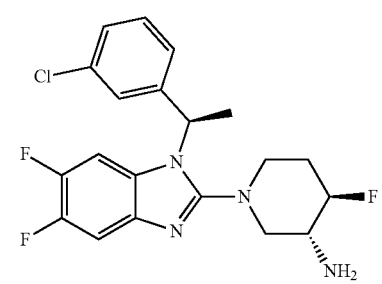 | (3R,4R)-1-(1-((1R)-1-(3-chlorophenyl)ethyl)-5,6-difluoro-1H-benzimidazol-2-yl)-4-fluoro-3-piperidinamine | 409.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 327 | 68 | | B | 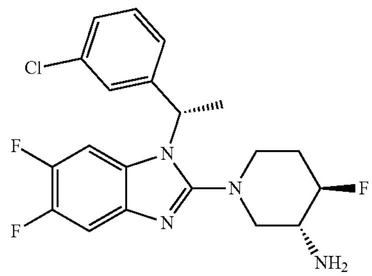 [SMILES: C[C@@H](c1cccc(Cl)c1)n1c(N2CC[C@@H](F)[C@H](N)C2)nc2cc(F)c(F)cc21] | (3R,4R)-1-(1-((1S)-1-(3-chlorophenyl)ethyl)-5,6-difluoro-1H-benzimidazol-2-yl)-4-fluoro-3-piperidinamine | 409.2 |
| 328 | 68 | | B | 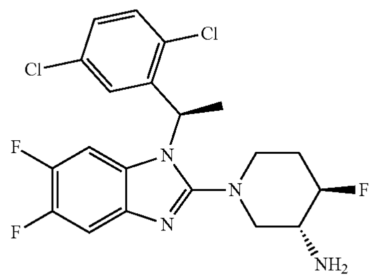 [SMILES: C[C@H](c1cc(Cl)ccc1Cl)n1c(N2CC[C@@H](F)[C@H](N)C2)nc2cc(F)c(F)cc21] | (3R,4R)-1-(1-((1R)-1-(2,5-dichlorophenyl)ethyl)-5,6-difluoro-1H-benzimidazol-2-yl)-4-fluoro-3-piperidinamine | 443.0 |
| 329 | 68 | | B | 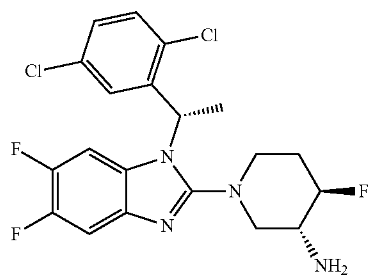 | (3R,4R)-1-(1-((1S)-1-(2,5-dichlorophenyl)ethyl)-5,6-difluoro-1H-benzimidazol-2-yl)-4-fluoro-3-piperidinamine | 443.0 |
| 330 | 68 | | B | 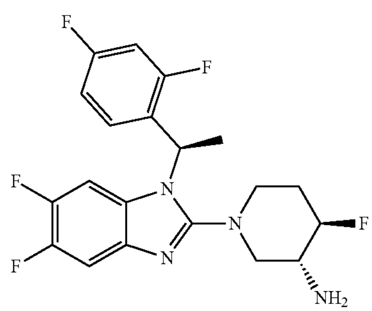 | (3R,4R)-1-(1-((1R)-1-(2,4-difluorophenyl)ethyl)-5,6-difluoro-1H-benzimidazol-2-yl)-4-fluoro-3-piperidinamine | 411.2 |
| 331 | 68 | | B | 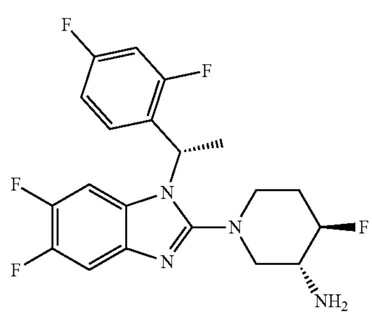 [SMILES: C[C@@H](c1ccc(F)cc1F)n1c(N2CC[C@@H](F)[C@H](N)C2)nc2cc(F)c(F)cc21] | (3R,4R)-1-(1-((1S)-1-(2,4-difluorophenyl)ethyl)-5,6-difluoro-1H-benzimidazol-2-yl)-4-fluoro-3-piperidinamine | 411.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 332 | 68 | | B | 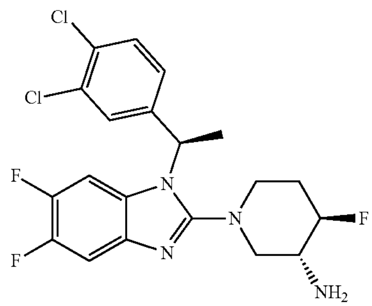 [SMILES: C[C@H](c1ccc(Cl)c(Cl)c1)n1c(N2CC[C@@H](F)[C@H](N)C2)nc2cc(F)c(F)cc21] | (3R,4R)-1-(1-((1R)-1-(3,4-dichlorophenyl)ethyl)-5,6-difluoro-1H-benzimidazol-2-yl)-4-fluoro-3-piperidinamine | 443.0 |
| 333 | 68 | | B | 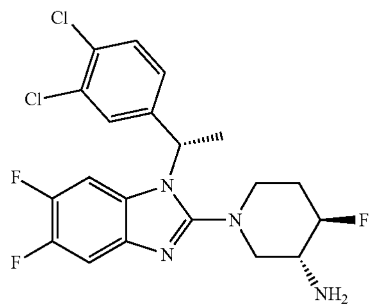 [SMILES: C[C@@H](c1ccc(Cl)c(Cl)c1)n1c(N2CC[C@@H](F)[C@H](N)C2)nc2cc(F)c(F)cc21] | (3R,4R)-1-(1-((1S)-1-(3,4-dichlorophenyl)ethyl)-5,6-difluoro-1H-benzimidazol-2-yl)-4-fluoro-3-piperidinamine | 443.0 |
| 334 | 68 | | B | 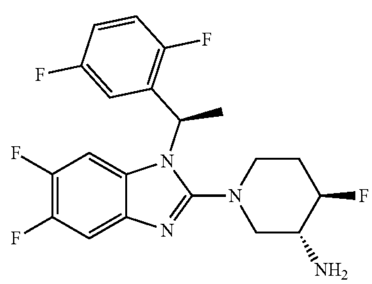 [SMILES: C[C@H](c1cc(F)ccc1F)n1c(N2CC[C@@H](F)[C@H](N)C2)nc2cc(F)c(F)cc21] | (3R,4R)-1-(1-((1R)-(2,5-difluorophenyl)ethyl)-5,6-difluoro-1H-benzimidazol-2-yl)-4-fluoro-3-piperidinamine | 411.2 |
| 335 | 68 | | B | 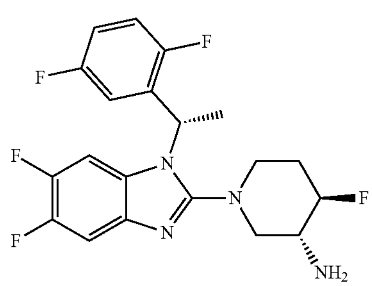 [SMILES: C[C@@H](c1cc(F)ccc1F)n1c(N2CC[C@@H](F)[C@H](N)C2)nc2cc(F)c(F)cc21] | (3R,4R)-1-(1-((1S)-1-(2,5-difluorophenyl)ethyl)-5,6-difluoro-1H-benzimidazol-2-yl)-4-fluoro-3-piperidinamine | 411.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 336 b | 68 | | B | 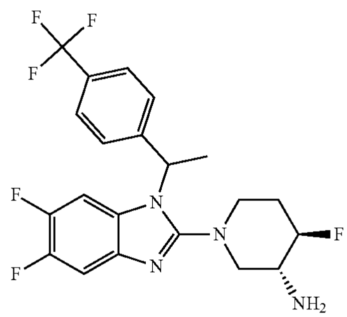 [SMILES: CC(c1ccc(C(F)(F)F)cc1)n1c(N2CC[C@@H](F)[C@H](N)C2)nc2cc(F)c(F)cc21] | (3R,4R)-1-(5,6-difluoro-1-((1R)-1-(4-(trifluoromethyl)phenyl)ethyl)-1H-benzimidazol-2-yl)-4-fluoro-3-piperidinamine | 443.2 |
| 337 b | 68 | | B | 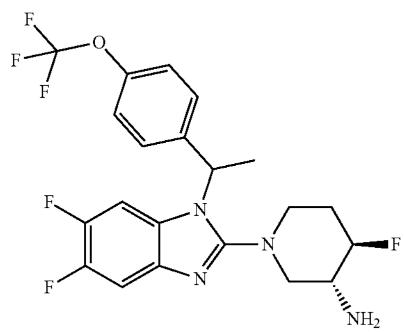 [SMILES: CC(c1ccc(OC(F)(F)F)cc1)n1c(N2CC[C@@H](F)[C@H](N)C2)nc2cc(F)c(F)cc21] | (3R,4R)-1-(5,6-difluoro-1-((1R)-1-(4-(trifluoromethoxy)phenyl)ethyl)-1H-benzimidazol-2-yl)-4-fluoro-3-piperidinamine | 459.2 |
| 338 | 68 | | B | 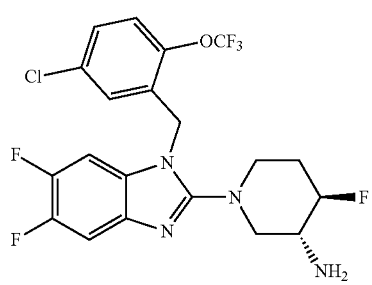 [SMILES: N[C@@H]1CN(c2nc3cc(F)c(F)cc3n2Cc2cc(Cl)ccc2OC(F)(F)F)CC[C@H]1F] | (3R,4R)-1-(1-(5-chloro-2-(trifluoromethoxy)benzyl)-5,6-difluoro-1H-benzimidazol-2-yl)-4-fluoro-3-piperidinamine | 479.2 |
| 339 | 68 | | B | 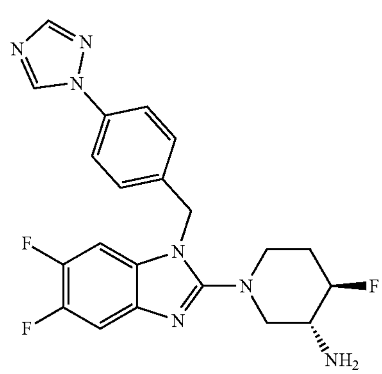 [SMILES: N[C@@H]1CN(c2nc3cc(F)c(F)cc3n2Cc2ccc(-n3cncn3)cc2)CC[C@H]1F] | (3R,4R)-1-(5,6-difluoro-1-(4-(1H-1,2,4-triazol-1-yl)benzyl)-1H-benzimidazol-2-yl)-4-fluoro-3-piperidinamine | 428.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 340 | 68 | 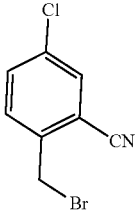 [SMILES: N#Cc1cc(Cl)ccc1CBr] | B | 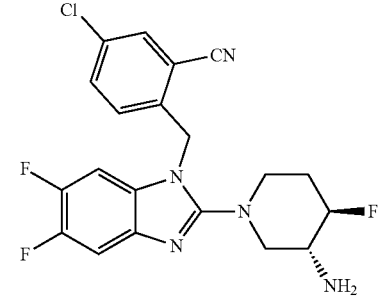 [SMILES: N#Cc1cc(Cl)ccc1Cn1c(N2CC[C@@H](F)[C@H](N)C2)nc2cc(F)c(F)cc21] | 2-((2-((3R,4R)-3-amino-4-fluoro-1-piperidinyl)-5,6-difluoro-1H-benzimidazol-1-yl)methyl)-5-chlorobenzonitrile | 420.2 |
| 341 | 68 | 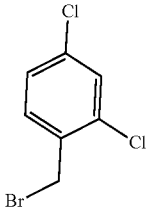 | B | 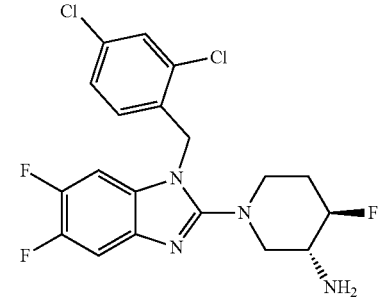 | (3R,4R)-1-(1-(2,4-dichlorobenzyl)-5,6-difluoro-1H-benzimidazol-2-yl)-4-fluoro-3-piperidinamine | 429.2 |
| 342 | 68 | 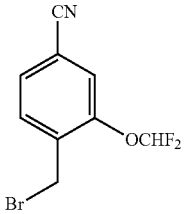 | B | 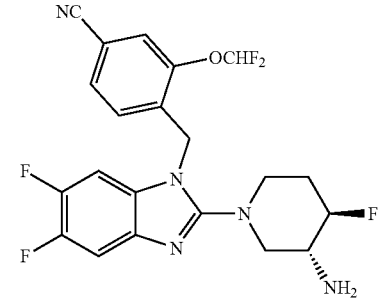 | 4-((2-((3R,4R)-3-amino-4-fluoro-1-piperidinyl)-5,6-difluoro-1H-benzimidazol-1-yl)methyl)-3-(difluoromethoxy)benzonitrile | 452.2 |
| 343 | 68 | 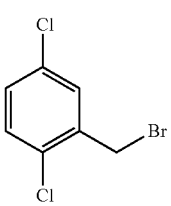 | B | 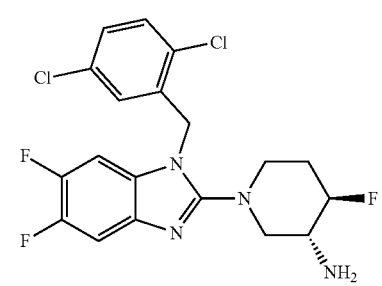 [SMILES: N[C@@H]1CN(c2nc3cc(F)c(F)cc3n2Cc2cc(Cl)ccc2Cl)CC[C@H]1F] | (3R,4R)-1-(1-(2,5-dichlorobenzyl)-5,6-difluoro-1H-benzimidazol-2-yl)-4-fluoro-3-piperidinamine | 429.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 344 | 68 | | B | 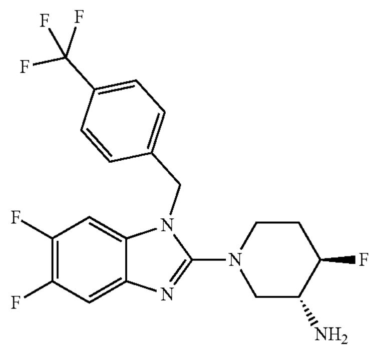 [SMILES: N[C@@H]1CN(c2nc3cc(F)c(F)cc3n2Cc2ccc(C(F)(F)F)cc2)CC[C@H]1F] | (3R,4R)-1-(1-(4-(1,1-difluoroethyl)benzyl)-5,6-difluoro-1H-benzimidazol-2-yl)-4-fluoro-3-piperidinamine | 425.2 |
| 345 | 68 | | B | 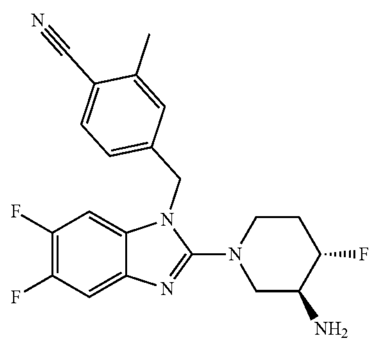 [SMILES: Cc1cc(Cn2c(N3CC[C@H](F)[C@@H](N)C3)nc3cc(F)c(F)cc32)ccc1C#N] | 4-((2-((3R,4R)-3-amino-4-fluoro-1-piperidinyl)-5,6-difluoro-1H-benzimidazol-1-yl)methyl)-2-methylbenzonitrile | 400.2 |
| 346 | 68 | | B | 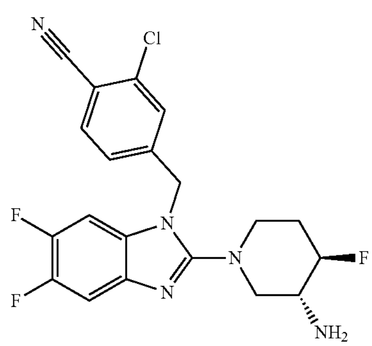 [SMILES: N#Cc1ccc(Cn2c(N3CC[C@@H](F)[C@H](N)C3)nc3cc(F)c(F)cc32)cc1Cl] | 4-((2-((3R,4R)-3-amino-4-fluoro-1-piperidinyl)-5,6-difluoro-1H-benzimidazol-1-yl)methyl)-2-chlorobenzonitrile | 420.2 |
| 347 | 68 | | B | 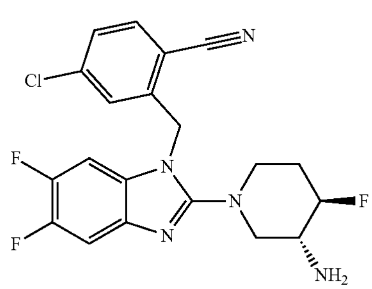 [SMILES: N#Cc1ccc(Cl)cc1Cn1c(N2CC[C@@H](F)[C@H](N)C2)nc2cc(F)c(F)cc21] | 2-((2-((3R,4R)-3-amino-4-fluoro-1-piperidinyl)-5,6-difluoro-1H-benzimidazol-1-yl)methyl)-4-chlorobenzonitrile | 420.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 348 | 68 | 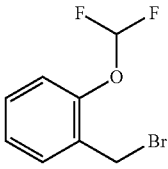 | B | 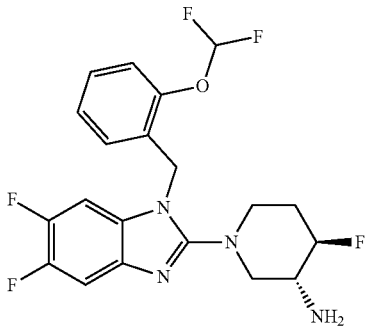 [SMILES: N[C@@H]1CN(c2nc3cc(F)c(F)cc3n2Cc2ccccc2OC(F)F)CC[C@H]1F] | (3R,4R)-1-(1-(2-(difluoromethoxy)benzyl)-5,6-difluoro-1H-benzimidazol-2-yl)-4-fluoro-3-piperidinamine | 427.2 |
| 349 | 68 | 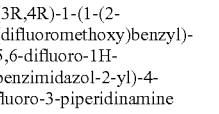 | B | 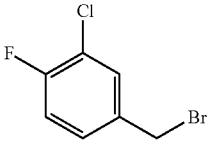 | (3R,4R)-1-(1-(3-chloro-4-fluorobenzyl)-5,6-difluoro-1H-benzimidazol-2-yl)-4-fluoro-3-piperidinamine | 413.0 |
| 350 | 68 | 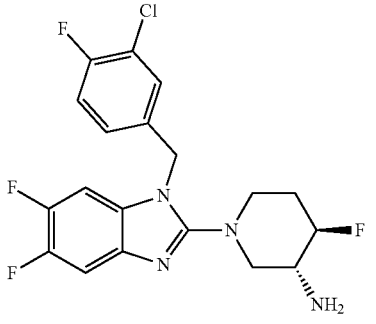 [SMILES: N[C@@H]1CN(c2nc3cc(F)c(F)cc3n2Cc2ccc(F)c(Cl)c2)CC[C@H]1F] | B | 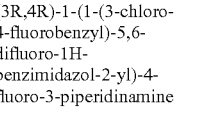 | (3R,4R)-1-(1-(4-chloro-2-methoxybenzyl)-5,6-difluoro-1H-benzimidazol-2-yl)-4-fluoro-3-piperidinamine | 425.2 |
| 351 | 68 | 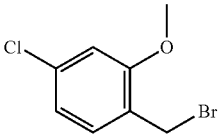 | B | 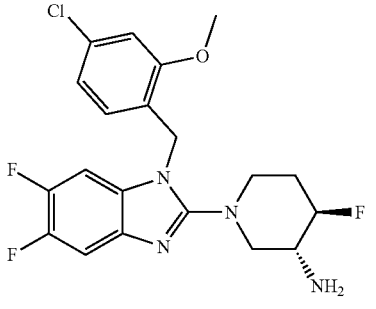 [SMILES: COc1cc(Cl)ccc1Cn1c(N2CC[C@@H](F)[C@H](N)C2)nc2cc(F)c(F)cc21] | (3R,4R)-1-(1-(2,4-difluorobenzyl)-5,6-difluoro-1H-benzimidazol-2-yl)-4-fluoro-3-piperidinamine | 397.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 352 | 68 | 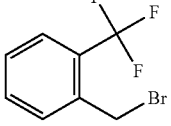 | B | 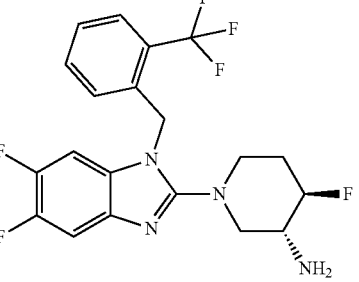 | (3R,4R)-1-(5,6-difluoro-1-(2-(trifluoromethyl)benzyl)-1H-benzimidazol-2-yl)-4-fluoro-3-piperidinamine | 429.2 |
| 353 | 68 | 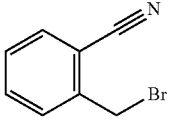 | B | 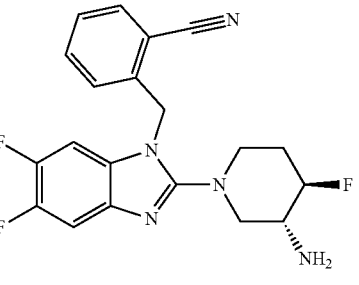 | 2-((2-((3R,4R)-3-amino-4-fluoro-1-piperidinyl)-5,6-difluoro-1H-benzimidazol-1-yl)methyl)benzonitrile | 386.2 |
| 354 | 68 | 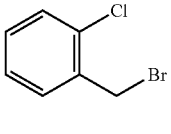 | B | 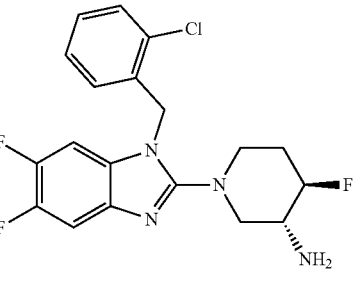 | (3R,4R)-1-(1-(2-chlorobenzyl)-5,6-difluoro-1H-benzimidazol-2-yl)-4-fluoro-3-piperidinamine | 395.0 |
| 355 | 68 | 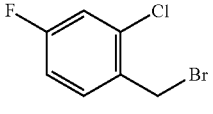 | B | 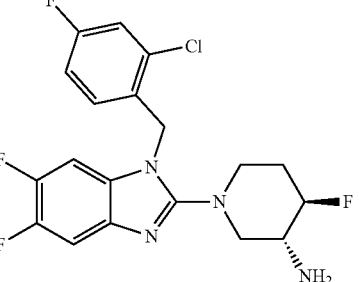 | (3R,4R)-1-(1-(2-chloro-4-fluorobenzyl)-5,6-difluoro-1H-benzimidazol-2-yl)-4-fluoro-3-piperidinamine | 413.0 |
| 356 | 68 | 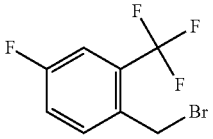 | B | 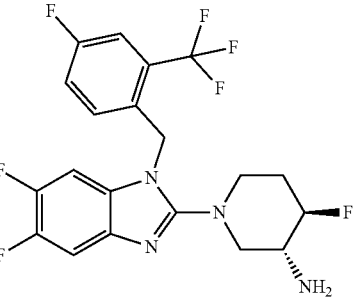 | (3R,4R)-1-(5,6-difluoro-1-(4-fluoro-2-(trifluoromethyl)benzyl)-1H-benzimidazol-2-yl)-4-fluoro-3-piperidinamine | 447.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 357 | 68 | 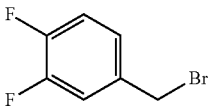 | B | 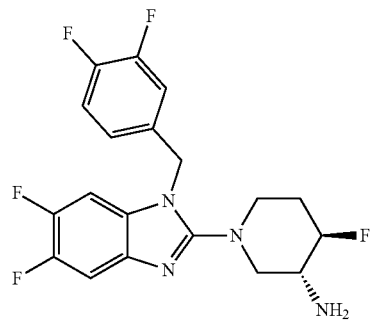 [SMILES: N[C@@H]1CN(c2nc3cc(F)c(F)cc3n2Cc2ccc(F)c(F)c2)CC[C@H]1F] | (3R,4R)-1-(1-(3,4-difluorobenzyl)-5,6-difluoro-1H-benzimidazol-2-yl)-4-fluoro-3-piperidinamine | 397.2 |
| 358 | 68 | 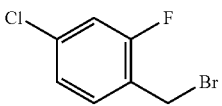 | B | 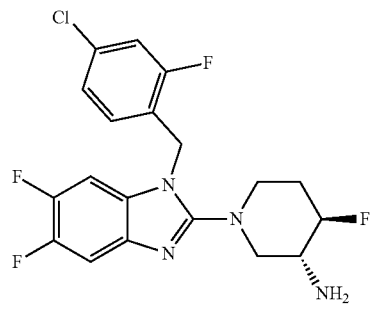 [SMILES: N[C@@H]1CN(c2nc3cc(F)c(F)cc3n2Cc2ccc(Cl)cc2F)CC[C@H]1F] | (3R,4R)-1-(1-(4-chloro-2-fluorobenzyl)-5,6-difluoro-1H-benzimidazol-2-yl)-4-fluoro-3-piperidinamine | 413.0 |
| 359 | 68 | 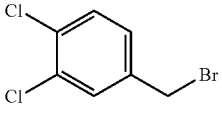 | B | 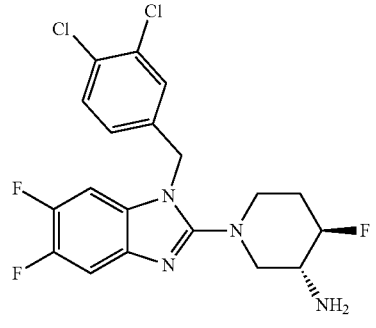 [SMILES: N[C@@H]1CN(c2nc3cc(F)c(F)cc3n2Cc2ccc(Cl)c(Cl)c2)CC[C@H]1F] | (3R,4R)-1-(1-(3,4-dichlorobenzyl)-5,6-difluoro-1H-benzimidazol-2-yl)-4-fluoro-3-piperidinamine | 429.0 |
| 360 | 68 | 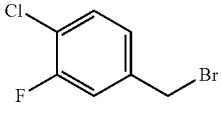 | B | 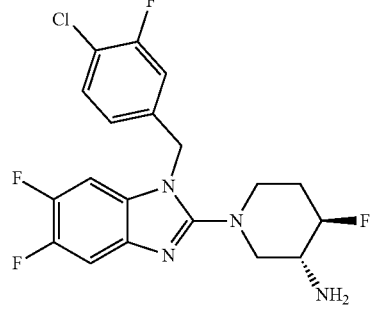 | (3R,4R)-1-(1-(4-chloro-3-fluorobenzyl)-5,6-difluoro-1H-benzimidazol-2-yl)-4-fluoro-3-piperidinamine | 413.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 361 | 68 | | B | 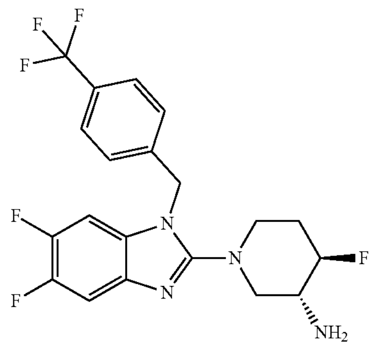 [SMILES: N[C@@H]1CN(c2nc3cc(F)c(F)cc3n2Cc2ccc(C(F)(F)F)cc2)CC[C@H]1F] | (3R,4R)-1-(5,6-difluoro-1-(4-(trifluoromethyl)benzyl)-1H-benzimidazol-2-yl)-4-fluoro-3-piperidinamine | 429.2 |
| 362 | 68 | | B | 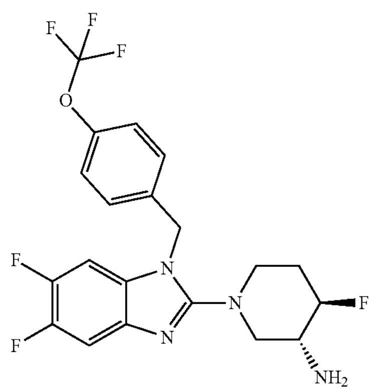 [SMILES: N[C@@H]1CN(c2nc3cc(F)c(F)cc3n2Cc2ccc(OC(F)(F)F)cc2)CC[C@H]1F] | (3R,4R)-1-(5,6-difluoro-1-(4-(trifluoromethoxy)benzyl)-1H-benzimidazol-2-yl)-4-fluoro-3-piperidinamine | 445.2 |
| 363 | 68 | | B | 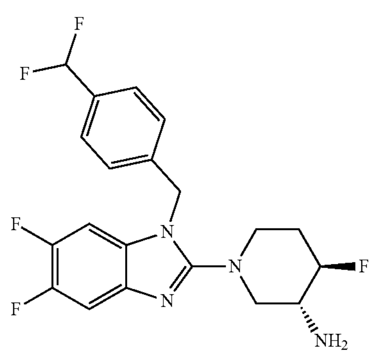 [SMILES: N[C@@H]1CN(c2nc3cc(F)c(F)cc3n2Cc2ccc(C(F)F)cc2)CC[C@H]1F] | (3R,4R)-1-(1-(4-(difluoromethyl)benzyl)-5,6-difluoro-1H-benzimidazol-2-yl)-4-fluoro-3-piperidinamine | 411.2 |
| 364 | 68 | | B | 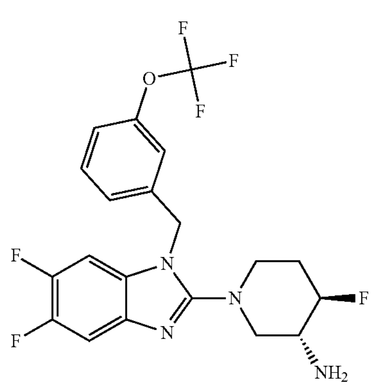 [SMILES: N[C@@H]1CN(c2nc3cc(F)c(F)cc3n2Cc2cccc(OC(F)(F)F)c2)CC[C@H]1F] | (3R,4R)-1-(5,6-difluoro-1-(3-(trifluoromethoxy)benzyl)-1H-benzimidazol-2-yl)-4-fluoro-3-piperidinamine | 445.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 365 | 68 | 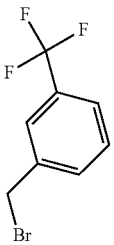 | B | 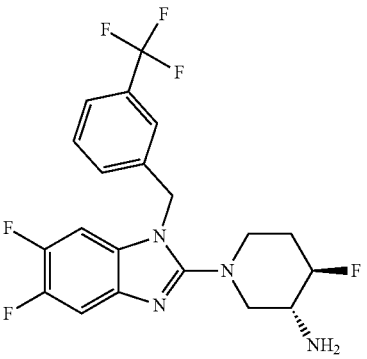 [SMILES: N[C@@H]1CN(c2nc3cc(F)c(F)cc3n2Cc2cccc(C(F)(F)F)c2)CC[C@H]1F] | (3R,4R)-1-(5,6-difluoro-1-(3-(trifluoromethyl)benzyl)-1H-benzimidazol-2-yl)-4-fluoro-3-piperidinamine | 429.2 |
| 366 | 68 | 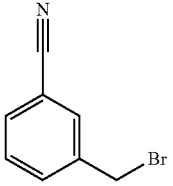 | B | 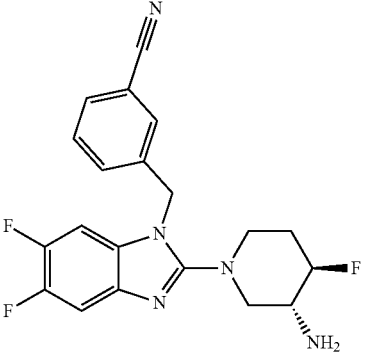 [SMILES: N#Cc1cccc(Cn2c(N3CC[C@@H](F)[C@H](N)C3)nc3cc(F)c(F)cc32)c1] | 3-((2-((3R,4R)-3-amino-4-fluoro-1-piperidinyl)-5,6-difluoro-1H-benzimidazol-1-yl)methyl)benzonitrile | 386.2 |
| 367 | 68 | 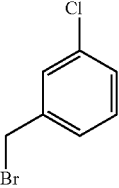 | B | 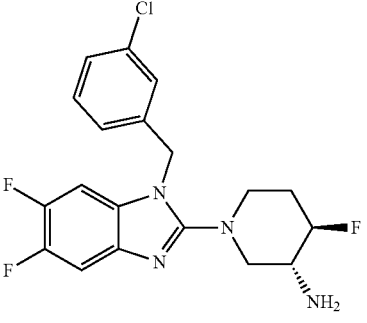 [SMILES: N[C@@H]1CN(c2nc3cc(F)c(F)cc3n2Cc2cccc(Cl)c2)CC[C@H]1F] | (3R,4R)-1-(1-(3-chlorobenzyl)-5,6-difluoro-1H-benzimidazol-2-yl)-4-fluoro-3-piperidinamine | 395.2 |
| 368 | 71 | 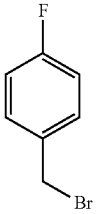 | B | 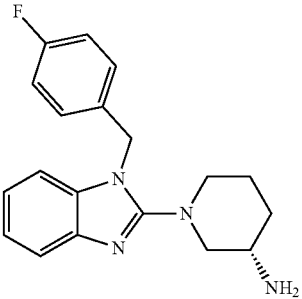 [SMILES: N[C@H]1CCCN(c2nc3ccccc3n2Cc2ccc(F)cc2)C1] | (S)-1-(1-(4-fluorobenzyl)-1H-benzo[d]imidazol-2-yl)piperidin-3-amine | 325.3 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 369 | 71 | | B | 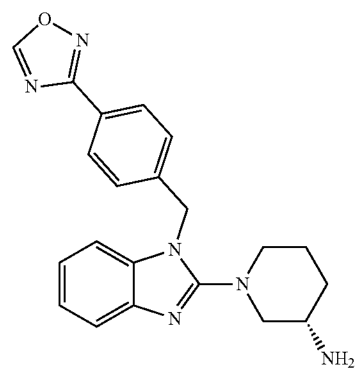 [SMILES: N[C@H]1CCCN(c2nc3ccccc3n2Cc2ccc(-c3ncon3)cc2)C1] | (S)-1-(1-(4-(1,2,4-oxadiazol-3-yl)benzyl)-1H-benzo[d]imidazol-2-yl)piperidin-3-amine | 375.2 |
| 370 | 72 | | B | 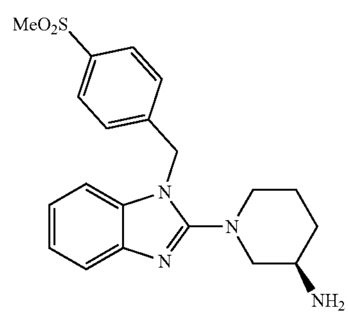 [SMILES: CS(=O)(=O)c1ccc(Cn2c(N3CCC[C@@H](N)C3)nc3ccccc32)cc1] | (R)-1-(1-(4-(methylsulfonyl)benzyl)-1H-benzo[d]imidazol-2-yl)piperidin-3-amine | 385.2 |
| 371 | 72 | | B | 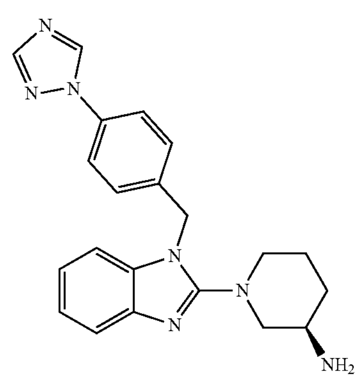 [SMILES: N[C@@H]1CCCN(c2nc3ccccc3n2Cc2ccc(-n3cncn3)cc2)C1] | (R)-1-(1-(4-(1H-1,2,4-triazol-1-yl)benzyl)-1H-benzo[d]imidazol-2-yl)piperidin-3-amine | 374.0 |
| 372 | 72 | | A | 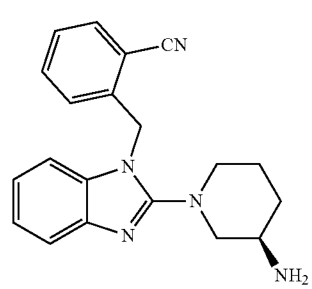 | (R)-2-((2-(3-aminopiperidin-1-yl)-1H-benzo[d]imidazol-1-yl)methyl)benzonitrile | 332.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 373 | 72 | 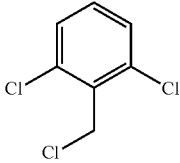 | A | 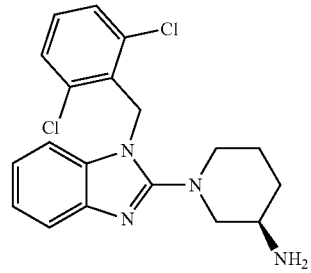 [SMILES: N[C@@H]1CCCN(c2nc3ccccc3n2Cc2c(Cl)cccc2Cl)C1] | (R)-1-(1-(2,6-dichlorobenzyl)-1H-benzo[d]imidazol-2-yl)piperidin-3-amine | 376.2 |
| 374 | 72 | 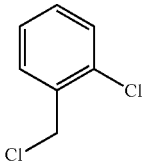 | A | 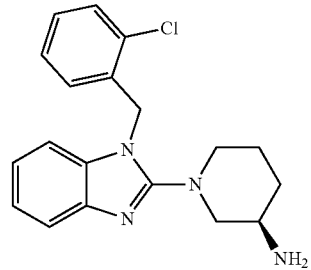 [SMILES: N[C@@H]1CCCN(c2nc3ccccc3n2Cc2ccccc2Cl)C1] | (R)-1-(1-(2-chlorobenzyl)-1H-benzo[d]imidazol-2-yl)piperidin-3-amine | 341.2 |
| 375 | 72 | 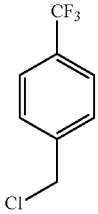 | A | 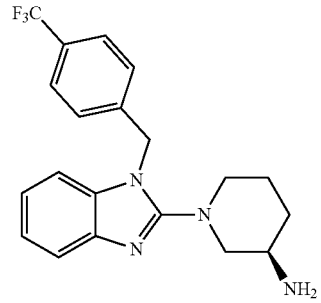 | (R)-1-(1-(4-(trifluoromethyl)benzyl)-1H-benzo[d]imidazol-2-yl)piperidin-3-amine | 375.2 |
| 376 | 72 | 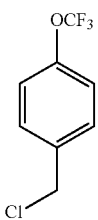 [SMILES: FC(F)(F)Oc1ccc(CCl)cc1] | A | 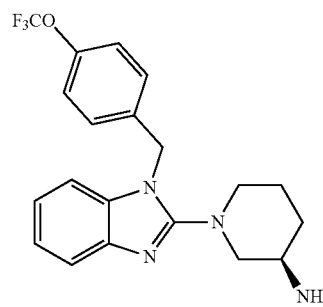 | (R)-1-(1-(4-(trifluoromethoxy)benzyl)-1H-benzo[d]imidazol-2-yl)piperidin-3-amine | 391.0 |
| 377 | 72 | 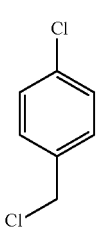 | A | 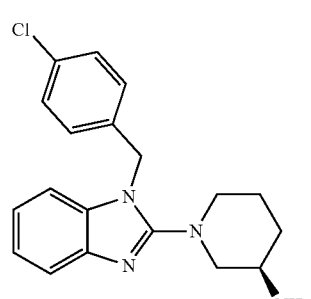 | (R)-1-(1-(4-chlorobenzyl)-1H-benzo[d]imidazol-2-yl)piperidin-3-amine | 341.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 378 | 72 | 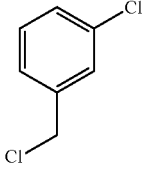 | A | 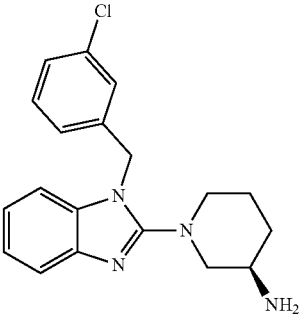 | (R)-1-(1-(3-chlorobenzyl)-1H-benzo[d]imidazol-2-yl)piperidin-3-amine | 341.2 |
| 379 | 72 | 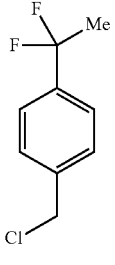 [SMILES: CC(F)(F)c1ccc(CCl)cc1] | A | 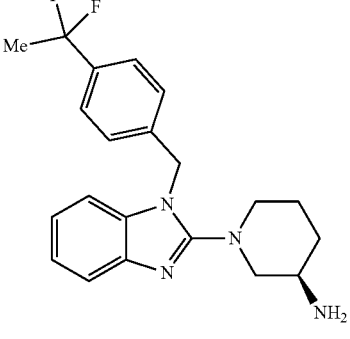 | (R)-1-(1-(4-(1,1-difluoroethyl)benzyl)-1H-benzo[d]imidazol-2-yl)piperidin-3-amine | 371.2 |
| 380 | 72 | 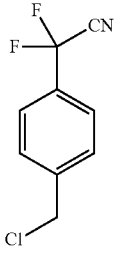 [SMILES: N#CC(F)(F)c1ccc(CCl)cc1] | A | 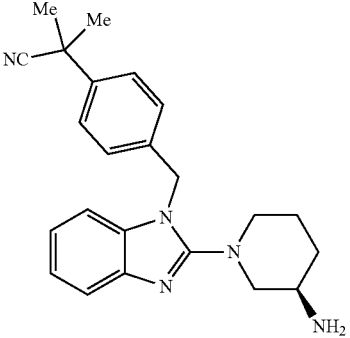 [SMILES: CC(C)(C#N)c1ccc(Cn2c(N3CCC[C@@H](N)C3)nc3ccccc32)cc1] | (R)-2-(4-((2-(3-aminopiperidin-1-yl)-1H-benzo[d]imidazol-1-yl)methyl)phenyl)-2-methylpropanenitrile | 374.2 |
| 381 | 72 | 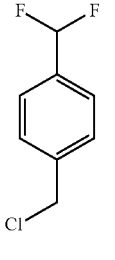 [SMILES: FC(F)c1ccc(CCl)cc1] | A | 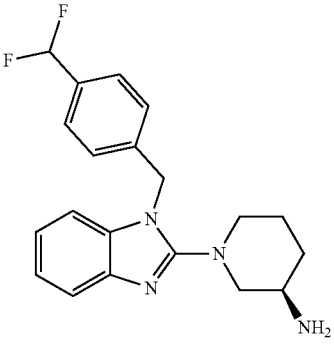 [SMILES: N[C@@H]1CCCN(c2nc3ccccc3n2Cc2ccc(C(F)F)cc2)C1] | (R)-1-(1-(4-(difluoromethyl)benzyl)-1H-benzo[d]imidazol-2-yl)piperidin-3-amine | 357.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 382 | 72 | 4-(chloromethyl)-N-methylbenzamide | A | 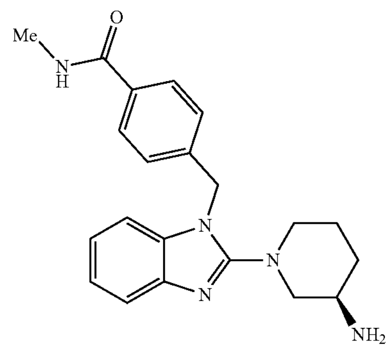 [SMILES: CNC(=O)c1ccc(Cn2c(N3CCC[C@@H](N)C3)nc3ccccc32)cc1] | (R)-4-((2-(3-aminopiperidin-1-yl)-1H-benzo[d]imidazol-1-yl)methyl)-N-methylbenzamide | 364.2 |
| 383 | 72 | 4-(chloromethyl)-3-fluorobenzonitrile | A | 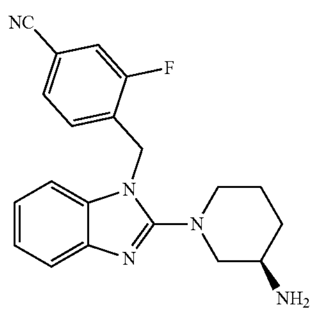 [SMILES: N#Cc1ccc(Cn2c(N3CCC[C@@H](N)C3)nc3ccccc32)c(F)c1] | (R)-4-((2-(3-aminopiperidin-1-yl)-1H-benzo[d]imidazol-1-yl)methyl)-3-fluorobenzonitrile | 350.2 |
| 384 | 72 | 2-(4-(chloromethyl)phenoxy)acetonitrile | A | 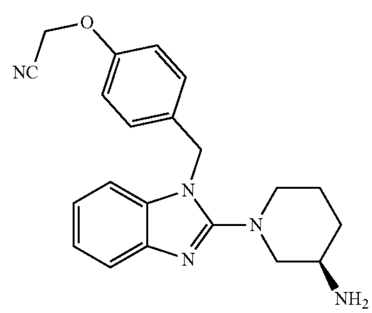 [SMILES: N#CCOc1ccc(Cn2c(N3CCC[C@@H](N)C3)nc3ccccc32)cc1] | (R)-2-(4-((2-(3-aminopiperidin-1-yl)-1H-benzo[d]imidazol-1-yl)methyl)phenoxy)acetonitrile | 362.2 |
| 385 | 72 | 4-(chloromethyl)-N,N-dimethylbenzenesulfonamide | A | 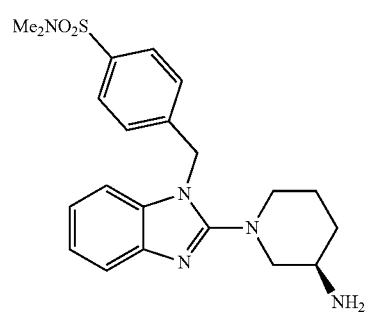 | (R)-4-((2-(3-aminopiperidin-1-yl)-1H-benzo[d]imidazol-1-yl)methyl)-N,N-dimethylbenzenesulfonamide | 414.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 386 | 72 | 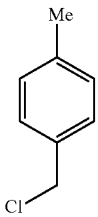 | A | 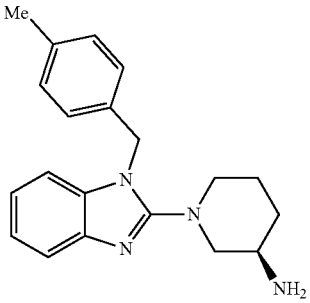 [SMILES: Cc1ccc(Cn2c(N3CCC[C@@H](N)C3)nc3ccccc32)cc1] | (R)-1-(1-(4-methylbenzyl)-1H-benzo[d]imidazol-2-yl)piperidin-3-amine | 321.2 |
| 387 | 72 | 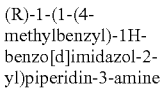 | A | 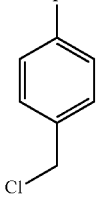 | (R)-1-(1-(4-fluorobenzyl)-1H-benzo[d]imidazol-2-yl)piperidin-3-amine | 324.4 |
| 388 | 72 | 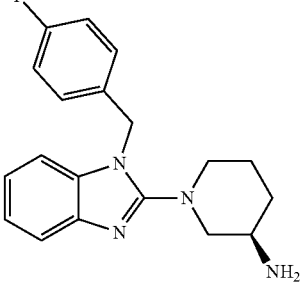 | A | 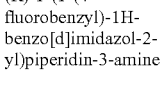 | (R)-1-(1-((1-methyl-1H-indazol-7-yl)methyl)-1H-benzo[d]imidazol-2-yl)piperidin-3-amine | 361.2 |
| 389 | 72 | 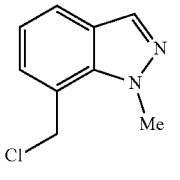 | A | 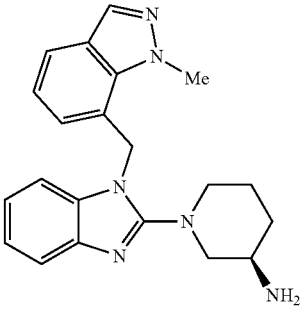 [SMILES: Cn1ncc2cccc(Cn3c(N4CCC[C@@H](N)C4)nc4ccccc43)c21] | (R)-1-(1-(2,4-difluorobenzyl)-1H-benzo[d]imidazol-2-yl)piperidin-3-amine | 343.2 | ized
TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 390 | 72 | 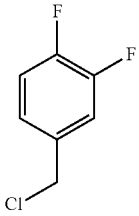 | A | 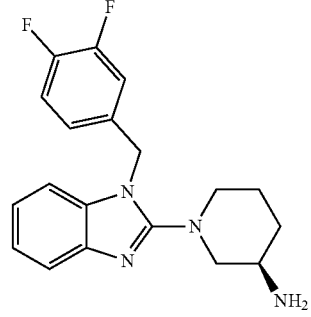 [SMILES: N[C@@H]1CCCN(c2nc3ccccc3n2Cc2ccc(F)c(F)c2)C1] | (R)-1-(1-(3,4-difluorobenzyl)-1H-benzo[d]imidazol-2-yl)piperidin-3-amine | 343.2 |
| 391 | 72 | 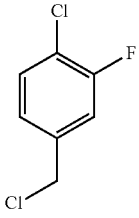 | A | 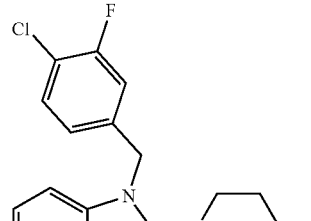 | (R)-1-(1-(4-chloro-3-fluorobenzyl)-1H-benzo[d]imidazol-2-yl)piperidin-3-amine | 359.2 |
| 392 | 72 | 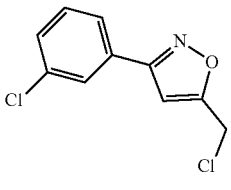 [SMILES: ClCc1cc(-c2cccc(Cl)c2)no1] | A | 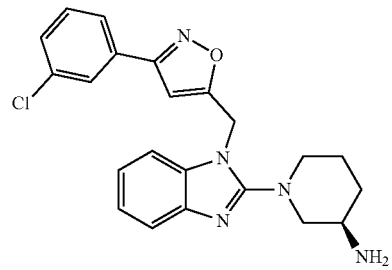 [SMILES: N[C@@H]1CCCN(c2nc3ccccc3n2Cc2cc(-c3cccc(Cl)c3)no2)C1] | (R)-1-(1-((3-(3-chlorophenyl)isoxazol-5-yl)methyl)-1H-benzo[d]imidazol-2-yl)piperidin-3-amine | 408.2 |
| 393 | 72 | 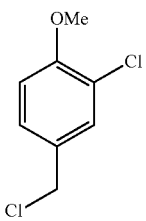 [SMILES: COc1ccc(CCl)cc1Cl] | A | 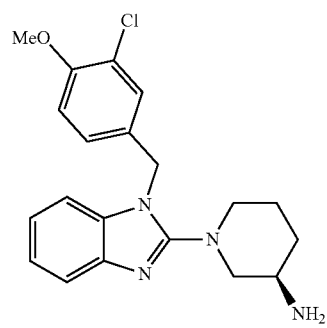 [SMILES: COc1ccc(Cn2c(N3CCC[C@@H](N)C3)nc3ccccc32)cc1Cl] | (R)-1-(1-(3-chloro-4-methoxybenzyl)-1H-benzo[d]imidazol-2-yl)piperidin-3-amine | 371.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 394 | 72 | | A | 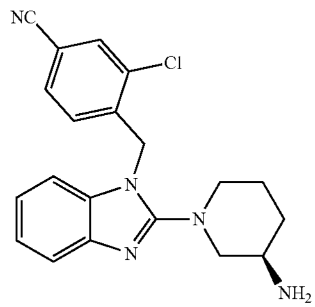 [SMILES: N#Cc1ccc(Cn2c(N3CCC[C@@H](N)C3)nc3ccccc32)c(Cl)c1] | (R)-4-((2-(3-aminopiperidin-1-yl)-1H-benzo[d]imidazol-1-yl)methyl)-3-chlorobenzonitrile | 366.2 |
| 395 | 72 | | A | 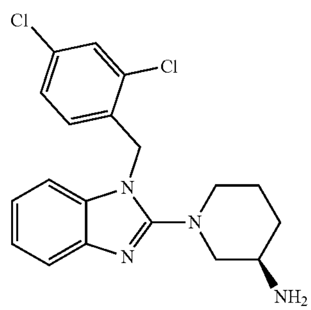 | (R)-1-(1-(2,4-dichlorobenzyl)-1H-benzo[d]imidazol-2-yl)piperidin-3-amine | 376.2 |
| 396 | 72 | | A | 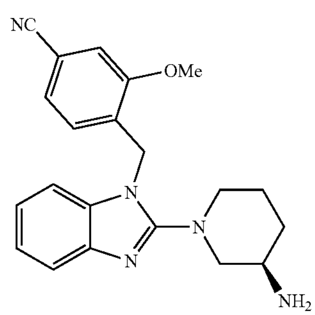 [SMILES: COc1cc(C#N)ccc1Cn1c(N2CCC[C@@H](N)C2)nc2ccccc21] | (R)-4-((2-(3-aminopiperidin-1-yl)-1H-benzo[d]imidazol-1-yl)methyl)-3-methoxybenzonitrile | 362.2 |
| 397 | 72 | | A | 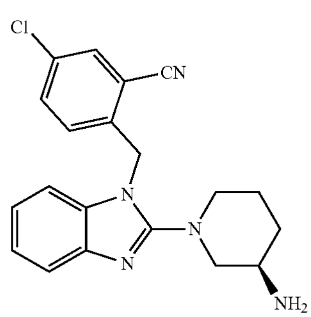 [SMILES: N#Cc1cc(Cl)ccc1Cn1c(N2CCC[C@@H](N)C2)nc2ccccc21] | (R)-2-((2-(3-aminopiperidin-1-yl)-1H-benzo[d]imidazol-1-yl)methyl)-5-chlorobenzonitrile | 366.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 398 | 72 | 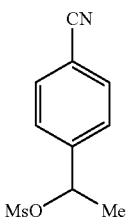 | A | 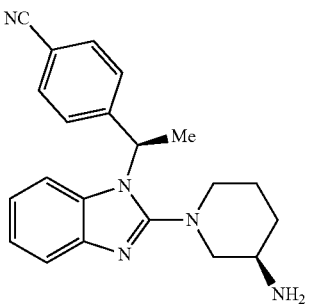 [SMILES: C[C@H](c1ccc(C#N)cc1)n1c(N2CCC[C@@H](N)C2)nc2ccccc21] | 4-((R)-1-(2-((R)-3-aminopiperidin-1-yl)-1H-benzo[d]imidazol-1-yl)ethyl)benzonitrile | 347.2 |
| 399 | 71 | 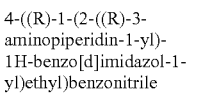 | A | 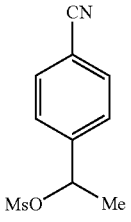 | 4-(1-(2-((S)-3-aminopiperidin-1-yl)-1H-benzo[d]imidazol-1-yl)ethyl)benzonitrile | 346.2 |
| 400 | 72 | 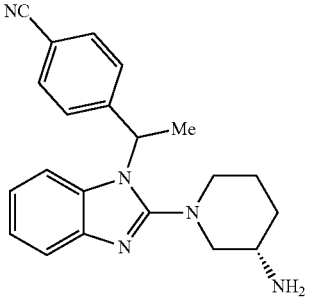 [SMILES: CC(c1ccc(C#N)cc1)n1c(N2CCC[C@H](N)C2)nc2ccccc21] | A | 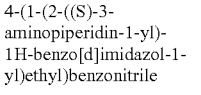 | (R)-3-((2-(3-aminopiperidin-1-yl)-1H-benzo[d]imidazol-1-yl)methyl)benzonitrile | 332.2 |
| 494 | | 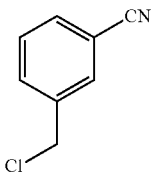 | B | 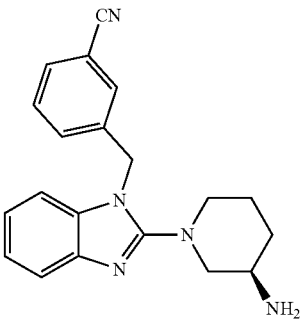 [SMILES: N#Cc1cccc(Cn2c(N3CCC[C@@H](N)C3)nc3ccccc32)c1] | (3R,4R)-3-amino-1-(1-((5-chloropyrimidin-2-yl)methyl)-5-fluoro-1H-benzo[d]imidazol-2-yl)piperidin-4-ol | 377.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 495 | | chloroacetyl morpholine | B | 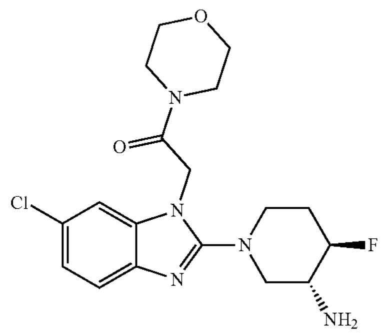 [SMILES: N[C@@H]1CN(c2nc3ccc(Cl)cc3n2CC(=O)N2CCOCC2)CC[C@H]1F] | 2-(2-((3R,4R)-3-amino-4-fluoropiperidin-1-yl)-6-chloro-1H-benzo[d]imidazol-1-yl)-1-morpholinoethanone | 396.2 |
| 496 | 75 | 5-chloro-2-(mesyloxymethyl)pyrimidine | B | 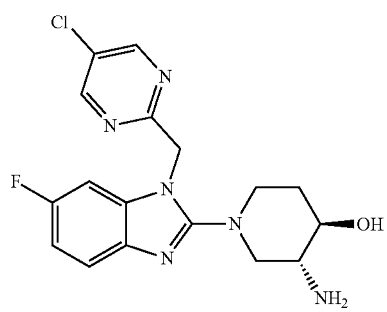 [SMILES: N[C@@H]1CN(c2nc3ccc(F)cc3n2Cc2ncc(Cl)cn2)CC[C@H]1O] | (3R,4R)-3-amino-1-(1-((5-chloropyrimidin-2-yl)methyl)-6-fluoro-1H-benzo[d]imidazol-2-yl)piperidin-4-ol | 377.2 |
| 497 | 69 | chloroacetyl morpholine | B | 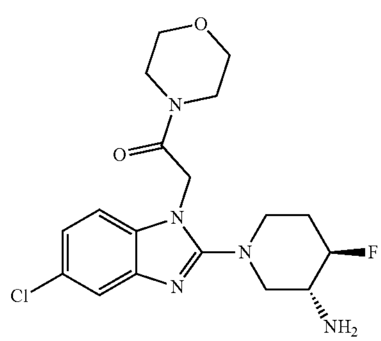 [SMILES: N[C@@H]1CN(c2nc3cc(Cl)ccc3n2CC(=O)N2CCOCC2)CC[C@H]1F] | -(2-((3R,4R)-3-amino-4-fluoropiperidin-1-yl)-5-chloro-1H-benzo[d]imidazol-1-yl)-1-morpholinoethanone | 396.2 |
| 498 | 68 | 5-chloro-2-(1-chloroethyl)pyrimidine | B | 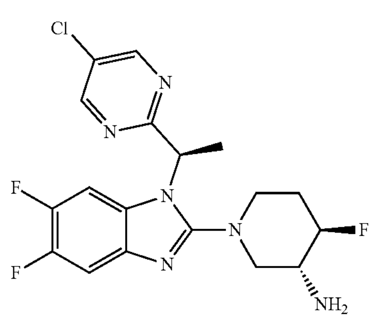 [SMILES: C[C@H](c1ncc(Cl)cn1)n1c(N2CC[C@@H](F)[C@H](N)C2)nc2cc(F)c(F)cc21] | (3R,4R)-1-(1-((R)-1-(5-chloropyrimidin-2-yl)ethyl)-5,6-difluoro-1H-benzo[d]imidazol-2-yl)-4-fluoropiperidin-3-amine | 411.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 499 | 81 | 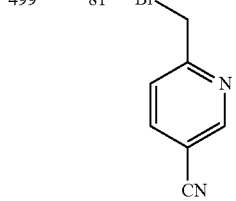 | B | 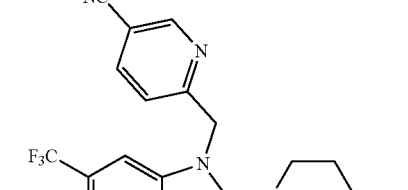 | 6-((2-((3R,4R)-3-amino-4-fluoropiperidin-1-yl)-6-(trifluoromethyl)-1H-imidazo[4,5-b]pyridin-1-yl)methyl)nicotinonitrile | 420.2 |
| 500 | 68 | 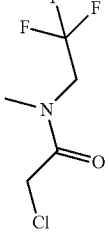 | B | 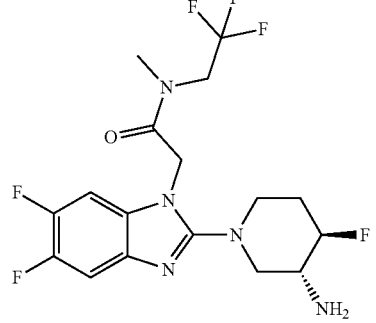 | 2-(2-((3R,4R)-3-amino-4-fluoropiperidin-1-yl)-5,6-difluoro-1H-benzo[d]imidazol-1-yl)-N-methyl-N-(2,2,2-trifluoroethyl)acetamide | 424.2 |
| 501 | 68 | 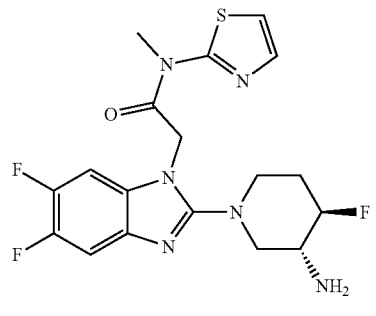 | B | 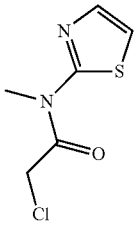 | 2-(2-((3R,4R)-3-amino-4-fluoropiperidin-1-yl)-5,6-difluoro-1H-benzo[d]imidazol-1-yl)-N-methyl-N-(thiazol-2-yl)acetamide | 425.2 |
| 502 | 69 | 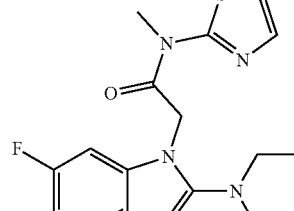 | B | 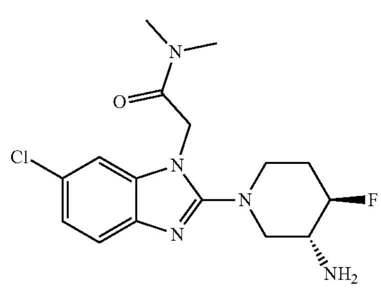 [SMILES: CN(C)C(=O)Cn1c(N2CC[C@@H](F)[C@H](N)C2)nc2ccc(Cl)cc21] | 2-(2-((3R,4R)-3-amino-4-fluoropiperidin-1-yl)-6-chloro-1H-benzo[d]imidazol-1-yl)-N,N-dimethylacetamide | 354.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 503 | 65 | 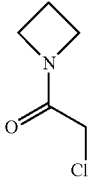 | B | 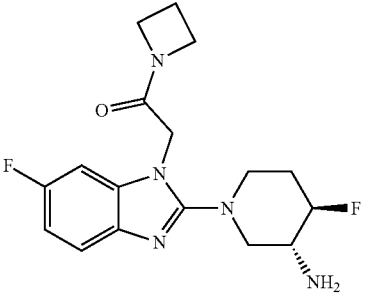 [SMILES: N[C@@H]1CN(c2nc3ccc(F)cc3n2CC(=O)N2CCC2)CC[C@H]1F] | 2-(2-((3R,4R)-3-amino-4-fluoropiperidin-1-yl)-6-fluoro-1H-benzo[d]imidazol-1-yl)-1-(azetidin-1-yl)ethan-1-one | 350.2 |
| 504 | 68 | 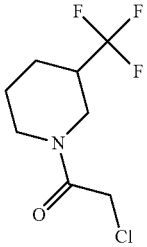 [SMILES: O=C(CCl)N1CCCC(C(F)(F)F)C1] | B | 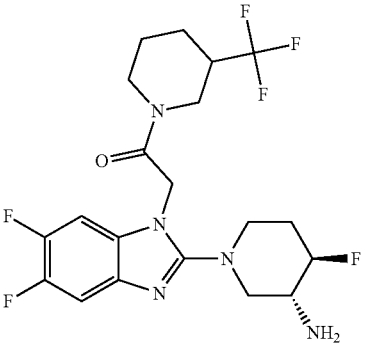 [SMILES: N[C@@H]1CN(c2nc3cc(F)c(F)cc3n2CC(=O)N2CCCC(C(F)(F)F)C2)CC[C@H]1F] | 2-(2-((3R,4R)-3-amino-4-fluoropiperidin-1-yl)-5,6-difluoro-1H-benzo[d]imidazol-1-yl)-1-(3-(trifluoromethyl)piperidin-1-yl)ethan-1-one | 464.2 |
| 505 | 68 | 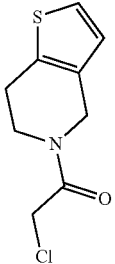 [SMILES: O=C(CCl)N1CCc2sccc2C1] | B | 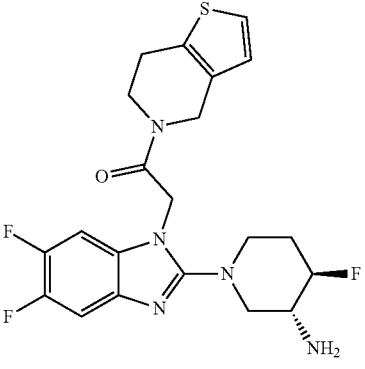 [SMILES: N[C@@H]1CN(c2nc3cc(F)c(F)cc3n2CC(=O)N2CCc3sccc3C2)CC[C@H]1F] | 2-(2-((3R,4R)-3-amino-4-fluoropiperidin-1-yl)-5,6-difluoro-1H-benzo[d]imidazol-1-yl)-1-(6,7-dihydrothieno[3,2-c]pyridin-5(4H)-yl)ethan-1-one | 450.2 |
| 506 | 69 | 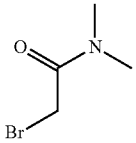 | B | 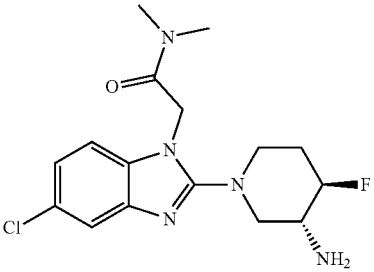 [SMILES: CN(C)C(=O)Cn1c(N2CC[C@@H](F)[C@H](N)C2)nc2cc(Cl)ccc21] | 2-(2-((3R,4R)-3-amino-4-fluoropiperidin-1-yl)-5-chloro-1H-benzo[d]imidazol-1-yl)-N,N-dimethylacetamide | 354.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 507 | 68 | | B | 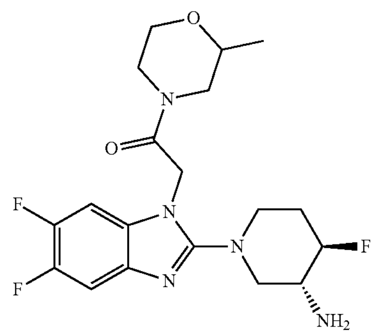 [SMILES: CC1CN(C(=O)Cn2c(N3CC[C@@H](F)[C@H](N)C3)nc3cc(F)c(F)cc32)CCO1] | 2-(2-((3R,4R)-3-amino-4-fluoropiperidin-1-yl)-5,6-difluoro-1H-benzo[d]imidazol-1-yl)-1-(2-methyl)morpholino)ethan-1-one | 412.2 |
| 508 | 68 | | B | 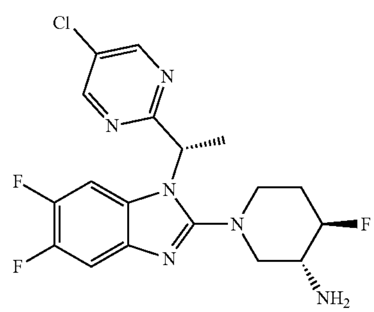 [SMILES: C[C@@H](c1ncc(Cl)cn1)n1c(N2CC[C@@H](F)[C@H](N)C2)nc2cc(F)c(F)cc21] | (3R,4R)-1-(1-((R)-1-(5-chloropyrimidin-2-yl)ethyl)-5,6-difluoro-1H-benzo[d]imidazol-2-yl)-4-fluoropiperidin-3-amine | 411.0 |
| 509 | 82 | | B | 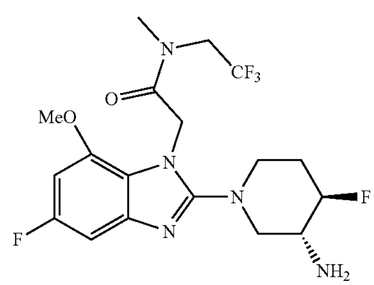 [SMILES: COc1cc(F)cc2nc(N3CC[C@@H](F)[C@H](N)C3)n(CC(=O)N(C)CC(F)(F)F)c12] | 2-(2-((3R,4R)-3-amino-4-fluoropiperidin-1-yl)-5-fluoro-7-methoxy-1H-benzo[d]imidazol-1-yl)-N-methyl-N-(2,2,2-trifluoroethyl)acetamide | 436.2 |
| 510 | 68 | | B | 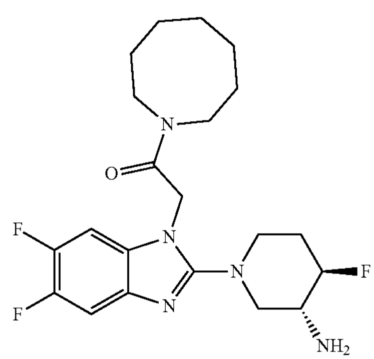 [SMILES: N[C@@H]1CN(c2nc3cc(F)c(F)cc3n2CC(=O)N2CCCCCCC2)CC[C@H]1F] | 2-(2-((3R,4R)-3-amino-4-fluoropiperidin-1-yl)-5,6-difluoro-1H-benzo[d]imidazol-1-yl)-1-(azocan-1-yl)ethan-1-one | 424.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 511 | 68 | | B | 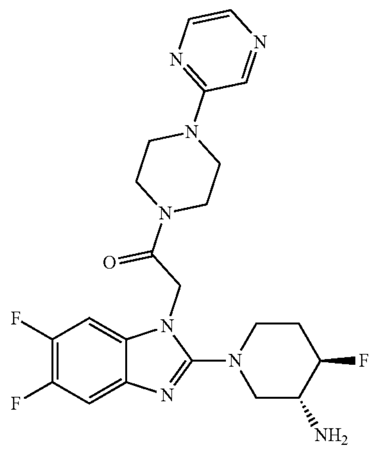 [SMILES: N[C@@H]1CN(c2nc3cc(F)c(F)cc3n2CC(=O)N2CCN(c3cnccn3)CC2)CC[C@H]1F] | 2-(2-((3R,4R)-3-amino-4-fluoropiperidin-1-yl)-5,6-difluoro-1H-benzo[d]imidazol-1-yl)-1-(4-(pyrazin-2-yl)piperazin-1-yl)ethan-1-one | 475.2 |
| 512 | 68 | | B | 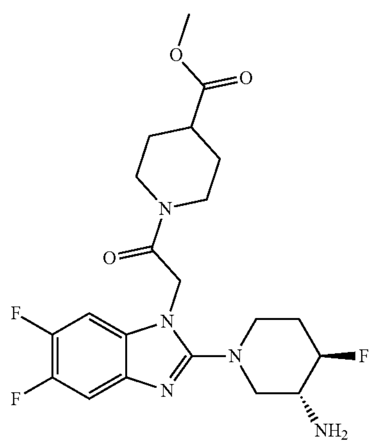 [SMILES: COC(=O)C1CCN(C(=O)Cn2c(N3CC[C@@H](F)[C@H](N)C3)nc3cc(F)c(F)cc32)CC1] | methyl 1-(2-(2-((3R,4R)-3-amino-4-fluoropiperidin-1-yl)-5,6-difluoro-1H-benzo[d]imidazol-1-yl)acetyl)piperidine-4-carboxylate | 454.2 |
| 513 | 68 | | B | 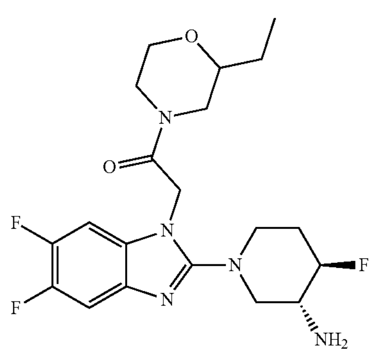 [SMILES: CCC1CN(C(=O)Cn2c(N3CC[C@@H](F)[C@H](N)C3)nc3cc(F)c(F)cc32)CCO1] | 2-(2-((3R,4R)-3-amino-4-fluoropiperidin-1-yl)-5,6-difluoro-1H-benzo[d]imidazol-1-yl)-1-(2-ethylmorpholino)ethan-1-one | 426.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 514 | 65 | 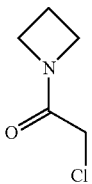 | B | 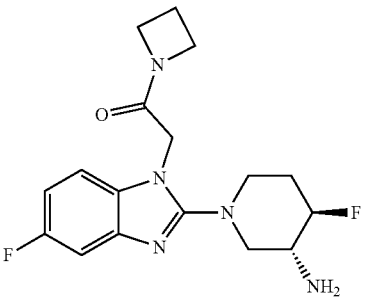 | 2-(2-((3R,4R)-3-amino-4-fluoropiperidin-1-yl)-5-fluoro-1H-benzo[d]imidazol-1-yl)-1-(azetidin-1-yl)ethan-1-one | 350.2 |
| 515 | 68 | 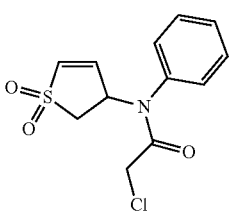 [SMILES: O=C(CCl)N(c1ccccc1)C1C=CS(=O)(=O)C1] | B | 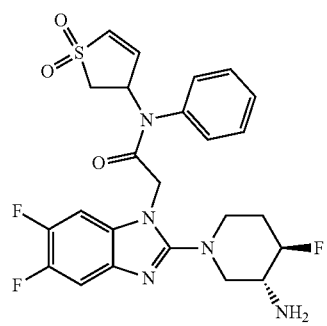 [SMILES: N[C@@H]1CN(c2nc3cc(F)c(F)cc3n2CC(=O)N(c2ccccc2)C2C=CS(=O)(=O)C2)CC[C@H]1F] | 2-(2-((3R,4R)-3-amino-4-fluoropiperidin-1-yl)-5,6-difluoro-1H-benzo[d]imidazol-1-yl)-N-(1,1-dioxido-2,3-dihydrothiophen-3-yl)-N-phenylacetamide | 520.2 |
| 516 | 68 | 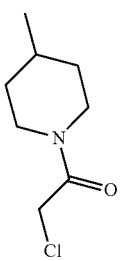 | B | 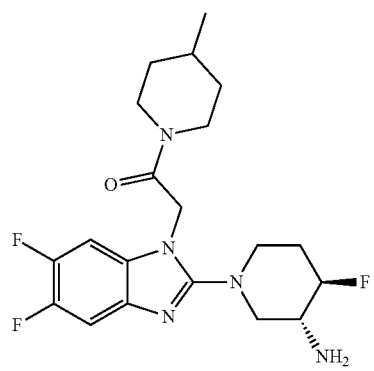 [SMILES: CC1CCN(C(=O)Cn2c(N3CC[C@@H](F)[C@H](N)C3)nc3cc(F)c(F)cc32)CC1] | 2-(2-((3R,4R)-3-amino-4-fluoropiperidin-1-yl)-5,6-difluoro-1H-benzo[d]imidazol-1-yl)-1-(4-methylpiperidin-1-yl)ethan-1-one | 410.2 |
| 517 | 65 | 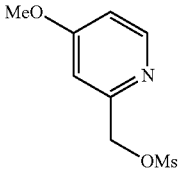 [SMILES: COc1ccnc(COS(C)(=O)=O)c1] | B | 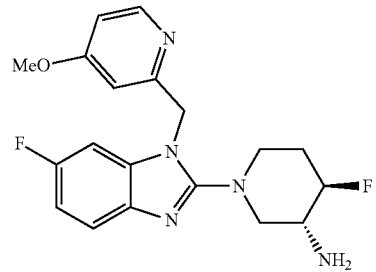 | (3R,4R)-4-fluoro-1-(6-fluoro-1-((4-methoxypyridin-2-yl)methyl)-1H-benzo[d]imidazol-2-yl)piperidin-3-amine | 375.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 518 | 68 | | B | 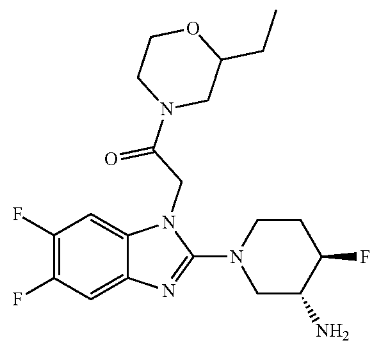 [SMILES: CCC1CN(C(=O)Cn2c(N3CC[C@@H](F)[C@H](N)C3)nc3cc(F)c(F)cc32)CCO1] | 2-(2-((3R,4R)-3-amino-4-fluoropiperidin-1-yl)-5,6-difluoro-1H-benzo[d]imidazol-1-yl)-1-(2-ethylmorpholino)ethan-1-one | 426.2 |
| 519 | 81 | | B | 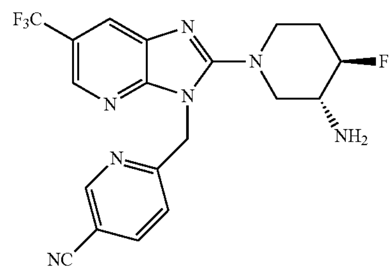 [SMILES: N#Cc1ccc(Cn2c(N3CC[C@@H](F)[C@H](N)C3)nc3cc(C(F)(F)F)cnc32)nc1] | 6-((2-((3R,4R)-3-amino-4-fluoropiperidin-1-yl)-6-(trifluoromethyl)-3H-imidazo[4,5-b]pyridin-3-yl)methyl)nicotinonitrile | 420.2 |
| 520 | 65 | | B | 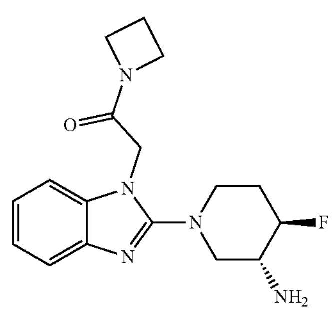 [SMILES: N[C@@H]1CN(c2nc3ccccc3n2CC(=O)N2CCC2)CC[C@H]1F] | 2-(2-((3R,4R)-3-amino-4-fluoropiperidin-1-yl)-1H-benzo[d]imidazol-1-yl)-1-(azetidin-1-yl)ethan-1-one | 332.2 |
| 521 | 68 | | B | 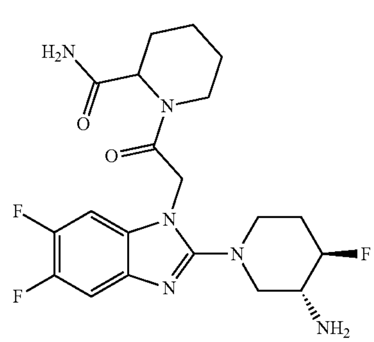 [SMILES: NC(=O)C1CCCCN1C(=O)Cn1c(N2CC[C@@H](F)[C@H](N)C2)nc2cc(F)c(F)cc21] | 1-(2-(2-(3R,4R)-3-amino-4-fluoropiperidin-1-yl)-5,6-difluoro-1H-benzo[d]imidazol-1-yl)acetyl)piperidine-2-carboxamide | 439.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 522 | 68 | 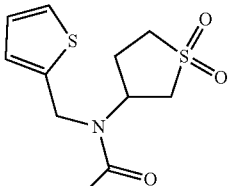 | B | 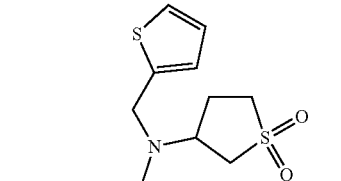 | 2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-(thiophen-2-ylmethyl)acetamide | 542.2 |
| 523 | 68 | 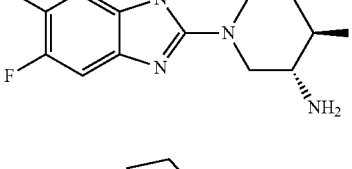 | B | 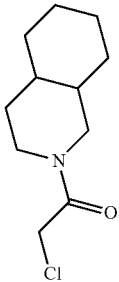 [SMILES: O=C(CCl)N1CCC2CCCCC2C1] | 2-(2-((3R,4R)-3-amino-4-fluoropiperidin-1-yl)-5,6-difluoro-1H-benzo[d]imidazol-1-yl)-1-(octahydroisoquinolin-2(1H)-yl)ethan-1-one | 450.2 |
| 524 | 65 | 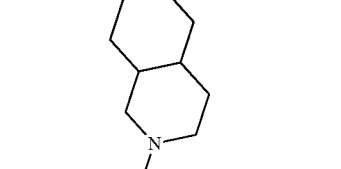 | B | 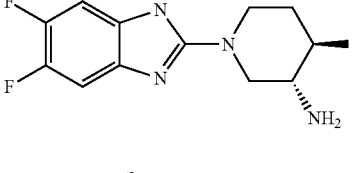 | (3R,4R)-4-fluoro-1-(5-fluoro-1-((4-methoxypyridin-2-yl)methyl)-1H-benzo[d]imidazol-2-yl)piperidin-3-amine | 375.2 |
| 525 | 68 | 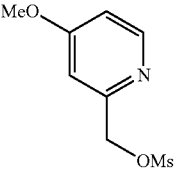 [SMILES: COc1ccnc(COS(C)(=O)=O)c1] | B | 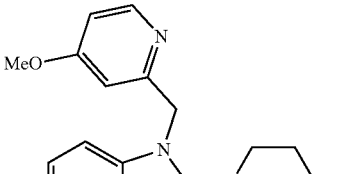 | 2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-methylacetamide | 460.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 526 | 68 | 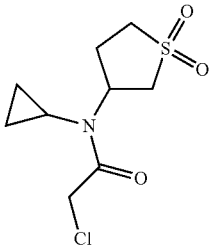 [SMILES: O=C(CCl)N(C1CC1)C1CCS(=O)(=O)C1] | B | 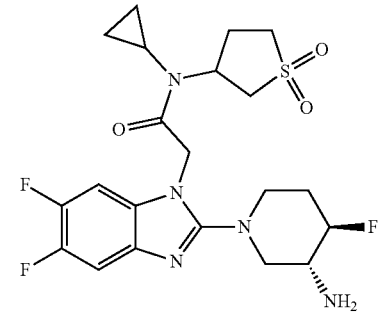 [SMILES: N[C@@H]1CN(c2nc3cc(F)c(F)cc3n2CC(=O)N(C2CC2)C2CCS(=O)(=O)C2)CC[C@H]1F] | 2-(2-((3R,4R)-3-amino-4-fluoropiperidin-1-yl)-5,6-difluoro-1H-benzo[d]imidazol-1-yl)-N-cyclopropyl-N-(1,1-dioxidotetrahydrothiophen-3-yl)acetamide | 486.2 |
| 527 | 68 | 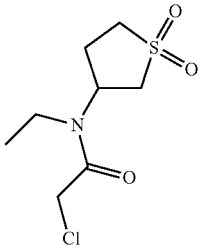 | B | 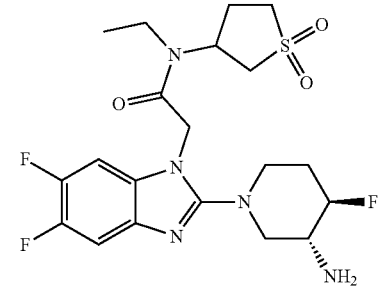 [SMILES: CCN(C(=O)Cn1c(N2CC[C@@H](F)[C@H](N)C2)nc2cc(F)c(F)cc21)C1CCS(=O)(=O)C1] | 2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-ethylacetamide | 474.2 |
| 528 | 68 | 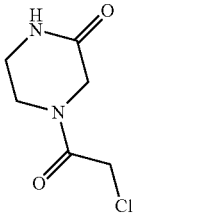 [SMILES: O=C1CN(C(=O)CCl)CCN1] | B | 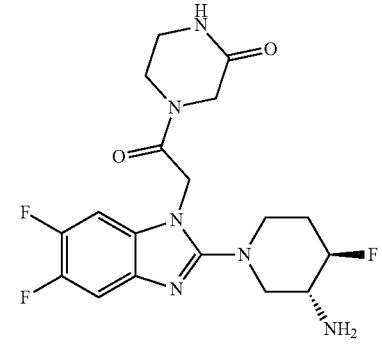 [SMILES: N[C@@H]1CN(c2nc3cc(F)c(F)cc3n2CC(=O)N2CCNC(=O)C2)CC[C@H]1F] | 4-(2-(2-((3R,4R)-3-amino-4-fluoropiperidin-1-yl)-5,6-difluoro-1H-benzo[d]imidazol-1-yl)acetyl)piperazin-2-one | 411.2 |
| 529 | 68 | 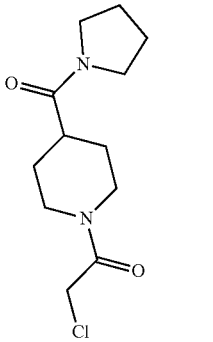 [SMILES: O=C(CCl)N1CCC(C(=O)N2CCCC2)CC1] | B | 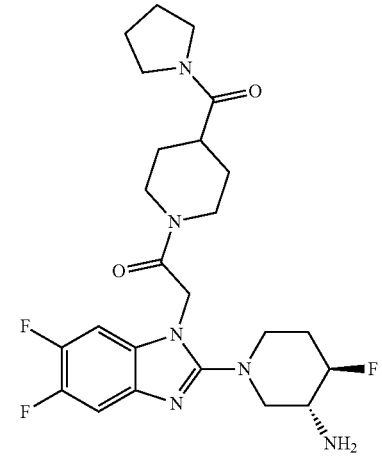 [SMILES: N[C@@H]1CN(c2nc3cc(F)c(F)cc3n2CC(=O)N2CCC(C(=O)N3CCCC3)CC2)CC[C@H]1F] | 2-(2-((3R,4R)-3-amino-4-fluoropiperidin-1-yl)-5,6-difluoro-1H-benzo[d]imidazol-1-yl)-1-(4-(pyrrolidine-1-carbonyl)piperidin-1-yl)ethan-1-one | 493.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 530 | 68 | | B | 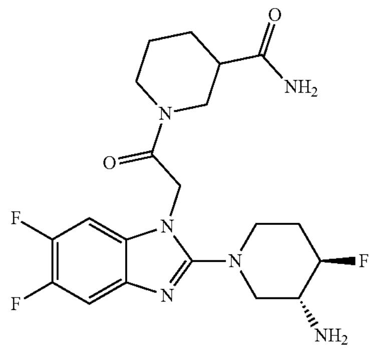 [SMILES: NC(=O)C1CCCN(C(=O)Cn2c(N3CC[C@@H](F)[C@H](N)C3)nc3cc(F)c(F)cc32)C1] | 1-(2-(2-((3R,4R)-3-amino-4-fluoropiperidin-1-yl)-5,6-difluoro-1H-benzo[d]imidazol-1-yl)acetyl)piperidine-3-carboxamide | 439.2 |
| 531 | 68 | | B | 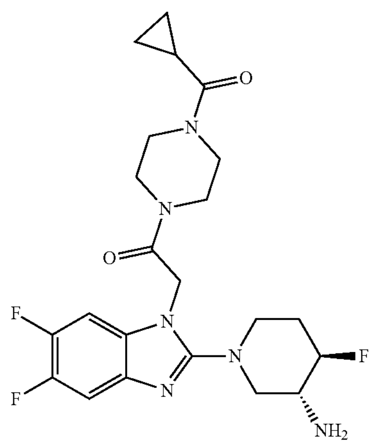 [SMILES: N[C@@H]1CN(c2nc3cc(F)c(F)cc3n2CC(=O)N2CCN(C(=O)C3CC3)CC2)CC[C@H]1F] | 2-(2-((3R,4R)-3-amino-4-fluoropiperidin-1-yl)-5,6-difluoro-1H-benzo[d]imidazol-1-yl)-1-(4-(cyclopropanecarbonyl)piperazin-1-yl)ethan-1-one | 465.2 |
| 532 | 68 | | B | 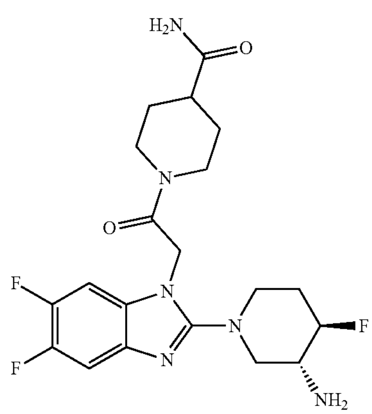 [SMILES: NC(=O)C1CCN(C(=O)Cn2c(N3CC[C@@H](F)[C@H](N)C3)nc3cc(F)c(F)cc32)CC1] | 1-(2-(2-((3R,4R)-3-amino-4-fluoropiperidin-1-yl)-5,6-difluoro-1H-benzo[d]imidazol-1-yl)acetyl)piperidine-4-carboxamide | 439.2 |
| 533 | 68 | | B | 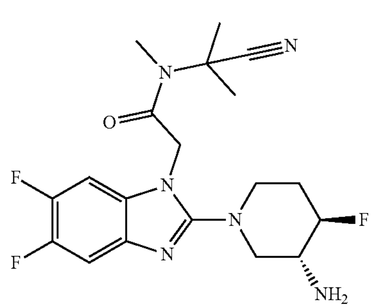 [SMILES: CN(C(=O)Cn1c(N2CC[C@@H](F)[C@H](N)C2)nc2cc(F)c(F)cc21)C(C)(C)C#N] | 2-(2-((3R,4R)-3-amino-4-fluoropiperidin-1-yl)-5,6-difluoro-1H-benzo[d]imidazol-1-yl)-N-(2-cyanopropan-2-yl)-N-methylacetamide | 409.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 534 | 68 | | B | 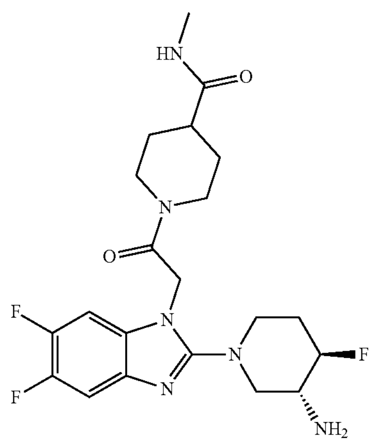 | 1-(2-(2-((3R,4R)-3-amino-4-fluoropiperidin-1-yl)-5,6-difluoro-1H-benzo[d]imidazol-1-yl)acetyl)-N-methylpiperidine-4-carboxamide | 453.2 |
| 535 | 68 | | B | 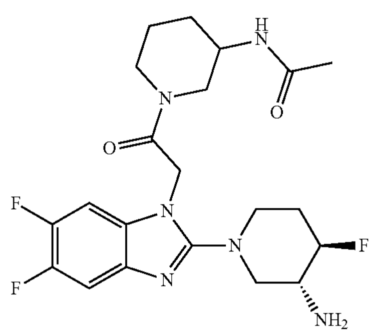 [SMILES: CC(=O)NC1CCCN(C(=O)Cn2c(N3CC[C@@H](F)[C@H](N)C3)nc3cc(F)c(F)cc32)C1] | N-(1-(2-(2-((3R,4R)-3-amino-4-fluoropiperidin-1-yl)-5,6-difluoro-1H-benzo[d]imidazol-1-yl)acetyl)piperidin-3-yl)acetamide | 453.2 |
| 536 | 68 | | B | 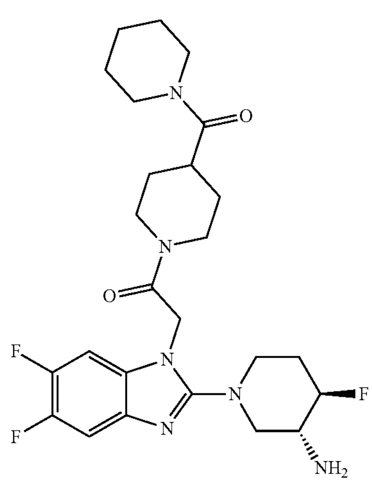 [SMILES: N[C@@H]1CN(c2nc3cc(F)c(F)cc3n2CC(=O)N2CCC(C(=O)N3CCCCC3)CC2)CC[C@H]1F] | 2-(2-((3R,4R)-3-amino-4-fluoropiperidin-1-yl)-5,6-difluoro-1H-benzo[d]imidazol-1-yl)-1-(4-(piperidine-1-carbonyl)piperidin-1-yl)ethan-1-one | 507.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 537 | 68 | | B | 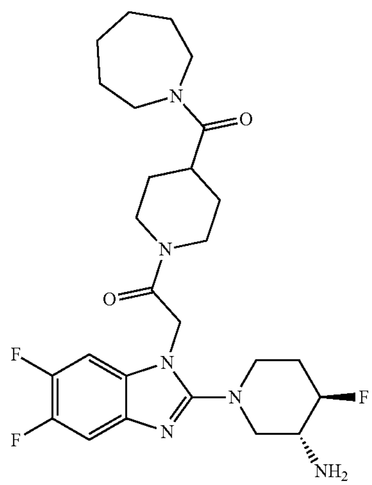 [SMILES: N[C@@H]1CN(c2nc3cc(F)c(F)cc3n2CC(=O)N2CCC(C(=O)N3CCCCCC3)CC2)CC[C@H]1F] | 2-(2-((3R,4R)-3-amino-4-fluoropiperidin-1-yl)-5,6-difluoro-1H-benzo[d]imidazol-1-yl)-1-(4-(azepane-1-carbonyl)piperidin-1-yl)ethan-1-one | 521.2 |
| 538 | 68 | | B | 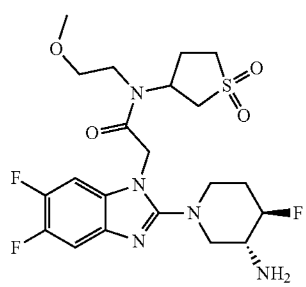 [SMILES: COCCN(C(=O)Cn1c(N2CC[C@@H](F)[C@H](N)C2)nc2cc(F)c(F)cc21)C1CCS(=O)(=O)C1] | 2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-(2-methoxyethyl)acetamide | 504.2 |
| 539 | 68 | | B | 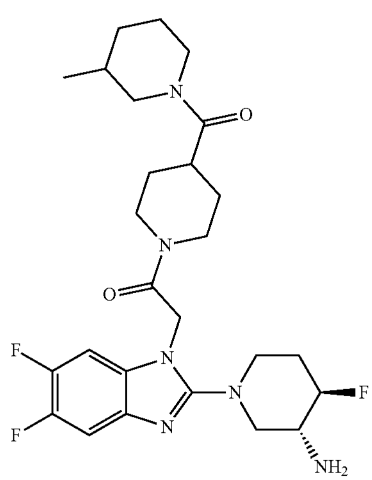 [SMILES: CC1CCCN(C(=O)C2CCN(C(=O)Cn3c(N4CC[C@@H](F)[C@H](N)C4)nc4cc(F)c(F)cc43)CC2)C1] | 2-(2-((3R,4R)-3-amino-4-fluoropiperidin-1-yl)-5,6-difluoro-1H-benzo[d]imidazol-1-yl)-1-(4-(3-methylpiperidine-1-carbonyl)piperidin-1-yl)ethan-1-one | 521.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 540 | 68 | | B | 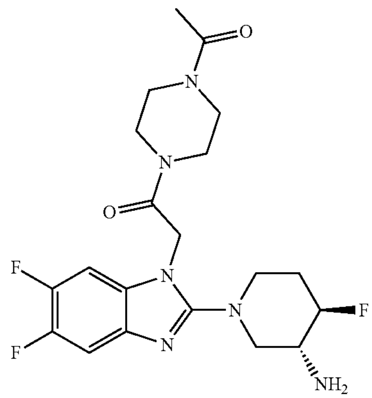 [SMILES: CC(=O)N1CCN(C(=O)Cn2c(N3CC[C@@H](F)[C@H](N)C3)nc3cc(F)c(F)cc32)CC1] | 1-(4-acetylpiperazin-1-yl)-2-(2-((3R,4R)-3-amino-4-fluoropiperidin-1-yl)-5,6-difluoro-1H-benzo[d]imidazol-1-yl)ethan-1-one | 439.2 |
| 541 | 68 | | B | 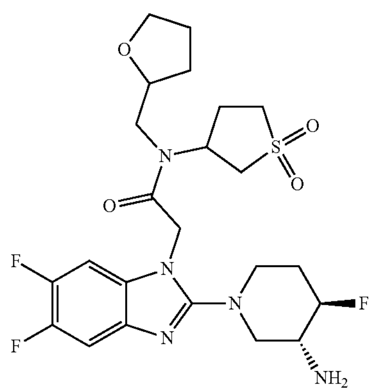 [SMILES: N[C@@H]1CN(c2nc3cc(F)c(F)cc3n2CC(=O)N(CC2CCCO2)C2CCS(=O)(=O)C2)CC[C@H]1F] | 2-(2-((3R,4R)-3-amino-4-fluoropiperidin-1-yl)-5,6-difluoro-1H-benzo[d]imidazol-1-yl)-N-(1,1-dioxidotetrahydrothiophen-3-yl)-N-((tetrahydrofuran-2-yl)methyl)acetamide | 530.2 |
| 542 | 68 | | B | 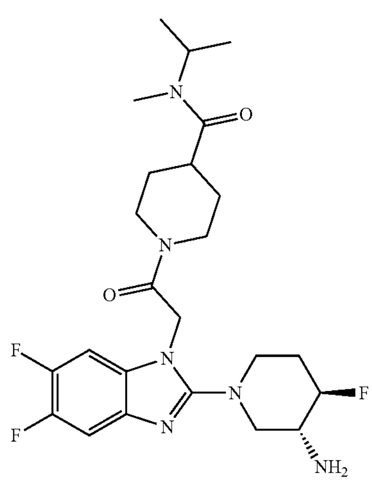 [SMILES: CC(C)N(C)C(=O)C1CCN(C(=O)Cn2c(N3CC[C@@H](F)[C@H](N)C3)nc3cc(F)c(F)cc32)CC1] | 1-(2-(2-((3R,4R)-3-amino-4-fluoropiperidin-1-yl)-5,6-difluoro-1H-benzo[d]imidazol-1-yl)acetyl)-N-isopropyl-N-methylpiperidine-4-carboxamide | 495.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 543 | 68 | | B | 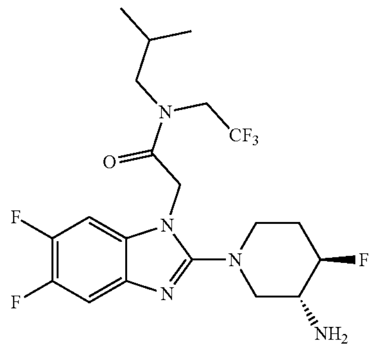 [SMILES: CC(C)CN(CC(F)(F)F)C(=O)Cn1c(N2CC[C@@H](F)[C@H](N)C2)nc2cc(F)c(F)cc21] | 2-(2-((3R,4R)-3-amino-4-methoxypiperidin-1-yl)-6-fluoro-1H-benzo[d]imidazol-1-yl)-N-methyl-N-(2,2,2-trifluoroethyl)acetamide | 418.2 |
| 544 | 82 | | B | 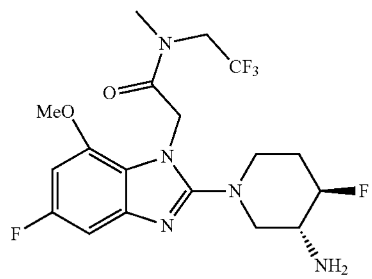 [SMILES: COc1cc(F)cc2nc(N3CC[C@@H](F)[C@H](N)C3)n(CC(=O)N(C)CC(F)(F)F)c12] | 2-(2-((3R,4R)-3-amino-4-fluoropiperidin-1-yl)-5-fluoro-7-methoxy-1H-benzo[d]imidazol-1-yl)-N-methyl-N-(2,2,2-trifluoroethyl)acetamide | 436.2 |
| 545 | 82 | | B | 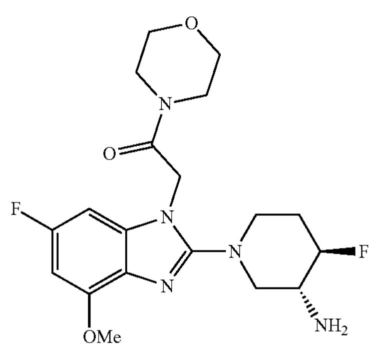 [SMILES: COc1cc(F)cc2c1nc(N1CC[C@@H](F)[C@H](N)C1)n2CC(=O)N1CCOCC1] | 2-(2-((3R,4R)-3-amino-4-fluoropiperidin-1-yl)-6-fluoro-4-methoxy-1H-benzo[d]imidazol-1-yl)-1-morpholinoethan-1-one | 410.2 |
| 546 | 82 | | B | 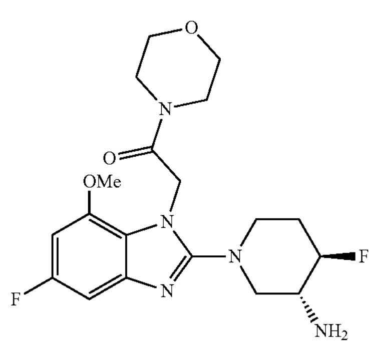 [SMILES: COc1cc(F)cc2nc(N3CC[C@@H](F)[C@H](N)C3)n(CC(=O)N3CCOCC3)c12] | 2-(2-((3R,4R)-3-amino-4-fluoropiperidin-1-yl)-5-fluoro-7-methoxy-1H-benzo[d]imidazol-1-yl)-1-morpholinoethan-1-one | 410.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 547 | 68 | 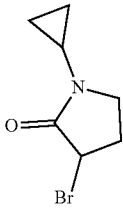 | A | 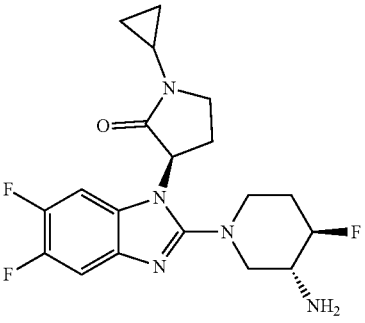 [SMILES: N[C@@H]1CN(c2nc3cc(F)c(F)cc3n2[C@@H]2CCN(C3CC3)C2=O)CC[C@H]1F] | (R)-3-(2-((3R,4R)-3-amino-4-fluoropiperidin-1-yl)-5,6-difluoro-1H-benzo[d]imidazol-1-yl)-1-cyclopropylpyrrolidin-2-one | 394.2 |
| 548 | 68 | 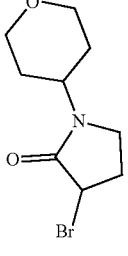 | A | 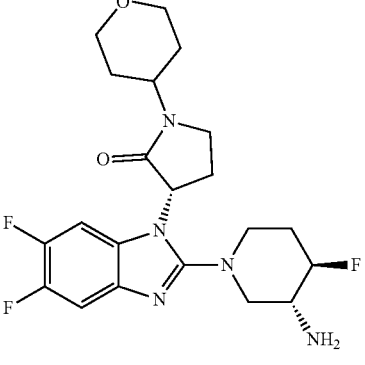 | (S)-3-(2-((3R,4R)-3-amino-4-fluoropiperidin-1-yl)-5,6-difluoro-1H-benzo[d]imidazol-1-yl)-1-(tetrahydro-2H-pyran-4-yl)pyrrolidin-2-one | 438.2 |
| 549 | 68 | 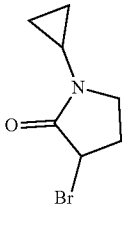 | A | 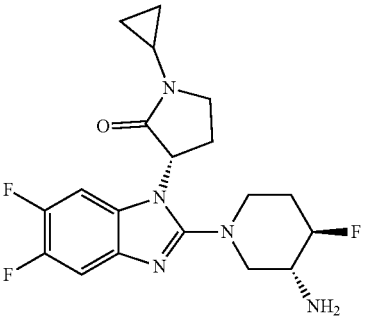 [SMILES: N[C@@H]1CN(c2nc3cc(F)c(F)cc3n2[C@H]2CCN(C3CC3)C2=O)CC[C@H]1F] | (S)-3-(2-((3R,4R)-3-amino-4-fluoropiperidin-1-yl)-5,6-difluoro-1H-benzo[d]imidazol-1-yl)-1-cyclopropylpyrrolidin-2-one | 394.2 |
| 550 | 68 | 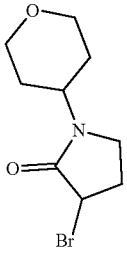 [SMILES: O=C1C(Br)CCN1C1CCOCC1] | A | 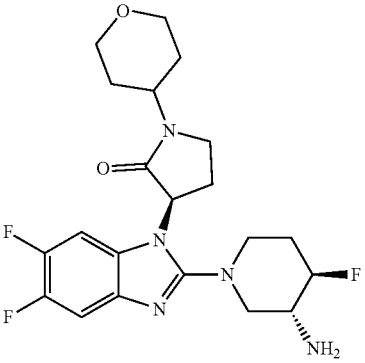 [SMILES: N[C@@H]1CN(c2nc3cc(F)c(F)cc3n2[C@@H]2CCN(C3CCOCC3)C2=O)CC[C@H]1F] | (R)-3-(2-((3R,4R)-3-amino-4-fluoropiperidin-1-yl)-5,6-difluoro-1H-benzo[d]imidazol-1-yl)-1-(tetrahydro-2H-pyran-4-yl)pyrrolidin-2-one | 438.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 551 | 68 | 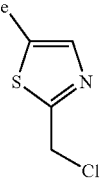 | B | 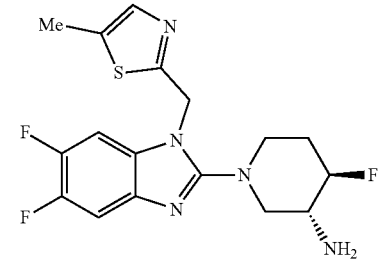 | (3R,4R)-1-(5,6-difluoro-1-((5-methylthiazol-2-yl)methyl)-1H-benzo[d]imidazol-2-yl)-4-fluoropiperidin-3-amine | 382.2 |
| 552 | 62 | 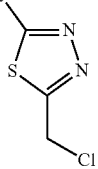 | B | 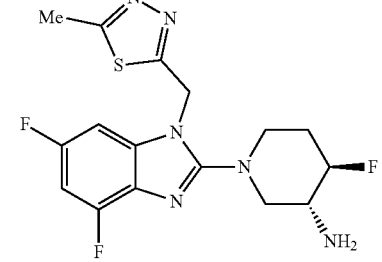 | (3R,4R)-1-(4,6-difluoro-1-((5-methyl-1,3,4-thiadiazol-2-yl)methyl)-1H-benzo[d]imidazol-2-yl)-4-fluoropiperidin-3-amine | 383.2 |
| 553 | 68 | 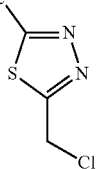 | B | 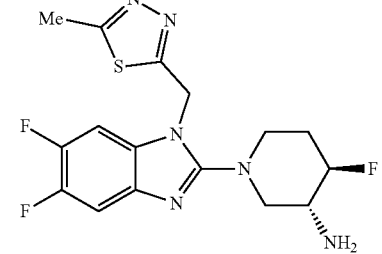 | (3R,4R)-1-(5,6-difluoro-1-((5-methyl-1,3,4-thiadiazol-2-yl)methyl)-1H-benzo[d]imidazol-2-yl)-4-fluoropiperidin-3-amine | 383.2 |
| 554 | 83 | 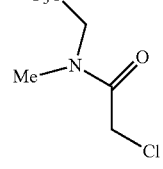 | B | 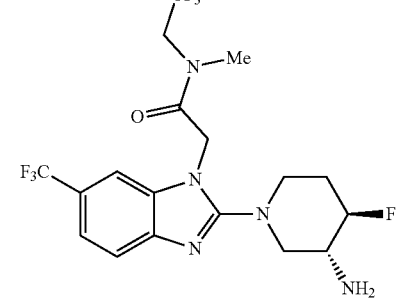 | 2-(2-((3R,4R)-3-amino-4-fluoropiperidin-1-yl)-6-(trifluoromethyl)-1H-benzo[d]imidazol-1-yl)-N-methyl-N-(2,2,2-trifluoroethyl)acetamide | 456.2 |
| 555 | 84 | 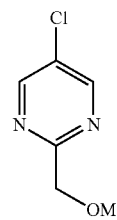 | B | 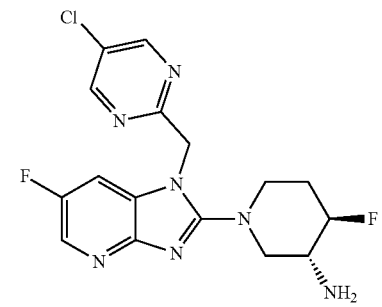 [SMILES: N[C@@H]1CN(c2nc3ncc(F)cc3n2Cc2ncc(Cl)cn2)CC[C@H]1F] | (3R,4R)-1-(1-((5-chloropyrimidin-2-yl)methyl)-6-fluoro-1H-imidazo[4,5-b]pyridin-2-yl)-4-fluoropiperidin-3-amine | 380.0 |

TABLE 5-continued

Compounds made following schemes 9-10

| Ex. # | SnAr Inter- mediate | Electrophile | Boc Depro- tection Pro- cedure | Structure | Compound Name | MS MH+ |
|---|---|---|---|---|---|---|
| 556 | 62 | 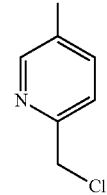 | B | 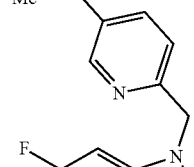 | (3R,4R)-1-(4,6-difluoro-1-((5-(methylsulfonyl)pyridin-2-yl)methyl)-1H-benzo[d]imidazol-2-yl)-4-fluoropiperidin-3-amine | 440.2 |
| 557 | 62 | 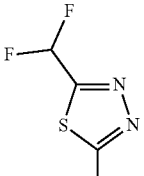 | B | 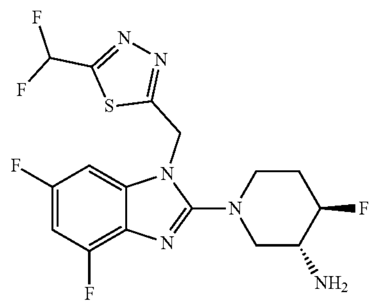 [SMILES: N[C@@H]1CN(c2nc3c(F)cc(F)cc3n2Cc2nnc(C(F)F)s2)CC[C@H]1F] | (3R,4R)-1-(1-((5-(difluoromethyl)-1,3,4-thiadiazol-2-yl)methyl)-4,6-difluoro-1H-benzo[d]imidazol-2-yl)-4-fluoropiperidin-3-amine | 419.2 |
| 558 | 62 | 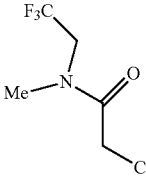 | B | 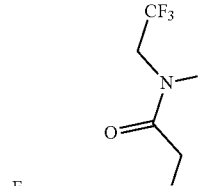 | 2-(2-((3R,4R)-3-amino-4-fluoropiperidin-1-yl)-4,6-difluoro-1H-benzo[d]imidazol-1-yl)-N-methyl-N-(2,2,2-trifluoroethyl)acetamide | 424.2 |
| 559 | 69 | 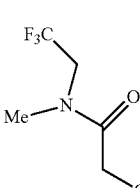 | B | 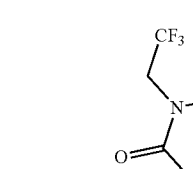 | 2-(2-((3R,4R)-3-amino-4-fluoropiperidin-1-yl)-6-chloro-1H-benzo[d]imidazol-1-yl)-N-methyl-N-(2,2,2-trifluoroethyl)acetamide | 422.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 560 | 68 | | B | 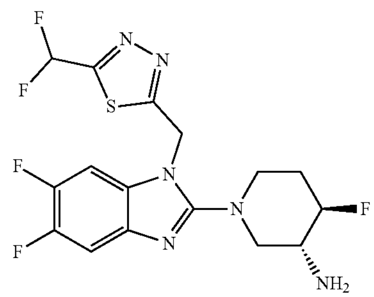 [SMILES: N[C@@H]1CN(c2nc3cc(F)c(F)cc3n2Cc2nnc(C(F)F)s2)CC[C@H]1F] | (3R,4R)-1-(1-((5-(difluoromethyl)-1,3,4-thiadiazol-2-yl)methyl)-5,6-difluoro-1H-benzo[d]imidazol-2-yl)-4-fluoropiperidin-3-amine | 419.0 |
| 561 | 65 | | B | 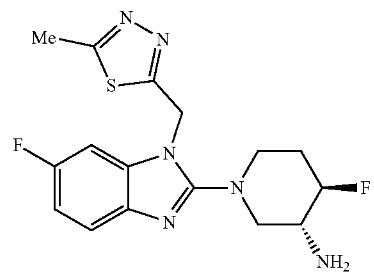 [SMILES: Cc1nnc(Cn2c(N3CC[C@@H](F)[C@H](N)C3)nc3ccc(F)cc32)s1] | (3R,4R)-4-fluoro-1-(6-fluoro-1-((5-methyl-1,3,4-thiadiazol-2-yl)methyl)-1H-benzo[d]imidazol-2-yl)piperidin-3-amine | 365.2 |
| 562 | 68 | | B | 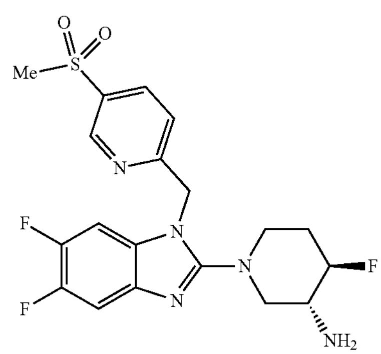 [SMILES: CS(=O)(=O)c1ccc(Cn2c(N3CC[C@@H](F)[C@H](N)C3)nc3cc(F)c(F)cc32)nc1] | (3R,4R)-1-(5,6-difluoro-1-((5-(methylsulfonyl)pyridin-2-yl)methyl)-1H-benzo[d]imidazol-2-yl)-4-fluoropiperidin-3-amine | 440.2 |
| 563 | 83 | | B | 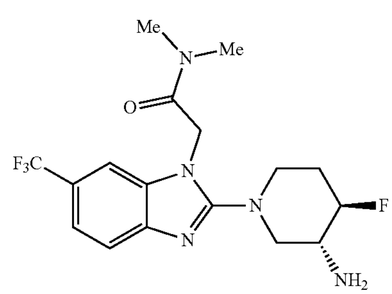 [SMILES: CN(C)C(=O)Cn1c(N2CC[C@@H](F)[C@H](N)C2)nc2ccc(C(F)(F)F)cc21] | 2-(2-((3R,4R)-3-amino-4-fluoropiperidin-1-yl)-6-(trifluoromethyl)-1H-benzo[d]imidazol-1-yl)-N,N-dimethylacetamide | 388.2 |
| 564 | 68 | | B | 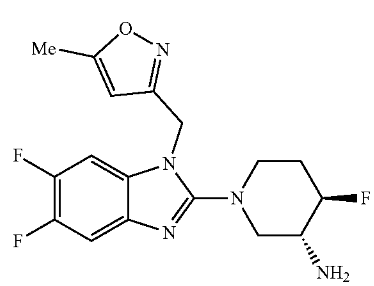 | (3R,4R)-1-(5,6-difluoro-1-((5-methylisoxazol-3-yl)methyl)-1H-benzo[d]imidazol-2-yl)-4-fluoropiperidin-3-amine | 366.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 565 | 62 | | B | 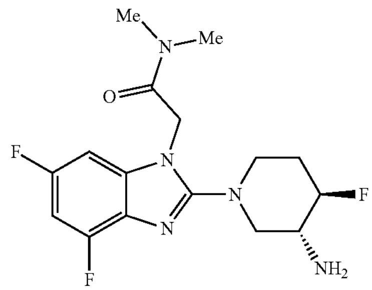 [SMILES: CN(C)C(=O)Cn1c(N2CC[C@@H](F)[C@H](N)C2)nc2c(F)cc(F)cc21] | 2-(2-((3R,4R)-3-amino-4-fluoropiperidin-1-yl)-4,6-difluoro-1H-benzo[d]imidazol-1-yl)-N,N-dimethylacetamide | 356.2 |
| 566 | 65 | | B | 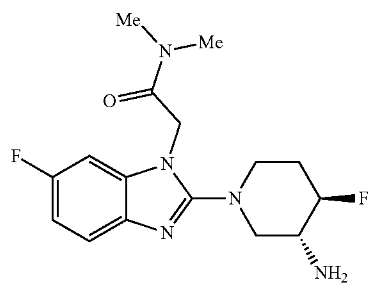 [SMILES: CN(C)C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-N,N-dimethylacetamide | 338.2 |
| 567 | 68 | | B | 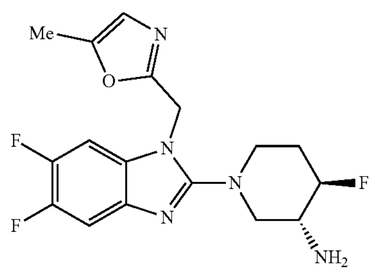 [SMILES: Cc1cnc(Cn2c(N3CC[C@@H](F)[C@H](N)C3)nc3cc(F)c(F)cc32)o1] | (3R,4R)-1-(5,6-difluoro-1-((5-methyloxazol-2-yl)methyl)-1H-benzo[d]imidazol-2-yl)-4-fluoropiperidin-3-amine | 366.2 |
| 568 | 68 | | B | 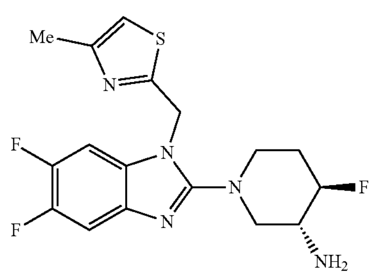 [SMILES: Cc1csc(Cn2c(N3CC[C@@H](F)[C@H](N)C3)nc3cc(F)c(F)cc32)n1] | (3R,4R)-1-(5,6-difluoro-1-((4-methylthiazol-2-yl)methyl)-1H-benzo[d]imidazol-2-yl)-4-fluoropiperidin-3-amine | 382.0 |
| 569 | 65 | | B | 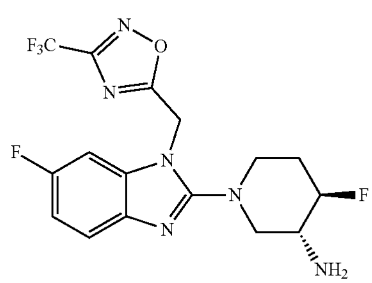 [SMILES: N[C@@H]1CN(c2nc3ccc(F)cc3n2Cc2nc(C(F)(F)F)no2)CC[C@H]1F] | (3R,4R)-4-fluoro-1-(6-fluoro-1-((3-(trifluoromethyl)-1,2,4-oxadiazol-5-yl)methyl)-1H-benzo[d]imidazol-2-yl)piperidin-3-amine | 403.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 570 | 69 | | B | 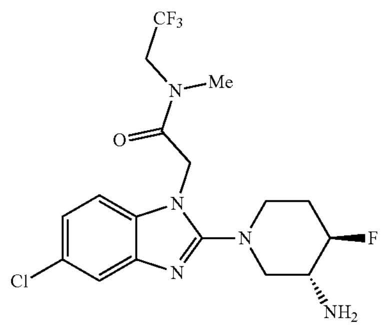 [SMILES: CN(CC(F)(F)F)C(=O)Cn1c(N2CC[C@@H](F)[C@H](N)C2)nc2cc(Cl)ccc21] | 2-(2-((3R,4R)-3-amino-4-fluoropiperidin-1-yl)-5-chloro-1H-benzo[d]imidazol-1-yl)-N-methyl-N-(2,2,2-trifluoroethyl)acetamide | 422.2 |
| 571 | 68 | | B | 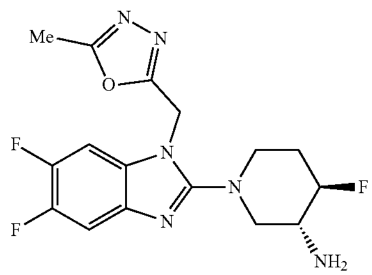 | (3R,4R)-1-(5,6-difluoro-1-((5-methyl-1,3,4-oxadiazol-2-yl)methyl)-1H-benzo[d]imidazol-2-yl)-4-fluoropiperidin-3-amine | 367.2 |
| 572 | 68 | | B | 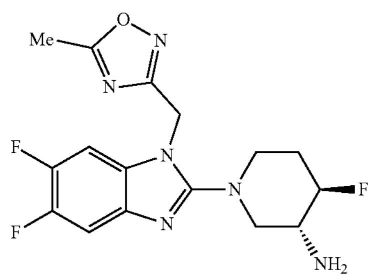 [SMILES: Cc1nc(Cn2c(N3CC[C@@H](F)[C@H](N)C3)nc3cc(F)c(F)cc32)no1] | (3R,4R)-1-(5,6-difluoro-1-((5-methyl-1,2,4-oxadiazol-3-yl)methyl)-1H-benzo[d]imidazol-2-yl)-4-fluoropiperidin-3-amine | 367.2 |
| 573 | 65 | | B | 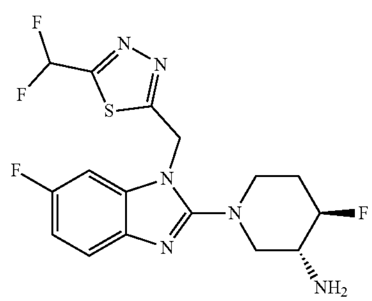 [SMILES: N[C@@H]1CN(c2nc3ccc(F)cc3n2Cc2nnc(C(F)F)s2)CC[C@H]1F] | (3R,4R)-1-(1-((5-(difluoromethyl)-1,3,4-thiadiazol-2-yl)methyl)-6-fluoro-1H-benzo[d]imidazol-2-yl)-4-fluoropiperidin-3-amine | 401.2 |
| 574 | 84 | | B | 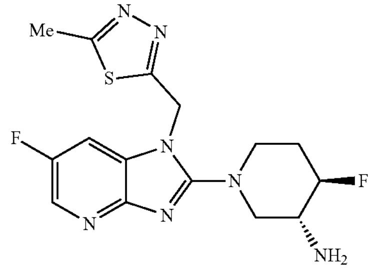 [SMILES: Cc1nnc(Cn2c(N3CC[C@@H](F)[C@H](N)C3)nc3ncc(F)cc32)s1] | (3R,4R)-4-fluoro-1-(6-fluoro-1-((5-methyl-1,3,4-thiadiazol-2-yl)methyl)-1H-imidazo[4,5-b]pyridin-2-yl)piperidin-3-amine | 366.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 575 | 68 | 2-(chloromethyl)-4,5-dimethyloxazole | B | 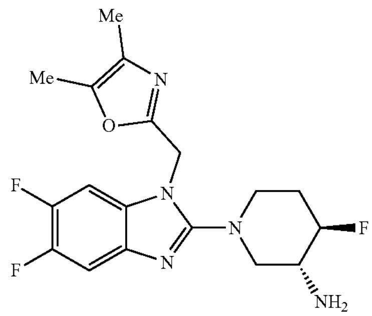 [SMILES: Cc1nc(Cn2c(N3CC[C@@H](F)[C@H](N)C3)nc3cc(F)c(F)cc32)oc1C] | (3R,4R)-1-(1-((4,5-dimethyloxazol-2-yl)methyl)-5,6-difluoro-1H-benzo[d]imidazol-2-yl)-4-fluoropiperidin-3-amine | 380.2 |
| 576 | 65 | 2-chloro-N,N-dimethylacetamide | B | 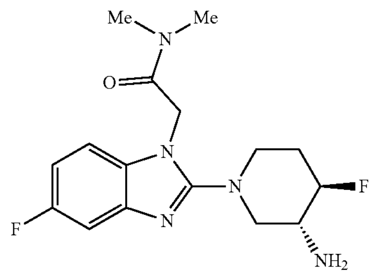 [SMILES: CN(C)C(=O)Cn1c(N2CC[C@@H](F)[C@H](N)C2)nc2cc(F)ccc21] | 2-(2-((3R,4R)-3-amino-4-fluoropiperidin-1-yl)-5-fluoro-1H-benzo[d]imidazol-1-yl)-N,N-dimethylacetamide | 338.2 |
| 577 | 68 | 3-(chloromethyl)-5-ethyl-1,2,4-oxadiazole | B | 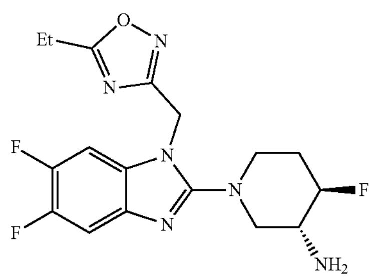 [SMILES: CCc1nc(Cn2c(N3CC[C@@H](F)[C@H](N)C3)nc3cc(F)c(F)cc32)no1] | (3R,4R)-1-(1-((5-ethyl-1,2,4-oxadiazol-3-yl)methyl)-5,6-difluoro-1H-benzo[d]imidazol-2-yl)-4-fluoropiperidin-3-amine | 381.2 |
| 578 | 68 | 3-(chloromethyl)-5-cyclopropyl-1,2,4-oxadiazole | B | 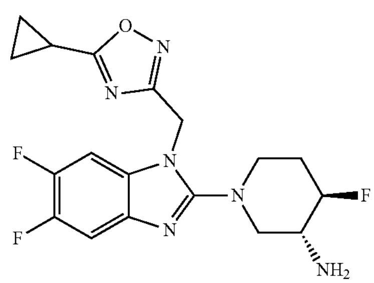 [SMILES: N[C@@H]1CN(c2nc3cc(F)c(F)cc3n2Cc2noc(C3CC3)n2)CC[C@H]1F] | (3R,4R)-1-(1-((5-cyclopropyl-1,2,4-oxadiazol-3-yl)methyl)-5,6-difluoro-1H-benzo[d]imidazol-2-yl)-4-fluoropiperidin-3-amine | 393.2 |
| 579 | 68 | 5-(chloromethyl)-3-methylisoxazole | B | 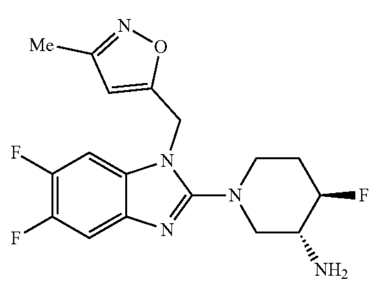 [SMILES: Cc1cc(Cn2c(N3CC[C@@H](F)[C@H](N)C3)nc3cc(F)c(F)cc32)on1] | (3R,4R)-1-(5,6-difluoro-1-((3-methylisoxazol-5-yl)methyl)-1H-benzo[d]imidazol-2-yl)-4-fluoropiperidin-3-amine | 366.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 580 | 83 | | B | 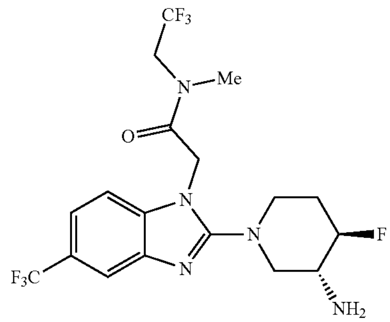 [SMILES: CN(CC(F)(F)F)C(=O)Cn1c(N2CC[C@@H](F)[C@H](N)C2)nc2cc(C(F)(F)F)ccc21] | 2-(2-((3R,4R)-3-amino-4-fluoropiperidin-1-yl)-5-(trifluoromethyl)-1H-benzo[d]imidazol-1-yl)-N-methyl-N-(2,2,2-trifluoroethyl)acetamide | 456.2 |
| 581 | 68 | | B | 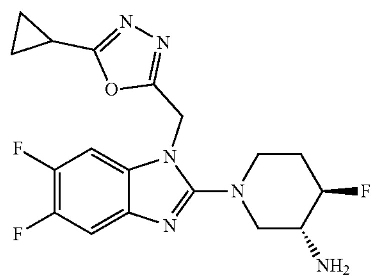 [SMILES: N[C@@H]1CN(c2nc3cc(F)c(F)cc3n2Cc2nnc(C3CC3)o2)CC[C@H]1F] | (3R,4R)-1-(1-((5-cyclopropyl-1,3,4-oxadiazol-2-yl)methyl)-5,6-difluoro-1H-benzo[d]imidazol-2-yl)-4-fluoropiperidin-3-amine | 393.2 |
| 582 | 65 | | B | 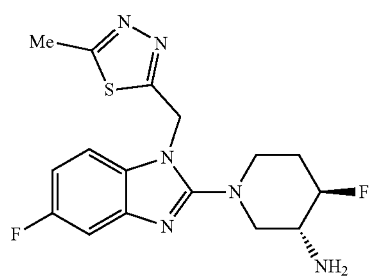 | (3R,4R)-4-fluoro-1-(5-fluoro-1-((5-methyl-1,3,4-thiadiazol-2-yl)methyl)-1H-benzo[d]imidazol-2-yl)piperidin-3-amine | 365.2 |
| 583 | 84 | | B | 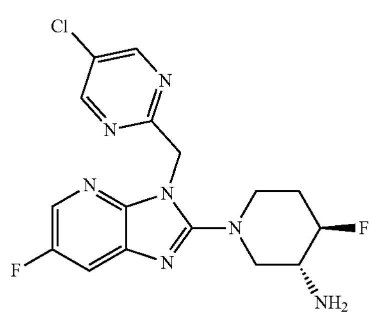 [SMILES: N[C@@H]1CN(c2nc3cc(F)cnc3n2Cc2ncc(Cl)cn2)CC[C@H]1F] | (3R,4R)-1-(3-((5-chloropyrimidin-2-yl)ethyl)-6-fluoro-3H-imidazo[4,5-b]pyridin-2-yl)-4-fluoropiperidin-3-amine | 380.2 |
| 584 | 65 | | B | 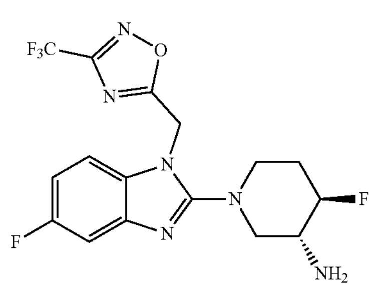 [SMILES: N[C@@H]1CN(c2nc3cc(F)ccc3n2Cc2nc(C(F)(F)F)no2)CC[C@H]1F] | (3R,4R)-4-fluoro-1-(5-fluoro-1-((3-(trifluoromethyl)-1,2,4-oxadiazol-5-yl)methyl)-1H-benzo[d]imidazol-2-yl)piperidin-3-amine | 403.0 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 585 | 65 | 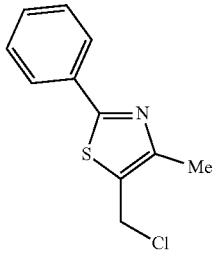 [SMILES: Cc1nc(-c2ccccc2)sc1CCl] | B | 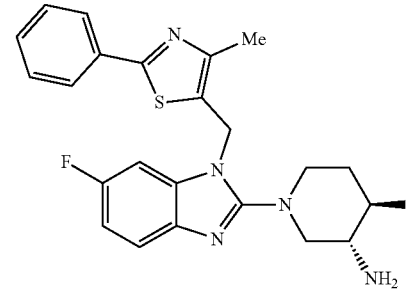 | (3R,4R)-4-fluoro-1-(6-fluoro-1-((4-methyl-2-phenylthiazol-5-yl)methyl)-1H-benzo[d]imidazol-2-yl)piperidin-3-amine | 440.2 |
| 586 | 68 | 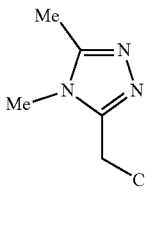 | B | 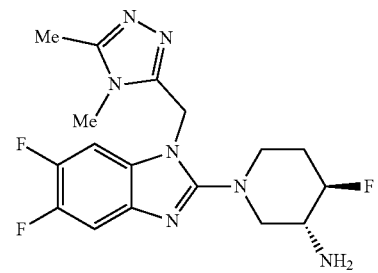 [SMILES: Cc1nnc(Cn2c(N3CC[C@@H](F)[C@H](N)C3)nc3cc(F)c(F)cc32)n1C] | (3R,4R)-1-(1-((4,5-dimethyl-4H-1,2,4-triazol-3-yl)methyl)-5,6-difluoro-1H-benzo[d]imidazol-2-yl)-4-fluoropiperidin-3-amine | 380.2 |
| 587 | 65 | 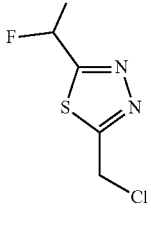 | B | 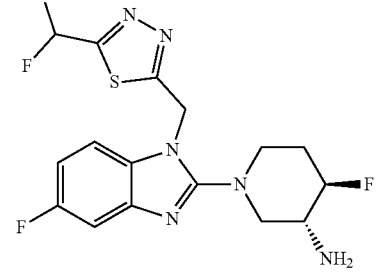 | (3R,4R)-1-(1-((5-(difluoromethyl)-1,3,4-thiadiazol-2-yl)methyl)-5-fluoro-1H-benzo[d]imidazol-2-yl)-4-fluoropiperidin-3-amine | 401.2 |
| 588 | 85 | 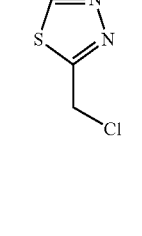 | B | 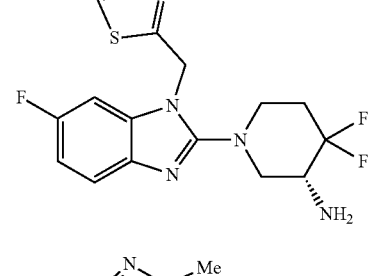 | (R)-4,4-difluoro-1-(6-fluoro-1-((5-methyl-1,3,4-thiadiazol-2-yl)methyl)-1H-benzo[d]imidazol-2-yl)piperidin-3-amine | 383.2 |
| 589 | 65 | 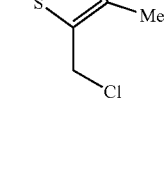 | B | 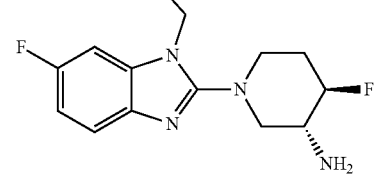 | (3R,4R)-1-(1-((2,4-dimethylthiazol-5-yl)methyl)-6-fluoro-1H-benzo[d]imidazol-2-yl)-4-fluoropiperidin-3-amine | 378.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 590 | 84 | | B | 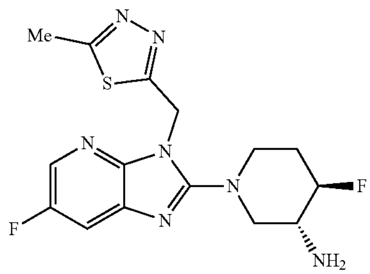 [SMILES: Cc1nnc(Cn2c(N3CC[C@@H](F)[C@H](N)C3)nc3cc(F)cnc32)s1] | (3R,4R)-4-fluoro-1-(6-fluoro-3-((5-methyl-1,3,4-thiadiazol-2-yl)methyl)-3H-imidazo[4,5-b]pyridin-2-yl)piperidin-3-amine | 366.2 |
| 591 | 62 | | B | 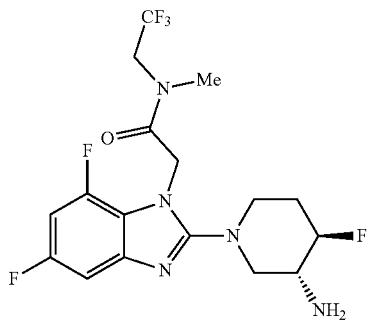 [SMILES: CN(CC(F)(F)F)C(=O)Cn1c(N2CC[C@@H](F)[C@H](N)C2)nc2cc(F)cc(F)c21] | 2-(2-((3R,4R)-3-amino-4-fluoropiperidin-1-yl)-5,7-difluoro-1H-benzo[d]imidazol-1-yl)-N-methyl-N-(2,2,2-trifluoroethyl)acetamide | 424.2 |
| 592 | 83 | | B | 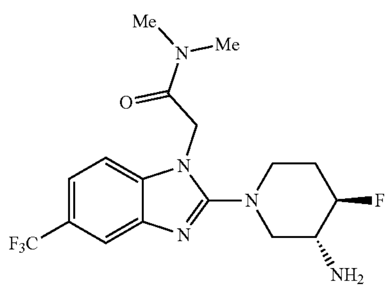 [SMILES: CN(C)C(=O)Cn1c(N2CC[C@@H](F)[C@H](N)C2)nc2cc(C(F)(F)F)ccc21] | 2-(2-((3R,4R)-3-amino-4-fluoropiperidin-1-yl)-5-(trifluoromethyl)-1H-benzo[d]imidazol-1-yl)-N,N-dimethylacetamide | 388.2 |
| 593 | 65 | | B | 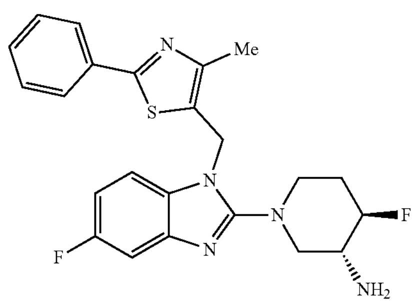 [SMILES: Cc1nc(-c2ccccc2)sc1Cn1c(N2CC[C@@H](F)[C@H](N)C2)nc2cc(F)ccc21] | (3R,4R)-4-fluoro-1-(5-fluoro-1-((4-methyl-2-phenylthiazol-5-yl)methyl)-1H-benzo[d]imidazol-2-yl)piperidin-3-amine | 440.2 |
| 594 | 62 | | B | 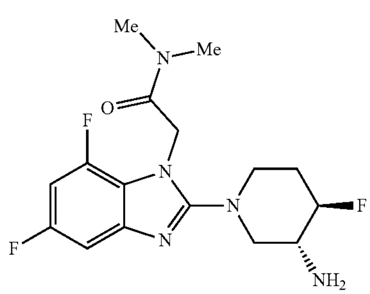 [SMILES: CN(C)C(=O)Cn1c(N2CC[C@@H](F)[C@H](N)C2)nc2cc(F)cc(F)c21] | 2-(2-((3R,4R)-3-amino-4-fluoropiperidin-1-yl)-5,7-difluoro-1H-benzo[d]imidazol-1-yl)-N,N-dimethylacetamide | 356.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 595 | 62 | 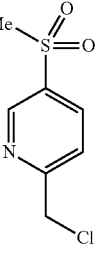 | B | 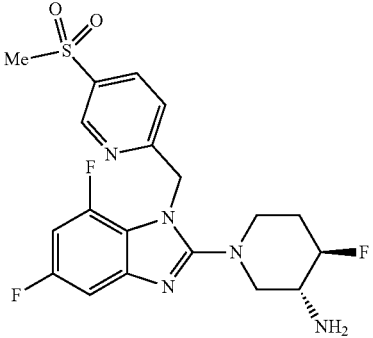 [SMILES: CS(=O)(=O)c1ccc(Cn2c(N3CC[C@@H](F)[C@H](N)C3)nc3cc(F)cc(F)c32)nc1] | (3R,4R)-1-(5,7-difluoro-1-((5-(methylsulfonyl)pyridin-2-yl)methyl)-1H-benzo[d]imidazol-2-yl)-4-fluoropiperidin-3-amine | 440.2 |
| 596 | 65 | 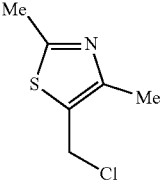 | B | 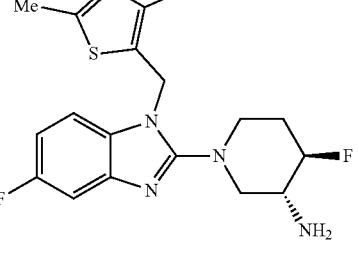 | (3R,4R)-1-(1-((2,4-dimethylthiazol-5-yl)methyl)-5-fluoro-1H-benzo[d]imidazol-2-yl)-4-fluoropiperidin-3-amine | 378.2 |
| 597 | 85 | 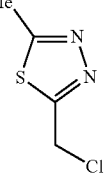 | B | 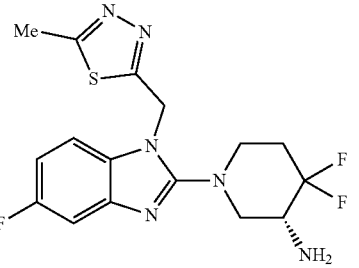 | (R)-4,4-difluoro-1-(5-fluoro-1-((5-methyl-1,3,4-thiadiazol-2-yl)methyl)-1H-benzo[d]imidazol-2-yl)piperidin-3-amine | 383.2 |
| 598 | 62 | 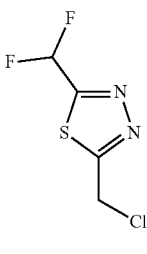 | B | 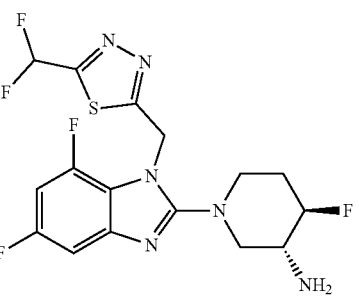 | (3R,4R)-1-(1-((5-(difluoromethyl)-1,3,4-thiadiazol-2-yl)methyl)-5,7-difluoro-1H-benzo[d]imidazol-2-yl)-4-fluoropiperidin-3-amine | 419.2 |

TABLE 5-continued

Compounds made following schemes 9-10

| Ex. # | SnAr Intermediate | Electrophile | Boc Deprotection Procedure | Structure | Compound Name | MS MH+ |
|---|---|---|---|---|---|---|
| 599 | 62 | Me-thiadiazole-CH2Cl | B | (structure) | (3R,4R)-1-(5,7-difluoro-1-((5-methyl-1,3,4-thiadiazol-2-yl)methyl)-1H-benzo[d]imidazal-2-yl)-4-fluoropiperidin-3-amine | 383.2 |

<sup>a</sup>Boc was removed using TFA. The free base was redissolved in DCM, and HCl was added to crash out the HCl salt.
b unspecified stereochemistry denotes a mixture of enantiomers or diastereomers.

TABLE 6

Characterization data for compounds made following schemes 9-10
The column "Separation Stage" indicates after which process step regioisomers formed due to asymmetric benzimidazole substitution at $R^1$ in Scheme 10 were separated during the preparation of the tabulated final compound. (I = after preparation of the N-aralkyl-2-piperidinyl-benzimidazole intermediate in the first step of Scheme 10 (where at least one $R^1$ is not hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 187 | 500 MHz d$_4$-MeOH | 8.80 (s, 2H), 7.65-7.69 (m, 1H), 7.54-7.61 (m, 1H), 7.49 (d, J = 8.30 Hz, 1H), 5.57 (s, 2H), 4.42-4.60 (m, 1H), 3.72-3.80 (m, 1H), 3.64 (br d, J = 13.23 Hz, 1H), 3.15-3.27 (m, 2H), 3.06 (dd, J = 9.21, 12.59 Hz, 1H), 2.13-2.27 (m, 1H), 1.80-1.99 (m, 1H) | B | Chiralpak AD-H, 25% IPA, peak 1 |
| 188 | 500 MHz d$_4$-MeOH | 8.68-8.74 (s, 2H), 7.47-7.52 (m, 1H), 7.14-7.20 (m, 2H), 7.08-7.13 (m, 1H), 5.53 (s, 2H), 4.34-4.52 (m, 1H), 3.64 (dtd, J = 1.95, 4.14, 12.36 Hz, 1H), 3.48-3.57 (m, 1H), 3.04-3.21 (m, 2H), 2.98 (dd, J = 8.82, 12.20 Hz, 1H), 2.12-2.25 (m, 1H), 1.82-1.92 (m, 1H) | — | — |
| 189 | 400 MHz d$_4$-MeOH | 8.40 (d, J = 2.90 Hz, 1H), 7.47-7.58 (m, 2H), 7.21 (dd, J = 4.35, 8.71 Hz, 1H), 7.13-7.17 (m, 1H), 7.06-7.13 (m, 2H), 4.32-4.55 (m, 1H), 3.62 (dtd, J = 1.66, 4.17, 12.39 Hz, 1H), 3.41-3.52 (m, 1H), 3.04-3.18 (m, 2H), 2.92-3.01 (m, 1H), 2.07-2.22 (m, 1H), 1.80-1.97 (m, 1H) | — | — |
| 190 | 400 MHz d$_4$-MeOH | 8.40 (d, J = 2.90 Hz, 1H), 7.61 (dt, J = 2.90, 8.50 Hz, 1H), 7.52-7.56 (m, 2H), 7.42-7.46 (m, 1H), 7.40 (dd, J = 4.35, 8.71 Hz, 1H), 5.46 (s, 2H), 4.32-4.54 (m, 1H), 3.67-3.75 (m, 1H), 3.55-3.65 (m, 1H), 3.21 (ddd, J = 2.90, 10.21, 12.80 Hz, 1H), 3.06-3.14 (m, 1H), 2.98-3.05 (m, 1H), 2.10-2.25 (m, 1H), 1.89 (ddd, J = 3.52, 9.69, 13.53 Hz, 1H) | B | Chiralpak AD-H, 20% MeOH, Peak 1 |
| 191 | 400 MHz d$_4$-MeOH | 8.39 (d, J = 2.90 Hz, 1H), 7.75-7.78 (m, 1H), 7.61 (dt, J = 2.90, 8.50 Hz, 1H), 7.35-7.42 (m, 2H), 7.27 (d, J = 8.29 Hz, 1H), 5.45-5.50 (m, 2H), 4.32-4.54 (m, 1H), 3.68 (dtd, J = 1.66, 4.02, 12.28 Hz, 1H), 3.51-3.63 (m, 1H), 3.15-3.25 (m, 1H), 3.10 (ddd, J = 3.94, 7.72, 9.48 Hz, 1H), 2.96-3.06 (m, 1H), 2.13-2.27 (m, 1H), 1.81-1.97 (m, 1H) | B | Chiralpak AD-H, 20% MeOH, Peak 2 |
| 192 | 500 MHz d$_4$-MeOH | 8.98 (s, 2H), 7.42-7.47 (m, 1H), 7.07-7.15 (m, 2H), 7.01-7.06 (m, 1H), 5.49 (s, 2H), 4.33-4.51 (m, 1H), 3.37-3.50 (m, 2H), 2.99-3.07 (m, 2H), 2.82 (br dd, J = 8.95, 12.07 Hz, 1H), 2.00-2.16 (m, 1H), 1.65-1.79 (m, 1H) | — | — |
| 193 | 400 MHz CDCl$_3$ | 8.97 (s, 2H), 7.60-7.67 (m, 1H), 7.16-7.23 (m, 1H), 7.03-7.15 (m, 2H), 5.45-5.56 (m, 2H), 4.29-4.56 (m, | | |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 1H), 3.64-3.76 (m, 1H), 3.51-3.63 (m, 1H), 3.14-3.33 (m, 2H), 3.03 (dd, J = 8.60, 12.54 Hz, 1H), 2.08-2.24 (m, 1H), 1.83-2.03 (m, 1H) | | |
| 194 | 400 MHz CDCl$_3$ | 8.36-8.39 (m, 2H), 7.60 (d, J = 8.50 Hz, 1H), 7.14-7.20 (m, 2H), 7.06-7.14 (m, 1H), 5.36 (d, J = 2.07 Hz, 2H), 4.34-4.56 (m, 1H), 3.90 (s, 3H), 3.63-3.78 (m, 2H), 3.14-3.31 (m, 2H), 3.04 (dd, J = 8.40, 12.54 Hz, 1H), 2.11-2.25 (m, 1H), 1.90-2.05 (m, 1H) | — | — |
| 195 | 400 MHz d$_4$-MeOH | 8.76 (s, 2H), 7.44-7.54 (m, 1H), 7.06-7.19 (m, 3H), 5.50 (br s, 2H), 4.32-4.53 (m, 1H), 3.62 (br d, J = 12.23 Hz, 1H), 3.51 (br d, J = 12.02 Hz, 1H), 3.02-3.21 (m, 2H), 2.89-3.01 (m, 1H), 2.12-2.26 (m, 1H), 1.81-1.98 (m, 1H) | — | — |
| 196 | 500 MHz d$_4$-MeOH | 8.70-8.75 (m, 2H), 7.65-7.69 (m, 1H), 7.58 (d, J = 8.30 Hz, 1H), 7.45-7.52 (m, 1H), 5.58 (s, 2H), 4.43-4.65 (m, 1H), 3.76-3.83 (m, 1H), 3.67 (br d, J = 12.98 Hz, 1H), 3.16-3.32 (m, 2H), 3.09 (dd, J = 9.34, 12.46 Hz, 1H), 2.15-2.29 (m, 1H), 1.86-1.99 (m, 1H) | B | Chiralpak AD-H, 20% MeOH, peak 1 |
| 197 | 500 MHz d$_4$-MeOH | 8.72 (s, 2H), 7.77-7.82 (m, 1H), 7.41-7.45 (m, 1H), 7.32-7.38 (m, 1H), 5.59 (s, 2H), 4.33-4.51 (m, 1H), 3.65-3.71 (m, 1H), 3.53-3.63 (m, 1H), 3.16-3.24 (m, 1H), 3.05-3.14 (m, 1H), 2.96-3.04 (m, 1H), 2.14-2.28 (m, 1H), 1.89 (ddd, J = 3.63, 9.67, 13.43 Hz, 1H) | B | Chiralpak AD-H, 20% MeOH, peak 2 |
| 198 | 400 MHz d$_4$-MeOH | 8.70-8.89 (m, 1H), 7.72-7.98 (m, 1H), 7.17-7.54 (m, 2H), 5.31-5.67 (m, 2H), 4.39-4.66 (m, 1H), 3.57-3.82 (m, 2H), 3.01-3.25 (m, 3H), 2.15-2.35 (m, 1H), 1.93 (td, J = 1.22, 9.80 Hz, 1H) | B | Chiralpak AD-H, 25% IPA, peak 2 |
| 199 | 400 MHz d$_4$-MeOH | 8.90 (d, J = 1.45 Hz, 1H), 8.75-8.78 (m, 1H), 7.48-7.56 (m, 1H), 7.08-7.23 (m, 4H), 5.66 (s, 2H), 3.39-3.59 (m, 3H), 3.13-3.30 (m, 2H), 2.25-2.40 (m, 1H), 2.04-2.25 (m, 1H) | — | — |
| 200 | 400 MHz d$_4$-MeOH | 8.88 (s, 2H), 7.63-7.68 (m, 1H), 7.53-7.59 (m, 1H), 7.45-7.50 (m, 1H), 5.53 (s, 2H), 4.36-4.58 (m, 1H), 3.72 (br dd, J = 1.45, 12.65 Hz, 1H), 3.58-3.66 (m, 1H), 3.10-3.26 (m, 2H), 2.99-3.07 (m, 1H), 2.13-2.27 (m, 1H), 1.82-1.95 (m, 1H) | B | Chiralpak AD-H, 25% IPA, peak 1 |
| 201 | 400 MHz d$_4$-MeOH | 8.86-8.90 (m, 2H), 7.80-7.84 (m, 1H), 7.45 (dd, J = 1.24, 8.29 Hz, 1H), 7.34-7.39 (m, 1H), 5.56 (s, 2H), 4.33-4.53 (m, 1H), 3.62-3.70 (m, 1H), 3.53-3.60 (m, 1H), 3.14-3.23 (m, 1H), 3.02-3.13 (m, 1H), 2.94-3.02 (m, 1H), 2.18-2.26 (m, 1H), 1.80-1.96 (m, 1H) | B | Chiralpak AD-H, 25% IPA, peak 1 |
| 202 | 400 MHz CDCl$_3$ | 9.11 (s, 1H), 8.92 (s, 1H), 8.30-8.39 (m, 3H), 7.47-7.53 (m, 1H), 7.23 (d, J = 7.88 Hz, 1H), 7.14-7.19 (m, 1H), 7.11 (d, J = 7.26 Hz, 1H), 5.68 (s, 2H), 4.81-4.92 (m, 1H), 3.59-3.74 (m, 2H), 3.45-3.55 (m, 1H), 3.03-3.16 (m, 2H), 2.14-2.24 (m, 1H), 1.80-1.93 (m, 1H) | — | — |
| 203 | 500 MHz d$_4$-MeOH | 8.79 (s, 2 H), 7.75-7.89 (m, 1 H), 7.45 (dd, J = 8.30, 1.30 Hz, 1 H), 7.36 (d, J = 8.04 Hz, 1 H), 5.55-5.60 (m, 2 H), 3.44-3.54 (m, 2 H), 3.35-3.42 (m, 2 H), 3.06-3.25 (m, 3 H), 1.89-2.18 (m, 2 H) | B | Chiralpak OJ, 15% MeOH, peak 1 |
| 204 | 500 MHz d$_4$-MeOH | 8.80 (s, 2 H), 7.65-7.69 (m, 1 H), 7.56-7.61 (m, 1 H), 7.51 (dd, J = 8.30, 1.56 Hz, 1 H), 5.57 (s, 2 H), 3.37-3.57 (m, 3 H), 3.06-3.26 (m, 3 H), 2.09-2.18 (m, 1 H), 1.90-2.08 (m, 2 H) | B | Chiralpak OJ, 15% MeOH, peak 2 |
| 205 | 500 MHz d$_4$-MeOH | 8.78 (s, 2H), 7.39-7.48 (m, 1H), 6.99 (dd, J = 2.47, 8.95 Hz, 1H), 6.90-6.95 (m, 1H), 5.48 (s, 2H), 3.64 (dd, J = 1.82, 7.79 Hz, 1H), 3.42-3.53 (m, 2H), 3.05 (dt, J = 2.60, 12.07 Hz, 1H), 2.83-2.90 (m, 2H), 2.01 (qd, J = 3.62, 13.01 Hz, 1H), 1.62-1.71 (m, 1H) | B | Chiralpak AD-H, 25% MeOH, peak 2 |
| 206 | 500 MHz d$_4$-MeOH | 8.75-8.79 (m, 2H), 7.12-7.22 (m, 2H), 6.82-6.93 (m, 1H), 5.49 (s, 2H), 3.65-3.72 (m, 1H), 3.53-3.62 (m, 1H), 3.44-3.52, (m, 1H), 3.08 (dt, J = 2.60, 12.20 Hz, | B | Chiralpak AD-H, 25% MeOH, peak 1 |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 1H), 2.86-2.97 (m, 2H), 2.02 (qd, J = 3.61, 13.04 Hz, 1H), 1.62-1.75 (m, 1H) | | |
| 207 | 500 MHz d$_4$-MeOH | 8.82-8.85 (m, 1H), 8.09-8.15 (m, 1H), 7.36 (d, J = 8.04 Hz, 1H), 7.18 (dd, J = 2.34, 9.34 Hz, 1H), 7.09 (dd, J = 4.54, 8.69 Hz, 1H), 6.87 (dt, J = 2.47, 9.28 Hz, 1H), 5.46-5.51 (m, 2H), 3.58-3.66 (m, 1H), 3.46-3.54 (m, 1H), 3.38-3.44 (m, 1H), 3.02-3.14 (m, 1H), 2.73-2.90 (m, 2H), 1.93-2.04 (m, 1H), 1.58-1.72 (m, 1H) | B | Chiralpak AD-H, 25% IPA, peak 1 |
| 208 | 500 MHz d$_4$-MeOH | 8.84 (d, J = 1.30 Hz, 1H), 8.09-8.18 (m, 1H), 7.41-7.47 (m, 1H), 7.37 (d, J = 8.30 Hz, 1H), 6.90-7.00 (m, 2H), 5.48 (s, 2H), 3.50-3.59 (m, 1H), 3.36-3.47 (m, 2H), 3.04 (dt, J = 2.60, 11.94 Hz, 1H), 2.72-2.87 (m, 2H), 1.91-2.04 (m, 1H), 1.56-1.69 (m, 1H) | B | Chiralpak AD-H, 25% IPA, peak 2 |
| 209 | 400 MHz d$_6$-DMSO | 8.56 (d, J = 2.1 Hz, 1H), 7.93 (dd, J = 2.5, 8.4 Hz, 1H), 7.52-7.31 (m, 2H), 7.25 (d, J = 8.4 Hz, 1H), 7.14-7.01 (m, 2H), 5.47-5.34 (m, 2H), 3.55 (br dd, J = 3.2, 12.2 Hz, 1H), 3.27-3.18 (m, 2H), 3.17-2.90 (m, 2H), 2.01-1.89 (m, 1H), 1.79 (br dd, J = 3.4, 9.9 Hz, 1H), 1.64-1.45 (m, 2H) | — | — |
| 210 | 400 MHz d$_6$-DMSO | 8.72 (d, J = 1.66 Hz, 1H), 8.31 (br s, 2H), 8.02 (d, J = 8.09 Hz, 1H), 7.83-7.89 (m, 1H), 7.57 (d, J = 7.77 Hz, 1H), 7.27 (m, 3H), 5.54-5.61 (m, 2H), 3.70 (br dd, J = 2.80, 12.44 Hz, 1H), 3.48 (br s, 1H), 3.27-3.44 (m, 2H), 3.07-3.16 (m, 1H), 1.96-2.10 (m, 1H), 1.83-1.94 (m, 1H), 1.59-1.73 (m, 2H) | — | — |
| 211 | 400 MHz d$_6$-DMSO | 8.92 (br s, 3H), 8.55 (d, J = 2.18 Hz, 1H), 8.03 (dd, J = 2.49, 8.40 Hz, 1H), 7.67 (d, J = 8.40 Hz, 1H), 7.60 (d, J = 7.77 Hz, 1H), 7.28-7.44 (m, 3H), 5.64-5.78 (m, 2H), 4.88-5.10 (m, 1H), 4.18 (br d, J = 12.65 Hz, 1H), 3.77 (br d, J = 13.58 Hz, 1H), 3.54-3.63 (m, 1H), 3.43-3.53 (m, 1H), 3.21-3.42 (m, 1H), 2.26-2.37 (m, 1H), 1.82-1.94 (m, 1H) | — | — |
| 212 | 400 MHz d$_6$-DMSO | 9.12 (br s, 3H), 8.94 (s, 1H), 8.40 (d, J = 8.19 Hz, 1H), 7.77 (d, J = 8.19 Hz, 1H), 7.61 (d, J = 7.88 Hz, 1H), 7.25-7.39 (m, 3H), 5.72-5.93 (m, 2H), 4.03 (br d, J = 12.75 Hz, 2H), 3.57-3.70 (m, 2H), 3.42 (br t, J = 10.78 Hz, 1H), 2.53-2.62 (m, 1H), 2.23-2.38 (m, 1H) | — | — |
| 213 | 500 MHz DMSO-d$_6$ | 8.57 (br s, 2H), 8.50-8.55 (m, 1H), 7.94-8.00 (m, 2H), 7.43-7.51 (m, 2H), 7.35 (d, J = 8.30 Hz, 1H), 5.54 (d, J = 7.66 Hz, 2H), 4.81 (dt, J = 4.87, 9.11 Hz, 1H), 3.83-3.92 (m, 1H), 3.50-3.58 (m, 2H), 3.16 (br dd, J = 10.19, 12.65 Hz, 1H), 3.06 (br t, J = 11.74 Hz, 1H), 2.20 (br t, J = 9.54 Hz, 1H), 1.76-1.88 (m, 1H) | B | Chiralpak AD-H, 25% IPA, peak 2 |
| 214 | 500 MHz DMSO-d$_6$ | 8.66 (br s, 2H), 8.54 (d, J = 2.21 Hz, 1H), 7.98 (dd, J = 2.34, 8.43 Hz, 1H), 7.78 (s, 1H), 7.57-7.63 (m, J = 8.30 Hz, 1H), 7.51-7.57 (m, J = 8.30 Hz, 1H), 7.46 (d, J = 8.43 Hz, 1H), 5.49-5.62 (m, 2H), 4.79-4.99 (m, 1H), 3.95 (br d, J = 12.98 Hz, 1H), 3.71-3.84 (m, 2H), 3.20 (br t, J = 11.48 Hz, 1H), 3.07 (br t, J = 11.81 Hz, 1H), 2.21 (br t, J = 9.67 Hz, 1H), 1.80 (br t, J = 9.93 Hz, 1H) | B | Chiralpak AD-H, 25% IPA, peak 2 |
| 215 | 500 MHz DMSO-d$_6$ | 8.59 (br d, J = 2.47 Hz, 1H), 7.86-7.91 (m, 1H), 7.45 (d, J = 7.91 Hz, 1H), 7.33 (s, 1H), 7.27-7.32 (m, 1H), 7.02-7.09 (m, 1H), 6.92-6.97 (m, 2H), 5.86 (q, J = 6.96 Hz, 1H), 4.76-4.99 (m, 1H), 3.65-3.76 (m, 2H), 3.37 (br s, 1H), 3.14-3.22 (m, 1H), 3.07 (br t, J = 11.16 Hz, 1H), 2.19-2.27 (m, 1H), 1.89-1.98 (m, 1H), 1.86 (d, J = 7.14 Hz, 3H) | B | Chiralpak IC, 20% methanol, peak 1 |
| 216 | 500 MHz DMSO-d$_6$ | 8.63 (d, J = 1.95 Hz, 1H), 7.89 (br dd, J = 1.88, 8.50 Hz, 1H), 7.47 (d, J = 7.92 Hz, 1H), 7.28 (d, J = 8.43 Hz, 1H), 7.07 (t, J = 6.55 Hz, 1H), 6.94-7.00 (m, 2H), 5.87 (q, J = 7.01 Hz, 1H), 4.71-4.90 (m, 1H), 3.66-3.77 (m, 1H), 3.58-3.64 (m, 1H), 3.40-3.48 (m, 1H), | B | Chiralpak IC, 20% methanol, peak 2 |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 217 | 500 MHz DMSO-d$_6$ | 3.02-3.18 (m, 2H), 2.20-2.28 (m, 1H), 1.96-2.02 (m, 1H), 1.92 (d, J = 7.14 Hz, 3H) 8.56 (d, J = 2.34 Hz, 1H), 8.53 (br s, 2H), 7.90 (dd, J = 2.47, 8.43 Hz, 1H), 7.50 (dd, J = 7.59, 10.96 Hz, 1H), 7.39 (d, J = 8.43 Hz, 1H), 7.13 (dd, J = 7.33, 10.83 Hz, 1H), 5.83 (q, J = 7.09 Hz, 1H), 4.75-4.93 (m, 1H), 3.65 (br dd, J = 4.48, 9.15 Hz, 2H), 3.29 (br d, J = 11.94 Hz, 1H), 3.07-3.18 (m, 1H), 3.02 (br t, J = 11.03 Hz, 1H), 2.16-2.24 (m, 1H), 1.85-1.92 (m, 1H), 1.83 (d, J = 7.14 Hz, 3H) | B | Chiralcel OZ-H, 15% methanol, peak 1 |
| 218 | 500 MHz DMSO-d$_6$ | 8.65 (br s, 2H), 8.62 (d, J = 2.34 Hz, 1H), 7.94 (dd, J = 2.47, 8.56 Hz, 1H), 7.55 (dd, J = 7.66, 11.03 Hz, 1H), 7.39 (d, J = 8.56 Hz, 1H), 7.15-7.21 (m, 1H), 5.87 (q, J = 7.09 Hz, 1H), 4.80-4.97 (m, 1H), 3.62-3.79 (m, 2H), 3.16 (dd, J = 10.12, 11.94 Hz, 1H), 3.03 (br t, J = 11.55 Hz, 1H), 2.25 (br t, J = 9.41 Hz, 1H), 1.94-2.03 (m, 1H), 1.91 (d, J = 7.27 Hz, 3H) | B | Chiralcel OZ-H, 15% methanol, peak 2 |
| 219 | 500 MHz DMSO-d$_6$ | 8.58 (br s, 1H), 8.58 (br s, 2H), 7.91 (dd, J = 2.47, 8.56 Hz, 1H), 7.44 (d, J = 8.36 Hz, 1H), 7.39 (d, J = 8.39 Hz, 1H), 7.02-7.09 (m, 2H), 5.84 (q, J = 7.09 Hz, 1H), 4.73-4.97 (m, 1H), 3.68 (br dd, J = 4.09, 10.70 Hz, 2H), 3.32 (br d, J = 11.42 Hz, 1H), 3.10-3.21 (m, 1H), 3.05 (br t, J = 11.03 Hz, 1H), 2.16-2.27 (m, 1H), 1.86-1.93 (m, 1H), 1.83 (d, J = 7.14 Hz, 3H) | B | Regis Whelk-O s, s, 20% methanol, peak 1 |
| 220 | 500 MHz DMSO-d$_6$ | 8.64 (d, J = 2.46 Hz, 1H), 8.56 (br s, 2H), 7.95 (dd, J = 2.47, 8.56 Hz, 1H), 7.46-7.51 (m, J = 8.43 Hz, 1H), 7.35-7.43 (m, J = 8.56 Hz, 1H), 7.05-7.16 (m, 2H), 5.87 (q, J = 7.14 Hz, 1H), 4.78-4.99 (m, 1H), 3.75 (br d, J = 12.20 Hz, 2H), 3.37-3.50 (m, 1H), 3.13-3.21 (m, 1H), 3.07 (br t, J = 11.55 Hz, 1H), 2.25 (br t, J = 9.34 Hz, 1H), 1.95-2.04 (m, 1H), 1.92 (d, J = 7.14 Hz, 3H) | B | Regis Whelk-O s, s, 20% methanol, peak 2 |
| 221 | 500 MHz DMSO-d$_6$ | 8.62 (br s, 1H), 8.60 (br s, 2H), 7.95 (dd, J = 2.47, 8.43 Hz, 1H), 7.54 (d, J = 1.56 Hz, 1H), 7.40 (d, J = 8.56 Hz, 1H), 6.97-7.05 (m, 2H), 5.88 (q, J = 7.01 Hz, 1H), 4.77-5.04 (m, 1H), 3.76 (br s, 3H), 3.57 (s, 1H), 3.44 (br d, J = 12.07 Hz, 1H), 3.18-3.32 (m, 1H), 3.13 (br t, J = 11.16 Hz, 1H), 2.23-2.32 (m, 1H), 1.92-2.01 (m, 1H), 1.89 (d, J = 7.01 Hz, 3H) | B | Regis Whelk-O s, s, 20% methanol, peak 3 |
| 222 | 500 MHz DMSO-d$_6$ | 8.62 (br d, J = 2.34 Hz, 3H), 7.92 (dd, J = 2.47, 8.56 Hz, 1H), 7.54 (s, 1H), 7.35 (d, J = 8.56 Hz, 1H), 6.99-7.05 (m, 2H), 5.87 (q, J = 7.01 Hz, 1H), 4.80-5.01 (m, 1H), 3.78 (br dd, J = 5.00, 11.87 Hz, 2H), 3.44-3.53 (m, 1H), 3.20 (dd, J = 10.38, 12.07 Hz, 1H), 3.10 (br t, J = 11.48 Hz, 1H), 2.27 (br t, J = 9.41 Hz, 1H), 1.95-2.04 (m, 1H), 1.92 (d, J = 7.14 Hz, 3H) | B | Regis Whelk-O s, s, 20% methanol, peak 4 |
| 223 | 500 MHz DMSO-d$_6$ | 9.00 (s, 1H), 8.63 (br s, 3H), 8.38 (dd, J = 1.69, 8.30 Hz, 1H), 7.58-7.70 (m, 3H), 7.52 (d, J = 8.30 Hz, 1H), 6.00 (q, J = 7.01 Hz, 1H), 4.81-5.00 (m, 1H), 3.74-3.83 (m, 1H), 3.65-3.74 (m, 1H), 3.42 (br d, J = 11.68 Hz, 1H), 3.24 (br dd, J = 9.80, 12.39 Hz, 1H), 3.13 (br t, J = 11.16 Hz, 1H), 2.23-2.32 (m, 1H), 1.94 (br d, J = 7.14 Hz, 4H) | B | Phenomenex Lux Cellulose-2, 20% isopropanol, peak 1 |
| 224 | 500 MHz DMSO-d$_6$ | 9.00 (s, 1H), 8.69-8.73 (m, 2H), 8.36 (dd, J = 1.88, 8.24 Hz, 1H), 8.00 (s, 1H), 7.66 (d, J = 8.30 Hz, 1H), 7.41 (d, J = 8.43 Hz, 1H), 7.17 (d, J = 8.43 Hz, 1H), 6.04 (q, J = 6.96 Hz, 1H), 4.86-5.04 (m, 1H), 3.77 (br d, J = 12.72 Hz, 1H), 3.65-3.73 (m, 1H), 3.42 (br d, J = 11.94 Hz, 1H), 3.26 (br dd, J = 9.60, 12.59 Hz, 1H), 3.12, (br t, J = 11.09 Hz, 1H), 2.25-2.34 (m, 1H), 1.90-1.99 (m, 4H) | B | Phenomenex Lux Cellulose-2, 20% isopropanol, peak 2 |
| 225 | 500 MHz DMSO-d$_6$ | 8.98-9.02 (m, 1H), 8.62 (br d, J = 3.24 Hz, 2H), 8.36 (dd, J = 1.88, 8.24 Hz, 1H), 7.63 (dd, J = 3.18, 8.24 Hz, 2H), 7.59 (s, 1H), 7.52 (d, J = 8.17 Hz, 1H), 5.96 (q, J = 6.96 Hz, 1H), 4.79-4.98 (m, 1H), 3.74-3.86 (m, 1H), 3.68-3.72 (m, 1H), 3.46 (br d, J = 11.94 Hz, | B | Phenomenex Lux Cellulose-2, 20% isopropanol, peak 3 |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
|  |  | 1H), 3.14-3.26 (m, 1H), 3.09 (br t, J = 12.00 Hz, 1H), 2.19-2.30 (m, 1H), 1.97 (br d, J = 7.27 Hz, 4H) |  |  |
| 226 | 500 MHz DMSO-d$_6$ | 8.92-8.96 (m, 1H), 8.58 (br s, 3H), 8.28 (dd, J = 1.95, 8.30 Hz, 1H), 7.94 (s, 1H), 7.53 (d, J = 8.30 Hz, 1H), 7.34 (dd, J = 1.30, 8.43 Hz, 1H), 7.23 (s, 1H), 7.07-7.16 (m, 2H), 7.03 (s, 1H), 5.94 (q, J = 6.92 Hz, 1H), 4.72-4.93 (m, 1H), 3.68-3.79 (m, 1H), 3.58-3.68 (m, 1H), 3.40 (br d, J = 12.85 Hz, 1H), 3.15 (br t, J = 11.35 Hz, 1H), 3.04 (br t, J = 11.74 Hz, 1H), 2.20 (br t, J = 9.54 Hz, 1H), 1.95 (m, 1H), 1.91 (d, J = 7.01 Hz, 3H) | B | Phenomenex Lux Cellulose-2, 20% isopropanol, peak 4 |
| 227 | 500 MHz DMSO-d$_6$ | 8.54 (br d, J = 2.21 Hz, 1H), 8.52 (br s, 2H), 7.96 (dd, J = 2.47, 8.43 Hz, 1H), 7.54 (dd, J = 7.53, 10.90 Hz, 1H), 7.33-7.44 (m, 2H), 5.37-5.52 (m, 2H), 4.73-4.92 (m, 1H), 3.75-3.83 (m, 1H), 3.51-3.62 (m, 1H), 3.45 (br d, J = 12.20 Hz, 1H), 3.12 (br dd, J = 10.64, 12.33 Hz, 1H), 3.01 (br t, J = 11.61 Hz, 1H), 2.14-2.23 (m, 1H), 1.76-1.90 (m, 1H) | B | — |
| 228 | 500 MHz DMSO-d$_6$ | 8.52 (br s, 2H), 8.49 (d, J = 2.85 Hz, 1H), 7.76 (dt, J = 2.98, 8.69 Hz, 1H), 7.53 (dd, J = 7.40, 11.03 Hz, 1H), 7.44 (t, J = 6.74 Hz, 1H), 7.37 (t, J = 8.28 Hz, 1H), 5.38-5.51 (m, 2H), 4.73-4.95 (m, 1H), 3.75-3.83 (m, 1H), 3.47 (br d, J = 12.98 Hz, 1H), 3.12 (dd, J = 10.19, 12.52 Hz, 1H), 3.01 (br t, J = 11.42 Hz, 1H), 2.15-2.23 (m, 1H), 1.77-1.87 (m, 1H) | B | — |
| 229 | 400 MHz DMSO-d$_6$ | 8.80 (br s, 2H), 8.52 (d, J = 2.38 Hz, 1H), 7.96 (dd, J = 2.44, 8.45 Hz, 1H), 7.39 (d, J = 8.40 Hz, 1H), 7.21 (dd, J = 2.13, 9.17 Hz, 1H), 6.95 (t, J = 10.40 Hz, 1H), 5.45-5.58 (m, 2H), 3.76 (br d, J = 12.02 Hz, 1H), 3.31-3.47 (m, 2H), 3.17-3.26 (m, 1H), 2.33 (m, 3H) | B | Regis Whelk-O s, s, 15% methanol, peak 1 |
| 230 | 500 MHz DMSO-d$_6$ | 8.87 (br s, 2H), 8.55 (s, 1H), 7.97 (br d, J = 8.17 Hz, 1H), 7.46 (br d, J = 8.30 Hz, 1H), 6.95-7.04 (m, 2H), 5.41-5.63 (m, 2H), 3.95-4.06 (m, 1H), 3.77 (br d, J = 12.20 Hz, 1H), 3.30-3.45 (m, 2H), 3.18 (br t, J = 10.19 Hz, 1H), 2.19-2.35 (m, 1H) | B | Regis Whelk-O s, s, 15% methanol, peak 2 |
| 231 | 500 MHz d$_4$-MeOH | 7.86 (s, 1H), 7.65 (d, J = 8.04 Hz, 1H), 7.55 (d, J = 7.79 Hz, 1H), 7.42 (t, J = 7.66 Hz, 1H), 7.16-7.26 (m, 2H), 6.64 (br dd, J = 1.82, 9.08 Hz, 1H), 6.27 (br t, J = 8.69 Hz, 1H), 4.89-5.03 (m, 1H), 4.13-4.24 (m, 1H), 3.92-4.01 (m, 1H), 3.79-3.90 (m, 1H), 3.50-3.64 (m, 2H), 3.39-3.48 (m, 1H), 3.24-3.30 (m, 1H), 2.97-3.08 (m, 1H), 2.70 (qd, J = 9.45, 13.43 Hz, 1H), 2.52 (dt, J = 4.67, 7.79 Hz, 1H), 2.17-2.34 (m, 1H) | B | Phenomenex Lux Cellulose-2, 30% MeOH Peak 1 |
| 232 | 500 MHz d$_4$-MeOH | 7.86 (s, 1H), 7.64 (d, J = 8.04 Hz, 1H), 7.54 (d, J = 7.78 Hz, 1H), 7.40 (t, J = 7.79 Hz, 1H), 7.14-7.22 (m, 2H), 6.65 (br d, J = 7.53 Hz, 1H), 6.27 (br t, J = 9.08 Hz, 1H), 4.88-5.00 (m, 1H), 4.08-4.16 (m, 1H), 3.86-3.99 (m, 2H), 3.39-3.58 (m, 3H), 3.24-3.30 (m, 1H), 3.01-3.11 (m, 1H), 2.62-2.77 (m, 1H), 2.44-2.56 (m, 1H), 2.10-2.27 (m, 1H) | B | Phenomenex Lux Cellulose-2, 30% MeOH Peak 2 |
| 233 | 500 MHz d$_4$-MeOH | 8.90 (d, J = 1.30 Hz, 1H), 8.82 (d, J = 1.30 Hz, 1H), 7.46 (d, J = 8.56 Hz, 1H), 7.28 (d, J = 2.08 Hz, 1H), 7.18 (dd, J = 1.95, 8.43 Hz, 1H), 5.65 (s, 2H), 3.38-3.51 (m, 2H), 3.28 (br d, J = 3.37 Hz, 1H), 3.16-3.25 (m, 1H), 3.08-3.15 (m, 1H), 2.23-2.36 (m, 1H), 2.07-2.22 (m, 1H) | B | Chiralpak IC, 15% MeOH, Peak 1 |
| 234 | 500 MHz d$_4$-MeOH | 8.91 (d, J = 1.30 Hz, 1H), 8.82 (d, J = 1.04 Hz, 1H), 7.50 (d, J = 1.82 Hz, 1H), 7.15-7.19 (m, 1H), 7.09-7.15 (m, 1H), 5.67 (s, 2H), 3.42.-3.55 (m, 2H), 3.33-3.38 (m, 1H), 3.20-3.28 (m, 1H), 3.13-3.20 (m, 1H), 2.25-2.38 (m, 1H), 2.09-2.23 (m, 1H) | B | Chiralpak IC, 15% MeOH, Peak 2 |
| 235 | 600 MHz d$_6$-DMSO | 8.30 (br d, J = 7.79 Hz, 1H), 7.46 (dd, J = 7.47, 11.21 Hz, 1H), 7.36 (dd, J = 7.32, 10.74 Hz, 1H), 4.64 (s, 2H), 4.30-4.46 (m, 1H), 3.84-3.93 (m, 1H), 3.37-3.43 (m, 1H), 2.93-3.05 (m, 2H), 2.79 (dd, J = 8.72, | — | — |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 12.46 Hz, 1H), 2.06-2.17 (m, 1H), 1.75-1.85 (m, 1H) 1.10 (dd, J = 1.87, 6.54 Hz, 6H) | | |
| 236 | 600 MHz d$_6$-DMSO | 7.46 (dd, J = 7.47, 11.21 Hz, 1H), 7.38 (dd, J = 7.32, 10.74 Hz, 1H), 4.73 (s, 2H), 4.33-4.47 (m, 1H), 4.27 (dt, J = 4.67, 7.63 Hz, 2H), 3.89-3.99 (m, 2H), 3.34-3.40 (m, 2H), 2.95-3.06 (m, 2H), 2.80 (dd, J = 8.25, 12.61 Hz, 1H), 2.26-2.34 (m, 2H), 2.06-2.18 (m, 1H), 1.75-1.85 (m, 1H) | — | — |
| 237 | 600 MHz d$_6$-DMSO | 7.44-7.52 (m, 1H), 7.28-7.38 (m, 1H), 5.02-5.12 (m, 2H), 4.32-4.47 (m, 1H), 3.55-3.86 (m, 2H), 3.18-3.55 (m, 5H), 2.93-3.07 (m, 2H), 2.74-2.84 (m, 1H), 2.03-2.17 (m, 1H), 1.71-1.84 (m, 1H), 1.01-1.36 (m, 6H) (mixture of 2 diastereomers/rotamers) | — | — |
| 238 | 600 MHz d$_6$-DMSO | 7.53 (dd, J = 7.47, 11.21 Hz, 1H), 7.09-7.20 (m, 1H), 5.28 (t, J = 9.96 Hz, 1H), 4.30-4.48 (m, 1H), 3.56-3.64 (m, 1H), 3.42-3.50 (m, 1H), 3.30-3.42 (m, 2H), 2.97-3.09 (m, 2H), 2.88 (s, 3H), 2.76-2.85 (m, 1H), 2.54-2.59 (m, 1H), 2.27-2.37 (m, 1H), 2.07-2.19 (m, 1H), 1.76-1.93 (m, 1H) | — | — |
| 239 | 600 MHz d$_6$-DMSO | 7.45-7.54 (m, 2H), 7.39-7.44 (m, 2H), 7.35-7.38 (m, 2H), 7.27 (dt, J = 0.93, 7.32 Hz, 1H), 5.21-5.32 (m, 1H), 4.32-4.50 (m, 1H), 4.08-4.20 (m, 1H), 3.61-3.68 (m, 1H), 3.29-3.39 (m, 2H), 2.97-3.11 (m, 2H), 2.73-2.90 (m, 1H), 2.51-2.63 (m, 1H), 2.07-2.32 (m, 4H), 1.82-1.92 (m, 1H) | — | — |
| 240 | 600MHz d$_6$-DMSO | 7.76-7.81 (m, 2H), 7.53-7.58 (m, 1H), 7.48-7.53 (m, 2H), 7.34-7.41 (m, 1H), 5.59 (dd, J = 9.65, 11.21 Hz, 1H), 4.34-4.49 (m, 1H), 4.06 (br t, J = 9.19 Hz, 1H), 3.92-4.00 (m, 1H), 3.34-3.43 (m, 2H), 3.01-3.09 (m, 2H), 2.82 (ddd, J = 8.88, 12.69, 14.87 Hz, 1H), 2.64-2.72 (m, 1H), 2.54-2.61 (m, 1H), 2.10-2.20 (m, 1H), 1.80-1.90 (m, 1H) | — | — |
| 241 | 500 MHz d$_4$-MeOH | 8.51 (s, 2H), 7.95 (d, J = 0.78 Hz, 1H), 7.65-7.70 (m, 1H), 7.59-7.64 (m, 1H), 5.57-5.68 (m, 2H), 4.77-4.95 (m, 1H), 4.23-4.32 (m, 1H), 3.98-4.06 (m, 1H), 3.95 (s, 3H), 3.71-3.80 (m, 1H), 3.42-3.53 (m, 2H), 2.34-2.44 (m, 1H), 2.01-2.15 (m, 1H) | B | Chiralcel OJ-H, 15% MeOH Peak 2 |
| 242 | 500 MHz d$_4$-MeOH | 8.52 (s, 2H), 7.94 (s, 1H), 7.66-7.74 (m, 2H), 5.54-5.67 (m, 2H), 4.77-4.93 (m, 1H), 4.21-4.30 (m, 1H), 4.01 (br d, J = 12.98 Hz, 1H), 3.96 (s, 3H), 3.71-3.78 (m, 1H), 3.43-3.50 (m, 2H), 2.32-2.46 (m, 1H), 1.98-2.14 (m, 1H) | B | Chiralcel OJ-H, 15% MeOH Peak 1 |
| 243 | 600 MHz d$_6$-DMSO | 8.82 (br d, J = 3.89 Hz, 3H), 8.73 (s, 1H), 7.94 (d, J = 1.04 Hz, 1H), 7.86-7.90 (m, 1H), 7.80-7.85 (m, 1H), 7.64-7.68 (m, 1H), 7.56-7.63 (m, 1H), 5.58-5.72 (m, 2H), 4.87-5.04 (m, 1H), 3.94-4.03 (m, 1H), 3.57-3.64 (m, 2H), 3.31 (dd, J = 10.12, 12.98 Hz, 1H), 3.16 (br t, J = 11.42 Hz, 1H), 2.20-2.32 (m, 1H), 1.79-1.96 (m, 1H) | B | Chiralpak AD-H, 20% MeOH Peak 1 |
| 244 | 600 MHz d$_6$-DMSO | 8.73 (br d, J = 4.15 Hz, 3H), 8.71 (d, J = 1.56 Hz, 1H), 8.01 (d, J = 1.30 Hz, 1H), 7.83-7.91 (m, 1H), 7.79 (dd, J = 1.43, 8.17 Hz, 1H), 7.51-7.60 (m, 1H), 7.37-7.51 (m, 1H), 5.55-5.73 (m, 2H), 4.81-5.03 (m, 1H), 3.85-3.96 (m, 1H), 3.58-3.66 (m, 1H), 3.49-3.54 (m, 1H), 3.25 (dd, J = 9.86, 12.98 Hz, 1H), 3.11 (br t, J = 11.42 Hz, 1H), 2.20-2.31 (m, 1H), 1.82-1.95 (m, 1H) | B | Chiralpak AD-H, 20% MeOH Peak 2 |
| 245 | 500 MHz d$_4$-MeOH | 7.36 (dd, J = 7.27, 10.64 Hz, 1H), 7.06 (dd, J = 7.01, 10.12 Hz, 1H), 5.39 (t, J = 9.99 Hz, 1H), 4.34-4.52 (m, 1H), 3.67-3.74 (m, 1H), 3.57-3.65 (m, 1H), 3.48 (br dd, J = 7.14 Hz, 2H), 3.08-3.20 (m, 2H), 3.01 (s, 3H), 2.95 (dd, J = 8.95, 12.33 Hz, 1H), 2.64-2.74 (m, 1H), 2.46 (qd, J = 9.81, 12.88 Hz, 1H), 2.18-2.29 (m, 1H), 1.92-2.03 (m, 1H) | F | Chiralpak IC, 25% MeOH, w/0.2% DEA Peak 1 |
| 246 | 500 MHz d$_4$- | 7.36 (dd, J = 7.27, 10.64 Hz, 1H), 7.06 (dd, J = 7.01, 10.12 Hz, 1H), 5.39 (t, J = 9.99 Hz, 1H), 4.36-4.52 | F | Chiralpak IC, 25% MeOH, |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | MeOH | (m, 1H), 3.67-3.74 (m, 1H), 3.58-3.65 (m, 1H), 3.52-3.58 (m, 1H), 3.38-3.46 (m, 1H), 3.11-3.20 (m, 2H), 3.01 (s, 3H), 2.93 (dd, J = 8.56, 12.46 Hz, 1H), 2.61-2.71 (m, 1H), 2.45 (qd, J = 9.74, 13.07 Hz, 1H), 2.18-2.29 (m, 1H), 1.92-2.04 (m, 1H) | | w/0.2% DEA Peak 2 |
| 247 | 500 MHz d$_4$-MeOH | 7.78 (d, J = 9.08 Hz, 2H), 7.46 (d, J = 9.08 Hz, 2H), 7.40 (dd, J = 7.27, 10.64 Hz, 1H), 7.21 (br dd, J = 6.88, 10.25 Hz, 1H), 5.63 (dd, J = 9.47, 11.03 Hz, 1H), 4.37-4.55 (m, 1H), 4.06-4.20 (m, 2H), 3.55-3.63 (m, 1H), 3.41-3.49 (m, 1H), 3.14-3.23 (m, 2H), 2.96 (dd, J = 8.82, 12.20 Hz, 1H), 2.75-2.84 (m, 1H), 2.58-2.73 (m, 1H), 2.19-2.33 (m, 1H), 1.92-2.06 (m, 1H) | F | Chiralcel OD-H, 30% MeOH, w/0.2% DEA Peak 1 |
| 248 | 500 MHz d$_4$-MeOH | 7.77 (d, J = 8.82 Hz, 2H), 7.43-7.49 (m, 2H), 7.40 (dd, J = 7.27, 10.64 Hz, 1H), 7.17-7.24 (m, 1H), 5.59-5.67 (m, 1H), 4.37-4.54 (m, 1H), 4.06-4.20 (m, 2H), 3.48-3.56 (m, 2H), 3.12-3.21 (m, 2H), 2.95-3.07 (m, 1H), 2.78-2.87 (m, 1H), 2.62-2.72 (m, 1H), 2.20-2.31 (m, 1H), 1.94-2.06 (m, 1H) | F | Chiralcel OD-H, 30% MeOH, w/0.2% DEA Peak 2 |
| 249 | DMSO-d$_6$ | 9.09 (d, J = 1.48 Hz, 1H), 8.96 (d, J = 1.40 Hz, 1H), 7.78 (d, J = 1.48 Hz, 1H), 7.56 (d, J = 8.29 Hz, 1H), 7.50 (d, J = 8.50 Hz, 1H), 5.66-5.76 (m, 2H), 4.39-4.37 (m, 1H), 3.39-3.49 (m, 2H), 3.06-3.17 (m, 1H), 2.80-2.95 (m, 2H), 2.00-2.14 (m, 2H), 1.67-1.83 (m, 1H) | B | SFC: Chiralpak AD-H, 30% methanol. |
| 250 | DMSO-d$_6$ | 9.08 (d, J = 1.40 Hz, 1H), 8.97 (d, J = 1.40 Hz, 1H), 7.93 (d, J = 1.48 Hz, 1H), 7.46 (d, J = 8.36 Hz, 1H), 7.39 (d, J = 8.21 Hz, 1H), 5.67-5.76 (m, 2H), 4.38-4.34 (m, 1H), 3.37-3.46 (m, 2H), 3.02-3.12 (m, 1H), 2.79-2.98 (m, 2H), 2.00-2.16 (m, 1H), 1.68-1.79 (m, 1H) | B | SFC: Chiralpak AD-IL 25% methanol |
| 251 | DMSO-d$_6$ | 9.10 (d, J = 1.40 Hz, 1H), 8.97 (d, J = 1.32 Hz, 1H), 7.17 (dd, J = 2.18, 9.26 Hz, 1H), 6.89 (t, J = 10.46 Hz, 1H), 5.63-5.70 (m, 2H), 4.26-4.31 (m, 1H), 3.37-3.51 (m, 2H), 3.03-3.12 (m, 1H), 2.92-3.01 (m, 1H), 2.79-2.91 (m, 1H), 1.99-2.17 (m, 1H), 1.70-1.84 (m, 1H) | B | SFC: Chiralpak AD-H, 30% methanol |
| 252 | DMSO-d$_6$ | 9.02-9.15 (m, 1H), 8.93-8.98 (m, 1H), 7.17 (d, J = 8.96 Hz, 1H), 6.82-6.94 (m, 1H), 5.61-5.70 (m, 2H), 4.34 (dt, J = 4.28, 8.25 Hz, 1H), 3.37-3.44 (m, 1H), 3.03-3.10 (m, 1H), 2.87-2.886 (m, 2H), 2.32-2.47 (m, 1H), 2.02-2.18 (m, 1H), 1.69-1.83 (m, 1H) | B | SFC: Chiralpak AD-H, 25% methanol |
| 253 | DMSO-d$_6$ | 10.99-11.51 (m, 1H), 8.46-8.48 (m, 1H), 7.65-7.72 (m, 1H), 7.51-7.57 (m, 1H), 7.13-7.20 (m, 2H), 6.84-6.95 (m, 2H), 4.09-4.26 (m, 1H), 3.88-4.08 (m, 1H), 3.74-3.82 (m, 2H), 2.80-3.00 (m, 2H), 2.58-2.67 (m, 1H), 2.20-2.26 (m, 3H), 1.93-2.00 (m, 1H), 1.74-1.84 (m, 1H), 1.47-1.55 (m, 2H) | — | — |
| 254 | DMSO-d$_6$ | 8.48-8.64 (s, 1H), 7.83-7.99 (m, 1H), 7.43-7.58 (m, 1H), 7.26 (d, J = 8.30 Hz, 1H), 7.01-7.20 (m, 2H), 6.89 (br dd, J = 3.05, 5.51 Hz, 2H), 4.55 (s, 1H), 4.01 (br d, J = 12.20 Hz, 1H), 3.74-3.83 (m, 1H), 3.55-3.69 (m, 1H), 2.82-3.04 (m, 2H), 2.58-2.66 (m, 1H), 2.35-2.47 (m, 1H), 2.25 (s, 2H), 1.95 (br s, 1H), 1.80 (br dd, J = 3.18, 6.16 Hz, 1H), 1.44-1.63 (m, 1H), | — | — |
| 255 | DMSO-d$_6$ | 9.04 (d, J = 2.02 Hz, 1H), 8.30 (d, J = 8.16 Hz, 1H), 7.40-7.47 (m, 2H), 7.05 (t, J = 7.59 Hz, 1H), 6.92-7.00 (m, 2H), 5.81-5.87 (m, 1H), 3.37-3.48 (m, 1H), 2.85-2.94 (m, 2H), 2.52-2.69 (m, 3H), 2.37-2.47 (m, 1H), 2.15 (s, 3H), 1.85-1.95 (m, 2H), 1.71-1.82 (m, 1H), 1.59-1.69 (m, 1H), 1.14-1.26 (m, 1H) | B | SFC: Chiralpak IC, 25% methanol |
| 256 | DMSO-d$_6$ | 9.04 (d, J = 1.48 Hz, 1H), 8.29 (d, J = 8.18 Hz, 1H), 7.45 (d, J = 8.80 Hz, 1H), 7.41 (d, J = 8.07 Hz, 1H), 7.05 (ddd, J = 1.87, 6.46, 8.02 Hz, 1H), 6.90-7.00 (m, 2H), 5.80-5.88 (m, 1H), | B | SFC: Chiralpak IC, 25% methanol |

TABLE 6-continued

Characterization data for compounds made following schemes 9-10
The column "Separation Stage" indicates after which
process step regioisomers formed due to asymmetric
benzimidazole substitution at R$^1$ in Scheme
10 were separated during the preparation of the tabulated
final compound. (I = after preparation of the
N-aralkyl-2-piperidinyl-benzimidazole intermediate
in the first step of Scheme 10 (where at least one R$^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 3.38-3.50 (m, 2H), 3.21-3.28 (m, 1H), 2.82-2.94 (m, 1H), 2.67 (dd, J = 9.07, 11.64 Hz, 1H), 2.51-2.62 (m, 2H), 2.25 (s, 2H), 2.15 (s, 1H), 1.91 (d, J = 7.16 Hz, 4H), 1.62-1.80 (m, 2H), 1.18-1.28 (m, 1H) | | |
| 257 | DMSO-d$_6$ | 8.92 (s, 2H), 7.15 (dd, J = 2.18, 9.34 Hz, 1H), 6.86 (t, J = 10.48 Hz, 1H), 5.51-5.60 (m, 2H), 4.298-4.44 (m, 1H), 3.34-3.42 (m, 2H), 3.02-3.10 (m, 1H), 2.88-2.97 (m, 1H), 2.81 (dd, J = 8.45, 12.57 Hz, 1H), 2.04-2.12 (m, 1H), 1.66-1.82 (m, 1H) | B | SFC/MS with MeOH as co-solvent at 10% iso-cratic Column: 4-Ethylpyridine 21.2 × 150 mm |
| 258 | DMSO-d$_6$ | 8.92 (s, 2H), 7.06 (dd, J = 2.26, 8.88 Hz, 1H), 6.95 (dt, J = 2.18, 10.63 Hz, 1H), 5.50-5.57 (m, 2H), 4.26-4.43 (m, 1H), 3.25-3.42 (m, 1H), 2.93-3.09 (m, 2H), 2.86 (br s, 1H), 2.76 (br dd, J = 8.60, 12.34 Hz, 1H), 2.00-2.09 (m, 1H), 1.62-1.73 (m, 1H) | B | SFC/MS with MeOH as co-solvent at 10% iso-cratic Column: 4-Ethylpyridine 21.2 × 150 mm |
| 259 | DMSO-d$_6$ | 7.85 (d, J = 0.78 Hz, 1H), 7.57 (d, J = 8.49 Hz, 1H), 7.50 (dd, J = 7.43, 11.17 Hz, 1H), 7.33 (dd, J = 7.08, 8.41 Hz, 1H), 7.25 (dd, J = 7.32, 10.67 Hz, 1H), 6.77 (d, J = 6.70 Hz, 1H), 5.59-5.66 (m, 2H), 4.27-4.41 (m, 2H), 4.03 (s, 3H), 3.42-3.59 (m, 1H), 2.99-3.12 (m, 1H), 2.89-2.98 (m, 1H), 2.83 (dd, J = 8.68, 12.57 Hz, 1H), 2.29-2.47 (m, 1H), 1.94-2.11 (m, 1H), 1.67-1.77 (m, 1H) | — | — |
| 260 | DMSO-d$_6$ | 8.97 (dd, J = 1.56, 4.20 Hz, 1H), 8.61 (d, J = 8.02 Hz, 1H), 7.97 (d, J = 8.49 Hz, 1H), 7.67 (t, J = 7.95 Hz, 1H), 7.61-7.65 (m, 1H), 7.53 (dd, J = 7.47, 11.13 Hz, 1H), 7.25 (dd, J = 7.32, 10.67 Hz, 1H), 7.00 (d, J = 7.19 Hz, 1H), 5.79-5.86 (m, 2H), 4.27-4.40 (m, 1H), 3.37-3.52 (m, 2H), 3.01-3.10 (m, 1H), 2.89-2.99 (m, 1H), 2.83 (dd, J = 8.49, 12.53 Hz, 1H), 2.02 (dddd, J = 4.28, 8.60, 12.62, 16.77 Hz, 1H), 1.67-1.83 (m, 1H) | — | — |
| 261 | DMSO-d$_6$ | 8.91 (dd, J = 1.71, 4.13 Hz, 1H), 8.40 (dd, J = 1.48, 8.25 Hz, 1H), 7.98 (d, J = 8.10 Hz, 1H), 7.87 (d, J = 7.16 Hz, 1H), 7.65 (t, J = 7.71 Hz, 1H), 7.57 (dd, J = 4.17, 8.21 Hz, 1H), 7.37-7.52 (m, 2H), 6.75 (q, J = 7.19 Hz, 1H), 4.33-4.41 (m, 1H), 3.35-3.46 (m, 2H), 2.96-3.09 (m, 2H), 2.72 (dd, J = 8.76, 12.34 Hz, 1H), 2.52-2.56 (m, 1H), 1.97-2.10 (m, 4H), 1.63-1.79 (m, 1H) | B | SFC: Chiralpak IC column, 20% methanol. |
| 262 | DMSO-d$_6$ | 8.91 (dd, J = 1.71, 4.13 Hz, 1H), 8.39 (dd, J = 1.56, 8.25 Hz, 1H), 7.98 (d, J = 8.02 Hz, 1H), 7.86 (d, J = 7.16 Hz, 1H), 7.65 (t, J = 7.71 Hz, 1H), 7.56 (dd, J = 4.13, 8.25 Hz, 1H), 7.46 (dd, J = 7.63, 11.13 Hz, 1H), 7.39 (dd, J = 7.36, 11.25 Hz, 1H), 6.73 (q, J = 7.14 Hz, 1H), 4.28-4.36 (m, 1H), 3.36-3.46 (m, 1H), 3.14-3.28 (m, 2H), 2.83-2.97 (m, 2H), 2.52-2.55 (m, 1H), 2.38 (br s, 1H), 1.91-2.05 (m, 4H), 1.68-1.85 (m, 1H) | B | SFC: Chiralpak IC column, 20% methanol. |
| 263 | DMSO-d$_6$ | 7.92 (t, J = 1.71 Hz, 1H), 7.84 (td, J = 1.31, 7.65 Hz, 1H), 7.51-7.59 (m, 4H), 7.14 (s, 1H), 5.57 (s, 2H), 4.29-4.50 (m, 1H), 3.36-3.49 (m, 3H), 2.99-3.13 (m, 1H), 2.87 (dd, J = 8.37, 12.57 Hz, 1H), 2.04-2.20 (m, 1H), 1H), 1.77-1.92 (m, 1H) | — | — |
| 264 | DMSO-d$_6$ | 8.06 (s, 1H), 7.68 (d, J = 8.02 Hz, 1H), 7.54 (t, J = 9.20 Hz, 1H), 7.18 (dd, J = 7.59, 10.47 Hz, 1H), 6.99 (t, J = 7.59 Hz, 1H), 6.48 (d, J = 7.30 Hz, 1H), 5.98 (d, J = 17.36 Hz, 1H), 5.91 (d, J = 17.36 Hz, 1H), 4.36-4.45 (m, 1H), 4.31-4.35 (m, 3H), 3.40-3.57 (m, 2H), 3.08-3.13 (m, 1H), 2.90-2.97 (m, 1H), 2.86 (dd, J = 8.14, 12.57 Hz, 1H), 2.54-2.66 (m, 1H), 1.99-2.07 (m, 1H), 1.67-1.83 (m, 1H) | — | — |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 265 | DMSO-$d_6$ | 7.47-7.56 (m, 3H), 7.42 (dd, J = 7.67, 8.52 Hz, 1H), 6.75 (dd, J = 7.24, 10.82 Hz, 1H), 5.50-5.56 (m, 2H), 4.29-4.47 (m, 1H), 3.40-3.51 (m, 1H), 3.35-3.40 (m, 1H), 3.01-3.14 (m, 1H), 2.91-3.01 (m, 1H), 2.82 (dd, J = 8.76, 12.42 Hz, 1H), 2.08-2.17 (m, 1H), 1.72-1.84 (m, 1H) | — | — |
| 266 | DMSO-$d_6$ | 7.37-7.41 (m, 1H), 7.18 (d, J = 7.38 Hz, 1H), 7.07 (t, J = 6.39 Hz, 2H), 4.62-4.71 (m, 2H), 4.25 (t, J = 7.63 Hz, 2H), 3.89-3.97 (m, 2H), 3.40-3.48 (m, 1H), 3.23-3.29 (m, 1H), 2.83-2.91 (m, 1H), 2.52-2.65 (m, 1H), 2.25-2.32 (m, 1H), 1.83-1.93 (m, 1H), 1.71-1.79 (m, 1H), 1.60-1.69 (m, 1H), 1.21-1.33 (m, 1H) | — | — |
| 267 | DMSO-$d_6$ | 9.53 (br s, 1H), 8.97 (d, J = 1.63 Hz, 1H), 8.33 (d, J = 8.66 Hz, 1H), 7.55 (d, J = 8.47 Hz, 1H), 7.23 (dd, J = 2.22, 9.07 Hz, 1H), 6.88 (t, J = 10.52 Hz, 1H), 5.82-5.96 (m, 1H), 4.02 (br dd, J = 3.93, 7.90 Hz, 2H), 3.61-3.79 (m, 1H), 3.57 (br s, 1H), 3.50 (br dd, J = 4.09, 12.42 Hz, 1H), 3.28 (br s, 1H), 3.13-3.26 (m, 1H), 3.09 (br d, J = 12.77 Hz, 1H), 2.51-2.66 (m, 2H), 1.97 (br s, 2H), 1.84-1.93 (m, 3H) | B | SFC: Chiralpak IC, 15% methanol (initial purification). Chiralpak AD-H, 10% methanol (reprocess of fraction A). - |
| 268 | DMSO-$d_6$ | 9.46 (br s, 1H), 8.93-9.04 (m, 1H), 8.33 (d, J = 8.76 Hz, 1H), 7.55 (d, J = 8.51 Hz, 1H), 7.23 (dd, J = 2.18, 9.03 Hz, 1H), 6.89 (t, J = 10.51 Hz, 1H), 5.85-5.96 (m, 1H), 3.92-4.07 (m, 2H), 3.83 (br s, 2H), 3.55-3.79 (m, 1H), 3.50 (br dd, J = 4.13, 12.46 Hz, 1H), 3.25-3.33 (m, 1H), 3.13-3.25 (m, 1H), 3.09 (br d, J = 12.53 Hz, 1H), 2.51-2.56 (m, 2H), 1.96 (br s, 2H), 1.83-1.92 (m, 3H) | B | SFC: Chiralpak IC, 15% methanol (initial purification). Chiralpak AD-H, 10% methanol (reprocess of fraction A). |
| 269 | DMSO-$d_6$ | 9.44 (br s, 1H), 8.94-8.99 (m, 1H), 8.30-8.35 (m, 1H), 7.49-7.56 (m, 1H), 7.23 (dd, J = 2.26, 9.03 Hz, 1H), 6.89 (t, J = 10.49 Hz, 1H), 5.86-5.94 (m, 1H), 3.95-4.09 (m, 2H), 3.71-3.80 (m, 2H), 3.57-3.69 (m, 1H), 3.50 (br dd, J = 4.09, 12.26 Hz, 1H), 3.12-3.26 (m, 2H), 3.09 (br d, J = 12.77 Hz, 1H), 2.51-2.62 (m, 2H), 1.91-1.97 (m, 1H), 1.85-1.91 (m, 3H) | B | SFC: Chiralpak IC, 15% methanol (initial purification). - Lux-Cellulose 2, 15% methanol (reprocess of fraction B). - |
| 270 | DMSO-$d_6$ | 9.45 (br s, 1H), 8.97 (d, J = 1.48 Hz, 1H), 8.29-8.36 (m, 1H), 7.48-7.56 (m, 1H), 7.23 (dd, J = 2.18, 9.03 Hz, 1H), 6.89 (t, J = 10.48 Hz, 1H), 5.85-5.94 (m, 1H), 3.97-4.07 (m, 2H), 3.71-3.80 (m, 2H), 3.57-3.69 (m, 1H), 3.29 (br s, 1H), 3.12-3.26 (m, 1H), 3.09 (br d, J = 12.53 Hz, 1H), 2.52-2.55 (m, 2H), 1.96-2.06 (m, 1H), 1.94 (br s, 1H), 1.83-1.91 (m, 3H) | B | SFC: Chiralpak IC, 15% methanol (initial purification). - Lux-Cellulose 2, 15% methanol (reprocess of fraction B). |
| 271 | DMSO-$d_6$ | 9.32 (br s, 1H), 8.86 (br s, 1H), 8.32-8.37 (m, 1H), 7.55-7.59 (m, 1H), 6.99 (dt, J = 2.06, 10.53 Hz, 1H), 6.79 (dd, J = 1.99, 8.99 Hz, 1H), 5.92 (q, J = 7.16 Hz, 1H), 3.95-4.10 (m, 2H), 3.81 (br d, J = 9.50 Hz, 1H), 3.70-3.78 (m, 1H), .61-3.69 (m, 1H), 3.39-3.48 (m, 2H), 3.07-3.17 (m, 1H), 2.52-2.55 (m, 2H), 1.87-1.99 (m, 5H) | B | SFC: Chiralpak IC, 15% methanol (initial purification). - Chiralcel OZ-H, 25% methanol (reprocess of fraction C). - |
| 272 | DMSO-$d_6$ | 9.33 (br s, 1H), 8.88 (br s, 1H), 8.35 (br d, J = 8.17 Hz, 1H), 7.57 (d, J = 8.25 Hz, 1H), 6.97-7.10 (m, 1H), 6.79 (br d, J = 8.88 Hz, 1H), 5.89-5.98 (m, 1H), | B | SFC: Chiralpak IC, 15% methanol |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 3.99-4.07 (m, 2H), 3.78-3.84 (m, 1H), 3.70-3.78 (m, 1H), 3.64 (br t, J = 11.29 Hz, 1H), 3.41-3.53 (m, 1H), 3.24 (br s, 1H), 3.07-3.17 (m, 1H), 2.54 (s, 2H), 1.86-1.99 (m, 5H) | | (initial purification). - fraction C). Regis Whelk-O s, s, 20% methanol (reprocess of peaks C1-C3). |
| 273 | DMSO-d$_6$ | 9.33 (br s, 1H), 8.90 (br d, J = 18.92 Hz, 1H), 8.32-8.37 (m, 1H), 7.57 (dd, J = 6.89, 7.67 Hz, 1H), 6.99 (t, J = 10.22 Hz, 1H), 6.79 (br d, J = 8.95 Hz, 1H), 5.87-5.94 (m, 1H), 3.97-4.09 (m, 2H), 3.81 (br d, J = 8.95 Hz, 1H), 3.70-3.78 (m, 1H), 3.61-3.69 (m, 1H), 3.57-3.69 (m, 1H), 3.29 (br s, 1H), 3.15 (br d, J = 14.09 Hz, 1H), 2.52-2.56 (m, 2H), 2.00 (br d, J = 5.99 Hz, 1H), 1.92 (d, J = 7.16 Hz, 4H) | B | SFC: Chiralpak IC, 15% methanol (initial purification). - Regis Whelk-O s, s, 30% methanol (reprocess of fraction D). |
| 274 | DMSO-d$_6$ | 9.33 (br s, 1H), 8.80-8.96 (m, 1H), 8.32-8.37 (m, 1H), 7.57 (t, J = 7.49 Hz, 1H), 6.99 (dt, J = 2.02, 10.51 Hz, 1H), 6.79 (br d, J = 9.03 Hz, 1H), 5.87-5.94 (m, 1H), 3.96-4.08 (m, 2H), 3.80 (br s, 1H), 3.70-3.78 (m, 1H), 3.55-3.69 (m, 1H), 3.40-3.53 (m, 1H), 3.15 (br d, J = 14.17 Hz, 1H), 3.10 (br d, J = 13.39 Hz, 1H), 2.51-2.55 (m, 2H), 1.92 (d, J = 7.16 Hz, 5H) | B | SFC: Chiralpak IC, 15% methanol (initial purification). - Regis Whelk-O s, s, 30% methanol (reprocess of fraction D). |
| 275 | DMSO-d$_6$ | 8.27 (br d, J = 7.21 Hz, 1H), 7.47 (dd, J = 7.47, 11.21 Hz, 1H), 7.34 (dd, J = 7.32, 10.67 Hz, 1H), 4.62-4.69 (m, 2H), 4.32-4.44 (m, 2H), 3.33-3.50 (m, 1H), 3.17 (br s, 1H), 2.96-3.11 (m, 2H), 2.77-2.85 (m, 1H), 2.66 (d, J = 4.59 Hz, 3H), 2.07-2.15 (m, 1H), 1.75-1.83 (m, 1H) | — | — |
| 276 | DMSO-d$_6$ | 7.46 (t, J = 9.25 Hz, 1H), 7.40 (t, J = 8.98 Hz, 1H), 4.98-5.07 (m, 2H), 4.35-4.47 (m, 1H), 3.63-3.73 (m, 2H), 3.56-3.62 (m, 4H), 3.38-3.54 (m, 2H), 3.22-3.37 (m, 2H), 3.17 (br s, 1H), 2.94-3.10 (m, 1H), 2.80 (dd, J = 8.14, 12.57 Hz, 1H), 2.06-2.17 (m, 1H), 1.75-1.84 (m, 1H) | — | — |
| 277 | DMSO-d$_6$ | 7.46 (dd, J = 7.47, 11.13 Hz, 1H), 7.38 (dd, J = 7.32, 10.74 Hz, 1H), 4.84-4.94 (m, 2H), 4.35-4.44 (m, 1H), 3.51-3.66 (m, 2H), 3.23-3.41 (m, 2H), 2.94-3.11 (m, 4H), 2.80 (dd, J = 8.21, 12.57 Hz, 2H), 2.29-2.47 (m, 2H), 2.02-2.18 (m, 2H), 1.96 (quin, J = 6.83 Hz, 1H), 1.75-1.86 (m, 1H) | — | — |
| 278 | DMSO-d$_6$ | 7.46 (dd, J = 7.47, 11.21 Hz, 1H), 7.37 (dd, J = 7.36, 10.78 Hz, 1H), 4.93-5.02 (m, 2H), 4.32-4.44 (m, 1H), 3.24-3.42 (m, 1H), 3.17 (br s, 1H), 3.11 (s, 6H), 2.94-3.06 (m, 1H), 2.88 (s, 1H), 2.79 (dd, J = 8.21, 12.65 Hz, 1H), 2.05-2.16 (m, 1H), 1.74-1.84 (m, 1H) | — | — |
| 279 | DMSO-d$_6$ | 7.53 (dd, J = 7.55, 11.13 Hz, 1H), 7.39 (dd, J = 7.43, 11.09 Hz, 1H), 5.51 (q, J = 6.98 Hz, 1H), 4.39-4.47 (dt, J = 4.13, 7.94 Hz, 1H), 3.07-3.26 (m, 3H), 2.72-2.81 (m, 7H), 2.52-2.56 (m, 1H), 2.10-2.28 (m, 1H), 1.71-1.86 (m, 1H), 1.61 (d, J = 7.01 Hz, 3H) | B | SFC: Chiralpak IC analytical column, 15% methanol with 0.2% DEA |
| 280 | DMSO d$_6$ | 7.53 (dd, J = 7.55, 11.13 Hz, 1H), 7.39 (dd, J = 7.43, 11.09 Hz, 1H), 5.51 (q, J = 6.98 Hz, 1H), 4.39-4.47 (dt, J = 4.13, 7.94 Hz, 1H), 3.07-3.26 (m, 3H), 2.72-2.81 (m, 7H), 2.52-2.56 (m, 1H), 2.10-2.28 (m, 1H), 1.71-1.86 (m, 1H), 1.61 (d, J = 7.01 Hz, 3H) | B | SFC: Chiralpak IC analytical column, 15% methanol with 0.2% DEA |
| 281 | DMSO-d$_6$ | 7.46 (dd, J = 7.47, 11.21 Hz, 1H), 7.37 (dd, J = 7.36, 10.78 Hz, 1H), 4.99 (d, J = 2.34 Hz, 2H), 4.31-4.39 | — | — |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | (m, 1H), 3.40-3.54 (m, 3H), 3.19-3.29 (m, 1H), 2.93-3.04 (m, 2H), 2.78 (dd, J = 8.25, 12.53 Hz, 1H), 2.06-2.16 (m, 1H), 1.71-1.83 (m, 3H), 1.54-1.66 (m, 4H), 1.40-1.53 (m, 2H) | | |
| 282 | DMSO-d$_6$ | 8.31-8.41 (m, 1H), 7.47 (dd, J = 7.47, 11.21 Hz, 1H), 7.35 (dd, J = 7.28, 10.70 Hz, 1H), 4.61-4.68 (m, 2H), 4.32-4.47 (m, 1H), 3.35-3.45 (m, 1H), 3.11-3.28 (m, 2H), 2.95-3.08 (m, 2H), 2.80 (dd, J = 8.68, 12.65 Hz, 1H), 2.03-2.18 (m, 1H), 1.99 (br s, 1H), 1.56-1.91 (m, 1H), 1.06 (t, J = 7.24 Hz, 3H) | — | — |
| 283 | DMSO-d$_6$ | 8.94 (s, 2H), 7.80 (d, J = 1.09 Hz, 1H), 7.55 (d, J = 8.39 Hz, 1H), 7.50 (d, J = 8.39 Hz, 1H), 5.54-5.62 (m, 2H), 4.44-4.57 (m, 1H), 3.45-3.56 (m, 2H), 3.07-3.13 (m, 1H), 2.81 (dd, J = 8.56, 12.92 Hz, 1H), 2.52-2.64 (m, 1H), 2.17 (s, 3H), 1.95-2.10 (m, 1H), 1.70-1.82 (m, 1H) | B | SFC: Chiralpak AD-H analytical column, 30% methanol |
| 284 | DMSO-d$_6$ | 8.94 (s, 2H), 7.91 (d, J = 1.01 Hz, 1H), 7.46 (dd, J = 1.56, 8.25 Hz, 1H), 7.39 (d, J = 8.25 Hz, 1H), 5.60 (s, 2H), 4.42-4.57 (m, 1H), 3.47-3.54 (m, 1H), 3.37-3.46 (m, 1H), 3.04-3.11 (m, 1H), 2.79 (dd, J = 8.52, 12.81 Hz, 1H), 2.52-2.65 (m, 1H), 2.18 (s, 3H), 1.95-2.11 (m, 1H), 1.71-1.84 (m, 1H) | B | SFC: Chiralpak AD-H analytical column, 30% methanol |
| 285 | DMSO-d$_6$ | 7.42 (d, J = 8.49 Hz, 1H), 7.38 (d, J = 2.02 Hz, 1H), 7.12-7.15 (m, 1H), 4.73-4.80 (m, 2H), 4.57-4.69 (m, 1H), 3.95 (t, J = 7.71 Hz, 2H), 3.51-3.56 (m, 1H), 3.31-3.44 (m, 2H), 3.28 (br s, 1H), 3.17 (s, 1H), 2.99-3.10 (m, 1H), 2.95 (br dd, J = 9.34, 12.61 Hz, 1H), 2.25-2.32 (m, 2H), 2.06-2.23 (m, 1H), 1.72-1.89 (m, 1H) | B | SFC: Chiralpak IC analytical column, 45% methanol. |
| 286 | DMSO-d$_6$ | 7.47 (d, J = 1.95 Hz, 1H), 7.25 (d, J = 8.49 Hz, 1H), 7.13 (dd, J = 1.95, 8.49 Hz, 1H), 4.72-4.79 (m, 2H), 4.58-4.70 (dt, J = 4.59, 8.68 Hz, 1H), 4.23-4.29 (m, 1H), 3.94 (t, J = 7.71 Hz, 1H), 3.51-3.59 (m, 1H), 3.31-3.47 (m, 2H), 3.28 (br s, 1H), 3.17 (s, 1H), 3.01-3.12 (m, 1H), 2.96 (br dd, J = 9.23, 12.65 Hz, 2H), 2.13-2.31 (m, 1H), 1.79-1.89 (m, 1H) | B | SFC: Chiralpak IC analytical column, 45% methanol. |
| 287 | DMSO-d$_6$ | 7.77 (d, J = 1.01 Hz, 1H), 7.46-7.54 (m, 2H), 4.74-4.86 (m, 3H), 4.25-4.36 (m, 2H), 3.96 (t, J = 7.71 Hz, 2H), 3.12-3.29 (m, 3H), 3.01-3.09 (m, 2H), 2.30 (quin, J = 7.69 Hz, 2H), 2.01-2.08 (m, 1H), 1.80-1.99 (m, 1H) | B | SFC: Chiralpak IC analytical column, 35% methanol |
| 288 | DMSO-d$_6$ | 7.86-7.92 (m, 1H), 7.46-7.52 (m, 1H), 7.33-7.42, (m, 1H), 4.74-4.86 (m, 3H), 4.25-4.36 (m, 2H), 3.96 (t, J = 7.71 Hz, 2H), 3.12-3.29 (m, 3H), 3.01-3.09 (m, 2H), 2.30 (quin, J = 7.69 Hz, 2H), 2.01-2.08 (m, 1H), 1.80-1.99 (m, 1H) | B | SFC: Chiralpak IC analytical column, 35% methanol |
| 289 | DMSO-d$_6$ | 8.92 (s, 2H), 7.42 (dd, J = 4.87, 8.68 Hz, 1H), 7.11 (dd, J = 2.49, 9.26 Hz, 1H), 6.92 (ddd, J = 2.57, 8.68, 10.08 Hz, 1H), 5.47-5.56 (m, 2H), 4.26-4.42 (m, 1H), 3.35-3.49 (m, 2H), 2.93-3.03 (m, 1H), 2.82-2.92 (m, 1H), 2.74 (dd, J = 8.60, 12.42 Hz, 1H), 1.97-2.12 (m, 1H), 1.64-1.82 (m, 1H) | B | SFC: Chiralcel OD-H, 15% isopropanol |
| 290 | DMSO d$_6$ | 8.92 (s, 2H), 7.24 (dd, J = 2.45, 9.77 Hz, 1H), 7.14 (dd, J = 4.75, 8.72 Hz, 1H), 6.87 (ddd, J = 2.49, 8.70, 9.91 Hz, 1H), 5.51 (d, J = 2.10 Hz, 2H), 4.27-4.34 (m, 1H), 3.35-3.44 (m, 2H), 2.98-3.06 (m, 1H), 2.83-2.93 (m, 1H), 2.78 (dd, J = 8.60, 12.57 Hz, 1H), 1.99-2.09 (m, 1H), 1.64-1.79 (m, 1H) | B | SFC: Chiralcel OD-H, 15% isopropanol |
| 291 | 500 MHz DMSO-d$_6$ | 8.96 (s, 1H), 8.28 (br dd, J = 1.95, 8.17 Hz, 1H), 7.36-7.50 (m, 1H), 7.32 (br d, J = 8.04 Hz, 1H), 7.05-7.20 (m, 2H), 6.98-7.05 (m, 1H), 5.47 (s, 2H), 3.3 (m, 1H), 2.83 (br t, J = 10.06 Hz, 2H), 2.74 (br s, 1H), 2.60-2.67 (m, 1H), 1.79 (br d, J = 8.30 Hz, 1H), 1.66 (br s, 1H), 1.51 (br d, J = 10.77 Hz, 1H), 1.15 (br d, J = 10.64 Hz, 1H) | — | — |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 292 | 500 MHz DMSO-d$_6$ | 8.67 (d, J = 1.66 Hz, 1H), 8.02 (br d, J = 7.98 Hz, 3H), 7.77 (dd, J = 1.97, 8.09 Hz, 1H), 7.52 (d, J = 7.77 Hz, 1H), 7.13-7.28 (m, 3H), 5.54 (s, 2H), 3.57-3.65 (m, 1H), 3.45 (br s, 1H), 3.30 (br d, J = 12.75 Hz, 1H), 3.18 (dd, J = 8.50, 12.44 Hz, 1H), 2.98-3.07 (m, 1H), 1.99 (br d, J = 9.02 Hz, 1H), 1.83 (br s, 1H), 1.54-1.70 (m, 2H) | — | — |
| 293 | 500 MHz DMSO-d$_6$ | 9.23 (s, 1H), 8.48 (br d, J = 5.71 Hz, 1H), 7.95 (br d, J = 8.17 Hz, 1H), 7.88 (s, 1H), 7.79 (br d, J = 5.58 Hz, 1H), 7.57 (br d, J = 8.43 Hz, 1H), 7.44 (br d, J = 7.66 Hz, 1H), 7.17 (br d, J = 7.91 Hz, 1H), 7.08 (br t, J = 7.46 Hz, 1H), 6.97-7.04 (m, 1H), 5.49 (s, 2H), 2.78-2.95 (m, 2H), 2.53-2.72 (m, 2H), 1.82 (br d, J = 10.25 Hz, 2H), 1.68 (br s, 1H), 1.61 (br s, 1H), 1.18 (br d, J = 9.73 Hz, 1H) | — | — |
| 294 | 500 MHz DMSO-d$_6$ | 8.05 (s, 1H), 7.67 (br d, J = 7.92 Hz, 1H), 7.46 (br d, J = 7.78 Hz, 1H), 7.08 (br t, J = 6.75 Hz, 1H), 6.92-7.03 (m, 3H), 6.59 (br d, J = 6.88 Hz, 1H), 5.83-5.96 (m, 2H), 4.32 (s, 3H), 3.37-3.59 (m, 1H), 2.86-2.99 (m, 1H), 2.82 (br s, 1H), 2.53-2.76 (m, 1H), 1.78 (br s, 2H), 1.65 (br s, 1H), 1.58 (br s, 1H), 1.19 (br d, J = 9.99 Hz, 1H) | — | — |
| 295 | 500 MHz DMSO-d$_6$ | 9.03 (s, 1H), 8.29 (br d, J = 6.74 Hz, 1H), 7.36-7.51 (m, 2H), 6.99-7.12 (m, 1H), 6.94 (d, J = 3.94 Hz, 2H), 5.82-5.99 (m, 1H), 4.03 (q, J = 7.15 Hz, 1H), 3.39 (br d, J = 10.78 Hz, 1H), 3.17 (br d, J = 12.65 Hz, 1H), 2.81-3.05 (m, 2H), 1.75-1.95 (m, 4H), 1.54-1.70 (m, 1H), 1.31-1.47 (m, 1H), 1.17 (t, J = 7.10 Hz, 1H) | B | SFC: Chiralpak IC, 20% methanol w/0.2% DEA |
| 296 | 500 MHz DMSO-d$_6$ | 9.04 (d, J = 1.55 Hz, 1H), 8.24-8.31 (m, 1H), 7.36-7.48 (m, 2H), 7.01-7.09 (m, 1H), 6.89-6.99 (m, 2H), 5.83-5.96 (m, 1H), 3.35-3.53 (m, 2H), 3.21 (br d, J = 12.13 Hz, 1H), 3.12 (br s, 1H), 2.77-3.02 (m, 2H), 1.75-1.95 (m, 1H), 1.67 (br d, J = 9.23 Hz, 1H), 1.29-1.46 (m, 1H). | B | SFC: Chiralpak IC, 20% methanol w/0.2% DEA |
| 297 | 500 MHz DMSO-d$_6$ | 9.03 (d, J = 1.55 Hz, 1H), 8.80 (br s, 3H), 8.36 (dd, J = 2.07, 8.29 Hz, 1H), 7.66 (br d, J = 8.29 Hz, 1H), 7.56 (d, J = 7.98 Hz, 1H), 7.39 (br s, 1H), 7.00-7.15 (m, 2H), 6.04 (q, J = 6.77 Hz, 1H), 4.92-5.05 (m, 1H), 3.84 (br d, J = 12.75 Hz, 1H), 3.75 (br s, 1H), 3.62-3.71 (m, 1H), 3.32-3.54 (m, 1H), 3.06-3.30 (m, 1H), 2.77-3.05 (m, 1H), 2.53-2.75 (m, 1H), 2.27-2.47 (m, 1H), 1.91-2.02 (m, 4H). | B | SFC: Chiralpak IC, 20% methanol w/0.2% DEA |
| 298 | 500 MHz DMSO-d$_6$ | 9.02 (d, J = 1.45 Hz, 1H), 8.80 (br s, 3H), 8.35 (dd, J = 2.18, 8.29 Hz, 1H), 7.63 (d, J = 7.56 Hz, 1H), 7.58 (d, J = 7.48 Hz, 1H), 7.20-7.29 (m, 1H), 7.03-7.15 (m, 2H), 6.01 (q, J = 6.91 Hz, 1H), 4.90-5.02 (m, 1H), 3.91 (s, 1H), 3.87 (br s, 1H), 3.65-3.81 (m, 1H), 3.59-3.64 (m, 1H), 3.26 (br t, J = 11.25 Hz, 1H), 2.32 (br d, J = 3.84 Hz, 1H), 2.01 (d, J = 7.05 Hz, 4H) | B | SFC: Chiralpak IC, 20% methanol w/0.2% DEA |
| 299 | 500 MHz DMSO-d$_6$ | 9.07 (d, J = 1.55 Hz, 1H), 8.36-8.52 (m, 4H), 7.84 (d, J = 8.19 Hz, 1H), 7.63 (d, J = 7.98 Hz, 1H), 7.28-7.39 (m, 1H), 7.21 (br d, J = 3.63 Hz, 2H), 5.90 (br dd, J = 4.77, 10.47 Hz, 1H), 4.02 (br d, J = 14.10 Hz, 1H), 3.89 (br s, 1H), 3.59-3.81 (m, 1H), 3.33-3.54 (m, 2H), 3.10-3.32 (m, 2H), 2.56 (br dd, J = 7.20, 13.73 Hz, 1H), 2.31 (qd, J = 7.03, 10.63 Hz, 1H), 2.08 (br s, 1H), 1.96-2.05 (m, 1H), 1.74 (br d, J = 8.60 Hz, 1H), 1.60 (br d, J = 4.35 Hz, 1H), 0.59 (br t, J = 7.15 Hz, 3H) | B | SFC: Chiralpak IC, 25% methanol w/0.2% DEA |
| 300 | 500 MHz DMSO-d$_6$ | 9.06 (d, J = 1.56 Hz, 1H), 8.51 (br s, 3H), 8.38-8.48 (m, 1H), 7.79 (br d, J = 8.40 Hz, 1H), 7.61 (d, J = 8.09 Hz, 1H), 7.26-7.34 (m, 1H), 7.13-7.22 (m, 2H), 5.71 (br dd, J = 5.65, 9.80 Hz, 1H), 3.67-3.78 (m, 1H), 3.42-3.50 (m, 1H), 3.16 (s, 1H), 3.10 (br s, 1H), 2.55-2.69 (m, 1H), 2.26-2.45 (m, 2H), 1.98-2.12 (m, | B | SFC: Chiralpak IC, 25% methanol w/0.2% DEA |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 1H), 1.86 (br s, 2H), 1.65 (br s, 1H), 1.10-1.31 (m, 1H), 0.64-0.71 (m, 3H). | | |
| 301 | 500 MHz DMSO-d$_6$ | 8.87 (s, 2H), 8.40 (br s, 2H), 7.53 (dd, J = 7.43, 11.02 Hz, 1H), 7.39 (t, J = 8.98 Hz, 1H), 5.50-5.60 (m, 2H), 4.72-4.84 (m, 1H), 3.62-3.75 (m, 1H), 3.42-3.59 (m, 1H), 3.17-3.29 (m, 1H), 2.95-3.08 (m, 2H), 2.13-2.20 (m, 1H), 1.73-1.82 (m, 1H) | — | — |
| 302 | 500 MHz DMSO-d$_6$ | 7.85 (s, 1H), 7.77 (d, J = 7.71 Hz, 1H), 7.49-7.56 (m, 2H), 7.44 (d, J = 8.32 Hz, 1H), 7.20 (t, J = 8.97 Hz, 1H), 5.83 (q, J = 7.08 Hz, 1H), 4.36-4.46 (m, 1H), 4.03-4.16 (m, 1H), 3.35-3.39 (m, 1H), 3.14-3.19 (m, 1H), 2.99-3.13 (m, 1H), 2.78-2.92 (m, 1H), 2.08-2.20 (m, 1H), 1.76-1.94 (m, 4H) | — | — |
| 303 | 500 MHz DMSO-d$_6$ | 8.88 (s, 2H), 7.50 (dd, J = 7.43, 11.09 Hz, 1H), 7.38 (t, J = 8.94 Hz, 1H), 5.49-5.58 (m, 2H), 4.45-4.54 (dt, J = 4.55, 8.66 Hz, 1H), 3.43-3.61 (m, 1H), 3.38-3.42 (m, 1H), 3.05-3.24 (m, 1H), 2.95-3.03 (m, 1H), 2.86 (dd, J = 9.19, 12.61 Hz, 1H), 1.98-2.11 (m, 1H), 1.66-1.76 (m, 1H) | — | — |
| 304 | 500 MHz DMSO-d$_6$ | 8.50 (d, J = 2.88 Hz, 1H), 7.73 (dt, J = 2.96, 8.72 Hz, 1H), 7.48 (dd, J = 7.47, 11.21 Hz, 1H), 7.30-7.38 (m, 2H), 5.36-5.43 (m, 2H), 4.65-4.82 (m, 1H), 63.16-3.29 (m, 2H), 3.04-3.14 (m, 1H), 2.88-3.00 (m, 2H), 1.94-2.01 (m, 1H), 1.80-1.92 (m, 1H). | — | — |
| 305 | 500 MHz DMSO-d$_6$ | 8.88 (s, 2H), 7.65 (s, 1H), 7.58 (d, J = 8.43 Hz, 1H), 7.41 (dd, J = 1.25, 8.33 Hz, 1H), 5.59-5.67 (m, 2H), 4.66-4.73 (m, 1H), 3.24-3.30 (m, 2H), 3.07-3.18 (m, 1H), 2.83-2.99 (m, 2H), 1.92-2.00 (m, 1H), 1.75-1.90 (m, 1H). | B | SFC: Chiralpak AD-H, 25% methanol |
| 306 | 500 MHz DMSO-d$_6$ | 8.88 (s, 2H), 7.75 (s, 1H), 7.36 (s, 2H), 5.55-5.64 (m, 2H), 4.70-4.76-4.81 (m, 1H), 3.24-3.31 (m, 2H), 3.08-3.18 (m, 1H), 2.86-3.00 (m, 2H), 1.93-2.03 (m, 1H), 1.76-1.92 (m, 1H). | B | SFC: Chiralpak AD-H, 25% methanol |
| 307 | 500 MHz DMSO-d$_6$ | 8.46-8.51 (m, 1H), 7.74 (t, J = 8.73 Hz, 1H), 7.51 (t, J = 9.21 Hz, 1H), 7.41 (d, J = 8.81 Hz, 1H), 7.34 (t, J = 9.19 Hz, 1H), 5.40-5.47 (m, 2H), 3.50 (br d, J = 12.46 Hz, 1H), 3.15-3.23 (m, 1H), 3.10 (td, J = 4.45, 16.87 Hz, 1H), 2.97-3.02 (m, 1H), 2.52-2.59 (m, 1H), 2.18-2.29 (m, 1H), 1.98-2.11 (m, 1H). | — | — |
| 308 | 500 MHz DMSO-d$_6$ | 7.63 (s, 1H), 7.56 (d, J = 8.25 Hz, 1H), 7.41 (dd, J = 1.28, 8.29 Hz, 1H), 4.76-4.89 (m, 3H), 4.26-4.33 (m, 2H), 3.96 (t, J = 7.75 Hz, 2H), 3.15-3.29 (m, 2H), 2.97-3.13 (m, 2H), 2.30 (td, J = 7.66, 15.43 Hz, 2H), 1.90-2.09 (m, 1H) | B | SFC: Chiralpak IC, 15% methanol. |
| 309 | 500 MHz DMSO-d$_6$ | 7.73 (s, 1H), 7.41 (s, 2H), 4.75-4.88 (m, 3H), 4.24-4.34 (m, 2H), 3.95 (t, J = 7.71 Hz, 2H), 3.14-3.28 (m, 3H), 2.98-3.12 (m, 2H), 2.29 (td, J = 7.69, 15.45 Hz, 2H), 1.91-2.09 (m, 2H) | B | SFC: Chiralpak IC, 15% methanol. |
| 310 | 500 MHz DMSO-d$_6$ | 7.45 (dd, J = 7.47, 11.13 Hz, 1H), 7.37 (dd, J = 7.32, 10.74 Hz, 1H), 4.77-4.86 (m, 2H), 4.32-4.46 (m, 1H), 3.59-3.67 (m, 2H), 2.94-3.12 (m, 2H), 2.78 (dd, J = 8.29, 12.57 Hz, 1H), 2.00-2.13 (m, 1H), 1.84-1.94 (m, 3H), 1.71-1.84 (m, 4H), 1.35 (d, J = 2.96 Hz, 6H). | — | — |
| 311 | 500 MHz MeOD | 8.86 (s, 1H), 8.14-8.20 (m, 1H), 7.48 (br dd, J = 5.06, 8.69 Hz, 1H), 7.43 (br d, J = 8.30 Hz, 1H), 6.93-7.01 (m, 2H), 5.46-5.58 (m, 2H), 3.94-4.01 (m, 1H), 3.34-3.48 (m, 3H), 3.20-3.26 (m, 1H), 3.09 (br dd, J = 5.32, 12.07 Hz, 1H), 1.87 (q, J = 5.71 Hz, 2H) | B | Cel2, 20% MeOH, 0.2% DEA, peak 1 |
| 312 | 500 MHz MeOD | 8.86 (s, 1H), 8.16 (br dd, J = 1.95, 8.17 Hz, 1H), 7.42 (br d, J = 8.56 Hz, 1H), 7.21 (br dd, J = 2.34, 9.34 Hz, 1H), 7.11 (br dd, J = 4.54, 8.69 Hz, 1H), 6.86-6.94 (m, 1H), 5.48-5.58 (m, 2H), 3.95-4.06 (m, 1H), 3.35-3.52 (m, 3H), 3.11-3.20 (m, 1H), 1.81-1.92 (m, 2H) | B | Cel2, 20% MeOH, 0.2% DEA, peak 2 |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 313 | 400 MHz d$_6$-DMSO | 8.45 (br s, 2H), 7.89 (d, J = 8.40 Hz, 2H), 7.55-7.64 (m, 3H), 7.31 (t, J = 7.62 Hz, 1H), 7.18 (t, J = 7.62 Hz, 1H), 7.08 (d, J = 8.19 Hz, 1H), 5.98 (q, J = 6.98 Hz, 1H), 3.64-3.74 (m, 2H), 3.44-3.51 (m, 1H), 3.31-3.38 (m, 1H), 3.11-3.20 (m, 1H), 1.96-2.05 (m, 2H), 1.93 (d, J = 7.05 Hz, 3H), 1.64-1.79 (m, 2H) | B | Chiralpak IC, 30% IPA Peak 1 |
| 314 | 400 MHz d$_6$-DMSO | 8.40 (br s, 3H), 7.85 (d, J = 8.50 Hz, 2H), 7.55-7.61 (m, 1H), 7.52 (d, J = 8.29 Hz, 2H), 7.25 (br t, J = 7.62 Hz, 1H), 7.04-7.15 (m, 2H), 5.89 (q, J = 7.05 Hz, 1H), 3.72-3.78 (m, 2H), 3.31-3.38 (m, 2H), 3.13-3.22 (m, 1H), 2.02-2.08 (m, 1H), 2.00 (d, J = 7.05 Hz, 3H), 1.89-1.97 (m, 1H), 1.62-1.79 (m, 2H) | B | Chiralpak IC, 30% IPA Peak 2 |
| 315 | 400 MHz d$_6$-DMSO | 8.43 (br s, 3H), 7.97 (dd, J = 1.14, 10.06 Hz, 1H), 7.70 (d, J = 7.59 Hz, 1H), 7.58 (d, J = 7.88 Hz, 1H), 7.39-7.48 (m, 1H), 7.23-7.38 (m, 3H), 5.52-5.65 (m, 2H), 3.79 (br d, J = 10.16 Hz, 1H), 3.34-3.51 (m, 3H), 3.11-3.22 (m, 1H), 1.95-2.04 (m, 1H), 1.83-1.95 (m, 1H), 1.58-1.75 (m, 2H) | — | — |
| 316 | 400 MHz d$_6$-DMSO | 8.55 (br s, 3H), 7.60 (d, J = 7.77 Hz, 1H), 7.45 (d, J = 7.92 Hz, 2H), 7.27-7.39 (m, 5H), 5.47-5.62 (m, 2H), 3.92 (br d, J = 10.37 Hz, 1H), 3.64-3.74 (m, 1H), 3.41-3.53 (m, 2H), 3.18-3.29 (m, 1H), 1.96-2.05 (m, 1H), 1.86-1.96 (m, 1H), 1.57-1.76 (m, 2H) | — | — |
| 317 | 400 MHz d$_6$-DMSO | 8.67 (br s, 3H), 7.87 (d, J = 8.40 Hz, 2H), 7.51-7.62 (m, 3H), 7.26 (t, J = 7.00 Hz, 1H), 7.04-7.17 (m, 2H), 5.94-6.01 (m, 1H), 5.10-5.30 (m, 1H), 3.84-3.97 (m, 1H), 3.57-3.68 (m, 2H), 3.23-3.37 (m, 2H), 2.18-2.29 (m, 1H), 2.07-2.18 (m, 1H), 1.95 (d, J = 7.05 Hz, 3H) | B | Chiralpak IC, 25% IPA Peak 1 |
| 318 | 400 MHz d$_6$-DMSO | 8.85 (br s, 3H), 7.85 (d, J = 8.40 Hz, 2H), 7.52-7.63 (m, 3H), 7.22-7.35 (m, 1H), 7.06-7.18 (m, 2H), 5.94 (q, J = 7.05 Hz, 1H), 5.13-5.34 (m, 1H), 3.83-4.00 (m, 1H), 3.72-3.80 (m, 1H), 3.51-3.61 (m, 1H), 3.40 (br s, 2H), 2.24 (br d, J = 2.38 Hz, 2H), 1.99-2.05 (m, 3H) | B | Chiralpak IC, 25% IPA Peak 2 |
| 319 | 400 MHz d$_6$-DMSO | 8.83 (br s, 3H), 7.87 (d, J = 8.40 Hz, 2H), 7.53-7.62 (m, 3H), 7.28 (t, J = 7.06 Hz, 1H), 7.14 (t, J = 7.77 Hz, 1H), 7.05 (d, J = 8.09 Hz, 1H), 5.98 (q, J = 6.88 Hz, 1H), 4.89-5.11 (m, 1H), 3.87 (br d, J = 12.75 Hz, 1H), 3.78 (br d, J = 6.84 Hz, 1H), 3.42-3.61 (m, 2H), 3.18-3.29 (m, 1H), 2.29-2.38 (m, 1H), 1.98-2.07 (m, 1H), 1.95 (d, J = 6.95 Hz, 3H) | B | Chiralpak IC, 25% IPA Peak 1 |
| 320 | 400 MHz d$_6$-DMSO | 8.86 (br s, 3H), 7.85 (d, J = 8.40 Hz, 2H), 7.50-7.61 (m, 3H), 7.25 (t, J = 7.52 Hz, 1H), 7.04-7.15 (m, 2H), 5.94 (q, J = 6.81 Hz, 1H), 4.87-5.09 (m, 1H), 3.91 (br d, J = 12.75 Hz, 1H), 3.79 (br s, 1H), 3.47-3.55 (m, 1H), 3.35-3.44 (m, 1H), 3.22-3.31 (m, 1H), 2.27-2.38 (m, 1H), 2.02-2.08 (m, 1H), 1.99 (d, J = 7.15 Hz, 3H) | B | Chiralpak IC, 25% IPA Peak 2 |
| 321 | 400 MHz d$_6$-DMSO | 8.48 (br s, 3H), 8.21 (d, J = 1.45 Hz, 1H), 7.84 (dd, J = 1.45, 8.09 Hz, 1H), 7.61 (d, J = 7.98 Hz, 1H), 7.31-7.45 (m, 2H), 7.19-7.29 (m, 2H), 5.45-5.60 (m, 2H), 3.73-3.82 (m, 2H), 3.42-3.54 (m, 2H), 3.34 (br d, J = 13.06 Hz, 1H), 3.17 (br t, J = 9.43 Hz, 1H), 1.95-2.06 (m, 1H), 1.83-1.94 (m, 1H), 1.59-1.78 (m, 2H) | — | — |
| 322 | 600 MHz DMSO-d$_6$ | 7.91 (d, J = 8.49 Hz, 2H), 7.48-7.56 (m, 2H), 7.19 (dd, J = 7.32, 10.90 Hz, 1H), 5.88 (q, J = 7.06 Hz, 1H), 4.32-4.48 (m, 1H), 3.35-3.41 (m, 1H), 3.24-3.28 (m, 1H), 3.17-3.22 (m, 3H), 2.99-3.09 (m, 1H), 2.87 (dd, J = 8.52, 12.50 Hz, 1H), 2.51-2.57 (m, 1H), 2.08-2.19 (m, 1H), 1.98 (br d, J = 7.08 Hz, 1H), 1.74-1.90 (m, 1H) | B | SFC: Chiralcel OJ-H, 15% methanol. |
| 323 | 600 MHz DMSO-d$_6$ | 7.90 (d, J = 7.91 Hz, 2H), 7.47-7.56 (m, 2H), 7.20 (dd, J = 7.28, 10.86 Hz, 1H), 5.88 (q, J = 7.06 Hz, 1H), 4.32-4.41 (m, 1H), 3.36-3.43 (m, 1H), 3.16- | B | SFC: Chiralcel OJ-H, 15% |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
|  |  | 3.27 (m, 1H), 2.99-3.13 (m, 1H), 2.80 (dd, J = 8.56, 12.46 Hz, 1H), 2.51-2.62 (m, 1H), 2.08-2.26 (m, 1H), 1.93 (d, J = 7.16 Hz, 3H), 1.79-1.91 (m, 1H) |  | methanol. |
| 324 | 600 MHz DMSO-$d_6$ | 7.74 (d, J = 7.73 Hz, 1H), 7.42-7.52 (m, 3H), 7.33-7.41 (m, 2H), 5.87 (q, J = 7.14 Hz, 1H), 4.31-4.42 (m, 1H), 3.20-3.27 (m, 1H), 3.17 (s, 1H), 2.91-3.00 (m, 2H), 2.78 (dd, J = 8.88, 12.30 Hz, 1H), 1.99-2.14 (m, 1H), 1.94 (d, J = 7.24 Hz, 4H), 1.69-1.87 (m, 1H) | B | SFC: Chiralpak AD-H, 10% methanol |
| 325 | 600 MHz DMSO-$d_6$ | 7.72 (d, J = 8.01 Hz, 1H), 7.51 (dd, J = 7.67, 11.09 Hz, 1H), 7.41-7.46 (m, 2H), 7.32-7.40 (m, 2H), 5.87 (q, J = 7.11 Hz, 1H), 4.31-4.41 (m, 1H), 3.25-3.40 (m, 1H), 3.17 (s, 1H), 3.11 (br d, J = 12.61 Hz, 1H), 2.92-3.07 (m, 1H), 2.74 (dd, J = 8.99, 12.34 Hz, 1H), 2.01-2.17 (m, 1H), 1.94 (d, J = 7.16 Hz, 4H), 1.71-1.89 (m, 1H) | B | SFC: Chiralpak AD-H, 10% methanol. |
| 326 | 600 MHz DMSO-$d_6$ | 7.52 (dd, J = 7.63, 11.06 Hz, 1H), 7.33-7.39 (m, 3H), 7.19 (dd, J = 7.28, 10.94 Hz, 1H), 7.08-7.15 (m, 1H), 5.74-5.82 (m, 1H), 4.34-4.45 (m, 1H), 3.35-3.42 (m, 1H), 2.97-3.08 (m, 2H), 2.86 (dd, J = 8.68, 12.42 Hz, 1H), 2.05-2.20 (m, 1H), 1.78-1.96 (m, 5H) | B | SFC: Chiralpak AD-H, 10% methanol. |
| 327 | 600 MHz DMSO-$d_6$ | 7.52 (dd, J = 7.59, 11.09 Hz, 1H), 7.34-7.38 (m, 3H), 7.19 (dd, J = 7.32, 10.90 Hz, 1H), 7.08-7.16 (m, 1H), 5.73-5.82 (m, 1H), 4.35-4.45 (m, 1H), 3.34-3.43 (m, 2H), 3.21-3.28 (m, 1H), 3.00-3.10 (m, 1H), 2.81 (dd, J = 8.52, 12.42 Hz, 1H), 2.07-2.21 (m, 1H), 1.78-1.96 (m, 5H) | B | SFC: Chiralpak AD-H, 10% methanol. |
| 328 | 600 MHz DMSO-$d_6$ | 7.77 (s, 1H), 7.41-7.54 (m, 4H), 5.83 (q, J = 7.14 Hz, 1H), 4.28-4.40 (m, 1H), 3.10 (br d, J = 12.38 Hz, 1H), 2.90-3.04 (m, 2H), 2.72 (dd, J = 8.87, 12.30 Hz, 1H), 2.00-2.16 (m, 1H), 1.95 (d, J = 7.16 Hz, 3H), 1.68-1.87 (m, 2H) | B | SFC: Chiralcel OD-H column, 10% isopropanol. |
| 329 | 600 MHz DMSO-$d_6$ | 7.79 (s, 1H), 7.42-7.54 (m, 4H), 5.84 (q, J = 7.14 Hz, 1H), 4.27-4.41 (m, 1H), 3.16-3.27 (m, 1H), 2.87-3.00 (m, 2H), 2.78 (dd, J = 9.03, 12.38 Hz, 1H), 2.00-2.13 (m, 1H), 1.95 (d, J = 7.16 Hz, 3H), 1.69-1.86 (m, 2H) | B | SFC: Chiralcel OD-H column, 10% isopropanol. |
| 330 | 600 MHz DMSO-$d_6$ | 7.75-7.80 (m, 1H), 7.48 (dd, J = 7.63, 11.06 Hz, 1H), 7.26 (dd, J = 7.28, 11.02 Hz, 1H), 7.14-7.20 (m, 2H), 5.89 (q, J = 6.95 Hz, 1H), 4.40-4.47 (m, 1H), 4.33-4.39 (m, 1H), 3.27-3.30 (m, 2H), 2.94-3.01 (m, 2H), 2.86 (dd, J = 8.95, 12.46 Hz, 1H), 2.02-2.14 (m, 1H), 1.85-2.00 (m, 5H) | B | SFC: 15 Chiralpak AD-H, 15% isopropanol |
| 331 | 600 MHz DMSO-$d_6$ | 7.74-7.82 (m, 1H), 7.48 (dd, J = 7.67, 11.09 Hz, 1H), 7.26 (dd, J = 7.32, 11.05 Hz, 1H), 7.14-7.20 (m, 2H), 5.88 (q, J = 7.11 Hz, 1H), 4.34-4.48 (m, 1H), 3.28-3.39 (m, 1H), 3.23 (br dd, J = 5.41, 7.43 Hz, 2H), 3.03-3.13 (m, 1H), 2.78 (dd, J = 8.37, 12.42 Hz, 1H), 2.07-2.22 (m, 1H), 1.94 (d, J = 7.16 Hz, 3H), 1.64-1.86 (m, 1H) | B | SFC: 15 Chiralpak AD-H, 15% isopropanol |
| 332 | 600 MHz DMSO-$d_6$ | 7.57 (s, 1H), 7.59 (d, J = 11.19 Hz, 1H), 7.52 (dd, J = 7.59, 11.09 Hz, 1H), 7.26 (dd, J = 7.28, 10.94 Hz, 1H), 7.10 (d, J = 8.54 Hz, 1H), 5.77 (q, J = 7.16 Hz, 1H), 4.32-4.45 (m, 1H), 3.24-3.38 (m, 1H), 2.96-3.09 (m, 2H), 2.85 (dd, J = 8.56, 12.46 Hz, 1H), 2.05-2.21 (m, 1H), 1.77-1.94 (m, 5H) | B | SFC: Chiralpak AD-H 25 cm column, 20% isopropanol |
| 333 | 600 MHz DMSO-$d_6$ | 7.51-7.61 (m, 3H), 7.26 (t, J = 9.06 Hz, 1H), 7.10 (d, J = 8.29 Hz, 1H), 5.74-5.81 (m, 1H), 4.31-4.45 (m, 1H), 3.21-3.28 (m, 1H), 2.98-3.12 (m, 2H), 2.80 (dd, J = 8.49, 12.46 Hz, 1H), 2.09-2.20 (m, 1H), 1.78-1.93 (m, 5H) | B | SFC: Chiralpak AD-H 25 cm column, 20% isopropanol |
| 334 | 600 MHz DMSO-$d_6$ | 7.62 (ddd, J = 3.15, 5.99, 9.15 Hz, 1H), 7.48 (dd, J = 7.59, 11.09 Hz, 1H), 7.35 (dd, J = 7.32, 11.05 Hz, 1H), 7.13-7.25 (m, 2H), 5.91 (q, J = 7.14 Hz, 1H), 4.32-4.44 (m, 1H), 3.25-3.29 (m, 1H), 2.92-3.03 (m, 2H), 2.87 (dd, J = 8.84, 12.26 Hz, 1H), 1.99-2.14 (m, 1H), 1.86-1.96 (m, 5H), 1.83 (br s, 1H) | B | SFC: Chiralpak AD-H, 15% isopropanol. |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 335 | 600 MHz DMSO-d$_6$ | 7.72 (d, J = 8.17 Hz, 2H), 7.53 (dd, J = 7.55, 10.90 Hz, 1H), 7.45 (br d, J = 7.08 Hz, 2H), 7.17 (t, J = 8.84 Hz, 1H), 5.87 (q, J = 6.95 Hz, 1H), 4.31-4.40 (m, 1H), 3.35-3.41 (m, 2H), 3.21-3.26 (m, 1H), 3.17 (s, 1H), 2.97-3.10 (m, 2H), 2.77-2.94 (m, 1H), 2.02-2.18 (m, 1H), 1.93 (d, J = 7.16 Hz, 3H), 1.72-1.90 (m, 3H) | B | SFC: Chiralpak AD-H, 15% isopropanol. |
| 336 | 600 MHz DMSO-d$_6$ | 7.72 (d, J = 8.17 Hz, 2H), 7.53 (dd, J = 7.55, 10.90 Hz, 1H), 7.45 (br d, J = 7.08 Hz, 2H), 7.17 (t, J = 8.84 Hz, 1H), 5.87 (q, J = 6.95 Hz, 1H), 4.31-4.45 (m, 1H), 3.21-3.26 (m, 1H), 3.17 (s, 1H), 2.97-3.10 (m, 1H), 2.77-2.94 (m, 1H), 2.02-2.18 (m, 1H), 1.93 (d, J = 7.16 Hz, 3H), 1.72-1.90 (m, 2H) | B | SFC: Regis Whelk-O s, s, 15% methanol. |
| 337 | 600 MHz DMSO-d$_6$ | 7.51 (dd, J = 7.59, 10.78 Hz, 1H), 7.32-7.39 (m, 4H), 7.15 (dd, J = 7.32, 10.90 Hz, 1H), 5.81 (q, J = 7.08 Hz, 1H), 4.34-4.45 (m, 1H), 3.22-3.39 (m, 1H), 2.96-3.12 (m, 2H), 2.77-2.94 (m, 1H), 2.07-2.19 (m, 1H), 1.78-1.93 (m, 5H) | B | SFC: Regis Whelk-O s, s, 15% methanol. |
| 338 | 600 MHz DMSO-d$_6$ | 8.87 (s, 2H), 7.48 (dd, J = 7.47, 11.13 Hz, 1H), 7.37 (dd, J = 7.32, 10.74 Hz, 1H), 5.39-5.55 (m, 2H), 4.68-4.77 (m, 1H), 3.14-3.28 (m, 1H), 3.01-3.11 (m, 1H), 2.83-2.94 (m, 2H), 1.88-2.01 (m, 1H), 1.69-1.87 (m, 1H), 1.63 (br s, 1H) | B | — |
| 339 | 600 MHz DMSO-d$_6$ | 8.50 (d, J = 2.88 Hz, 1H), 7.73 (dt, J = 2.96, 8.72 Hz, 1H), 7.48 (dd, J = 7.47, 11.21 Hz, 1H), 7.30-7.38 (m, 2H), 5.36-5.43 (m, 2H), 4.75-4.82 (m, 1H), 4.65-4.74 (m, 1H), 3.16-3.29 (m, 1H), 3.04-3.14 (m, 1H), 2.88-3.00 (m, 2H), 1.94-2.01 (m, 1H), 1.80-1.92 (m, 1H), 1.59 (br s, 1H) | B | — |
| 340 | 600 MHz DMSO-d$_6$ | 8.12 (d, J = 2.26 Hz, 1H), 7.71 (dd, J = 2.26, 8.49 Hz, 1H), 7.54 (dd, J = 7.47, 11.06 Hz, 1H), 7.36 (t, J = 8.91 Hz, 1H), 6.97 (d, J = 8.56 Hz, 1H), 5.45-5.54 (m, 3H), 4.36-4.43 (m, 1H), 4.28-4.35 (m, 1H), 3.27-3.35 (m, 1H), 3.17 (s, 1H), 2.99-3.07 (m, 1H), 2.86-2.98 (m, 1H), 2.76 (dd, J = 8.68, 12.57 Hz, 1H), 2.01-2.17 (m, 1H), 1.66-1.82 (m, 1H) | B | — |
| 341 | 600 MHz DMSO-d$_6$ | 8.12 (d, J = 2.26 Hz, 1H), 7.71 (dd, J = 2.26, 8.49 Hz, 1H), 7.54 (dd, J = 7.47, 11.06 Hz, 1H), 7.36 (t, J = 8.91 Hz, 1H), 6.97 (d, J = 8.56 Hz, 1H), 5.45-5.54 (m, 2H), 4.28-4.43 (m, 1H), 3.27-3.35 (m, 1H), 3.17 (s, 1H), 2.99-3.07 (m, 1H), 2.86-2.98 (m, 1H), 2.76 (dd, J = 8.68, 12.57 Hz, 1H), 2.01-2.17 (m, 1H), 1.66-1.82 (m, 1H) | B | — |
| 342 | 600 MHz DMSO-d$_6$ | 7.80 (s, 1H), 7.65 (dd, J = 1.44, 7.98 Hz, 1H), 7.49-7.57 (m, 1H), 7.38 (s, 1H), 7.32, (dd, J = 7.24, 10.67 Hz, 1H), 6.97 (d, J = 8.02 Hz, 1H), 5.33-5.40 (m, 2H), 4.29-4.42 (m, 1H), 3.36-3.45 (m, 1H), 3.16-3.28 (m, 1H), 2.98-3.05 (m, 1H), 2.86-2.95 (m, 1H), 2.76 (dd, J = 8.72, 12.61 Hz, 1H), 1.98-2.10 (m, 1H), 1.65-1.79 (m, 1H) | B | — |
| 343 | 600 MHz DMSO-d$_6$ | 7.51-7.59 (m, 2H), 7.44 (dd, J = 2.57, 8.56 Hz, 1H), 7.37 (dd, J = 7.28, 10.70 Hz, 1H), 6.89 (d, J = 2.49 Hz, 1H), 5.31-5.38 (m, 2H), 4.29-4.41 (m, 1H), 3.35-3.46 (m, 1H), 3.25-3.29 (m, 1H), 2.99-3.05 (m, 1H), 2.85-2.96 (m, 1H), 2.77 (dd, J = 8.64, 12.53 Hz, 1H), 1.91-2.09 (m, 1H), 1.65-1.76 (m, 1H) | B | — |
| 344 | 600 MHz DMSO-d$_6$ | 7.48-7.56 (m, 3H), 7.39 (dd, J = 7.32, 10.67 Hz, 1H), 7.24 (d, J = 8.25 Hz, 2H), 5.33-5.42 (m, 2H), 4.31-4.43 (m, 1H), 3.43 (ddd, J = 3.39, 7.07, 8.86 Hz, 1H), 3.36-3.39 (m, 1H), 3.17 (d, J = 4.75 Hz, 1H), 2.92-3.08 (m, 1H), 2.81 (dd, J = 8.56, 12.61 Hz, 1H), 1.98-2.11 (m, 1H), 1.93 (t, J = 18.84 Hz, 3H), 1.63-1.87 (m, 1H) | B | — |
| 345 | 600 MHz DMSO-d$_6$ | 7.74 (s, 1H), 7.52-7.60 (m, 2H), 7.22 (dd, J = 7.36, 10.63 Hz, 1H), 6.68 (d, J = 8.02 Hz, 1H), 5.31-5.40 (m, 2H), 4.09-4.41 (m, 1H), 3.36-3.45 (m, 1H), 3.15-3.24 (m, 1H), 3.00-3.07 (m, | B | — |

TABLE 6-continued

Characterization data for compounds made following schemes 9-10
The column "Separation Stage" indicates after which
process step regioisomers formed due to asymmetric
benzimidazole substitution at R¹ in Scheme
10 were separated during the preparation of the tabulated
final compound. (I = after preparation of the
N-aralkyl-2-piperidinyl-benzimidazole intermediate
in the first step of Scheme 10 (where at least one R¹ is not
hydrogen); B = prior to boc deprotection; or F = final compound).

| Ex. # | Freq., Solvent | ¹HNMR Data (δ ppm) | Separation Stage | SFC Isomer Separation Conditions |
|---|---|---|---|---|
| | | 1H), 2.87-2.98 (m, 1H), 2.78 (dd, J = 8.33, 12.61 Hz, 1H), 2.34-2.39 (m, 3H), 1.98-2.10 (m, 1H), 1.61-1.79 (m, 1H) | | |
| 346 | 600 MHz DMSO-d₆ | 8.16 (d, J = 1.63 Hz, 1H), 7.75 (dd, J = 1.60, 8.06 Hz, 1H), 7.55 (dd, J = 7.43, 11.09 Hz, 1H), 7.37 (dd, J = 7.32, 10.67 Hz, 1H), 6.89 (d, J = 8.10 Hz, 1H), 5.38-5.46 (m, 2H), 4.29-4.40 (m, 1H), 3.26 (br s, 2H), 2.98-3.06 (m, 1H), 2.83-2.97 (m, 1H), 2.75 (dd, J = 8.60, 12.57 Hz, 1H), 1.98-2.16 (m, 1H), 1.62-1.79 (m, 1H) | B | — |
| 347 | 600 MHz DMSO-d₆ | 8.12 (d, J = 2.26 Hz, 1H), 7.71 (dd, J = 2.26, 8.49 Hz, 1H), 7.54 (dd, J = 7.44, 11.09 Hz, 1H), 7.36 (dd, J = 7.28, 10.70 Hz, 1H), 6.97 (d, J = 8.56 Hz, 1H), 5.46-5.53 (m, 2H), 4.24-4.43 (m, 1H), 3.09-3.24 (m, 2H), 2.99-3.06 (m, 1H), 2.83-2.98 (m, 1H), 2.76 (dd, J = 8.60, 12.57 Hz, 1H), 2.02-2.10 (m, 1H), 1.67-1.86 (m, 1H) | B | — |
| 348 | 600 MHz DMSO-d₆ | 7.51 (dd, J = 7.47, 11.21 Hz, 1H), 7.35-7.42 (m, 1H), 7.15-7.28 (m, 4H), 6.86 (d, J = 7.65 Hz, 1H), 5.30 (s, 2H), 4.19-4.43 (m, 1H), 3.37-3.49 (m, 2H), 2.98-3.09 (m, 1H), 2.89-2.97 (m, 1H), 2.78 (dd, J = 8.80, 12.61 Hz, 1H), 1.95-2.09 (m, 1H), 1.65-1.83 (m, 1H) | B | — |
| 349 | 600 MHz DMSO-d₆ | 7.44-7.52 (m, 3H), 7.36 (t, J = 8.95 Hz, 1H), 7.09 (ddd, J = 2.18, 4.63, 8.52 Hz, 1H), 5.28-5.35 (m, 2H), 4.27-4.47 (m, 1H), 3.38-3.47 (m, 1H), 3.09-3.23 (m, 1H), 2.93-3.07 (m, 2H), 2.80 (dd, J = 8.60, 12.57 Hz, 1H), 2.00-2.14 (m, 1H), 1.69-1.88 (m, 1H) | B | — |
| 350 | 600 MHz DMSO-d₆ | 7.49 (dd, J = 7.43, 11.17 Hz, 1H), 7.25 (dd, J = 7.32, 10.67 Hz, 1H), 7.14 (d, J = 1.95 Hz, 1H), 6.93 (dd, J = 1.95, 8.17 Hz, 1H), 6.71 (d, J = 8.17 Hz, 1H), 5.18 (s, 2H), 4.24-4.43 (m, 1H), 3.84 (s, 3H), 3.36-3.48 (m, 1H), 3.11-3.28 (m, 1H), 2.97-3.06 (m, 1H), 2.89-2.97 (m, 1H), 2.77 (dd, J = 8.80, 12.61 Hz, 1H), 1.96-2.09 (m, 1H), 1.64-1.82, (m, 1H) | B | — |
| 351 | 600 MHz DMSO-d₆ | 7.50 (dd, J = 7.47, 11.13 Hz, 1H), 7.39 (dd, J = 7.24, 10.74 Hz, 1H), 7.29 (t, J = 9.79 Hz, 1H), 7.00-7.08 (m, 2H), 5.34 (s, 2H), 4.29-4.45 (m, 1H), 3.37-3.50 (m, 2H), 2.99-3.07 (m, 1H), 2.90-2.98 (m, 1H), 2.78 (dd, J = 8.64, 12.53 Hz, 1H), 2.04-2.12 (m, 1H), 1.69-1.87 (m, 1H) | B | — |
| 352 | 600 MHz DMSO-d₆ | 7.84 (d, J = 7.55 Hz, 1H), 7.51-7.61 (m, 3H), 7.30 (t, J = 8.69 Hz, 1H), 6.75 (d, J = 7.71 Hz, 1H), 5.45 (s, 2H), 4.22-4.39 (m, 1H), 3.34-3.42 (m, 1H), 3.22-3.28 (m, 1H), 2.95-3.09 (m, 1H), 2.83-2.92 (m, 1H), 2.62-2.78 (m, 1H), 1.89-2.03 (m, 1H), 1.58-1.74 (m, 1H) | B | — |
| 353 | 600 MHz DMSO-d₆ | 7.91 (dd, J = 1.01, 7.71 Hz, 1H), 7.64 (dt, J = 1.21, 7.73 Hz, 1H), 7.49-7.56 (m, 2H), 7.33 (dd, J = 7.28, 10.70 Hz, 1H), 6.98 (d, J = 7.86 Hz, 1H), 5.49-5.55 (m, 2H), 4.26-4.42 (m, 1H), 3.36-3.46 (m, 1H), 3.09-3.26 (m, 1H), 2.99-3.07 (m, 1H), 2.86-2.96 (m, 1H), 2.77 (dd, J = 8.68, 12.57 Hz, 1H), 1.92-2.09 (m, 1H), 1.64-1.82 (m, 1H) | B | — |
| 354 | 600 MHz DMSO-d₆ | 7.54 (s, 1H), 7.51-7.53 (m, 1H), 7.35 (dt, J = 1.56, 7.67 Hz, 1H), 7.23-7.31 (m, 2H), 6.78-6.82 (m, 1H), 5.32-5.40 (m, 2H), 4.24-4.44 (m, 1H), 3.36-3.51 (m, 1H), 2.99-3.14 (m, 1H), 2.87-2.96 (m, 1H), 2.77 (dd, J = 8.60, 12.57 Hz, 1H), 2.00-2.07 (m, 1H), 1.85-1.98 (m, 1H), 1.65-1.78 (m, 1H) | B | — |
| 355 | 600 MHz DMSO-d₆ | 7.50-7.57 (m, 2H), 7.29 (t, J = 9.13 Hz, 1H), 7.17 (dt, J = 2.65, 8.49 Hz, 1H), 6.86-6.90 (m, 1H), 5.29-5.36 (m, 2H), 4.19-4.46 (m, 1H), 3.35-3.48 (m, 1H), 3.26-3.29 (m, 1H), 2.99-3.14 (m, | B | — |

TABLE 6-continued

Characterization data for compounds made following schemes 9-10
The column "Separation Stage" indicates after which
process step regioisomers formed due to asymmetric
benzimidazole substitution at R¹ in Scheme
10 were separated during the preparation of the tabulated
final compound. (I = after preparation of the
N-aralkyl-2-piperidinyl-benzimidazole intermediate
in the first step of Scheme 10 (where at least one R¹ is not
hydrogen); B = prior to boc deprotection; or F = final compound).

| Ex. # | Freq., Solvent | ¹HNMR Data (δ ppm) | Separation Stage | SFC Isomer Separation Conditions |
|---|---|---|---|---|
| | | 1H), 2.87-2.95 (m, 1H), 2.77 (dd, J = 8.72, 12.61 Hz, 1H), 2.01-2.09 (m, 1H), 1.63-1.79 (m, 1H) | | |
| 356 | 600 MHz DMSO-d₆ | 7.76 (dd, J = 2.65, 9.03 Hz, 1H), 7.57 (dd, J = 7.47, 11.13 Hz, 1H), 7.46 (dt, J = 2.65, 8.45 Hz, 1H), 7.33 (dd, J = 7.28, 10.63 Hz, 1H), 6.81 (dd, J = 5.29, 8.64 Hz, 1H), 5.38-5.45 (m, 2H), 4.25-4.41 (m, 1H), 3.34-3.49 (m, 1H), 3.23-3.29 (m, 1H), 2.95-3.01 (m, 1H), 2.83-2.91 (m, 1H), 2.74 (dd, J = 8.91, 12.57 Hz, 1H), 1.97-2.04 (m, 1H), 1.62-1.80 (m, 1H) | B | — |
| 357 | 600 MHz DMSO-d₆ | 7.36-7.52 (m, 3H), 7.29 (t, J = 9.45 Hz, 1H), 6.92-6.98 (m, 1H), 5.27-5.34 (m, 2H), 4.26-4.48 (m, 1H), 3.38-3.49 (m, 1H), 3.36-3.38 (m, 1H), 2.93-3.07 (m, 2H), 2.81 (dd, J = 8.60, 12.57 Hz, 1H), 2.05-2.13 (m, 1H), 1.71-1.89 (m, 1H) | B | — |
| 358 | 600 MHz DMSO-d₆ | 7.46-7.54 (m, 2H), 7.39 (dd, J = 7.32, 10.67 Hz, 1H), 7.24 (dd, J = 1.87, 8.33 Hz, 1H), 6.96 (t, J = 8.29 Hz, 1H), 5.35 (s, 2H), 4.27-4.44 (m, 1H), 3.36-3.49 (m, 2H), 3.00-3.17 (m, 1H), 2.89-2.98 (m, 1H), 2.78 (dd, J = 8.68, 12.57 Hz, 1H), 2.02-2.13 (m, 1H), 1.67-1.84 (m, 1H) | B | — |
| 359 | 600 MHz DMSO-d₆ | 7.58 (d, J = 8.33 Hz, 1H), 7.44-7.53 (m, 3H), 7.04 (dd, J = 2.02, 8.33 Hz, 1H), 5.30-5.36 (m, 2H), 4.30-4.46 (m, 1H), 3.38-3.51 (m, 2H), 2.93-3.07 (m, 2H), 2.80 (dd, J = 8.64, 12.61 Hz, 1H), 2.05-2.13 (m, 1H), 1.68-1.86 (m, 1H) | B | — |
| 360 | 600 MHz DMSO-d₆ | ¹H NMR (600 MHz, DMSO-d6) δ 7.55 (t, J = 8.15 Hz, 1H), 7.51 (t, J = 9.00 Hz, 1H), 7.43 (t, J = 8.77 Hz, 1H), 7.26 (dd, J = 1.87, 10.20 Hz, 1H), 6.94 (dd, J = 1.44, 8.29 Hz, 1H), 5.30-5.37 (m, 2H), 4.32-4.46 (m, 1H), 3.38-3,52 (m, 2H), 3.00-3.08 (m, 1H), 2.92-3.00 (m, 1H), 2.80 (dd, J = 8.60, 12.57 Hz, 1H), 1.96-2.13 (m, 1H), 1.69-1.87 (m, 1H) | B | — |
| 361 | 600 MHz DMSO-d₆ | 7.68-7.74 (m, J = 8.17 Hz, 2H), 7.52 (dd, J = 7.43, 11.17 Hz, 1H), 7.41 (dd, J = 7.32, 10.67 Hz, 1H), 7.31-7.36 (m, J = 8.02 Hz, 2H), 5.40-5.47 (m, 2H), 4.31-4.45 (m, 1H), 3.39-3.53 (m, 2H), 3.00-3.07 (m, 1H), 2.91-2.99 (m, 1H), 2.80 (dd, J = 8.60, 12.57 Hz, 1H), 2.03-2.11 (m, 1H), 1.66-1.83 (m, 1H) | B | — |
| 362 | 600 MHz DMSO-d₆ | 7.50 (dd, J = 7.43, 11.17 Hz, 1H), 7.43 (dd, J = 7.32, 10.74 Hz, 1H), 7.34 (d, J = 8.17 Hz, 2H), 7.27 (d, J = 8.06 Hz, 2H), 5.32-5.40 (m, 2H), 4.23-4.50 (m, 1H), 3.39-3.46 (m, 1H), 3.36 (br s, 1H), 2.99-3.11 (m, 1H), 2.91-2.99 (m, 1H), 2.80 (dd, J = 8.68, 12.57 Hz, 1H), 1.99-2.12 (m, 1H), 1.65-1.81 (m, 1H) | B | — |
| 363 | 600 MHz DMSO-d₆ | 7.48-7.58 (m, 3H), 7.38 (dd, J = 7.32, 10.67 Hz, 1H), 7.27 (d, J = 8.10 Hz, 2H), 7.00 (t, J = 55.86 Hz, 1H), 5.35-5.43 (m, 2H), 4.20-4.48 (m, 1H), 3.42 (ddd, J = 3.39, 7.08, 8.91 Hz, 1H), 3.36-3.38 (m, 1H), 2.99-3.08 (m, 1H), 2.91-2.99 (m, 1H), 2.80 (dd, J = 8.60, 12.57 Hz, 1H), 1.98-2.11 (m, 1H), 1.65-1.82 (m, 1H) | B | — |
| 364 | 600 MHz DMSO-d₆ | 7.43-7.52 (m, 3H), 7.27 (br d, J = 8.17 Hz, 1H), 7.19 (s, 1H), 7.11 (d, J = 7.79 Hz, 1H), 5.35-5.43 (m, 2H), 4.31-4.42 (m, 1 H), 3.39-3.47 (m, 1H), 3.36-3.38 (m, 1H), 2.98-3.07 (m, 1H), 2.94 (tdd, J = 4.20, 7.94, 14.40 Hz, 1H), 2.80 (dd, J = 8.68, 12.57 Hz, 1H), 1.69-1.86 (m, 1H) | B | — |
| 365 | 600 MHz DMSO-d₆ | ¹H NMR (600 MHz, DMSO-d₆) δ 7.65 (d, J = 8.23 Hz, 1H), 7.62, (s, 1H), 7.46-7.57 (m, 3H), 7.34 (d, J = 7.71 Hz, 1H), 5.39-5.47 (m, 2H), 4.20-4.48 (m, 1H), 3.39-3.47 (m, 1H), 3.35-3.38 (m, 1H), 2.91-3.06 (m, 2H), 2.80 (dd, J = 8.68, 12.57 Hz, 1H), 1.98-2.11 (m, 1H), 1.69-1.85 (m, H) | B | — |
| 366 | 600 MHz DMSO-d₆ | 7.76 (d, J = 7.71 Hz, 1H), 7.70 (s, 1H), 7.48-7.57 (m, 2H), 7.44 (t, J = 8.87 Hz, 1H), 7.40 (d, J = 8.08 Hz, 1H), 5.34-5.42 (m, 2H), 4.27-4.50 (m, 1H), 3.38- | B | — |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 3.48 (m, 1H), 3.15-3.26 (m, 1H), 3.00-3.13 (m, 1H), 2.91-3.00 (m, 1H), 2.80 (dd, J = 8.60, 12.57 Hz, 1H), 1.99-2.16 (m, 1H), 1.72-1.87 (m, 1H) | | |
| 367 | 600 MHz DMSO-d$_6$ | 7.50 (dd, J = 7.43, 11.17 Hz, 1H), 7.43 (dd, J = 7.32, 10.74 Hz, 1H), 7.35 (s, 1H), 7.35 (d, J = 5.66 Hz, 1H), 7.27 (s, 1H), 7.01-7.06 (m, 1H), 5.30-5.37 (m, 2H), 4.26-4.51 (m, 1H), 3.39-3.49 (m, 1H), 3.36-3.38 (m, 1H), 2.92-3.07 (m, 2H), 2.80 (dd, J = 8.64, 12.53 Hz, 1H), 1.96-2.14 (m, 1H), 1.72-1.84 (m, 1H) | B | — |
| 368 | 400 MHz d$_4$-MeOH | 7.47-7.53 (m, 1H), 7.09-7.23 (m, 5H), 7.00-7.08 (m, 2H), 5.30 (s, 2H), 3.48-3.55 (m, 1H), 3.24-3.30 (m, 1H), 2.92-3.06 (m, 2H), 2.86 (dd, J = 8.81, 11.71 Hz, 1H), 1.92-2.04 (m, 1H), 1.82 (td, J = 4.07, 13.42 Hz, 1H), 1.64-1.76 (m, 1H), 1.30-1.45 (m, 1H) | — | — |
| 369 | 600 MHz d$_6$-DMSO | 7.98-8.03 (m, 2H), 7.44 (d, J = 7.79 Hz, 1H), 7.34 (d, J = 8.41 Hz, 2H), 7.16-7.18 (m, 1H), 7.07-7.11 (m, 1H), 6.99-7.04 (m, 1H), 5.39 (s, 2H), 2.81-2.95 (m, 2H), 2.69 (br d, J = 2.49 Hz, 2H), 1.81-1.88 (m, 1H), 1.68-1.77 (m, 1H), 1.54-1.65 (m, 1H), 1.16-1.28 (m, 1H) | — | — |
| 370 | 500 MHz d$_6$-DMSO | 7.89 (br d, J = 8.04 Hz, 2H), 7.44 (br d, J = 7.53 Hz, 1H), 7.39 (br d, J = 8.04 Hz, 2H), 7.15 (br d, J = 7.79 Hz, 1H), 7.09 (br t, J = 7.14 Hz, 1H), 6.99-7.05 (m, 1H), 5.41 (s, 2H), 3.40 (br d, J = 10.38 Hz, 1H), 3.25-3.30 (m, 1H), 2.83-2.92 (m, 2H), 2.63-2.71 (m, 1H), 1.82 (br dd, J = 3.37, 8.04 Hz, 1H), 1.71 (br dd, J = 4.54, 8.69 Hz, 1H), 1.52-1.65 (m, 1H), 1.15-1.27 (m, 1H) | — | — |
| 371 | 500 MHz d$_6$-DMSO | 9.23 (s, 1H), 8.21 (s, 1H), 7.81 (br d, J = 8.56 Hz, 2H), 7.43 (br d, J = 7.27 Hz, 1H), 7.33 (br d, J = 8.56 Hz, 2H), 7.19 (br d, J = 7.53 Hz, 1H), 6.99-7.12 (m, 2H), 5.35 (s, 2H), 3.43 (br d, J = 9.86 Hz, 1H), 2.83-2.95 (m, 2H), 2.61-2.71 (m, 1H), 1.81-1.91 (m, 1H), 1.72 (br dd, J = 3.63, 9.08 Hz, 1H), 1.56-1.65 (m, 1H), 1.15-1.30 (m, 1H) | — | — |
| 372 | 500 MHz d$_6$-DMSO | 7.90 (br d, J = 7.01 Hz, 1H), 7.62 (br t, J = 7.27 Hz, 1H), 7.42-7.53 (m, 2H), 7.10 (br dd, J = 4.80, 7.14 Hz, 2H), 7.00-7.06 (m, 1H), 6.97 (br d, J = 7.78 Hz, 1H), 5.48 (s, 2H), 3.30-3.43 (m, 2H), 2.76-2.91 (m, 3H), 2.61 (br dd, J = 9.08, 11.68 Hz, 1H), 1.77-1.87 (m, 1H), 1.65-1.74 (m, 1H), 1.52-1.62 (m, 1H) | — | — |
| 373 | 500 MHz d$_6$-DMSO | 7.48 (br d, J = 8.04 Hz, 2H), 7.38 (br d, J = 8.04 Hz, 2H), 6.98 (br t, J = 7.27 Hz, 2H), 6.86 (br t, J = 7.40 Hz, 1H), 6.75 (br d, J = 8.04 Hz, 1H), 5.44-5.54 (m, 2H), 3.41 (br d, J = 8.82 Hz, 2H), 2.80-2.94 (m, 2H), 2.61-2.69 (m, 1H), 1.86 (br dd, J = 3.76, 8.43 Hz, 1H), 1.74-1.81 (m, 1H), 1.58-1.70 (m, 1H), 1.14-1.30 (m, 1H) | — | — |
| 374 | 500 MHz d$_6$-DMSO | 7.52 (br d, J = 7.01 Hz, 1H), 7.45 (br d, J = 7.79 Hz, 1H), 7.32 (br t, J = 7.01 Hz, 1H), 7.22-7.28 (m, 1H), 6.96-7.13 (m, 3H), 6.79 (br d, J = 6.75 Hz, 1H), 5.32 (s, 2H), 2.75-2.90 (m, 3H), 2.61 (br dd, J = 9.08, 11.68 Hz, 1H), 1.77-1.87 (m, 1H), 1.67 (br dd, J = 3.76, 9.21 Hz, 1H), 1.47-1.61 (m, 1H), 1.10-1.26 (m, 1H) | — | — |
| 375 | 500 MHz d$_6$-DMSO | 7.70 (br d, J = 7.79 Hz, 2H), 7.43 (br d, J = 7.79 Hz, 1H), 7.34 (br d, J = 8.04 Hz, 2H), 7.14 (br d, J = 7.79 Hz, 1H), 7.08 (br t, J = 7.14 Hz, 1H), 6.99-7.05 (m, 1H), 5.39 (s, 2H), 3.39 (br d, J = 9.60 Hz, 2H), 2.78-2.91 (m, 3H), 2.63 (br dd, J = 9.34, 11.68 Hz, 1H), 1.81 (br dd, J = 3.89, 8.04 Hz, 1H), 1.66-1.76 (m, 1H), 1.52-1.64 (m, 1H), 1.12-1.26 (m, 1H) | — | — |
| 376 | 500 MHz d$_6$-DMSO | 7.40-7.47 (m, 1H), 7.23-7.37 (m, 4H), 7.17 (br d, J = 8.04 Hz, 1H), 6.96-7.12 (m, 2H), 5.25-5.41 (m, 2H), 3.39 (br d, J = 10.90 Hz, 2H), 2.77-2.89 (m, | | |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 377 | 500 MHz $d_6$-DMSO | 2H), 2.62 (br dd, J = 9.21, 11.81 Hz, 1H), 1.78-1.88 (m, 1H), 1.54-1.75 (m, 2H), 1.12-1.23 (m, 1H) 7.34-7.46 (m, 3H), 7.12-7.21 (m, 3H), 6.96-7.11 (m, 2H), 5.23-5.31 (m, 2H), 3.35-3.42 (m, 2H), 2.78-2.90 (m, 3H), 2.57-2.68 (m, 1H), 1.79-1.88 (m, 1H), 1.66-1.77 (m, 1H), 1.53-1.64 (m, 1H), 1.11-1.24 (m, 1H) | — | — |
| 378 | 500 MHz $d_6$-DMSO | 7.43 (br d, J = 7.79 Hz, 1H), 7.30-7.37 (m, 2H), 7.25 (s, 1H), 7.19 (br d, J = 7.79 Hz, 1H), 6.99-7.12 (m, 3H), 5.24-5.36 (m, 2H), 3.39 (br d, J = 10.12 Hz, 2H), 2.78-2.92 (m, 2H), 2.62 (br dd, J = 9.08, 11.68 Hz, 1H), 1.79-1.89 (m, 1H), 1.70 (br d, J = 3.63 Hz, 1H), 1.53-1.66 (m, 1H), 1.18 (br d, J = 10.38 Hz, 1H) | — | — |
| 379 | 500 MHz $d_6$-DMSO | 7.52 (br d, J = 8.30 Hz, 1H), 7.47-7.59 (m, 1H), 7.42 (br d, J = 7.79 Hz, 1H), 7.25 (br d, J = 7.78 Hz, 2H), 6.95-7.18 (m, 3H), 5.25-5.40 (m, 2H), 3.40 (br d, J = 11.68 Hz, 2H), 2.79-2.90 (m, 2H), 2.64 (br dd, J = 9.21, 11.55 Hz, 1H), 1.92 (br t, J = 18.81 Hz, 3H), 1.82 (br dd, J = 3.37, 9.08 Hz, 1H), 1.71 (br dd, J = 4.02, 9.21 Hz, 1H), 1.60 (br s, 1H), 1.09-1.2.4 (m, 1H) | — | — |
| 380 | 500 MHz $d_6$-DMSO | 7.39-7.49 (m, 3H), 7.22 (br d, J = 8.30 Hz, 2H), 7.15 (br d, J = 7.79 Hz, 1H), 6.97-7.10 (m, 2H), 5.23-5.34 (m, 2H), 3.41 (br d, J = 11.68 Hz, 2H), 2.78-2.91 (m, 2H), 2.59-2.69 (m, 1H), 1.79-1.86 (m, 1H), 1.68-1.76 (m, 1H), 1.59-1.68 (m, 6H), 1.12-1.24 (m, 1H) | — | — |
| 381 | 500 MHz $d_6$-DMSO | 7.53 (br d, J = 7.78 Hz, 2H), 7.43 (br d, J = 7.53 Hz, 1H), 7.27 (br d, J = 7.79 Hz, 2H), 6.96-7.16 (m, 4H), 5.28-5.39 (m, 2H), 3.40 (br d, J = 9.86 Hz, 2H), 2.76-2.91 (m, 3H), 2.59-2.68 (m, 1H), 1.83 (br dd, J = 3.76, 8.17 Hz, 1H), 1.70 (br dd, J = 4.41, 9.34 Hz, 1H), 1.51-1.62 (m, 1H), 1.11-1.25 (m, 1H) | — | — |
| 382 | 500 MHz $d_6$-DMSO | 8.37 (br d, J = 4.41 Hz, 1H), 7.76 (br d, J = 8.30 Hz, 2H), 7.39-7.47 (m, 1H), 7.21 (br d, J = 8.04 Hz, 2H), 6.97-7.17 (m, 3H), 5.33 (s, 2H), 3.40 (br d, J = 9.08 Hz, 2H), 2.78-2.91 (m, 2H), 2.63 (br dd, J = 9.47, 11.29 Hz, 1H), 1.53-1.92 (m, 3H), 1.09-1.24 (m, 1H) | — | — |
| 383 | 500 MHz $d_6$-DMSO | 7.86-7.94 (m, 1H), 7.57-7.66 (m, 1H), 7.36-7.50 (m, 1H), 6.93-7.23 (m, 5H), 5.41 (s, 2H), 2.72-2.93 (m, 3H), 2.57-2.66 (m, 1H), 1.81 (br dd, J = 3.11, 4.93 Hz, 1H), 1.65-1.74 (m, 1H), 1.51-1.63 (m, 1H), 1.10-1.26 (m, 1H) | — | — |
| 384 | 500 MHz $d_6$-DMSO | 7.41 (br d, J = 7.53 Hz, 1H), 7.13-7.20 (m, 3H), 6.96-7.08 (m, 4H), 5.20-5.27 (m, 2H), 5.11 (s, 2H), 3.41 (br d, J = 12.20 Hz, 2H), 2.81-2.89 (m, 2H), 2.63 (br dd, J = 9.08, 11.68 Hz, 1H), 1.79-1.88 (m, 1H), 1.72 (br dd, J = 3.89, 8.56 Hz, 1H), 1.61 (br dd, J = 3.89, 10.90 Hz, 1H), 1.18 (br d, J = 10.38 Hz, 1H) | — | — |
| 385 | 500 MHz $d_6$-DMSO | 7.71 (br d, J = 8.30 Hz, 2H), 7.44 (br d, J = 7.78 Hz, 1H), 7.38 (br d, J = 8.04 Hz, 2H), 7.18 (br d, J = 7.79 Hz, 1H), 6.99-7.12 (m, 2H), 5.36-5.45 (m, 2H), 3.37 (br d, J = 11.68 Hz, 2H), 2.71-2.89 (m, 2H), 1.76-1.84 (m, 1H), 1.65-1.73 (m, 1H), 1.48-1.61 (m, 2H), 1.11-1.22 (m, 1H) | — | — |
| 386 | 500 MHz $d_6$-DMSO | 7.41 (br d, J = 7.79 Hz, 1H), 6.96-7.16 (m, 5H), 7.16 (br s, 1H), 5.15-5.29 (m, 2H), 3.40 (br d, J = 11.42 Hz, 2H), 2.79-2.89 (m, 2H), 2.58-2.67 (m, 1H), 2.24 (s, 3H), 1.79-1.87 (m, 1H), 1.69 (br d, J = 3.63 Hz, 1H), 1.54-1.65 (m, 1H), 1.13-1.22 (m, 1H) | — | — |
| 387 | 500 MHz $d_6$-DMSO | 7.41 (br d, J = 7.53 Hz, 1H), 7.11-7.27 (m, 5H), 6.97-7.09 (m, 2H), 5.21-5.35 (m, 2H), 3.39 (br d, J = 11.94 Hz, 2H), 2.79-2.89 (m, 2H), 2.62 (br dd, J = 9.21, 11.55 Hz, 1H), 1.78-1.88 (m, 1H), 1.71 (br dd, J = 3.63, 8.56 Hz, 1H), 1.54-1.65 (m, 1H), 1.08-1.25 (m, 1H) | — | — |

TABLE 6-continued

Characterization data for compounds made following schemes 9-10
The column "Separation Stage" indicates after which
process step regioisomers formed due to asymmetric
benzimidazole substitution at R[1] in Scheme
10 were separated during the preparation of the tabulated
final compound. (I = after preparation of the
N-aralkyl-2-piperidinyl-benzimidazole intermediate
in the first step of Scheme 10 (where at least one R[1] is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 388 | 500 MHz d$_6$-DMSO | 8.05 (s, 1H), 7.64-7.71 (m, 1H), 7.46 (br d, J = 7.79 Hz, 1H), 7.02-7.12 (m, 1H), 6.90-7.02 (m, 3H), 6.56-6.64 (m, 1H), 5.90 (br d, J = 5.97 Hz, 2H), 4.32 (s, 3H), 3.40 (br d, J = 10.90 Hz, 2H), 2.89-2.96 (m, 1H), 2.78-2.86 (m, 1H), 2.70 (br dd, J = 8.69, 11.81 Hz, 1H), 1.74-1.82 (m, 1H), 1.64-1.70 (m, 1H), 1.50-1.60 (m, 1H), 1.11-1.26 (m, 1H) | — | — |
| 389 | 500 MHz d$_6$-DMSO | 7.40-7.45 (m, 1H), 7.24-7.32 (m, 1H), 7.16 (br d, J = 7.79 Hz, 1H), 6.96-7.11 (m, 3H), 5.26-5.33 (m, 1H), 3.37 (br d, J = 1.56 Hz, 2H), 2.77-2.91 (m, 2H), 2.58-2.65 (m, 1H), 1.80-1.87 (m, 1H), 1.67-1.76 (m, 1H), 1.52-1.64 (m, 1H), 1.09-1.24 (m, 1H) | — | — |
| 390 | 500 MHz d$_6$-DMSO | 7.33-7.45 (m, 2H), 7.16-7.30 (m, 2H), 7.00-7.11 (m, 2H), 6.95 (br s, 1H), 5.22-5.33 (m, 2H), 3.39 (br d, J = 11.16 Hz, 2H), 2.85 (br d, J = 9.611 Hz, 2H), 2.63 (br dd, J = 9.34, 11.68 Hz, 1H), 1.78-1.88 (m, 1H), 1.71 (br d, J = 3.63 Hz, 1H), 1.59 (br dd, J = 2.47, 10.51 Hz, 1H), 1.12-1.24 (m, 1H) | — | — |
| 391 | 500 MHz d$_6$-DMSO | 7.53 (br t, J = 7.91 Hz, 1H), 7.43 (br d, J = 7.53 Hz, 1H), 7.23 (br d, J = 8.82 Hz, 1H), 7.18 (br d, J = 7.78 Hz, 1H), 6.99-7.12 (m, 2H), 6.94 (br d, J = 7.78 Hz, 1H), 5.25-5.34 (m, 2H), 3.38 (br d, J = 11.42 Hz, 2H), 2.80-2.91 (m, 2H), 2.63 (br dd, J = 9.34, 11.68 Hz, 1H), 1.78-1.88 (m, 1H), 1.67-1.77 (m, 1H), 1.60 (br s, 1H), 1.12-1.24 (m, 1H) | — | — |
| 392 | 500 MHz d$_6$-DMSO | 7.92 (s, 1H), 7.84 (br d, J = 7.53 Hz, 1H), 7.49-7.59 (m, 2H), 7.44 (br d, J = 7.01 Hz, 1H), 7.35 (br d, J = 7.01 Hz, 1H), 7.04-7.16 (m, 3H), 5.47-5.57 (m, 2H), 3.38-3.46 (m, 2H), 2.85-2.96 (m, 2H), 2.69 (br dd, J = 9.08, 11.42 Hz, 1H), 1.81-1.90 (m, 1H), 1.77 (br dd, J = 4.15, 8.82 Hz, 1H), 1.61-1.70 (m, 1H), 1.18-1.29 (m, 1H) | — | — |
| 393 | 500 MHz d$_6$-DMSO | 7.41 (br d, J = 7.53 Hz, 1H), 7.29 (s, 1H), 7.20 (br d, J = 7.53 Hz, 1H), 6.99-7.12 (m, 4H), 5.17-5.25 (m, 2H), 3.80 (s, 3H), 3.40 (br d, J = 9.86 Hz, 2H), 2.79-2.91 (m, 2H), 2.62 (br dd, J = 9.34, 11.68 Hz, 1H), 1.84 (br dd, J = 4.02, 8.17 Hz, 1H), 1.72 (br d, J = 3.37 Hz, 1H), 1.53-1.66 (m, 2H), 1.10-1.25 (m, 1H) | — | — |
| 394 | 500 MHz d$_6$-DMSO | 8.15 (br d, J = 1.30 Hz, 1H), 7.75 (br dd, J = 1.17, 7.91 Hz, 1H), 7.46 (br d, J = 8.04 Hz, 1H), 7.00-7.14 (m, 3H), 6.88 (br d, J = 8.04 Hz, 1H), 5.33-5.44 (m, 2H), 3.15-3.24 (m, 2H), 2.74-2.89 (m, 2H), 2.60 (br dd, J = 9.34, 11.42 Hz, 1H), 1.77-1.85 (m, 1H), 1.63-1.73 (m, 1H), 1.46-1.57 (m, 1H), 1.09-1.25 (m, 1H) | — | — |
| 395 | 500 MHz d$_6$-DMSO | 7.66-7.74 (m, 1H), 7.42-7.48 (m, 1H), 7.31-7.38 (m, 1H), 7.00-7.16 (m, 3H), 6.79 (br d, J = 8.30 Hz, 1H), 5.30 (s, 2H), 3.14-3.27 (m, 2H), 2.73-2.91 (m, 2H), 2.60 (br dd, J = 9.21, 11.81 Hz, 1H), 1.77-1.86 (m, 1H), 1.67-1.74 (m, 1H), 1.50-1.61 (m, 1H), 1.09-1.20 (m, 1H) | — | — |
| 396 | 500 MHz d$_6$-DMSO | 7.54-7.58 (m, 1H), 7.44 (br d, J = 7.27 Hz, 1H), 7.33 (br d, J = 8.04 Hz, 1H), 6.98-7.14 (m, 3H), 6.71-6.77 (m, 1H), 5.20-5.27 (m, 1H), 5.18-5.28 (m, 1H), 3.10-3.23 (m, 2H), 2.75-2.88 (m, 2H), 2.58-2.64 (m, 1H), 1.79-1.84 (m, 1H), 1.64-1.71 (m, 1H), 1.51-1.58 (m, 1H), 1.16 (br dd, J = 8.04, 10.90 Hz, 1H) | — | — |
| 397 | 500 MHz d$_6$-DMSO | 8.11 (br d, J = 2.08 Hz, 1H), 7.67-7.74 (m, 1H), 7.46 (br d, J = 8.30 Hz, 1H), 7.07-7.15 (m, 2H), 7.04 (br d, J = 7.53 Hz, 1H), 6.95 (br d, J = 8.56 Hz, 1H), 5.46 (s, 2H), 3.17-3.26 (m, 2H), 2.78-2.88 (m, 2H), 2.57-2.65 (m, 1H), 1.77-1.86 (m, 1H), 1.66-1.75 (m, 1H), 1.53-1.62 (m, 1H), 1.14-1.22 (m, 1H) | — | — |
| 398 | 400 MHz MeOD | 7.69-7.76 (m, 2H), 7.50-7.56 (m, 1H), 7.46 (d, J = 8.09 Hz, 2H), 7.11-7.19 (m, 1H), 6.95-7.07 (m, 2H), 5.91 (q, J = 7.12 Hz, 1H), 3.43 (dd, J = 3.73, 11.61 Hz, 1H), 3.27-3.31 (m, 1H), 2.95-3.08 (m, | — | — |

TABLE 6-continued

Characterization data for compounds made following schemes 9-10
The column "Separation Stage" indicates after which
process step regioisomers formed due to asymmetric
benzimidazole substitution at R¹ in Scheme
10 were separated during the preparation of the tabulated
final compound. (I = after preparation of the
N-aralkyl-2-piperidinyl-benzimidazole intermediate
in the first step of Scheme 10 (where at least one R¹ is not
hydrogen); B = prior to boc deprotection; or F = final compound).

| Ex. # | Freq., Solvent | ¹HNMR Data (δ ppm) | Separation Stage | SFC Isomer Separation Conditions |
|---|---|---|---|---|
| | | 2H), 2.87 (dd, J = 8.91, 11.61 Hz, 1H), 1.96-2.00 (m, 2H), 1.95-2.01 (m, 1H), 1.86-1.94 (m, 1H), 1.69-1.83 (m, 1H), 1.33-1.47 (m, 1H) | | |
| 399 | 400 MHz MeOD | Mixture of diasteromers: 7.70-7.78 (m, 2H), 7.52 (d, J = 7.88 Hz, 1H), 7.45 (dd, J = 6.32, 7.98 Hz, 2H), 7.15 (dt, J = 1.24, 7.57 Hz, 1H), 6.94-7.07 (m, 2H), 5.86-5.98 (m, 1H), 3.40-3.54 (m, 1H), 3.36 (s, 2H), 2.97-3.09 (m, 2H), 2.86 (ddd, J = 8.91, 11.51, 16.27 Hz, 1H), 2.00 (dd, J = 7.36, 8.19 Hz, 3H), 1.68-1.92 (m, 2H), 1.32-1.45 (m, 1H | — | — |
| 400 | 400 MHz d₆-DMSO | 8.03 (br s, 3H), 7.79 (d, J = 7.67 Hz, 1H), 7.72 (s, 1H), 7.55-7.62 (m, 1H), 7.47-7.54 (m, 2H), 7.11-7.25 (m, 3H), 5.44 (s, 2H), 3.66 (br dd, J = 3.01, 12.54 Hz, 1H), 3.47 (br d, J = 2.90 Hz, 1H), 3.25-3.34 (m, 1H), 3.21 (dd, J = 8.50, 12.23 Hz, 1H), 2.98-3.09 (m, 1H), 1.95-2.03 (m, 1H), 1.79-1.90 (m, 1H), 1.53-1.71 (m, 2H) | — | — |
| 494 | 500 MHz d₄-MeOH | 8.77 (s, 2H), 7.39-7.45 (m, 1H), 6.98 (dd, J = 2.34, 8.82 Hz, 1H), 6.85-6.93 (m, 1H), 5.50 (s, 2H), 3.90 (td, J = 3.60, 7.07 Hz, 1H), 3.31-3.44 (m, 3H), 3.22-3.29 (m, 1H), 3.06-3.15 (m, 1H), 3.03 (td, J = 3.50, 7.01 Hz, 1H), 1.77-1.93 (m, 2H) | B | Chiralpak ID, 25% IPA w/0.2% DEA, peak 1 |
| 495 | 500 MHz d₄-MeOH | 7.42-7.47 (m, 1H), 7.31 (d, J = 1.82 Hz, 1H), 7.18 (dd, J = 1.95, 8.43 Hz, 1H), 5.08 (s, 2H), 4.38-4.55 (m, 1H), 3.75-3.81 (m, 2H), 3.71-3.75 (m, 2H), 3.67-3.70 (m, 2H), 3.59-3.65 (m, 2H), 3.53 (br d, J = 12.46 Hz, 1H), 3.38 (s, 1H), 3.16-3.22 (m, 1H), 3.07-3.15 (m, 1H), 2.97 (dd, J = 8.56, 12.46 Hz, 1H), 2.18-2.29 (m, 1H), 1.89-2.01 (m, 1H) | B | Chiralpak IC, 35% MeOH, peak 1 |
| 496 | 500 MHz d₄-MeOH | 8.77 (s, 2H), 7.15-7.19 (m, 1H), 7.10-7.14 (m, 1H), 6.83-6.90 (m, 1H), 5.50 (s, 2H), 3.90 (td, J = 3.44, 7.14 Hz, 1H), 3.24-3.45 (m, 4H), 3.11-3.18 (m, 1H), 2.99-3.05 (m, 1H), 1.79-1.95 (m, 2H) | B | Chiralpak ID, 25% IPA w/0.2% DEA, peak 2 |
| 497 | 500 MHz d₄-MeOH | 7.45-7.50 (m, 1H), 7.20-7.24 (m, 1H), 7.13-7.20 (m, 1H), 5.08 (s, 2H), 4.41-4.58 (m, 1H), 3.75-3.81 (m, 2H), 3.70 (td, J = 4.57, 16.28 Hz, 4H), 3.60-3.66 (m, 2H), 3.56 (dtd, J = 1.95, 4.23, 12.42 Hz, 1H), 3.41-3.48 (m, 1H), 3.18-3.26 (m, 1H), 3.10-3.16 (m, 1H), 2.99 (dd, J = 8.69, 12.59 Hz, 1H), 2.18-2.30 (m, 1H), 1.89-2.02 (m, 1H) | B | Chiralpak IC, 35% MeOH, peak 2 |
| 498 | 600 MHz DMSO-d₆ | 8.97 (s, 2H), 7.50 (dd, J = 7.59, 11.09 Hz, 1H), 7.13 (dd, J = 7.36, 10.94 Hz, 1H), 5.93 (q, J = 7.19 Hz, 1H), 4.36-4.57 (m, 1H), 3.38-3.56 (m, 1H), 3.22 (br d, J = 7.24 Hz, 1H), 2.94-3.00 (m, 1H), 2.88 (dd, J = 8.76, 12.34 Hz, 1H), 2.37-2.47 (m, 1H), 2.07-2.14 (m, 1H), 1.88 (d, J = 7.16 Hz, 4H) | B | Chiralpak AD-H, 25% IPA, peak 1 |
| 499 | 600 MHz DMSO-d₆ | 8.92-8.95 (m, 1H), 8.53-8.56 (m, 1H), 8.35 (dd, J = 2.10, 8.17 Hz, 1H), 8.01 (d, J = 2.10 Hz, 1H), 7.60 (d, J = 8.17 Hz, 1H), 5.69 (s, 2H), 4.33-4.44 (m, 1H), 3.51-3.70 (m, 1H), 3.14-3.19 (m, 1H), 2.81-2.91 (m, 1H), 2.51-2.55 (m, 1H), 2.37-2.47 (m, 1H), 2.02-2.09 (m, 1H), 1.62-1.76 (m, 1H). | B | Chiralpak AD-H, 25% IPA, peak 1 |
| 500 | 600 MHz DMSO-d₆ | 7.45-7.54 (m, 1H), 7.26-7.42 (m, 1H), 5.01-5.18 (m, 2H), 4.35-4.54 (m, 2H), 4.22 (q, J = 9.60 Hz, 2H), 3.32-3.41 (m, 1H), 3.20-3.26 (m, 1H), 2.94-3.07 (m, 3H), 2.81 (dd, J = 8.17, 12.59 Hz, 1H), 2.65-2.74 (m, 1H), 2.02-2.19 (m, 1H), 1.77 (br d, J = 9.86 Hz, 1H) | — | — |
| 501 | 600 MHz DMSO-d₆ | 7.57-7.62 (m, 2H), 7.51 (dd, J = 7.40, 11.13 Hz, 1H), 7.32 (d, J = 3.50 Hz, 1H), 5.37-5.43 (m, 2H), 4.36-4.48 (m, 1H), 3.83 (s, 3H), 3.51 (br d, J = 13.00 Hz, 1H), 3.13-3.23 (m, 2H), 2.99-3.10 (m, 1H), 2.79-2.84 (m, 1H), 2.07-2.14 (m, 1H), 1.75-1.84 (m, 1H) | — | — |
| 502 | 600 MHz DMSO-d₆ | 8.43 (br s, 2H), 7.44 (d, J = 8.51 Hz, 1H), 7.41 (s, 1H), 7.14 (dd, J = 2.06, 8.45 Hz, 2H), 4.98-5.07 (m, 2H), 4.73-4.92 (m, 1H), 3.65-3.72 (m, 2H), 3.34 (br | B | Chiralpak AD-H, 25% IPA, peak 1 |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | s, 1H), 2.77-3.13 (m, 6H), 2.51-2.55 (m, 2H), 2.16-2.24 (m, 1H), 1.81-1.90 (m, 1H) | | |
| 503 | 600 MHz DMSO-d$_6$ | $^1$ 7.41 (dd, J = 4.87, 8.68 Hz, 1H), 7.15 (dd, J = 2.49, 9.19 Hz, 1H), 6.94 (ddd, J = 2.53, 8.64, 10.08 Hz, 1H), 4.67-4.80 (m, 2H), 4.50-4.65 (m, 1H), 4.22-4.33 (m, 2H), 3.94 (t, J = 7.71 Hz, 2H), 3.39-3.57 (m, 1H), 3.23-3.39 (m, 1H), 2.96-3.10 (m, 1H), 2.88 (dd, J = 8.99, 12.57 Hz, 1H), 2.52-2.55 (m, 1H), 2.29 (quin, J = 7.69 Hz, 2H), 2.11-2.20 (m, 1H), 1.80-1.88 (m, 1H) | B | Chiralpak AD-H, 25% IPA, peak 1 |
| 504 | 600 MHz DMSO-d$_6$ | 7.35-7.48 (m, 2H), 4.99-5.12 (m, 2H), 4.40-4.47 (m, 1H), 4.30-4.39 (m, 1H), 3.90 (br d, J = 13.23 Hz, 1H), 3.15-3.30 (m, 4H), 2.94-3.04 (m, 2H), 2.90 (br t, J = 11.64 Hz, 1H), 2.69-2.84 (m, 2H), 2.04-2.16 (m, 1H), 1.91-2.03 (m, 1H), 1.71-1.89 (m, 1H), 1.54-1.67 (m, 2H) | — | — |
| 505 | 600 MHz DMSO-d$_6$ | 7.40-7.52 (m, 3H), 6.92 (dd, J = 5.14, 10.98 Hz, 1H), 5.14-5.18 (m, 1H), 5.08-5.12 (m, 1H), 4.75 (s, 1H), 4.57 (s, 1H), 3.78-3.89 (m, 2H), 3.20-3.29 (m, 2H), 2.93-3.03 (m, 2H), 2.75-2.83 (m, 2H), 2.37-2.46 (m, 1H), 1.92-2.11 (m, 2H), 1.70-1.79 (m, 1H) | — | — |
| 506 | 600 MHz DMSO-d$_6$ | 7.45 (d, J = 1.87 Hz, 1H), 7.20 (d, J = 8.49 Hz, 1H), 7.08 (dd, J = 2.02, 8.49 Hz, 1H), 4.94-5.04 (m, 2H), 4.33-4.48 (m, 1H), 3.28-3.38 (m, 1H), 2.96-3.13 (m, 6H), 2.88 (s, 3H), 2.76-2.85 (m, 1H), 1.99-2.16 (m, 1H), 1.74-1.87 (m, 1H) | B | Chiralpak AD-H, 25% IPA, peak 2 |
| 507 | 600 MHz DMSO-d$_6$ | 7.46 (dd, J = 7.43, 11.17 Hz, 1H), 7.39 (t, J = 8.84 Hz, 1H), 5.06-5.19 (m, 1H), 4.93 (br t, J = 18.33 Hz, 1H), 4.06-4.13 (m, 1H), 3.80-3.93 (m, 2H), 3.49-3.60 (m, 1H), 3.36-3.48 (m, 1H), 3.28-3.30 (m, 1H), 3.20-3.28 (m, 2H), 3.17 (d, J = 5.06 Hz, 1H), 2.88-3.05 (m, 2H), 2.73-2.83 (m, 1H), 2.42-2.48 (m, 1H), 2.00-2.16 (m, 1H), 1.92 (br s, 1H), 1.73-1.89 (m, 1H), 1.06-1.18 (m, 3H) | — | — |
| 508 | 600 MHz DMSO-d$_6$ | 8.97 (s, 2H), 7.50 (dd, J = 7.59, 11.09 Hz, 1H), 7.13 (dd, J = 7.36, 10.94 Hz, 1H), 5.93 (q, J = 7.19 Hz, 1H), 4.36-4.57 (m, 1H), 3.38-3.56 (m, 1H), 3.22 (br d, J = 7.24 Hz, 1H), 2.94-3.00 (m, 1H), 2.88 (dd, J = 8.76, 12.34 Hz, 1H), 2.37-2.47 (m, 1H), 2.07-2.14 (m, 1H), 1.88 (d, J = 7.16 Hz, 4H) | B | Chiralpak AD-H, 25% IPA, peak 2 |
| 509 | 600 MHz DMSO-d$_6$ | 6.73 (dd, J = 2.26, 8.95 Hz, 1H), 6.56-6.64 (m, 1H), 5.03-5.12 (m, 2H), 4.29-4.49 (m, 1H), 4.22 (q, J = 9.58 Hz, 2H), 3.89 (s, 3H), 3.26 (s, 3H), 3.18 (br d, J = 12.53 Hz, 1H), 2.89-3.00 (m, 3H), 2.68-2.77 (m, 1H), 2.07 (ddd, J = 4.01, 8.91, 13.08 Hz, 1H), 1.70-1.86 (m, 1H) | B | SFC: Whelk-01, 25% methanol Peak 2 |
| 510 | 600 MHz DMSO-d$_6$ | 7.47 (dd, J = 7.47, 11.13 Hz, 1H), 7.35 (dd, J = 7.36, 10.70 Hz, 1H), 4.99 (s, 2H), 4.33-4.445 (m, 1H), 3.49-3.57 (m, 2H), 3.38-3.45 (m, 1H), 3.25-3.30 (m, 1H), 2.91-3.04 (m, 2H), 2.78 (dd, J = 8.64, 12.53 Hz, 1H), 2.06-2.14 (m, 1H), 1.71-1.87 (m, 5H), 1.57-1.66 (m, 4H), 1.43-1.57 (m, 4H) | — | — |
| 511 | 600 MHz DMSO-d$_6$ | 8.39 (d, J = 1.32 Hz, 1H), 8.13 (dd, J = 1.52, 2.61 Hz, 1H), 7.89 (d, J = 2.57 Hz, 1H), 7.46 (t, J = 9.08 Hz, 1H), 7.42 (t, J = 8.88 Hz, 1H), 5.04-5.14 (m, 2H), 4.34-4.35 (m, 1H), 3.67-3.79 (m, 4H), 3.58-3.66 (m, 4H), 3.23-3.28 (m, 1H), 2.96-3.05 (m, 2H), 2.80 (dd, J = 8.06, 12.57 Hz, 1H), 2.07-2.15 (m, 1H), 1.74-1.92 (m, 2H) | — | — |
| 512 | 600 MHz DMSO-d$_6$ | 7.46 (t, J = 9.16 Hz, 1H), 7.39 (t, J = 9.02 Hz, 1H), 4.95-5.07 (m, 2H), 4.36-4.44 (m, 1H), 4.18 (br t, J = 11.64 Hz, 1H), 3.83-3.97 (m, 1H), 3.63 (s, 2H), 3.13-3.26 (m, 3H), 2.93-3.05 (m, 2H), 2.73-2.89 (m, 2H), 2.68 (tt, J = 3.97, 10.94 Hz, 1H), 2.51-2.56 (m, 1H), 2.09 (br d, J = 13.16 Hz, 1H), 1.89-1.98 (m, | — | — |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | 1H), 1.74-1.89 (m, 2H), 1.60-1.70 (m, 1H), 1.40-1.50 (m, 1H) | | |
| 513 | 600 MHz DMSO-d$_6$ | 7.46 (dd, J = 7.43, 11.02 Hz, 1H), 7.39 (dd, J = 7.55, 10.35 Hz, 1H), 5.07-5.18 (m, 1H), 4.93 (dd, J = 14.95, 17.28 Hz, 1H), 4.33-4.48 (m, 1H), 4.09-4.16 (br d, J = 13.00 Hz, 1H), 3.82-3.93 (m, 2H), 3.53 (dt, J = 2.37, 11.46 Hz, 1H), 3.19-3.30 (m, 2H), 2.90-3.05 (m, 2H), 2.69-2.84 (m, 2H), 2.44-2.48 (m, 1H), 2.06-2.16 (m, 1H), 1.72-1.90 (m, 2H), 1.39-1.52 (m, 2H), 0.85-0.97 (m, 3H) | — | — |
| 514 | 600 MHz DMSO-d$_6$ | 7.20-7.26 (m, 2H), 6.95 (ddd, J = 2.49, 8.74, 9.87 Hz, 1H), 4.71-4.77 (m, 2H), 4.63-4.55 (m, 1H), 4.23-4.29 (m, 2H), 3.94 (t, J = 7.71 Hz, 2H), 3.45-3.63 (m, 1H), 3.39-3.45 (m, 1H), 3.14-3.35 (m, 1H), 2.98-3.12 (m, 1H), 2.93 (dd, J = 9.19, 12.69 Hz, 1H), 2.28 (quin, J = 7.69 Hz, 2H), 2.08-2.23 (m, 1H), 1.79-1.89 (m, 1H) | B | SFC: Chiralpak IC, 40% methanol peak 2 |
| 515 | 600 MHz DMSO-d$_6$ | 7.69 (d, J = 8.32 Hz, 2H), 7.48-7.65 (m, 7H), 5.67-5.99 (m, 1H), 5.17-5.57 (m, 1H), 4.36-4.51 (m, 2H), 3.86 (br s, 1H), 3.49 (br d, J = 11.99 Hz, 1H), 3.38-3.44 (m, 1H), 2.90-3.03 (m, 2H), 2.67-2.84 (m, 1H), 2.12 (br s, 1H), 1.68-1.84 (m, 1H) | — | — |
| 516 | 600 MHz DMSO-d$_6$ | 7.46 (dd, J = 7.47, 11.13 Hz, 1H), 7.37 (dd, J = 7.32, 10.74 Hz, 1H), 4.94-5.04 (m, 2H), 4.28 (br d, J = 12.85 Hz, 1H), 3.93 (br d, J = 13.23 Hz, 1H), 3.21-3.29 (m, 2H), 3.09 (br t, J = 11.91 Hz, 1H), 2.93-3.03 (m, 2H), 2.78 (dt, J = 8.41, 12.53 Hz, 1H), 2.59-2.65 (m, 1H), 2.07-2.14 (m, 1H), 1.67-1.82 (m, 4H), 1.63 (br d, J = 10.98 Hz, 2H), 1.10-1.18 (m, 1H), 0.90-1.00 (m, 3H) | — | — |
| 517 | 600 MHz DMSO-d$_6$ | 8.47 (d, J = 5.76 Hz, 1H), 7.41 (dd, J = 4.87, 8.68 Hz, 1H), 7.13 (dd, J = 2.49, 9.26 Hz, 1H), 6.91 (ddd, J = 2.57, 8.68, 10.08 Hz, 1H), 6.85 (d, J = 5.84 Hz, 1H), 5.36 (s, 2H), 4.27-4.43 (m, 1H), 3.74 (s, 3H), 3.37-3.48 (m, 2H), 2.98-3.06 (m, 1H), 2.91 (tdd, J = 4.17, 7.93, 14.39 Hz, 1H), 2.80 (dd, J = 8.64, 12.46 Hz, 1H), 1.93-2.09 (m, 1H), 1.65-1.79 (m, 1H) | B | SFC: Chiralpak OD analytical column, 15% isopropanol Peak 1 |
| 518 | 600 MHz DMSO-d$_6$ | 7.46 (t, J = 8.90 Hz, 1H), 7.40 (t, J = 9.01 Hz, 1H), 5.13 (dd, J = 12.96, 17.56 Hz, 1H), 4.93 (br t, J = 16.66 Hz, 1H), 4.32-4.49 (m, 1H), 4.02-4.21 (m, 1H), 3.82-3.93 (m, 2H), 3.36-3.43 (m, 1H), 3.19-3.28 (m, 3H), 2.90-3.06 (m, 3H), 2.72-2.83 (m, 2H), 2.00-2.15 (m, 1H), 1.79 (br s, 1H), 1.39-1.54 (m, 1H), 0.86-0.97 (m, 3H) | — | — |
| 519 | 600 MHz DMSO-d$_6$ | 8.81-9.03 (m, 1H), 8.27-8.41 (m, 2H), 7.63-7.75 (m, 1H), 7.38-7.55 (m, 1H), 5.85-5.99 (m, 2H), 4.19-4.51 (m, 3H), 2.83-2.95 (m, 1H), 2.63-2.78 (m, 1H), 1.94-2.14 (m, 1H), 1.69-1.86 (m, 1H), 1.41-1.58 (m, 1H) | B | SFC: Regis Whelk-O analytical column, 35% isopropanol. Peak 2 |
| 520 | 600 MHz DMSO-d$_6$ | 8.63 (br s, 2H), 7.22-7.35 (m, 2H), 7.11-7.22 (m, 2H), 4.74-4.85 (m, 2H), 4.28 (t, J = 7.63 Hz, 1H), 3.94 (br t, J = 7.71 Hz, 1H), 3.43-3.78 (m, 6H), 3.04-3.20 (m, 1H), 2.38-2.59 (m, 3H), 2.21-2.32 (m, 1H), 1.81-1.98 (m, 1H) | — | — |
| 521 | 600 MHz DMSO-d$_6$ | 7.34-7.51 (m, 4H), 7.24 (br s, 1H), 4.91-5.16 (m, 3H), 4.66 (br dd, J = 2.65, 17.20 Hz, 1H), 4.32-4.48 (m, 1H), 3.84-3.90 (m, 1H), 3.17 (d, J = 4.13 Hz, 1H), 2.93-3.05 (m, 2H), 2.61-2.74 (m, 1H), 2.07-2.22 (m, 1H), 1.74-1.89 (m, 2H), 1.64 (br d, J = 12.77 Hz, 2H), 1.42-1.57 (m, 1H), 1.26-1.38 (m, 2H) | — | — |
| 522 | 600 MHz DMSO-d$_6$ | 7.48 (dd, J = 7.51, 10.78 Hz, 1H), 7.33-7.43 (m, 1H), 7.04 (d, J = 2.73 Hz, 2H), 7.04 (m, 1H), 5.20-5.38 (m, 1H), 4.90-5.05 (m, 2H), 4.75-4.87 (m, 1H), 4.68 | | |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | (dd, J = 6.85, 15.88 Hz, 1H), 3.67 (dt, J = 8.25, 13.04 Hz, 1H), 3.38-3.52 (m, 1H), 3.26 (br d, J = 5.22 Hz, 1H), 3.09-3.23 (m, 3H), 2.88-3.05 (m, 1H), 2.79-2.86 (m, 1H), 2.57-2.70 (m, 1H), 2.51-2.57 (m, 1H), 2.31-2.47 (m, 2H), 1.95-2.11 (m, 1H), 1.71-1.87 (m, 1H). | | |
| 523 | 600 MHz DMSO-d$_6$ | 7.44-7.63 (m, 1H), 7.32-7.40 (m, 1H), 4.96-5.13 (m, 2H), 4.24-4.50 (m, 1H), 3.41 (br s, 1H), 3.21 (br s, 1H), 2.96-3.03 (m, 2H), 2.33-2.46 (m, 2H), 2.17-2.32 (m, 1H), 2.10 (br d, J = 10.20 Hz, 1H), 1.88 (br d, J = 6.85 Hz, 1H), 1.77 (br d, J = 8.49 Hz, 1H), 1.67 (br d, J = 9.81 Hz, 1H), 1.62 (br s, 1H), 1.56 (br s, 2H), 1.43-1.53 (m, 1H), 1.30-1.42 (m, 3H), 1.21-1.30 (m, 2H) 1.07-1.21 (m, 2H) 0.90-1.06 (m, 1H). | — | — |
| 524 | 600 MHz DMSO-d$_6$ | 8.47 (d, J = 5.84 Hz, 1H), 7.23 (d, J = 9.56 Hz, 1H), 7.18-7.21 (m, 1H), 6.83-6.89 (m, 2H), 5.32-5.40 (m, 2H), 4.37-4.44 (m, 1H), 4.28-4.35 (m, 1H), 3.75 (s, 3H), 3.45-3.54 (m, 2H), 3.03-3.10 (m, 1H), 2.83 (dd, J = 8.68, 12.50 Hz, 1H), 2.03-2.10 (m, 1H), 1.65-1.80 (m, 1H) | B | SFC: Chiralpak OD analytical column, 15% isopropanol |
| 525 | 600 MHz DMSO-d$_6$ | 7.36-7.49 (m, 2H), 5.09-5.19 (m, 2H), 4.93-5.05 (m, 2H), 4.36-4.44 (m, 1H), 3.61 (td, J = 8.79, 13.18 Hz, 1H), 3.37-3.49 (m, 1H), 3.24-3.30 (m, 1H), 3.10-3.24 (m, 3H), 3.07 (s, 3H), 2.93-3.05 (m, 3H), 2.74-2.83 (m, 3H), 2.18-2.34 (m, 1H), 2.05-2.15 (m, 1H), 1.73-1.91 (m, 1H) | — | — |
| 526 | 600 MHz DMSO-d$_6$ | 7.45-7.58 (m, 2H), 5.02-5.14 (m, 2H), 4.40-4.49 (m, 1H), 4.33-4.40 (m, 1H), 3.36-3.51 (m, 1H), 3.22-3.29 (m, 3H), 3.17 (s, 1H), 2.93-3.12 (m, 4H), 2.77 (ddd, J = 4.17, 8.31, 12.59 Hz, 1H), 2.34-2.47 (m, 2H), 2.08-2.17 (m, 1H), 1.74-1.92 (m, 1H), 1.06 (br d, J = 8.33 Hz, 2H), 0.94-1.03 (m, 2H) | — | — |
| 527 | 600 MHz DMSO-d$_6$ | 7.36-7.51 (m, 2H), 4.95-5.24 (m, 2H), 4.71-4.86 (m, 1H), 4.45-4.54 (m, 1H), 4.32-4.38 (m, 1H), 3.45-3.55 (m, 1H), 3.35-3.44 (m, 2H), 3.24-3.31 (m, 2H), 3.09-3.22 (m, 2H), 2.92-3.04 (m, 2H), 2.73-2.81 (m, 1H), 2.23-2.39 (m, 2H), 2.04-2.15 (m, 1H), 1.65-1.92 (m, 3H), 1.25 (t, J = 7.05 Hz, 2H), 1.05 (br t, J = 6.77 Hz, 1H) | — | — |
| 528 | 600 MHz DMSO-d$_6$ | 7.46-7.54 (m, 2H), 5.00-5.15 (m, 2H), 4.68-4.86 (m, 1H), 4.23 (s, 1H), 3.91-4.00 (m, 1H), 3.75 (br t, J = 5.29 Hz, 1H), 3.57-3.68 (m, 3H), 3.20-3.26 (m, 2H), 2.95-3.06 (m, 2H), 2.51-2.65 (m, 1H), 2.15-2.22 (m, 1H), 1.82-1.92 (m, 1H) | — | — |
| 529 | 600 MHz DMSO-d$_6$ | 7.46 (dd, J = 7.51, 11.09 Hz, 1H), 7.38 (dd, J = 7.32, 10.74 Hz, 1H), 4.95-5.08 (m, 2H), 4.28-4.38 (m, 1H), 3.99 (br d, J = 13.31 Hz, 1H), 3.46-3.55 (m, 2H), 3.24-3.30 (m, 4H), 3.11-3.23 (m, 1H), 2.93-3.10 (m, 2H), 2.68-2.82 (m, 3H), 2.11 (ddd, J = 4.48, 8.31, 12.59 Hz, 1H), 1.89 (quin, J = 6.79 Hz, 2H), 1.68-1.82 (m, 5H), 1.64 (dt, J = 3.43, 12.26 Hz, 1H), 1.35-1.45 (m, 1H) | — | — |
| 530 | 600 MHz DMSO-d$_6$ | 7.40-7.48 (m, 1H), 7.31-7.40 (m, 1H), 4.94-5.09 (m, 2H), 3.73-3.91 (m, 2H), 3.42-3.57 (m, 1H), 3.08-3.22 (m, 3H), 2.97-3.05 (m, 3H), 2.79 (tt, J = 8.44, 12.15 Hz, 2H), 2.33-2.48 (m, 1H), 2.01-2.16 (m, 1H), 1.86-1.98 (m, 1H), 1.68-1.84 (m, 2H), 1.58-1.66 (m, 1H) | — | — |
| 531 | 600 MHz DMSO-d$_6$ | 7.46 (t, J = 9.14 Hz, 1H), 7.41 (t, J = 8.98 Hz, 1H), 5.00-5.12 (m, 2H), 4.35-4.46 (m, 1H), 3.82 (br s, 1H), 3.49-3.82 (m, 7H), 3.23-3.30 (m, 1H), 2.94-3.11 (m, 2H), 2.79 (dd, J = 8.06, 12.57 Hz, 1H), 2.06-2.17 (m, 1H), 2.00 (br s, 1H), 1.73-1.92 (m, 2H), 0.71-0.80 (m, 4H) | — | — |
| 532 | 600 MHz DMSO- | 7.46 (dd, J = 7.47, 11.13 Hz, 1H), 7.37 (dd, J = 7.40, 10.74 Hz, 1H), 7.30 (br d, J = 5.37 Hz, 1H), 6.82 (br | | |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | | s, 1H), 4.95-5.06 (m, 2H), 4.31-4.45 (m, 1H), 4.22-4.30 (m, 1H), 3.97 (br d, J = 13.16 Hz, 1H), 3.10-3.22 (m, 2H), 2.91-3.09 (m, 3H), 2.66-2.82 (m, 2H), 2.35-2.47 (m, 1H), 2.00-2.16 (m, 1H), 1.77-1.85 (m, 2H), 1.71-1.77 (m, 1H), 1.56-1.68 (m, 1H), 1.36-1.44 (m, 1H) | | |
| 533 | 600 MHz DMSO-d$_6$ | 7.36 (t, J = 9.19 Hz, 1H), 6.93 (s, 1H), 6.89 (s, 1H), 6.80 (dt, J = 7.32, 10.20 Hz, 1H), 4.27-4.45 (m, 1H), 3.63-3.75 (m, 2H), 3.59 (br d, J = 11.83 Hz, 1H), 3.11-3.25 (m, 1H), 2.98-2.74-2.92 (m, 3H), 1.90-2.05 (m, 1H), 1.58-1.72 (m, 2H), 1.44 (d, J = 7.08 Hz, 3H), 1.36 (d, J = 7.24 Hz, 3H) | — | — |
| 534 | 600 MHz DMSO-d$_6$ | 7.77 (br dd, J = 4.44, 7.32 Hz, 1H), 7.46 (dd, J = 7.43, 11.09 Hz, 1H), 7.37 (dd, J = 7.36, 10.70 Hz, 1H), 4.94-5.07 (m, 2H), 4.32-4.44 (m, 1H), 4.24-4.31 (m, 1H), 3.98 (br d, J = 13.23 Hz, 1H), 3.26 (br s, 1H), 3.09-3.21 (m, 1H), 2.92-3.07 (m, 2H), 2.66-2.81 (m, 2H), 2.58 (d, J = 4.59 Hz, 3H), 2.32-2.47 (m, 2H), 2.10 (br dd, J = 3.54, 13.20 Hz, 1H), 1.57-1.86 (m, 4H), 1.33-1.46 (m, 1H) | — | — |
| 535 | 600 MHz DMSO-d$_6$ | 7.32-7.49 (m, 2H), 4.89-5.05 (m, 2H), 4.34-4.45 (m, 1H), 3.69-3.85 (m, 2H), 3.16-3.27 (m, 1H), 2.95-3.12 (m, 4H), 2.72-2.88 (m, 1H), 1.98-2.16 (m, 2H), 1.86 (br d, J = 1.71 Hz, 4H), 1.70-1.84 (m, 3H), 1.40-1.59 (m, 2H) | — | — |
| 536 | 600 MHz DMSO-d$_6$ | 7.46 (dd, J = 7.47, 11.13 Hz, 1H), 7.38 (dd, J = 7.36, 10.70 Hz, 1H), 4.95-5.08 (m, 2H), 4.35-4.44 (m, 3H), 3.98 (br d, J = 13.31 Hz, 1H), 3.49 (br s, 2H), 3.38-3.45 (m, 3H), 3.16-3.28 (m, 2H), 2.91-3.04 (m, 3H), 2.71-2.83 (m, 2H), 1.97-2.15 (m, 1H), 1.73-1.91 (m, 1H), 1.57-1.70 (m, 4H), 1.51 (br s, 2H), 1.36-1.46 (m, 3H) | — | — |
| 537 | 600 MHz DMSO-d$_6$ | 7.46 (dd, J = 7.43, 11.09 Hz, 1H), 7.38 (dd, J = 7.40, 10.74 Hz, 1H), 4.95-5.08 (m, 2H), 4.28-4.39 (m, 1H), 3.99 (br d, J = 13.39 Hz, 1H), 3.52 (br t, J = 5.99 Hz, 2H), 3.37-3.44 (m, 2H), 3.25-3.30 (m, 1H), 3.13-3.25 (m, 2H), 2.94-3.05 (m, 2H), 2.85-2.93 (m, 1H), 2.70-2.85 (m, 2H), 2.11 (ddd, J = 4.44, 8.19, 12.51 Hz, 1H), 1.74-1.84 (m, 2H), 1.63-1.72 (m, 5H), 1.58 (quin, J = 5.90 Hz, 2H), 1.40-1.53 (m, 5H) | — | — |
| 538 | 600 MHz DMSO-d$_6$ | 7.47 (dd, J = 7.43, 11.17 Hz, 1H), 7.31 (dd, J = 7.28, 10.70 Hz, 1H), 5.03 (br s, 2H), 4.31-4.46 (m, 2H), 3.55-3.71 (m, 4H), 3.34-3.42 (m, 4H), 3.21-3.28 (m, 3H), 3.04-3.20 (m, 2H), 2.92-3.03 (m, 2H), 2.69-2.81 (m, 1H), 2.26-2.40 (m, 2H), 1.99-2.14 (m, 1H), 1.70-1.86 (m, 1H) | — | — |
| 539 | 600 MHz DMSO-d$_6$ | 7.46 (dd, J = 7.47, 11.13 Hz, 1H), 7.38 (dd, J = 7.40, 10.74 Hz, 1H), 5.01 (dq, J = 9.61, 17.43 Hz, 2H), 4.43 (td, J = 4.02, 7.61 Hz, 1H), 4.31-4.38 (m, 1H), 4.29 (br s, 1H), 3.98 (br d, J = 13.23 Hz, 1H), 3.83-3.92 (m, 1H), 3.15-3.29 (m, 2H), 2.92-3.04 (m, 4H), 2.73-2.81 (m, 2H), 2.51-2.62 (m, 1H), 2.06-2.15 (m, 1H), 1.71-1.88 (m, 4H), 1.59-1.71 (m, 4.H), 1.39 (br s, 2H), 1.09-1.17 (m, 1H), 0.90 (br d, J = 6.38 Hz, 2H), 0.85 (br d, J = 6.46 Hz, 2H) | — | — |
| 540 | 600 MHz DMSO-d$_6$ | 7.46 (t, J = 9.12 Hz, 1H), 7.40 (t, J = 9.00 Hz, 1H), 5.00-5.11 (m, 2H), 4.33-4.44 (m, 1H), 3.51-3.63 (m, 5H), 3.43-3.49 (m, 3H), 3.23-3.30 (m, 1H), 2.94-3.06 (m, 2H), 2.79 (dd, J = 8.06, 12.57 Hz, 1H), 2.02-2.17 (m, 4H), 1.75-1.93 (m, 2H) | — | — |
| 541 | 600 MHz DMSO-d$_6$ | 7.47 (t, J = 9.15 Hz, 1H), 7.30-7.41 (m, 1H), 4.99-5.17 (m, 2H), 4.30-4.44 (m, 1H), 4.06-4.15 (m, 1H), 3.85-3.93 (m, 1H), 3.71-3.79 (m, 1H), 3.45-3.64 (m, 2H), 3.35-3.42(m, 1H), 3.17 (d, J = 4.98 Hz, 1H), 3.05-3.13 (m, 1H), 2.93-3.04 (m, 2H), 2.69-2.80 (m, | | |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 542 | 600 MHz DMSO-d$_6$ | 1H), 2.30-2.47 (m, 2H), 2.02-2.13 (m, 2H), 1.91-1.96 (m, 1H), 1.74-1.90 (m, 4H), 1.46-1.54 (m, 1H) 7.46 (dd, J = 7.47, 11.13 Hz, 1H), 7.38 (dd, J = 7.32, 10.74 Hz, 1H), 4.95-5.07 (m, 2H), 4.67 (spt, J = 6.76 Hz, 1H), 4.29-4.37 (m, 1H), 4.25 (td, J = 3.24, 6.52 Hz, 1H), 3.99 (br d, J = 13.47 Hz, 1H), 3.17-3.35 (m, 1H), 2.92-3.05 (m, 3H), 2.86 (s, 2H), 2.69-2.83 (m, 2H), 2.66 (s, 1H), 2.06-2.16 (m, 1H), 1.74-1.91 (m, 3H), 1.59-1.70 (m, 3H), 1.35-1.47 (m, 1H), 1.16 (dd, J = 2.57, 6.31 Hz, 3H), 1.02 (dd, J = 3.58, 6.62 Hz, 3H) | — | — |
| 543 | 600 MHz DMSO-d$_6$ | 7.47-7.55 (m, 1H), 7.26-7.33 (m, 1H), 5.06-5.14 (m, 2H), 4.38-4.56 (m, 2H), 4.11-4.27 (m, 1H), 3.36-3.46 (m, 1H), 3.11-3.28 (m, 3H), 2.93-3.09 (m, 2H), 2.79 (br s, 1H), 1.99-2.16 (m, 2H), 1.74 (br t, J = 9.42 Hz, 1H), 0.98 (d, J = 6.54 Hz, 3H), 0.83 (dd, J = 2.34, 6.62 Hz, 3H) | — | — |
| 544 | 600 MHz DMSO-d$_6$ | 6.80-6.88 (m, 1H), 6.56-6.63 (m, 1H), 5.03-5.14 (m, 2H), 4.38-4.53 (m, 1H), 4.30-4.37 (m, 1H), 4.23 (q, J = 9.52 Hz, 2H), 3.73-3.77 (m, 3H), 3.24 (s, 3H), 2.92-3.04 (m, 3H), 2.72-2.82 (m, 1H), 2.03-2.13 (m, 1H), 1.73-1.90 (m, 1H) | B | SFC: Chiralpak IC, 20% methanol. Peak 1 |
| 545 | 600 MHz DMSO-d$_6$ | 6.83 (dd, J = 2.18, 9.42 Hz, 1H), 6.61 (dd, J = 2.18, 11.99 Hz, 1H), 4.96-5.07 (m, 2H), 4.34-4.44 (m, 1H), 3.80 (s, 3H), 3.63-3.70 (m, 2H), 3.59 (br d, J = 4.83 Hz, 4H), 3.40-3.52 (m, 3H), 3.22-3.28 (m, 1H), 2.94-3.11 (m, 2H), 2.77 (dd, J = 8.49, 12.53 Hz, 1H), 2.02-2.19 (m, 1H), 1.75-1.84 (m, 1H) | B | SFC: Chiralpak IC, 35% methanol Peak 1 |
| 546 | 600 MHz DMSO-d$_6$ | 6.74 (dd, J = 2.26, 8.95 Hz, 1H), 6.57 (dd, J = 2.22, 12.18 Hz, 1H), 4.94-5.02 (m, 2H), 4.35-4.43 (m, 1H), 3.89 (s, 3H), 3.61-3.70 (m, 2H), 3.59 (br s, 3H), 3.36-3.53 (m, 3H), 3.16-3.28 (m, 2H), 2.92-3.02 (m, 2H), 2.74 (dd, J = 8.17, 12.46 Hz, 1H), 1.98-2.14 (m, 1H), 1.74-1.86 (m, 1H) | B | SFC: Chiralpak IC, 35% methanol Peak 2 |
| 547 | 500 MHz, METHANOL-d4 | 7.35 (dd, J = 7.53, 10.64 Hz, 1H), 7.01 (dd, J = 6.88, 10.25 Hz, 1H), 5.38 (t, J = 10.12 Hz, 1H), 4.34-4.52 (m, 1H), 3.59-3.69 (m, 1H), 3.55 (dt, J = 7.40, 9.67 Hz, 1H), 3.41-3.51 (m, 2H), 3.05-3.22 (m, 2H), 2.94 (dd, J = 8.82, 12.46 Hz, 1H), 2.79-2.87 (m, 1H), 2.61-2.70 (m, 1H), 2.37-2.48 (m, 1H), 2.18-2.30 (m, 1H), 1.91-2.03 (m, 1H), 0.80-0.94 (m, 4H) | B | SC: Regis Whelk-O, 30% IPA, Peak 1 |
| 548 | 500 MHz, CHLOROFORM-d | 7.39 (dd, J = 7.27, 10.64 Hz, 1H), 6.69 (dd, J = 7.01, 9.86 Hz, 1H), 5.21 (t, J = 9.99 Hz, 1H), 4.27-4.46 (m, 2H), 4.04-4.16 (m, 2H), 3.48-3.70 (m, 6H), 3.14-3.24 (m, 1H), 2.96-3.11 (m, 2H), 2.53-2.63 (m, 1H), 2.41 (qd, J = 9.54, 13.43 Hz, 1H), 2.18-2.26 (m, 1H), 1.92-2.08 (m, 2H), 1.69-1.91 (m, 3H) | B | SC: Chiralpak IC, 20% methanol, Peak 1 |
| 549 | 500 MHz, METHANOL-d4 | 7.36 (dd, J = 7.27, 10.64 Hz, 1H), 7.02 (dd, J = 7.01, 10.38 Hz, 1H), 5.39 (t, J = 10.12 Hz, 1H), 4.35-4.53 (m, 1H), 3.64 (dt, J = 1.04, 9.73 Hz, 1H), 3.50-3.60 (m, 2H), 3.41 (br dd, J = 5.19, 7.27 Hz, 1H), 3.11-3.21 (m, 2H), 2.93 (dd, J = 8.56, 12.46 Hz, 1H), 2.79-2.87 (m, 1H), 2.57-2.67 (m, 1H), 2.42 (qd, J = 9.87, 12.94 Hz, 1H), 2.17-2.30 (m, 1H), 1.94-2.04 (m, 1H), 0.78-0.94 (m, 4H) | B | SC: Regis Whelk-O, 30% IPA, Peak 2 |
| 550 | 500 MHz, CHLOROFORM-d | 7.39 (dd, J = 7.40, 10.51 Hz, 1H), 6.69 (dd, J = 6.75, 9.86 Hz, 1H), 5.19 (t, J = 9.86 Hz, 1H), 4.35-4.47 (m, 2H), 4.02-4.19 (m, 2H), 3.40-3.71 (m, 6H), 3.16-3.38 (m, 2H), 2.89 (dd, J = 8.69, 12.59 Hz, 1H), 2.58 (dddd, J = 1.30, 7.72, 9.34, 13.30 Hz, 1H), 2.40 (qd, J = 9.68, 13.27 Hz, 1H), 2.16-2.32 (m, 1H), 1.90-2.04 (m, 2H), 1.72-1.90 (m, 3H) | B | SC: Chiralpak IC, 2.0% methanol, Peak 2 |
| 551 | 600 MHz, DMSO-d$_6$ | 7.46-7.56 (m, 2H), 7.38-7.45 (m, 1H), 5.56 (s, 2H), 4.32-4.50 (m, 1H), 3.37-3.51 (m, 2H), 3.04-3.12 (m, 1H), 2.94-3.04 (m, 1H), 2.80-2.90 (m, 1H), 2.07-2.17 (m, 1H), 1.73-1.85 (m, 1H) | — | — |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 552 | 500 MHz, METHANOL-d$_4$ | 7.06-7.14 (m, 1H), 6.80-6.91 (m, 1H), 5.76 (s, 2H), 4.54-4.72 (m, 1H), 3.66-3.79 (m, 1H), 3.52-3.61 (m, 1H), 3.41-3.52 (m, 1H), 3.32 (t, J = 1.62 Hz, 3H), 3.15-3.24 (m, 1H), 3.07-3.15 (m, 1H), 2.22-2.34 (m, 1H), 1.93-2.09 (m, 1H) | B | Regis Whelk-O s, s, 25% MeOH, peak 2 |
| 553 | 600 MHz, DMSO-d$_6$ | 7.46-7.63 (m, 2H), 5.68-5.79 (m, 2H), 4.32-4.52 (m, 1H), 3.37-3.47 (m, 2H), 2.98-3.11 (m, 2H), 2.79-2.88 (m, 1H), 2.62-2.69 (m, 3H), 2.07-2.17 (m, 1H), 1.75-1.85 (m, 1H) | — | — |
| 554 | 500 MHz, METHANOL-d$_4$ | 7.54-7.67 (m, 2H), 7.43-7.53 (m, 1H), 5.21 (s, 2H), 4.10-4.57 (m, 3H), 3.52-3.62 (m, 1H), 3.39-3.47 (m, 1H), 3.35 (s, 3H), 3.13 (m, 2H), 2.92-3.06 (m, 1H), 2.12-2.28 (m, 1H), 1.86-2.03 (m, 1H) | F | Chiralpak AD-H, 15% MeOH/DEA, peak 1 |
| 555 | 500 MHz, METHANOL-d$_4$ | 8.81 (s, 2H), 8.16 (t, J = 2.34 Hz, 1H), 7.58 (dd, J = 2.59, 8.43 Hz, 1H), 5.54 (s, 2H), 4.36-4.56 (m, 1H), 3.68-3.79 (m, 1H), 3.58-3.68 (m, 1H), 3.10-3.25 (m, 2H), 2.96-3.10 (m, 1H), 2.10-2.27 (m, 1H), 1.81-1.97 (m, 1H) | F | Chiralpak IC, 40% MeOH with 0.2% DEA, peak 2 |
| 556 | 600 MHz, DMSO-d$_6$ | 8.98 (d, J = 1.79 Hz, 1H), 8.29-8.34 (m, 1H), 7.53 (d, J = 8.25 Hz, 1H), 7.01-7.06 (m, 1H), 6.97 (td, J = 10.59, 2.18 Hz, 1H), 5.57 (s, 2H), 4.32-4.40 (m, 1H), 3.36-3.51 (m, 2H), 3.31 (s, 3H), 2.98-3.09 (m, 1H), 2.86-2.95 (m, 1H), 2.80 (dd, J = 12.46, 8.49 Hz, 1H), 2.01-2.09 (m, 1H), 1.68-1.76 (m, 1H) | B | Lux Cellulose-2, 30% MeOH, peak 2 |
| 557 | 500 MHz, METHANOL-d$_4$ | 7.2.1-7.40 (m, 1H), 7.07-7.17 (m, 1H), 6.81-6.93 (m, 1H), 5.83-5.96 (m, 2H), 4.63-4.80 (m, 1H), 3.73-3.86 (m, 1H), 3.54-3.72 (m, 2H), 3.12-3.25 (m, 2H), 2.24-2.36 (m, 1H), 1.98-2.10 (m, 1H) | B | Regis Whelk-O s, s, 10% MeOH, peak 2 |
| 558 | 500 MHz, METHANOL-d$_4$ | 7.00-7.08 (m, 1H), 6.74-6.84 (m, 1H), 5.19 (s, 2H), 4.38-4.56 (m, 1H), 4.06-4.28 (m, 3H), 3.48-3.58 (m, 1H), 3.38-3.46 (m, 1H), 3.33 (s, 3H), 3.14-3.20 (m, 1H), 2.88-3.02 (m, 1H), 2.14-2.27 (m, 1H), 1.88-2.00 (m, 1H) | F | Regis Whelk-O s, s, 15% MeOH, peak 1 |
| 559 | 500 MHz, METHANOL-d$_4$ | 7.39-7.50 (m, 1H), 7.22-7.34 (m, 1H), 7.09-7.23 (m, 1H), 5.10 (s, 2H), 4.11-4.53 (m, 3H), 3.44-3.55 (m, 1H), 3.34-3.41 (m, 1H), 3.34 (s, 3H), 3.05-3.16 (m, 2H), 2.87-2.98 (m, 1H), 2.12-2.25 (m, 1H), 1.82-2.00 (m, 1H) | F | Chiralpak AD-H, 25% MeOH/DEA, peak 1 |
| 560 | 600 MHz DMSO-d$_6$ | 7.42-7.68 (m, 3H), 5.84-5.98 (m, 2H), 4.30-4.51 (m, 1H), 3.34-3.49 (m, 2H), 3.04-3.13 (m, 1H), 2.93-3.02 (m, 1H), 2.79-2.90 (m, 1H), 2.08-2.18 (m, 1H), 1.73-1.86 (m, 1H) | — | — |
| 561 | 500 MHz, METHANOL-d$_4$ | 7.43-7.54 (m, 1H), 7.16-7.27 (m, 1H), 6.94-7.04 (m, 1H), 5.75 (s, 2H), 4.54-4.74 (m, 1H), 3.66-3.75 (m, 1H), 3.51-3.59 (m, 1H), 3.43-3.49 (m, 1H), 3.28-3.36 (m, 3H), 3.06-3.24 (m, 2H), 2.22-2.39 (m, 1H), 1.96-2.14 (m, 1H) | B | Chiralpak AZ-H, 30% MeOH, peak 2 |
| 562 | 600 MHz, DMSO-d$_6$ | 8.92-9.00 (m, 1H), 8.26-8.35 (m, 1H), 7.44-7.57 (m, 2H), 7.32-7.42, (m, 1H), 5.55 (s, 2H), 4.29-4.48 (m, 1H), 3.38-3.47 (m, 2H), 3.31 (s, 3H), 2.99-3.09 (m, 1H), 2.89-2.98 (m, 1H), 2.75-2.84 (m, 1H), 2.00-2.11 (m, 1H), 1.65-1.78 (m, 1H) | — | — |
| 563 | 600 MHz, DMSO-d$_6$ | 7.64 (s, 1H), 7.56 (d, J = 8.33 Hz, 1H), 7.40 (dd, J = 8.33, 1.25 Hz, 1H), 5.06-5.15 (m, 2H), 4.38-4.46 (m, 1H), 3.39-3.41 (m, 2H), 3.07-3.15 (m, 4H), 2.99 (m, 1H), 2.90 (s, 3H), 2.84 (dd, J = 12.69, 8.17 Hz, 1H), 2.01-2.17 (m, 1H), 1.74-1.85 (m, 1H) | B | Chiralpak IC, 15% MeOH, peak 1 |
| 564 | 600 MHz, DMSO-d$_6$ | 7.47-7.52 (m, 1H), 7.42-7.46 (m, 1H), 6.07-6.14 (m, 1H), 5.34 (s, 2H), 4.31-4.55 (m, 1H), 3.40-3.51 (m, 2H), 2.98-3.12 (m, 2H), 2.79-2.89 (m, 1H), 2.36 (s, 3H), 2.07-2.18 (m, 1H), 1.75-1.85 (m, 1H) | — | — |
| 565 | 600 MHz, DMSO-d$_6$ | 7.02-7.09 (m, 1H), 6.90-6.98 (m, 1H), 4.94-5.05 (m, 2H), 4.31-4.49 (m, 1H), 3.32 (s, 2H), 3.12 (s, 3H), 2.93-3.07 (m, 2H), 2.88 (s, 3H), 2.75-2.82 (m, 1H), 2.04-2.18 (m, 1H), 1.77-1.83 (m, 1H) | B | Phenomenex CEL 2, 25% MeOH, peak 1 |

TABLE 6-continued

Characterization data for compounds made following schemes 9-10
The column "Separation Stage" indicates after which
process step regioisomers formed due to asymmetric
benzimidazole substitution at R$^1$ in Scheme
10 were separated during the preparation of the tabulated
final compound. (I = after preparation of the
N-aralkyl-2-piperidinyl-benzimidazole intermediate
in the first step of Scheme 10 (where at least one R$^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| 566 | 600 MHz, DMSO-d$_6$ | 7.35-7.44 (m, 1H), 7.07-7.13 (m, 1H), 6.84-6.95 (m, 1H), 4.90-5.04 (m, 2H), 4.31-4.49 (m, 1H), 3.24-3.25 (m, 2H), 3.12 (s, 3H), 2.93-3.03 (m, 2H), 2.89 (s, 3H), 2.72-2.81 (m, 1H), 2.03-2.17 (m, 1H), 1.73-1.86 (m, 1H) | B | Phenomenex CEL 2, 25% MeOH, peak 1 |
| 567 | 600 MHz, DMSO-d$_6$ | 7.49-7.54 (m, 1H), 7.40-7.46 (m, 1H), 6.77-6.87 (m, 1H), 5.40 (s, 2H), 4.30-4.48 (m, 1H), 3.37-3.50 (m, 2H), 3.03-3.13 (m, 1H), 2.91-3.00 (m, 1H), 2.80-2.88 (m, 1H), 2.26 (d, J = 1.09 Hz, 3H), 2.06-2.15 (m, 1H), 1.72-1.81 (m, 1H) | — | — |
| 568 | 600 MHz, DMSO-d$_6$ | 7.47-7.57 (m, 2H), 7.18-7.28 (m, 1H), 5.59 (s, 2H), 4.31-4.48 (m, 1H), 3.38-3.51 (m, 2H), 3.03-3.12 (m, 1H), 2.92-3.01 (m, 1H), 2.79-2.88 (m, 1H), 2.32 (s, 3H), 2.04-2.17 (m, 1H), 1.73-1.81 (m, 1H) | — | — |
| 569 | 600 MHz, DMSO-d$_6$ | 7.45-7.53 (m, 1H), 7.35-7.42 (m, 1H), 6.96-7.06 (m, 1H), 5.89 (s, 2H), 4.28-4.47 (m, 1H), 3.32 (m, 2H), 2.97-3.06 (m, 1H), 2.87-2.95 (m, 1H), 2.73-2.82 (m, 1H), 2.04-2.14 (m, 1H), 1.67-1.77 (m, 1H) | B | Chiralcel OD-H, 15% isopropanol, peak 1 |
| 570 | 500 MHz, METHANOL-d$_4$ | 7.42-7.52 (m, 1H), 7.09-7.21 (m, 2H), 5.11 (s, 2H), 4.09-4.53 (m, 3H), 3.46-3.56 (m, 1H), 3.35-3.45 (m, 1H), 3.34 (s, 3H), 3.05-3.15 (m, 2H), 2.87-2.98 (m, 1H), 2.13-2.26 (m, 1H), 1.85-1.97 (m, 1H) | F | Chiralpak AD-H 25% MeOH/DEA, peak 2 |
| 571 | 600 MHz, DMSO-d$_6$ | 7.48-7.57 (m, 2H), 5.59 (s, 2H), 4.32-4.50 (m, 1H), 3.39-3.46 (m, 2H), 3.02-3.10 (m, 1H), 2.94-3.02 (m, 1H), 2.76-2.88 (m, 1H), 2.47 (s, 3H), 2.06-2.17 (m, 1H), 1.73-1.82 (m, 1H) | — | — |
| 572 | 600 MHz, DMSO-d$_6$ | 7.48-7.56 (m, 1H), 7.39-7.47 (m, 1H), 5.44 (s, 2H), 4.31-4.50 (m, 1H), 3.35-3.48 (m, 2H), 3.02-3.13 (m, 1H), 2.91-3.01 (m, 1H), 2.78-2.89 (m, 1H), 2.57 (s, 3H), 2.06-2.16 (m, 1H), 1.72-1.80 (m, 1H) | — | — |
| 573 | 500 MHz, METHANOL-d$_4$ | 7.47-7.56 (m, 1H), 7.10-7.37 (m, 2H), 6.99-7.07 (m, 1H), 5.90 (s, 2H), 4.65-4.84 (m, 1H), 3.75-3.84 (m, 1H), 3.53-3.70 (m, 2H), 3.13-3.23 (m, 2H), 2.26-2.37 (m, 1H), 2.00-2.11 (m, 1H) | B | Chiralcel OD-H, 15% isopropanol, peak 1 |
| 574 | 500 MHz, METHANOL-d$_4$ | 8.18-8.24 (m, 1H), 7.68-7.75 (m, 1H), 5.73-5.82 (m, 2H), 4.54-4.74 (m, 1H), 3.77-3.88 (m, 1H), 3.41-3.77 (m, 2H), 3.32 (td, J = 1.62, 3.24 Hz, 1H), 3.06-3.22 (m, 1H), 2.68-2.79 (m, 3H), 2.21 (s, 1H), 1.90-2.05 (m, 1H) | B | Chiralpak IC, 35% MeOH, peak 1 |
| 575 | 600 MHz, DMSO-d$_6$ | 7.47-7.55 (m, 1H), 7.36-7.46 (m, 1H), 5.35 (s, 2H), 4.32-4.48 (m, 1H), 3.39-3.49 (m, 2H), 3.03-3.12 (m, 1H), 2.93-3.02 (m, 1H), 2.79-2.89 (m, 1H), 2.18 (s, 3H), 2.05-2.14 (m, 1H), 1.97 (s, 3H), 1.70-1.82 (m, 1H) | — | — |
| 576 | 600 MHz, DMSO-d$_6$ | 7.20-7.24 (m, 1H), 7.12-7.19 (m, 1H), 6.86-6.95 (m, 1H), 4.91-5.05 (m, 2H), 4.31-4.48 (m, 1H), 3.33-3.39 (m, 2H), 3.12 (s, 3H), 2.93-3.06 (m, 2H), 2.89 (s, 3H), 2.74-2.82 (m, 1H), 2.05-2.15 (m, 1H), 1.74-1.82, (m, 1H) | B | Chiralpak IC, 15% MeOH, peak 2 |
| 577 | 600 MHz, DMSO-d$_6$ | 7.42-7.54 (m, 2H), 5.45 (s, 2H), 4.29-4.49 (m, 1H), 3.37-3.50 (m, 2H), 3.03-3.13 (m, 1H), 2.92 (m, 3H), 2.77-2.87 (m, 1H), 2.06-2.17 (m, 1H), 1.71-1.80 (m, 1H), 1.24 (t, J = 7.55 Hz, 3H) | — | — |
| 578 | 600 MHz, DMSO-d$_6$ | 7.43-7.56 (m, 2H), 5.37-5.45 (m, 2H), 4.31-4.49 (m, 1H), 3.36-3.47 (m, 2H), 3.03-3.11 (m, 1H), 2.90-2.99 (m, 1H), 2.75-2.86 (m, 1H), 2.29-2.37 (m, 1H), 2.05-2.17 (m, 1H), 1.69-1.82 (m, 1H), 1.20-1.27 (m, 3H), 1.03-1.10 (m, 3H) | — | — |
| 579 | 600 MHz, DMSO-d$_6$ | 7.45-7.58 (m, 2H), 6.28-6.36 (m, 1H), 5.45 (s, 2H), 4.32-4.51 (m, 1H), 3.39-3.47 (m, 1H), 3.35-3.39 (m, 1H), 3.04-3.13 (m, 1H), 2.94-3.03 (m, 1H), 2.79-2.89 (m, 1H), 2.19 (s, 3H), 2.08-2.16 (m, 1H), 1.78-1.84 (m, 1H) | — | — |
| 580 | 500 MHz, METHANOL-d$_4$ | 7.70-7.83 (m, 1H), 7.42-7.53 (m, 1H), 7.27-7.41 (m, 1H), 5.21 (s, 2H), 4.13-4.56 (m, 3H), 3.51-3.62 (m, 1H), 3.40-3.48 (m, 1H), 3.37 (s, 3H), 3.12 (s, 2H), | F | Chiralpak AD-H, 15% MeOH/DEA, peak 2 |

TABLE 6-continued

Characterization data for compounds made following schemes 9-10
The column "Separation Stage" indicates after which
process step regioisomers formed due to asymmetric
benzimidazole substitution at R¹ in Scheme
10 were separated during the preparation of the tabulated
final compound. (I = after preparation of the
N-aralkyl-2-piperidinyl-benzimidazole intermediate
in the first step of Scheme 10 (where at least one R¹ is not
hydrogen); B = prior to boc deprotection; or F = final compound).

| Ex. # | Freq., Solvent | ¹HNMR Data (δ ppm) | Separation Stage | SFC Isomer Separation Conditions |
|---|---|---|---|---|
| | | 2.93-3.05 (m, 1H), 2.14-2.30 (m, 1H), 1.88-2.03 (m, 1H) | | |
| 581 | 600 MHz, DMSO-d₆ | 7.47-7.61 (m, 2H), 5.48-5.60 (m, 2H), 4.30-4.49 (m, 1H), 3.37-3.46 (m, 2H), 2.99-3.08 (m, 1H), 2.90-2.98 (m, 1H), 2.78-2.86 (m, 1H), 2.18-2.25 (m, 1H), 2.06-2.16 (m, 1H), 1.72-1.81 (m, 1H), 1.08-1.15 (m, 2H), 0.91-0.99 (m, 2H) | — | — |
| 582 | 500 MHz, METHANOL-d₄ | 7.33-7.40 (m, 1H), 7.16-7.25 (m, 1H), 6.92-7.01 (m, 1H), 5.70-5.80 (m, 2H), 4.48-4.68 (m, 1H), 3.65-3.75 (m, 1H), 3.50-3.59 (m, 1H), 3.36 (s, 3H), 3.30-3.34 (m, 1H), 3.14-3.25 (m, 1H), 3.02-3.12 (m, 1H), 2.22-2.34 (m, 1H), 1.93-2.07 (m, 1H) | B | Chiralpak AZ-H, 30% MeOH, peak 1 |
| 583 | 500 MHz, METHANOL-d₄ | 8.70-8.80 (m, 2H), 7.94-8.04 (m, 1H), 7.56-7.66 (m, 1H), 5.62 (s, 2H), 4.39-4.61 (m, 1H), 3.63-3.87 (m, 2H), 3.13-3.25 (m, 2H), 2.95-3.09 (m, 1H), 2.12-2.26 (m, 1H), 1.74-1.92 (m, 1H) | F | Chiralpak IC, 40% MeOH with 0.2% DEA, peak 2 |
| 584 | 600 MHz, DMSO-d₆ | 7.37-7.45 (m, 1H), 7.26-7.35 (m, 1H), 6.95-7.06 (m, 1H), 5.89 (s, 2H), 4.30-4.49 (m, 1H), 3.32-3.44 (m, 2H), 3.00-3.11 (m, 1H), 2.86-2.97 (m, 1H), 2.75-2.84 (m, 1H), 2.06-2.17 (m, 1H), 1.67-1.77 (m, 1H) | B | Chiralcel OD-H, 15% isopropanol, peak 2 |
| 585 | 600 MHz, DMSO-d₆ | 7.77-7.84 (m, 2H), 7.39-7.47 (m, 4H), 7.30 (dd, J = 9.23, 2.45 Hz, 1H), 6.95 (ddd, J = 10.02, 8.66, 2.57 Hz, 1H), 5.48-5.55 (m, 2H), 4.34-4.48 (m, 1H), 3.37-3.51 (m, 2H), 3.03-3.12 (m, 2H), 2.84 (dd, J = 12.42, 8.91 Hz, 1H), 2.52 (s, 3H), 2.12-2.21 (m, 1H), 1.79-1.97 (m, 1H) | B | Chiralcel OJ-H, 30% MeOH, peak 1 |
| 586 | 600 MHz, DMSO-d₆ | 7.46-7.55 (m, 1H), 7.26-7.35 (m, 1H), 5.45 (s, 2H), 4.30-4.49 (m, 1H), 3.39 (s, 5H), 2.96-3.11 (m, 2H), 2.78-2.88 (m, 1H), 2.26-2.32 (m, 3H), 2.06-2.18 (m, 1H), 1.77-1.86 (m, 1H) | — | — |
| 587 | 500 MHz, METHANOL-d₄ | 7.35-7.42 (m, 1H), 7.23 (s, 2H), 6.95-7.03 (m, 1H), 5.90 (s, 2H), 4.50-4.70 (m, 1H), 3.67-3.77 (m, 1H), 3.54-3.63 (m, 1H), 3.37-3.49 (m, 1H), 3.15-3.25 (m, 1H), 3.02-3.13 (m, 1H), 2.21-2.33 (m, 1H), 1.94-2.08 (m, 1H) | B | Chiralcel OD-H, 15% isopropanol, peak 2 |
| 588 | 500 MHz, METHANOL-d₄ | 7.43-7.52 (m, 1H), 7.17-7.25 (m, 1H), 6.95-7.04 (m, 1H), 5.77 (d, J = 1.95 Hz, 2H), 3.50-3.61 (m, 1H), 3.40-3.49 (m, 1H), 3.29-3.35 (m, 2H), 3.14-3.25 (m, 1H), 2.73 (s, 3H), 2.29-2.45 (m, 1H), 2.14-2.30 (m, 1H) | B | Chiralcel OD-H, 10% isopropanol, peak 1 |
| 589 | 600 MHz, DMSO-d₆ | 7.37-7.44 (m, 1H), 7.19-7.27 (m, 1H), 6.89-6.97 (m, 1H), 5.34-5.44 (m, 2H), 4.30-4.49 (m, 1H), 3.37-3.47 (m, 2H), 2.97-3.11 (m, 2H), 2.75-2.85 (m, 1H), 2.46-2.48 (m, 3H), 2.39 (s, 3H), 2.09-2.19 (m, 1H), 1.81-1.91 (m, 1H) | B | Chiralcel OJ-H, 10% isopropanol, peak 1 |
| 590 | 500 MHz, METHANOL-d₄ | 7.86-7.98 (m, 1H), 7.34-7.49 (m, 1H), 6.05 (s, 2H), 4.65-4.85 (m, 2H), 4.48-4.63 (m, 1H), 3.13-3.48 (m, 3H), 2.75 (s, 3H), 2.25-2.38 (m, 1H), 1.77-1.94 (m, 1H) | B | Chiralpak IC, 35% MeOH, peak 2 |
| 591 | 500 MHz, METHANOL-d₄ | 6.87-6.95 (m, 1H), 6.74-6.86 (m, 1H), 5.07-5.21 (m, 2H), 4.12-4.56 (m, 3H), 3.45-3.59 (m, 1H), 3.36 (s, 3H), 2.89-3.23 (m, 4H), 2.11-2.28 (m, 1H), 1.84-1.99 (m, 1H) | F | Regis Whelk-O s, s, 15% MeOH, peak 2 |
| 592 | 600 MHz, DMSO-d₆ | 7.73 (s, 1H), 7.39 (s, 2H), 5.03-5.12 (m, 2H), 4.37-4.46 (m, 1H), 3.36-3.44 (m, 2H), 3.14 (s, 3H), 2.96-3.12 (m, 2H), 2.89 (s, 3H), 2.84 (dd, J = 12.57, 8.29 Hz, 1H), 2.08-2.17 (m, 1H), 1.81-1.92 (m, 1H) | B | Chiralpak IC, 15% MeOH, peak 2 |
| 593 | 600 MHz, DMSO-d₆ | 7.76-7.83 (m, 2H), 7.39-7.46 (m, 3H), 7.36 (dd, J = 8.76, 4.71 Hz, 1H), 7.25 (dd, J = 9.73, 2.49 Hz, 1H), 6.95 (ddd, J = 9.85, 8.80, 2.53 Hz, 1H), 5.52 (s, 2H), 4.35-4.49 (m, 1H), 3.39-3.54 (m, 2H), 3.03-3.15 (m, 2H), 2.87 (dd, J = 12.42, 8.91 Hz, 1H), 2.47 (s, 3H), 2.12-2.22 (m, 1H), 1.78-1.94 (m, 1H) | B | Chiralcel OJ-H, 30% MeOH, peak 2 |
| 594 | 600 MHz, DMSO- | 7.09-7.17 (m, 1H), 6.86-6.96 (m, 1H), 4.96-5.09 (m, 2H), 4.32-4.50 (m, 1H), 3.22-3.43 (m, 2H), 3.10 (s, | B | Phenomenex CEL 2, 25% |

TABLE 6-continued

Characterization data for compounds made following schemes 9-10
The column "Separation Stage" indicates after which
process step regioisomers formed due to asymmetric
benzimidazole substitution at $R^1$ in Scheme
10 were separated during the preparation of the tabulated
final compound. (I = after preparation of the
N-aralkyl-2-piperidinyl-benzimidazole intermediate
in the first step of Scheme 10 (where at least one $R^1$ is not
hydrogen); B = prior to boc deprotection; or F = final compound).

| Ex. # | Freq., Solvent | $^1$HNMR Data (δ ppm) | Separation Stage | SFC Isomer Separation Conditions |
|---|---|---|---|---|
| | d$_6$ | 3H), 2.96-3.07 (m, 2H), 2.89 (s, 3H), 2.77-2.85 (m, 1H), 2.07-2.18 (m, 1H), 1.74-1.87 (m, 1H) | | MeOH, peak 2 |
| 595 | 600 MHz, DMSO-d$_6$ | 8.97 (d, J = 1.79 Hz, 1H), 8.32 (dd, J = 8.25, 2.34 Hz, 1H), 7.55 (d, J = 8.33 Hz, 1H), 7.17 (dd, J = 9.26, 2.18 Hz, 1H), 6.88 (J = 10.33 Hz, 1H), 5.54-5.61 (m, 2H), 4.31-4.45 (m, 1H), 3.39-3.45 (m, 2H), 3.04-3.14 (m, 1H), 2.92-3.03 (m, 1H), 2.85 (dd, J = 12.61, 8.49 Hz, 1H), 2.03-2.20 (m, 1H), 1.73-1.82 (m, 1H) | B | Lux Cellulose-2, 30% MeOH, peak 1 |
| 596 | 600 MHz, DMSO-d$_6$ | 7.28-7.34 (m, 1H), 7.20-7.26 (m, 1H), 6.90-6.98 (m, 1H), 5.40 (s, 2H), 4.33-4.49 (m, 1H), 3.40-3.53 (m, 2H), 3.01-3.14 (m, 2H), 2.80-2.89 (m, 1H), 2.45-2.48 (m, 3H), 2.39 (s, 3H), 2.10-2.21 (m, 1H), 1.80-1.89 (m, 1H) | B | Chiralcel OJ-H, 10% isopropanol, peak 2 |
| 597 | 500 MHz, METHANOL-d$_4$ | 7.33-7.40 (m, 1H), 7.16-7.26 (m, 1H), 6.93-7.04 (m, 1H), 5.77 (d, J = 1.56 Hz, 2H), 3.54-3.63 (m, 1H), 3.44-3.52 (m, 1H), 3.37-3.43 (m, 1H), 3.32 (s, 1H), 3.18-3.27 (m, 1H), 2.68-2.77 (m, 3H), 2.31-2.44 (m, 1H), 2.14-2.30 (m, 1H) | B | Chiralcel OD-H, 10% isopropanol, peak 2 |
| 598 | 500 MHz, METHANOL-d$_4$ | 7.24 (t, J = 55 Hz, 1H), 7.08-7.16 (m, 1H), 6.83-6.92 (m, 1H), 5.94 (s, 2H), 4.70-4.86 (m, 1H), 3.85-3.93 (m, 1H), 3.73-3.83 (m, 1H), 3.64-3.72 (m, 1H), 3.24 (dd, J = 10.45, 12.65 Hz, 2H), 2.25-2.38 (m, 1H), 2.08 (br dd, J = 1.36, 2.92 Hz, 1H) | B | Regis Whelk-O s, s, 10% MeOH, peak 1 |
| 599 | 500 MHz, METHANOL-d$_4$ | 7.04-7.11 (m, 1H), 6.80-6.92 (m, 1H), 5.79 (s, 2H), 4.58-4.79 (m, 1H), 3.74-3.84 (m, 1H), 3.52-3.68 (m, 2H), 3.12-3.27 (m, 2H), 2.74 (s, 3H), 2.24-2.36 (m, 1H), 1.99-2.10 (m, 1H) | B | Regis Whelk-O s, s, 25% MeOH, peak 1 |

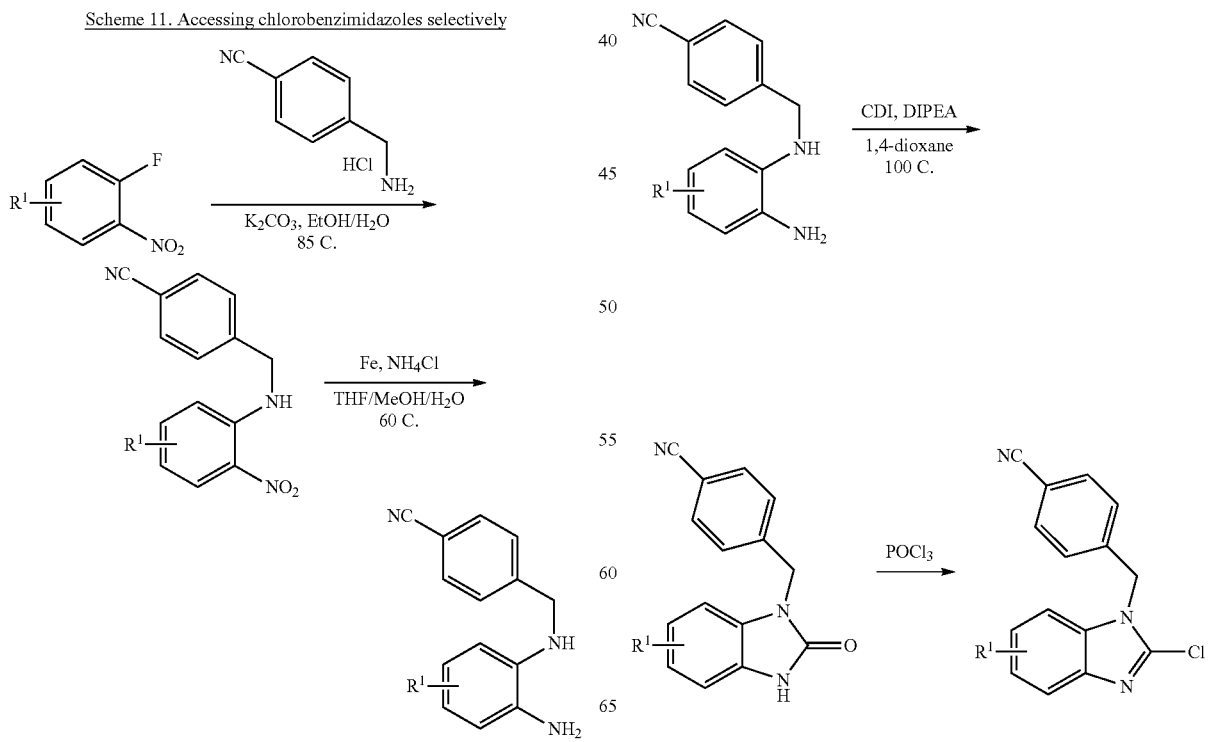

Scheme 11. Accessing chlorobenzimidazoles selectively

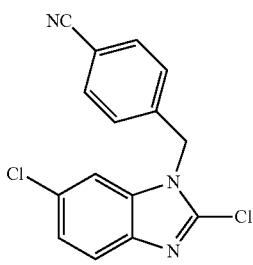 [SMILES: N#Cc1ccc(Cn2c(Cl)nc3ccc(Cl)cc32)cc1]

Intermediate 86: 4-((2,6-dichloro-1H-benzo[d]imidazol-1-yl)methyl)benzonitrile

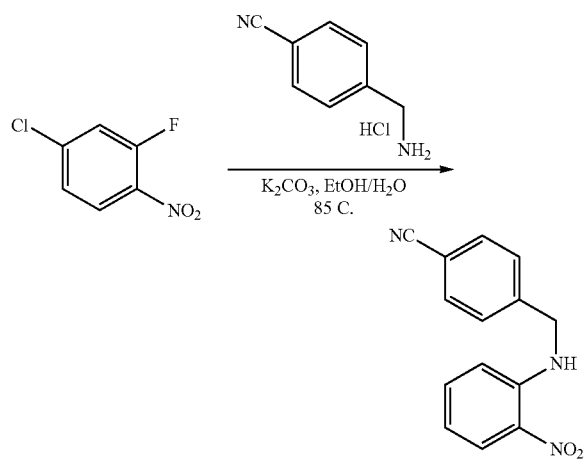

Step 1. 4-(((5-chloro-2-nitrophenyl)amino)methyl)benzonitrile

To a stirred solution of 4-chloro-2-fluoro-1-nitrobenzene (8.0 g, 45.6 mmol, 1 equiv) in ethanol (104.0 mL) and water (80.0 mL) was added 4-(aminomethyl)benzonitrile hydrochloride (8.45 g, 50.1 mmol, 1.1 equiv) followed by addition of potassium carbonate (11.34 g, 82.0 mmol, 1.8 equiv). The reaction mixture was heated to 85° C. for 10 h then stirred for 8 h at ambient temperature. After completion (monitored by TLC), the reaction mixture was diluted with water (100 mL) and solids were filtered. The obtained solid was dried under high vacuum to provide 4-(((5-chloro-2-nitrophenyl)amino)methyl)benzonitrile (9 g, 68.6% yield) as yellow solid. $^1$H NMR (400 MHz, DMSO-d$_6$): δ 8.85 (t, J=6.3 Hz, 1H), 8.08-8.13 (m, 1H), 7.86-7.79 (m, 2H), 7.56 (d, J=8.0 Hz, 2H), 6.90 (t, J=2.4 Hz, 1H), 6.77-6.66 (m, 1H), 4.76 (d, J=6.3 Hz, 2H).

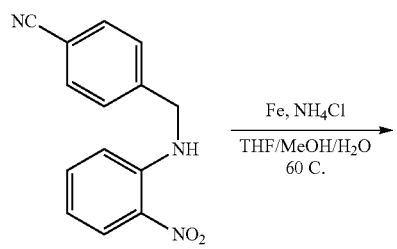

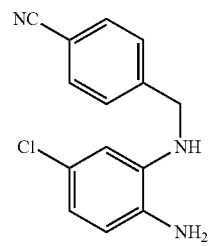

Step 2. 4-(((2-amino-5-chlorophenyl)amino)methyl)benzonitrile

To a stirred solution of 4-(((5-chloro-2-nitrophenyl)amino)methyl)benzonitrile (9.0 g, 31.3 mmol, 1.0 equiv) in mixture of tetrahydrofuran (90.0 mL), methanol (90.0 mL) and water (60.0 mL) was added iron powder (7.51 g, 135.0 mmol, 4.3 equiv) followed by ammonium chloride (7.53 g, 141.0 mmol, 4.5 equiv). The resulting reaction mixture was heated to 60° C. for 2 h. After completion (monitored by TLC), the reaction mixture was filtered through celite pad and was washed with ethyl acetate (100 mL). The filtrate was diluted with water (100 mL) and layers were separated, aqueous layer was washed with ethyl acetate (2×200 mL). The combined organic layers were washed with water (2×200 mL), brine (2×200 mL), dried over sodium sulphate, filtered and concentrate under reduced pressure to provide 4-(((2-amino-5-chlorophenyl)amino)methyl)benzonitrile (7.5 g, 93% yield) as light yellow solid which was sufficiently pure to use in the next step. $^1$H NMR (400 MHz, DMSO-d$_6$): δ 7.81 (dd, J=8.3, 2.3 Hz, 2H), 7.65-7.45 (m, 2H), 6.53 (dd, J=8.2, 2.2 Hz, 1H), 6.40 (dt, J=8.1, 2.4 Hz, 1H), 6.19 (d, J=2.4 Hz, 1H), 5.58 (t, J=7.2 Hz, 1H), 4.75 (s, 2H), 4.54-4.28 (m, 2H).

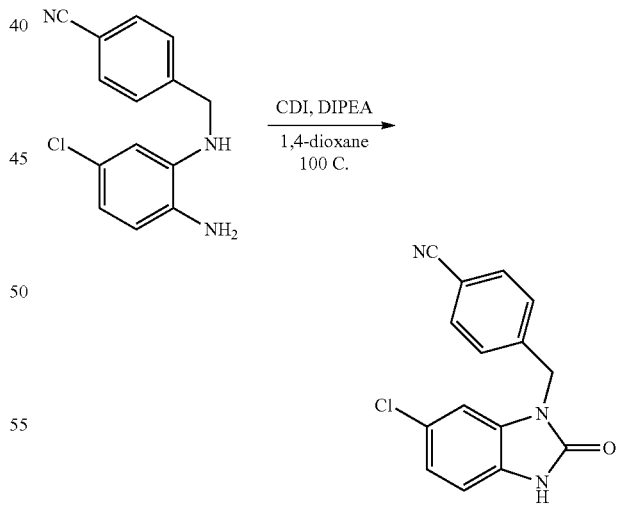

Step 3. 4-((6-chloro-2-oxo-2,3-dihydro-1H-benzo[d]imidazol-1-yl)methyl)benzonitrile To a stirred solution of 4-(((2-amino-5-chlorophenyl)amino)methyl)benzonitrile (7.5 g, 29.1 mmol, 1.0 equiv) in 1,4-dioxane (120.0 mL) was added DIPEA (7.62 mL, 43.7 mmol, 1.5 equiv) and CDI (11.80 g, 72.8 mmol, 2.5 equiv)

portion wise. The resulting reaction mixture was heated to 100° C. for 1 h. After completion (monitored by TLC), the reaction mixture was cooled to ambient temperature and slowly quenched with ice cold water (100 mL). The reaction mixture was extracted with ethyl acetate (2×150 mL). The combined organic layers were washed with water (2×150 mL) and brine solution (2×100 mL), dried over sodium sulphate, filtered and concentrate under reduced pressure to provide 4-((6-chloro-2-oxo-2,3-dihydro-1H-benzo[d]imidazol-1-yl)methyl)benzonitrile (6 g, 72.7% yield) as light brown solid which was sufficiently pure to use in next step as such. $^1$H NMR (400 MHz, DMSO-d$_6$): δ 11.21 (s, 1H), 7.86-7.79 (m, 2H), 7.54-7.40 (m, 2H), 7.23 (d, J=1.7 Hz, 1H), 7.06-6.97 (m, 2H), 5.12 (s, 2H). MS: (ESI neg. ion) m/z: 282 [M−1]

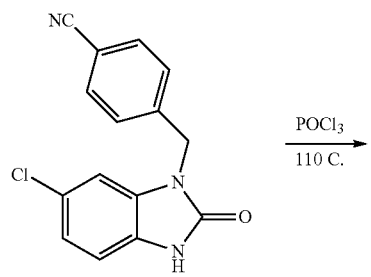

POCl$_3$
110 C.

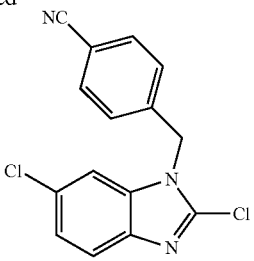

Step 4. 4-((2,6-dichloro-1H-benzo[d]imidazol-1-yl)methyl)benzonitrile

To a stirred solution of 4-((6-chloro-2-oxo-2,3-dihydro-1H-benzo[d]imidazol-1-yl)methyl)benzonitrile (6.0 g, 21.15 mmol, 1.0 equiv) in POCl3 (60.0 mL) was heated to 110° C. for 5 h. After completion (monitored by TLC), the reaction mixture was concentrated under high vacuum pressure. The obtained residue was diluted with DCM and slowly neutralized with 10% aqueous sodium bicarbonate solution at 0° C. The layers were separated and aqueous layer was extracted with DCM (2×150 mL). The combined organic layers were washed with water (200 mL), brine (200 mL), dried over sodium sulphate, filtered and concentrated under reduced pressure. The obtained crude was purified on silica gel 230-400 mesh using petroleum ether and ethyl acetate as an eluent (15-20%) to afford 4-((2,6-dichloro-1H-benzo[d]imidazol-1-yl)methyl)benzonitrile (2.5 g, 39.1% yield) as an off white solid. $^1$H NMR (400 MHz, DMSO-d$_6$): δ 7.91-7.79 (m, 3H), 7.68 (d, J=8.7 Hz, 1H), 7.39-7.28 (m, 3H), 5.67 (s, 2H). MS: (ESI pos. ion) m/z: 302.0 [M+1]

TABLE 7

Intermediates accessed using the sequence outlines in Scheme 11

| Int # | Structure | Compound Name | $^1$H NMR | MS MH+ |
|---|---|---|---|---|
| 86 | (structure) | 4-((2,6-dichloro-1H-benzo[d]imidazol-1-yl)methyl)benzonitrile | $^1$H NMR (400 MHz, DMSO-d$_6$): δ 7.91-7.79 (m, 3H), 7.68 (d, J = 8.7 Hz, 1H), 7.39-7.28 (m, 3H), 5.67 (s, 2H) | 302.0 |
| 87 | (structure) | 4-((2-chloro-6-ethoxy-1H-benzo[d]imidazol-1-yl)methyl)benzonitrile | $^1$H NMR (400 MHz, DMSO-d$_6$): δ 7.84 (dq, J = 8.5, 1.9 Hz, 2H), 7.52 (dd, J = 8.8, 1.2 Hz, 1H), 7.34 (d, J = 8.2 Hz, 2H), 7.22 (d, J = 2.3 Hz, 1H), 6.88 (dt, J = 8.8, 1.8 Hz, 1H), 5,62 (s, 2H), 4.02 (q, J = 7.0 Hz, 2H), 1.32 (t, J = 7.0 Hz, 3H) | 312.0 |

TABLE 7-continued

Intermediates accessed using the sequence outlines in Scheme 11

| Int # | Structure | Compound Name | ¹H NMR | MS MH+ |
|---|---|---|---|---|
| 88 | 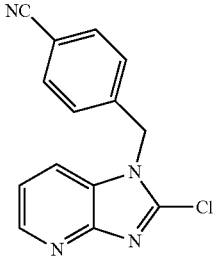 [SMILES: N#Cc1ccc(Cn2c(Cl)nc3ncccc32)cc1] | 4-((2-chloro-1H-imidazo[4,5-b]pyridin-1-yl)methyl)benzonitrile | ¹H NMR (400 MHz, DMSO-d$_6$): δ 11.74 (s, 1H), 7.93 (d, J = 5.1 Hz, 1H), 7.82 (d, J = 7.9 Hz, 2H), 7.49 (d, J = 7.8 Hz, 2H), 7.38 (d, J = 7.5 Hz, 1H), 6.99 (dd, J = 7.7, 5.1 Hz, 1H), 5.14 (s, 2H) | 251.2 |
| 89 | 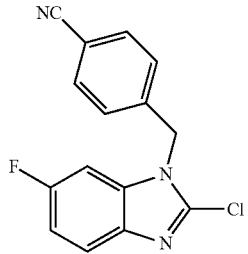 | 4-((2-chloro-6-fluoro-1H-benzo[d]imidazol-1-yl)methyl)benzonitrile | ¹H NMR (400 MHz, DMSO-d$_6$): δ 7.87-7.81 (m, 2H), 7.71-7.59 (m, 2H), 7.39-7.33 (m, 2H), 7.15 (ddd, J = 10.0, 8.9, 2.5 Hz, 1H), 5.64 (s, 2H) | 286.0 |
| 90 | 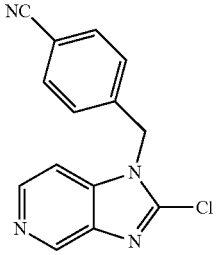 [SMILES: N#Cc1ccc(Cn2c(Cl)nc3cnccc32)cc1] | 4-((2-chloro-1H-imidazo[4,5-c]pyridin-1-yl)methyl)benzonitrile | — | 269.2 |
| 91 | 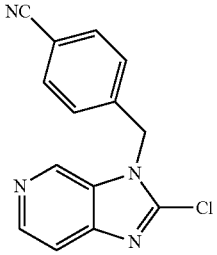 [SMILES: N#Cc1ccc(Cn2c(Cl)nc3ccncc32)cc1] | 4-[(2-chloro-3H-imidazo[4,5-c]pyridin-3-yl)methyl)benzonitrile | — | 269.2 |
| 92 | 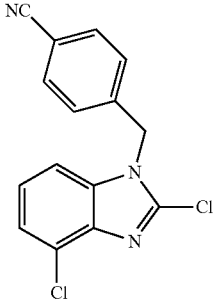 [SMILES: N#Cc1ccc(Cn2c(Cl)nc3c(Cl)cccc32)cc1] | 4-((2,4-dichloro-1H-benzo[d]imidazol-1-yl)methyl)benzonitrile | ¹H NMR (400 MHz, DMSO-d$_6$): δ 7.87-7.80 (m, 2H), 7.65-7.58 (m, 1H), 7.42-7.27 (m, 4H), 5.70 (d, J = 2.8 Hz, 2H) | 302.1 |

TABLE 7-continued

Intermediates accessed using the sequence outlines in Scheme 11

| Int # | Structure | Compound Name | ¹H NMR | MS MH+ |
|---|---|---|---|---|
| 93 | 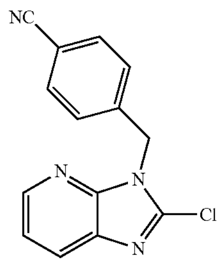 [SMILES: N#Cc1ccc(Cn2c(Cl)nc3cccnc32)cc1] | 4-((2-chloro-3H-imidazo[4,5-b]pyridin-3-yl)methyl)benzonitrile | ¹H NMR (400 MHz, DMSO-d$_6$): δ 8.41 (dd, J = 4.7, 2.0 Hz, 1H), 8.13 (dt, J = 8.1, 1.7 Hz, 1H), 7.83 (dd, J = 8.3, 2.3 Hz, 2H), 7.46-7.34 (m, 3H), 5.64 (d, J = 2.2 Hz, 2H) | 269.0 |
| 94 | 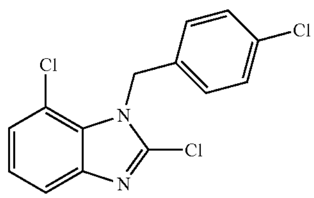 [SMILES: Clc1ccc(Cn2c(Cl)nc3cccc(Cl)c32)cc1] | 4-((2,7-dichloro-1H-benzo[d]imidazol-1-yl)methyl)benzonitrile | 1H NMR (400 MHz, DMSO-d6): δ 7.84 (d, J = 8.1 Hz, 2H), 7.69 (dd, J = 7.8, 1.1 Hz, 1H), 7.36 (dd, J = 7.9, 1.2 Hz, 1H), 7.32 (d, J = 7.8 Hz, 1H), 7.25 (d, J = 8.1 Hz, 2H), 5.89 (s, 2H) | 302.1 |
| 95 | 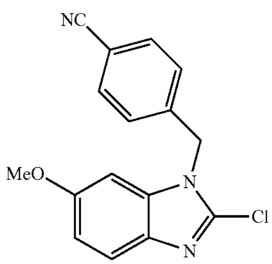 [SMILES: COc1ccc2nc(Cl)n(Cc3ccc(C#N)cc3)c2c1] | 4-((2-chloro-6-methoxy-1H-benzo[d]imidazol-1-yl)methyl)benzonitrile | — | 298.2 |
| 96 | 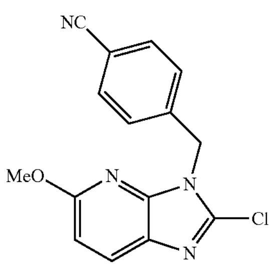 [SMILES: COc1ccc2nc(Cl)n(Cc3ccc(C#N)cc3)c2n1] | 4-((2-chloro-5-methoxy-3H-imidazo[4,5-b]pyridin-3-yl)methyl)benzonitrile | — | 299.2 |
| 97 | 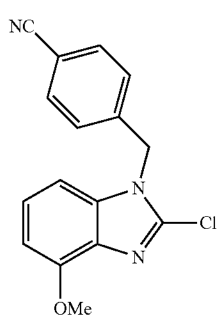 [SMILES: COc1cccc2c1nc(Cl)n2Cc1ccc(C#N)cc1] | 4-((2-chloro-4-methoxy-1H-benzo[d]imidazol-1-yl)methyl)benzonitrile | ¹H NMR (400 MHz, DMSO-d$_6$): δ 7.87-7.80 (m, 2H), 7.36-7.27 (m, 2H), 7.26-7.14 (m, 2H), 6.81 (dd, J = 7.7, 1.3 Hz, 1H), 5.62 (s, 2H), 3.93 (s, 3H) | 298.2 |

TABLE 7-continued

Intermediates accessed using the sequence outlines in Scheme 11

| Int # | Structure | Compound Name | ¹H NMR | MS MH+ |
|---|---|---|---|---|
| 98 | 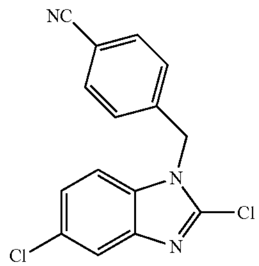 [SMILES: N#Cc1ccc(Cn2c(Cl)nc3cc(Cl)ccc32)cc1] | 4-((2,5-dichloro-1H-benzo[d]imidazol-1-yl)methyl)benzonitrile | — | 302.2 |

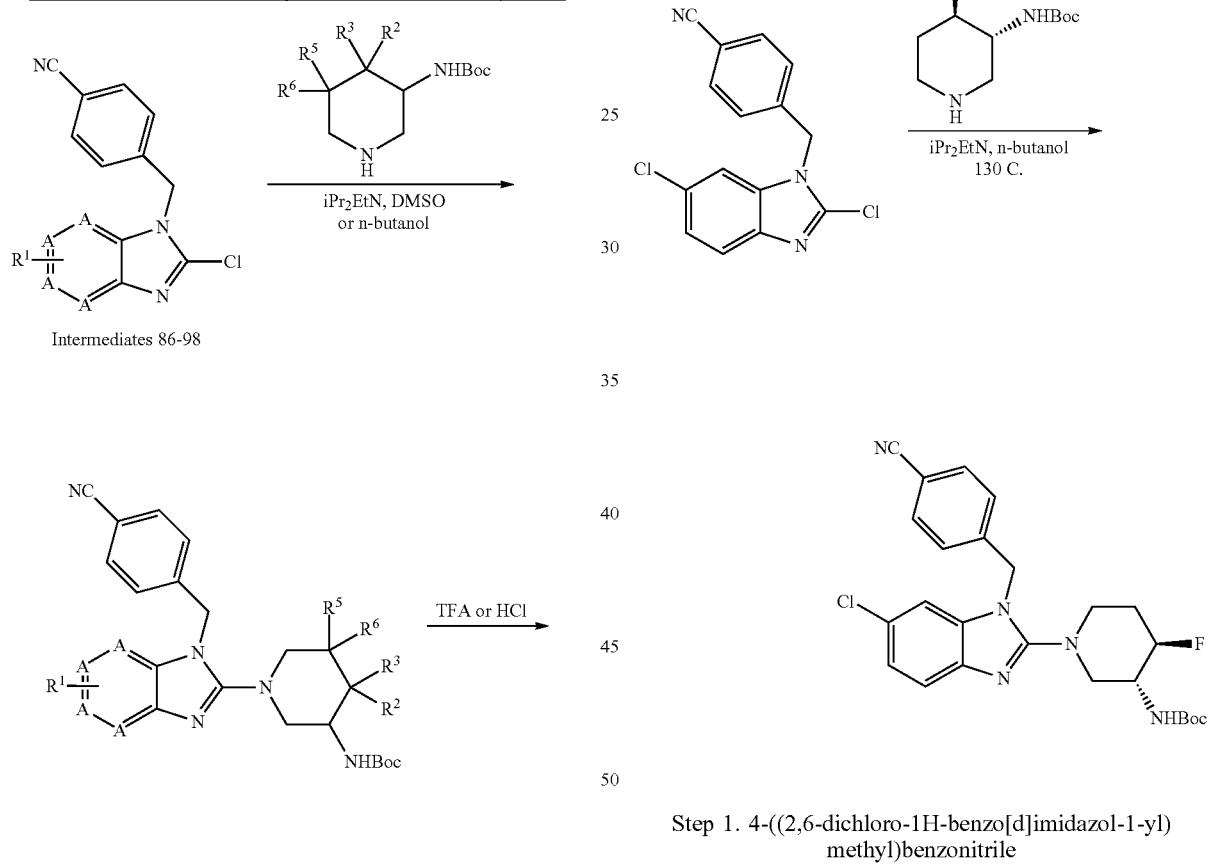

Scheme 12. Advancement of benzylated intermediates to final products

Step 1. 4-((2,6-dichloro-1H-benzo[d]imidazol-1-yl)methyl)benzonitrile

To a suspension of 4-((2,6-dichloro-1H-benzo[d]imidazol-1-yl)methyl)benzonitrile (50 mg, 0.165 mmol, 1 equiv) and tert-butyl ((3R,4R)-4-fluoropiperidin-3-yl)carbamate (72.2 mg, 0.331 mmol, 2 equiv) in 1-butanol (662 μl, 0.25 M) in a microwave vial was added DIEA (43.4 μl, 0.248 mmol, 1.5 equiv). The vial was heated to 130° C. for 12 hours. The reaction mixture was cooled to room temperature, concentrated, and loaded onto a 12 g RediSep ISCO cartridge, eluting with 20-80% ethyl acetate in heptane, to provide tert-butyl ((3R,4R)-1-(6-chloro-1-(4-cyanobenzyl)-1H-benzo[d]imidazol-2-yl)-4-fluoropiperidin-3-yl)carbamate (40 mg, 49.9% yield) as a white solid. MS (ESI pos. ion) m/z: 484.0 (M+H).

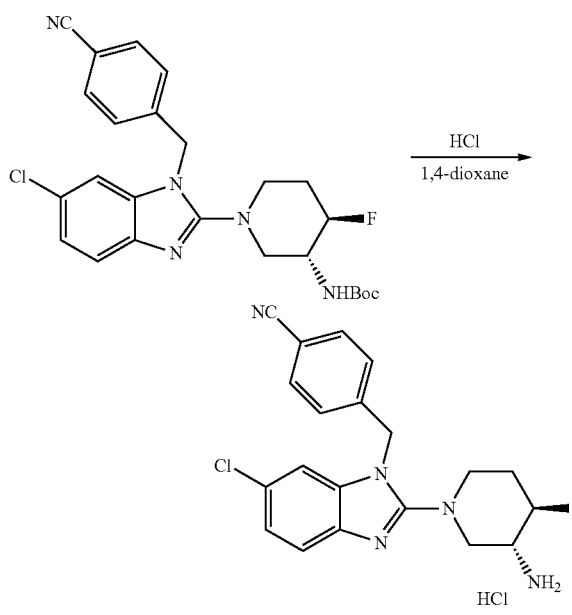

Step 2. 4-((2-((3R,4R)-3-amino-4-fluoropiperidin-1-yl)-6-chloro-1H-benzo[d]imidazol-1-yl)methyl)benzonitrile To a solution of tert-butyl ((3R,4R)-1-(6-chloro-1-(4-cyanobenzyl)-1H-benzo[d]imidazol-2-yl)-4-fluoropiperidin-3-yl)carbamate (40 mg, 0.083 mmol, 1 equiv) in 1,4-dioxane (1 mL) was added 4 N HCl in dioxane (0.517 mL, 2.066 mmol, 25 equiv). The reaction was stirred at ambient temperature for 6 hours at which time the reaction mixture was concentrated to provide 4-((2-((3R,4R)-3-amino-4-fluoropiperidin-1-yl)-6-chloro-1H-benzo[d]imidazol-1-yl)methyl)benzonitrile hydrochloride as a white solid. NMR (400 MHz, DMSO-$d_6$) 8.78 (br s, 2H), 7.87-7.80 (m, 2H), 7.55 (d, J=8.5 Hz, 1H), 7.49-7.35 (m, 3H), 7.31-7.21 (m, 1H), 5.65-5.49 (m, 2H), 5.05-4.91 (m, 1H), 3.95 (br d, J=12.3 Hz, 1H), 3.79-3.61 (m, 1H), 3.52-3.44 (m, 1H), 3.35-3.22 (m, 1H), 3.12 (br t, J=11.5 Hz, 1H), 2.32-2.15 (m, 1H), 1.99-1.79 (m, 1H). MS (ESI pos. ion) m/z: 384.0 (M+H).

TABLE 8

Examples prepared in a manner analogous to Schemes 11-12

| Ex. # | Benzimidazole Intermediate | Amine | Structure | Compound Name | MS MH+ |
|---|---|---|---|---|---|
| 401 | 86 | (structure: F, NHBoc piperidine) | HCl (structure) | 4-((2-((3R,4S)-3-amino-4-fluoropiperidin-1-yl)-6-chloro-1H-benzo[d]imidazol-1-yl)methyl)benzonitrile hydrochloride | 384.0 |
| 402 | 95 | (structure: NHBoc piperidine) | HCl (structure) | (S)-4-((2-(3-aminopiperidin-1-yl)-6-methoxy-1H-benzo[d]imidazol-1-yl)methyl)benzonitrile hydrochloride | 362.0 |

TABLE 8-continued

Examples prepared in a manner analogous to Schemes 11-12

| Ex. # | Benzimidazole Intermediate | Amine | Structure | Compound Name | MS MH+ |
|---|---|---|---|---|---|
| 403 | 95 | 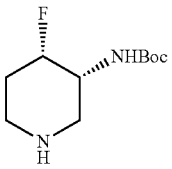 [SMILES: CC(C)(C)OC(=O)N[C@@H]1CNCC[C@@H]1F] | 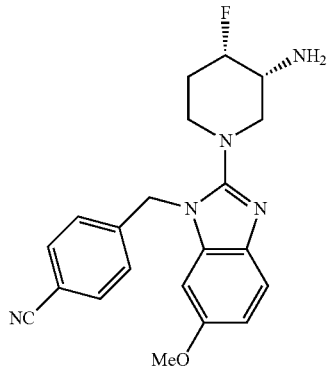 [SMILES: COc1ccc2nc(N3CC[C@H](F)[C@H](N)C3)n(Cc3ccc(C#N)cc3)c2c1] | 4-((2-((3R,4S)-3-amino-4-fluoropiperidin-1-yl)-6-methoxy-1H-benzo[d]imidazol-1-yl)methyl)benzonitrile | 380.0 |
| 404 | 95 | 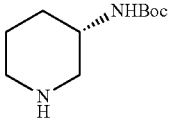 [SMILES: CC(C)(C)OC(=O)N[C@H]1CCCNC1] HCl | 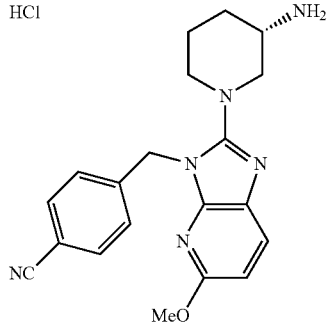 [SMILES: Cl ; COc1ccc2nc(N3CCC[C@H](N)C3)n(Cc3ccc(C#N)cc3)c2n1] | (S)-4-((2-(3-aminopiperidin-1-yl)-5-methoxy-3H-imidazo[4,5-b]pyridin-3-yl)methyl)benzonitrile hydrochloride | 363.0 |
| 405 | 86 | 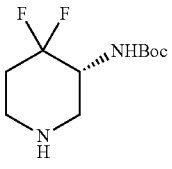 [SMILES: CC(C)(C)OC(=O)N[C@@H]1CNCCC1(F)F] | 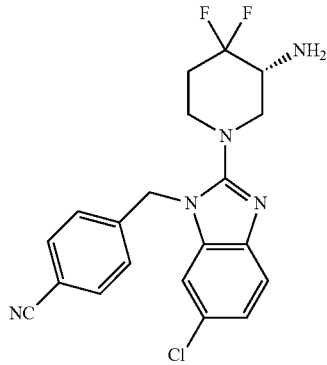 [SMILES: N#Cc1ccc(Cn2c(N3CCC(F)(F)[C@H](N)C3)nc3ccc(Cl)cc32)cc1] | (R)-4-((2-(1-amino-4,4-difluoropiperidin-1-yl)-6-chloro-1H-benzo[d]imidazol-1-yl)methyl)benzonitrile | 402.0 |
| 406 | 95 | 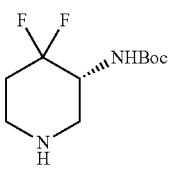 [SMILES: CC(C)(C)OC(=O)N[C@@H]1CNCCC1(F)F] | 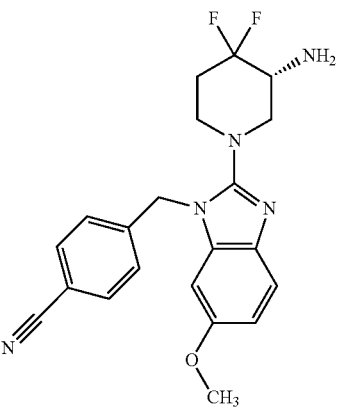 [SMILES: COc1ccc2nc(N3CCC(F)(F)[C@H](N)C3)n(Cc3ccc(C#N)cc3)c2c1] | (R)-4-((2-(3-amino-4,4-difluoropiperidin-1-yl)-6-methoxy-1H-benzo[d]imidazol-1-yl)methyl)benzonitrile | 398.0 |

TABLE 8-continued

Examples prepared in a manner analogous to Schemes 11-12

| Ex. # | Benzim- idazole Inter- mediate | Amine | Structure | Compound Name | MS MH+ |
|---|---|---|---|---|---|
| 407 | 92 | 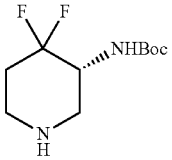 [SMILES: CC(C)(C)OC(=O)N[C@@H]1CNCCC1(F)F] | 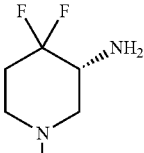 | (R)-4-((2-(3-amino-4,4-difluoropiperidin-1-yl)-4-chloro-1H-benzo[d]imidazol-1-yl)methyl)benzonitrile | 402.0 |
| 408 | 97 | 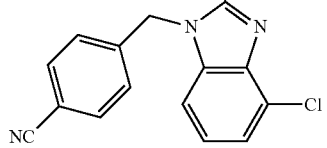 | 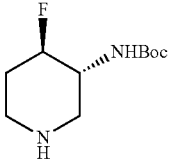 [SMILES: CC(C)(C)OC(=O)N[C@@H]1CNCC[C@H]1F] | 4-((2-((3R,4R)-3-amino-4-fluoropiperidin-1-yl)-4-chloro-1H-benzo[d]imidazol-1-yl)methyl)benzonitrile | 384.0 |
| 409 | 92 | 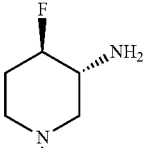 | 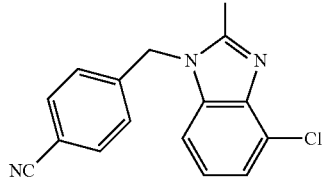 | 4-((2-(3R,4S)-3-amino-4-fluoropiperidin-1-yl)-4-chloro-1H-benzo[d]imidazol-1-yl)methyl)benzonitrile | 384.0 |
| 410 | 97 | 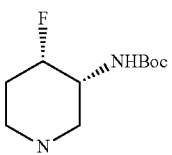 | 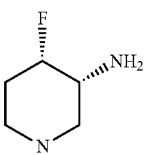 | (R)-4-((2-(3-amino-4,4-difluoropiperidin-1-yl)-4-methoxy-1H-benzo[d]imidazol-1-yl)methyl)benzonitrile | 398.0 |

TABLE 8-continued

Examples prepared in a manner analogous to Schemes 11-12

| Ex. # | Benzimidazole Intermediate | Amine | Structure | Compound Name | MS MH+ |
|---|---|---|---|---|---|
| 411 | 97 | | 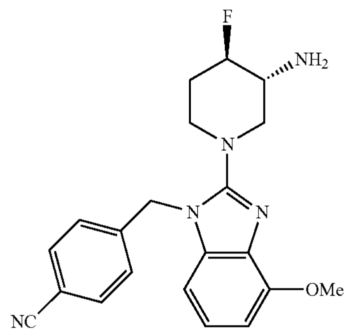 [SMILES: COc1cccc2c1nc(N1CC[C@@H](F)[C@H](N)C1)n2Cc1ccc(C#N)cc1] | 4-((2-((3R,4R)-3-amino-4-fluoropiperidin-1-yl)-4-methoxy-1H-benzo[d]imidazol-1-yl)methyl)benzonitrile | 380.2 |
| 412 | 90 | | 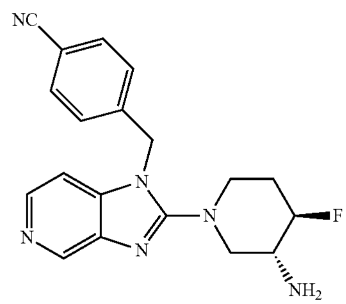 [SMILES: N#Cc1ccc(Cn2c(N3CC[C@@H](F)[C@H](N)C3)nc3cnccc32)cc1] | 4-((2-((3R,4R)-3-amino-4-fluoropiperidin-1-yl)-1H-imidazo[4,5-c]pyridin-1-yl)methyl)benzonitrile | 351.2 |
| 413 | 91 | | 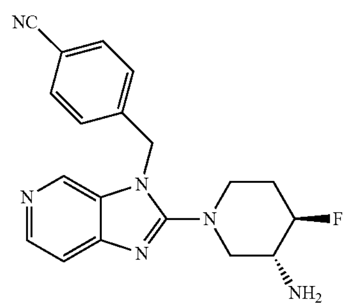 | 4-((2-((3R,4R)-3-amino-4-fluoropiperidin-1-yl)-3H-imidazo[4,5-c]pyridin-3-yl)methyl)benzonitrile | 351.2 |
| 414 | 87 | | 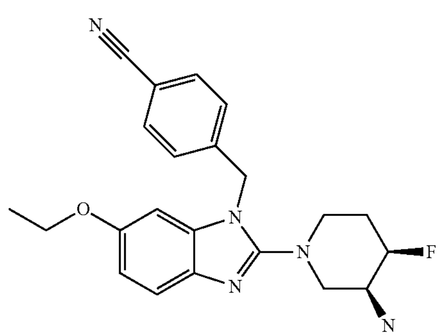 [SMILES: CCOc1ccc2nc(N3CC[C@@H](F)[C@@H](N)C3)n(Cc3ccc(C#N)cc3)c2c1] | 4-((2-((3R,4R)-3-amino-4-fluoro-1-piperidinyl)-6-ethoxy-1H-benzimidazol-1-yl)methyl)benzonitrile | 394.2 |

TABLE 8-continued

Examples prepared in a manner analogous to Schemes 11-12

| Ex. # | Benzim-idazole Intermediate | Amine | Structure | Compound Name | MS MH+ |
|---|---|---|---|---|---|
| 415 | 88 | | 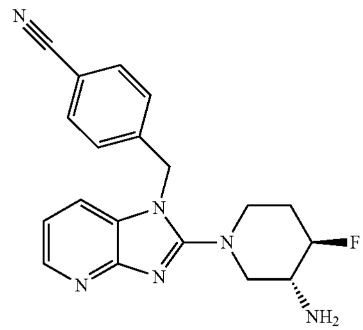 [SMILES: N#Cc1ccc(Cn2c(N3CC[C@@H](F)[C@H](N)C3)nc3ncccc32)cc1] | 4-((2-((3R,4S)-3-amino-4-fluoropiperidin-1-yl)-1H-imidazo[4,5-b]pyridin-1-yl)methyl)benzonitrile | 351.2 |
| 416 | 89 | | 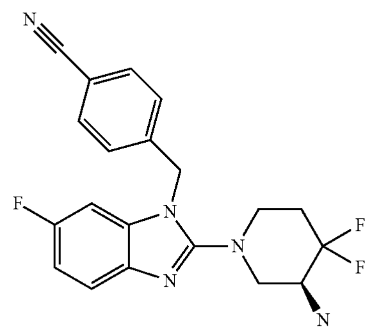 [SMILES: N#Cc1ccc(Cn2c(N3CCC(F)(F)[C@@H](N)C3)nc3ccc(F)cc32)cc1] | 4-((2-((3R)-3-amino-4,4-difluoro-1-piperidinyl)-6-fluoro-1H-benzimidaz-1-yl)methyl)benzonitrile | 386.2 |
| 417 | 88 | | 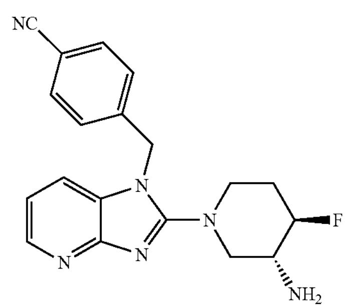 [SMILES: N#Cc1ccc(Cn2c(N3CC[C@@H](F)[C@H](N)C3)nc3ncccc32)cc1] | 4-((2-((3R,4R)-3-amino-4-fluoropiperidin-1-yl)-1H-imidazo[4,5-b]pyridin-1-yl)methyl)benzonitrile | 351.2 |
| 418 | 92 | | 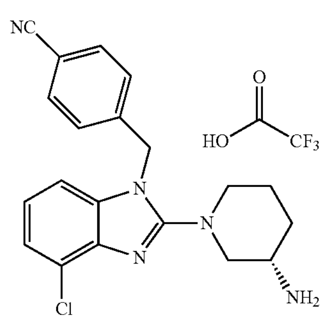 | (S)-4-((2-(3-aminopiperidin-1-yl)-4-chloro-1H-benzo[d]imidazol-1-yl)methyl)benzonitrile 2,2,2-trifluoroacetate | 366.0 |

TABLE 8-continued

Examples prepared in a manner analogous to Schemes 11-12

| Ex. # | Benzimidazole Intermediate | Amine | Structure | Compound Name | MS MH+ |
|---|---|---|---|---|---|
| 419 | 93 | 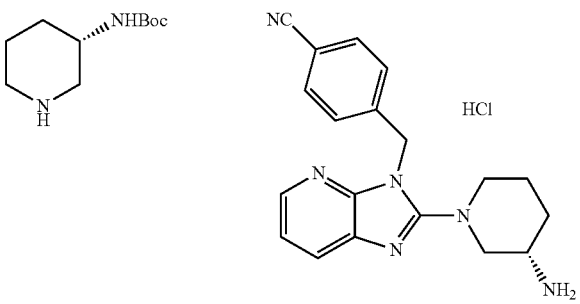 | 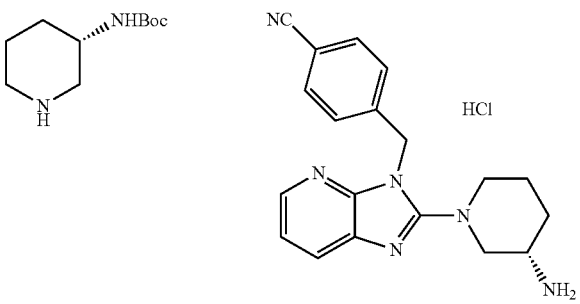 | (S)-4-((2-(3-aminopiperidin-1-yl)-3H-imidazo[4,5-b]pyridin-3-yl)methyl)benzonitrile hydrochloride | 333.2 |
| 420 | 86 | 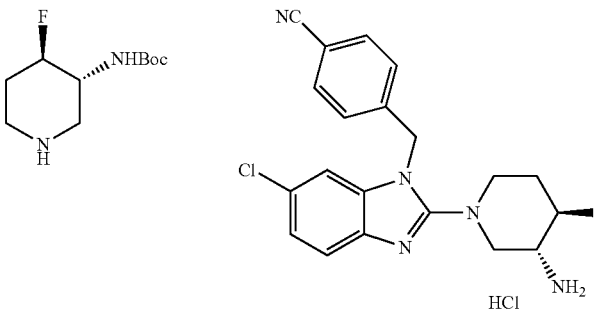 | 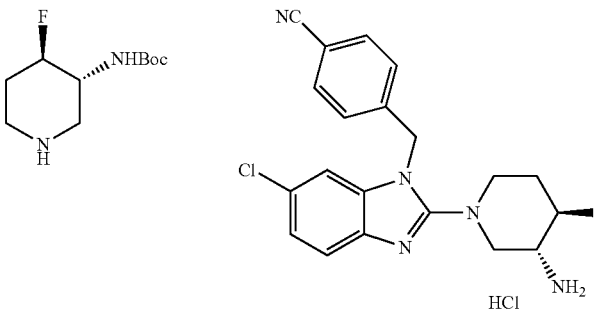 | 4-((2-((3R,4R)-3-amino-4-fluoropiperidin-1-yl)-6-chloro-1H-benzo[d]imidazol-1-yl)methyl)benzonitrile hydrochloride | 384.2 |
| 421 | 86 | 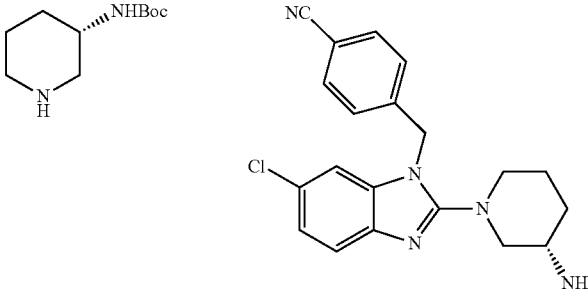 | 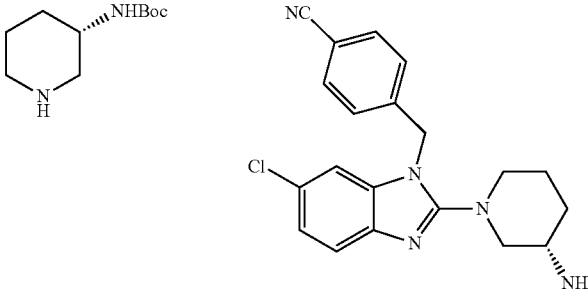 | (S)-4-((2-(3-aminopiperidin-1-yl)-6-chloro-1H-benzo[d]imidazol-1-yl)methyl)benzonitrile | 366.2 |
| 422 | 98 | 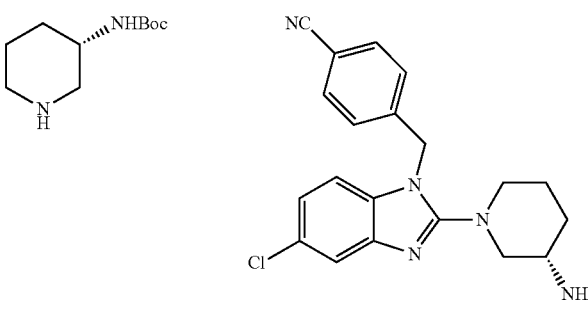 | 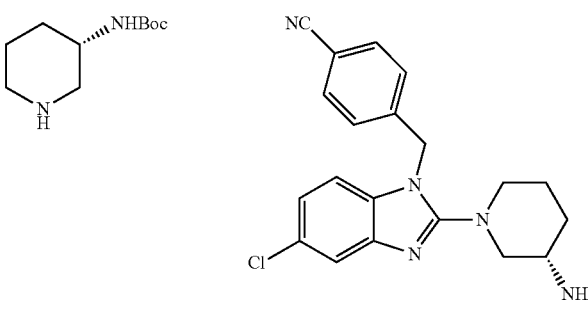 | (S)-4-((2-(3-aminopiperidin-1-yl)-5-chloro-1H-benzo[d]imidazol-1-yl)methyl)benzonitrile | 366.2 |

TABLE 9

Characterization data for compounds following Schemese 11-12.

| Ex. # | Freq., Solvent | ¹HNMR Data (δ ppm) |
|---|---|---|
| 401 | 400 MHz d₆-DMSO | 8.57 (br s, 2H), 7.81-7.86 (m, 1H), 7.83 (d, J = 7.30 Hz, 1H), 7.50-7.55 (m, 1H), 7.40-7.43 (m, 1H), 7.34-7.39 (m, 2H), 7.23 (dd, J = 1.92, 8.34 Hz, 1H), 5.49-5.60 (m, 2H), 5.22-5.04 (m, 1H), 3.61-3.69 (m, 4H), 3.34-3.44 (m, 4H), 3.22-3.31 (m, 1H), 3.08-3.22 (m, 1H), 2.05-2.16 (m, 1H), 1.93-2.05 (m, 1H) |
| 402 | 400 MHz d₆-DMSO | 8.45 (br s, 3H), 7.87 (d, J = 8.29 Hz, 2H), 7.49 (t, J = 8.91 Hz, 3H), 6.95-7.02 (m, 2H), 5.56-5.72(m, 2H), 3.72 (s, 3H), 3.37(br d, J = 7.67 Hz, 4H), 3.12 (br t, J = 10.05 Hz, 1H), 1.97 (br d, J = 8.40 Hz, 1H), 1.88 (br dd, J = 3.63, 9.64 Hz, 1H), 1.62-1.70 (m, 1H), 1.56 (br dd, J = 4.09, 9.38 Hz, 1H) |
| 403 | 400 MHz d₆-DMSO | 7.80 (d, J = 8.29 Hz, 2H), 7.27-7.37 (m, 3H), 6.81 (d, J = 2.38 Hz, 1H), 6.73 (dd, J = 2.44, 8.66 Hz, 1H), 5.40 (s, 2H), 4.66-4.87 (m, 1H), 3.68 (s, 3H), 3.14-3.21 (m, 2H), 3.00-3.10 (m, 3H), 2.90-2.99 (M, 2H), 1.81-2.03 (m, 2H) |
| 404 | 400 MHz d₆-DMSO | 8.40 (br s, 3H), 7.79-7.89 (m, 3H), 7.52 (d, J = 7.98 Hz, 2H), 6.75 (d, J = 8.60 Hz, 1H), 5.45-5.59 (m, 2H), 3.79 (s, 3H), 3.64-3.76 (m, 1H), 3.48 (br dd, J = 4.25, 11.30 Hz, 2H), 3.21-3.31 (m, 1H), 3.00 (br t, J = 10.21 Hz, 1H), 1.93-2.02 (m 1H), 1.80-1.93 (m, 1H), 1.46-1.69 (m, 2H) |
| 405 | 400 MHz d₆-DMSO | 7.82 (d, J = 7.88 Hz, 2H), 7.47 (d, J = 8.40 Hz, 1H), 7.29-7.35 (m, 3H), 7.14 (d, J = 8.50 Hz, 1H), 5.49 (s, 2H), 3.26-3.40 (m, 2H), 3.08-3.24 (m, 2H), 2.93-3.05 (m, 1H), 2.18-2.32 (m, 1H), 1.90-2.15 (m, 1H), 1.77 (br s, 2H) |

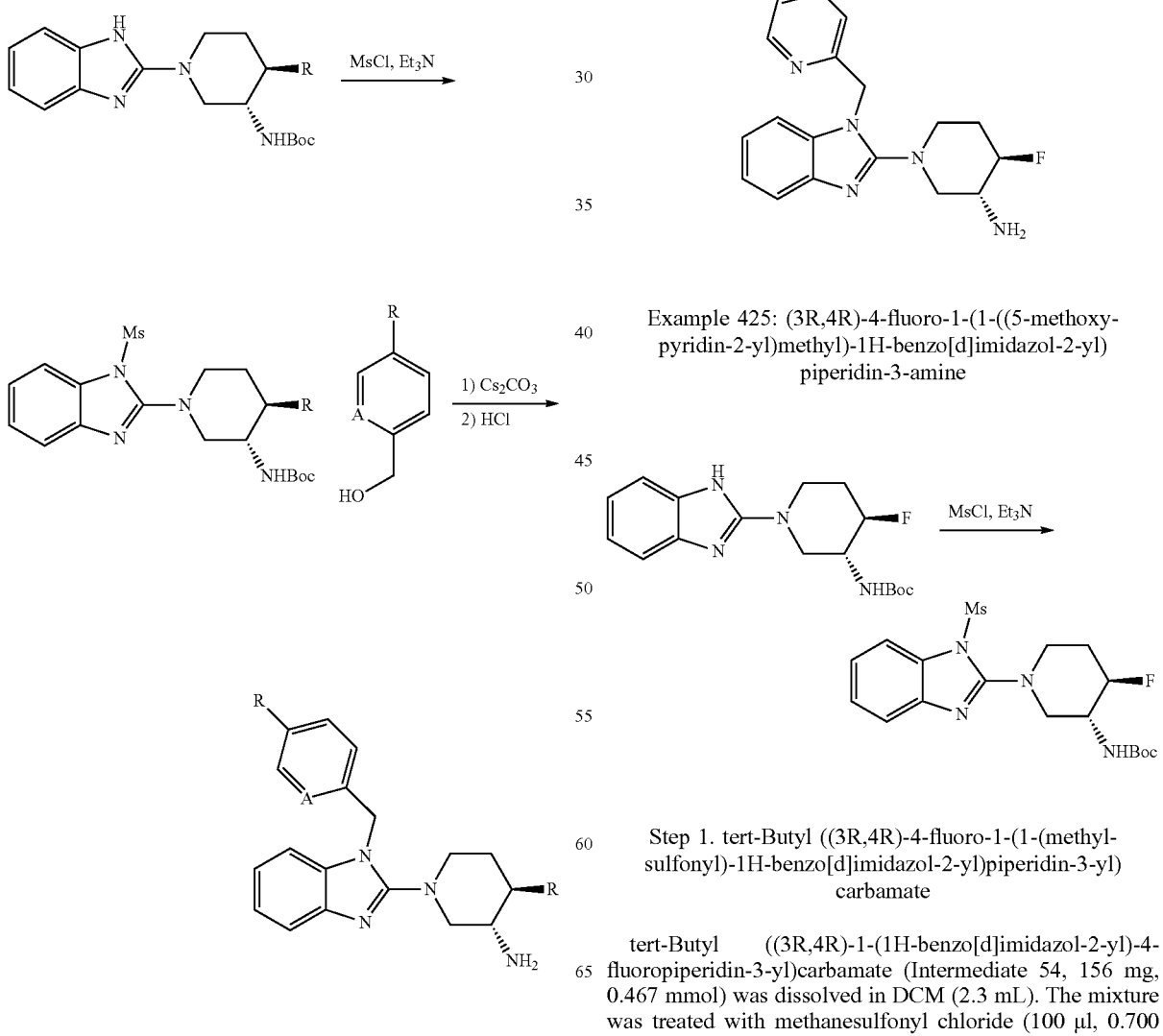

Example 425: (3R,4R)-4-fluoro-1-(1-((5-methoxy-pyridin-2-yl)methyl)-1H-benzo[d]imidazol-2-yl)piperidin-3-amine Step 1. tert-Butyl ((3R,4R)-4-fluoro-1-(1-(methyl-sulfonyl)-1H-benzo[d]imidazol-2-yl)piperidin-3-yl)carbamate tert-Butyl ((3R,4R)-1-(1H-benzo[d]imidazol-2-yl)-4-fluoropiperidin-3-yl)carbamate (Intermediate 54, 156 mg, 0.467 mmol) was dissolved in DCM (2.3 mL). The mixture was treated with methanesulfonyl chloride (100 µl, 0.700 mmol, 2 equiv) and triethylamine, anhydrous (197 μl, 1.400 mmol). The resulting yellow solution was left to stir overnight. The reaction was quenched with NH4Cl (aq), diluted with DCM, extracted into DCM, dried over MgSO4, filtered, concentrated to give the crude as an oil. The oil was purified on column chromatography (25 g SiO2, 0-45% ethyl acetate in heptane), to give tert-butyl ((3R,4R)-4-fluoro-1-(1-(methylsulfonyl)-1H-benzo[d]imidazol-2-yl)piperidin-3-yl)carbamate as a colorless solid. (ESL pos. ion) m/z: 413.2 [M+1].

EtOAc in heptane) to afford tert-butyl ((3R,4R)-4-fluoro-1-(1-((5-methoxypyridin-2-yl)methyl)-1H-benzo[d]imidazol-2-yl)piperidin-3-yl)carbamate as a colorless oil. (ESI, pos. ion) m/z: 456.2 [M+1].

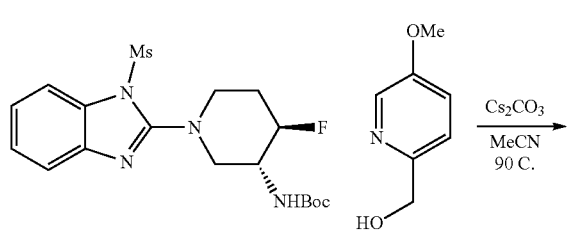

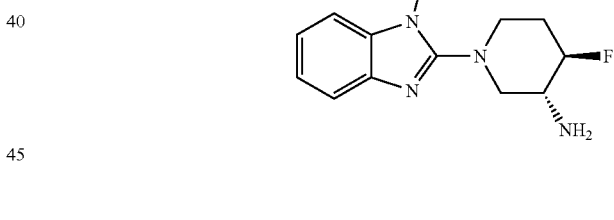

Step 3. (3R,4R)-4-fluoro-1-(1-((5-methoxypyridin-2-yl)methyl)-1H-benzo[d]imidazol-2-yl)piperidin-3-amine (Example 425)

Step 2. Tert-butyl ((3R,4R)-4-fluoro-1-(1-((5-methoxypyridin-2-yl)methyl)-1H-benzo[d]imidazol-2-yl)piperidin-3-yl)carbamate A vial was charged with (S)-1-(1-(methylsulfonyl)-1H-benzo[d]imidazol-2-yl)piperidin-3-amine (150 mg, 0.38 mmol), 1-hydroxy-2,3-dihydro-1H-indene-5-carbonitrile (67 mg, 1.1 equiv), and Cs2CO3 (150 mg, 1.2 equiv). The vial was fitted with a stirring bar, capped, and MeCN (1.3 ml) was added. The mixture was placed into a heating block set at 90° C. for 18 h. The reaction was diluted with EtOAc and NH4Cl$_{(aq)}$, the mixture was extracted into EtOAc. The combined organic extracts were dried over MgSO4, filtered, and concentrated to give the reaction crude. Crude material was purified on column chromatography (4 g SiO2, 0-30% tert-butyl ((3R,4R)-4-fluoro-1-(1-((5-methoxypyridin-2-yl)methyl)-1H-benzo[d]imidazol-2-yl)piperidin-3-yl)carbamate (32 mg, 1 equiv) was dissolved in DCM (5 mL). HCl in dioxane (10 equiv) was added, and the mixture was allowed to stir overnight. The solution was concentrated, then purified using reverse phase HPLC to provide the title compound. $^1$H NMR (600 MHz, d6-DMSO) δ 7.79 (s, 1H), 7.50 (t, J=7.53 Hz, 2H), 7.11 (t, J=7.66 Hz, 1H), 6.96 (d, J=7.79 Hz, 1H), 6.88-6.94 (m, 1H), 6.39-6.49 (m, 1H), 6.19 (t, J=8.95 Hz, 1H), 3.54-3.62 (m, 1H), 3.36-3.43 (m, 1H), 3.18-3.24 (m, 3H), 3.00-3.13 (m, 2H), 2.74-2.87 (m, 1H), 2.52-2.63 (m, 1H), 1.91-2.12 (m, 2H), 1.77-1.89 (m, 1H), 1.47-1.56 (m, 1H). (ESI, pos. ion) m/z: 356.2 [M+1].

TABLE 10

Compounds made following Scheme 13 and analogous to preparation of Example 425

| Ex. # | Alcohol | Structure | Compound Name | MS MH+ |
|---|---|---|---|---|
| 423 | | 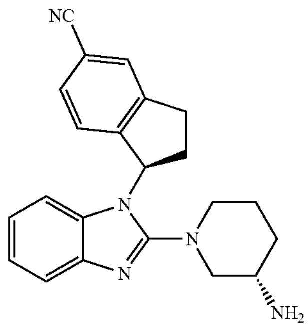 [SMILES: N#Cc1ccc2c(c1)CC[C@H]2n1c(N2CCC[C@H](N)C2)nc2ccccc21] | (R)-1-(2-((S)-3-aminopiperidin-1-yl)-1H-benzo[d]imidazol-1-yl)-2,3-dihydro-1H-indene-5-carbonitrile | 358.2 |
| 424 | | 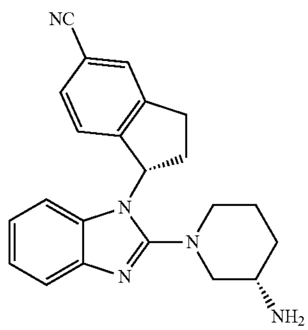 [SMILES: N#Cc1ccc2c(c1)CC[C@@H]2n1c(N2CCC[C@H](N)C2)nc2ccccc21] | (S)-1-(2-((S)-3-aminopiperidin-1-yl)-1H-benzo[d]imidazol-1-yl)-2,3-dihydro-1H-indene-5-carbonitrile | 358.2 |
| 425 | | 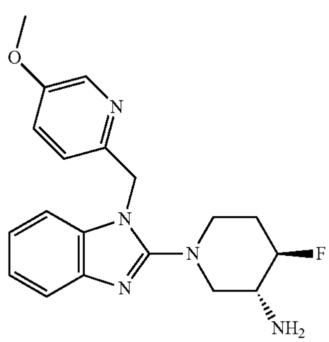 [SMILES: COc1ccc(Cn2c(N3CC[C@@H](F)[C@H](N)C3)nc3ccccc32)nc1] | (3R,4R)-4-fluoro-1-(1-((5-methoxypyridin-2-yl)methyl)-1H-benzo[d]imidazol-2-yl)piperidin-3-amine | 356.2 |

TABLE 11

Characterization data for compounds made following scheme 13

| Ex. # | Freq., Solvent | ¹HNMR Data (δ ppm) | Separation Stage | SFC Isomer Separation Conditions |
|---|---|---|---|---|
| 423 | 500 MHz d₄-MeOH | 7.79 (s, 1H), 7.50 (t, J = 7.53 Hz, 2H), 7.11 (t, J = 7.66 Hz, 1H), 6.96 (d, J = 7.79 Hz, 1H), 6.88-6.94 (m, 1H), 6.39-6.49 (m, 1H), 6.19 (t, J = 8.95 Hz, 1H), 3.54-3.62 (m, 1H), 3.36-3.43 (m, 1H), 3.18-3.24 (m, 3H), 3.00-3.13 (m, 2H), 2.74-2.87 (m, 1H), 2.52-2.63 (m, 1H), 1.91-2.12 (m, 2H), 1.77-1.89 (m, 1H), 1.47-1.56 (m, 1H) | B | Phenomenex Lux Cellulose-2, 30% MeOH, Chiralcel OD, 25% MeOH Peak 1 |
| 424 | 500 MHz d₄-MeOH | 7.79 (s, 1H), 7.49 (dd, J = 7.91, 11.03 Hz, 2H), 7.06-7.14 (m, 1H), 6.86-6.96 (m, 2H), 6.45 (br d, J = 5.71 Hz, 1H), 6.19 (br t, J = 8.95 Hz, 1H), 3.53-3.62 (m, 1H), 3.35-3.44 (m, 2H), 3.11-3.24 (m, 3H), 2.81-2.96 (m, 2H), 2.51-2.65 (m, 1H), 1.90-2.10 (m, 2H), 1.73-1.88 (m, 1H), 1.42-1.53 (m, 1H) | B | Phenomenex Lux Cellulose-2, 30% MeOH, Peak 3 |

TABLE 11-continued

Characterization data for compounds made following scheme 13

| Ex. # | Freq., Solvent | ¹HNMR Data (δ ppm) | Separation Stage | SFC Isomer Separation Conditions |
|---|---|---|---|---|
| 425 | 600 MHz, d₆-DMSO | 8.22 (d, J = 2.80 Hz, 1H), 7.42 (d, J = 7.79 Hz, 1H), 7.37 (dd, J = 3.11, 8.72 Hz, 1H), 7.17 (d, J = 8.72 Hz, 1H), 7.11 (d, J = 7.79 Hz, 1H), 7.04-7.09 (m, 1H), 6.98-7.03 (m, 1H), 5.31 (s, 2H), 4.32-4.47 (m, 1H), 3.79 (s, 3H), 3.40-3.52 (m, 2H), 2.96-3.09 (m, 2H), 2.84 (dd, J = 8.72, 12.46 Hz, 1H), 2.04-2.14 (m, 1H), 1.73-1.84 (m, 1H) | — | — |

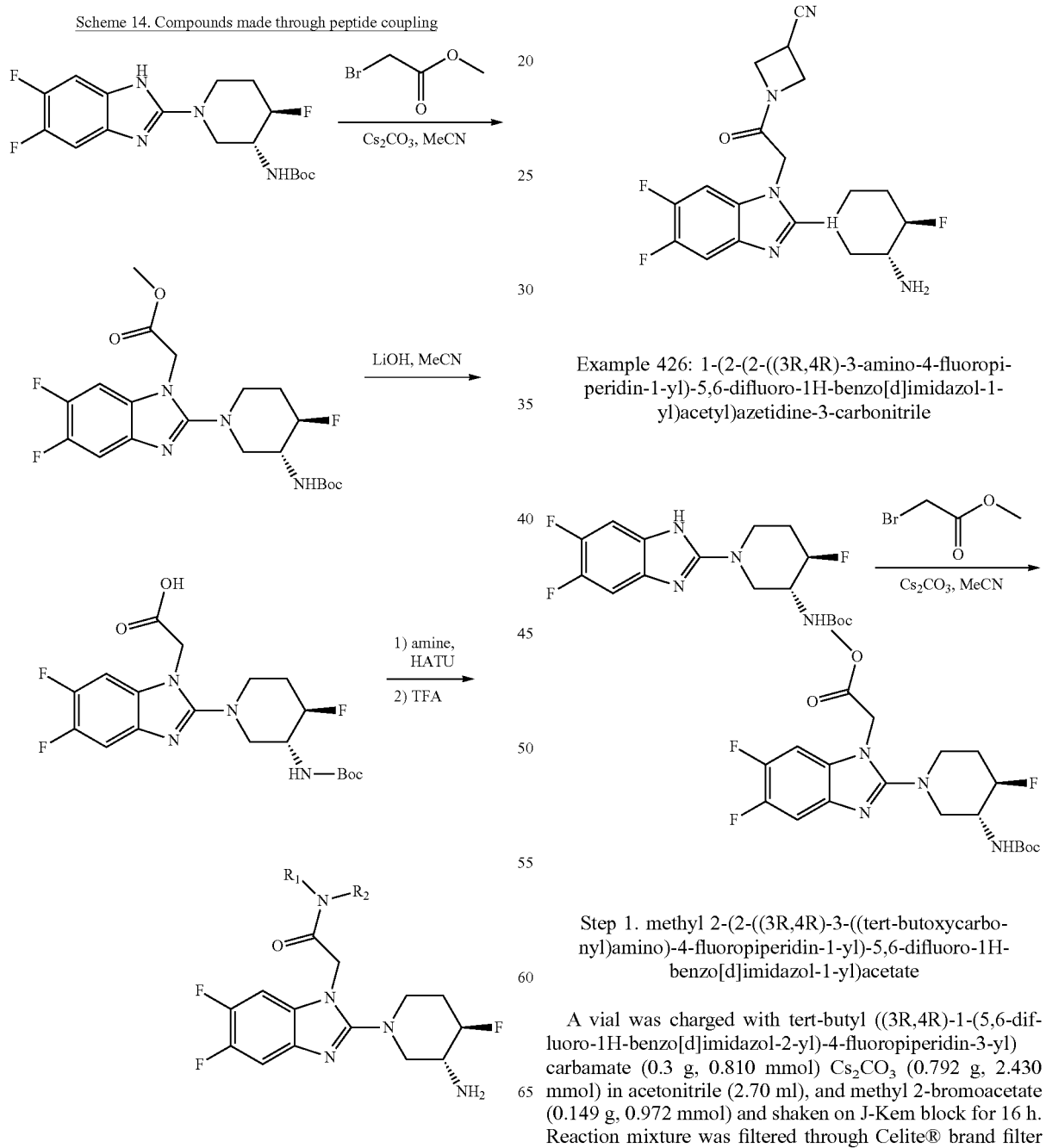

Example 426: 1-(2-(2-(((3R,4R)-3-amino-4-fluoropiperidin-1-yl)-5,6-difluoro-1H-benzo[d]imidazol-1-yl)acetyl)azetidine-3-carbonitrile Step 1. methyl 2-(2-((3R,4R)-3-((tert-butoxycarbonyl)amino)-4-fluoropiperidin-1-yl)-5,6-difluoro-1H-benzo[d]imidazol-1-yl)acetate A vial was charged with tert-butyl ((3R,4R)-1-(5,6-difluoro-1H-benzo[d]imidazol-2-yl)-4-fluoropiperidin-3-yl) carbamate (0.3 g, 0.810 mmol) Cs₂CO₃ (0.792 g, 2.430 mmol) in acetonitrile (2.70 ml), and methyl 2-bromoacetate (0.149 g, 0.972 mmol) and shaken on J-Kem block for 16 h. Reaction mixture was filtered through Celite® brand filter agent plug and purified by reverse phase HPLC to obtain methyl 2-(2-((3R,4R)-3-((tert-butoxycarbonyl)amino)-4-fluoropiperidin-1-yl)-5,6-difluoro-1H-benzo[d]imidazol-1-yl)acetate. ¹H NMR (600 MHz, DMSO-d₆) δ 7.56 (t, J=9.06 Hz, 1H), 7.51 (t, J=8.85 Hz, 1H), 7.19 (br d, J=8.25 Hz, 1H), 4.94-5.03 (m, 2H), 4.51-4.59 (dt, J=4.63, 9.01 Hz, 1H), 3.68-3.77 (m, 3H), 3.35-3.46 (m, 2H), 3.24-3.30 (m, 1H), 2.95 (br t, J=10.63 Hz, 1H), 2.73-2.89 (m, 1H), 2.13-2.21 (m, 1H), 1.79-1.89 (m, 1H), 1.39 (s, 9H). MS: (ESI pos. ion) m/z: 443.2 [M+1].

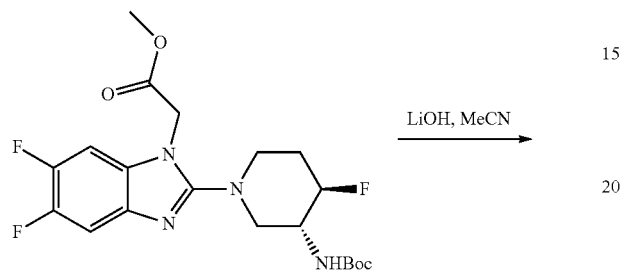

Step 2. 2-(2-((3R,4R)-3-((tert-butoxycarbonyl)amino)-4-fluoropiperidin-1-yl)-5,6-difluoro-1H-benzo[d]imidazol-1-yl)acetic acid Methyl 2-(2-((3R,4R)-3-((tert-butoxycarbonyl)amino)-4-fluoropiperidin-1-yl)-5,6-difluoro-1H-benzo[d]imidazol-1-yl)acetate was saponified using LiOH (0.097 g, 4.05 mmol) in dioxane (1 mL) and water (1 mL). Reaction mixture was stirred at ambient temperature for 1 h. Reaction mixture was acidified using acetic acid and the resulting off white precipitate was filtered to obtain 2-(2-((3R,4R)-3-((tert-butoxycarbonyl)amino)-4-fluoropiperidin-1-yl)-5,6-difluoro-1H-benzo[d]imidazol-1-yl)acetic acid. MS: (ESI pos. ion) m/z: 429.2 [M+1].

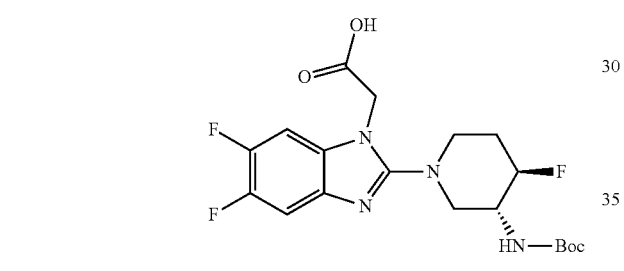

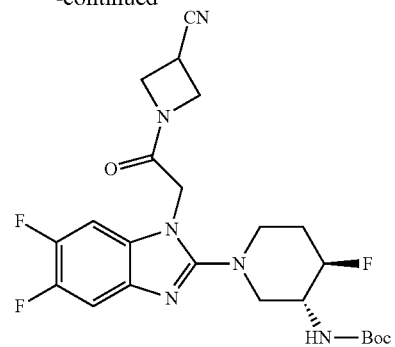

Step 3. tert-butyl ((3R,4R)-1-(1-(2-(3-cyanoazetidin-1-yl)-2-oxoethyl)-5,6-difluoro-1H-benzo[d]imidazol-2-yl)-4-fluoropiperidin-3-yl)carbamate A solution of 2-(2-((3R,4R)-3-((tert-butoxycarbonyl)amino)-4-fluoropiperidin-1-yl)-5,6-difluoro-1H-benzo[d]imidazol-1-yl)acetic acid (0.015 g, 0.035 mmol), 3-cyanoazetidine hydrochloride (4.15 mg, 0.035 mmol) and 2-(1h-benzotriazole-1-yl)-1,1,3,3-tetramethyluronium hexaflurophosphate (0.013 g, 0.035 mmol) in dimethyl sulfoxide (0.117 ml) and DIPEA (0.024 ml, 0.140 mmol) was shaken at ambient temperature. The reaction mixture was purified by reverse phase HPLC to obtain tert-butyl ((3R,4R)-1-(1-(2-(3-cyanoazetidin-1-yl)-2-oxoethyl)-5,6-difluoro-1H-benzo[d]imidazol-2-yl)-4-fluoropiperidin-3-yl)carbamate. MS: (ESI pos. ion) m/z: 493.2 [M+1].

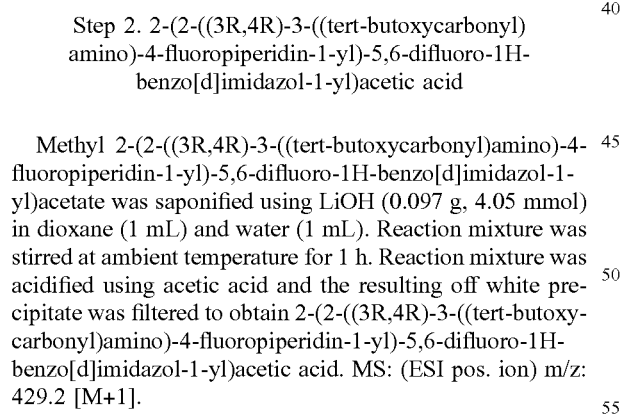

Step 4. 1-(2-(2-((3R,4R)-3-amino-4-fluoropiperidin-1-yl)-5,6-difluoro-1H-benzo[d]imidazol-1-yl)acetyl)azetidine-3-carbonitrile (Example 426)

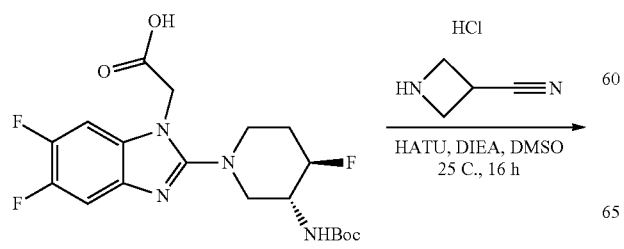

tert-Butyl ((3R,4R)-1-(1-(2-(3-cyanoazetidin-1-yl)-2-oxoethyl)-5,6-difluoro-1H-benzo[d]imidazol-2-yl)-4-fluoropiperidin-3-yl)carbamate was treated with TFA (0.5 mL) in DCM (0.5 mL). Mixture was concentrated and purified using reverse phase HPLC to obtain the title compound. $^1$H NMR (600 MHz, DMSO-$d_6$) δ 7.34-7.60 (m, 2H), 4.73-4.80 (m, 2H), 4.48-4.60 (m, 2H), 4.31-4.48 (m, 1H), 4.17-4.28 (m, 1H), 4.06-4.15 (m, 1H), 3.82-3.94 (m, 1H), 2.96-3.06 (m, 2H), 2.74-2.84 (m, 1H), 2.06-2.17 (m, 1H), 1.64-1.88 (m, 3H). MS: (ESI pos. ion) m/z: 393.2 [M+1].

The following compounds were made following an analogous procedure to that described for Example 426 and general Scheme 14 above:

TABLE 12

Compounds made following Scheme 14

| Ex. # | Amine | Structure | Compound Name | MS MH+ |
|---|---|---|---|---|
| 426 | HCl 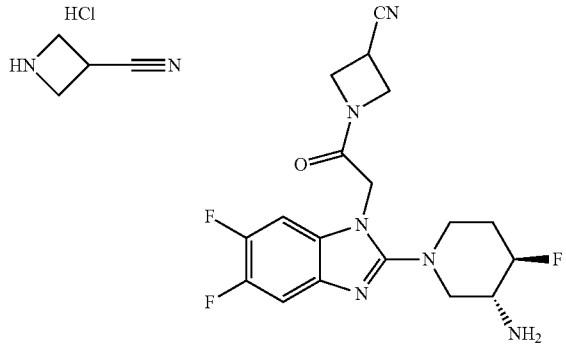 | 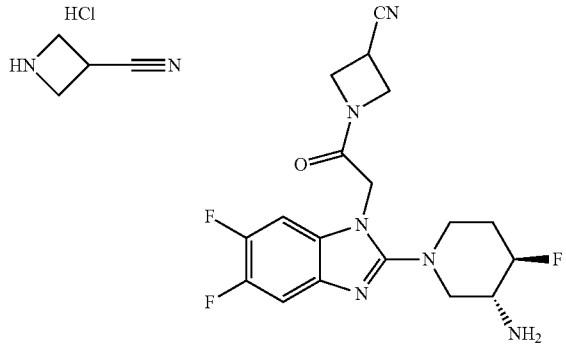 | 1-(2-(2-((3R,4R)-3-amino-4-fluoropiperidin-1-yl)-5,6-difluoro-1H-benzo[d]imidazol-1-yl)acetyl)azetidine-3-carbonitrile | 393.2 |
| 427 | 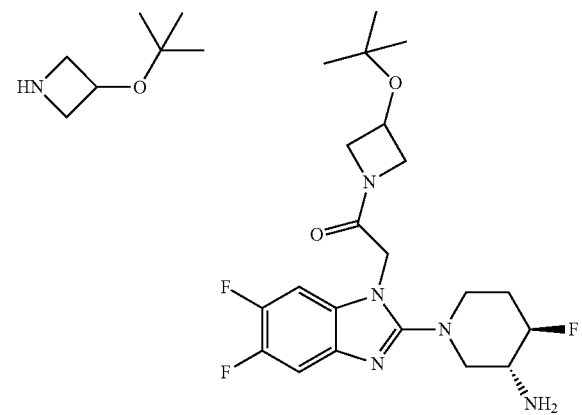 | 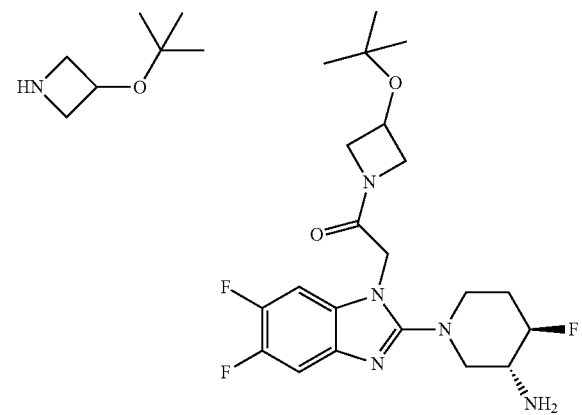 | 2-(2-((3R,4R)-3-amino-4-fluoropiperidin-1-yl)-5,6-difluoro-1H-benzo[d]imidazol-1-yl)-1-(3-(tert-butoxy)azetidin-1-yl)ethan-1-one | 440.2 |
| 428 | 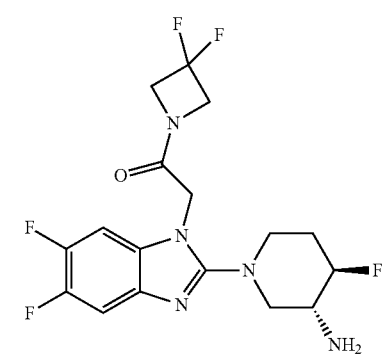 [SMILES: N[C@@H]1CN(c2nc3cc(F)c(F)cc3n2CC(=O)N2CC(F)(F)C2)CC[C@H]1F] | 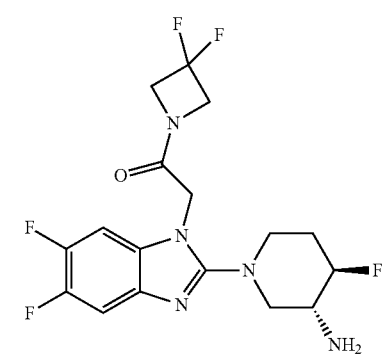 [SMILES: N[C@@H]1CN(c2nc3cc(F)c(F)cc3n2CC(=O)N2CC(F)(F)C2)CC[C@H]1F] | 2-(2-((3R,4R)-3-amino-4-fluoropiperidin-1-yl)-5,6-difluoro-1H-benzo[d]imidazol-1-yl)-1-(3,3-difluoroazetidin-1-yl)ethanone | 404.2 |

TABLE 12-continued

Compounds made following Scheme 14

| Ex. # | Amine | Structure | Compound Name | MS MH+ |
|---|---|---|---|---|
| 429 |  | 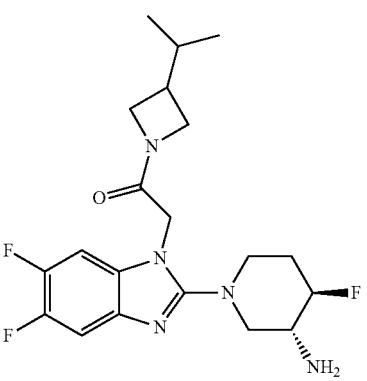 [SMILES: CC(C)C1CN(C(=O)Cn2c(N3CC[C@@H](F)[C@H](N)C3)nc3cc(F)c(F)cc32)C1] | 2-(2-((3R,4R)-3-amino-4-fluoropiperidin-1-yl)-5,6-difluoro-1H-benzo[d]imidazol-1-yl)-1-(3-isopropylazetidin-1-yl)ethanone | 410.2 |
| 430 | 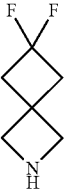 | 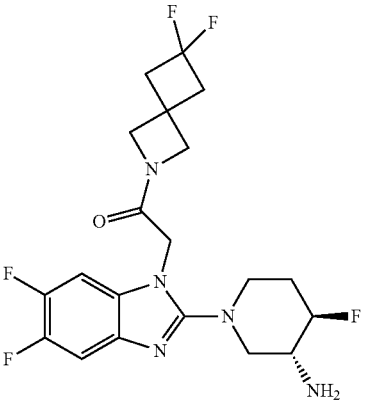 [SMILES: N[C@@H]1CN(c2nc3cc(F)c(F)cc3n2CC(=O)N2CC3(C2)CC(F)(F)C3)CC[C@H]1F] | 2-(2-((3R,4R)-3-amino-4-fluoropiperidin-1-yl)-5,6-difluoro-1H-benzo[d]imidazol-1-yl)-1-(6,6-difluoro-2-azaspiro[3.3]heptan-2-yl)ethanone | 444.2 |
| 431 |  | 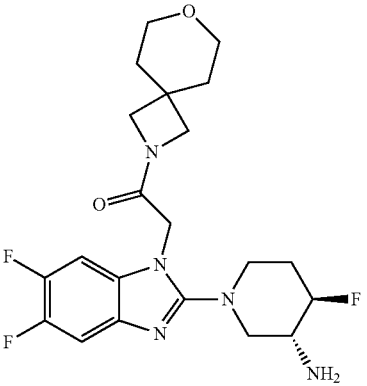 [SMILES: N[C@@H]1CN(c2nc3cc(F)c(F)cc3n2CC(=O)N2CC3(CCOCC3)C2)CC[C@H]1F] | 2-(2-((3R,4R)-3-amino-4-fluoropiperidin-1-yl)-5,6-difluoro-1H-benzo[d]imidazol-1-yl)-1-(7-oxa-2-azaspiro[3.5]nonan-2-yl)ethanone | 438.2 |

TABLE 13

Characterization data for compounds made following scheme 14

| Ex. # | Freq., Solvent | ¹HNMR Data (δ ppm) | Separation Stage | SFC Isomer Separation Conditions |
|---|---|---|---|---|
| 426 | 600 MHz, DMSO-$d_6$ | 7.34-7.60 (m, 2H), 4.73-4.80 (m, 2H), 4.48-4.60 (m, 2H), 4.31-4.48 (m, 1H), 4.17-4.28 (m, 1H), 4.06-4.15 (m, 1H), 3.82-3.94 (m, 1H), 2.96-3.06 (m, 2H), 2.74-2.84 (m, 1H), 2.06-2.17 (m, 1H), 1.64-1.88 (m, 3H), | — | — |
| 427 | 600 MHz, DMSO-$d_6$ | 7.46 (dd, J = 7.43, 11.17 Hz, 1H), 7.40 (dd, J = 7.36, 10.39 Hz, 1H), 4.72-4.79 (m, 2H), 4.56-4.64 (m, 1H), 4.41-4.49 (m, 2H), 4.36 (br s, 1H), 4.16 (dd, J = 7.20, 9.77 Hz, 3H), 4.08 (dt, J = 4.98, 8.25 Hz, 1H), 3.70 (dd, J = 4.71, 10.00 Hz, 1H), 2.95-3.06 (m, 2H), 2.78 (ddd, J = 5.02, 8.10, 12.73 Hz, 1H), 2.02-2.16 (m, 1H), 1.89 (br s, 1H), 1.72-1.87 (m, 1H), 1.15 (s, 9H), | — | — |
| 428 | 600 MHz, DMSO-$d_6$ | 7.37-7.50 (m, 2H), 4.87 (s, 1H), 4.76-4.85 (m, 2H), 4.34-4.47 (m, 2H), 3.20-3.27 (m, 1H), 3.14-3.19 (m, 1H), 2.98-3.11 (m, 2H), 2.87-2.97 (m, 1H), 2.79 (dd, J = 8.37, 12.57 Hz, 1H), 2.03-2.18 (m, 1H), 1.96 (dt, J = 4.67, 9.19 Hz, 1H), 1.78-1.91 (m, 1H) | — | — |
| 429 | 600 MHz, DMSO-$d_6$ | 7.46 (dd, J = 7.47, 11.13 Hz, 1H), 7.38 (dd, J = 7.32, 10.67 Hz, 1H), 4.70-4.79 (m, 2H), 4.32-4.47 (m, 1H), 4.25-4.30 (m, 1H), 3.92-3.99 (m, 2H), 3.62 (dd, J = 5.92, 9.65 Hz, 1H), 3.34-3.43 (m, 1H), 2.96-3.05 (m, 2H), 2.76-2.82 (m, 1H), 2.31-2.47 (m, 1H), 2.08-2.16 (m, 1H), 1.74-1.91 (m, 3H), 0.86 (t, J = 5.57 Hz, 6H) | — | — |
| 430 | 600 MHz, DMSO-$d_6$ | 7.47 (t, J = 9.20 Hz, 1H), 7.39 (dd, J = 7.36, 10.70 Hz, 1H), 4.74 (d, J = 1.79 Hz, 2H), 4.32-4.46 (m, 3H), 4.03-4.10 (m, 2H), 3.37-3.54 (m, 1H), 2.92-3.05 (m, 3H), 2.88 (t, J = 12.38 Hz, 4H), 2.74-2.83 (m, 1H), 2.11 (ddd, J = 3.97, 8.10,17.13 Hz, 1H), 1.74-1.93 (m, 1H), | — | — |
| 431 | 600 MHz, DMSO-$d_6$ | 7.47 (dd, J = 7.43, 11.17 Hz, 1H), 7.39 (dd, J = 7.36, 10.70 Hz, 1H), 4.72-4.80 (m, 2H), 4.34-4.47 (m, 1H), 4.02 (q, J = 8.33 Hz, 2H), 3.69 (s, 2H), 3.46-3.59 (m, 4H), 3.34-3.36 (m, 1H), 2.96-3.06 (m, 2H), 2.80 (dd, J = 8.21, 12.50 Hz, 1H), 2.08-2.16 (m, 1H), 1.70-1.88 (m, 6H) | — | — |

Example 432: (R)-6-((2-(4,4-difluoro-3-(methylamino)piperidin-1-yl)-6-fluoro-1H-benzo[d]imidazol-1-yl)methyl)nicotinonitrile

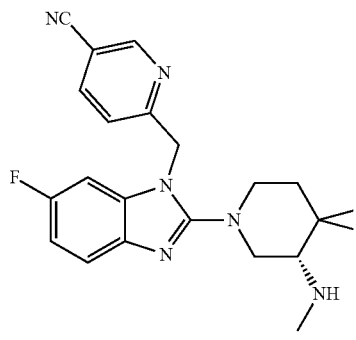

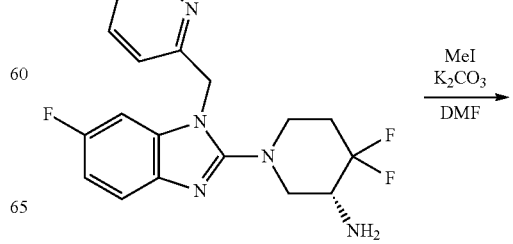

-continued

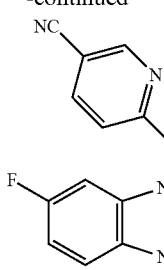

A vial was charged with (R)-6-((2-(3-amino-4,4-difluoropiperidin-1-yl)-6-fluoro-1H-benzo[d]imidazol-1-yl)methyl)nicotinonitrile (100 mg, 0.259 mmol). The vial was fitted with a stirring bar and DMF (1.3 mL) was added. Potassium carbonate (53.7 mg, 0.388 mmol) was added, followed by iodomethane (40.4 mg, 0.285 mmol). The mixture was left to stir at room temperature for 2 hours. Formation of the mono and bis-methylated amine was observed by LCMS. The reaction was worked up by diluting with EtOAc and NH$_4$Cl (aq). The mixture was extracted with EtOAc, the organic extracts were combined, dried over MgSO$_4$, filtered and concentrated to give the crude mixture. The crude was purified on HPLC to afford the title compound. MS: (ESI pos. ion) m/z: 401.2 [M+1]; $^1$H NMR (600 MHz, d$_6$-DMSO) δ 8.95 (dd, J=0.62, 2.18 Hz, 1H), 8.33 (dd, J=2.18, 8.10 Hz, 1H), 7.51 (d, J=8.10 Hz, 1H), 7.46 (dd, J=4.98, 8.72 Hz, 1H), 7.11 (dd, J=2.49, 9.03 Hz, 1H), 6.95 (ddd, J=2.49, 8.72, 9.96 Hz, 1H), 5.54 (s, 2H), 3.35-3.41 (m, 1H), 3.28-3.32 (m, 1H), 3.10-3.16 (m, 1H), 2.91-2.96 (m, 1H), 2.88 (td, J=3.66, 13.23 Hz, 1H), 2.25 (s, 3H), 2.13-2.23 (m, 1H), 2.01-2.13 (m, 1H).

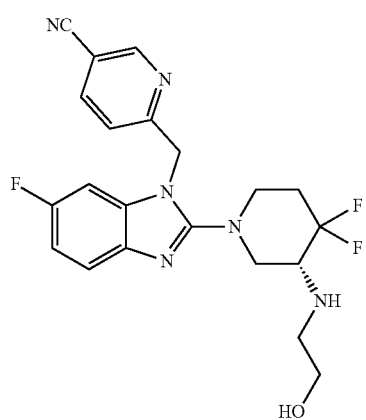 [SMILES: N#Cc1ccc(Cn2c(N3CCC(F)(F)[C@H](NCCO)C3)nc3ccc(F)cc32)nc1]

Example 433: (R)-6-((2-(4,4-difluoro-3-((2-hydroxyethyl)amino)piperidin-1-yl)-6-fluoro-1H-benzo[d]imidazol-1-yl)methyl)nicotinonitrile

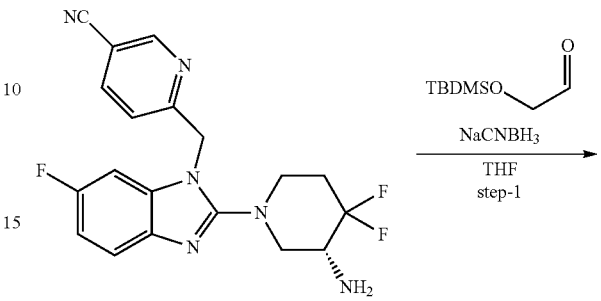

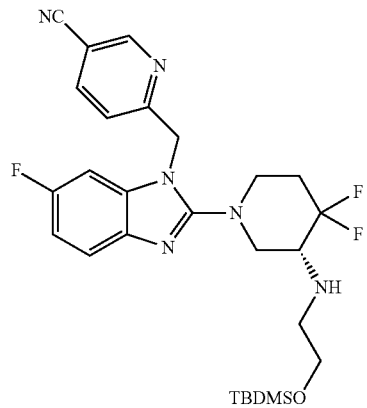

Step 1. (R)-6-((2-(3-((2-((tert-butyldimethylsilyl)oxy)ethyl)amino)-4,4-difluoropiperidin-1-yl)-6-fluoro-1H-benzo[d]imidazol-1-yl)methyl)nicotinonitrile (R)-6-((2-(3-amino-4,4-difluoropiperidin-1-yl)-6-fluoro-1H-benzo[d]imidazol-1-yl)methyl)nicotinonitrile (89.4 mg, 0.231 mmol) was combined with (tert-butyldimethylsilyloxy)acetaldehyde (63.7 µl, 0.301 mmol) in a vial. Tetrahydrofuran (2.3 mL) and sodium cyanoborohydride (24.2 µl, 0.463 mmol) were added. The mixture was allowed to stir at room temperature for 2 hours, at which time starting material was fully consumed. The reaction was quenched with NH$_4$Cl (aq), extracted into EtOAc, washed with brine, dried over MgSO$_4$, filtered and concentrated to give (R)-6-((2-(3-((2-((tert-butyldimethylsilyl)oxy)ethyl)amino)-4,4-difluoropiperidin-1-yl)-6-fluoro-1H-benzo[d]imidazol-1-yl)methyl)nicotinonitrile, which was used in the next step without further purification.

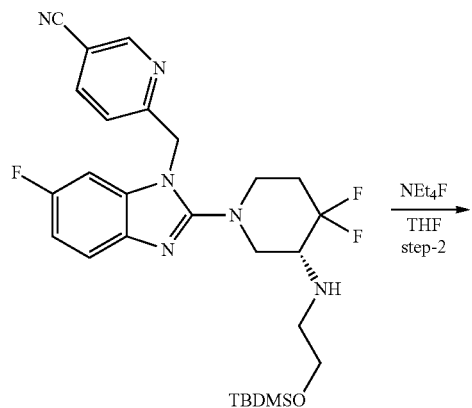

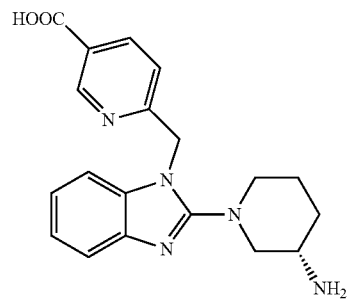 [SMILES: N[C@H]1CCCN(c2nc3ccccc3n2Cc2ccc(C(=O)O)cn2)C1]

Example 434: (S)-6-((2-(3-aminopiperidin-1-yl)-1H-benzo[d]imidazol-1-yl)methyl)nicotinic acid

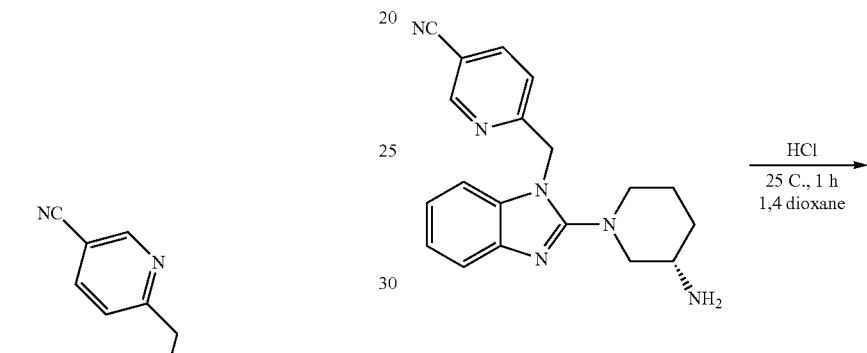

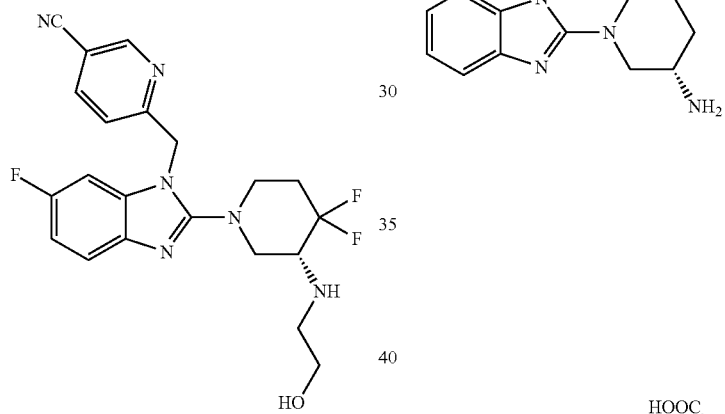

Step 2. (R)-6-((2-(4,4-difluoro-3-((2-hydroxyethyl)amino)piperidin-1-yl)-6-fluoro-1H-benzo[d]imidazol-1-yl)methyl)nicotinonitrile (Example 433)

(R)-6-((2-(3-((2-((tert-butyldimethylsilyl)oxy)ethyl)amino)-4,4-difluoropiperidin-1-yl)-6-fluoro-1H-benzo[d]imidazol-1-yl)methyl)nicotinonitrile was dissolved in THF (2.3 mL), and tetrabutylammonium fluoride (1.0 M solution in THF, 301 µl, 0.301 mmol) was added. The mixture was left to stir at rt for 16 h. Clean deprotection was observed by LCMS. The resulting mixture was worked up by diluting with water and EtOAc, extracting into EtOAc, drying over MgSO$_4$, filtering and concentrating. The crude was purified by column chromatography (4 g SiO$_2$, 0-70% EtOAc in heptane) to furnish the title compound. MS: (ESI pos. ion) m/z: 431.2 [M+1]. $^1$H NMR (500 MHz, d$_4$-MeOH) δ 8.82 (br s, 1H), 8.13-8.25 (m, 1H), 7.59 (d, J=8.30 Hz, 1H), 7.55 (dd, J=4.67, 8.30 Hz, 1H), 6.98-7.06 (m, 2H), 5.58 (s, 2H), 4.17 (dtd, J=4.80, 8.63, 12.98 Hz, 1H), 4.06 (br d, J=13.23 Hz, 1H), 3.84-3.95 (m, 2H), 3.53-3.66 (m, 2H), 3.38-3.47 (m, 1H), 3.32-3.37 (m, 2H), 2.25-2.42 (m, 2H).

A vial was charged with (S)-6-((2-(3-aminopiperidin-1-yl)-1H-benzo[d]imidazol-1-yl)methyl)nicotinonitrile (0.03 g, 0.09 mmol) and 3.99 N aqueous hydrochloric acid (0.075 ml, 0.451 mmol) in 1,4-dioxane (0.301 ml), and shaken at ambient temperature for 1 h. The reaction mixture was concentrated and purified by reverse phase HPLC. $^1$H NMR (600 MHz, DMSO-d$_6$) δ 13.23-13.65 (br s, 1H), 8.98 (d, J=1.40 Hz, 1H), 8.29 (br d, J=6.85 Hz, 1H), 8.12-8.19 (m, 1H), 8.11 (br s, 1H), 7.51 (br d, J=7.71 Hz, 1H), 7.21 (br s, 1H), 7.15 (br s, 1H), 5.57-5.61 (br s, 2H), 3.58-3.76 (m, 1H), 3.44-3.57 (m, 1H), 3.16-3.29 (m, 2H), 3.06 (br s, 1H), 2.52-2.55 (m, 1H), 1.95 (br s, 1H), 1.83 (br s, 1H), 1.53-1.64 (m, 1H). MS: (ESI pos. ion) m/z: 352.2 [M+1].

547

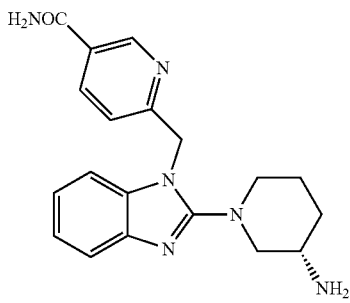 [SMILES: NC(=O)c1ccc(Cn2c(N3CCC[C@H](N)C3)nc3ccccc32)nc1]

Example 435: (S)-6-((2-(3-aminopiperidin-1-yl)-1H-benzo[d]imidazol-1-yl)methyl)nicotinamide

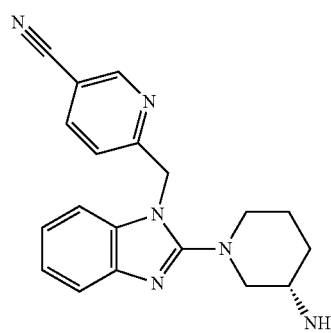

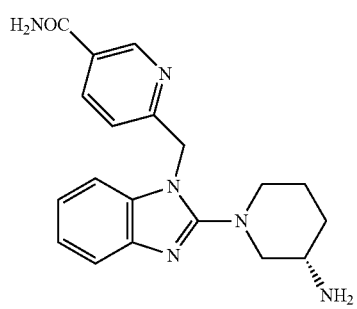

A vial containing (S)-6-((2-(3-aminopiperidin-1-yl)-1H-benzo[d]imidazol-1-yl)methyl)nicotinonitrile (0.03 g, 0.090 mmol) and NaOH (1 M in water) (0.271 ml, 0.271 mmol) in methanol (0.30 mL) was shaken at rt for 3 h. The reaction mixture was diluted with EtOAc, filtered, concentrated, and purified by reverse phase HPLC to afford the title compound. $^1$H NMR (600 MHz, DMSO-d$_6$) δ 8.94 (s, 1H), 8.16 (dd, J=2.22, 8.14 Hz, 1H), 8.11 (br s, 1H), 7.56 (br s, 1H), 7.43 (d, J=7.79 Hz, 1H), 7.18 (d, J=8.17 Hz, 1H), 6.98-7.11 (m, 3H), 5.38-5.44 (m, 2H), 3.37-3.43 (m, 1H), 2.76-2.89 (m, 2H), 2.57-2.66 (m, 1H), 2.52-2.56 (m, 1H), 1.78-1.84 (m, 1H), 1.65-1.74 (m, 1H), 1.50-1.58 (m, 1H), 1.14-1.28 (m, 1H). MS: (ESI pos. ion) m/z: 351.2 [M+1].

548

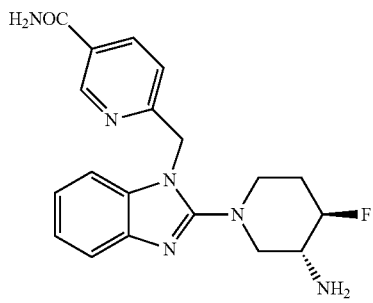 [SMILES: NC(=O)c1ccc(Cn2c(N3CC[C@@H](F)[C@H](N)C3)nc3ccccc32)nc1]

Example 436: 6-((2-((3R,4R)-3-amino-4-fluoropiperidin-1-yl)-1H-benzo[d]imidazol-1-yl)methyl)nicotinamide

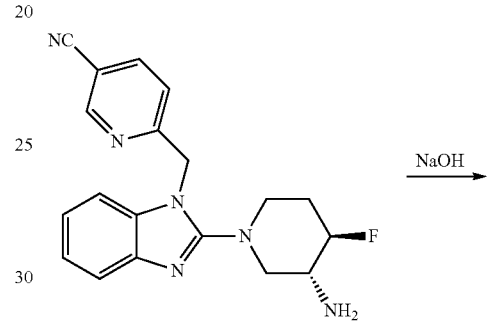

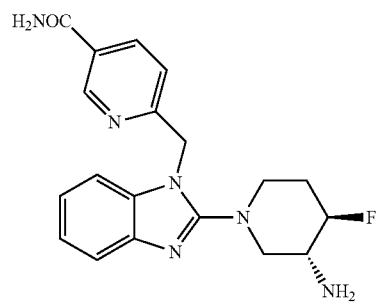

A vial containing 6-((2-((3R,4R)-3-amino-4-fluoropiperidin-1-yl)-1H-benzo[d]imidazol-1-yl)methyl)nicotinonitrile (0.03 g, 0.090 mmol) and NaOH (1 M in water) (0.271 ml, 0.271 mmol) in methanol (0.301 ml) was shaken at ambient temperature for 3 h. The reaction mixture was diluted with EtOAc, filtered concentrated and purified by reverse phase HPLC to afford the title compound. $^1$H NMR (500 MHz, MeOH-d4) δ 8.84-9.04 (m, 1H), 8.08-8.27 (m, 1H), 7.48-7.58 (m, 1H), 7.06-7.34 (m, 4H), 5.51 (br d, J=6.75 Hz, 3H), 4.29-4.50 (m, 1H), 3.61 (br dd, J=3.89, 7.79 Hz, 1H), 3.39-3.50 (m, 1H), 2.87-3.19 (m, 3H), 2.10-2.27 (m, 1H), 1.78-1.97 (m, 1H), 0.79-0.98 (m, 1H). MS: (ESI pos. ion) m/z: 369.2 [M+1].

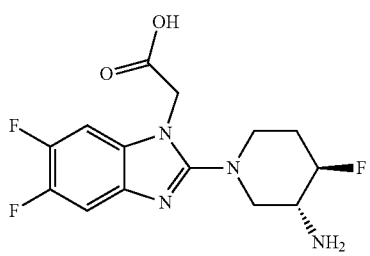 [SMILES: N[C@@H]1CN(c2nc3cc(F)c(F)cc3n2CC(=O)O)CC[C@H]1F]

Example 437: 2-(2-((3R,4R)-3-amino-4-fluoropiperidin-1-yl)-5,6-difluoro-1H-benzo[d]imidazol-1-yl)acetic acid

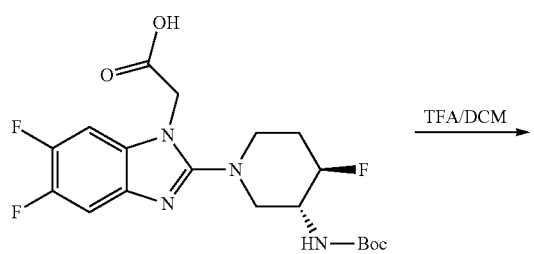

TFA/DCM

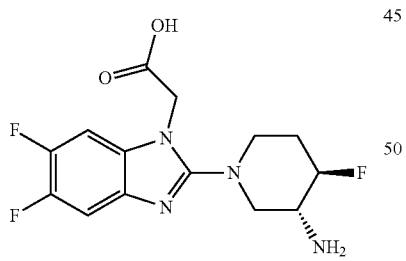

2-(2-((3R,4R)-3-((tert-butoxycarbonyl)amino)-4-fluoropiperidin-1-yl)-5,6-difluoro-1H-benzo[d]imidazol-1-yl) acetic acid was treated with TFA (0.5 mL) in DCM (1 mL) and stirred at rt for 1 h. Reaction mixture was concentrated and purified via reverse phase HPLC to obtain the title compound. $^1$H NMR (600 MHz, DMSO-d6) δ 7.47-7.60 (m, 2H), 4.82-4.92 (m, 2H), 4.51-4.59 (dt, J=4.63, 9.01 Hz, 1H), 3.35-3.46 (m, 2H), 3.24-3.30 (m, 1H), 2.95 (br t, J=10.63 Hz, 1H), 2.73-2.89 (m, 1H), 2.13-2.21 (m, 1H), 1.79-1.89 (m, 1H). MS: ESI pos. ion) m/z: 329.0 [M+1].

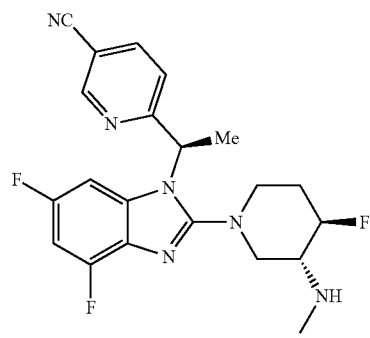

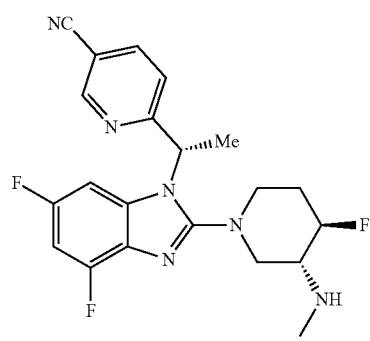

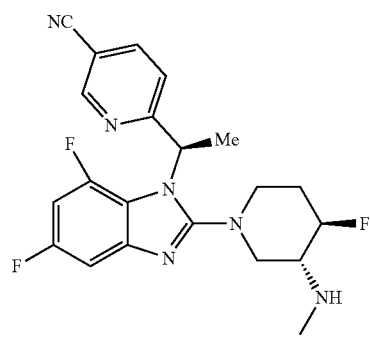

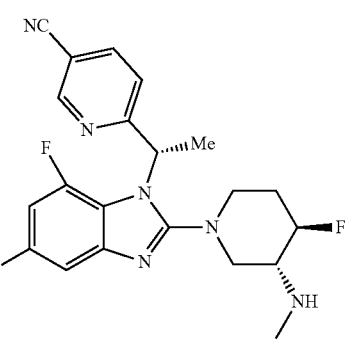

Examples 438-441: 6-((R)-1-(4,6-difluoro-2-((3R,4R)-4-fluoro-3-(methylamino)piperidin-1-yl)-1H-benzo[d]imidazol-1-yl)ethyl)nicotinonitrile (Example 596) and 6-((S)-1-(4,6-difluoro-2-((3R,4R)-4-fluoro-3-(methylamino)piperidin-1-yl)-1H-benzo[d]imidazol-1-yl)ethyl)nicotinonitrile (Example 597) and 6-((R)-1-(5,7-difluoro-2-((3R,4R)-4-fluoro-3-(methylamino)piperidin-1-yl)-1H-benzo[d]imidazol-1-yl)ethyl)nicotinonitrile (Example 598) and 6-((S)-1-(5,7-difluoro-2-((3R,4R)-4-fluoro-3-(methylamino)piperidin-1-yl)-1H-benzo[d]imidazol-1-yl)ethyl)nicotinonitrile (Example 599)

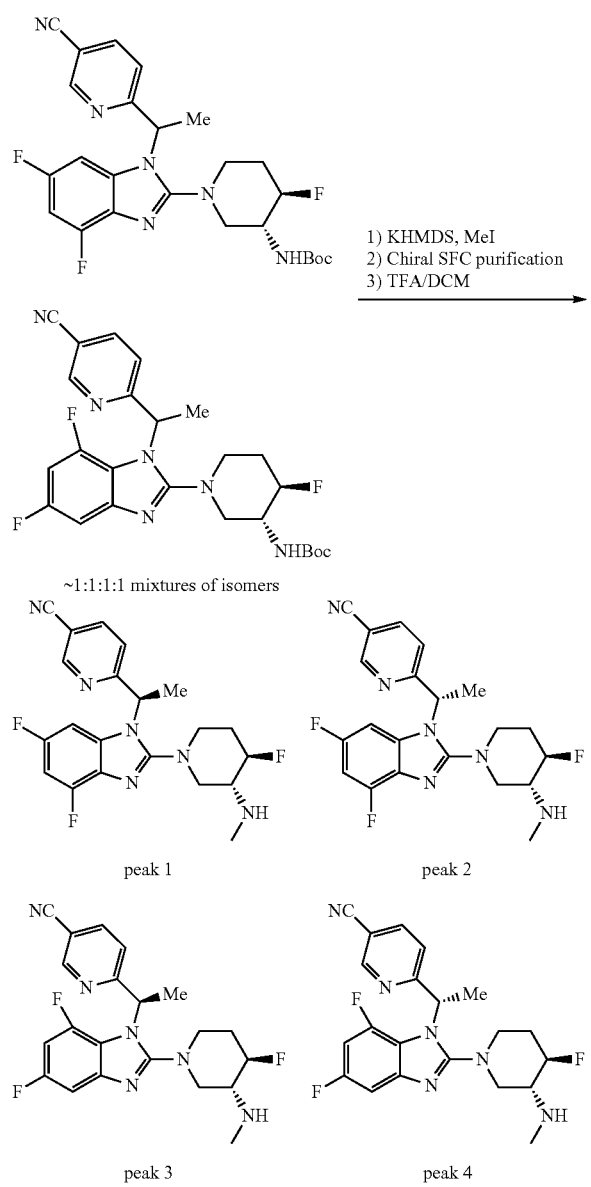

Step 1. tert-butyl ((3R,4R)-1-(1-(1-(5-cyanopyridin-2-yl)ethyl)-4,6-difluoro-1H-benzo[d]imidazol-2-yl)-4-fluoropiperidin-3-yl)carbamate (1.05 g, 2.098 mmol, mixture of 4 isomers) and methyl iodide (0.144 ml, 2.308 mmol) were dissolved in THF and cooled to 0 C. potassium bis(trimethylsilyl)amide solution, 1 m in tetrahydrofuran (2.203 ml, 2.203 mmol) was added slowly and the reaction stirred for 1 hour. Conversion stalled, so the reaction was quenched with ammonium chloride, then extracted with DCM (3×). The organics were combined, dried over Na2SO4, filtered, and concentrated to provide a mixture of methylated and N—H products.

Step 2. Isomers were separated using chiral SFC: Chiralpak Cel2, 15% MeOH, 0.2% DEA.

Step 3. Each individual isomer (100 mg, 1 equiv), was dissolved in DCM (5 mL), then TFA (0.5 mL) was added. After 1 hour, the solutions were poured onto pre-wetted SCX columns and flushed with methanol. The products were eluted with methanolic ammonia.

Peak 1: 6-((R)-1-(4,6-difluoro-2-((3R,4R)-4-fluoro-3-(methylamino)piperidin-1-yl)-1H-benzo[d]imidazol-1-yl)ethyl)nicotinonitrile (Example 438): $^1$H NMR (500 MHz, METHANOL-d4) δ ppm 1.88-2.08 (m, 4H) 2.22-2.33 (m, 1H) 2.41-2.50 (m, 3H) 2.99 (dd, J=12.72, 9.34 Hz, 1H) 3.16-3.30 (m, 2H) 3.50-3.64 (m, 1H) 3.77-3.95 (m, 1H) 4.53-4.76 (m, 1H) 5.97 (q, J=7.01 Hz, 1H) 6.63-6.78 (m, 1H) 7.04-7.16 (m, 1H) 7.62 (d, J=8.30 Hz, 1H) 8.19 (dd, J=8.30, 2.08 Hz, 1H) 8.84 (d, J=1.56 Hz, 1H). MS: (ESI pos. ion) m/z: 415.2 [M+1].

Peak 2: 6-((S)-1-(4,6-difluoro-2-((3R,4R)-4-fluoro-3-(methylamino)piperidin-1-yl)-1H-benzo[d]imidazol-1-yl)ethyl)nicotinonitrile (Example 597): $^1$H NMR (500 MHz, METHANOL-d4) δ ppm 1.97 (d, J=7.01 Hz, 3H) 2.03-2.28 (m, 2H) 2.52 (s, 3H) 2.99-3.21 (m, 3H) 3.59 (br d, J=12.98 Hz, 1H) 3.71-3.80 (m, 1H) 4.54-4.75 (m, 1H) 5.97 (q, J=7.01 Hz, 1H) 6.64-6.75 (m, 1H) 7.10 (dd, J=8.82, 2.08 Hz, 1H) 7.58 (d, J=8.30 Hz, 1H) 8.18 (dd, J=8.30, 2.08 Hz, 1H) 8.76-8.87 (m, 1H). MS: (ESI pos. ion) m/z: 415.2 [M+1].

Peak 3: 6-((R)-1-(5,7-difluoro-2-((3R,4R)-4-fluoro-3-(methylamino)piperidin-1-yl)-1H-benzo[d]imidazol-1-yl)ethyl)nicotinonitrile (Example 598): $^1$H NMR (500 MHz, METHANOL-d4) δ ppm 2.01 (d, J=7.27 Hz, 4H) 2.18-2.33 (m, 1H) 2.49 (s, 3H) 2.98 (dd, J=12.46, 9.34 Hz, 1H) 3.14-3.28 (m, 2H) 3.47 (br dd, J=12.85, 1.95 Hz, 1H) 3.79 (dtd, J=8.40, 4.04, 4.04, 2.47 Hz, 1H) 4.57-4.76 (m, 1H) 5.91-6.04 (m, 1H) 6.67-6.85 (m, 2H) 7.63 (d, J=8.30 Hz, 1H) 8.13-8.25 (m, 1H) 8.84-8.96 (m, 1H). MS: (ESI pos. ion) m/z: 415.2 [M+1].

Peak 4: 6-((S)-1-(5,7-difluoro-2-((3R,4R)-4-fluoro-3-(methylamino)piperidin-1-yl)-1H-benzo[d]imidazol-1-yl)ethyl)nicotinonitrile (Example 599): $^1$H NMR (500 MHz, METHANOL-d4) δ ppm 2.02 (d, J=7.01 Hz, 3H) 2.16-2.35 (m, 1H) 2.51-2.68 (m, 3H) 2.98-3.20 (m, 3H) 3.46-3.60 (m, 1H) 3.65-3.78 (m, 1H) 4.54-4.78 (m, 1H) 5.99 (q, J=7.27 Hz, 1H) 6.64-6.85 (m, 2H) 7.58 (d, J=8.30 Hz, 1H) 8.19 (dd, J=8.17, 2.21 Hz, 1H) 8.83-8.96 (m, 1H). MS: (ESI pos. ion) m/z: 415.2 [M+1].

Scheme 15. Compounds made through mixed anhydride

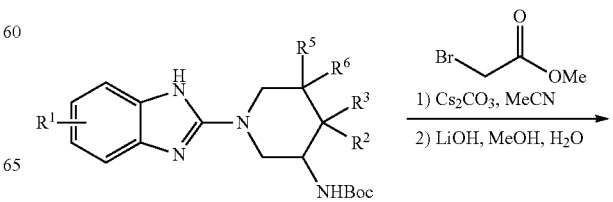

553
-continued

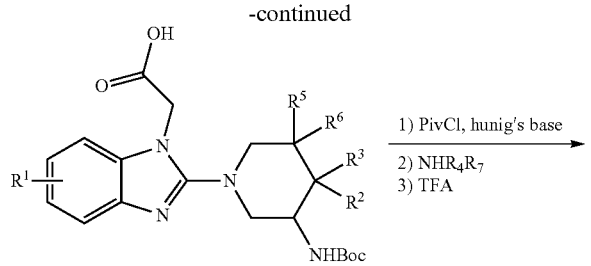

1) PivCl, hunig's base
2) NHR₄R₇
3) TFA

554
-continued

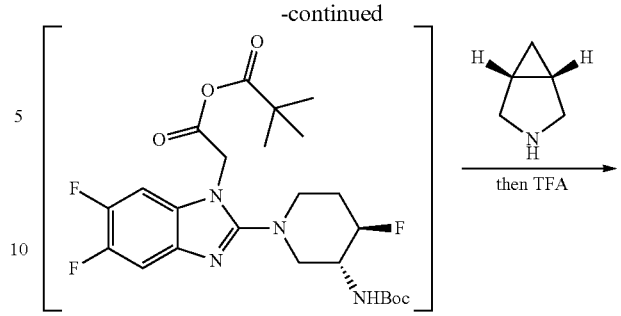

then TFA

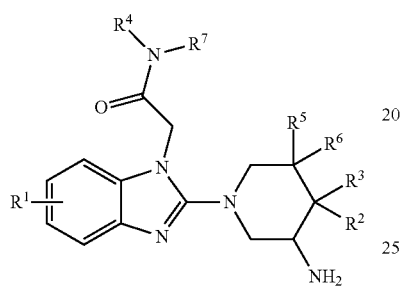

Example 607: 2-(2-((3R,4R)-3-amino-4-fluoropiperidin-1-yl)-5,6-difluoro-1H-benzo[d]imidazol-1-yl)-1-((1R,5S)-3-azabicyclo[3.1.0]hexan-3-yl)ethanone

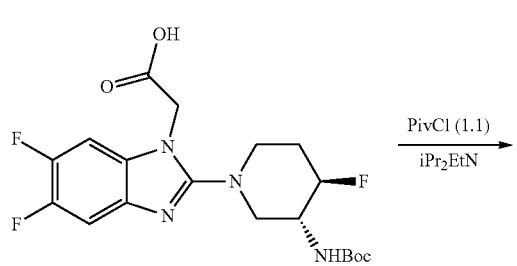

PivCl (1.1)
iPr₂EtN

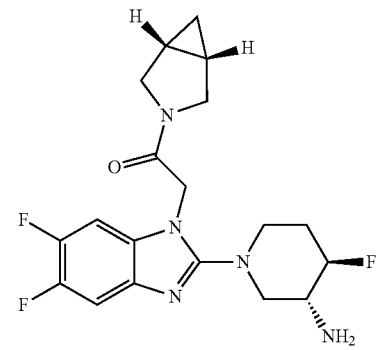

Step 1. 2-(2-((3R,4R)-3-amino-4-fluoropiperidin-1-yl)-5,6-difluoro-1H-benzo[d]imidazol-1-yl)-1-((1R, 5S)-3-azabicyclo[3.1.0]hexan-3-yl)ethanone 2-(2-((3R,4R)-3-((tert-butoxycarbonyl)amino)-4-fluoropiperidin-1-yl)-5,6-difluoro-1H-benzo[d]imidazol-1-yl) acetic acid (110 mg, 0.257 mmol), 1,1'-dimethyltriethylamine (135 µl, 0.770 mmol), and tetrahydrofuran (1284 µl) were combined in a vial and cooled to 0 C. trimethyl acetyl chloride (24.12 µl, 0.282 mmol) was added dropwise and the mixture stirred for 15 minutes. LCMS showed full conversion to mixed anhydride (appears as methyl ester by LCMS from MeOH displacement). 3-azabicyclo[3.1.0]hexane (1.5 equiv) was added and allowed to stir for 1 hour. The mixture was concentrated down, then redissovled in DCM/TFA (1:1) and allowed to stir for 1 hour. The mixture was reconcentrated, then redissolved in 1 mL DMSO, filtered, and purified by reverse phase HPLC to provide the desired product.

TABLE 14

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 600 | (2-methylazetidine) | B | (structure) | 2-(2-((3R,4R)-3-amino-4-fluoropiperidin-1-yl)-5,6-difluoro-1H-benzo[d]imidazol-1-yl)-1-(2-methylazetidin-1-yl)ethanone | 382.0 |
| 601 | (N-methyl-2,2-difluoroethylamine) | B | (structure) | 2-(2-((3R,4R)-3-amino-4-fluoropiperidin-1-yl)-5,6-difluoro-1H-benzo[d]imidazol-1-yl)-N-(2,2-difluoroethyl)-N-methylacetamide | 406.2 |
| 602 | (N-methylcyclopropylamine) | B | (structure) | 2-(2-((3R,4R)-3-amino-4-fluoropiperidin-1-yl)-5,6-difluoro-1H-benzo[d]imidazol-1-yl)-N-cyclopropyl-N-methylacetamide | 382.2 |
| 603 | (N-methyl-(R)-1-cyanoethylamine) | B | (structure) | 2-(2-((3R,4R)-3-amino-4-fluoropiperidin-1-yl)-5,6-difluoro-1H-benzo[d]imidazol-1-yl)-N-((R)-1-cyanoethyl)-N-methylacetamide | 395.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 604 | | B | 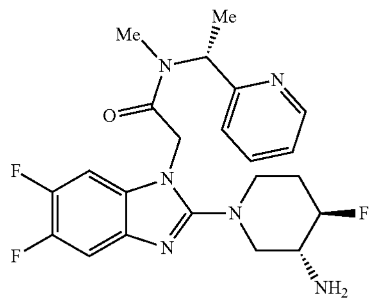 [SMILES: C[C@H](c1ccccn1)N(C)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-methyl-N-((R)-1-pyridin-2-yl)ethyl)acetamide | 447.0 |
| 605 | | B | 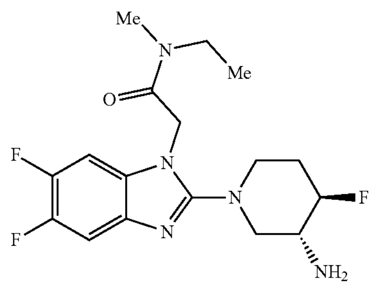 [SMILES: CCN(C)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-ethyl-N-methylacetamide | 370.2 |
| 606 | | B | 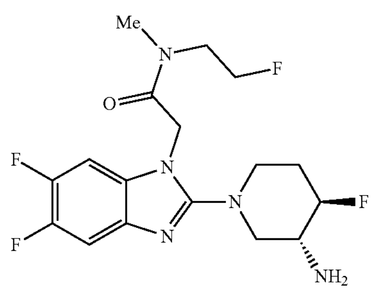 [SMILES: CN(CCF)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-(2-fluoroethyl)-N-methylacetamide | 388.2 |
| 607 | | B | 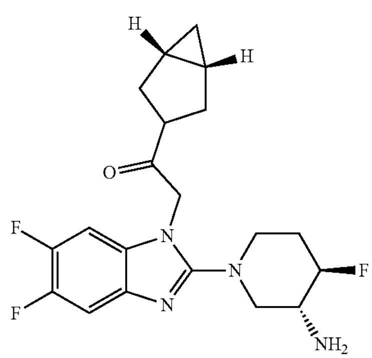 [SMILES: N[C@@H]1CN(c2nc3cc(F)c(F)cc3n2CC(=O)C2C[C@@H]3C[C@@H]3C2)CC[C@H]1F] | 2-(2-((3R,4R)-3-amino-4-fluoropiperidin-1-yl)-5,6-difluoro-1H-benzo[d]imidazol-1-yl)-1-((1R,5S)-3-azabicyclo[3.1.0]hexan-3-yl)ethanone | 394.0 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 608 | | B | 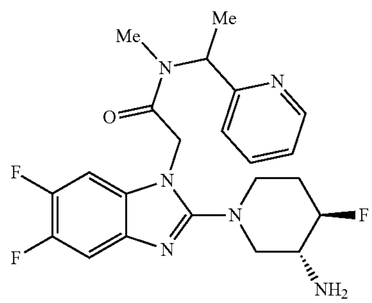 [SMILES: CC(c1ccccn1)N(C)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-methyl-N-(1-(pyridin-2-yl)ethyl)acetamide | 447.2 |
| 609 | | B | 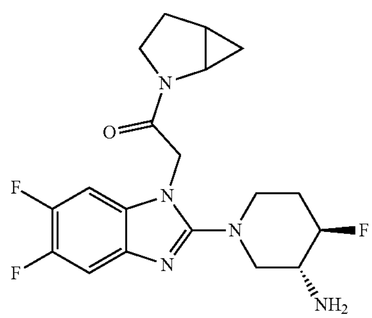 [SMILES: N[C@@H]1CN(c2nc3cc(F)c(F)cc3n2CC(=O)N2CCC3CC32)CC[C@H]1F] | 2-(2-((3R,4R)-3-amino-4-fluoropiperidin-1-yl)-5,6-difluoro-1H-benzo[d]imidazol-1-yl)-1-(2-azabicyclo[3.1.0]hexan-2-yl)ethanone | 394.2 |
| 610 | | B | 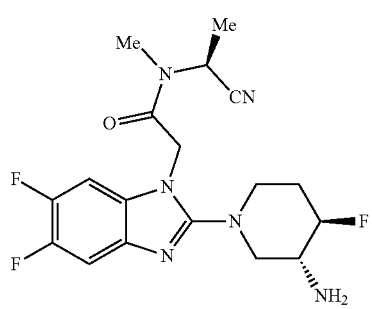 [SMILES: C[C@@H](C#N)N(C)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-((S)-1-cyanoethyl)-N-methylacetamide | 395.4 |
| 611 | | B | 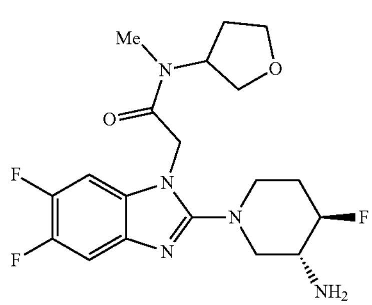 [SMILES: CN(C(=O)Cn1c(N2CC[C@@H](F)[C@H](N)C2)nc2cc(F)c(F)cc21)C1CCOC1] | 2-(2-((3R,4R)-3-amino-4-fluoropiperidin-1-yl)-5,6-difluoro-1H-benzo[d]imidazol-1-yl)-N-methyl-N-(tetrahydrofuran-3-yl)acetamide | 412.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 612 | 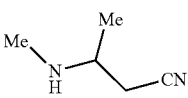 | B | 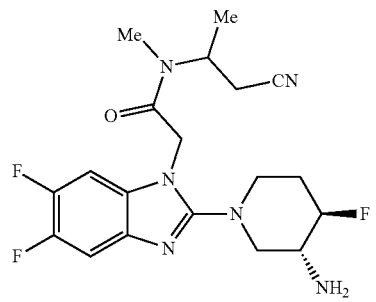 [SMILES: CC(CC#N)N(C)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-(1-cyanopropan-2-yl)-N-methylacetamide | 409.2 |
| 613 | 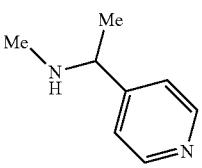 | B | 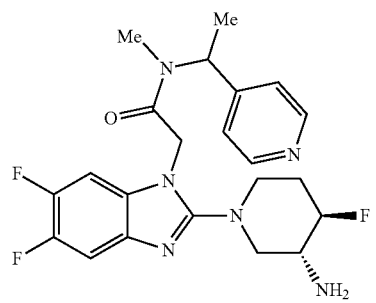 | 2-(2-((3R,4R)-3-amino-4-fluoropiperidin-1-yl)-5,6-difluoro-1H-benzo[d]imidazol-1-yl)-N-methyl-N-(1-(pyridin-4-yl)ethyl)acetamide | 447.2 |
| 614 | 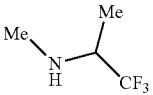 | B | 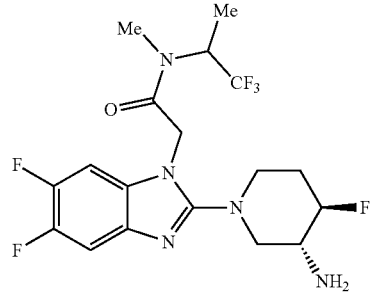 [SMILES: CC(N(C)C(=O)Cn1c(N2CC[C@@H](F)[C@H](N)C2)nc2cc(F)c(F)cc21)C(F)(F)F] | 2-(2-((3R,4R)-3-amino-4-fluoropiperidin-1-yl)-5,6-difluoro-1H-benzo[d]imidazol-1-yl)-N-methyl-N-(1,1,1-trifluoropropan-2-yl)acetamide | 438.2 |
| 615 | 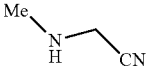 | B | 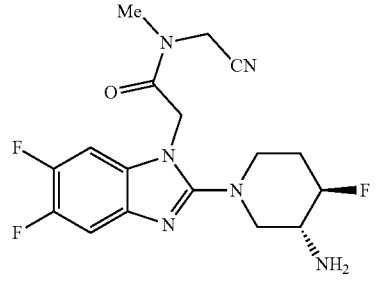 | 2-(2-((3R,4R)-3-amino-4-fluoropiperidin-1-yl)-5,6-difluoro-1H-benzo[d]imidazol-1-yl)-N-(cyanomethyl)-N-methylacetamide | 381.2 |
| 616 | 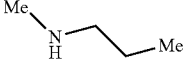 | B | 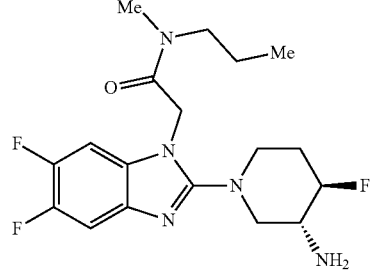 | 2-(2-((3R,4R)-3-amino-4-fluoropiperidin-1-yl)-5,6-difluoro-1H-benzo[d]imidazol-1-yl)-N-methyl-N-propylacetamide | 384.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 617 | | B | 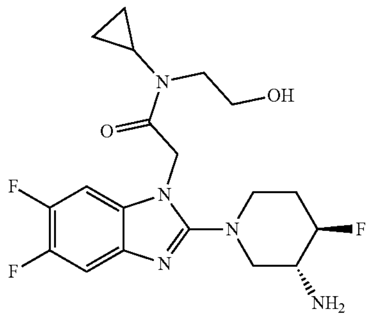 [SMILES: N[C@@H]1CN(c2nc3cc(F)c(F)cc3n2CC(=O)N(CCO)C2CC2)CC[C@H]1F] | 2-(2-((3R,4R)-3-amino-4-fluoropiperidin-1-yl)-5,6-difluoro-1H-benzo[d]imidazol-1-yl)-N-cyclopropyl-N-(2-hydroxyethyl)acetamide | 412.0 |
| 618 | | B | 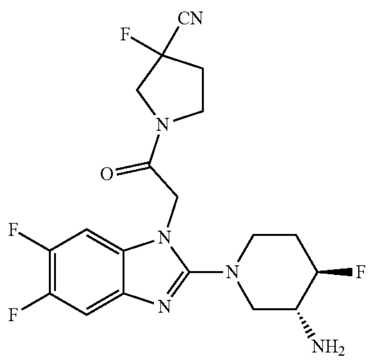 [SMILES: N#CC1(F)CCN(C(=O)Cn2c(N3CC[C@@H](F)[C@H](N)C3)nc3cc(F)c(F)cc32)C1] | 1-(2-(2-((3R,4R)-3-amino-4-fluoropiperidin-1-yl)-5,6-difluoro-1H-benzo[d]imidazol-1-yl)acetyl)-3-fluoropyrrolidine-3-carbonitrile | 425.2 |
| 619 | | B | 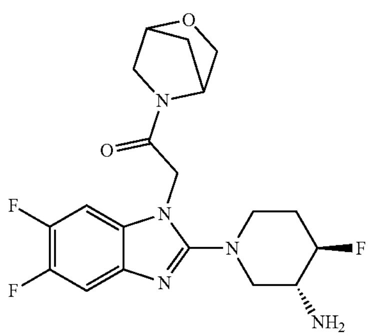 [SMILES: N[C@@H]1CN(c2nc3cc(F)c(F)cc3n2CC(=O)N2CC3CC2CO3)CC[C@H]1F] | 2-(2-((3R,4R)-3-amino-4-fluoropiperidin-1-yl)-5,6-difluoro-1H-benzo[d]imidazol-1-yl)-1-(2-oxa-5-azabicyclo[2.2.1]heptan-5-yl)ethanone | 410.0 |
| 620 | | B | 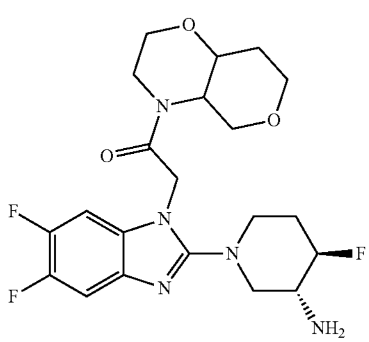 [SMILES: N[C@@H]1CN(c2nc3cc(F)c(F)cc3n2CC(=O)N2CCOC3CCOCC32)CC[C@H]1F] | 2-(2-((3R,4R)-3-amino-4-fluoropiperidin-1-yl)-5,6-difluoro-1H-benzo[d]imidazol-1-yl)-1-(hexahydropyrano[4,3-b][1,4]oxazin-4(7H)-yl)ethanone | 454.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 621 | 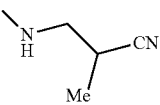 | B | 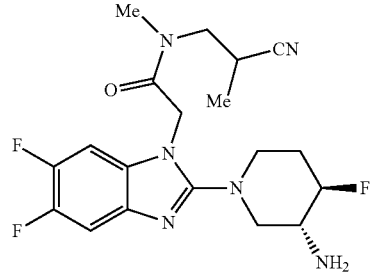 [SMILES: CC(C#N)CN(C)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-(2-cyanopropyl)-N-methylacetamide | 409.2 |
| 622 | 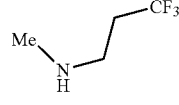 | B | 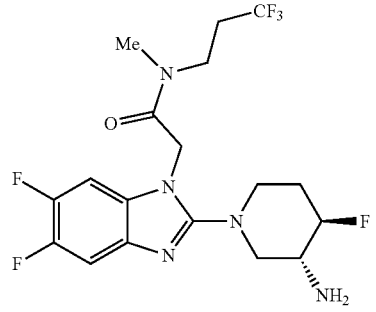 [SMILES: CN(CCC(F)(F)F)C(=O)Cn1c(N2CC[C@@H](F)[C@H](N)C2)nc2cc(F)c(F)cc21] | -(2-((3R,4R)-3-amino-4-fluoropiperidin-1-yl)-5,6-difluoro-1H-benzo[d]imidazol-1-yl)-N-methyl-N-(3,3,3-trifluoropropyl)acetamide | 438.2 |
| 623 | 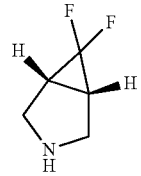 | B | 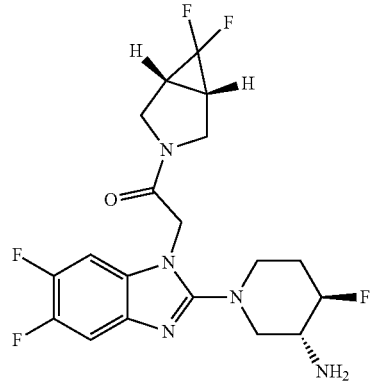 [SMILES: N[C@@H]1CN(c2nc3cc(F)c(F)cc3n2CC(=O)N2C[C@@H]3[C@H](C2)C3(F)F)CC[C@H]1F] | 2-(2-((3R,4R)-3-amino-4-fluoropiperidin-1-yl)-5,6-difluoro-1H-benzo[d]imidazol-1-yl)-1-((1R,5S)-6,6-difluoro-3-azabicyclo[3.1.0]hexan-3-yl)ethanone | 430.2 |
| 624 | 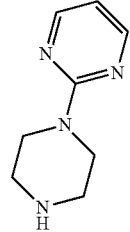 [SMILES: c1cnc(N2CCNCC2)nc1] | B | 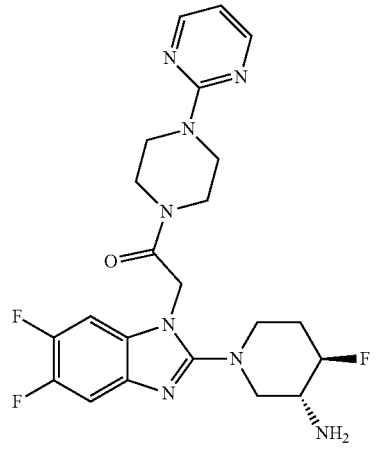 [SMILES: N[C@@H]1CN(c2nc3cc(F)c(F)cc3n2CC(=O)N2CCN(c3ncccn3)CC2)CC[C@H]1F] | 2-(2-((3R,4R)-3-amino-4-fluoropiperidin-1-yl)-5,6-difluoro-1H-benzo[d]imidazol-1-yl)-1-(4-(pyrimidin-2-yl)piperazin-1-yl)ethanone | 475.0 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 625 | | B | 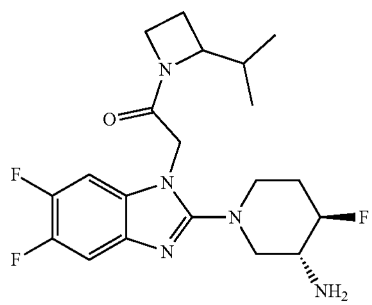 [SMILES: CC(C)C1CCN1C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-1-(2-isopropylazetidin-1-yl)ethanone | 410.2 |
| 626 | | B | 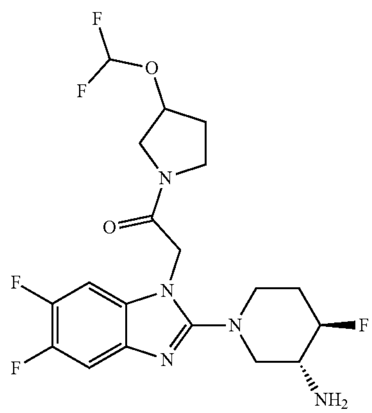 [SMILES: N[C@@H]1CN(c2nc3cc(F)c(F)cc3n2CC(=O)N2CCC(OC(F)F)C2)CC[C@H]1F] | 2-(2-((3R,4R)-3-amino-4-fluoropiperidin-1-yl)-5,6-difluoro-1H-benzo[d]imidazol-1-yl)-1-(3-(difluoromethoxy)pyrrolidin-1-yl)ethanone | 448.2 |
| 627 | | B | 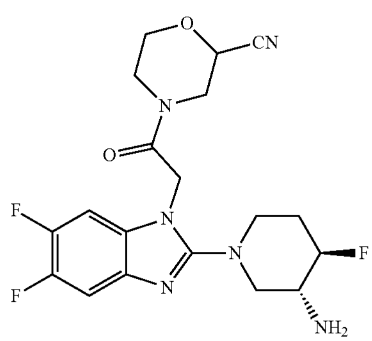 [SMILES: N#CC1CN(C(=O)Cn2c(N3CC[C@@H](F)[C@H](N)C3)nc3cc(F)c(F)cc32)CCO1] | 4-(2-(2-((3R,4R)-3-amino-4-fluoropiperidin-1-yl)-5,6-difluoro-1H-benzo[d]imidazol-1-yl)acetyl)morpholine-2-carbonitrile | 423.0 |
| 628 | | B | 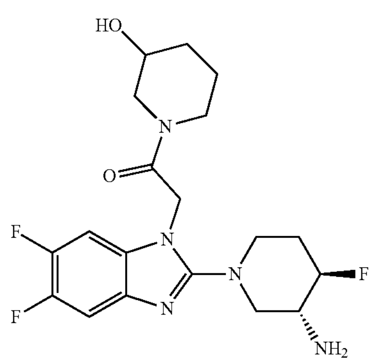 [SMILES: N[C@@H]1CN(c2nc3cc(F)c(F)cc3n2CC(=O)N2CCCC(O)C2)CC[C@H]1F] | 2-(2-((3R,4R)-3-amino-4-fluoropiperidin-1-yl)-5,6-difluoro-1H-benzo[d]imidazol-1-yl)-1-(3-hydroxypiperidin-1-yl)ethanone | 412.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 629 | 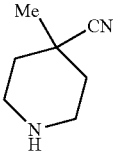 | B | 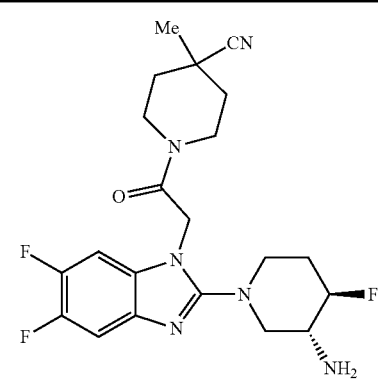 | 1-(2-(2-((3R,4R)-3-amino-4-fluoropiperidin-1-yl)-5,6-difluoro-1H-benzo[d]imidazol-1-yl)acetyl)-4-methylpiperidine-4-carbonitrile | 435.2 |
| 630 | 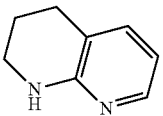 | B | 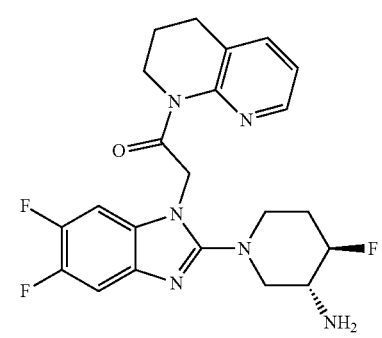 [SMILES: N[C@@H]1CN(c2nc3cc(F)c(F)cc3n2CC(=O)N2CCCc3cccnc32)CC[C@H]1F] | 2-(2-((3R,4R)-3-amino-4-fluoropiperidin-1-yl)-5,6-difluoro-1H-benzo[d]imidazol-1-yl)-1-(3,4-dihydro-1,8-naphthyridin-1(2H)-yl)ethanone | 445.0 |
| 631 | 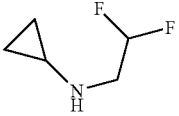 | B | 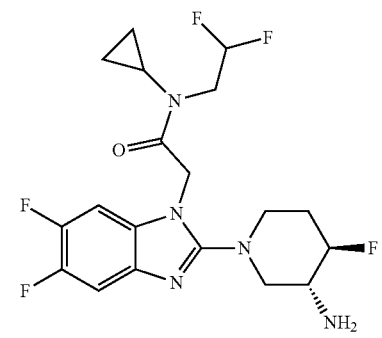 [SMILES: N[C@@H]1CN(c2nc3cc(F)c(F)cc3n2CC(=O)N(CC(F)F)C2CC2)CC[C@H]1F] | 2-(2-((3R,4R)-3-amino-4-fluoropiperidin-1-yl)-5,6-difluoro-1H-benzo[d]imidazol-1-yl)-N-cyclopropyl-N-(2,2-difluoroethyl)acetamide | 432.2 |
| 632 | 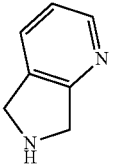 | B | 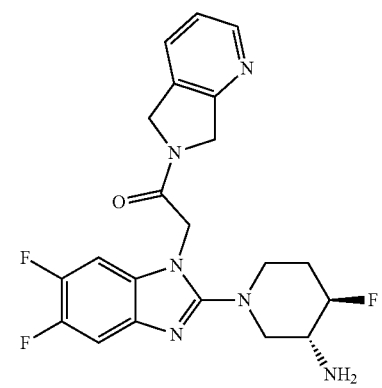 [SMILES: N[C@@H]1CN(c2nc3cc(F)c(F)cc3n2CC(=O)N2Cc3cccnc3C2)CC[C@H]1F] | 2-(2-((3R,4R)-3-amino-4-fluoropiperidin-1-yl)-5,6-difluoro-1H-benzo[d]imidazol-1-yl)-1-(5H-pyrrolo[3,4-b]pyridin-6(7H)-yl)ethanone | 431.2 |

TABLE 14-continued

The following compounds were made following an analogous procedure to that described for
Example 607 and general Scheme 15 above:

| Ex. # | Amine | Boc Deprotection Procedure | Structure | Compound Name | MS MH+ |
|---|---|---|---|---|---|
| 633 | | B | 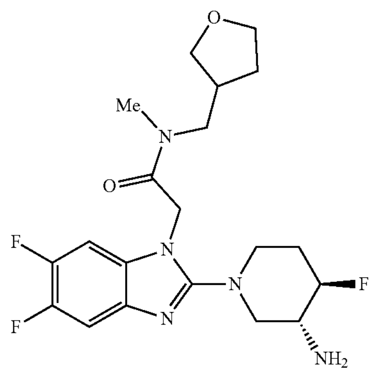 [SMILES: CN(CC1CCOC1)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-methyl-N-((tetrahydrofuran-3-yl)methyl)acetamide | 426.0 |
| 634 | | B | 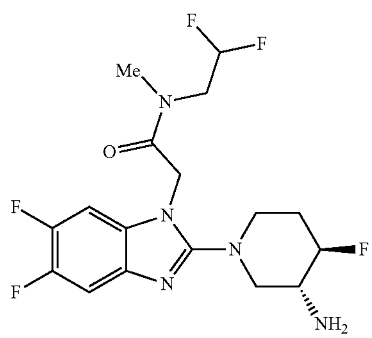 [SMILES: CN(CC(F)F)C(=O)Cn1c(N2CC[C@@H](F)[C@H](N)C2)nc2cc(F)c(F)cc21] | -(2-((3R,4R)-3-amino-4-fluoropiperidin-1-yl)-5,6-difluoro-1H-benzo[d]imidazol-1-yl)-N-(2,2-difluoroethyl)-N-methylacetamide | 406.2 |
| 635 | | B | 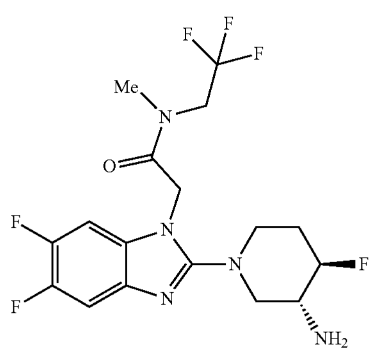 [SMILES: CN(CC(F)(F)F)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-methyl-N-(2,2,2-trifluoroethyl)acetamide | 424.2 |
| 636 | | B | 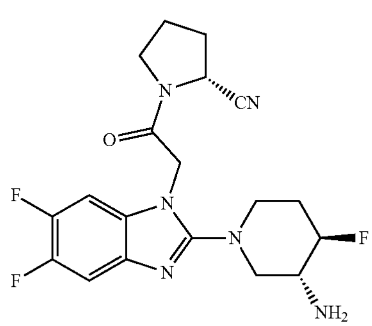 [SMILES: N#C[C@H]1CCCN1C(=O)Cn1c(N2CC[C@@H](F)[C@H](N)C2)nc2cc(F)c(F)cc21] | (R)-1-(2-(2-((3R,4R)-3-amino-4-fluoropiperidin-1-yl)-5,6-difluoro-1H-benzo[d]imidazol-1-yl)acetyl)pyrrolidine-2-carbonitrile | 407.0 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 637 | 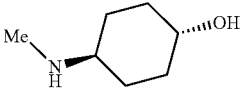 | B | 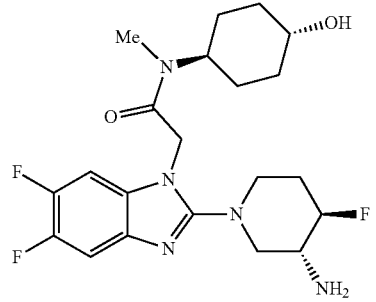 [SMILES: CN(C(=O)Cn1c(N2CC[C@@H](F)[C@H](N)C2)nc2cc(F)c(F)cc21)[C@H]1CC[C@H](O)CC1] | 2-(2-((3R,4R)-3-amino-4-fluoropiperidin-1-yl)-5,6-difluoro-1H-benzo[d]imidazol-1-yl)-N-((1r,4R)-4-hydroxycyclohexyl)-N-methylacetamide | 440.0 |
| 638 | 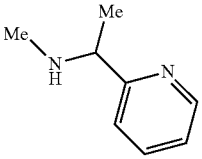 | B | 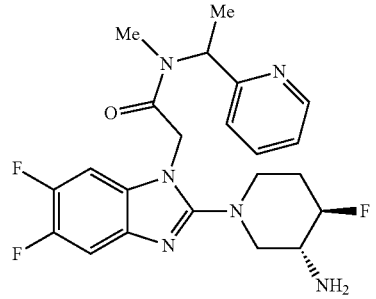 [SMILES: CC(c1ccccn1)N(C)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-methyl-N-((S)-1-(pyridin-2-yl)ethyl)acetamide | 447.2 |
| 639 | 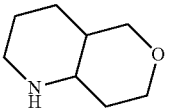 | B | 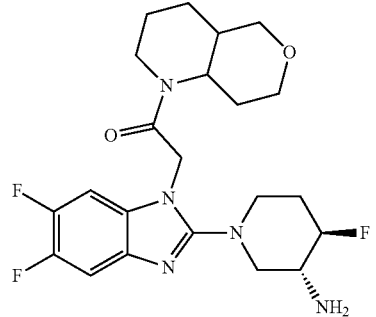 [SMILES: N[C@@H]1CN(c2nc3cc(F)c(F)cc3n2CC(=O)N2CCCC3COCCC32)CC[C@H]1F] | 2-(2-((3R,4R)-3-amino-4-fluoropiperidin-1-yl)-5,6-difluoro-1H-benzo[d]imidazol-1-yl)-1-(octahydro-1H-pyrano[4,3-b]pyridin-1-yl)ethanone | 452.2 |
| 640 | 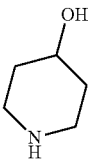 | B | 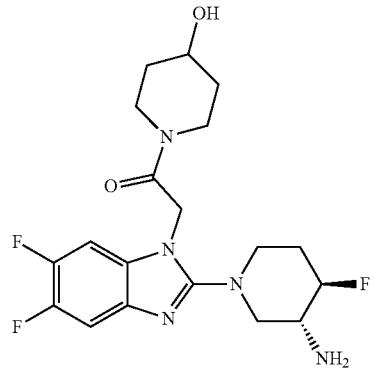 [SMILES: N[C@@H]1CN(c2nc3cc(F)c(F)cc3n2CC(=O)N2CCC(O)CC2)CC[C@H]1F] | 2-(2-((3R,4R)-3-amino-4-fluoropiperidin-1-yl)-5,6-difluoro-1H-benzo[d]imidazol-1-yl)-1-(4-hydroxypiperidin-1-yl)ethanone | 412.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 641 | | B | 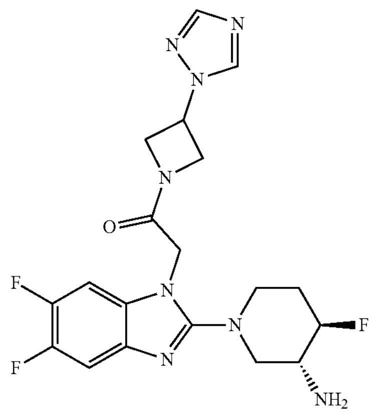 [SMILES: N[C@@H]1CN(c2nc3cc(F)c(F)cc3n2CC(=O)N2CC(n3cncn3)C2)CC[C@H]1F] | 1-(3-(1H-1,2,4-triazol-1-yl)azetidin-1-yl)-2-(2-((3R,4R)-3-amino-4-fluoropiperidin-1-yl)-5,6-difluoro-1H-benzo[d]imidazol-1-yl)ethanone | 435.2 |
| 642 | | B | 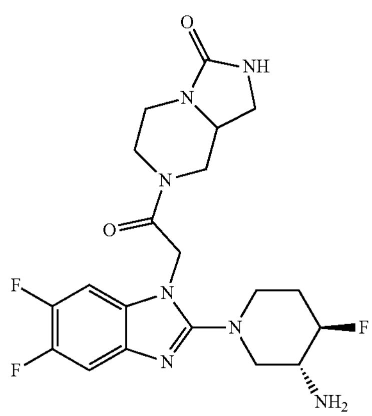 [SMILES: N[C@@H]1CN(c2nc3cc(F)c(F)cc3n2CC(=O)N2CCN3C(=O)NCC3C2)CC[C@H]1F] | 7-(2-(2-((3R,4R)-3-amino-4-fluoropiperidin-1-yl)-5,6-difluoro-1H-benzo[d]imidazol-1-yl)acetyl)hexahydroimidazo[1,5-a]pyrazin-3(2H)-one | 452.2 |
| 643 | | B | 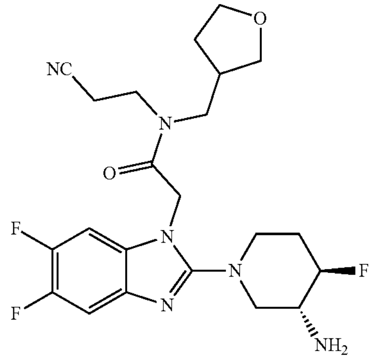 [SMILES: N#CCCN(CC1CCOC1)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-(2-cyanoethyl)-N-((tetrahydrofuran-3-yl)methyl)acetamide | 465.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 644 | | B | 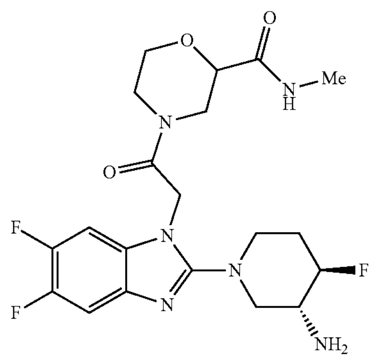 [SMILES: CNC(=O)C1CN(C(=O)Cn2c(N3CC[C@@H](F)[C@H](N)C3)nc3cc(F)c(F)cc32)CCO1] | 4-(2-(2-((3R,4R)-3-amino-4-fluoropiperidin-1-yl)-5,6-difluoro-1H-benzo[d]imidazol-1-yl)acetyl)-N-methylmorpholine-2-carboxamide | 455.2 |
| 645 | | B | 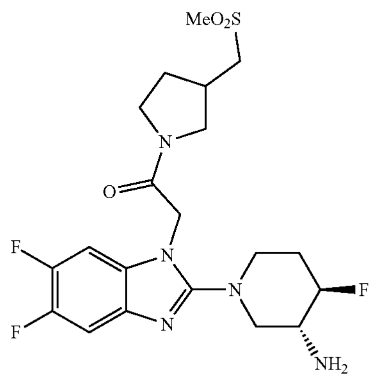 [SMILES: CS(=O)(=O)CC1CCN(C(=O)Cn2c(N3CC[C@@H](F)[C@H](N)C3)nc3cc(F)c(F)cc32)C1] | 2-(2-((3R,4R)-3-amino-4-fluoropiperidin-1-yl)-5,6-difluoro-1H-benzo[d]imidazol-1-yl)-1-(3-((methylsulfonyl)methyl)pyrrolidin-1-yl)ethanone | 474.2 |
| 646 | | B | 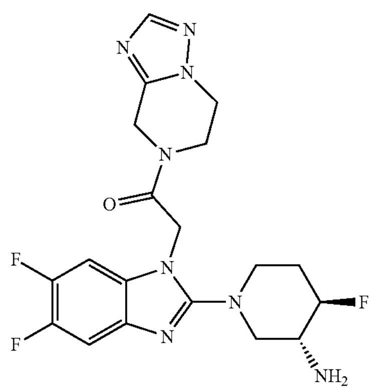 [SMILES: N[C@@H]1CN(c2nc3cc(F)c(F)cc3n2CC(=O)N2CCn3ncnc3C2)CC[C@H]1F] | 2-(2-((3R,4R)-3-amino-4-fluoropiperidin-1-yl)-5,6-difluoro-1H-benzo[d]imidazol-1-yl)-1-(5,6-dihydro-[1,2,4]triazolo[1,5-a]pyrazin-7(8H)-yl)ethanone | 435.2 |
| 647 | | B | 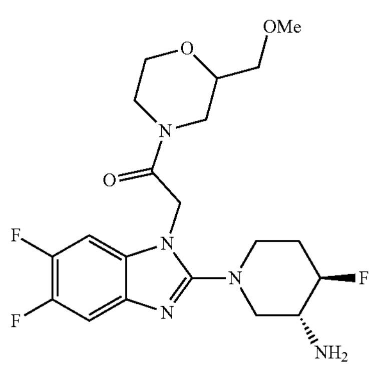 [SMILES: COCC1CN(C(=O)Cn2c(N3CC[C@@H](F)[C@H](N)C3)nc3cc(F)c(F)cc32)CCO1] | 2-(2-((3R,4R)-3-amino-4-fluoropiperidin-1-yl)-5,6-difluoro-1H-benzo[d]imidazol-1-yl)-1-(2-(methoxymethyl)morpholino)ethanone | 442.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 648 | | B | 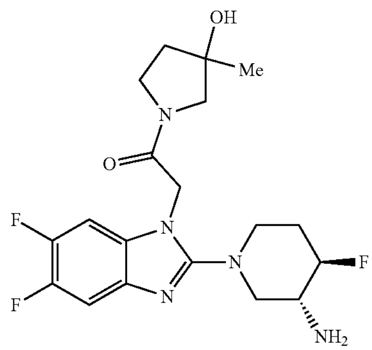 [SMILES: CC1(O)CCN(C(=O)Cn2c(N3CC[C@@H](F)[C@H](N)C3)nc3cc(F)c(F)cc32)C1] | 2-(2-((3R,4R)-3-amino-4-fluoropiperidin-1-yl)-5,6-difluoro-1H-benzo[d]imidazol-1-yl)-1-(3-hydroxy-3-methylpyrrolidin-1-yl)ethanone | 412.2 |
| 649 | | B | 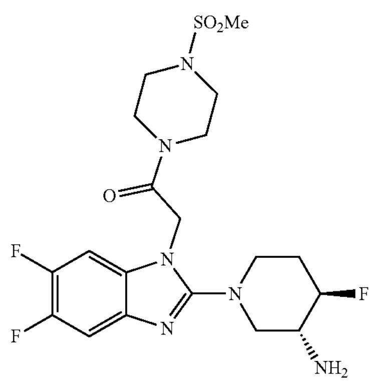 [SMILES: CS(=O)(=O)N1CCN(C(=O)Cn2c(N3CC[C@@H](F)[C@H](N)C3)nc3cc(F)c(F)cc32)CC1] | 2-(2-((3R,4R)-3-amino-4-fluoropiperidin-1-yl)-5,6-difluoro-1H-benzo[d]imidazol-1-yl)-1-(4-(methylsulfonyl)piperazin-1-yl)ethanone | 475.2 |
| 650 | | B | 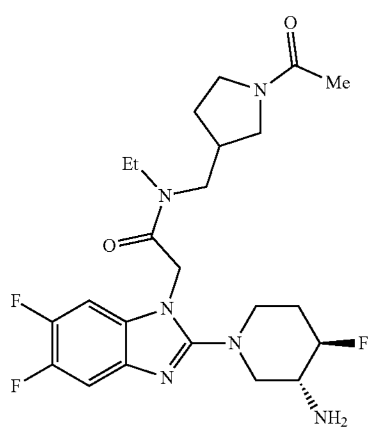 [SMILES: CCN(CC1CCN(C(C)=O)C1)C(=O)Cn1c(N2CC[C@@H](F)[C@H](N)C2)nc2cc(F)c(F)cc21] | N-((1-acetylpyrrolidin-3-yl)methyl)-2-(2-((3R,4R)-3-amino-4-fluoropiperidin-1-yl)-5,6-difluoro-1H-benzo[d]imidazol-1-yl)-N-ethylacetamide | 481.2 |
| 651 | | B | 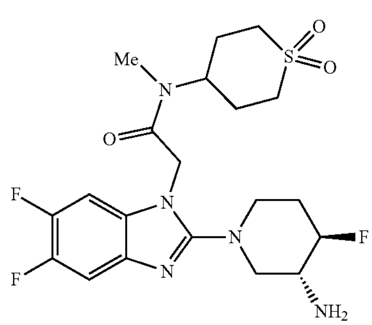 [SMILES: CN(C(=O)Cn1c(N2CC[C@@H](F)[C@H](N)C2)nc2cc(F)c(F)cc21)C1CCS(=O)(=O)CC1] | 2-(2-((3R,4R)-3-amino-4-fluoropiperidin-1-yl)-5,6-difluoro-1H-benzo[d]imidazol-1-yl)-N-(1,1-dioxidotetrahydro-2H-thiopyran-4-yl)-N-methylacetamide | 474.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 652 | | B | 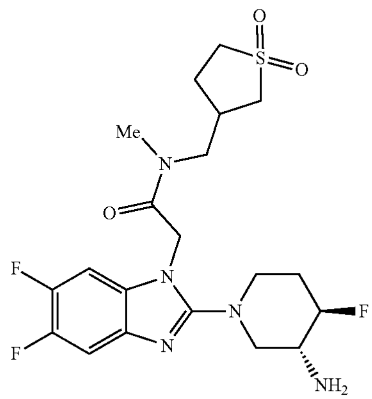 [SMILES: CN(CC1CCS(=O)(=O)C1)C(=O)Cn1c(N2CC[C@@H](F)[C@H](N)C2)nc2cc(F)c(F)cc21] | 2-(2-((3R,4R)-3-amino-4-fluoropiperidin-1-yl)-5,6-difluoro-1H-benzo[d]imidazol-1-yl)-N-((1,1-dioxidotetrahydrothiophen-3-yl)methyl)-N-methylacetamide | 474.0 |
| 653 | | B | 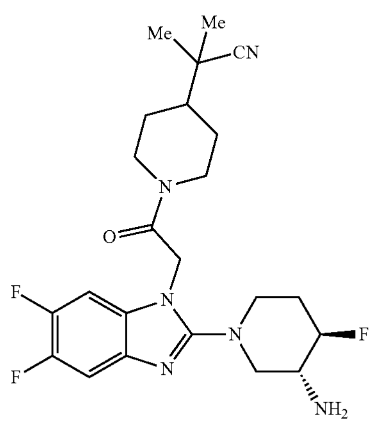 [SMILES: CC(C)(C#N)C1CCN(C(=O)Cn2c(N3CC[C@@H](F)[C@H](N)C3)nc3cc(F)c(F)cc32)CC1] | 2-(1-(2-(2-((3R,4R)-3-amino-4-fluoropiperidin-1-yl)-5,6-difluoro-1H-benzo[d]imidazol-1-yl)acetyl)piperidin-4-yl)-2-methylpropanenitrile | 463.0 |
| 654 | | B | 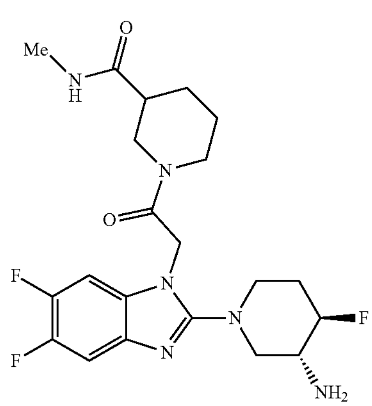 [SMILES: CNC(=O)C1CCCN(C(=O)Cn2c(N3CC[C@@H](F)[C@H](N)C3)nc3cc(F)c(F)cc32)C1] | 1-(2-(2-((3R,4R)-3-amino-4-fluoropiperidin-1-yl)-5,6-difluoro-1H-benzo[d]imidazol-1-yl)acetyl)-N-methylpiperidine-3-carboxamide | 453.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 655 | | B | 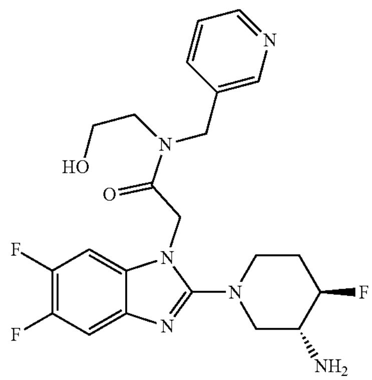 [SMILES: N[C@@H]1CN(c2nc3cc(F)c(F)cc3n2CC(=O)N(CCO)Cc2cccnc2)CC[C@H]1F] | 2-(2-((3R,4R)-3-amino-4-fluoropiperidin-1-yl)-5,6-difluoro-1H-benzo[d]imidazol-1-yl)-N-(2-hydroxyethyl)-N-(pyridin-3-ylmethyl)acetamide | 463.2 |
| 656 | | B | 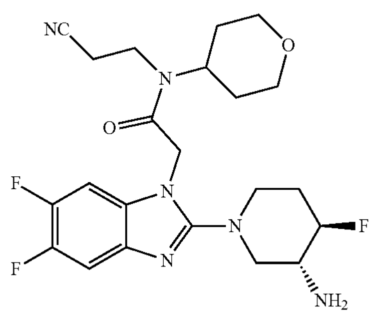 [SMILES: N#CCCN(C(=O)Cn1c(N2CC[C@@H](F)[C@H](N)C2)nc2cc(F)c(F)cc21)C1CCOCC1] | 2-(2-((3R,4R)-3-amino-4-fluoropiperidin-1-yl)-5,6-difluoro-1H-benzo[d]imidazol-1-yl)-N-(2-cyanoethyl)-N-ttetrahydro-2H-pyran-4-yl)acetamide | 465.2 |
| 657 | | B | 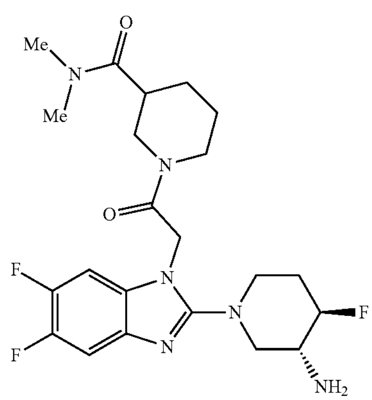 [SMILES: CN(C)C(=O)C1CCCN(C(=O)Cn2c(N3CC[C@@H](F)[C@H](N)C3)nc3cc(F)c(F)cc32)C1] | 1-(2-(2-((3R,4R)-3-amino-4-fluoropiperidin-1-yl)-5,6-difluoro-1H-benzo[d]imidazol-1-yl)acetyl)-N,N-dimethylpiperidine-3-carboxamide | 467.2 |
| 658 | | B | 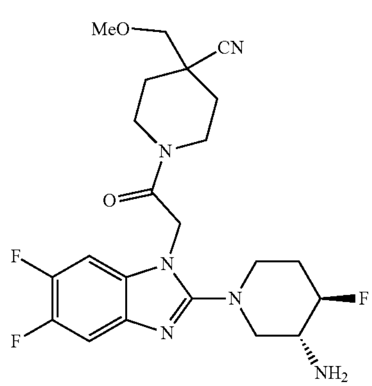 [SMILES: COCC1(C#N)CCN(C(=O)Cn2c(N3CC[C@@H](F)[C@H](N)C3)nc3cc(F)c(F)cc32)CC1] | 1-(2-(2-((3R,4R)-3-amino-4-fluoropiperidin-1-yl)-5,6-difluoro-1H-benzo[d]imidazol-1-yl)acetyl)-4-(methoxymethyl)piperidine-4-carbonitrile | 465.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 659 | 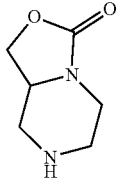 | B | 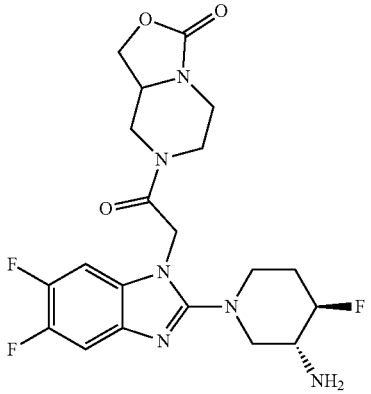 [SMILES: N[C@@H]1CN(c2nc3cc(F)c(F)cc3n2CC(=O)N2CCN3C(=O)OCC3C2)CC[C@H]1F] | 7-(2-(2-((3R,4R)-3-amino-4-fluoropiperidin-1-yl)-5,6-difluoro-1H-benzo[d]imidazol-1-yl)acetyl)tetrahydro-1H-oxazolo[3,4-a]pyrazin-3(5H)-one | 453.2 |
| 660 | 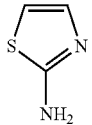 | B | 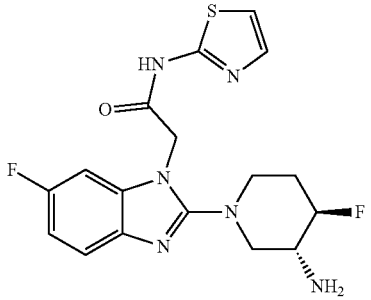 [SMILES: N[C@@H]1CN(c2nc3ccc(F)cc3n2CC(=O)Nc2nccs2)CC[C@H]1F] | 2-(2-((3R,4R)-3-amino-4-fluoropiperidin-1-yl)-6-fluoro-1H-benzo[d]imidazol-1-yl)-N-(thiazol-2-yl)acetamide | 393.0 |
| 661 | 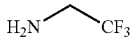 | B | 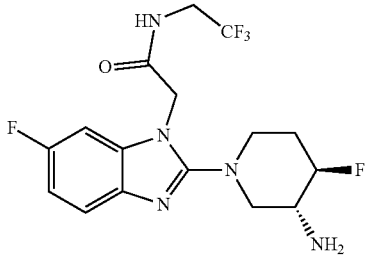 [SMILES: N[C@@H]1CN(c2nc3ccc(F)cc3n2CC(=O)NCC(F)(F)F)CC[C@H]1F] | 2-(2-((3R,4R)-3-amino-4-fluoropiperidin-1-yl)-6-fluoro-1H-benzo[d]imidazol-1-yl)-N-(2,2,2-trifluoroethyl)acetamide | 392.2 |
| 662 | 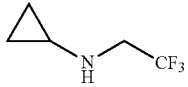 | B | 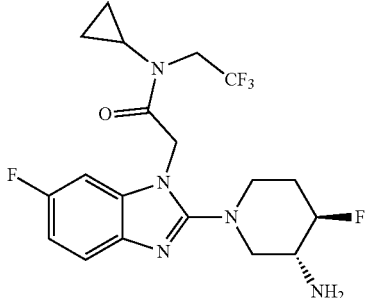 | 2-(2-((3R,4R)-3-amino-4-fluoropiperidin-1-yl)-6-fluoro-1H-benzo[d]imidazol-1-yl)-N-cyclopropyl-N-(2,2,2-trifluoroethyl)acetamide | 432.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 663 | Me-NH-CH2CH2-OMe | B | 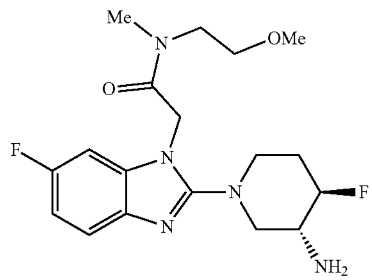 [SMILES: COCCN(C)C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-N-(2-methoxyethyl)-N-methylacetamide | 382.2 |
| 664 | Me-NH-(tetrahydrofuran-3-yl) | B | 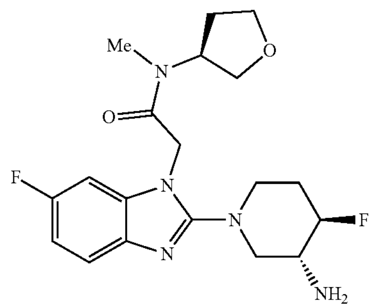 [SMILES: CN(C(=O)Cn1c(N2CC[C@@H](F)[C@H](N)C2)nc2ccc(F)cc21)[C@H]1CCOC1] | 2-(2-((3R,4R)-3-amino-4-fluoropiperidin-1-yl)-6-fluoro-1H-benzo[d]imidazol-1-yl)-N-methyl-N-((S)-tetrahydrofuran-3-yl)acetamide | 394.2 |
| 665 | Me-NH-(tetrahydrofuran-3-yl) | B | 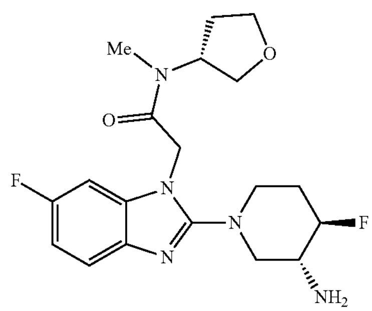 [SMILES: CN(C(=O)Cn1c(N2CC[C@@H](F)[C@H](N)C2)nc2ccc(F)cc21)[C@@H]1CCOC1] | 2-(2-((3R,4R)-3-amino-4-fluoropiperidin-1-yl)-6-fluoro-1H-benzo[d]imidazol-1-yl)-N-methyl-N-((R)-tetrahydrofuran-3-yl)acetamide | 394.2 |
| 666 | H2N-CH(Me)-(pyridin-2-yl) | B | 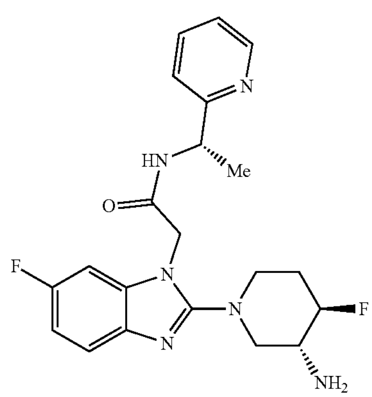 [SMILES: C[C@H](NC(=O)Cn1c(N2CC[C@@H](F)[C@H](N)C2)nc2ccc(F)cc21)c1ccccn1] | 2-(2-((3R,4R)-3-amino-4-fluoropiperidin-1-yl)-6-fluoro-1H-benzo[d]imidazol-1-yl)-N-((S)-1-(pyridin-2-yl)ethyl)acetamide | 415.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 667 | | B | 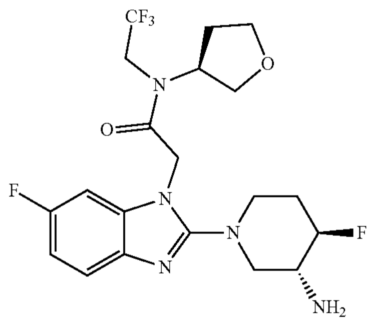 [SMILES: N[C@@H]1CN(c2nc3ccc(F)cc3n2CC(=O)N(CC(F)(F)F)[C@H]2CCOC2)CC[C@H]1F] | 2-(2-((3R,4R)-3-amino-4-fluoropiperidin-1-yl)-6-fluoro-1H-benzo[d]imidazol-1-yl)-N-((S)-tetrahydrofuran-3-yl)-N-(2,2,2-trifluoroethyl)acetamide | 462.2 |
| 668 | | B | 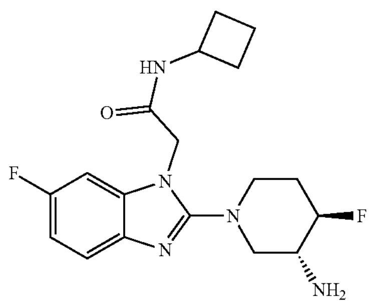 [SMILES: N[C@@H]1CN(c2nc3ccc(F)cc3n2CC(=O)NC2CCC2)CC[C@H]1F] | 2-(2-((3R,4R)-3-amino-4-fluoropiperidin-1-yl)-6-fluoro-1H-benzo[d]imidazol-1-yl)-N-cyclobutylacetamide | 364.2 |
| 669 | | B | 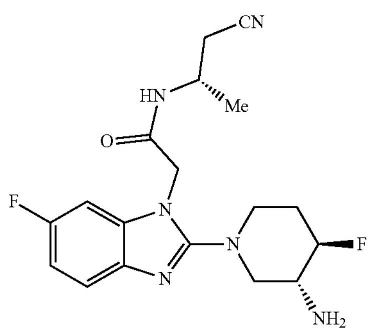 [SMILES: C[C@@H](CC#N)NC(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-N-((S)-1-cyanopropan-2-yl)acetamide | 377.2 |
| 670 | | B | 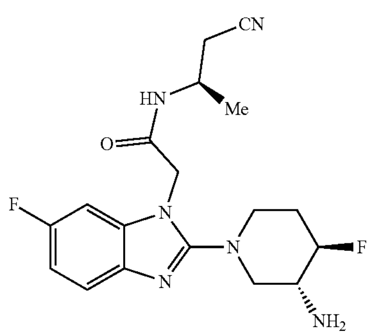 [SMILES: C[C@H](CC#N)NC(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-N-((R)-1-cyanopropan-2-yl)acetamide | 377.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 671 | Et-NH-CH2CH2-OMe | B | 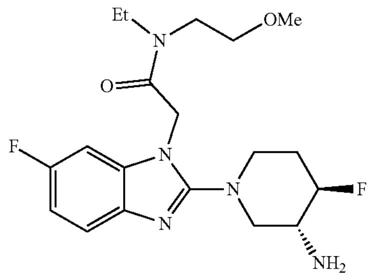 [SMILES: CCN(CCOC)C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-N-ethyl-N-(2-methoxyethyl)acetamide | 396.2 |
| 672 | CF3CH2-NH-(tetrahydrofuran-3-yl) | B | 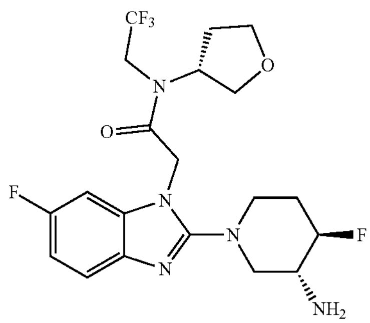 [SMILES: N[C@@H]1CN(c2nc3ccc(F)cc3n2CC(=O)N(CC(F)(F)F)[C@@H]2CCOC2)CC[C@H]1F] | 2-(2-((3R,4R)-3-amino-4-fluoropiperidin-1-yl)-6-fluoro-1H-benzo[d]imidazol-1-yl)-N-((R)-tetrahydrofuran-3-yl)-N-(2,2,2-trifluoroethyl)acetamide | 462.2 |
| 673 | H2N-CH2CH2-CF3 | B | 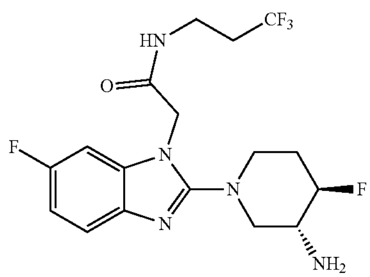 [SMILES: N[C@@H]1CN(c2nc3ccc(F)cc3n2CC(=O)NCCC(F)(F)F)CC[C@H]1F] | 2-(2-((3R,4R)-3-amino-4-fluoropiperidin-1-yl)-6-fluoro-1H-benzo[d]imidazol-1-yl)-N-(3,3,3-trifluoropropyl)acetamide | 406.2 |
| 674 | H2N-CH(Me)-(pyridin-2-yl) | B | 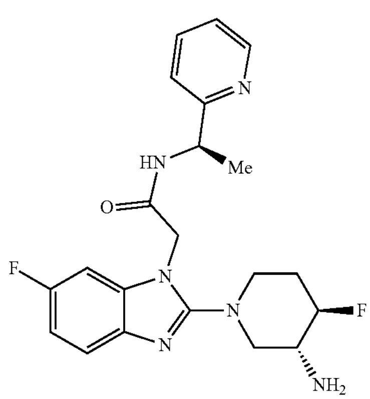 [SMILES: C[C@@H](NC(=O)Cn1c(N2CC[C@@H](F)[C@H](N)C2)nc2ccc(F)cc21)c1ccccn1] | 2-(2-((3R,4R)-3-amino-4-fluoropiperidin-1-yl)-6-fluoro-1H-benzo[d]imidazol-1-yl)-N-((R)-1-(pyridin-2-yl)ethyl)acetamide | 415.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 675 | H₂N-(tetrahydrofuran-3-yl) | B | 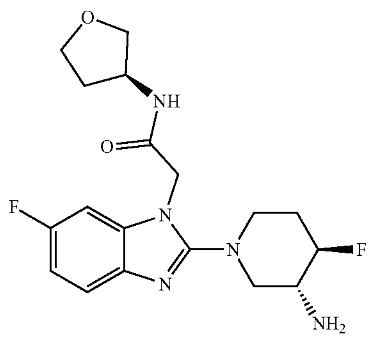 [SMILES: N[C@@H]1CN(c2nc3ccc(F)cc3n2CC(=O)N[C@H]2CCOC2)CC[C@H]1F] | 2-(2-((3R,4R)-3-amino-4-fluoropiperidin-1-yl)-6-fluoro-1H-benzo[d]imidazol-1-yl)-N-((S)-tetrahydrofuran-3-yl)acetamide | 380.2 |
| 676 | H₂N-(tetrahydrofuran-3-yl) | B | 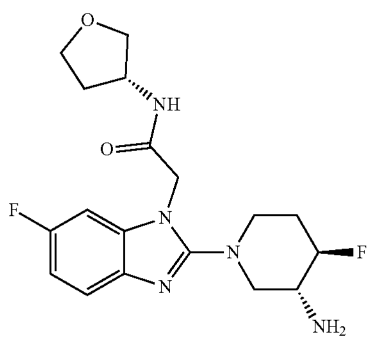 [SMILES: N[C@@H]1CN(c2nc3ccc(F)cc3n2CC(=O)N[C@@H]2CCOC2)CC[C@H]1F] | 2-(2-((3R,4R)-3-amino-4-fluoropiperidin-1-yl)-6-fluoro-1H-benzo[d]imidazol-1-yl)-N-((R)-tetrahydrofuran-3-yl)acetamide | 380.2 |
| 677 | 2-methylazetidine | B | 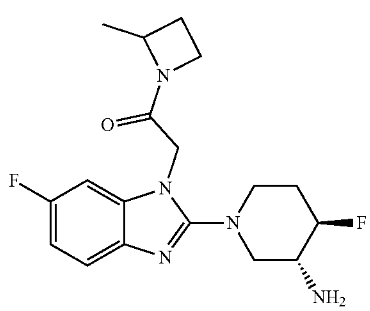 [SMILES: CC1CCN1C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-1-(2-methylazetidin-1-yl)ethan-1-one | 464.2 |
| 678 | (S)-3-methylmorpholine | B | 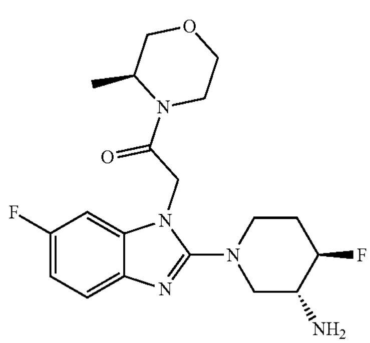 [SMILES: C[C@H]1COCCN1C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-1-((S)-3-methylmorpholino)ethan-1-one | 394.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 679 | | B | 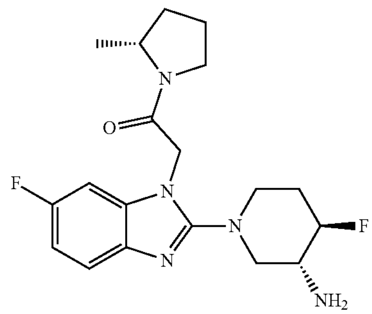 [SMILES: C[C@@H]1CCCN1C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-1-((R)-3-methylpyrrolidin-1-yl)ethan-1-one | 378.2 |
| 680 | | B | 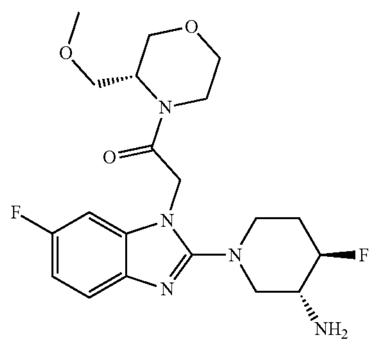 [SMILES: COC[C@@H]1COCCN1C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-1-((R)-3-(methoxymethyl)morpholino)ethan-1-one | 424.2 |
| 681 | | B | 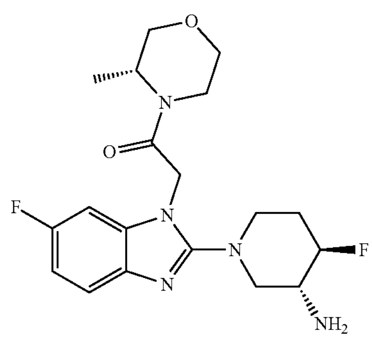 | 2-(2-((3R,4R)-3-amino-4-fluoropiperidin-1-yl)-6-fluoro-1H-benzo[d]imidazol-1-yl)-1-((R)-3-methylmorpholino)ethan-1-one | 394.2 |
| 682 | | B | 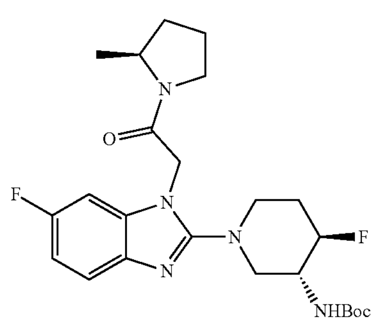 [SMILES: C[C@H]1CCCN1C(=O)Cn1c(N2CC[C@@H](F)[C@H](NC(=O)OC(C)(C)C)C2)nc2ccc(F)cc21] | 2-(2-((3R,4R)-3-amino-4-fluoropiperidin-1-yl)-6-fluoro-1H-benzo[d]imidazol-1-yl)-1-((S)-2-methylpyrrolidin-1-yl)ethan-1-one | 378.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 683 | | B | 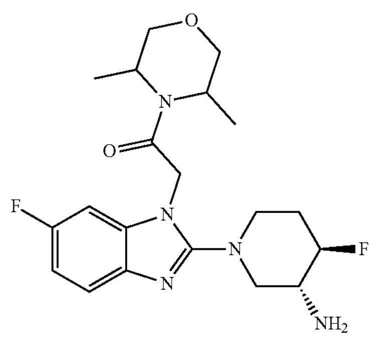 [SMILES: CC1COCC(C)N1C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-1-(3,5-dimethylmorpholino)ethan-1-one | 408.2 |
| 684 | | B | 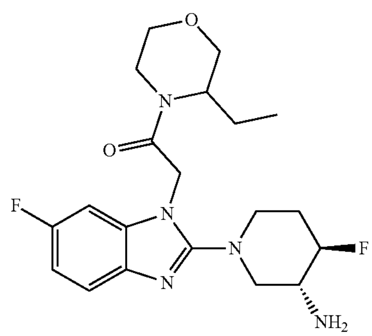 [SMILES: CCC1COCCN1C(=O)Cn1c(N2CC[C@@H](F)[C@H](N)C2)nc2ccc(F)cc21] | 2-(2-((3R,4R)-3-amino-4-fluoropiperidin-1-yl)-6-fluoro-1H-benzo[d]imidazol-1-yl)-1-(3-ethylmorpholino)ethan-1-one | 408.2 |
| 685 | | B | 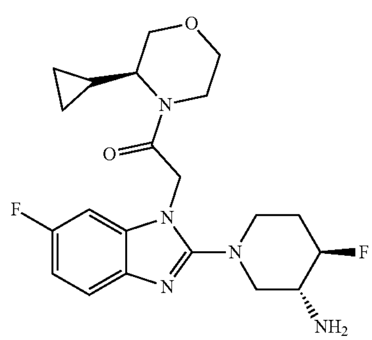 [SMILES: N[C@@H]1CN(c2nc3ccc(F)cc3n2CC(=O)N2CCOC[C@@H]2C2CC2)CC[C@H]1F] | 2-(2-((3R,4R)-3-amino-4-fluoropiperidin-1-yl)-6-fluoro-1H-benzo[d]imidazol-1-yl)-1-((S)-3-cyclopropylmorpholino)ethan-1-one | 420.2 |
| 686 | | B | 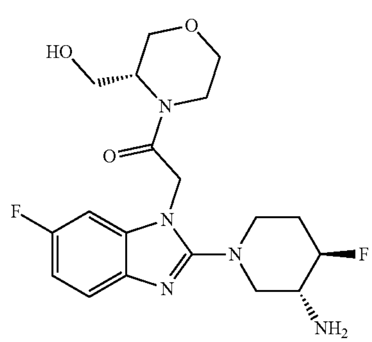 [SMILES: N[C@@H]1CN(c2nc3ccc(F)cc3n2CC(=O)N2CCOC[C@H]2CO)CC[C@H]1F] | 2-(2-((3R,4R)-3-amino-4-fluoropiperidin-1-yl)-6-fluoro-1H-benzo[d]imidazol-1-yl)-1-((R)-3-(hydroxymethyl)morpholino)ethan-1-one | 410.2 |

TABLE 14-continued

The following compounds were made following an analogous procedure to that described for Example 607 and general Scheme 15 above:

| Ex. # | Amine | Boc Deprotection Procedure | Structure | Compound Name | MS MH+ |
|---|---|---|---|---|---|
| 687 | (structure) | B | (structure) | 2-(2-((3R,4R)-3-amino-4-fluoropiperidin-1-yl)-6-fluoro-1H-benzo[d]imidazol-1-yl)-1-(3,3-dimethylmorpholino)ethan-1-one | 408.2 |

TABLE 15

Characterization data for compounds tabulated in Table 14 8.
The column "Separation Stage" indicates after which process step regioisomers formed due to asymmetric benzimidazole substitution at $R^1$ in Scheme 15 were separated during the preparation of the tabulated final compound (I = after preparation of the acetic acid intermediate (where at least one $R^1$ is not hydrogen); B = prior to boc deprotection or F = final compound).

| Ex. # | Freq., Solvent | ¹HNMR Data (δ ppm) | Separation Stage | SFC Isomer Separation Conditions |
|---|---|---|---|---|
| 600 | 600 MHz, DMSO-d6 | 7.42-7.56 (m, 1H), 7.38 (dd, J = 7.47, 10.59 Hz, 1H), 4.60-4.88 (m, 2H), 4.55-4.90 (m, 3H), 4.32-4.52 (m, 2H), 4.11-4.21 (m, 1H), 3.76-3.90 (m, 1H), 2.96-3.09 (m, 2H), 2.71-2.88 (m, 1H), 2.37-2.46 (m, 1H), 2.12 (dt, J = 3.11, 13.08 Hz, 1H), 1.73-1.90 (m, 3H), 1.53 (d, J = 6.23 Hz, 1H), 1.35 (dd, J = 1.87, 6.23 Hz, 2H) | — | — |
| 601 | 600 MHz, DMSO-d6 | 7.44-7.53 (m, 1H), 7.25-7.43 (m, 1H), 6.02-6.55 (m, 1H), 4.99-5.11 (m, 2H), 4.30-4.48 (m, 1H), 3.93-4.03 (m, 1H), 3.78 (dt, J = 3.74, 15.41 Hz, 1H), 3.22 (s, 2H), 2.94-3.04 (m, 3H), 2.71-2.82 (m, 1H), 2.01-2.15 (m, 1H), 1.70-1.87 (m, 3H) | — | — |
| 602 | 600 MHz, DMSO-d6 | 7.35-7.53 (m, 2H), 4.99-5.15 (m, 2H), 4.30-4.46 (m, 1H), 3.28 (br d, J = 3.43 Hz, 1H), 2.95-3.10 (m, 3H), 2.86 (s, 3H), 2.79 (br dd, J = 8.25, 12.61 Hz, 1H), 2.02-2.18 (m, 1H), 1.71-1.88 (m, 3H), 0.86-1.01 (m, 4H) | — | — |
| 603 | 500 MHz d₄-MeOH | 7.31-7.40 (m, 1H), 7.18-7.30 (m, 1H), 5.58 (q, J = 7.18 Hz, 1H), 5.02-5.19 (m, 2H), 4.42-4.61 (m, 1H), 3.53 (dtd, J = 1.56, 4.18, 12.39 Hz, 1H), 3.39 (br d, J = 12.98 Hz, 1H), 3.28 (s, 2H), 3.21-3.30 (m, 1H), 3.04-3.15 (m, 1H), 3.07 (br s, 1H), 2.98 (dd, J = 8.82, 12.46 Hz, 1H), 2.17-2.29 (m, 1H), 1.89-2..03 (m, 1H), 1.56 (d, J = 7.01 Hz, 3H) | B | Chiralpak OJ, 10% MeOH, peak 2 |
| 604 | 500 MHz d₄-MeOH | mixture of rotamers: 8.68 (d, J = 4.67 Hz, 1H), 8.53-8.62 (m, 1H), 7.90 (dt, J = 1.82, 7.79 Hz, 1H), 7.83 (dt, J = 1.82, 7.79 Hz, 1H), 7.54 (d, J = 7.79 Hz, 1H), 7.27-7.46 (m, 3H), 5.83 (q, J = 7.01 Hz, 1H), 5.20-5.48 (m, 1H), 5.09 (d, J = 2.34 Hz, 1H), 4.37-4.57 (m, 1H), 3.48-3.57 (m, 1H), 3.34-3.46 (m, 1H), 3.05-3.21 (m, 2H), 3.03 (s, 2H), 2.90-3.01 (m, 1H), 2.77 (s, 1H), 2.12-2.27 (m, 1H), 1.88-2.01 (m, 1H), 1.80 (d, J = 7.01 Hz, 1H), 1.64 (d, J = 7.01 Hz, 2H) | B | Chiralpak AD, 20% MeOH, peak 2 |
| 605 | 600 MHz, DMSO-d6 | Mixture of rotamers: 7.41-7.52 (m, 1H), 7.29-7.40 (m, 1H), 4.94-5.01 (m, 2H), 4.26-4.49 (m, 1H), 3.42-3.50 (m, 1H), 3.07-3.11 (m, 2H), 2.93-3.05 (m, 2H), 2.85 (s, 3H), 2.75-2.82 (m, 1H), 2.03-2.15 (m, 1H), 1.64-1.83 (m, 3H), 1.00-1.24 (m, 3H) | — | — |
| 606 | 600 MHz, DMSO- | Mixture of rotamers: 7.43-7.50 (m, 1H), 7.23-7.41 (m, 1H), 4.98-5.05 (m, 2H), 4.66-4.77 (m, 1H), | | |

TABLE 15-continued

Characterization data for compounds tabulated in Table 14 8.
The column "Separation Stage" indicates alter which process step regioisomers formed due to asymmetric benzimidazole substitution at $R^1$ in Scheme 15 were separated during the preparation of the tabulated final compound (I = after preparation of the acetic acid intermediate (where at least one $R^1$ is not hydrogen); B = prior to boc deprotection or F = final compound).

| Ex. # | Freq., Solvent | $^1$HNMR Data (δ ppm) | Separation Stage | SFC Isomer Separation Conditions |
|---|---|---|---|---|
| | d6 | 4.49-4.61 (m, 1H), 4.30-4.47 (m, 1H), 3.75-3.86 (m, 1H), 3.60-3.69 (m, 1H), 3.18 (s, 2H), 2.94-3.04 (m, 2H), 2.93 (s, 1H), 2.77 (ddd, J = 8.56, 12.61, 18.68 Hz, 1H), 1.97-2.14 (m, 1H), 1.71-1.85 (m, 3H) | | |
| 607 | 600 MHz, DMSO-d6 | 7.34-7.50 (m, 2H), 4.91 (dd, J = 14.95, 17.44 Hz, 1H), 4.71-4.83 (m, 1H), 4.32-4.48 (m, 1H), 3.76 (dd, J = 8.25, 9.81 Hz, 1H), 3.56-3.70 (m, 2H), 3.20-3.30 (m, 2H), 2.91-3.06 (m, 2H), 2.73-2.83 (m, 1H), 2.06-2.16 (m, 1H), 1.82-1.96 (m, 1H), 1.73-1.82 (m, 1H), 1.69 (br dd, J = 3.74, 7.47 Hz, 1H), 1.57 (td, J = 3.62, 7.40 Hz, 1H), 0.70-0.80 (m, 1H), 0.20 (d, J = 4.36 Hz, 1H) | — | — |
| 608 | 600 MHz, DMSO-d6 | Mixture of diasteromers: 8.46-8.53 (m, 2H), 7.68-7.76 (m, 1H), 7.44-7.52 (m, 3H), 5.74-5.81 (m, 1H), 4.97-5.13 (m, 2H), 4.32-4.48 (m, 1H), 2.94-3.07 (m, 2H), 2.89 (d, J = 3.43 Hz, 3H), 2.76-2.84 (m, 1H), 2.04-2.15 (m, 1H), 1.76-1.86 (m, 3H), 1.68 (br t, J = 6.85 Hz, 1H), 1.53 (dd, J = 2.49, 7.16 Hz, 3H) | — | — |
| 609 | 600 MHz, DMSO-d6 | Mixture of diasteromers: 7.43-7.53 (m, 1H), 7.38 (qd, J = 7.06, 10.59 Hz, 1H), 5.18 (dd, J = 7.63, 17.59 Hz, 1H), 4.88-5.03 (m, 2H), 4.27-4.49 (m, 1H), 3.69-3.78 (m, 1H), 3.62 (dtd, J = 2.96, 5.98, 8.76 Hz, 1H), 3.10-3.20 (m, 1H), 2.94-3.08 (m, 3H), 2.75-2.86 (m, 1H), 2.08-2.20 (m, 2H), 1.90 (ddd, J = 3.43, 8.88, 12.61 Hz, 1H), 1.71-1.83 (m, 4H), 0.81-0.90 (m, 1H) | — | — |
| 610 | 500 MHz, d$_4$-MeOH | 7.35 (dd, J = 7.27, 10.64 Hz, 1H), 7.28 (dd J = 7.14, 10.25 Hz, 1H), 5.48-5.60 (m, 1H), 5.01-5.19 (m, 2H), 4.51-4.66 (m, 1H), 3.56-3.64 (m, 1H), 3.38-3.45 (m, 2H), 3.28 (s, 3H), 3.03-3.13 (m, 1H), 2.17-2.31 (m, 1H), 1.90-2.05 (m, 1H), 1.56 (d, J = 7.27 Hz, 3H) | B | Chiralpak OJ, 10% MeOH, peak 1 |
| 611 | 600 MHz, DMSO-d6 | 7.25-7.58 (m, 2H), 4.90-5.18 (m, 3H), 4.28-4.49 (m, 1H), 3.93-4.00 (m, 1H), 3.54-3.79 (m, 3H), 2.89-3.08 (m, 4H), 2.71-2.84 (m, 2H), 2.07-2.23 (m, 2H), 1.71-1.89 (m, 2H), 1.66-2.00 (m, 1H) | — | — |
| 612 | 600 MHz, DMSO-d6 | Mixture of diasteroemers: 7.43-7.51 (m, 1H), 7.28-7.41 (m, 1H), 4.93-5.20 (m, 2H), 4.74-4.85 (m, 1H), 4.30-4.55 (m, 1H), 3.21-3.29 (m, 2H), 3.01-3.05 (m, 3H), 2.96-3.00 (m, 1H), 2.75-2.90 (m, 4H), 2.75-2.88 (m, 3H), 2.04-2.20 (m, 1H), 1.70-1.87 (m, 3H), 1.14-1.35 (m, 3H) | — | — |
| 613 | 600 MHz, DMSO-d6 | 8.53-8.60 (m, 2H), 7.43-7.51 (m, 2H), 7.31 (dd, J = 5.45, 8.56 Hz, 2H), 5.69 (qum, J = 6.54 Hz, 1H), 4.99-5.18 (m, 2H), 4.34-4.52 (m, 1H), 2.93-3.09 (m, 2H), 2.90 (d, J = 4.67 Hz, 3H), 2.75-2.86 (m, 1H), 2.05-2.18 (m, 1H), 1.76-1.88 (m, 3H), 1.51 (dd, J = 2.96, 7.01 Hz, 3H) | — | — |
| 614 | 600 MHz, DMSO-d6 | Mixture of diasteromers: 7.45-7.53 (m, 1H), 7.30-7.43 (m, 1H), 5.17-5.30 (m, 1H), 5.02-5.17 (m, 2H), 4.30-4.48 (m, 1H), 3.20-3.26 (m, 1H), 3.11 (s, 3H), 2.91-3.04 (m, 2H), 2.73-2.82 (m, 1H), 2.03-2.15 (m, 1H), 1.80-1.86 (m, 1H), 1.68-1.79 (m, 1H), 1.33-1.53 (m, 3H) | — | — |
| 615 | 600 MHz, DMSO-d6 | 7.40-7.55 (m, 2H), 5.02-5.15 (m, 2H), 4.46 (s, 2H), 4.31-4.44 (m, 1H), 3.27-3.30 (m, 2H), 3.23 (s, 3H), 2.97-3.06 (m, 1H), 2.93-3.05 (m, 1H), 2.78 (dd, J = 8.10, 12.46 Hz, 1H), 2.06-2.18 (m, 1H), 1.71-1.82 (m, 1H) | — | — |
| 616 | 600 MHz, DMSO-d6 | 7.41-7.52 (m, 1H), 7.29-7.40 (m, 1H), 4.94-5.01 (m, 2H), 4.26-4.49 (m, 1H), 3.42-3.50 (m, 1H), 3.07-3.11 (m, 2H), 2.93-3.05 (m, 2H), 2.85 (s, 1H), 2.75-2.82 (m, 1H), 2.03-2.15 (m, 1H), 1.64-1.83 (m, 3H), 1.00-1.24 (m, 3H) | — | — |
| 617 | 600 MHz, DMSO-d6 | 7.45 (ddd, J = 7.47, 10.98, 14.25 Hz, 2H), 5.00-5.14 (m, 2H), 4.31-4.50 (m, 1H), 3.49-3.54 (m, 2H), 3.38-3.48 (m, 4H), 3.19-3.24 (m, 1H), 2.93-3.06 (m, 3H), 2.77 (dd, J = 8.41, 12.46 Hz, 1H), 2.03- | — | — |

TABLE 15-continued

Characterization data for compounds tabulated in Table 14 8.
The column "Separation Stage" indicates alter which process step regioisomers formed due to asymmetric benzimidazole substitution at $R^1$ in Scheme 15 were separated during the preparation of the tabulated final compound (I = after preparation of the acetic acid intermediate (where at least one $R^1$ is not hydrogen); B = prior to boc deprotection or F = final compound).

| Ex. # | Freq., Solvent | ¹HNMR Data (δ ppm) | Separation Stage | SFC Isomer Separation Conditions |
|---|---|---|---|---|
| | | 2.21 (m, 1H), 1.73-1.88 (m, 1H), 0.88-1.03 (m, 4H) | | |
| 618 | 600 MHz, DMSO-d6 | 7.45-7.51 (m, 1H), 7.33-7.44 (m, 1H), 4.82-5.09 (m, 2H), 4.42-4.54 (m, 1H), 4.26-4.39 (m, 1H), 3.91-4.21 (m, 2H), 3.71-3.86 (m, 2H), 3.43 (dt, J = 7.32, 10.98 Hz, 1H), 3.16-3.26 (m, 1H), 2.97-3.07 (m, 2H), 2.75-2.86 (m, 2H), 2.52-2.73 (m, 2H), 2.05-2.14 (m, 1H), 1.74-1.85 (m, 1H) | — | — |
| 619 | 600 MHz, DMSO-d6 | 7.44-7.50 (m, 1H), 7.32-7.43 (m, 1H), 4.84-5.14 (m, 2H), 4.61-4.79 (m, 2H), 4.33-4.49 (m, 1H), 3.74-3.86 (m, 1H), 3.71 (s, 1H), 3.60 (s, 1H), 3.25-3.30 (m, 2H), 3.23 (br d, J = 11.52 Hz, 1H), 2.91-3.06 (m, 2H), 2.80 (dd, J = 8.25, 12.61 Hz, 1H), 2.07-2.18 (m, 1H), 1.73-1.96 (m, 5H) | — | — |
| 620 | 600 MHz, DMSO-d6 | Mixture of isomers: 7.39-7.49 (m, 2H), 4.91-5.08 (m, 2H), 4.33-4.52 (m, 2H), 3.87-3.96 (m, 2H), 3.74-3.85 (m, 2H), 3.58-3.67 (m, 1H), 3.51 (t, J = 11.05 Hz, 1H), 3.43 (dt, J = 3.11, 9.65 Hz, 1H), 3.21-3.27 (m, 2H), 2.94-3.05 (m, 2H), 2.79 (td, J = 8.10, 12.46 Hz, 1H), 2.07-2.17 (m, 1H), 1.73-1.85 (m, 3H), 1.52-1.61 (m, 1H) | — | — |
| 621 | 600 MHz, DMSO-d6 | Mixture of diasteromers: 7.42-7.51 (m, 1H), 7.38 (dd, J = 7.47, 10.59 Hz, 1H), 4.93-5.13 (m, 2H), 4.29-4.47 (m, 1H), 3.65-3.88 (m, 1H), 3.40-3.57 (m, 1H), 3.19-3.23 (m, 3H), 2.95-3.07 (m, 2H), 2.67-2.86 (m, 1H), 2.04-2.17 (m, 1H), 1.71-1.85 (m, 3H) | — | — |
| 622 | 600 MHz, DMSO-d6 | 7.42-7.51 (m, 1H), 7.30-7.39 (m, 1H), 4.91-5.10 (m, 2H), 4.32-4.49 (m, 1H), 3.53-3.74 (m, 2H), 3.26 (br dd, J = 5.14, 7.32 Hz, 1H), 3.15 (s, 1H), 3.11-3.21 (m, 1H), 2.93-3.05 (m, 2H), 2.78 (dd, J = 8.25, 12.61 Hz, 1H), 2.52-2.57 (m, 1H), 2.04-2.15 (m, 1H), 1.71-1.82 (m, 3H) | — | — |
| 623 | 600 MHz, DMSO-d6 | 7.43-7.52 (m, 1H), 7.33 (dd, J = 7.16, 10.59 Hz, 1H), 4.93-5.01 (m, 1H), 4.81-4.90 (m, 1H), 4.31-4.48 (m, 1H), 4.02-4.12 (m, 1H), 3.91-4.01 (m, 1H), 3.80 (br d, J = 12.46 Hz, 1H), 3.58-3.70 (m, 1H), 3.17-3.26 (m, 1H), 2.91-3.03 (m, 2H), 2.72-2.85 (m, 2H), 2.56-2.65 (m, 1H), 2.02-2.20 (m, 1H), 1.68-1.81 (m, 2H) | — | — |
| 624 | 600 MHz, DMSO-d6 | 8.32-8.47 (m, 2H), 7.35-7.53 (m, 2H), 6.61-6.74 (m, 1H), 5.03-5.16 (m, 2H), 4.32-4.48 (m, 1H), 3.83-3.93 (m, 2H), 3.77 (br t, J = 4.20 Hz, 2H), 3.67-3.73 (m, 4H), 3.60-3.64 (m, 2H), 2.95-3.06 (m, 2H), 2.81 (dd, J = 7.94, 12.61 Hz, 1H), 2.05-2.19 (m, 1H), 1.75-1.86 (m, 1H) | — | — |
| 625 | 600 MHz, DMSO-d6 | Mixture of Rotamers: 7.44-7.53 (m, 1H), 7.36 (dd, J = 7.32, 10.74 Hz, 1H), 4.66-4.90 (m, 2H), 4.50-4.65 (m, 1H), 4.31-4.48 (m, 1H), 4.10-4.28 (m, 2H), 3.99-4.09 (m, 1H), 2.91-3.09 (m, 2H), 2.79 (dt, J = 8.56, 13.16 Hz, 1H), 2.20-2.32 (m, 1H), 2.08-2.16 (m, 2H), 2.00 (td, J = 5.61, 15.26 Hz, 1H), 1.69-1.89 (m, 3H), 0.77-0.92 (m, 6H) | — | — |
| 626 | 600 MHz, DMSO-d6 | Mixture of Rotamers: 7.47 (dd, J = 7.47, 11.21 Hz, 1H), 7.39 (dd, J = 7.16, 10.59 Hz, 1H), 6.61-6.99 (m, 1H), 4.79-5.01 (m, 3H), 4.30-4.48 (m, 1H), 3.63-3.94 (m, 3H), 3.51-3.61 (m, 2H), 2.96-3.07 (m, 2H), 2.79 (ddd, J = 1.25, 8.33, 12.53 Hz, 1H), 2.17-2.31 (m, 1H), 1.98-2.15 (m, 3H), 1.73-1.81 (m, 1H) | — | — |
| 627 | 600 MHz, DMSO-d6 | Mixture of diastereomers: 7.43-7.53 (m, 1H), 7.28-7.40 (m, 1H), 4.98-5.28 (m, 3H), 4.30-4.51 (m, 1H), 4.01-4.26 (m, 1H), 3.74-3.98 (m, 4H), 3.44-3.53 (m, 1H), 3.40-3.59 (m, 1H), 2.94-3.10 (m, 3H), 2.72-2.87 (m, 1H), 2.06-2.19 (m, 1H), 1.71-1.94 (m, 1H) | — | — |
| 628 | 600 MHz, DMSO-d6 | Mixture of diastereomers: 7.23-7.49 (m, 2H), 4.91-5.18 (m, 4H), 4.29-4.49 (m, 1H), 3.49-4.15 (m, 4H), 2.92-3.09 (m, 3H), 2.71-2.82 (m, 1H), 2.04-2.16 (m, 1H), 1.29-1.90 (m, 8H) | — | — |

TABLE 15-continued

Characterization data for compounds tabulated in Table 14 8.
The column "Separation Stage" indicates alter which process step regioisomers formed due to asymmetric benzimidazole substitution at R¹ in Scheme 15 were separated during the preparation of the tabulated final compound (I = after preparation of the acetic acid intermediate (where at least one R¹ is not hydrogen); B = prior to boc deprotection or F = final compound),

| Ex. # | Freq., Solvent | ¹HNMR Data (δ ppm) | Separation Stage | SFC Isomer Separation Conditions |
|---|---|---|---|---|
| 629 | 600 MHz, DMSO-d6 | 7.44-7.52 (m, 1H), 7.41 (dd, J = 7.32, 10.74 Hz, 1H), 4.94-5.14 (m, 2H), 4.34-4.49 (m, 1H), 4.23-4.32 (m, 1H), 3.97-4.06 (m, 1H), 3.21 (br d, J = 1.25 Hz, 1H), 2.95-3.05 (m, 2H), 2.74-2.91 (m, 2H), 2.06-2.16 (m, 1H), 2.01 (td, J = 2.76, 5.99 Hz, 1H), 1.88-1.96 (m, 2H), 1.72-1.85 (m, 2H), 1.60-1.72 (m, 1H), 1.43-1.53 (m, 1H), 1.40 (s, 3H) | — | — |
| 630 | 600 MHz, DMSO-d6 | 8.35-8.57 (m, 1H), 7.59-7.69 (m, 1H), 7.26-7.53 (m, 2H), 7.24 (dd, J = 4.83, 7.63 Hz, 1H), 5.02-5.21 (m, 2H), 4.66-4.93 (m, 1H), 4.60-4.95 (m, 1H), 4.25-4.48 (m, 1H), 3.92 (br t, J = 5.92 Hz, 1H), 3.80-3.87 (m, 1H), 2.71-3.14 (m, 5H), 1.97-2.15 (m, 1H), 1.62-1.80 (m, 1H) | — | — |
| 631 | 600 MHz, DMSO-d6 | 7.19-7.28 (m, 2H), 6.88-6.96 (m, 1H), 6.00-6.28 (m, 1H), 5.11-5.23 (m, 2H), 4.31-4.50 (m, 1H), 3.76 (dt, J = 3.74, 15.26 Hz, 2H), 2.92-3.08 (m, 3H), 2.81 (dd, J = 8.25, 12.61 Hz, 1H), 2.07-2.18 (m, 1H), 1.70-1.84 (m, 1H), 0.89-1.07 (m, 4H) | — | — |
| 632 | 600 MHz, DMSO-d6 | 8.49-8.55 (m, 1H), 7.81-7.90 (m, 1H), 7.42-7.51 (m, 2H), 7.33-7.40 (m, 1H), 5.00-5.17 (m, 4H), 4.67-4.79 (m, 2H), 4.32-4.47 (m, 1H), 3.36-3.42 (m, 1H), 2.95-3.09 (m, 2H), 2.82 (dd, J = 7.94, 12.61 Hz, 1H), 2.05-2.16 (m, 1H), 1.76-1.87 (m, 2H) | — | — |
| 633 | 600 MHz, DMSO-d6 | Mixture of diasteromers: 7.43-7.52 (m, 1H), 7.29-7.41 (m, 1H), 4.91-5.05 (m, 2H), 4.29-4.50 (m, 1H), 3.55-3.89 (m, 3H), 3.36-3.49 (m, 2H), 3.19-3.28 (m, 1H), 3.14 (s, 2H), 2.94-3.05 (m, 2H), 2.87 (s, 1H), 2.73-2.83 (m, 1H), 2.51-2.66 (m, 1H), 2.02-2.15 (m, 1H), 1.86-1.94 (m, 1H), 1.72-1.84 (m, 2H), 1.43-1.64 (m, 1H) | — | — |
| 634 | 600 MHz, DMSO-d6 | 7.22-7.29 (m, 1H), 7.06-7.21 (m, 1H), 6.87-6.96 (m, 1H), 6.01-6.52 (m, 1H), 4.97-5.13 (m, 2H), 4.29-4.50 (m, 1H), 3.68-4.05 (m, 2H), 3.57 (q, J = 7.16 Hz, 1H), 3.40 (br d, J = 7.16 Hz, 1H), 2.93-3.06 (m, 2H), 2.71-2.89 (m, 1H), 2.06-2.15 (m, 1H), 1.78 (ddd, J = 3.58, 6.46, 9.58 Hz, 1H), 1.24 (t, J = 7.16 Hz, 2H), 1.06 (t, J = 7.01 Hz, 1H) | — | — |
| 635 | 600 MHz, DMSO-d6 | 7.21-7.27 (m, 1H), 7.16 (dd, J = 4.67, 8.72 Hz, 1H), 7.08 (dd, J = 4.67, 8.72 Hz, 1H), 6.88-6.98 (m, 1H), 4.98-5.20 (m, 2H), 4.15-4.52 (m, 1H), 4.21 (q, J = 9.65 Hz, 1H), 3.63 (q, J = 7.06 Hz, 2H), 3.42 (brd, J = 6.85 Hz, 1H), 2.89-3.07 (m, 2H), 2.69-2.85 (m, 1H), 2.03-2.13 (m, 1H), 1.69-1.81 (m, 1H), 1.28 (t, J = 7.16 Hz, 2H), 1.07 (t, J = 7.01 Hz, 1H) | — | — |
| 636 | 600 MHz, DMSO-d6 | 7.39-7.56 (m, 2H), 4.92 (br d, J = 3.43 Hz, 3H), 4.81 (dd, J = 3.43, 7.47 Hz, 1H), 4.34-4.49 (m, 1H), 3.81 (ddd, J = 3.89, 7.71, 9.58 Hz, 1H), 3.56-3.71 (m, 1H), 2.98-3.09 (m, 3H), 2.80 (dd, J = 8.10, 12.77 Hz, 1H), 2.05-2.30 (m, 8H) | — | — |
| 637 | 600 MHz, DMSO-d6 | 7.43-7.50 (m, 1H), 7.37 (dd, J = 7.16, 10.59 Hz, 1H), 4.99-5.11 (m, 1H), 4.88-4.99 (m, 1H), 4.53-4.62 (m, 1H), 4.30-4.48 (m, 1H), 4.15 (tt, J = 3.89, 11.99 Hz, 1H), 2.98-3.05 (m, 1H), 2.91-2.98 (m, 3H), 2.78 (td, J = 7.43, 12.53 Hz, 1H), 2.72 (s, 1H), 2.07-2.14 (m, 1H), 1.86 (br d, J = 11.21 Hz, 3H), 1.73-1.80 (m, 1H), 1.66 (br d, J = 8.41 Hz, 2H), 1.52-1.60 (m, 1H), 1.48 (br dd, J = 3.11, 9.34 Hz, 1H), 1.29-1.37 (m, 1H), 1.13-1.26 (m, 2H) | — | — |
| 638 | 600 MHz, DMSO-d6 | Mixture of rotamers: 8.68 (dd, J = 0.78, 4.67 Hz, 1H), 8.58 (dd, J = 0.78, 4.93 Hz, 1H), 7.79-7.95 (m, 1H), 7.54 (d, J = 7.79 Hz, 1H), 7.26-7.46 (m, 3H), 5.83 (q, J = 7.18 Hz, 1H), 5.41 (d, J = 6.75 Hz, 1H), 5.22-5.37 (m, 1H), 5.04-5.14 (m, 1H), 4.35-4.61 (m, 1.H), 3.50-3.61 (m, 1H), 3.35-3.47 (m, 1H), 3.05-3.20 (m, 2H), 3.02 (s, 1H), 2.89-2.98 (m, 1H), 2.76 (s, 1H), 2.12-2.28 (m, 1H), 1.86-2.01 (m, 1H), 1.80 (d, J = 6.75 Hz, 1H), 1.63 (d, J = 7.27 Hz, 1H) | B | Chiralpak AD, 20% MeOH, peak 1 |

TABLE 15-continued

Characterization data for compounds tabulated in Table 14 8.
The column "Separation Stage" indicates alter which process step regioisomers formed due to asymmetric benzimidazole substitution at R¹ in Scheme 15 were separated during the preparation of the tabulated final compound (I = after preparation of the acetic acid intermediate (where at least one R¹ is not hydrogen); B = prior to boc deprotection or F = final compound).

| Ex. # | Freq., Solvent | $^1$HNMR Data (δ ppm) | Separation Stage | SFC Isomer Separation Conditions |
|---|---|---|---|---|
| 639 | 600 MHz, DMSO-d6 | 7.42-7.52 (m, 1H), 7.32-7.41 (m, 1H), 5.04-5.26 (m, 1H), 4.83-5.02 (m, 1H), 4.55-4.65 (m, 1H), 4.31-4.48 (m, 1H), 4.10-4.26 (m, 1H), 3.85-3.95 (m, 1H), 3.77 (br d, J = 11.21 Hz, 1H), 3.58-3.68 (m, 1H), 3.46-3.56 (m, 1H), 3.13-3.21 (m, 1H), 2.92-3.07 (m, 2H), 2.76-2.87 (m, 1H), 2.59-2.71 (m, 1H), 2.02-2.26 (m, 2H), 1.86-1.93 (m, 1H), 1.66-1.82 (m, 3H), 1.50-1.60 (m, 2H), 1.21-1.35 (m, 1H) | — | — |
| 640 | 600 MHz, DMSO-d6 | 7.46 (dd, J = 7.47, 10.90 Hz, 1H), 7.37 (dd, J = 7.47, 10.90 Hz, 1H), 4.91-5.08 (m, 3H), 4.30-4.49 (m, 1H), 3.69-3.94 (m, 4H), 3.05-3.15 (m, 1H), 2.93-3.05 (m, 3H), 2.79 (dd, J = 8.25, 12.61 Hz, 1H), 2.04-2.17 (m,2H), 1.67-1.86 (m, 4H), 1.41-1.50 (m, 1H), 1.24-1.33 (m, 1H) | — | — |
| 641 | 600 MHz, DMSO-d6 | 8.66-8.70 (m, 1H), 8.13 (s, 1H), 7.42-7.51 (m, 2H), 5.44-5.53 (m, 1H), 4.81-4.90 (m, 2H), 4.77 (q, J = 9.03 Hz, 1H), 4.55 (dt, J = 5.29, 8.88 Hz, 1H), 4.33-4.49 (m, 2H), 4.24 (dd, J = 5.29, 10.28 Hz, 1H), 3.15-3.28 (m, 1H), 3.01-3.08 (m, 2H), 2.82 (dd, J = 8.41, 12.46 Hz, 1H), 2.10-2.17 (m, 1H), 1.90-2.07 (m, 1H), 1.79-1.87 (m, 1H) | — | — |
| 642 | 600 MHz, DMSO-d6 | 7.45-7.50 (m, 1H), 7.41 (br t, J = 8.25 Hz, 1H), 6.50-6.64 (m, 1H), 5.07-5.19 (m, 1H), 4.94-5.03 (m, 1H), 4.21-4.50 (m, 2H), 3.91-4.05 (m, 1H), 3.73-3.85 (m, 1H), 3.53-3.69 (m, 2H), 2.91-3.10 (m, 5H), 2.71-2.86 (m, 2H), 2.56-2.65 (m, 1H), 2.11-2.18 (m, 1H), 1.74-1.82 (m, 1H) | — | — |
| 643 | 600 MHz, DMSO-d6 | 7.48 (dd, J = 7.47, 11.21 Hz, 1H), 7.35 (ddd, J = 5.61, 7.08, 10.67 Hz, 1H), 4.92-5.18 (m, 2H), 4.30-4.47 (m, 1H), 3.74-3.92 (m, 2H), 3.57-3.73 (m, 3H), 3.47-3.53 (m, 1H), 3.32-3.44 (m, 6H), 3.22-3.27 (m, 1H), 2.93-3.05 (m, 3H), 2.74-2.80 (m, 2H), 2.01-2.16 (m, 2H), 1.73-1.91 (m, 3H), 1.47-1.67 (m, 1H) | — | — |
| 644 | 600 MHz, DMSO-d6 | 7.81-8.03 (m, 1H), 7.44-7.50 (m, 1H), 7.40 (dd, J = 7.47, 10.59 Hz, 1H), 4.92-5.22 (m, 2H), 4.10-4.47 (m, 2H), 3.77-4.02 (m, 3H), 3.47-3.60 (m, 1H), 3.44-3.71 (m, 1H), 3.13-3.25 (m, 2H), 2.99-3.09 (m, 2H), 2.73-2.86 (m, 2H), 2.59-2.69 (m, 3H), 2.05-2.19 (m, 1H), 1.70-1.85 (m, 1H) | — | — |
| 645 | 600 MHz, DMSO-d6 | 7.42-7.52 (m, 1H), 7.31-7.42 (m, 1H), 4.72-5.01 (m, 2H), 4.32-4.53 (m, 1H), 3.89-4.17 (m, 1H), 3.71-3.85 (m, 1H), 3.53-3.67 (m, 1H), 3.43 (br dd, J = 5.92, 14.01 Hz, 1H), 3.36-3.40 (m, 2H), 3.17 (d, J = 4.98 Hz, 1H), 3.11-3.22 (m, 1H), 2.97-3.08 (m, 5H), 2.75-2.83 (m, 1H), 2.59-2.71 (m, 1H), 2.09-2.31 (m, 2H), 1.74-1.88 (m, 2H) | — | — |
| 646 | 600 MHz, DMSO-d6 | 7.96-8.09 (m, 1H), 7.41-7.53 (m, 2H), 5.08-5.27 (m, 2H), 5.03 (s, 1H), 4.75-4.86 (m, 1H), 4.33-4.49 (m, 2H), 4.13-4.22 (m, 2H), 3.96-4.07 (m, 1H), 3.24-3.28 (m, 1H), 2.94-3.05 (m, 2H), 2.75-2.83 (m, 1H), 2.01-2.15 (m, 1H), 1.72-1.84 (m, 2H) | — | — |
| 647 | 600 MHz, DMSO-d6 | Mixture of Diasteromers: 7.44-7.50 (m, IB), 7.37-7.43 (m, 1H), 5.13 (dt J = 6.23, 18.22 Hz, 1H), 4.94 (br dd, J = 13.86, 17.28 Hz, 1H), 4.31-4.50 (m, 1H), 4.06-4.21 (m, 1H), 3.80-3.94 (m, 2H), 3.48-3.69 (m, 2H), 3.39-3.46 (m, 3H), 3.25 (s, 3H), 3.07-3.11 (m, 1H), 2.94-3.03 (m, 2H), 2.74-2.86 (m, 2H), 2.58-2.64 (m, 1H), 2.06-2.15 (m, IB), 1.71-1.87 (m, 1H) | — | — |
| 648 | 600 MHz, DMSO-d6 | 7.46 (dd, J = 7.47, 10.90 Hz, 1H), 7.36 (dd, J = 7.32, 10.74 Hz, 1H), 4.76-5.01 (m, 3H), 4.29-4.47 (m, 1H), 3.67-3.77 (m, 1H), 3.42-3.55 (m, 2H), 2.95-3.18 (m, 3H), 2.74-2.84 (m, 1H), 2.04-2.15 (m, 1H), 1.73-1.98 (m, 4H), 1.28-1.37 (m, 3H) | — | — |
| 649 | 600 MHz, DMSO-d6 | 7.44-7.51 (m, 1H), 7.32-7.41 (m, 1H), 4.99-5.14 (m, 2H), 4.29-4.48 (m, 1H), 3.54-3.75 (m, 5H), 3.18-3.26 (m, 3H), 3.11-3.17 (m, 2H), 2.97-3.06 | | |

TABLE 15-continued

Characterization data for compounds tabulated in Table 14 8.
The column "Separation Stage" indicates alter which process step regioisomers formed due to asymmetric benzimidazole substitution at $R^1$ in Scheme 15 were separated during the preparation of the tabulated final compound (I = after preparation of the acetic acid intermediate (where at least one $R^1$ is not hydrogen); B = prior to boc deprotection or F = final compound).

| Ex. # | Freq., Solvent | ¹HNMR Data (δ ppm) | Separation Stage | SFC Isomer Separation Conditions |
|---|---|---|---|---|
| | | (m, 2H), 2.94 (s, 3H), 2.74-2.83 (m, 1H), 2.08-2.19 (m, 1H), 1.75-1.95 (m, 3H) | | |
| 650 | 600 MHz, DMSO-d6 | Mixture of Diasteromers: 7.31-7.53, (m, 2H), 4.93-5.22 (m, 2H), 4.49-4.64 (m, 1H), 4.31-4.46 (m, 1H), 3.73-3.82 (m, 3H), 3.44-3.69 (m, 5H), 2.94-3.06 (m, 3H), 2.72-2.85 (m, 1H), 2.05-2.30 (m, 4H), 1.97 (d, 3=12.46 Hz, 3H), 1.86-1.92 (m, 2H), 3.25 (q, J = 7.16 Hz, 2H), 3.03 (q, J = 6.75 Hz, 2H) | — | — |
| 65' | 600 MHz, DMSO-d6 | 7.43-7.51 (m, 1H), 7.35-7.43 (m, 1H), 5.04-5.19 (m, 1H), 4.90-5.03 (m, 1H), 4.57 (tt, J = 3.35, 12.22 Hz, 1H), 4.33-4.48 (m, 1H), 3.35-3.45 (m, 3H), 3.17-3.28 (m, 3H), 3.06 (br d, J = 11.52 Hz, 1H), 3.00 (s, 3H), 2.73-2.83 (m, 2H), 2.06-2.31 (m, 4H), 1.88 (br d, J = 10.90 Hz, 2H), 1.71-1.83 (m, 1H) | — | — |
| 652 | 600 MHz, DMSO-d6 | Mixture of Diasteromers: 7.34-7.49 (m, 2H), 4.93-5.05 (m, 2H), 4.33-4.50 (m, 1H), 3.40-3.60 (m, 3H), 3.20-3.26 (m, 3H), 3.3.4-3.18 (m, 3H), 2.95-3.10 (m, 3H), 2.78 (ddd, J = 7.32, 8.95, 12.69 Hz, 3H), 2.05-2.24 (m, 2H), 1.65-1.91 (m, 2H) | — | — |
| 653 | 600 MHz, DMSO-d6 | 7.43-7.50 (m, 1H), 7.31-7.39 (m, 1H), 5.04-5.16 (m, 1H), 4.93-5.03 (m, 1H), 4.31-4.50 (m, 2H), 4.02-4.12 (m, 1H), 3.18-3.29 (m, 2H), 3.09 (br t, J = 12.77 Hz, 1H), 2.91-3.04 (m, 2H), 2.80 (td, J = 7.63, 12.77 Hz, 1H), 2.55-2.64 (m, 1H), 2.06-2.19 (m, 1H), 1.88 (br s, 1H), 1.75-1.84 (m, 3H), 1.62-1.72 (m, 1H), 1.31 (br d, J = 4.67 Hz, 6H), 1.07-1.15 (m, 1H) | — | — |
| 654 | 600 MHz, DMSO-d6 | 7.80-7.93 (m, 1H), 7.42-7.50 (m, 1H), 7.32-7.39 (m, 1H), 4.89-5.17 (m, 2H), 4.31-4.48 (m, 1H), 3.74-3.93 (m, 2H), 3.40 (br dd, J = 9.34, 13.70 Hz, 1H), 3.11-3.19 (m, 1H), 2.94-3.04 (m, 3H), 2.72-2.87 (m, 2H), 2.53-2.65 (m, 3H), 2.05-2.24 (m, 2H), 1.77-1.90 (m, 4H), 1.59-1.74 (m, 2H) | — | — |
| 655 | 600 MHz, DMSO-d6 | Mixture of Rotamers: 8.43-8.56 (m, 2H), 7.69 (td, J = 1.87, 7.79 Hz, 1H), 7.47 (dd, J = 7.32, 11.05 Hz, 1H), 7.33-7.39 (m, 1H), 7.25-7.31 (m, 1H), 5.25 (s, 2H), 4.62 (s, 2H), 4.32-4.50 (m, 1H), 3.64-3.72 (m, 2H), 3.53 (br t, J = 4.98 Hz, 2H), 3.36-3.42 (m, 2H), 2.93-3.06 (m, 2H), 2.71-2.82 (m, 1H), 2.01-2.13 (m, 1H) 1.72-1.89 (m, 1H) | — | — |
| 656 | 600 MHz, DMSO-d6 | Mixture of Rotamers: 7.47 (dd, J = 7.63, 11.06 Hz, 1H), 7.33-7.42 (m, 1H), 5.04-5.21 (m, 2H), 4.31-4.48 (m, 1H), 3.86-4.07 (m, 3H), 3.51 (t, J = 6.85 Hz, 1H), 3.41-3.46 (m, 1H), 3.41 (br s, 1H), 3.20-3.28 (m, 1H), 2.94-3.07 (m, 2H), 2.77-2.84 (m, 1H), 2.72 (t, J = 6.85 Hz, 1H), 2.04-2.17 (m, 1H), 1.69-1.87 (m, 5H) | — | — |
| 657 | 600 MHz, DMSO-d6 | Mixture of Roatmers: 7.36-7.50 (m, 2H), 4.92-5.14 (m, 2H), 4.30-4.50 (m, 1H), 4.03-4.24 (m, 1H), 3.76-3.96 (m, 1H), 3.12-3.24 (m, 1H), 2,98-3.08 (m, 4H), 2.77-2.89 (m, 5H), 2.61-2.73 (m, 1H), 2.09-2.21 (m, 1H), 1.76-1.94 (m, 4H), 1.48-1.67 (m, 2H) | — | — |
| 658 | 600 MHz, DMSO-d6 | 7.44-7.50 (m, 1H), 7.34-7.42 (m, 1H), 4.95-5.13 (m, 2H), 4.29-4.47 (m, 2H), 4.00-4.11 (m, 1H), 3.48 (d, J = 1.56 Hz, 2H), 3.36 (s, 3H), 3.22-3.28 (m, 2H), 2.93-3.07 (m, 2H), 2.54-2.87 (m, 2H), 2.08-2.19 (m, 1H), 1.98-2.05 (m, 1H), 1.94 (br d, J = 13.39 Hz, 1H), 1.76-1.88 (m, 3H), 1.63-1.73 (m, 1H), 1.44-1.53 (m, 1H) | — | — |
| 659 | 600 MHz, DMSO-d6 | 7.37-7.51 (m, 2H), 4.93-5.21 (m, 2H), 4.32-4.51 (m, 3H), 3.95-4.07 (m, 2H), 3.59-3.69 (m, 1H), 3.09-3.22 (m, 2H), 2.93-3.07 (m, 3H), 2.61-2.83 (m, 2H), 2.04-2.23 (m, 1H), 1.74-1.96 (m, 3H) | — | — |
| 660 | 600 MHz, DMSO-d6 | 7.51 (d, 3=3.58 Hz, 1H), 7.24-7.29 (m, 3H), 6.91-6.97 (m, 1H), 5.07 (s, 2H), 4.31-4.46 (m, 1H), 3.31-3.43 (m, 2H), 2.95-3.10 (m, 2H), 2.78-2.87 (m, 1H), 2.07-2.16 (m, 1H), 1.73-1.84 (m, 1H) | I | SFC: Chiralpak AY-H, 10% IPA Peak 1 |

TABLE 15-continued

Characterization data for compounds tabulated in Table 14 8.
The column "Separation Stage" indicates alter which process step regioisomers formed due to asymmetric benzimidazole substitution at R¹ in Scheme 15 were separated during the preparation of the tabulated final compound (I = after preparation of the acetic acid intermediate (where at least one R¹ is not hydrogen); B = prior to boc deprotection or F = final compound).

| Ex. # | Freq., Solvent | ¹HNMR Data (δ ppm) | Separation Stage | SFC Isomer Separation Conditions |
|---|---|---|---|---|
| 661 | 600 MHz, DMSO-d₆ | 9.04-9.14 (m, 1H), 7.21-7.27 (m, 1H), 7.13-7.20 (m, 1H), 6.89-6.97 (m, 1H), 4.80 (s, 2H), 4.30-4.51 (m, 1H), 3.93-4.06 (m, 2H), 3.37-3.47 (m, 2H), 2.97-3.08 (m, 2H), 2.77-2.87 (m, 1H), 2.04-2.16 (m, 1H), 1.72-1.88 (m, 1H) | I | SFC: Chiralpak AY-H, 10% IPA Peak 1 |
| 662 | 600 MHz, DMSO-d₆ | 7.18-7.27 (m, 2H), 6.93 (ddd, J = 9.85, 8.76, 2.49 Hz, 1H), 5.17-5.28 (m, 2H), 4.32-4.50 (m, 1H), 4.13-4.25 (m, 2H), 2.95-3.10 (m, 3H), 2.62-2.91 (m, 2H), 2.52-2.57 (m, 1H), 2.07-2.18 (m, 1H), 1.71-1.83 (m, 1H), 0.98-1.13 (m, 4H) | I | SFC: Chiralpak AY-H, 10% IPA Peak 1 |
| 663 | 600 MHz, DMSO-d₆ | 7.15-7.25 (m, 1H), 7.06 (dd, J = 8.68, 4.87 Hz, 1H), 6.91 (t, J = 9.22 Hz, 1H), 4.95-5.03 (m, 2H), 4.38-4.49 (m, 1H), 3.60-3.67 (m, 1H), 3.54-3.60 (m, 1H), 3.47-3.53 (m, 1H), 3.39-3.47 (m, 2H), 3.34-3.39 (m, 1H), 3.21-3.27 (m, 3H), 2.96-3.09 (m, 2H), 2.81 (dt J = 12.53, 9.26 Hz, 2H), 2.06-2.15 (m, 1H), 1.74-1.83 (m, 1H) | I | SFC: Chiralpak AY-H, 10% IPA Peak 1 |
| 664 | 500 MHz, METHANOL-d₄ | 7.13-7.24 (m, 2H), 6.87-7.00 (m, 1H), 4.96-5.14 (m, 2H), 4.34-4.55 (m, 1H), 4.04-4.17 (m, 1H), 3.64-3.97 (m, 3H), 3.47-3.57 (m, 1H), 3.38-3.46 (m, 1H), 3.30-3.34 (m, 2H), 3.06-3.21 (m, 4H), 2.93 (m, 1H), 2.16-2.44 (m, 2H), 1.87-2.10 (m, 2H) | F | Chiralpak IF, 30% MeOH w/ 0.2% DEA, peak 2 |
| 665 | 500 MHz, METHANOL-d₄ | 7.13-7.23 (m, 2H), 6.89-6.99 (m, 1H), 5.03 (s, 2H), 4.35-4.54 (m, 1H), 4.05-4.16 (m, 1H), 3.65-3.98 (m, 3H), 3.48-3.58 (m, 1H), 3.35-3.49 (m, 1H), 3.32 (td, J = 1.57, 3.21 Hz, 3H), 3.06-3.14 (m, 2H), 2.89-3.02 (m, 2H), 2.15-2.45 (m, 2H), 1.85-2.09 (m, 2H) | F | Chiralpak IF, 30% MeOH w/ 0.2% DEA, peak 1 |
| 666 | 600 MHz, DMSO-d₆ | 8.90-9.00 (m, 1H), 8.49-8.58 (m, 1H), 7.73-7.81 (m, 1H), 7.36-7.42 (m, 1H), 7.26-7.31 (m, 1H), 7.16-7.24 (m, 2H), 6.86-6.97 (m, 1H), 4.95-5.09 (m, 1H), 4.70-4.84 (m, 2H)5 4.27-4.47 (m, 1H), 3.38-3.48 (m, 1H), 3.33-3.38 (m, 1H), 2.94-3.07 (m, 2H), 2.76-2.84 (m, 1H), 2.03-2.16 (m, 1H), 1.74-1.81 (m, 1H), 1.38-1.49 (m, 3H) | B | Chiralpak IC 30% MeOH, peak 2 |
| 667 | 500 MHz, METHANOL-d₄ | 7.07-7.25 (m, 2H), 6.90-7.01 (m, 1H), 5.16-5.32 (m, 1H), 5.01-5.16 (m, 1H), 4.32-4.55 (m, 2H), 4.06-4.32 (m, 2H), 3.67-4.04 (m, 4H), 3.45-3.55 (m, 1H), 3.36-3.45 (m, 1H), 3.04-3.19 (m, 2H), 2.88-3.02 (m, 1H), 2.00-2.61 (m, 3H), 1.81-1.98 (m, 1H) | F | Chiralpak IF, AD-H, 15% MeOH with 0.2% DEA, peak 2 |
| 668 | 600 MHz, DMSO-d₆ | 8.63-8.71 (m, 1H), 7.20-7.25 (m, 1H), 7.13-7.20 (m, 1H), 6.87-6.98 (m, 1H), 4.63 (s, 2H), 4.31-4.48 (m, 1H), 4.16-4.28 (m, 1H), 3.35-3.47 (m, 1H), 2.95-3.10 (m, 2H), 2.76-2.88 (m, 1H), 2.15-2.24 (m, 2H), 2.05-2.14 (m, 1H), 1.86-1.99 (m, 3H), 1.76-1.86 (m, 1H), 1.57-1.71 (m, 2H) | I | SFC: Chiralpak AY-H, 10% IPA Peak 1 |
| 669 | 600 MHz, DMSO-d₆ | 8.61-8.72 (m, 1H), 7.15-7.29 (m, 2H), 6.85-6.97 (m, 1H), 4.69 (d, J = 9.19 Hz, 2H), 4.31-4.50 (m, 1H), 4.04-4.15 (m, 1H), 3.36-3.49 (m, 2H), 2.96-3.13 (m, 2H), 2.73-2.88 (m, 2H), 2,63-2.73 (m, 1H), 2.07-2.19 (m, 1H), 1.76-1.86 (m, 1H), 1.21 (d, J = 6.77 Hz, 3H) | I | SFC: Chiralpak AY-H, 10% IPA Peak 1 |
| 670 | 600 MHz, DMSO-d₆ | 8.63-8.74 (m, 1H), 7.16-7.29 (m, 2H), 6.85-6.96 (m, 1H), 4.61-4.77 (m, 2H), 4.30-4.50 (m, 1H), 4.04-4.15 (m, 2H), 3.35-3.47 (m, 2H), 2.98-3.11 (m, 2H), 2.81-2.87 (m, 1H), 2.75-2.80 (m, 1H), 2.66-2.71 (m, 1H), 2.08-2.20 (m, 1H), 1.75-1.88 (m, 1H), 1.21 (d, J = 6.77 Hz, 3H) | I | SFC: Chiralpak AY-H, 10% IPA Peak 1 |
| 671 | 600 MHz, DMSO-d₆ | 7.23-7.34 (m, 1H), 7.12-7.14 (m, 2H), 6.98 (t, J = 9.31 Hz, 1H), 4.95-5.09 (m, 2H), 4.77-4.86 (m, 1 H), 3.66-3.76 (m, 1H), 3.57-3.62 (m, 1H), 3.46-3.56 (m, 4H), 3.37 (s, 3H), 3.31-3.35 (m, 2H), 3.07-3.12 (m, 2H), 2.91-3.05 (m, 1H), 2.16-2.23 (m, 1H), 1.76-1.88 (m, 1 H), 1.04 (t, J = 7.01 Hz, 3H) | I | SFC: Chiralpak AY-H, 10% IPA Peak 1 |
| 672 | 500 MHz, METHANOL-d₄ | 7.08-7.23 (m, 2H), 6.89-7.00 (m, 1H), 5.15-5.32 (m, 1H), 5.02-5.14 (m, 1H), 4.30-4.55 (m, 2H), 4.07-4.28 (m, 2H), 3.69-4.05 (m, 4H), 3.47-3.57 | F | SFC: Chiralpak AY-H, 10% |

TABLE 15-continued

Characterization data for compounds tabulated in Table 14 8.
The column "Separation Stage" indicates after which process step regioisomers formed due to asymmetric benzimidazole substitution at $R^1$ in Scheme 15 were separated during the preparation of the tabulated final compound (I = after preparation of the acetic acid intermediate (where at least one $R^1$ is not hydrogen); B = prior to boc deprotection or F = final compound).

| Ex. # | Freq., Solvent | ¹HNMR Data (δ ppm) | Separation Stage | SFC Isomer Separation Conditions |
|---|---|---|---|---|
| | | (m, 1H), 3.35-3.44 (m, 1H), 3.03-3.19 (m, 2H), 2.88-2.99 (m, 1H), 1.99-2.61 (m, 3H), 1.82-1.99 (m, 1H) | | IPA Peak 1 |
| 673 | 600 MHz, DMSO-d₆ | 8.55-8.63 (m, 1H), 7.20-7.27 (m, 1H), 7.13-7.19 (m, 1H), 6.88-6.99 (m, 1H), 4.63-4.71 (m, 2H), 4.31-4.49 (m, 1H), 3.35-3.47 (m, 4H), 2.96-3.11 (m, 2H), 2.79-2.87 (m, 1H), 2.41-2.48 (m, 2H), 2.07-2.15 (m, 1H), 1.74-1.86 (m, 1H) | I | SFC: Chiralpak AY-H, 10% IPA Peak 1 |
| 674 | 600 MHz, DMSO-d₆ | 8.86-9.01 (m, 1H), 8.49-8.62 (m, 1H), 7.71-7.82 (m, 1H), 7.34-7.43 (m, 1H), 7.26-7.32 (m, 1H), 7.14-7.24 (m, 2H), 6.86-6.96 (m, 1H), 4.97-5.07 (m, 1H), 4.68-4.86 (m, 2H), 4.30-4.48 (m, 1H), 3.35-3.47 (m, 2H), 2.95-3.08 (m, 2H), 2.76-2.86 (m, 1H), 2.03-2.15 (m, 1H), 1.72-1.83 (m, 1H), 1.43 (d, J = 7.01 Hz, 3H) | I | SFC: Chiralpak AY-H, 10% IPA Peak 1 |
| 675 | 600 MHz, DMSO-d₆ | 8.62-8.77 (m, 1H), 7.14-7.26 (m, 2H), 6.83-6.98 (m, 1H), 4.67 (d, J = 5.29 Hz, 2H), 4.33-4.48 (m, 1H), 4.26-4.32 (m, 1H), 3.79-3.86 (m, 1H), 3.73-3.78 (m, 1H), 3.67-3.73 (m, 1H) 3.50-3.56 (m, 1H), 3.37-3.46 (m, 2H), 2.97-3.09 (m, 2H), 2.76-2.85 (m, 1H), 2.07-2.17 (m, 2H), 1.74-1.85 (m, 2H) | B | Chiralpak AZ-H, 35% MeOH, peak 1 |
| 676 | 600 MHz, DMSO-d₆ | 8.65-8.73 (m, 1H), 7.16-7.27 (m, 2H), 6.89-6.97 (m, 1H), 4.67 (s, 2H), 4.33-4.47 (m, 1H), 4.25-4.32 (m, 1H), 3.80-3.88 (m, 1H), 3.73-3.79 (m, 1H), 3.66-3.73 (m, 1H), 3.49-3.57 (m, 1H), 3.37-3.46 (m, 2H), 2.96-3.10 (m, 2H), 2.77-2.87 (m, 1H), 2.07-2.18 (m, 2H), 1.74-1.86 (m, 2H) | B | Chiralpak AZ-H, 35% MeOH, peak 2 |
| 677 | 600 MHz DMSO-d₆ | 8.18 (s, 2H), 7.17-7.25 (m, 2H), 6.93 (t, J = 9.30 Hz, 1H), 4.59-4.76 (m, 2H), 4.44-4.53 (m, 1H), 4.34-4.43 (m, 1H), 4.07-4.22 (m, 1H), 3.84 (br t, J = 7.75 Hz, 1H), 3.28-3.47 (m, 2H), 3.01-3.21 (m, 4H), 2.79-2.95 (m, 1H), 2.52-2.57 (m, 1H), 2.40-2.48 (m, 1H), 2.09-2.17 (m, 1H), 1.77-1.90 (m, 2H), 1.53 (d, J = 6.23 Hz, 1H), 1.35 (dd, J = 1.40, 6.31 Hz, 1H) | I | SFC: Chiralpak AY-H, 10% IPA Peak 1 |
| 678 | 600 MHz DMSO-d₆ | 7.16-7.25 (m, 2H), 6.91 (t, J = 9.20 Hz, 1H), 5.08-5.23 (m, 1H), 4.81-4.95 (m, 1H), 4.45 (dt, J = 4.17, 7.88 Hz, 1H), 4.30-4.39 (m, 1H), 4.13 (br s, 1H), 4.00 (br d, J = 13.47 Hz, 1H), 3.82-3.93 (m, 1H), 3.60-3.73 (m, 2H), 3.41-3.53 (m, 2H), 2.96-3.07 (m, 2H), 2.77-2.86 (m, 1H), 2.12 (br s, 2H), 1.75-1.84 (m, 1H), 1.37 (br d, J = 5.61 Hz, 1H), 1.14-1.20 (m, 2H) | I | SFC: Chiralpak AY-H, 10% IPA Peak 1 |
| 679 | 600 MHz DMSO-d₆ | 7.15-7.25 (m, 2H), 6.91 (t, J = 9.32 Hz, 1H), 4.87 (s, 1H), 4.29-4.39 (m, 1H), 4.05 (dt, J = 2.61, 6.60 Hz, 1H), 3.61-3.75 (m, 1H), 3.42-3.59 (m, 3H), 2.95-3.12 (m, 2H), 2.77-2.85 (m, 1H), 2.52-2.55 (m, 1H), 2.06-2.18 (m, 1H), 1.89-2.06 (m, 2H), 1.75-1.87 (m, 1H), 1.45-1.63 (m, 1H), 1.22-1.29 (m, 1H), 1.11 (d, J = 6.31 Hz, 2H) | I | SFC: Chiralpak AY-H, 10% IPA Peak 1 |
| 680 | 600 MHz DMSO-d₆ | 7.15-7.27 (m, 1H) 7.08 (dd, J = 4.79, 8.60 Hz, 1H), 6.92 (t, J = 8.75 Hz, 1H), 5.11-5.20 (m, 1H), 4.86-4.94 (m, 1H), 4.41-4.53 (m, 1H), 4.28-4.41 (m, 1H), 4.09-4.25 (m, 1H), 4.01 (br d, J = 11.83 Hz, 1H), 3.77-3.90 (m, 3H), 3.64 (br dd, J = 3.31, 11.87 Hz, 1H), 3.44-3.60 (m, 2H), 3.34-3.43 (m, 3H), 3.32 (br s, 2H), 2.97-3.09 (m, 3H), 2.75-2.85 (m, 1H), 2.06-2.25 (m, 1H), 1.74-1.84 (m, 1H). | I | SFC: Chiralpak AY-H, 10% IPA Peak 1 |
| 681 | 600 MHz DMSO-d₆ | 7.22 (d, J = 9.53 Hz, 1H), 7.18 (t, J = 7.08 Hz, 1H), 6.91 (t, J = 9.33 Hz, 1H), 5.11 (br d, J = 17.36 Hz, 1H), 4.87 (br d, J = 17.05 Hz, 1H), 4.28-4.40 (m, 1H), 3.78-3.92 (m, 1H), 3.61-3.76 (m, 2H), 3.38-3.53 (m, 2H), 3.26-3.34 (m, 3H), 2.95-3.08 (m, 2H), 2.80 (dd, J = 8.29, 12.50 Hz, 1H), 2.02-2.20 (m, 2H), 1.75-1.85 (m, 1H), 1.36 (br d, J = 5.76 Hz, 1H), 1.13-1.21 (m, 2H) | I | SFC: Chiralpak AY-H, 10% IPA Peak 1 |
| 682 | 600 MHz DMSO-d₆ | 7.14-7.25 (m, 2H), 6.91 (t J = 9.19 Hz, 1H), 4.87 (q, J = 17.44 Hz, 2H), 4.28-4.40 (m, 1H), 3.97-4.13 (m, 1H), 3.61-3.71 (m, 1H), 3.47-3.60 (m, 1H), | I | SFC: Chiralpak AY-H, 10% |

TABLE 15-continued

Characterization data for compounds tabulated in Table 14 8.
The column "Separation Stage" indicates alter which process step regioisomers formed due to asymmetric benzimidazole substitution at $R^1$ in Scheme 15 were separated during the preparation of the tabulated final compound (I = after preparation of the acetic acid intermediate (where at least one $R^1$ is not hydrogen); B = prior to boc deprotection or F = final compound).

| Ex. # | Freq., Solvent | $^1$HNMR Data (δ ppm) | Separation Stage | SFC Isomer Separation Conditions |
|---|---|---|---|---|
| | | 3.37-3.46 (m, 3H), 2.95-3.11 (m, 2H), 2.75-2.89 (m, 1H), 2.52-1.91 (m, 4H), 1.49-1.60 (m, 1H), 1.23-1.29 (m, 1H), 1.11 (d, J = 6.31 Hz, 2H) | | IPA Peak 1 |
| 683 | 600 MHz DMSO-d$_6$ | 8.43 (br s, 2H), 7.20-7.30 (m, 2H), 6.94-7.05 (m, 1H), 4.78-5.18 (m, 2H), 3.95-4.13 (m, 2H), 3.82-3.93 (m, 1H), 3.68-3.81 (m, 1H), 3.56-3.68 (m, 2H), 3.32-3.48 (m, 2H), 2.99-3.37 (m, 1H), 1.98-2.21 (m, 1H), 1.40-1.51-2.0 (m, 1H), 1.13-1.30 (m, 7H) | I | SFC: Chiralpak AY-H, 10% IPA Peak 1 |
| 684 | 600 MHz DMSO-d$_6$ | 7.10-7.26 (m, 2H), 6.90-6.96 (m, 1H), 5.11-5.21 (m, 1H), 4.90-5.00 (m, 1H), 4.41-4.49 (m, 1H), 4.37 (br d, J= 6.07 Hz, 1B), 4.17 (br s, 1H), 3.70-3.87 (m, 2H), 3.61 (dt, J = 2.61, 11.50 Hz, 1H), 3.38-3.33 (m, 2H), 3.13-3.20 (m, 1H), 2.99-3.05 (m, 2H), 2.87-2.98 (m, 1H), 2.77-2.85 (m, 1H), 2.52-2.55 (m, 1H), 2.29-2.47 (m, 1H), 1.71-1.89 (m, 1H), 0.97 (t, J = 7.40 Hz, 1H), 0.81 (dt, J = 1.40, 7.40 Hz, 3H) | I | SFC: Chiralpak AY-H, 10% IPA Peak 1 |
| 685 | 600 MHz DMSO-d$_6$ | 7.22 (br d, J = 9.42 Hz, 1H), 7.16 (br d, J = 4.44 Hz, 1H), 6.92 (br t, J = 9.19 Hz, 1H), 5.04-5.19 (m, 1H), 4.93 (br d, J = 17.44 Hz, 1H), 4.36-4.38 (br m, 1H), 3.86-3.95 (m, 1H), 3.77-3.86 (m, 2H), 3.53-3.68 (m, 2H), 3.37-3.51 (m, 3H), 3.14-3.27 (m, 1H), 2.96-3.08 (m, 2H), 2.77-2.89 (m, 1H), 2.12 (br s, 1H), 1.99 (br s, 1H), 1.75-1.91 (m, 1H), 1.48 (br s, 1H), 0.62 (br s, 1H), 0.51 (br s, 1H), 0.42 (br s, 1H), 0.24-0.36 (m, 1H) | I | SFC: Chiralpak AY-H, 10% IPA Peak 1 |
| 686 | 600 MHz DMSO-d$_6$ | 7.14-7.24 (m, 1H), 7.11 (dd, J = 4.79, 8.60 Hz, 1H), 6.85-6.94 (m, 1H), 5.15 (br d, J = 17.52 Hz, 1H), 5.06 (d, J = 17.44 Hz, 1H), 4.42-4.58 (m, 1H), 3.96-4.04 (m, 1H), 3.77-3.94 (m, 2H), 3.59-3.74 (m, 2H), 3.44 (br d, J = 9.89 Hz, 1H), 3.24-3.41 (m, 2H), 2.97-3.23 (m, 1H), 2.65-2.94 (m, 2H), 2.52-2.56 (m, 1H), 2.07-2.16 (m, 1H), 1.74-1.84 (m, 1H), 1.07-1.19 (m, 2H) | I | SFC: Chiralpak AY-H, 10% IPA Peak 1 |
| 687 | 600 MHz DMSO-d$_6$ | 8.29-8.40 (br s, 2H), 7.21-7.30 (m, 1H), 6.99 (t, J = 9.33 Hz, 1H), 4.92-5.06 (m, 1H), 3.70-3.88 (m, 2H), 3.52-3.70 (m, 6H), 3.33-3.39 (m, 2H), 3.05-3.18 (m, 2H), 3.01 (br t, J = 11.99 Hz, 1H), 2.52-2.55 (m, 1H), 1.12-1.41 (m, 6H) | I | SFC: Chiralpak AY-H, 10% IPA Peak 1 |

Biological Example 1 TRPC6 Calcium Flux Assay

Potency of TRPC6 (Transient receptor potential channel family C6) inhibitors were measured by their inhibition of Calcium influx trigged by GAG (1-Oleoyl-2-acetyl-sn-glycerol, Millipore Sigma, O6754) stimulation on HEK293 cells stably transfected with human TRPC6 using a FLIPR tetra system. Cells were grown in a humidified environment at 37° C. under 5% $CO_2$ using the growth medium with the following selective reagents (Dulbecco's Modified Eagle's Medium (DMEM) high glucose, 10% Fetal Bovine Serum, 1×PSGlu (penicillin-streptomycin glutamine), 1×NEAA (Non-essential amino acid), 1× Na Pyruvate and 200 ug/ml Hygromycin). For general passage, cells were grown to 70-90% confluency; the media was removed, and the cells were gently washed 2 times with calcium and magnesium free PBS (phosphate-buffered saline). Trypsin (3 mL) was applied for 5 minutes at 37° C. The cells were dislodged by rapping flask against base of a hand and 7 mL of growth medium was added to deactivate trypsin and re-suspend cells. The usual splitting schedule was 1:5 every 2-3 days. Cells were plated the day before the assay, plating cell density is 1.0-1.5×10$^4$/25 μl/well in poly-D-lysine (PDL) coated 384-well plates using either multichannel pipettes or multidrop. These cells were first incubated with fluorescence dye at room temperature for 90-120 minutes after they were grown on PDL-coated 384-well black plates overnight (Dye loading buffer 10 ml example: 9 mL assay buffer, 1 mL, 10×PBX signal enhancer, 10 μL Calcium indicator). The cells were incubated with a dose of compounds for 25 minutes before being stimulated with TRPC6 agonist OAG. The OAG solution was prepared by adding OAG into assay buffer (Ca ringer solution base: 10 mM HEPES (4-(2-hydroxyethyl)-1-piperazine-ethanesulfonic acid), 4 mM $MgCl_2$, 120 mM NaCl, 5 mM KCl, pH=7.2 @25° C.)+0.1% BSA+2 mM $CaCl_2$) to the concentration of 0.2 mM/2% DMSO, which achieves a final on cell concentration of 50 uM/0.5% DMSO. 12.5 uL OAG mixture was added and the activation of the TRPC6 channel was measured by the change of intracellular Calcium levels on FLIPR terra system.

Data was acquired by measuring the fluorescent peak signal subtracted from the background during the 180 second imaging frame. Each data point is further normalized to 100% of OAG triggered signal vs. buffer. Table 16 provides the IC$_{50}$ for each compound, which data is obtained by plotting peak signal over the compound dose.

TABLE 16

| Ex. # | hTRPC6 Potency (μM) |
|---|---|
| 1 | 0.000696 |
| 2 | 0.0032 |
| 3 | 0.00199 |
| 4 | 0.00167 |
| 5 | 0.00292 |
| 6 | 0.0004002 |
| 7 | 0.0011733 |
| 8 | 0.00028336 |
| 9 | 0.0016133 |
| 10 | 0.00606 |
| 11 | 0.00179 |
| 12 | 0.000285 |
| 13 | 0.00687 |
| 14 | 0.000377 |
| 15 | 0.00439 |
| 16 | 0.224 |
| 17 | 0.118 |
| 18 | 0.00785 |
| 19 | 0.000956 |
| 20 | 0.00192 |
| 21 | 0.0006585 |
| 22 | 0.00162 |
| 23 | >3.75 |
| 24 | 0.145 |
| 25 | 0.21 |
| 26 | 0.161 |
| 27 | 0.0735 |
| 28 | >3.75 |
| 29 | 0.0448 |
| 30 | 1.94 |
| 31 | 0.000476 |
| 32 | 0.0472 |
| 33 | 0.0004325 |
| 34 | 0.0689 |
| 35 | 0.000491 |
| 36 | 0.00613 |
| 37 | 0.00692 |
| 38 | 0.00071978 |
| 39 | 0.000867 |
| 40 | 0.00461 |
| 41 | 0.0184 |
| 42 | 1.94 |
| 43 | 0.000581 |
| 44 | 0.000952 |
| 45 | 0.00236 |
| 46 | 0.001785 |
| 47 | 0.000686 |
| 48 | 0.002205 |
| 49 | 0.001095 |
| 50 | 0.000759 |
| 51 | 0.00647 |
| 52 | 0.0242 |
| 53 | 0.00152 |
| 54 | 0.00552 |
| 55 | 0.00397 |
| 56 | 0.0135 |
| 57 | 0.000784 |
| 58 | 0.000469 |
| 59 | 0.000256 |
| 60 | 0.000261 |
| 61 | 0.0027 |
| 62 | 0.0603 |
| 63 | 0.000389 |
| 64 | 0.132 |
| 65 | 0.000598 |
| 66 | 0.237 |
| 67 | 0.272 |
| 68 | 0.0018215 |
| 69 | 0.01471 |
| 70 | 0.002325 |
| 71 | 0.005615 |
| 72 | 0.000448 |

TABLE 16-continued

| Ex. # | hTRPC6 Potency (μM) |
|---|---|
| 73 | 0.0010945 |
| 74 | 0.38 |
| 75 | 0.0814 |
| 76 | 0.971 |
| 77 | 0.0109 |
| 78 | 0.0707 |
| 79 | 0.00509 |
| 80 | 0.0793 |
| 81 | 0.557 |
| 82 | 0.000504 |
| 83 | 0.000906 |
| 84 | 0.00127 |
| 85 | 0.00755 |
| 86 | 0.00137 |
| 87 | 0.000931 |
| 88 | 0.0006428 |
| 89 | 0.368 |
| 90 | 0.068 |
| 91 | 0.0329 |
| 92 | 0.0438 |
| 93 | 0.0068533 |
| 94 | 0.615 |
| 95 | >3.75 |
| 96 | 0.134 |
| 97 | >3.75 |
| 98 | >3.75 |
| 99 | >3.75 |
| 100 | 0.06 |
| 101 | >3.75 |
| 102 | >3.75 |
| 103 | >3.75 |
| 104 | 0.0618 |
| 105 | 2.48 |
| 106 | 0.0004496 |
| 107 | 0.00788 |
| 108 | 0.000433 |
| 109 | 0.0438 |
| 110 | 0.001232 |
| 111 | 0.0007875 |
| 112 | 0.00028147 |
| 113 | 0.0002855 |
| 114 | 0.000382 |
| 115 | 0.000446 |
| 116 | 0.00779 |
| 117 | >3.75 |
| 118 | 0.000855 |
| 119 | 0.00194 |
| 120 | 0.00321 |
| 121 | 0.00559 |
| 122 | 0.0299 |
| 123 | 0.252 |
| 124 | 0.000741 |
| 125 | 0.000389 |
| 126 | 0.00048 |
| 127 | 0.000492 |
| 128 | 0.04935 |
| 129 | >3.75 |
| 130 | 0.269 |
| 131 | 0.08255 |
| 132 | 0.042 |
| 133 | 0.00698 |
| 134 | 0.00471 |
| 135 | >3.75 [2] |
| 136 | 0.013945 |
| 137 | 0.0362 |
| 138 | 0.00052 |
| 139 | 0.001905 |
| 140 | 0.132 |
| 141 | 0.0135 |
| 142 | 0.0138 |
| 143 | 0.0068625 |
| 144 | 0.000462 |
| 145 | 0.014 |
| 146 | 0.000631 |
| 147 | 0.000433 |
| 148 | 0.0118 |

TABLE 16-continued

| Ex. # | hTRPC6 Potency (μM) |
|---|---|
| 149 | 0.00109 |
| 150 | 0.00902 |
| 151 | 0.00606 |
| 152 | 0.0677 |
| 153 | 0.072 |
| 154 | 0.00306 |
| 155 | 0.0162 |
| 156 | 0.0617 |
| 157 | 0.000501 |
| 158 | 0.00471 |
| 159 | 0.0164 |
| 160 | 0.0142 |
| 161 | 0.133 |
| 162 | 0.257 |
| 163 | 2.84 |
| 164 | 0.253 |
| 165 | 2.06 |
| 166 | 0.56 |
| 167 | 0.0019657 |
| 168 | 1.6 |
| 169 | 0.0142 |
| 170 | 0.0259 |
| 171 | 0.544 |
| 172 | 0.00222 |
| 173 | 0.00138 |
| 174 | 0.564 |
| 175 | 1.7 |
| 176 | 2.33 |
| 177 | 1.54 |
| 178 | 0.0471 |
| 179 | 0.326 |
| 180 | 0.0149 |
| 181 | 0.000907 |
| 182 | 0.314 |
| 183 | 0.655 |
| 184 | 0.143 |
| 185 | 0.003585 |
| 186 | 0.278 |
| 187 | 0.0015905 |
| 188 | 0.013025 |
| 189 | 0.0035867 |
| 190 | 0.004015 |
| 191 | 0.13985 |
| 192 | 0.001725 |
| 193 | 0.0485 |
| 194 | 0.0142 |
| 195 | 0.000664 |
| 196 | 0.00647 |
| 197 | 0.2555 |
| 198 | 0.07125 |
| 199 | 0.0281 |
| 200 | 0.00218 |
| 201 | 0.0439 |
| 202 | 0.002137 |
| 203 | 0.598 |
| 204 | 0.00492 |
| 205 | 0.003 |
| 206 | 0.0123 |
| 207 | 0.0496 |
| 208 | 0.0477 |
| 209 | 0.0038675 |
| 210 | 0.0691 |
| 211 | 0.001095 |
| 212 | 0.0034975 |
| 213 | 0.00993 |
| 214 | 0.00042 |
| 215 | 0.593 |
| 216 | 0.0114 |
| 217 | 0.0687 |
| 218 | 0.00082 |
| 219 | 0.0159 |
| 220 | 0.0009855 |
| 221 | 0.0549 |
| 222 | 0.002045 |
| 223 | 0.0515 |
| 224 | 0.158 |
| 225 | 0.00281 |
| 226 | 0.0137 |
| 227 | 0.00032823 |
| 228 | 0.00032 |
| 229 | 0.0422 |
| 230 | 0.00049 |
| 231 | 0.737 |
| 232 | 0.00216 |
| 233 | 0.00147 |
| 234 | 0.0269 |
| 235 | 0.15 |
| 236 | 0.0238 |
| 237 | 0.223 |
| 238 | 0.185 |
| 239 | 0.562 |
| 240 | 0.0107 |
| 241 | >3.75 |
| 242 | 0.0735 |
| 243 | 1.97 |
| 244 | >3.75 |
| 245 | 0.0625 |
| 246 | 2.92 |
| 247 | 0.0754 |
| 248 | 0.00507 |
| 249 | 0.00765 |
| 250 | 0.0785 |
| 251 | 0.0172 |
| 252 | 0.00876 |
| 253 | 0.406 |
| 254 | 0.0739 |
| 255 | 0.10145 |
| 256 | 0.0194 |
| 257 | 0.0524 |
| 258 | 0.0002881 |
| 259 | 1.43 |
| 260 | 0.376 |
| 261 | >3.75 |
| 262 | 0.28 |
| 263 | 0.765 |
| 264 | 0.217 |
| 265 | 2.86 |
| 266 | 15.8 |
| 267 | >3.75, >50.0 |
| 268 | >3.75, >50.0 |
| 269 | 0.002045 |
| 270 | 0.0515 |
| 271 | 0.158 |
| 272 | 0.00281 |
| 273 | 0.0137 |
| 274 | 0.00032823 |
| 275 | 0.00032 |
| 276 | 0.0422 |
| 277 | 0.00049 |
| 278 | 0.737 |
| 279 | 0.00716 |
| 280 | 0.00147 |
| 281 | 0.0269 |
| 282 | 0.15 |
| 283 | 0.0238 |
| 284 | 0.223 |
| 285 | 0.185 |
| 286 | 0.562 |
| 287 | 0.0107 |
| 288 | >3.75 |
| 289 | 0.0735 |
| 290 | 1.97 |
| 291 | >3.75 |
| 292 | 0.0625 |
| 293 | 2.92 |
| 294 | 0.0754 |
| 295 | 0.00507 |
| 296 | 0.00765 |
| 297 | 0.0785 |
| 298 | 0.0172 |

TABLE 16-continued

| Ex. # | hTRPC6 Potency (µM) |
|---|---|
| 299 | 0.00876 |
| 300 | 0.406 |
| 301 | 0.0739 |
| 102 | 0.10145 |
| 303 | 0.0194 |
| 304 | 0.0524 |
| 305 | 0.0002881 |
| 306 | 1.43 |
| 307 | 0.376 |
| 308 | >3.75 |
| 309 | 0.28 |
| 310 | 0.765 |
| 311 | 0.217 |
| 312 | 2.86 |
| 313 | 15.8 |
| 314 | >3.75, >50.0 |
| 315 | >3.75, >50.0 |
| 316 | 0.002045 |
| 317 | 1.36 |
| 318 | 0.0377 |
| 319 | 0.456 |
| 320 | 0.01205 |
| 321 | 0.00407 |
| 322 | 1.45 |
| 323 | >3.75 |
| 324 | >3.75 |
| 325 | 0.743 |
| 326 | 2.93 |
| 327 | 1.37 |
| 328 | >3.75 |
| 329 | >3.75 |
| 330 | 0.669 |
| 331 | 0.204 |
| 332 | 3.2 |
| 333 | 3.25 |
| 334 | 3.54 |
| 335 | >3.75 |
| 336 | >3.75 |
| 337 | >3.75 |
| 338 | >3.75 |
| 339 | 0.00323 |
| 340 | 0.000704 |
| 341 | 0.0258 |
| 342 | 0.0121 |
| 343 | 0.804 |
| 344 | 0.0853 |
| 345 | 0.0015 |
| 346 | 0.00139 |
| 347 | 0.00107 |
| 348 | 0.493 |
| 349 | 0.215 |
| 350 | 0.351 |
| 351 | 0.0103 |
| 352 | 0.328 |
| 353 | 0.0308 |
| 354 | 0.133 |
| 355 | 0.037 |
| 356 | 0.239 |
| 357 | 0.0245 |
| 358 | 0.00647 |
| 359 | 0.238 |
| 360 | 0.0429 |
| 361 | 0.0668 |
| 362 | 0.256 |
| 363 | 0.0313 |
| 364 | 1.02 |
| 365 | 2.96 |
| 366 | 0.232 |
| 367 | 0.354 |
| 368 | 0.0992 |
| 369 | 0.00865 |
| 370 | >50.0 |
| 371 | 6.83 |
| 372 | 14.1 |
| 373 | 5.85 |
| 374 | 3.41 |
| 375 | 2.77 |
| 376 | 3.05 |
| 377 | 1.65 |
| 378 | 3.08 |
| 379 | 4.44 |
| 380 | 17 |
| 381 | 5.68 |
| 382 | >50.0 |
| 383 | 0.319 |
| 384 | 16 |
| 385 | >50.0 |
| 386 | 4.26 |
| 387 | 5.36 |
| 388 | 9.75 |
| 389 | 4.58 |
| 390 | 3.57 |
| 391 | 1.82 |
| 392 | 2.24 |
| 393 | 5.05 |
| 394 | 0.732 |
| 395 | 1.12 |
| 396 | 18.2 |
| 397 | 1.58 |
| 398 | 0.0874 |
| 399 | 0.0205 |
| 400 | 16.5 |
| 401 | 0.00045573 |
| 402 | 0.00133 |
| 403 | 0.000395 |
| 404 | 0.00167 |
| 405 | 0.000708 |
| 406 | 0.000447 |
| 407 | 0.00585 |
| 408 | 0.000924 |
| 409 | 0.0010356 |
| 410 | 0.0105 |
| 411 | 0.00268 |
| 412 | 0.322 |
| 413 | 0.221 |
| 414 | 0.0015 |
| 415 | 0.274 |
| 416 | 0.00236 |
| 417 | 0.0127 |
| 418 | 0.000584 |
| 419 | 0.128 |
| 420 | 0.0006 |
| 421 | 0.0005404 |
| 422 | 0.00235 |
| 423 | 0.151 |
| 424 | 0.000707 |
| 425 | 0.113 |
| 426 | 0.933 |
| 427 | >1.75 |
| 428 | 0.0183 |
| 429 | >3.75 |
| 430 | 0.88 |
| 431 | >3.75 |
| 432 | 0.00777 |
| 433 | >3.75 |
| 434 | >3.75 |
| 415 | 1.16 |
| 436 | 0.0524 |
| 437 | >3.75 |
| 438 | 0.476 |
| 439 | 0.0367 |
| 440 | 1.34 |
| 441 | 0.002235 |
| 442 | 0.000319 |
| 443 | 0.000471 |
| 444 | 0.00442 |
| 445 | 0.0208 |
| 446 | 0.034 |
| 447 | 0.119 |
| 448 | 0.123 |

TABLE 16-continued

| Ex. # | hTRPC6 Potency (μM) |
|---|---|
| 449 | 1.16 |
| 450 | >3.75 |
| 451 | 0.000613 |
| 452 | 0.00117 |
| 453 | 0.00151 |
| 454 | 0.00152 |
| 455 | 0.00656 |
| 456 | 0.00844 |
| 457 | 0.0133 |
| 458 | 0.0163 |
| 459 | 0.0164 |
| 460 | 0.0242 |
| 461 | 0.0289 |
| 462 | 0.0294 |
| 463 | 0.0339 |
| 464 | 0.0631 |
| 465 | 0.0867 |
| 466 | 0.103 |
| 467 | 0.123 |
| 468 | 0.178 |
| 469 | 0.19 |
| 470 | 0.219 |
| 471 | 0.36 |
| 472 | 0.383 |
| 473 | 0.398 |
| 474 | 0.411 |
| 475 | 0.62 |
| 476 | 0.763 |
| 477 | 1.03 |
| 478 | 1.05 |
| 479 | 1.2 |
| 480 | 1.2 |
| 481 | 2.4 |
| 482 | 2.74 |
| 483 | 2.74 |
| 484 | >3.75 |
| 485 | >3.75 |
| 486 | >1.75 |
| 487 | >3.75 |
| 488 | >3.75 |
| 489 | >3.75 |
| 490 | >3.75 |
| 491 | >3.75 |
| 492 | >3.75 |
| 493 | >3.75 |
| 494 | 0.0126 |
| 495 | 0.0127 |
| 496 | 0.0611 |
| 497 | 0.094 |
| 498 | 0.00188 |
| 499 | 0.00258 |
| 500 | 0.005145 |
| 501 | 0.00621 |
| 502 | 0.009095 |
| 503 | 0.0256 |
| 504 | 0.0393 |
| 505 | 0.0432 |
| 506 | 0.0766 |
| 507 | 0.102 |
| 508 | 0.112 |
| 509 | 0.131 |
| 510 | 0.139 |
| 511 | 0.158 |
| 512 | 0.162 |
| 513 | 0.183 |
| 514 | 0.185 |
| 515 | 0.186 |
| 516 | 0.197 |
| 517 | 0.319 |
| 518 | 0.4 |
| 519 | 0.476 |
| 520 | 0.686 |
| 521 | 0.757 |
| 522 | 0.762 |
| 523 | 0.988 |
| 524 | 1.49 |

TABLE 16-continued

| Ex. # | hTRPC6 Potency (μM) |
|---|---|
| 525 | 1.78 |
| 526 | 2.85 |
| 527 | 3.01 |
| 528 | >3.75 |
| 529 | >1.75 |
| 530 | >3.75 |
| 531 | >3.75 |
| 532 | >3.75 |
| 533 | >3.75 |
| 534 | >3.75 |
| 535 | >3.75 |
| 536 | >3.75 |
| 537 | >1.75 |
| 538 | >3.75 |
| 539 | >3.75 |
| 540 | >3.75 |
| 541 | >3.75 |
| 542 | >3.75 |
| 543 | >3.75 |
| 544 | >3.75 |
| 545 | >3.75 |
| 546 | >3.75 |
| 547 | 0.0437 |
| 548 | 0.382 |
| 549 | 0.41 |
| 550 | >3.75 |
| 551 | 0.0061 |
| 552 | 0.00651 |
| 553 | 0.00669 |
| 554 | 0.0109 |
| 555 | 0.0116 |
| 556 | 0.0119 |
| 557 | 0.0128 |
| 558 | 0.0161 |
| 559 | 0.0166 |
| 560 | 0.0187 |
| 561 | 0.0198 |
| 562 | 0.0208 |
| 563 | 0.0216 |
| 564 | 0.0292 |
| 565 | 0.0322 |
| 566 | 0.0352 |
| 567 | 0.0398 |
| 568 | 0.04805 |
| 569 | 0.0784 |
| 570 | 0.0854 |
| 571 | 0.0932 |
| 572 | 0.106 |
| 573 | 0.117 |
| 574 | 0.153 |
| 575 | 0.155 |
| 576 | 0.169 |
| 577 | 0.184 |
| 578 | 0.251 |
| 579 | 0.312 |
| 580 | 0.365 |
| 581 | 0.368 |
| 582 | 0.376 |
| 583 | 0.42 |
| 584 | 0.546 |
| 585 | 0.579 |
| 586 | 0.747 |
| 587 | 0.765 |
| 588 | 0.811 |
| 589 | 1.01 |
| 590 | 1.44 |
| 591 | 1.59 |
| 592 | 1.73 |
| 593 | 2.12 |
| 594 | >3.75 |
| 595 | >3.75 |
| 596 | >3.75 |
| 597 | >3.75 |
| 598 | >3.75 |
| 599 | >3.75 |
| 600 | 0.00538 |

TABLE 16-continued

| Ex. # | hTRPC6 Potency (μM) |
|---|---|
| 601 | 0.00556 |
| 602 | 0.00575 |
| 603 | 0.00673 |
| 604 | 0.00778 |
| 605 | 0.0079 |
| 606 | 0.00806 |
| 607 | 0.0143 |
| 608 | 0.0183 |
| 609 | 0.0203 |
| 610 | 0.0212 |
| 611 | 0.0224 |
| 612 | 0.0224 |
| 613 | 0.0242 |
| 614 | 0.0248 |
| 615 | 0.0285 |
| 616 | 0.0323 |
| 617 | 0.0332 |
| 618 | 0.0483 |
| 619 | 0.0574 |
| 620 | 0.0604 |
| 621 | 0.0753 |
| 622 | 0.0789 |
| 623 | 0.089 |
| 624 | 0.102 |
| 625 | 0.105 |
| 626 | 0.117 |
| 627 | 0.122 |
| 628 | 0.132 |
| 629 | 0.158 |
| 630 | 0.174 |
| 631 | 0.225 |
| 632 | 0.23 |
| 633 | 0.24 |
| 634 | 0.26 |
| 635 | 0.304 |
| 636 | 0.326 |
| 637 | 0.341 |
| 638 | 0.425 |
| 639 | 0.657 |
| 640 | 0.809 |
| 641 | 1.28 |
| 642 | 1.65 |
| 643 | 1.82 |
| 644 | 1.91 |
| 645 | 2.3 |
| 646 | 2.31 |
| 647 | 3.17 |
| 648 | 3.35 |
| 649 | >3.75 |
| 650 | >1.75 |
| 651 | >3.75 |
| 652 | >3.75 |
| 653 | >3.75 |
| 654 | >3.75 |
| 655 | >3.75 |
| 656 | >3.75 |
| 657 | >3.75 |
| 658 | >3.75 |
| 659 | >3.75 |
| 660 | 0.005037 |
| 661 | 0.279 |
| 662 | 0.283 |
| 663 | 0.294 |
| 664 | 0.555 |
| 665 | 0.584 |
| 666 | 0.687 |
| 667 | 0.745 |
| 668 | 0.778 |
| 669 | 0.901 |
| 670 | 1.12 |
| 671 | 1.43 |
| 672 | 1.66 |
| 673 | >3.75 |
| 674 | >1.75 |
| 675 | >3.75 |
| 676 | >3.75 |

TABLE 16-continued

| Ex. # | hTRPC6 Potency (μM) |
|---|---|
| 677 | 0.0881 |
| 678 | 0.0983 |
| 679 | 0.15 |
| 680 | 0.153 |
| 681 | 0.168 |
| 682 | 0.259 |
| 683 | 0.29 |
| 684 | 0.524 |
| 685 | 1.16 |
| 686 | 1.57 |
| 687 | 2.08 |

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions. 11925336v.1

What is claimed is:

1. A compound or pharmaceutically acceptable salt thereof, according to Formula I:

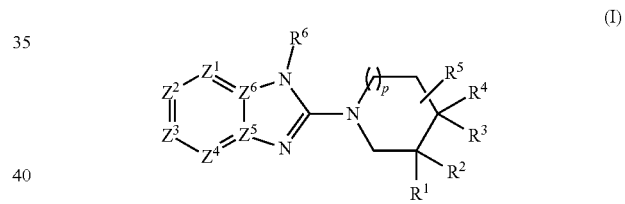

(I)

Wherein p is 0 or 1;

when p is 0, then $R^1$ and $R^3$, taken in combination, form a fused $C_3$-$C_6$cycloalkyl ring or a fused 4 to 6 member heterocycle ring having 1 or 2 ring heteroatoms independently selected from N, O or S, which cycloalkyl or heterocycle is optionally substituted with amino; $R^2$ is hydrogen, $C_1$-$C_6$alkyl or amino$C_1$-$C_4$alkyl; and $R^4$ is hydrogen; or when p is 1, then $R^1$ is $NHR^{1a}$; $R^{1a}$ is hydrogen, $C_1$-$C_4$alkyl, $C_3$-$C_7$cycloalkyl, hydroxy$C_1$-$C_4$alkyl, or 4 to 6 member heterocycloalkyl having one ring heteroatom selected from N, O or S; $R^2$ is hydrogen, $C_1$-$C_4$alkyl, hydroxy$C_1$-$C_4$alkyl or $C(O)NH_2$; $R^3$ is halogen, $C_1$-$C_4$alkyl, $C_1$-$C_4$alkoxy or hydroxy; and $R^4$ is hydrogen, $C_1$-$C_4$alkyl or halogen; or when p is 0 or 1, then $C(NHR^{1a})R^2$, taken in combination, form a spirocyclic 4 to 6 member heterocycloalkyl; $R^3$ is halogen $C_1$-$C_4$alkyl, $C_1$-$C_4$alkoxy, or hydroxy; and $R^4$ is hydrogen or halogen; or when p is 1, then $R^1$ and $R^3$, taken in combination, form a fused 4 to 6 member heterocycle or a fused 3 to 7 member carbocycle, which heterocycle comprises a ring nitrogen atom and optionally 0 or 1 additional ring heteroatoms selected from N, O and S, and which carbocycle is substituted with amino; and $R^2$ is hydrogen; and $R^4$ is hydrogen, halogen or hydroxy;

$R^5$ represents 1 or 2 substituents independently selected from hydrogen, halogen, hydroxy, amino, $C_1$-$C_6$alkyl or $C_1$-$C_6$alkoxy;

$R^6$ is —$(CR^7R_8)$-A;

A is 5 or 6 member heteroaryl, which heteroaryl comprises one ring heteroatom selected from N, O or S and 0, 1 or 2 additional ring nitrogen atoms, which heteroaryl is optionally substituted with 0, 1, 2, 3 or 4 groups independently selected from halogen, cyano, $C_1$-$C_6$alkyl, $C_2$-$C_6$alkenyl, $C_2$-$C_6$alkynyl, halo$C_1$-$C_6$alkyl, $C_1$-$C_6$alkoxy, halo$C_1$-$C_6$alkoxy, $C(O)NH_2$, $C(O)NHC_1$-$C_6$alkyl, phenyl or 5 or 6 member heteroaryl having one ring heteroatom selected from N, O or S and 0, 1 or 2 additional ring nitrogen atoms, wherein the optional heteroaryl or phenyl substituent is further substituted with 0, 1 or 2 $C_1$-$C_6$alkyl;

$R^7$ is hydrogen, $C_1$-$C_4$alkyl or amino;

$R^8$ is hydrogen or $C_1$-$C_4$alkyl; or $CR^7R^8$, taken in combination form a 3 to 6 member cycloalkandiyl group;

$Z^1$ is N or $CR^{11}$;
$Z^2$ is N or $CR^{12}$;
$Z^3$ is N or $CR^{13}$;
$Z^4$ is N or $CR^{14}$,
$Z^5$ and $Z^6$ are each independently N or C;

wherein 0, 1 or 2 of $Z^1$, $Z^2$, $Z^3$, $Z^4$, $Z^5$ and $Z^6$ are N;

each of $R^{11}$, $R^{12}$, $R^{13}$ and $R^{14}$ is independently selected from the group consisting of hydrogen, halogen, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, $C_3$-$C_7$cycloalkyl, cyano, $SO2C_1$-$C_6$alkyl, phenyl, and saturated, partially unsaturated or aromatic 5 or 6 member heterocycle having 1 or 2 ring heteroatoms independently selected from N, O and S, which heterocycle is optionally substituted with 1 or 2 substituents independently selected from $C_1$-$C_6$alkyl and halogen; and with the proviso that compounds of Formula I do not include 1-[7-fluoro-6-methoxy-1-[[2-(trifluoromethyl)phenyl]methyl]-1H-benzimidazol-2-yl]-3-piperidinamine.

2. The compound or pharmaceutically acceptable salt thereof of claim 1, wherein p is 0; $R^1$ and $R^3$, taken in combination, form a fused $C_3$-$C_6$cycloalkyl ring or a fused 4 to 6 member azacycle ring, which cycloalkyl or azacycle is optionally substituted with amino; and $R^2$ and $R^4$ are hydrogen.

3. The compound or pharmaceutically acceptable salt thereof of claim 1, wherein p is 1, $R^1$ is $NHR^{1a}$; $R^{1a}$ is hydrogen, $C_1$-$C_4$alkyl, $C_3$-$C_7$cycloalkyl or 4 to 6 member heterocycloalkyl having one ring heteroatom selected from N, O or S; $R^2$ is hydrogen or $C_1$-$C_4$alkyl; $R^3$ is halogen, $C_1$-$C_4$alkyl, $C_1$-$C_4$alkoxy, or hydroxy; and $R^4$ is hydrogen, halogen or $C_1$-$C_4$alkyl.

4. The compound or pharmaceutically acceptable salt thereof of claim 3, wherein $R^1$ is $NHR^{1a}$; $R^{1a}$ is hydrogen, methyl, ethyl, propyl, isopropyl or cyclopropyl; $R^2$ is hydrogen or methyl; $R^3$ is halogen, methyl, ethyl, methoxy, ethoxy, or hydroxy; and $R^4$ is hydrogen, halogen, methyl or ethyl.

5. The compound or pharmaceutically acceptable salt thereof of claim 3, wherein $R^1$ is $NH_2$; $R^2$ is hydrogen; $R^3$ is fluorine, methyl, or hydroxy; and $R^4$ is hydrogen, fluorine or methyl.

6. The compound or pharmaceutically acceptable salt thereof of claim 1, wherein $R^7$ is hydrogen or methyl; and $R^8$ is hydrogen.

7. The compound or pharmaceutically acceptable salt thereof of claim 1, wherein A is pyridin-2-yl, pyridin-3-yl, pyrimidin-2-yl, or pyrazin-2-yl, each of which is substituted with 1 to 3 groups independently selected from the group consisting of halogen, cyano, $C_1$-$C_4$alkyl, halo$C_1$-$C_4$alkyl, $C_1$-$C_4$alkoxy, halo$C_1$-$C_4$alkoxy, $C(O)NH_2$, $C(O)NHC_1$-$C_4$alkyl, phenyl or 5 member heteroaryl having one ring heteroatom selected from N, O or S and 0, 1 or 2 additional ring nitrogen atoms, wherein the optional heteroaryl or phenyl substituent is further substituted with 0, 1 or 2 $C_1$-$C_6$alkyl.

8. The compound or pharmaceutically acceptable salt thereof of claim 1, wherein
$Z^1$ is $CR^{11}$;
$Z^2$ is $CR^{12}$;
$Z^3$ is $CR^{13}$;
$Z^4$ is N or $CR^{14}$,
$Z^5$ and $Z^6$ are each C;
$R^{11}$ is hydrogen, halogen, cyano or $C_1$-$C_4$alkyl;
$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, halo$C_1$-$C_4$alkoxy $C_3$-$C_6$cycloalkyl or 5 member saturated, partially unsaturated or aromatic 5 or 6 member heterocycle having 1 or 2 ring heteroatoms independently selected from N, O and S; and
$R^{14}$ is hydrogen, halogen, cyano or $C_1$-$C_4$alkyl.

9. The compound or pharmaceutically acceptable salt thereof of claim 1 which is a compound of Formula III:

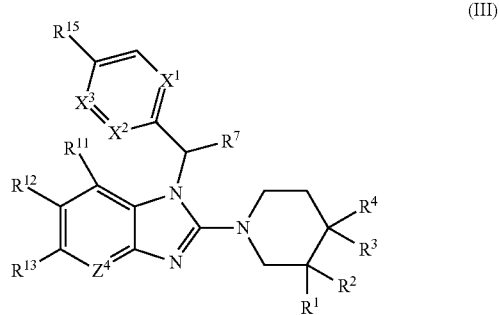

(III)

Wherein
$X^1$ is $CR^{16}$ or N;
$X^2$ is $CR^{17}$ or N;
$X^3$ is $CR^{18}$ or N;
$Z^4$ is N or $CR^{14}$;
$R^1$ is $NHR^{1a}$;
$R^{1a}$ is hydrogen or $C_1$-$C_4$alkyl;
$R^2$ is hydrogen or $C_1$-$C_4$alkyl;
$R^3$ is halogen;
$R^4$ is hydrogen or halogen;
$R^7$ is hydrogen, methyl or ethyl;
$R^{11}$ is hydrogen, halogen, cyano or $C_1$-$C_4$alkyl;
$R^{12}$ and $R^{13}$ are each independently selected from the group consisting of hydrogen, halogen, cyano, $C_1$-$C_4$alkyl, halo$C_1$-$C_4$alkyl, $C_1$-$C_4$alkoxy, or halo$C_1$-$C_4$alkoxy;
$R^{14}$ is hydrogen, halogen, cyano or $C_1$-$C_4$alkyl;
$R^{15}$ is hydrogen, halogen, cyano, $C_1$-$C_4$alkyl, $C_1$-$C_4$alkoxy, halo$C_1$-$C_4$alkyl, halo$C_1$-$C_4$alkoxy, $C(O)NH_2$, $C(O)NH(C_1$-$C_4$alkyl) or 5 member heteroaryl having one ring heteroatom selected from N, O or S and 0, 1 or 2 additional ring nitrogen atoms;

$R^{16}$ is hydrogen, halogen, cyano, $C_1$-$C_4$alkyl, $C_1$-$C_4$alkoxy, halo$C_1$-$C_4$alkyl or halo$C_1$-$C_4$alkoxy;
$R^{17}$ is hydrogen or halogen; and
$R^{18}$ is hydrogen, halogen, cyano, $C_1$-$C_4$alkyl, $C_1$-$C_4$alkoxy, halo$C_1$-$C_4$alkyl or halo$C_1$-$C_4$alkoxy, wherein at least one of $R^1$, $R^{16}$, $R^{17}$ or $R^{18}$ is not hydrogen.

10. The compound or pharmaceutically acceptable salt thereof of claim 9, wherein $R^{11}$ is hydrogen.

11. The compound or pharmaceutically acceptable salt thereof of claim 9, wherein $R^{1a}$ is hydrogen or methyl; $R^3$ is fluorine; and $R^4$ is hydrogen or fluorine.

12. A compound or pharmaceutically acceptable salt thereof, which compound is selected from the group consisting of
- 6-((2-((3R,4S)-3-amino-4-fluoropiperidin-1-yl)-6-chloro-1H-benzo[d]imidazol-1-yl)methyl)nicotinonitrile;
- 2-((3R,4R)-3-amino-4-fluoropiperidin-1-yl)-1-((5-chloropyrimidin-2-yl)methyl)-6-fluoro-1H-benzo[d]imidazole-4-carbonitrile;
- (3R,4R)-1-(4,6-difluoro-1-((5-fluoropyrimidin-2-yl)methyl)-1H-benzo[d]imidazol-2-yl)-4-fluoropiperidin-3-amine;
- 6-((2-((3R,4R)-3-amino-4-fluoropiperidin-1-yl)-1H-benzo[d]imidazol-1-yl)methyl)nicotinonitrile;
- (R)-6-((2-(3-amino-4,4-difluoropiperidin-1-yl)-4,6-difluoro-1H-benzo[d]imidazol-1-yl)methyl)nicotinonitrile hydrochloride;
- (R)-6-((2-(3-amino-4,4-difluoropiperidin-1-yl)-6-fluoro-1H-benzo[d]imidazol-1-yl)methyl)nicotinonitrile;
- 6-((2-((3R,4R)-3-amino-4-fluoro-1-piperidinyl)-4-methoxy-1H-benzimidazol-1-yl)methyl)-3-pyridinecarbonitrile;
- 2-((3R,4R)-3-amino-4-fluoropiperidin-1-yl)-1-((5-chloropyrimidin-2-yl)methyl)-1H-benzo[d]imidazole-6-carbonitrile;
- (3R,4R)-4-fluoro-1-(1-((5-fluoropyrimidin-2-yl)methyl)-1H-benzo[d]imidazol-2-yl)piperidin-3-amine; and
- (3R,4R)-1-(1-((5-chloropyrimidin-2-yl)methyl)-6-fluoro-1H-benzo[d]imidazol-2-yl)-4-fluoropiperidin-3-amine.

13. The compound or pharmaceutically acceptable salt thereof of claim 1 in a form of a pharmaceutically acceptable salt.

14. A pharmaceutical composition comprising a pharmaceutically acceptable excipient, carrier or adjuvant and at least one compound of claim 1.

15. A method of treating a disease or disorder mediated by TRPC6 in a mammal which method comprises administering to the mammal a therapeutically effective amount of at least one compound of claim 1, or a pharmaceutical salt thereof or a pharmaceutical composition thereof, wherein the disease or disorder mediated by TRPC6 is nephrotic syndrome or pulmonary hypertension.

16. A method for modulating TRPC6 activity in a mammal which method comprises administering to the mammal an amount of at least one compound of claim or a pharmaceutical salt thereof or a pharmaceutical composition thereof to modulate TRPC6 activity in the mammal.

* * * * *